United States Patent
Beskrovnaya et al.

(10) Patent No.: US 10,871,495 B2
(45) Date of Patent: Dec. 22, 2020

(54) BIOMARKERS OF POLYCYSTIC KIDNEY DISEASE AND USES THEREOF

(71) Applicant: Genzyme Corporation, Cambridge, MA (US)

(72) Inventors: Oxana Beskrovnaya, Bridgewater, NJ (US); Nikolai Bukanov, Bridgewater, NJ (US); Sarah Moreno, Bridgewater, NJ (US)

(73) Assignee: Genzyme Corporation, Cambridge, MA (US)

( * ) Notice: Subject to any disclaimer, the term of this patent is extended or adjusted under 35 U.S.C. 154(b) by 202 days.

(21) Appl. No.: 15/501,496

(22) PCT Filed: Aug. 3, 2015

(86) PCT No.: PCT/US2015/043497
§ 371 (c)(1),
(2) Date: Feb. 3, 2017

(87) PCT Pub. No.: WO2016/022500
PCT Pub. Date: Feb. 11, 2016

(65) Prior Publication Data
US 2017/0227551 A1    Aug. 10, 2017

Related U.S. Application Data

(60) Provisional application No. 62/033,031, filed on Aug. 4, 2014.

(51) Int. Cl.
*G01N 33/68*    (2006.01)
*G01N 33/49*    (2006.01)

(52) U.S. Cl.
CPC ....... *G01N 33/6893* (2013.01); *G01N 33/492* (2013.01); *G01N 2800/347* (2013.01); *G01N 2800/52* (2013.01); *G01N 2800/56* (2013.01); *G01N 2800/60* (2013.01)

(58) Field of Classification Search
CPC ......... G01N 2800/347; G01N 2800/52; G01N 2800/56; G01N 2800/60; G01N 33/492; G01N 33/6893
See application file for complete search history.

(56) References Cited

U.S. PATENT DOCUMENTS

| 2011/0229895 A1 | 9/2011 | Walz |
| 2013/0276513 A1* | 10/2013 | Sharma ................ G01N 33/48 73/23.35 |
| 2014/0079769 A1 | 3/2014 | Terzi et al. |

FOREIGN PATENT DOCUMENTS

| CN | 102018702 | 4/2011 |
| EP | 2341344 | 7/2011 |
| JP | 2003-500418 | 1/2003 |
| JP | 2008-507540 | 3/2008 |
| WO | WO 2000/71706 | 11/2000 |
| WO | WO 2006/012394 | 2/2006 |
| WO | WO 2010/141862 | 12/2010 |
| WO | WO 2014/006093 | 1/2014 |
| WO | WO 2014/043068 | 3/2014 |

OTHER PUBLICATIONS

Natoli et al., "Inhibition of glucosylceramide accumulation results in effective blockade of polycystic kidney disease in mouse models," Nature Medicine, 2010, vol. 16, pp. 788-792.*
Salih et al., "Urinary extracellular vesicles and the kidney: biomarkers and beyond," Am. J. Physiol. Renal Physiol., 2014, vol. 306, pp. F1251-F1259, Epub Apr. 2, 2014.*
Anderson et al., "2-Hydroxyestradiol slows progression of experimental polycystic kidney disease," Am. J. Physiol. Renal Physiol. 302(5):F636-F645, Dec. 7, 2011.
Belibi et al., "mTORC1/2 and rapamycin in female Han:SPRD rats with polycystic kidney disease," Am. J. Physiol. Renal Physiol. 300(1):F236-F244, dated Oct. 13, 2010.
Chinese Office Action in Application No. 2015-80053081.4, dated Sep. 29, 2018, 23 pages.
Columbia Office Action in Application No. NC2017/0001596, dated Nov. 13, 2018, 14 pages.
Singapore Written Opinion in Application No. 112017002905, dated Sep. 28, 2018, 6 pages.
Written Opinion in Singapore Patent Application No. 11201700290S, dated Oct. 26, 2017, 6 pages.
Hogan et al., "Characterization of PKD Protein-Positive Exosome-Like Vesicles," J. Am. Soc. Nephrol. 20(2):278-288, Jan. 28, 2009.

(Continued)

*Primary Examiner* — Galina M. Yakovleva
(74) *Attorney, Agent, or Firm* — Fish & Richardson P.C.

(57) ABSTRACT

Provided herein are methods for determining the efficacy of treatment for polycystic kidney disease (PKD) in a patient, diagnosing PKD in a patient, staging PKD in a patient, and monitoring PKD in a patient. These methods include determining a single or multiple levels of one or more markers selected from the group of Proliferating Cell Nuclear Antigen (PCNA), cyclin D1, cyclin D3, MAPKERK kinase 1 (MEK), ribosomal protein S6 (S6), phosphorylated ribosomal protein S6 (pS6), extracellular signal-regulated kinase (ERK), phosphorylated extracellular signal-regulated kinase (pERK), protein kinase B (Akt), phosphorylated protein kinase B (pAkt), caspase-2, total S6, and retinoblastoma binding protein (RBBP). Also provided are kits that include at least three antibodies that specifically bind to one or more of these markers.

4 Claims, 3 Drawing Sheets
Specification includes a Sequence Listing.

(56) References Cited

OTHER PUBLICATIONS

Hogan et al., "Identification of Biomarkers for PKD1 Using Urinary Exosomes," *J. Am. Soc. Nephrol.* 26(7):1661-1670, Dec. 2014.
International Preliminary Report on Patentability in International Application No. PCT/US2015/043497, dated Feb. 7, 2017, 14 pages.
International Search Report and Written Opinion in International Application No. PCT/US2015/043497, dated Feb. 24, 2016, 19 pages.
Jia et al., "Chronic treatment with Lisinopril decreases proliferative and apoptotic pathways in autosomal recessive polycystic kidney disease," *Pediatric Nephrol.* 25(6):1139-1146, Mar. 13, 2010.
Mathivanan et al., "Proteomics Analysis of A33 Immunoaffinity-purified Exosomes Released from The Human Colon Tumor Cell Line LIM10215 Reveals a Tissue-specific Protein Signature," *Mol. Cell. Proteomics* 9(2):197-208, Feb. 1, 2010.
Pisitkun et al., "Identification and proteomic profiling of exosomes in human urine," *Proc. Natl. Acad. Sci. U.S.A.* 101(36):13368-13373, Sep. 7, 2004.
Salih, "Third International Meeting of ISEV 2014," ISEV Meeting, p. 06C-251, dated Apr. 30, 2014.
Bukanov et al., "CDK inhibitors R-roscovitine and S-CR8 effectively block renal and hepatic cystogenesis in an orthologous model of ADPKD," Cell Cycle 11(21):4040-4046, Nov. 1, 2012.
Chinese Office Action in Application No. 201580053081.4, dated Jan. 19, 2018, 11 pages.
Columbia Office Action in Application No. NC2017/0001596, dated May 3, 2018, 10 pages.
Japanese Office Action in Patent Application No. 2017-506291, dated Aug. 6, 2019, 6 pages.
Chinese Office Action in Patent Application No. 201580053081.4, dated Apr. 2, 2019, 19 pages.
Columbia Office Action in Patent Application No. NC2017/0001596, dated Jul. 19, 2018, 23 pages.
Fischer et al., "Activation of the AKT/mTOR pathway in autosomal recessive polycystic kidney disease (ARPKD)," Nephrology Dialysis Transplantation 24(6):1819-1827, Jan. 2009.
Masoumi et al., "Potential pharmacological interventions in polycystic kidney disease," Drugs 67(17):2495-2510, Dec. 2007.
Natoli et al., "Loss of GM3 synthase gene, but not sphingosine kinase 1, is protective against murine nephronophthisis-related polycystic kidney disease," Human Molecular Genetics 21(15):3397-3407, May 2012.
Written Opinion in Russian Patent Application No. 2017106891, dated Mar. 13, 2019, 11 pages.
Chinese Office Action in Patent Application No. 201580053081.4, dated Oct. 28, 2019, 13 pages.
Chinese Office Action in Patent Application No. 201580053081.4, dated Apr. 2, 2020, 7 pages.
European Office Action in Patent Application No. 15757363.5, dated Oct. 23, 2019, 8 pages.

* cited by examiner

US 10,871,495 B2

BIOMARKERS OF POLYCYSTIC KIDNEY DISEASE AND USES THEREOF

CROSS-REFERENCE TO RELATED APPLICATIONS

This application is a National Stage application under 35 U.S.C. § 371 of International Patent Application No. PCT/US2015/043497, filed Aug. 3, 2015, which claims priority to U.S. Provisional Patent Application Ser. No. 62/033,031, filed Aug. 4, 2014, the entire contents which are herein incorporated by reference.

TECHNICAL FIELD

This invention relates to methods of molecular medicine and molecular biology.

BACKGROUND

Polycystic kidney disease (PKD) is a common genetic disorder characterized by the formation of fluid-filled epithelial-lined cysts in the kidneys of patients over time (Park et al., *BMB Reports* 44:359-368, 2011). The cysts in a PKD patient can increase in size and number over the decades, and displace and destroy adjacent renal parenchyma, which can ultimately lead to end-stage renal disease in the patient (Chapin et al., *J. Cell Biol.* 191:701-710, 2010). Multiple mechanisms have been shown to contribute to PKD, including increased proliferation and apoptosis, in addition to loss of differentiation and polarity (Belibi et al., *Expert. Opin. Invest. Drugs* 19:315-328, 2010). Many end-stage PKD patients depend on transplantation or hemodialysis to attenuate renal failure (Park et al., 2011; supra).

There are two types of PKD: autosomal dominant PKD (ADPKD) and autosomal recessive PKD (ARPKD). In the year 2006, about 500,000 people were diagnosed as having PKD in the U.S., with ADPKD affecting about 1 person out of 500 to 1,000 people, and ARPKD affecting about 1 person out of 20,000 to 40,000 people. ADPKD is the most common inherited disorder of the kidneys and accounts for ~5% of the end-stage renal disease patients in the U.S. (Pei et al., *Adv. Chronic Kidney Dis.* 17:140-152, 2010).

SUMMARY

The present invention is based, at least in part, on the discovery that levels of Proliferating Cell Nuclear Antigen (PCNA), cyclin D1, cyclin D3, MAPK-ERK kinase 1 (MEK), ribosomal protein S6 (S6), phosphorylated ribosomal protein S6 (pS6), extracellular signal-regulated kinase (ERK), phosphorylated extracellular signal-regulated kinase (pERK), protein kinase B (Akt), phosphorylated protein kinase B (pAkt), caspase-2, total ribosomal protein S6 (S6+pS6) and retinoblastoma binding protein (RBBP) are elevated in samples containing a biological fluid (e.g., a urine sample or a urine sample enriched for exosomes) from patients having PKD, are increased in samples containing a biological fluid (e.g., a urine sample or a urine sample enriched for exosomes) from patients with later stages of PKD as compared to the levels in patients having early stages of PKD, and are decreased in samples containing a biological fluid (e.g., a urine sample or a urine sample enriched for exosomes) from PKD subjects administered a therapeutically effective treatment of PKD. In view of this discovery, provided herein are methods for determining the efficacy of a treatment for PKD in a patient, diagnosing PKD in a patient, staging PKD in a patient, and monitoring PKD in a patient that include determining a level of one or more of PCNA, cyclin D1, cyclin D3, MEK, S6, pS6, ERK, pERK, Akt, pAkt, caspase-2, total ribosomal protein S6, and RBBP.

Provided here are methods of determining the efficacy of treatment for polycystic kidney disease (PKD) in a PKD patient that include: (a) providing a first sample including a biological fluid obtained from the PKD patient at a first time point; (b) concentrating the first sample for exosomes; (c) determining the level(s) of at least one marker selected from the group of Proliferating Cell Nuclear Antigen (PCNA), cyclin D1, cyclin D3, MAPK-ERK kinase 1 (MEK), ribosomal protein S6 (S6), phosphorylated ribosomal protein S6 (pS6), extracellular signal-regulated kinase (ERK), phosphorylated extracellular signal-regulated kinase (pERK), protein kinase B (Akt), phosphorylated protein kinase B (pAkt), caspase-2, total ribosomal protein S6, and retinoblastoma binding protein (RBBP) in the first sample; (d) administering a treatment for PKD to the PKD patient; (e) providing a second sample comprising a biological fluid obtained from the PKD patient at a second time point after step (d) and performing steps (b) and (c) on the second sample; and (f) identifying the administered treatment as being effective if the level is decreased at the second time point as compared to the first time point. In some embodiments of any of the method described herein, the administered treatment is administration of a glucosyl ceramide synthase (GCS) inhibitor. In some embodiments of any of the method described herein, the GCS inhibitor is selected from the group of: (S)-quinuclidin-3-yl (2-(4'-(2-methoxyethoxy)-[1,1'-biphenyl]-4-yl)propan-2-yl)carbamate; 4-fluoro-1-(5-fluoro-4-(4-((2-methoxyethoxy)methyl)phenyl)pyrimidin-2-yl)-N-(4-methyl-1-azabicyclo[3.2.2]nonan-4-yl)piperidine-4-carboxamide; 4-fluoro-1-(4-(4-((2-methoxyethoxy)methyl)phenyl)pyrimidin-2-yl)-N-(3-methylquinuclidin-3-yl)piperidine-4-carboxamide; 4-fluoro-1-(4-(4-((2-methoxyethoxy)methyl)phenyl)pyrimidin-2-yl)-N-(4-methyl-1-azabicyclo[3.2.2]nonan-4-yl)piperidine-4-carboxamide; 4-fluoro-1-(4-(4-(methoxymethyl)phenyl)pyrimidin-2-yl)-N-(3-methylquinuclidin-3-yl)piperidine-4-carboxamide; 4-fluoro-1-(4-(4-(methoxymethyl)phenyl)pyrimidin-2-yl)-N-(4-methyl-1-azabicyclo[3.2.2]nonan-4-yl)piperidine-4-carboxamide; 4-fluoro-1-(4-(4-(2-methoxyethoxy)phenyl)pyrimidin-2-yl)-N-(3-methylquinuclidin-3-yl)piperidine-4-carboxamide; 4-fluoro-1-(4-(4-(2-methoxyethoxy)phenyl)pyrimidin-2-yl)-N-(4-methyl-1-azabicyclo[3.2.2]nonan-4-yl)piperidine-4-carboxamide; 4-fluoro-1-(4-(4-(2-fluoroethoxy)phenyl)pyrimidin-2-yl)-N-(quinuclidin-3-yl)piperidine-4-carboxamide; and 4-fluoro-1-(4-(4-(2-fluoroethoxy)phenyl)pyrimidin-2-yl)-N-(4-methyl-1-azabicyclo[3.2.2]nonan-4-yl)piperidine-4-carboxamide.

Some embodiments of any of the methods described herein further include after (f): (g) administering additional doses of the administered GCS inhibitor identified as being effective to the PKD patient. In some embodiments of any of the methods described herein, in step (g) the PKD patient is administered additional doses of: (S)-quinuclidin-3-yl (2-(4'-(2-methoxyethoxy)-[1,1'-biphenyl]-4-yl)propan-2-yl) carbamate; 4-fluoro-1-(5-fluoro-4-(4-((2-methoxyethoxy)methyl)phenyl) pyrimidin-2-yl)-N-(4-methyl-1-azabicyclo[3.2.2]nonan-4-yl)piperidine-4-carboxamide; 4-fluoro-1-(4-(4-((2-methoxyethoxy)methyl)phenyl)pyrimidin-2-yl)-N-(3-methylquinuclidin-3-yl)piperidine-4-carboxamide; 4-fluoro-1-(4-(4-((2-methoxyethoxy)methyl)phenyl)pyrimidin-2-yl)-N-(4-methyl-1-azabicyclo[3.2.2]nonan-4-yl)piperidine-4-carboxamide; 4-fluoro-1-(4-(4-(methoxymethyl) phenyl) pyrimidin-2-yl)-N-(3-methylquinuclidin-3-yl) piperidine-4-carboxamide; 4-fluoro-1-(4-(4-(methoxymethyl) phenyl)pyrimidin-2-yl)-N-(4-methyl-1-azabicyclo[3.2.2]nonan-4-yl)piperidine-4-carboxamide; 4-fluoro-1-(4-(4-(2-methoxyethoxy)phenyl) pyrimidin-2-yl)-N-(3-methylquinuclidin-3-yl)piperidine-4-carboxamide; 4-fluoro-1-(4-(4-(2-methoxyethoxy)phenyl)pyrimidin-2-yl)-N-(4-methyl-1-azabicyclo[3.2.2]nonan-4-yl)piperidine-4-carboxamide; 4-fluoro-1-(4-(4-(2-fluoroethoxy)phenyl) pyrimidin-2-yl)-N-(quinuclidin-3-yl)piperidine-4-carboxamide; or 4-fluoro-1-(4-(4-(2-fluoroethoxy)phenyl)pyrimidin-2-yl)-N-(4-methyl-1-azabicyclo[3.2.2]nonan-4-yl)piperidine-4-carboxamide.

In some embodiments of any of the methods described herein, steps (c) and (e) include determining the levels of at least two markers selected from the group consisting of PCNA, cyclin D1, cyclin D3, MEK, S6, and pS6, and the administered treatment is identified as being effective if at least one of the two levels is decreased at the second time point as compared to the first time point. In some embodiments of any of the methods described herein, the administered treatment is identified as being effective if both levels are decreased at the second time point as compared to the first time point.

In some embodiments of any of the methods described herein, steps (c) and (e) include determining the levels of at least three markers selected from the group of PCNA, cyclin D1, cyclin D3, MEK, S6, and pS6, and the administered treatment is identified as being effective if at least one of the three levels is decreased at the second time point as compared to the first time point. In some embodiments of any of the methods described herein, the administered treatment is identified as being effective if all three levels are decreased at the second time point as compared to the first time point.

In some embodiments of any of the methods described herein, steps (c) and (e) include determining the levels of at least four markers selected from the group of PCNA, cyclin D1, cyclin D3, MEK, S6, and pS6, and the administered treatment is identified as being effective if at least one of the four levels is decreased at the second time point as compared to the first time point. In some embodiments of any of the methods described herein, the administered treatment is identified as being effective if all four levels are decreased at the second time point as compared to the first time point. In some embodiments of any of the methods described herein, the administered treatment is administration of a CDK inhibitor (e.g., R-roscovitine) to the PKD patient.

In some embodiments of any of the methods described herein, the concentrating in (b) and (e) includes ultracentrifuging the first and second samples, respectively. In some embodiments of any of the methods described herein, the first and second samples include urine.

In some embodiments of any of the methods described herein, determining the level(s) of at least one marker in (c) and (e) include determining the level of protein of the at least one marker. In some embodiments of any of the methods described herein, steps (c) and (e) include contacting the sample with antibodies that bind specifically to the protein of the at least one marker. In some embodiments of any of the methods described herein, steps (c) and (e) include determining the level of one or both of cyclin D1 and MEK.

Some embodiments of any of the methods described herein further include after (f): (g) administering additional doses of the administered treatment identified as being effective to the PKD patient. In some embodiments of any of the methods described herein, the administered treatment identified as being effective is a CDK inhibitor, and in step (g) the PKD patient is administered additional doses of the CDK inhibitor (e.g., S-CR8).

Also provided are methods of determining the efficacy of treatment in a patient identified as having polycystic kidney disease (PKD) that include: (a) providing a first sample including a biological fluid obtained from the PKD patient at a first time point; (b) determining the level(s) of at least one marker selected from the group of Proliferating Cell Nuclear Antigen (PCNA), cyclin D1, cyclin D3, MAPK-ERK kinase 1 (MEK), ribosomal protein S6 (S6), phosphorylated ribosomal protein S6 (pS6), extracellular signal-regulated kinase (ERK), phosphorylated extracellular signal-regulated kinase (pERK), protein kinase B (Akt), phosphorylated protein kinase B (pAkt), caspase-2, total S6, and retinoblastoma binding protein (RBBP) in the first sample; (c) administering a treatment for PKD to the PKD patient; (d) providing a second sample comprising a biological fluid obtained from the patient at a second time point after step (c) and performing step (b) on the second sample; and (e) identifying the administered treatment as being effective if the level is decreased at the second time point as compared to the level at the first time point. In some embodiments of any of the methods described herein, the administered treatment is administration of a glucosyl ceramide synthase (GCS) inhibitor. In some embodiments of any of the methods described herein, the GCS inhibitor is selected from the group consisting of: (S)-quinuclidin-3-yl (2-(4'-(2-methoxyethoxy)-[1,1'-biphenyl]-4-yl)propan-2-yl) carbamate; 4-fluoro-1-(5-fluoro-4-(4-((2-methoxyethoxy)methyl)phenyl)pyrimidin-2-yl)-N-(4-methyl-1-azabicyclo[3.2.2]nonan-4-yl) piperidine-4-carboxamide; 4-fluoro-1-(4-(4-((2-methoxyethoxy)methyl)phenyl) pyrimidin-2-yl)-N-(3-methylquinuclidin-3-yl)piperidine-4-carboxamide; 4-fluoro-1-(4-(4-((2-methoxyethoxy)methyl)phenyl)pyrimidin-2-yl)-N-(4-methyl-1-azabicyclo [3.2.2]nonan-4-yl)piperidine-4-carboxamide; 4-fluoro-1-(4-(4-(methoxymethyl) phenyl)pyrimidin-2-yl)-N-(3-methylquinuclidin-3-yl)piperidine-4-carboxamide; 4-fluoro-1-(4-(4-(methoxymethyl) phenyl)pyrimidin-2-yl)-N-(4-methyl-1-azabicyclo [3.2.2] nonan-4-yl)piperidine-4-carboxamide; 4-fluoro-1-(4-(4-(2-methoxyethoxy) phenyl)pyrimidin-2-yl)-N-(3-methylquinuclidin-3-yl)piperidine-4-carboxamide; 4-fluoro-1-(4-(4-(2-methoxyethoxy)phenyl)pyrimidin-2-yl)-N-(4-methyl-1-azabicyclo [3.2.2]nonan-4-yl)piperidine-4-carboxamide; 4-fluoro-1-(4-(4-(2-fluoroethoxy) phenyl) pyrimidin-2-yl)-N-(quinuclidin-3-yl)piperidine-4-carboxamide; and 4-fluoro-1-(4-(4-(2-fluoroethoxy)phenyl) pyrimidin-2-yl)-N-(4-methyl-1-azabicyclo[3.2.2]nonan-4-yl)piperidine-4-carboxamide.

Some embodiments of any of the methods described herein further include after (e): (f) administering additional doses of the administered GCS inhibitor identified as being effective to the PKD patient. In some embodiments of any of the methods described herein, in step (f) the PKD patient is administered additional doses of: (S)-quinuclidin-3-yl (2-(4'-(2-methoxyethoxy)-[1,1'-biphenyl]-4-yl)propan-2-yl) carbamate; 4-fluoro-1-(5-fluoro-4-(4-((2-methoxyethoxy) methyl)phenyl) pyrimidin-2-yl)-N-(4-methyl-1-azabicyclo [3.2.2]nonan-4-yl)piperidine-4-carboxamide; 4-fluoro-1-(4-(4-((2-methoxyethoxy)methyl)phenyl)pyrimidin-2-yl)-N-(3-methylquinuclidin-3-yl)piperidine-4-carboxamide; 4-fluoro-1-(4-(4-((2-methoxyethoxy) methyl)phenyl)pyrimidin-2-yl)-N-(4-methyl-1-azabicyclo [3.2.2]nonan-4-yl) piperidine-4-carboxamide; 4-fluoro-1-(4-(4-(methoxymethyl) phenyl)pyrimidin-2-yl)-N-(3-methylquinuclidin-3-yl) piperidine-4-carboxamide; 4-fluoro-1-(4-(4-

(methoxymethyl)phenyl)pyrimidin-2-yl)-N-(4-methyl-1-azabicyclo [3.2.2]nonan-4-yl)piperidine-4-carboxamide; 4-fluoro-1-(4-(4-(2-methoxyethoxy) phenyl)pyrimidin-2-yl)-N-(3-methylquinuclidin-3-yl)piperidine-4-carboxamide; 4-fluoro-1-(4-(4-(2-methoxyethoxy)phenyl)pyrimidin-2-yl)-N-(4-methyl-1-azabicyclo[3.2.2]nonan-4-yl)piperidine-4-carboxamide; 4-fluoro-1-(4-(4-(2-fluoroethoxy)phenyl) pyrimidin-2-yl)-N-(quinuclidin-3-yl)piperidine-4-carboxamide; or 4-fluoro-1-(4-(4-(2-fluoroethoxy)phenyl) pyrimidin-2-yl)-N-(4-methyl-1-azabicyclo[3.2.2]nonan-4-yl)piperidine-4-carboxamide.

In some embodiments of any of the methods described herein, steps (b) and (d) include determining the levels of at least two markers selected from the group of PCNA, cyclin D1, cyclin D3, MEK, S6, and pS6, and the administered treatment is identified as being effective if at least one of the two levels is decreased at the second time point as compared to the first time point. In some embodiments of any of the methods described herein, the administered treatment is identified being effective if both levels are decreased at the second time point as compared to the first time point.

In some embodiments of any of the methods described herein, steps (b) and (d) include determining the levels of at least three markers selected from the group consisting of PCNA, cyclin D1, cyclin D3, MEK, S6, and pS6, and the administered treatment is identified as being effective if at least one of the three levels is decreased at the second time point as compared to the first time point. In some embodiments of any of the methods described herein, the administered treatment is identified as being effective if all three levels are decreased at the second time point as compared to the first time point.

In some embodiments of any of the methods described herein, steps (b) and (d) include determining the levels of at least four markers selected from the group of PCNA, cyclin D1, cyclin D3, MEK, S6, and pS6, and the administered treatment is identified as being effective if at least one of the four levels is decreased at the second time point as compared to the first time point. In some embodiments of any of the methods described herein, the administered treatment is identified as being effective if all four levels are decreased at the second time point as compared to the first time point. In some embodiments of any of the methods described herein, the administered treatment is administration of a CDK inhibitor or R-roscovitine.

In some embodiments of any of the methods described herein, determining the level(s) of at least one marker in (b) and (d) includes determining the level of protein of the at least one marker. In some embodiments of any of the methods described herein, steps (b) and (d) include contacting the sample with antibodies that bind specifically to the protein of the at least one marker. In some embodiments of any of the methods described herein, steps (b) and (d) include determining the level of at least two of PCNA, cyclin D3, pERK, and Akt. Some embodiments of any of the methods described herein further include after (e): (f) administering additional doses of the administered treatment identified as being effective to the PKD patient. In some embodiments of any of the methods described herein, the administered treatment identified as being effective is a CDK inhibitor, and in step (f) the PKD patient is administered additional doses of the CDK inhibitor. In some embodiments of any of the methods described herein, in step (f) the PKD patient is administered additional doses of roscovitine.

Also provided are methods of diagnosing polycystic kidney disease (PKD) in a patient that include: (a) providing a sample including a biological fluid from a patient suspected of having PKD; (b) concentrating the sample for exosomes; (c) determining the level(s) of at least one marker selected from the group of Proliferating Cell Nuclear Antigen (PCNA), cyclin D1, cyclin D3, MAPK-ERK kinase 1 (MEK), ribosomal protein S6 (S6), phosphorylated ribosomal protein S6 (pS6), extracellular signal-regulated kinase (ERK), phosphorylated extracellular signal-regulated kinase (pERK), protein kinase B (Akt), phosphorylated protein kinase B (pAkt), caspase-2, total S6, and retinoblastoma binding protein (RBBP) in the sample; and (d) identifying the patient as having PKD if the level is elevated as compared to a control level. In some embodiments of any of the methods described herein, step (c) includes determining the levels of at least two markers selected from the group of PCNA, cyclin D1, cyclin D3, MEK, S6, and pS6, and the patient is identified as having PKD if at least one of the two levels are elevated as compared to control level(s). In some embodiments of any of the methods described herein, the patient is identified as having PKD if both levels are elevated as compared to control levels.

In some embodiments of any of the methods described herein, step (c) includes determining the levels of at least three markers selected from the group consisting of PCNA, cyclin D1, cyclin D3, MEK, S6, and pS6, and the patient is identified as having PKD if at least one of the three levels are elevated as compared to control levels. In some embodiments of any of the methods described herein, the patient is identified as having PKD if all three levels are elevated as compared to control levels.

In some embodiments of any of the methods described herein, step (c) includes determining the levels of at least four markers selected from the group of PCNA, cyclin D1, cyclin D3, MEK, S6, and pS6, and the patient is identified as having PKD if at least one of the four levels are elevated as compared to control levels. In some embodiments of any of the methods described herein, the patient is identified as having PKD if all four levels are elevated as compared to control levels.

In some embodiments of any of the methods described herein, concentrating in (b) includes ultracentrifuging the sample. In some embodiments of any of the methods described herein, the sample includes urine. In some embodiments of any of the methods described herein, determining the level(s) of at least one marker in (c) includes determining the level of protein of the at least one marker. In some embodiments of any of the methods described herein, step (c) includes contacting the sample with antibodies that bind specifically to the protein of the at least one marker.

In some embodiments of any of the methods described herein, step (c) includes determining the level of at least two of PCNA, cyclin D1, cyclin D3, MEK, S6, and phosphorylated S6. Some embodiments of any of the methods described herein further include after step (d): (e) administering a treatment for PKD to a patient identified as having PKD. In some embodiments of any of the methods described herein, the treatment is administering a glucosyl ceramide synthase (GCS) inhibitor to the patient. In some embodiments of any of the methods described herein, the GCS inhibitor is selected from the group of: (S)-quinuclidin-3-yl (2-(4'-(2-methoxyethoxy)-[1,1'-biphenyl]-4-yl)propan-2-yl) carbamate; 4-fluoro-1-(5-fluoro-4-(4-((2-methoxyethoxy) methyl)phenyl)pyrimidin-2-yl)-N-(4-methyl-1-azabicyclo [3.2.2]nonan-4-yl)piperidine-4-carboxamide; 4-fluoro-1-(4-(4-((2-methoxyethoxy)methyl) phenyl)pyrimidin-2-yl)-N-(3-methylquinuclidin-3-yl)piperidine-4-carboxamide;

4-fluoro-1-(4-(4-((2-methoxyethoxy)methyl)phenyl)pyrimidin-2-yl)-N-(4-methyl-1-azabicyclo[3.2.2]nonan-4-yl)piperidine-4-carboxamide; 4-fluoro-1-(4-(4-(methoxymethyl)phenyl)pyrimidin-2-yl)-N-(3-methylquinuclidin-3-yl) piperidine-4-carboxamide; 4-fluoro-1-(4-(4-(methoxymethyl)phenyl)pyrimidin-2-yl)-N-(4-methyl-1-azabicyclo[3.2.2]nonan-4-yl)piperidine-4-carboxamide; 4-fluoro-1-(4-(4-(2-methoxyethoxy)phenyl)pyrimidin-2-yl)-N-(3-methylquinuclidin-3-yl)piperidine-4-carboxamide; 4-fluoro-1-(4-(4-(2-methoxyethoxy)phenyl)pyrimidin-2-yl)-N-(4-methyl-1-azabicyclo[3.2.2]nonan-4-yl)piperidine-4-carboxamide; 4-fluoro-1-(4-(4-(2-fluoroethoxy)phenyl)pyrimidin-2-yl)-N-(quinuclidin-3-yl)piperidine-4-carboxamide; and 4-fluoro-1-(4-(4-(2-fluoroethoxy)phenyl)pyrimidin-2-yl)-N-(4-methyl-1-azabicyclo[3.2.2]nonan-4-yl)piperidine-4-carboxamide.

In some embodiments of any of the methods described herein, the treatment is administering a CDK inhibitor to the patient (e.g., S-CR8). Some embodiments of any of the methods described herein further include after (d): (e) imaging one or both kidney(s) in a patient identified as having PKD. In some embodiments of any of the methods described herein, the control level is a threshold level or a level in a healthy subject or a population of healthy subjects.

Also provided are methods of diagnosing polycystic kidney disease (PKD) in a patient that include: (a) providing a sample including kidney tissue from a patient suspected of having PKD; (b) determining the level(s) of at least one marker selected from the group consisting of Proliferating Cell Nuclear Antigen (PCNA), cyclin D1, cyclin D3, MAPK-ERK kinase 1 (MEK), ribosomal protein S6 (S6), phosphorylated ribosomal protein S6 (pS6), extracellular signal-regulated kinase (ERK), phosphorylated extracellular signal-regulated kinase (pERK), protein kinase B (Akt), phosphorylated protein kinase B (pAkt), caspase-2, total S6, and retinoblastoma binding protein (RBBP) in the sample; and (c) identifying the patient as having PKD if the level is elevated as compared to a control level. In some embodiments of any of the methods described herein, step (b) includes determining the levels of at least two markers selected from the group of PCNA, cyclin D1, cyclin D3, MEK, S6, and pS6, and the patient is identified as having PKD if at least one of the two levels are elevated as compared to control level(s). In some embodiments of any of the methods described herein, the patient is identified as having PKD if both levels are elevated as compared to control levels.

In some embodiments of any of the methods described herein, step (b) includes determining the levels of at least three markers selected from the group of PCNA, cyclin D1, cyclin D3, MEK, S6, and pS6, and the patient is identified as having PKD if at least one of the three levels are elevated as compared to control levels. In some embodiments of any of the methods described herein, the patient is identified as having PKD if all three levels are elevated as compared to control levels.

In some embodiments of any of the methods described herein, step (b) includes determining the levels of at least four markers selected from the group of PCNA, cyclin D1, cyclin D3, MEK, S6, and pS6, and the patient is identified as having PKD if at least one of the four levels are elevated as compared to control levels. In some embodiments of any of the methods described herein, the patient is identified as having PKD if all four levels are elevated as compared to control levels. In some embodiments of any of the methods described herein, determining the level(s) of at least one marker in (b) includes determining the level of protein of the at least one marker. In some embodiments of any of the methods described herein, step (b) includes contacting the sample with antibodies that bind specifically to the protein of the at least one marker. In some embodiments of any of the methods described herein, step (b) includes determining the level of at least two of cyclin D1, MEK, ERK, pAkt, Akt, S6, and pS6.

Some embodiments of any of the methods described herein further include after step (c): (d) administering a treatment for PKD to a patient identified as having PKD. In some embodiments of any of the methods described herein, the treatment is administering a glucosyl ceramide synthase (GCS) inhibitor to the patient. In some embodiments of any of the methods described herein, the GCS inhibitor is selected from the group of: (S)-quinuclidin-3-yl (2-(4'-(2-methoxyethoxy)-[1,1'-biphenyl]-4-yl)propan-2-yl)carbamate; 4-fluoro-1-(5-fluoro-4-(4-((2-methoxyethoxy)methyl)phenyl)pyrimidin-2-yl)-N-(4-methyl-1-azabicyclo[3.2.2]nonan-4-yl)piperidine-4-carboxamide; 4-fluoro-1-(4-(4-((2-methoxyethoxy)methyl)phenyl)pyrimidin-2-yl)-N-(3-methylquinuclidin-3-yl)piperidine-4-carboxamide; 4-fluoro-1-(4-(4-((2-methoxyethoxy)methyl)phenyl)pyrimidin-2-yl)-N-(4-methyl-1-azabicyclo[3.2.2]nonan-4-yl)piperidine-4-carboxamide; 4-fluoro-1-(4-(4-(methoxymethyl)phenyl)pyrimidin-2-yl)-N-(3-methylquinuclidin-3-yl)piperidine-4-carboxamide; 4-fluoro-1-(4-(4-(methoxymethyl) phenyl)pyrimidin-2-yl)-N-(4-methyl-1-azabicyclo[3.2.2]nonan-4-yl)piperidine-4-carboxamide; 4-fluoro-1-(4-(4-(2-methoxyethoxy)phenyl) pyrimidin-2-yl)-N-(3-methylquinuclidin-3-yl)piperidine-4-carboxamide; 4-fluoro-1-(4-(4-(2-methoxyethoxy)phenyl)pyrimidin-2-yl)-N-(4-methyl-1-azabicyclo[3.2.2]nonan-4-yl)piperidine-4-carboxamide; 4-fluoro-1-(4-(4-(2-fluoroethoxy)phenyl)pyrimidin-2-yl)-N-(quinuclidin-3-yl)piperidine-4-carboxamide; and 4-fluoro-1-(4-(4-(2-fluoroethoxy)phenyl)pyrimidin-2-yl)-N-(4-methyl-1-azabicyclo[3.2.2]nonan-4-yl)piperidine-4-carboxamide.

In some embodiments of any of the methods described herein, the treatment is administering a CDK inhibitor (e.g., S-CR8) to the patient. Some embodiments of any of the methods described herein further include after (c): (d) imaging one or both kidney(s) in a patient identified as having PKD.

Also provided are methods of determining the stage of polycystic kidney disease (PKD) in a patient that include: (a) providing a sample including a biological fluid from a patient suspected of having PKD or identified as having PKD; (b) concentrating the sample for exosomes; (c) determining the level(s) of at least one marker selected from the group of Proliferating Cell Nuclear Antigen (PCNA), cyclin D1, cyclin D3, MAPK-ERK kinase 1 (MEK), ribosomal protein S6 (S6), phosphorylated ribosomal protein S6 (pS6), extracellular signal-regulated kinase (ERK), phosphorylated extracellular signal-regulated kinase (pERK), protein kinase B (Akt), phosphorylated protein kinase B (pAkt), caspase-2, total S6, and retinoblastoma binding protein (RBBP) in the sample; and (d) determining the stage of PKD in the patient from the level. In some embodiments of any of the methods described herein, step (c) includes determining the levels of at least two markers selected from the group of PCNA, cyclin D1, cyclin D3, MEK, S6, and pS6, and the stage of PKD in the patient is determined from at least one of the two levels. In some embodiments of any of the methods described herein, the stage of PKD in the patient is determined from both levels.

In some embodiments of any of the methods described herein, step (c) includes determining the levels of at least three markers selected from the group of PCNA, cyclin D1, cyclin D3, MEK, S6, and pS6, and the stage of PKD in the patient is determined from at least one of the three levels. In some embodiments of any of the methods described herein, the stage of PKD in the patient is determined from all three levels.

In some embodiments of any of the methods described herein, step (c) includes determining the levels of at least four markers selected from the group of PCNA, cyclin D1, cyclin D3, MEK, S6, and pS6, and the stage of PKD in the patient is determined from at least one of the four levels. In some embodiments of any of the methods described herein, the stage of PKD in the patient is determined from all four levels. In some embodiments of any of the methods described herein, the concentrating in step (b) includes ultracentrifuging the sample. In some embodiments of any of the methods described herein, the sample comprises urine. In some embodiments of any of the methods described herein, determining the level(s) of at least one marker in (c) includes determining the level of protein of the at least one marker. In some embodiments of any of the methods described herein, step (c) includes contacting the sample with antibodies that bind specifically to the protein of the at least one marker.

In some embodiments of any of the methods described herein, step (c) includes determining the level of at least two of PCNA, cyclin D3, MEK, and phosphorylated S6. Some embodiments of any of the methods described herein further include after (d): (e) administering a treatment for stage I, stage II, stage III, stage IV, or stage V PKD to a patient identified to have stage I, stage II, stage III, stage IV, or stage V PKD, respectively. Some embodiments of any of the methods described herein further include after (d): (e) imaging one or both kidney(s) in a patient after (d) to confirm the stage of PKD in the patient.

Also provided are methods of monitoring polycystic kidney disease (PKD) patient that include: (a) providing a first sample including a biological fluid obtained from the PKD patient at a first time point; (b) concentrating the first sample for exosomes; (c) determining the level(s) of at least one marker selected from the group of Proliferating Cell Nuclear Antigen (PCNA), cyclin D1, cyclin D3, MAPK-ERK kinase 1 (MEK), ribosomal protein S6 (S6), phosphorylated ribosomal protein S6 (pS6), extracellular signal-regulated kinase (ERK), phosphorylated extracellular signal-regulated kinase (pERK), protein kinase B (Akt), phosphorylated protein kinase B (pAkt), caspase-2, total S6, and retinoblastoma binding protein (RBBP) in the first sample; (d) providing a second sample including a biological fluid obtained from the PKD patient at a second time point after the first time point, and performing steps (b) and (c) on the second sample; and (e) identifying the patient as having improving or static PKD if the level is not elevated at the second time point as compared to the level at the first time point. In some embodiments of any of the methods described herein, steps (c) and (d) include determining the levels of at least two markers selected from the group consisting of PCNA, cyclin D1, cyclin D3, MEK, S6, and pS6, and the patient is identified as having improving or static PKD if at least one of the two levels is not elevated at the second time point as compared to the first time point. In some embodiments of any of the methods described herein, the patient is identified as having improving or static PKD if both levels are not elevated at the second time point as compared to the first time point.

In some embodiments of any of the methods described herein, steps (c) and (d) include determining the levels of at least three markers selected from the group of PCNA, cyclin D1, cyclin D3, MEK, S6, and pS6, and the patient is identified as having improving or static PKD if at least one of the three levels is not elevated at the second time point as compared to the first time point. In some embodiments of any of the methods described herein, the patient is identified as having improving or static PKD if all three levels are not elevated at the second time point as compared to the first time point.

In some embodiments of any of the methods described herein, steps (c) and (d) include determining the levels of at least four markers selected from the group of PCNA, cyclin D1, cyclin D3, MEK, S6, and pS6, and the patient is identified as having improving or static PKD if at least one of the four levels are not elevated at the second time point as compared to the first time point. In some embodiments of any of the methods described herein, the patient is identified as having improving or static PKD if all four levels are not elevated at the second time point as compared to the first time point. In some embodiments of any of the methods described herein, the concentrating in (b) and (d) includes ultracentrifuging the sample. In some embodiments of any of the methods described herein, the first and second samples comprise urine. In some embodiments of any of the methods described herein, determining the level(s) of at least one marker in steps (c) and (d) include determining the level of protein of the at least one marker. In some embodiments of any of the methods described herein, steps (c) and (d) include contacting the sample with antibodies that bind specifically to the protein of the at least one marker. In some embodiments of any of the methods described herein, steps (c) and (d) include determining the level of at least two of PCNA, cyclin D3, MEK, and phosphorylated S6. Some embodiments of any of the methods described herein further include after (e): (f) administering the same treatment to a patient identified as having improving or static PKD.

Also provided are kits that include, consist essentially of, or consist of at least three antibodies selected from the group of: an antibody that specifically binds to Proliferating Cell Nuclear Antigen (PCNA), an antibody that specifically binds to cyclin D1, an antibody that specifically binds to cyclin D3, an antibody that specifically binds to MAPK-ERK kinase 1 (MEK), an antibody that specifically binds to ribosomal protein S6 (S6), an antibody that specifically binds to phosphorylated ribosomal protein S6 (pS6), an antibody that specifically binds to extracellular signal-regulated kinase (ERK), an antibody that specifically binds to phosphorylated extracellular signal-regulated kinase (pERK), an antibody that specifically binds to protein kinase B, an antibody that specifically binds to phosphorylated protein kinase B (pAkt), an antibody that specifically binds to caspase-2, and an antibody that specifically binds to retinoblastoma binding protein (RBBP).

As used herein, the word "a" before a noun represents one or more of the particular noun. For example, the phrase "a marker" represents "one or more markers."

The term "patient" means a vertebrate, including any member of the class mammalia, including humans, domestic and farm animals, and zoo, sports or pet animals, such as mouse, rabbit, pig, sheep, goat, cattle, horse (e.g., race horse), and higher primates. In preferred embodiments, the patient is a human.

The term "biological fluid" means any fluid obtained from a mammalian patient (e.g., blood, plasma, serum, or other blood fractions, lymph, urine, cerebrospinal fluid, ascites, saliva, breast milk, tears, vaginal discharge, amniotic fluid, lavage, semen, glandular secretions, exudate, and contents of cysts or feces). In preferred embodiments, the biological fluid is urine, blood, serum, or plasma.

The term "exosome" is art known and means a lipid-based microparticle or nanoparticle, or protein-rich aggregate, present in a sample (e.g., a biological fluid) obtained from a patient. Exosomes are also referred to in the art as extracellular vesicles, microvesicles, or nanovesicles. In the present disclosure, an extracellular vesicle can be between about 20 nm to about 1 m (e.g., 20 nm to about 90 nm) in diameter. The size of vesicles may also be much higher where the diameter is in the micron range, e.g. 1-10 m. Exosomes are secreted or shed from a variety of different mammalian cell types. Non-limiting examples of exosomes and methods for concentrating a sample (e.g., a biological fluid) for exosomes are described herein. Additional examples of exosomes and methods for concentrating a sample for exosomes are known in the art.

The phrase "concentrating a sample for exosomes" is art known and means one or more manipulations of a sample to increase the concentration of exosomes. The step of concentrating a sample for exosomes can, for example, include one or more of the following: centrifuging the sample (e.g, ultracentrifugation, optionally in a density gradient), passing the sample through a chromatography column (e.g., an affinity or molecular sieve chromatography column, such as a spin column), and the use of antibodies that specifically bind to an antigen on the surface of an exosome and/or a bead (e.g., a bead coated with the antibodies that specifically bind to the antigen on the surface of an exosome or a bead coated with a molecule that binds specifically to the antibody that specifically binds to the antigen on the surface of the exosome). Exemplary methods of concentrating a sample for examples are described herein and additional methods are known in the art.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
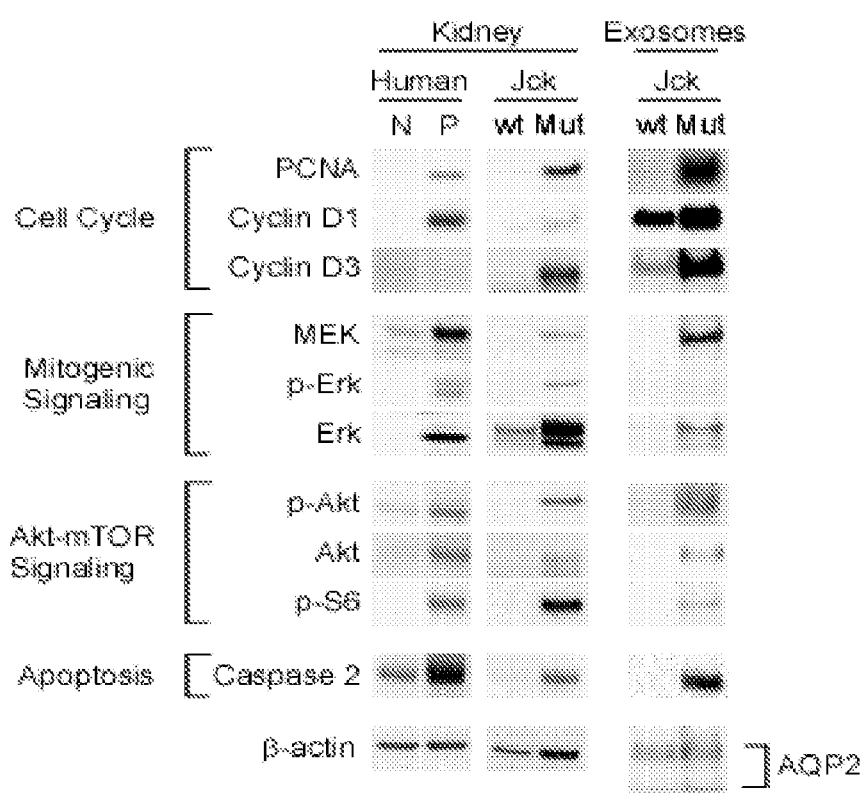
FIG. 1 is an immunoblot showing the levels of markers in kidney lysate samples from normal (N) and PKD (P) human patients, and from wildtype (wt) and jck mice (Mut), and in urinary exosomes from wildtype (wt) and jck mice (Mut). The loading control for the kidney lysate samples (β-actin) and for the urinary exosomes (aquaporin-2; AQP2) are shown.

Provided herein are methods for determining the efficacy of treatment for PKD in a patient, diagnosing PKD in a patient, staging PKD in a patient, and monitoring PKD in a patient that include determining a single or multiple levels of one or more markers selected from the group of Proliferating Cell Nuclear Antigen (PCNA), cyclin D1, cyclin D3, MAPK-ERK kinase 1 (MEK), ribosomal protein S6 (S6), phosphorylated ribosomal protein S6 (pS6), extracellular signal-regulated kinase (ERK), phosphorylated extracellular signal-regulated kinase (pERK), protein kinase B (Akt), phosphorylated protein kinase B (pAkt), caspase-2, total ribosomal protein S6, and retinoblastoma binding protein (RBBP). Also provided are kits comprising at least three antibodies selected from the group consisting of: an antibody that specifically binds to PCNA, an antibody that specifically binds to cyclin D1, an antibody that specifically binds to cyclin D3, an antibody that specifically binds to MEK, an antibody that specifically binds to S6, an antibody that specifically binds to pS6, an antibody that specifically binds to ERK, an antibody that specifically binds to pERK, an antibody that specifically binds to Akt, an antibody that specifically binds to pAkt, an antibody that specifically binds to caspase-2, and an antibody that specifically binds to RBBP. Non-limiting aspects of these methods are described below. As can be appreciated in the art, the various aspects described below can be used in any combination without limitation.

Polycystic Kidney Disease

The methods described herein can further include a step of identifying or diagnosing a patient as having PKD. Non-limiting examples of diagnosing a patient as having PKD are provided herein and are described below.

In other examples, a patient is identified as having PKD based on the observation or assessment of one or more symptoms of the following symptoms in a patient: high blood pressure, back or side pain, headache, increased size of abdomen, presence of blood in urine, frequent urination, kidney stones, kidney failure, urinary tract or kidney infections, cysts on the kidney, cysts on the liver, pancreatic cysts, mitral valve prolapse, aneurysms, nausea, vomiting, left ventricular hypertrophy, hernia, diverticulitis, fatigue, poor appetite, weight loss, trouble concentrating, dry/itchy skin, muscle cramps, swelling in feet and ankles, mild to moderate depression, and bubbly urine. PKD can also be diagnosed in a subject by performing a genetic test (see, e.g., PKD1 genetic diagnostic tests from a variety of vendors including Athena Diagnostics (Worcester, Mass.) and CGC Genetics (Porto, Portugal); PKD2 genetic diagnostic tests from a variety of ventors including Centrogene AG (Germany), PreventionGenetics (Marshfield, Wis.), GCG Genetics (Portugal), and InVitae Corporation (San Francisco, Calif.); and PKHD1 genetic diagnostic tests are available from a variety of vendors including Centrogene AG (Germany), Prevention Genetics (Marshfield, Wis.), Counsyl (San Francisco, Calif.), and Invitae (San Francisco, Calif.)). The detection of mutations or deletions of the PKD1 and/or PKD2 genes can be used to diagnose autosomal dominant PKD, and the detection of mutations or deletions in PKHD1 can be used to diagnose autosomal recessive PKD.

PKD (e.g., autosomal dominant PKD and autosomal recessive PKD) can be diagnosed by performing imaging studies. For example, ultrasound, computerized tomography (CT), and magnetic resonance imaging (MRI) can be used to look for cysts on the kidney(s) and to determine the total kidney volume (TKV) or height-adjusted total kidney volume (htTKV). For example, the detection of at least two cysts (e.g., at least three, four, five, or six cysts) on each kidney by age 30 in a patient (e.g., a patient with a family history of the disease) can confirm the diagnosis of PKD. The detection of a multicystic dysplastic kidney(s) in a fetus (e.g., a fetus that is greater than 14 weeks of gestation) can be used to diagnose autosomal recessive PKD. In addition, the amniotic fluid from a fetus can be used to detect a mutation or deletion in PKHD1 (e.g., using any of the genetic diagnostic tests for PKHD1 described herein or known in the art).

PKD can also be diagnosed or identified in a subject, in part, by determining a patient's kidney function. For example, PKD can be diagnosed and identified in part by measuring one or more of a patient's creatinine level (e.g., a level of creatinine greater than 1.3 mg/dL indicating that the patient has PKD), glomerular filtration rate (e.g., a rate that is below 80 mL/minutes indicates that the patient has PKD), and blood urea nitrogen (e.g., a blood urea nitrogen level of greater than 20 mg/dL).

The PKD patients described herein can be diagnosed or identified using any of the methods described or provided herein, or any methods known in the art. The PKD patient can be in utero (e.g., a fetus with a gestational age greater than 14 weeks, 15 weeks, 17 weeks, 20 weeks, 25 weeks, 30 weeks, or 35 weeks), an infant, an adolescent (between 13 and 18 years old (e.g., between 13 and 15 years old or between 15 and 18 years old), or an adult (greater than 18 years old (e.g., greater than 20, 22, 24, 26, 28, 30, 32, 34, 36, 38, 40, 45, 50, 55, 60, 65, 70, 75, 80, 85, 90, or 95 years old). The PKD patient can be a female (e.g., a pregnant female) or can be a male. The PKD patient may already be receiving a treatment for PKD. In other examples, the PKD patient may not have received a treatment for a PKD. In additional examples, the PKD patient may have received a previous treatment for PKD and the previous treatment was therapeutically unsuccessful (e.g., lead to the development of negative adverse side effects, did not reduce the rate of development and/or growth of cysts, and/or did not reduce the rate of loss in the function of the patient's kidney(s)). The PKD patient may be a participant in a clinical study.

PKD Treatments

Some examples of a treatment for PKD is the administration of one or more glucosylceramide synthase (GCS) inhibitors. Non-limiting examples of GSC inhibitors are described in Lee et al. (*J. Biol. Chem.* 274:14662-14669, 1999), Shayman et al. (*Methods Enzymol.* 311:373-387, 2000), Huang et al. (*FASEB J.* 25:3661-3673, 2011), Kolton et al. (*Bioorg. Med. Chem. Lett.* 21:6773-6777, 2011), Larsen et al. (*J. Lipid Res.* 53:282-291, 2012), Niino et al. (*Biochem. Biophys. Res. Comm.* 433:170-174, 2013), Richards et al. (*J. Med. Chem.* 55:4322-4325, 2012), Nietupski et al. (*Mol. Genet. Metab.* 105:621-628, 2012), Ashe et al. (*PLoS One* 6:e21758, 2011), Shayman (*Drugs Future* 35:613-620, 2010), Bijl et al. (*J. Pharmacol. Exp. Ther* 326:849-855, 2008), Treiber et al. (*Xenobiotica* 37:298-314, 2007), McEachern et al. (*Mol. Genet. Metab.* 91:259-267, 2007), Wennekes et al. (*Diabetes* 56:1341-1349, 2007), Jimbo et al. (*J. Biochem.* 127:485-291, 2000), Miura et al. (*Bioorg. Med. Chem.* 6:1481-1489, 1998), Abe et al. (*J. Biochem.* 111:191-196, 1992), Inokuchi et al. (*J. Cell Physiol.* 141:573-583, 1989), and Inokuchi et al. (*J. Lipid Res.* 28:565-571, 1987). Additional examples of GCS inhibitors are described in U.S. Patent Application Publication Nos. 2013/0225573, 2013/0137743, 2013/0095089, 2012/0322787, 2012/0322786, 2011/0184021, 2011/0166134, 2010/0256216, and 2007/0259918 (each of which is hereby incorporated by reference).

Additional examples of GCS inhibitors are described in WO 14/043068 (incorporated herein by reference). For example, a GCS inhibitor can have a structure represented by Formula I below.

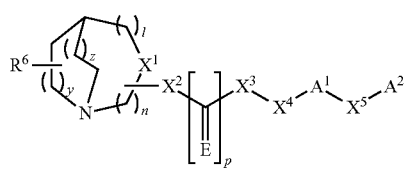

I wherein:
n is 1, 2, or 3;
m is 0 or 1;
p is 0 or 1;
t is 0, 1, or 2;
E is S, O, NH, NOH, NNO$_2$, NCN, NR, NOR or NSO$_2$R;
X$^1$ is CR$^1$ when m is 1 or N when m is 0;
X$^2$ is O, —NH, —CH$_2$, SO$_2$, NH—SO$_2$, CH(C$_1$-C$_6$) alkyl or —NR$^2$;
X$^3$ is a direct bond, O, —NH, —CH$_2$—, CO, —CH(C$_1$-C$_6$) alkyl, SO$_2$NH, —CO—NH—, or NR$^3$;
X$^4$ is a direct bond, CR$^4$R$^5$, CH$_2$CR$^4$R$^5$ or CH$_2$—(C$_1$-C$_6$) alkyl-CR$^4$R$^5$;
X$^5$ is a direct bond, O, S, SO$_2$, CR$^4$R$^5$, (C$_1$-C$_6$)alkyl, (C$_1$-C$_6$)alkyloxy, —O—(C$_1$-C$_6$)alkyl, (C$_1$-C$_6$)alkenyl, (C$_1$-C$_6$)alkenyloxy, —R$^7$—(C$_3$-C$_{10}$)cycloalkyl, (C$_3$-C$_{10}$)cycloalkyl-R$^7$—, —R$^7$—(C$_6$-C$_{12}$)aryl, (C$_6$-C$_{12}$)aryl-R$^7$—, —R$^7$—(C$_2$-C$_9$)heteroaryl, (C$_2$-C$_9$)heteroaryl-R$^7$—, —R$^7$—(C$_2$-C$_9$)heterocycloalkyl, and (C$_2$-C$_9$)heterocycloalkyl-R$^7$—, wherein R$^7$ is a direct bond, O, S, SO$_2$, CR$^4$R$^5$, (C$_1$-C$_6$)alkyl, (C$_1$-C$_6$)alkyloxy, —O—(C$_1$-C$_6$)alkyl, (C$_1$-C$_6$) alkenyl, (C$_1$-C$_6$)alkenyloxy; and further wherein when X$^5$ is defined as —R$^7$—(C$_3$-C$_{10}$)cycloalkyl, (C$_3$-C$_{10}$)cycloalkyl-R$^7$—, —R$^7$—(C$_6$-C$_{12}$)aryl, (C$_6$-C$_{12}$)aryl-R$^7$—, —R$^7$—(C$^2$-C$^9$)heteroaryl, (C$_2$-C$_9$)heteroaryl-R$^7$—, —R$^7$—(C$_2$-C$_9$) heterocycloalkyl, and (C$_2$-C$_9$)heterocycloalkyl-R$^7$—, wherein the $(C_3-C_{10})$cycloalkyl, $(C_6-C_{12})$ aryl, $(C_2-C_9)$heteroaryl, $(C_2-C_9)$ heterocycloalkyl groups are optionally substituted by one or more substituents selected from the group consisting of halo, $(C_1-C_6)$alkyl, $(C_1-C_6)$ alkylenyl, amino, $(C_1-C_6)$ alkylamino, $(C_1-C_6)$dialkylamino, $(C_1-C_6)$alkoxy, $O(C_3-C_6$ cycloalkyl), $(C_3-C_6)$ cycloalkoxy, nitro, CN, OH, $(C_1-C_6)$alkyloxy, $(C_3-C_6)$ cycloalkyl, $(C_1-C_6)$ alkoxycarbonyl, $(C_1-C_6)$ alkylcarbonyl, $(C_1-C_6)$halo alkyl, $(C_2-C_9)$heterocycloalkyl, $R^8R^9N$—CO— wherein $R^8$ and $R^9$ are each independently selected from the group consisting of hydrogen and $(C^1-C^6)$alkyl or $R^8$ and $R^9$ can be taken together with the nitrogen to which they are attached to form a $(C_2-C_9)$heterocycloalkyl or $(C_2-C_9)$heterocycloalkyl group optionally substituted by one to three halo groups, $(C_1-C_6)$ alkylsulfonyl optionally substituted by one or two groups selected from $(C_1-C_6)$alkoxy and $(C_3-C_{10})$cycloalkyl;

$(C_1-C_6)$alkyl substituted by one to four substituents selected from the group consisting of halo, hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy; and $(C_1-C_6)$alkyloxy substituted by one to four substituents selected from the group consisting of halo, hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy;

R is $(C_6-C_{12})$aryl, $(C_2-C_9)$heteroaryl, $(C_1-C_6)$alkyl, $(C_2-C_9)$heteroaryl$(C_1-C_6)$alkyl; $R^1$ is H, CN, $(C_1-C_6)$alkylcarbonyl, or $(C_1-C_6)$alkyl;

$R^2$ and $R^3$ are each independently —H, $(C_1-C_6)$alkyl optionally substituted by one or more substituents selected from the group consisting of halogen, $(C_1-C_6)$alkyl, $(C_6-C_{12})$aryl, $(C_2-C_9)$heteroaryl, $(C_1-C_6)$alkyl$(C_6-C_{12})$aryl, halo $(C_6-C_{12})$aryl, and halo$(C_2-C_9)$heteroaryl, or optionally when $X^2$ is —$NR^2$ and $X^3$ is —$NR^3$, $R^2$ and $R^3$ may be taken together with the nitrogen atoms to which they are attached form a non-aromatic heterocyclic ring optionally substituted by with one or more substituents selected from halogen, $(C_1-C_6)$alkyl, $(C_6-C_{12})$aryl, $(C_2-C_9)$heteroaryl, $(C_1-C_6)$alkyl$(C_6-C_{12})$aryl, halo$(C_6-C_{12})$aryl, and halo$(C_2-C_9)$heteroaryl;

$R^4$ and $R^5$ are independently selected from H, $(C_1-C_6)$ alkyl, or taken together with the carbon to which they are attached to form a spiro $(C_3-C_{10})$cycloalkyl ring or spiro $(C_3-C_{10})$cycloalkoxy ring;

$R^6$ is —H, halogen, —CN, $(C_6-C_{12})$aryl, $(C_6-C_{12})$aryloxy, $(C_1-C_6)$alkyloxy; $(C_1-C_6)$alkyl optionally substituted by one to four halo or $(C_1-C_6)$alkyl;

$A^1$ is $(C_2-C_6)$alkynyl; $(C_3-C_{10})$cycloalkyl, $(C_6-C_{12})$aryl, $(C_2-C_9)$heteroaryl, $(C_2-C_9)$heterocycloalkyl or benzo$(C_2-C_9)$heterocycloalkyl wherein $A^1$ is optionally substituted with one or more substituents selected from the group consisting of halo, $(C_1-C_6)$alkyl optionally substituted by one to three halo; $(C_1-C_6)$alkenyl, amino, $(C_1-C_6)$alkylamino, $(C_1-C_6)$ dialkylamino, $(C_1-C_6)$alkoxy, nitro, CN, —OH, $(C_1-C_6)$alkyloxy optionally substituted by one to three halo; $(C_1-C_6)$alkoxycarbonyl, and $(C_1-C_6)$ alkylcarbonyl;

$A^2$ is H, $(C_3-C_{10})$cycloalkyl, $(C_6-C_{12})$aryl, $(C_2-C_9)$heteroaryl, $(C_2-C_9)$heterocycloalkyl or benzo$(C_2-C_9)$heterocycloalkyl wherein $A^2$ is optionally substituted with one or more substituents selected from the group consisting of halo, $(C_1-C_6)$alkyl, $(C_1-C_6)$alkylenyl, amino, $(C_1-C_6)$ alkylamino, $(C_1-C_6)$dialkylamino, $(C_1-C_6)$alkoxy, $O(C_3-C_6$ cycloalkyl), $(C_3-C_6)$ cycloalkoxy, nitro, CN, OH, $(C_1-C_6)$alkyloxy, $(C_3-C_6)$ cycloalkyl, $(C_1-C_6)$alkoxycarbonyl, $(C_1-C_6)$ alkylcarbonyl, $(C_1-C_6)$ halo alkyl, $(C_2-C_9)$heterocycloalkyl, $R^8R^9N$—CO—, wherein $R^8$ and $R^9$ are each independently selected from the group consisting of hydrogen and $(C_1-C_6)$alkyl or R8 and R9 can be taken together with the nitrogen to which they are attached to form a $(C_2-C_9)$heterocycloalkyl or $(C_2-C_9)$heterocycloalkyl group optionally substituted by one to three halo groups, $(C_1-C_6)$alkylsulfonyl optionally substituted by one or two groups selected from $(C_1-C_6)$alkoxy and $(C_3-C_{10})$cycloalkyl;

$(C_1-C_6)$alkyl substituted by one to four substituents selected from the group consisting of halo, hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy; and $(C_1-C_6)$alkyloxy substituted by one to four substituents selected from the group consisting of halo, hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy;

with the proviso that the sum of n+t+Y+z is not greater than 6;

with the proviso that when p is 0; $X^2$ is NH—$SO^2$ and $X^3$ is NH;

with the proviso that when n is 1; t is O; y is 1; z is 1; $X^2$ is NH; E is O; $X^3$ is NH;

$A^2$ is H and $X^5$ is a direct bond; $A^1$ is not unsubstituted phenyl, halophenyl or isopropenyl phenyl;

with the proviso that when n is 1; t is O; y is 1; z is 1; $X^2$ is O; E is O; $X^3$ is NH; $A^1$ is $(C^6-C^{12})$aryl and $X^5$ is a direct bond; $A^2$ is H and $R^4$ is H then $R^5$ is not cyclohexyl;

with the proviso that when n is 1; t is O; y is 1; z is 1; $X^2$ is NH; E is O; $X^3$ is $CH_2$; $R^4$ and $R^5$ are both hydrogen; $A^2$ is H and $X^5$ is a direct bond; then $A^1$ is not unsubstituted phenyl; and with the proviso that when $X^3$ is O, —NH, —$CH_2$—, CO, —CH$(C_1-C_6)$ alkyl, $SO_2NH$, —CO—NH— or —$NR^3$; and $X^4$ is $CR^4R^5$, $CH_2CR^4R^5$ or $CH_2$—$(C_1-C_6)$ alkyl-$CR^4R^5$; then $A^2$ must be $(C_3-C_{10})$cycloalkyl, $(C_6-C_{12})$aryl, $(C_2-C_9)$ heteroaryl, $(C_2-C_9)$heterocycloalkyl or benzo$(C_2-C_9)$heterocycloalkyl substituted with one or more substituents selected from the group consisting of $(C_2-C_9)$heterocycloalkyl, $R^8R^9N$—CO— wherein $R^8$ and $R^9$ are each independently selected from the group consisting of hydrogen and $(C_1-C_6)$ alkyl or $R^8$ and $R^9$ can be taken together with the nitrogen to which they are attached to form a $(C_2-C_9)$heterocycloalkyl or $(C_2-C_9)$heterocycloalkyl group optionally substituted by one to three halo groups, $(C_1-C_6)$alkylsulfonyl optionally substituted by one or two groups selected from $(C_1-C_6)$ alkoxy and $(C_3-C_{10})$cycloalkyl;

$(C_1-C_6)$alkyl substituted by one to four substituents selected from the group consisting of hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy;

or $(C_1-C_6)$alkyloxy substituted by one to four substituents selected from the group consisting of hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy.

Additional exemplary GCS inhibitors include: 1-azabicyclo[2.2.2]oct-3-yl [2-(2,4'-difluorobiphenyl-4-yl)propan-2-yl]carbamate; 1-azabicyclo[2.2.2]oct-3-yl {2-[4-(1,3-benzothiazol-6-yl)phenyl]propan-2-yl} carbamate; 1-azabicyclo

[3.2.2]non-4-yl {1-[5-(4-fluorophenyl)pyridin-2-yl] cyclopropyl} carbamate; 1-azabicyclo[2.2.2]oct-3-yl {1-[3-(4-fluorophenoxy)phenyl]cyclopropyl} carbamate; 1-azabicyclo[2.2.2]oct-3-yl {1-[4-(1,3-benzothiazol-5-yl)phenyl] cyclopropyl} carbamate; 1-azabicyclo[2.2.2]oct-3-yl [1-(4'-fluoro-3'-methoxybiphenyl-4yl)cyclopropyl] carbamate; 1-azabicyclo [2.2.2]oct-3-yl [3-(4'-fluorobiphenyl-4-yl) oxetan-3-yl] carbamate; 1-azabicyclo[2.2.2]oct-3-yl {1-[6-(4-fluorophenoxy) pyridin-2-yl]cyclopropyl} carbamate; 1-azabicyclo[2.2.2]oct-3-yl [3-(4'-fluorobiphenyl-4-yl)pentan-3-yl] carbamate; 1-azabicyclo[2.2.2]oct-3-yl {2-[2-(4-fluorophenyl)-2H-indazol-6-yl]propan-2-yl} carbamate; 1-azabicyclo[2.2.2]oct-3-yl {2-[2-(IH-pyrrol-1-yl)pyridin-4-yl]propan-2-yl} carbamate; 1-(3-ethyl-1-azabicyclo [2.2.2]oct-3-yl)-3-[1-(4'-fluorobiphenyl-4-yl)cyclopropyl] urea; N—(I-azabicyclo [2.2.2]oct-3-yl)-N'—[I-(4'-fluorobiphenyl-4yl)cyclopropyl]ethanediamide; 1-azabicyclo [2.2.2]oct-3-yl (1-{4[(4,4difluorocyclohexyl)oxy]phenyl} cyclopropyl) carbamate; 1-(4-methyl-1-azabicyclo[3.2.2] non-4-yl)-3-[1-(5-phenylpyridin-2-yl)cyclopropyl]urea; 1-[1-(4'-fluorobiphenyl-4-yl)cyclopropyl]-I-methyl-3-(3-methyl-1-azabicyclo [2.2.2]oct-3-yl)urea; 1-[1-(4'-fluorobiphenyl-4-yl)cyclopropyl]-I-methyl-3-(3-methyl-1-azabicyclo[2.2.2]oct-3-yl)urea; 1-{2-[4'-(2-methoxyethoxy)biphenyl-4-yl]propan-2-yl}-3-(3-methyl-1azabicyclo[2.2.2] oct-3-yl)urea; 2-(1-azabicyclo [3.2.2]non-4-yl)-N-[1-(5-phenylpyridin-2-yl)cyclopropyl] acetamide; 3-(4'-fluorobiphenyl-4-yl)-3-methyl-N-(4-methyl-1-azabicyclo [3.2.2]non-4-5yl)butanamide; N-[2-(biphenyl-4-yl)propan-2-yl]-N'-(3-methyl-1-azabicyclo [2.2.2]oct-3-yl)sulfuric diamide; N-[2-(4'-fluorobiphenyl-4-yl)propan-2-yl]-N'-(3-methyl-1-azabicyclo[2.2.2]oct-3-yl)sulfuric diamide; 1-(3-butyl-1-azabicyclo [2.2.2]oct-3-yl)-3-{2-[1-(4-fluorophenyl)-IH-pyrazol-4-yl]propan-2-yl} urea; 1-azabicyclo[2.2.2] oct-3-yl [4-(4-fluorophenyl)-2-methylbut-3-yn-2-yl] carbamate; 1-(3-butyl-1-azabicyclo[2.2.2]oct-3-yl)-3-[4-(4-fluorophenyl)-2-methylbut-3-yn-2-yl]urea; N—[I-(4'-fluorobiphenyl-4-yl)cyclopropyl]-1,4-diazabicyclo[3.2.2] nonane-4-carboxamide; 1-(2-(4'-fluoro-[I, 1'-biphenyl]-4-yl) propan-2-yl)-3-(3-methyl-1-azabicyclo[3.2.2]nonan-3-yl) urea; 1-(2-(4'-fluoro-[I, 1'-biphenyl]-4-yl)propan-2-yl)-3-(4-methyl-1-azabicyclo[4.2.2]decan-4-yl)urea; 1-(2-(4'-fluoro-[I, 1'-biphenyl]-4-yl)propan-2-yl)-3-(3-methyl-1-azabicyclo [4.2.2]decan-3-yl)urea; and 1-(2-(4'-fluoro-[1, 1'-biphenyl]-4-yl)propan-2-yl)-3-(5-methyl-1-azabicyclo[4.2.2]decan-5-yl)urea.

Additional examples of GCS inhibitors are listed below.

((S)-Quinuclidin-3-yl (2-(4'-(2-methoxyethoxy)-[1, 1'-biphenyl]-4-yl)propan-2-yl)carbamate)

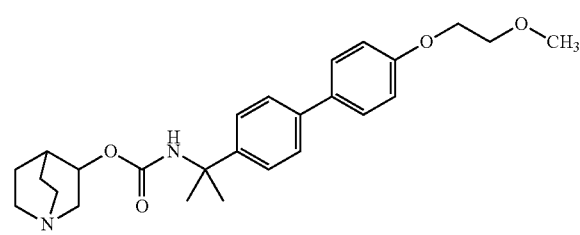 [SMILES: COCCOc1ccc(-c2ccc(C(C)(C)NC(=O)OC3CN4CCC3CC4)cc2)cc1]

(4-Fluoro-1-(5-fluoro-4-(4-((2-methoxyethoxy) methyl)phenyl)pyrimidin-2-yl)-N-(4-methyl-1-azabicyclo 13.2.21 nonan-4-yl)piperidine-4-carboxamide)

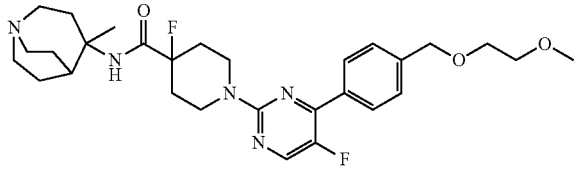 [SMILES: COCCOCc1ccc(-c2nc(N3CCC(F)(C(=O)NC4(C)CCN5CCC4CC5)CC3)ncc2F)cc1]

(4-Fluoro-1-(4-(4-((2-methoxyethoxy)methyl)phenyl)pyrimidin-2-yl)-N-(3-methylquinuclidin-3-yl) piperidine-4-carboxamide)

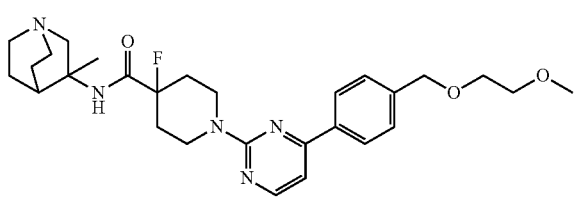 [SMILES: COCCOCc1ccc(-c2ccnc(N3CCC(F)(C(=O)NC4(C)CN5CCC4CC5)CC3)n2)cc1]

(4-Fluoro-1-(4-(4-((2-methoxyethoxy)methyl)phenyl)pyrimidin-2-yl)-N-(4-methyl-1-azabicyclo 13.2.21 nonan-4-yl)piperidine-4-carboxamide)

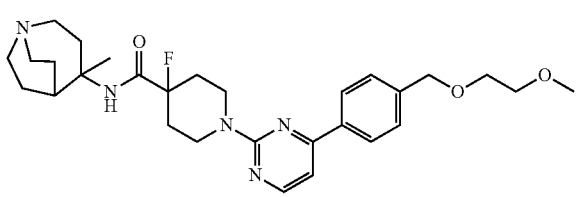

(4-Fluoro-1-(4-(4-(methoxymethyl)phenyl)pyrimidin-2-yl)-N-(3methylquinuclidin-3-yl)piperidine-4-carboxamide)

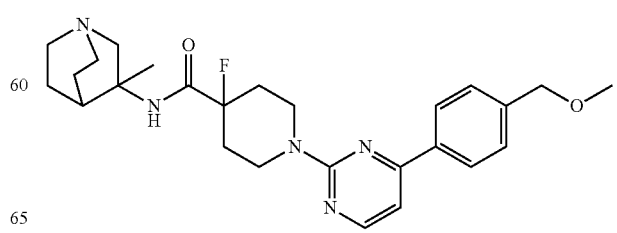

(4-Fluoro-1-(4-(4-(methoxymethyl)phenyl)pyrimidin-2-yl)-N-(4-methyl-1-azabicyclo[3.2.2]nonan-4-yl)piperidine-4-carboxamide)

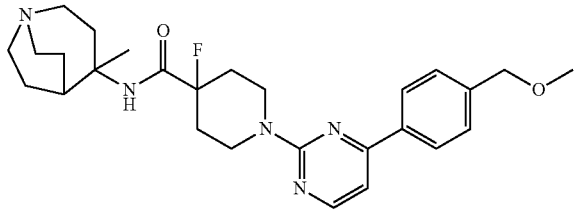

(4-Fluoro-1-(4-(4-(2-methoxyethoxy)phenyl)pyrimidin-2-yl)-N-(3-methylquinuclidin-3-yl)piperidine-4-carboxamide)

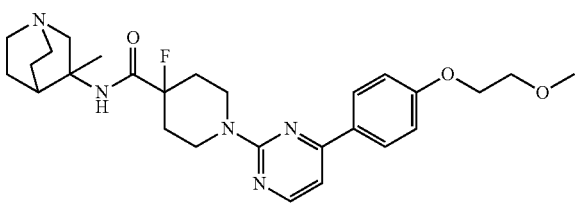 [SMILES: COCCOc1ccc(-c2ccnc(N3CCC(F)(C(=O)NC4(C)CN5CCC4CC5)CC3)n2)cc1]

(4-Fluoro-1-(4-(4-(2-methoxyethoxy)phenyl)pyrimidin-2-yl)-N-(4-methyl-1-azabicyclo[3.2.2]nonan-4-yl)piperidine-4-carboxamide)

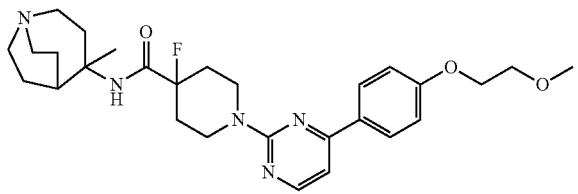

(4-Fluoro-1-(4-(4-(2-fluoroethoxy)phenyl)pyrimidin-2-yl)-N-(quinuclidin-3-yl)piperidine-4-carboxamide)

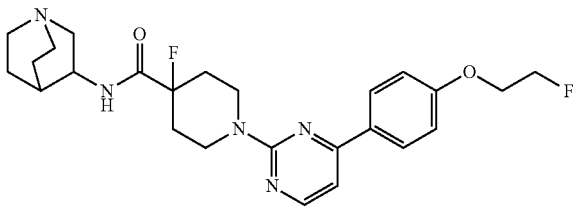 [SMILES: O=C(NC1CN2CCC1CC2)C1(F)CCN(c2nccc(-c3ccc(OCCF)cc3)n2)CC1]

(4-Fluoro-1-(4-(4-(2-fluoroethoxy)phenyl)pyrimidin-2-yl)-N-(4-methyl-1-azabicyclo[3.2.2]nonan-4-yl)piperidine-4-carboxamide)

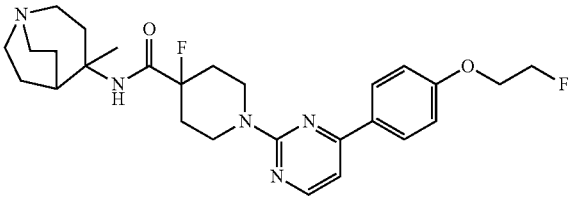

Some examples of a treatment for PKD include the administration of one or more cyclin dependent kinase (CDK) inhibitors. Non-limiting examples of CDK inhibitors include S-CR8, olomoucine, LEE011, palbociclib, P1446A-05, PD-0332991, and R-roscovitine. Additional examples of CDK inhibitors are described in Cicenas et al. (*J. Cancer Res. Clin. Oncol.* 138:1409-1418, 2011), Blachly et al. (*Leuk. Lymphoma* 54:2133-2143, 2013), Galons et al. (*Expert Opin. Ther. Pat.* 20:377-404, 2010), Geyer et al. (*Biochim. Biophys. Acta* 1754:160-170, 2005). Additional examples of CDK inhibitors are described in U.S. Patent Application Publication Nos. 2006/0178371, 2006/0173017, 2006/0173016, 2006/0135589, 2006/0128725, 2006/0106023, 2006/0041131, 2006/0040958, 2006/0030555, 2005/0261353, 2005/0130980, 2005/0004007, 2004/0248905, 2004/0209878, 2004/0198757, 2004/0116442, 2004/0110775, 2004/0106624, 2004/0102451, 2004/0097517, 2004/0097516, 2004/0073969, 2004/0072835, 2004/0063715, 2004/0048849, 2004/0006074, 2003/0073686, 2002/0065293, 2002/0042412, 2002/0013328, 2002/0002178, and 2001/0025379.

Another example of a treatment for PKD is hemodialysis or peritoneal dialysis. A further example of a treatment for PKD is the surgical transplantation of a kidney.

Markers

The methods provided herein include the determination of the level(s) of at least one marker selected from the group of: PCNA, cyclin D1, cyclin D3, MEK, S6, pS6, ERK, pERK, Akt, pAKT, caspase-2, total S6, and RBBP, in at least one sample from a patient (e.g., a PKD patient). For example, the level(s) of one or more marker can be determined in a sample containing a biological fluid (e.g., urine) from the patient (e.g., a PKD patient) (e.g., a sample containing a biological fluid that has been concentrated for exosomes). In some examples, the marker is a protein. In other examples, the marker is a mRNA encoding the marker protein.

Methods for determining the levels of the markers described herein are well understood in the art. For example, the protein level of each marker described herein can be determined using an antibody-based assay (e.g., an enzyme-linked immnosorbent assay, antibody array, antibody-labeled beads, and immunoblots). Exemplary antibodies that can be used in these antibody-based assays are described in the Examples. Additional antibodies that can be used in the antibody-based assays are known in the art. Methods of making antibodies that specifically bind to a marker are also well known in the art. Additional methods for determining the protein level of each marker include mass spectrometry, liquid chromatography (e.g., high performance liquid chromatography) mass spectrometry (LC-MS), and liquid chromatography (e.g., high performance liquid chromatography) tandem mass spectrometry (LC-MS/MS). Non-limiting examples of methods for determining the protein level of a marker in a sample containing a biological fluid (e.g., a sample containing a biological fluid that has been concentrated for exosomes) are described in Pisitkun et al. (*Proteomics Clin. Appl.* 6:268-278, 2012). These exemplary methods of determining the level(s) of the markers can be used in any of the methods provided herein.

The mRNA level of each marker described herein can be determined, e.g., using a polymerase chain reaction (PCR)-based assay (e.g., real-time PCR and reverse-transcriptase PCR). Additional methods for determining the mRNA level of each marker include the use of a gene chip. Further examples of methods for determining the mRNA level of a marker in a sample containing a biological fluid (e.g., a sample containing a biological fluid that has been concentrated for exosomes) are described in Chen et al. (*Lab Chip* 10:505-511, 2010), Schageman et al. (*BioMed Res. Int.*, Article ID 253957, 2013), and Alvarez et al. (*Kidney Inter.* 82:1024-1032, 2012). Additional methods for determining an mRNA level of a marker are well known in the art.

In some examples, a sample (e.g., a sample comprising a biological fluid) from a subject can be stored for a period of time (e.g., stored at least 1 hour (e.g., at least 2, 4, 6, 8, 12, or 24 hours, or at least 1, 2, 3, 4, 5, 6, 7, 14, or 21 days, e.g., at a temperature of about 10° C., about 0° C., about −20° C., about −40° C., about −70° C., or about −80° C.) before the level(s) of the at least one marker are determined in the sample. For example, a sample comprising a biological fluid and concentrated for exosomes can be stored for a period of time (e.g., stored for any of the times and/or temperatures described herein) before the level(s) of the at least one marker are determined in the sample. Some examples further include a step of concentrating a sample containing a biological fluid before the level(s) of the at least one marker (e.g., any marker or any combination of marker described herein) is determined. Non-limiting examples of methods of concentrating a sample containing a biological fluid for exosomes are described herein. In some examples, a biological sample containing a biological fluid that is concentrated for exosomes is stored for a period of time (e.g., stored for any of the times and/or temperatures described herein) before the level(s) of the at least one marker are determined in the sample.

The level(s) of any marker or any combination of markers described herein can be determined in a sample (e.g., a sample containing a biological fluid or a sample containing a biological fluid that has been concentrated for exosomes) in any of the methods described herein. Examples of combinations of markers or single markers that can be determined (i.e., the level determined) in a sample (e.g., a sample containing a biological fluid or a sample containing a biological fluid that has been concentrated for exosomes) in any of the methods described herein are shown in Table 1. A description of each of the markers described herein is provided below.

PCNA

Proliferating Cell Nuclear Antigen (PCNA) is a 28.8 kDa protein having 261 amino acids. The amino acid sequence of human PCNA is SEQ ID NO: 1. The protein level of PCNA described herein can include the forms of PCNA that are non-phosphorylated and phosphorylated at the tyrosine at amino acid position 248 in SEQ ID NO: 1, include only the form of PCNA phosphorylated at the tyrosine at amino acid position 248 in SEQ ID NO: 1, or include only the unphosphorylated form of PCNA.

Cyclin D1

Cyclin D1 is a 33.7 kDa protein having 295 amino acids. The amino acid sequence of human cyclin D1 is SEQ ID NO: 2. The protein level of cyclin D1 can include the forms of cyclin D1 that are non-phosphorylated and phosphorylated at the threonine at amino acid position 286 in SEQ ID NO: 2, include only the form of cyclin D1 phosphorylated at the threonine at amino acid position 286 in SEQ ID NO: 2, or include only the unphosphorylated form of cyclin D1.

Cyclin D3

Cyclin D3 is a protein having 292 amino acids. The amino acid sequence of human cyclin D3 is SEQ ID NO: 3. The protein level of cyclin D3 can include the forms of cyclin D3 that are non-phosphorylated and phosphorylated at the serine at amino acid position 279 in SEQ ID NO: 3, include only the form of cyclin D3 phosphorylated at the serine at amino acid position 279 in SEQ ID NO: 3, or include only the unphosphorylated form of cyclin D3.

MEK

MAPK-ERK kinase 1 (MEK) is a protein having two isoforms. The first isoform of human MEK has a sequence of 393 amino acids (SEQ ID NO: 4) and the second isoform of human MEK has a sequence of 367 amino acids (SEQ ID NO: 5). The protein level of MEK can include one or more of: the unphosphorylated form of the first isoform of MEK; the unphosphorylated form of the second isoform of MEK; one or more form(s) of the first isoform of MEK including one or more of a phosphorylation at the serine at amino acid position 218 in SEQ ID NO: 4, a phosphorylation at the serine at amino acid position 222 in SEQ ID NO: 4, a phosphorylation at the threonine at amino acid position 286 in SEQ ID NO: 4, a phosphorylation at the threonine at amino acid position 292 in SEQ ID NO: 4, and a phosphorylation at the serine at amino acid position 298 in SEQ ID NO: 4; and one or more form(s) of the second isoform of MEK including one or more of a phosphorylation at the serine at amino acid position 192 of SEQ ID NO: 5, a phosphorylation at the serine at amino acid position 196 of SEQ ID NO: 5, a phosphorylation at the threonine at amino acid position 260 in SEQ ID NO: 5, a phosphorylation at the threonine at amino acid position 266 in SEQ ID NO: 5, and a phosphorylation at the serine at amino acid position 272 in SEQ ID NO: 5.

S6, pS6, and total S6

Ribosomal protein S6 (S6) is a 28.7 kDa protein having 249 amino acids. The amino acid sequence of human S6 is SEQ ID NO: 6. The phrase "level of S6" or "level of ribosomal protein S6," when referring to a protein level, means the sum of the levels of all detectable forms (e.g., all phosphorylated forms and the unphosphorylated form) of S6. The phosphorylated forms of S6 protein can include one or more of: a phosphorylation of the serine at amino acid position 235 in SEQ ID NO: 6, a phosphorylation of the serine at amino acid position 236 in SEQ ID NO: 6, a phosphorylation of the serine at amino acid position 240 in SEQ ID NO: 6, a phosphorylation at the serine at amino acid position 242 in SEQ ID NO: 6, a phosphorylation at serine at amino acid position 244 in SEQ ID NO: 6, and a phosphorylation at the serine at amino acid position 247 in SEQ ID NO: 6. In some embodiments, the level of S6 can be determined through the use of an antibody that binds to an antigen that is common to all detectable forms (e.g., all phosphorylated forms and the unphosphorylated form) of S6.

The phrase "level of pS6" or "level of ribosomal protein pS6," when referring to a protein level, means the level (or sum of two or more of the levels) of one or more of a phosphorylated form of ribosomal S6 protein having a phosphorylation at serine at amino acid position 235 in SEQ ID NO: 6, a phosphorylation at serine at amino acid position 236 in SEQ ID NO: 6, or a phosphorylation in the serines at amino acid positions 235 and 236 in SEQ ID NO: 6. The level of pS6 can be determined, e.g., by using an antibody or antibodies that specifically bind to an epitope in S6 that includes the phosphorylated serine at amino acid position 235 in SEQ ID NO: 6 and/or the phosphorylated serine at amino acid position 236 in SEQ ID NO: 6.

ERK

The phrase "level of ERK," when referring to a protein level, means the sum of the levels of all detectable forms of ERK1 (e.g., all phosphorylated forms and unphosphorylated forms of each isoform of ERK1) and/or all detectable forms of ERK2 (e.g., all phosphorylated forms and unphorylated forms). The first isoform of human ERK1 has a sequence of 379 amino acids (SEQ ID NO: 7). The second isoform of human ERK1 has a sequence of 335 amino acids (SEQ ID NO: 8). The third isoform of human ERK1 has a sequence of 357 amino acids (SEQ ID NO: 9). The first isoform of human ERK2 has a sequence of 360 amino acids (SEQ ID NO: 10). The second isoform of human ERK2 has a sequence of 316 amino acids (SEQ ID NO: 11).

The phosphorylated forms of the first isoform of ERK1 can include one or more of: a phosphorylation of the serine at amino acid position 170 in SEQ ID NO: 7, a phosphorylation of the threonine at amino acid position 198 in SEQ ID NO: 7, a phosphorylation of the threonine at amino acid position 202 in SEQ ID NO: 7, a phosphorylation of the tyrosine at amino acid position 204 in SEQ ID NO: 7, and a phosphorylation of the threonine at amino acid position 207 in SEQ ID NO: 7. The phosphorylated forms of the second isoform of ERK1 can include one or more of: phosphorylation of the serine at amino acid position 170 in SEQ ID NO: 8, a phosphorylation of the threonine at amino acid position 198 in SEQ ID NO: 8, a phosphorylation of the threonine at amino acid position 202 in SEQ ID NO: 8, a phosphorylation of the tyrosine at amino acid position 204 in SEQ ID NO: 8, and a phosphorylation of the threonine at amino acid position 207 in SEQ ID NO: 8. The phosphorylated forms of the third isoform of ERK1 can include one or more of: a phosphorylation of the serine at amino acid position 170 in SEQ ID NO: 9, a phosphorylation of the threonine at amino acid position 198 in SEQ ID NO: 9, a phosphorylation of the threonine at amino acid position 202 in SEQ ID NO: 9, a phosphorylation of the tyrosine at amino acid position 204 in SEQ ID NO: 9, and a phosphorylation of the threonine at amino acid position 207 in SEQ ID NO: 9. All detectable forms of ERK1 can be identified, e.g., by using an antibody that specifically binds to an epitope that is shared between the unphosphorylated forms of the first, second, and third isoforms of ERK1 and all of the various phosphorylated forms of the first, second, and third isoforms of ERK1.

The phosphorylated forms of the first isoform of ERK2 can include one or more of: a phosphorylation at the serine at amino acid position 29 in SEQ ID NO: 10, a phosphorylation of the threonine at amino acid position 185 in SEQ ID NO: 10, a phosphorylation of the tyrosine at amino acid position 187 in SEQ ID NO: 10, a phosphorylation of the threonine at the amino acid position 190 in SEQ ID NO: 10, a phosphorylation of the serine at the amino acid position 246 in SEQ ID NO: 10, a phosphorylation of the serine at amino acid position 248, and a phosphorylation of the serine at amino acid position 284 in SEQ ID NO: 10. The phosphorylated forms of the second isoform of ERK2 can include one or more of: a phosphorylation at the serine at amino acid position 29 in SEQ ID NO: 11, a phosphorylation of the threonine at amino acid position 185 in SEQ ID NO: 11, a phosphorylation of the tyrosine at amino acid position 187 in SEQ ID NO: 11, and a phosphorylation of the threonine at the amino acid position 190 in SEQ ID NO: 11. All detectable forms of ERK2 can be identified, e.g., by using an antibody that specifically binds to an epitope that is shared between the unphosphorylated forms of the first and second isoforms of ERK2 and all of the various phosphorylated forms of the first and second isoforms of ERK2.

pERK

The phrase "level of pERK," when referring to a protein level, means the level (or sum of two or more of the levels) of one or more of: a form of the first isoform of ERK1 having a phosphorylation at the threonine at amino acid position 202 in SEQ ID NO: 7, a form of the first isoform of ERK1 having a phosphorylation at the tyrosine at amino acid position 204 in SEQ ID NO: 7, a first isoform of ERK1 having a phosphorylation at threonine at amino acid position 202 and tyrosine at amino acid position 204 in SEQ ID NO: 7, a form of the second isoform of ERK1 having a phosphorylation at the threonine at amino acid position 202 in SEQ ID NO: 8, a form of the second isoform of ERK1 having a phosphorylation at the tyrosine at amino acid position 204 in SEQ ID NO: 8, a form of the second isoform of ERK1 having a phosphorylation at the threonine at amino acid position 202 and the tyrosine at amino acid position 204 of SEQ ID NO: 8, a form of the third isoform of ERK1 having a phosphorylation at the threonine at amino acid position 202 in SEQ ID NO: 9, a form of the third isoform of ERK1 having a phosphorylation at the tyrosine at amino acid position 204 in SEQ ID NO: 9, a form of the third isoform of ERK1 having a phosphorylation at the threonine at amino acid position 202 and the tyrosine at amino acid position 204 in SEQ ID NO: 9, a form of the first isoform of ERK2 having a phosphorylation at the threonine at amino acid position 185 in SEQ ID NO: 10, a form of the first isoform of ERK2 having a phosphorylation at the tyrosine at amino acid position 187 of SEQ ID NO: 10, a form of the first isoform of ERK2 having a phosphorylation at the threonine at amino acid position 185 and the tyrosine at amino acid position 187 of SEQ ID NO: 10, a form of the second isoform of ERK2 having a phosphorylation at the threonine at amino acid position 185 in SEQ ID NO: 11, a form of the second isoform of ERK2 having a phosphorylation at the tyrosine at amino acid position 187 in SEQ ID NO: 11, and a form of the second isoform of ERK2 having a phosphorylation at the threonine at amino acid position 185 and the tyrosine at amino acid position 187 in SEQ ID NO: 11. The level of pERK can be determined, e.g., by using an antibody that specifically binds to an epitope in the first, second, or third isoforms of ERK1 that includes the phosphorylated threonine at amino acid position 202 in SEQ ID NO: 7, 8, or 9 and/or the phosphorylated tyrosine at amino acid position 204 in SEQ ID NO: 7, 8, or 9, respectively, or an antibody that specifically binds to an epitope on the first or second isoforms of ERK2 that includes the phosphorylated threonine at amino acid position 185 in SEQ ID NO: 10 or 11 and/or the phosphorylated tyrosine at amino acid position 187 in SEQ ID NO: 10 or 11, respectively.

Akt

Akt is a 55.7 kDa protein having 480 amino acids (SEQ ID NO: 12). The protein level of Akt can include two or more of: the unphosphorylated form of Akt and one or more form(s) of Akt including one or more of a phosphorylation at the serine at amino acid position 124 in SEQ ID NO: 12, a phosphorylation at the serine at amino acid position 126 in SEQ ID NO: 12, a phosphorylation at the serine at amino acid position 129 in SEQ ID NO: 12, a phosphorylation at the tyrosine at amino acid position 176 in SEQ ID NO: 12, a phosphorylation at the threonine at amino acid position 308 in SEQ ID NO: 12, a phosphorylation at the threonine at amino acid position 450 in SEQ ID NO: 12, a phosphorylation at the serine at amino acid position 473 in SEQ ID NO: 12, and a phosphorylation at the tyrosine at amino acid position 474 in SEQ ID NO: 12.

pAkt

The phrase "level of pAkt," when referring to a protein level, means the level (or sum of two or more of the levels) of one or more a form Akt having a phosphorylation at the serine at amino acid position 473 in SEQ ID NO: 12. The level of pAkt can be determined, e.g., by using an antibody that specifically binds to an epitope in Akt that includes the phosphorylated serine at amino acid position 473 in SEQ ID NO: 12.

Caspase-2

There are three different isoforms of caspase-2 in humans. The first isoform of caspase-2 in its unprocessed form has a total of 452 amino acids (SEQ ID NO: 13). After processing, the first isoform of caspase-2 forms three subunit peptides: amino acids 170-325 of SEQ ID NO: 13 (caspase-2 subunit p18), amino acids 334-452 of SEQ ID NO: 13 (caspase-2 subunit p13), and amino acids 348-452 of SEQ ID NO: 13 (caspase-2 subunit p12). Amino acids 2-169 of SEQ ID NO: 13 represent the prosequence of the unprocessed form of caspase-2. The second isoform has a total of 313 amino acids (SEQ ID NO: 14). The third isoform has a total of 91 amino acids (SEQ ID NO: 15). A phosphorylated form of the first isoform of caspase-2 has a phosphorylation at the serine at amino acid position 340 in SEQ ID NO: 13. The protein level of caspase-2 can include one or more of the unprocessed form of the first isoform of caspase-2, the caspase-2 subunit p18, the caspase-2 subunit p13, the caspase-2 subunit p12, the form of the first isoform of caspase-2 having a phosphorylation at the serine at amino acid position 340 in SEQ ID NO: 13, and a form of the caspase-2 subunit p13 having a phosphorylation at the serine at amino acid position 7 in caspase-2 subunit p13.

RBBP

Human retinoblastoma binding protein (RBBP) has 425 amino acids (SEQ ID NO: 16). A phosphorylated form of RBBP has a phosphorylation at the serine at amino acid position 110 in SEQ ID NO: 16. The protein level of RBBP can include one or both of: the unphosphorylated form of RBBP and a form of RBBP having a phosphorylation at the serine at amino acid position 110 in SEQ ID NO: 16.

Concentration of Exosomes in a Sample

Some of the methods described herein include a step of concentrating a biological sample containing a biological fluid (e.g., any of the biological fluids described herein) for exosomes. For example, a sample containing a biological fluid can be concentrated for exosomes by ultracentrifuging the sample (e.g., in a sucrose gradient or using differential centrifugation) (see, e.g., the methods described in Gonzalez et al., *J. Am. Soc. Nephrol.* 20:363-379, 2009, and Alvarez et al., Kidney Int. 82:1024-1032, 2012) and removing an aliquot of the sample or the entire sample containing concentrated exosomes. In other examples, a sample containing a biological fluid can be concentrated for exosomes through the use of ultrafiltration (e.g., nanofiltration) (see, e.g., the methods described in Cheruvanky et al., *Am. J. Physiol. Renal Physiol.* 292:F1657-F1661, 2007, and Alvarez et al., Kidney Int. 82:1024-1032, 2012), precipitation (see, e.g., the methods described in Alvarez et al., *Kidney Int.* 82:1024-1032, 2012), or affinity purification that includes the use of a chromatography resin (e.g., a heparin column) or bead that is coated with an antibody that specifically binds to an epitope on the surface of exosomes, microfluidics (see, e.g., the methods described in Chen et al., *Lap Chip* 10:505-511, 2010). Additional methods for concentrating a sample for exosomes is described in Schageman et al., *BioMed Research Int.*, Article 253957, 2013.

Exemplary methods for concentrating a sample containing a biological fluid for exosomes are also described in the Examples. Additional methods for concentrating a sample containing a biological fluid for exosomes are known in the art.

Methods of Determining the Efficacy of a Treatment of PKD

Provided herein are methods of determining the efficacy of a treatment for PKD in a PKD subject. In some examples, these methods include: (a) providing a first sample comprising a sample including a biological fluid (e.g., urine) obtained from a PKD patient at a first time point; (b) concentrating the first sample for exosomes; (c) determining the level(s) of at least one (e.g., two, three, four, five, six, seven, eight, nine, ten, eleven, or twelve in any combination) marker selected from the group of: PCNA, cyclin D1, cyclin D3, MEK, S6, pS6, ERK, pERK, Akt, pAkt, caspase-2, total S6, and RBBP in the first sample; (d) administering a treatment for PKD to the PKD patient; (e) providing a second sample including a biological fluid obtained from the PKD patient as a second time point after step (d) and performing steps (b) and (c) on the second sample; and (f) identifying the administered treatment as being effective if the level is decreased at the second time point as compared to the first time point. Some embodiments further include after (f): (g) administering additional doses of the administered GCS inhibitor identified as being effective (e.g., (S)-quinuclidin-3-yl (2-(4'-(2-methoxyethoxy)-[1,1'-biphenyl]-4-yl)propan-2-yl)carbamate; 4-fluoro-1-(5-fluoro-4-(4-((2-methoxyethoxy)methyl)phenyl) pyrimidin-2-yl)-N-(4-methyl-1 azabicyclo[3.2.2] nonan-4-yl)piperidine-4-carboxamide; 4-fluoro-1-(4-(4-((2-methoxyethoxy)methyl) phenyl)pyrimidin-2-yl)-N-(3-methylquinuclidin-3-yl)piperidine-4-carboxamide; 4-fluoro-1-(4-(4-((2-methoxyethoxy)methyl)phenyl)pyrimidin-2-yl)-N-(4-methyl-1-azabicyclo[3.2.2]nonan-4-yl)piperidine-4-carboxamide; 4-fluoro-1-(4-(4-(methoxymethyl)phenyl) pyrimidin-2-yl)-N-(3-methylquinuclidin-3-yl)piperidine-4-carboxamide; 4-fluoro-1-(4-(4-(methoxymethyl)phenyl)pyrimidin-2-yl)-N-(4-methyl-1-azabicyclo [3.2.2]nonan-4-yl)piperidine-4-carboxamide; 4-fluoro-1-(4-(4-(2-methoxyethoxy) phenyl)pyrimidin-2-yl)-N-(3-methylquinuclidin-3-yl)piperidine-4-carboxamide; 4-fluoro-1-(4-(4-(2-methoxyethoxy)phenyl)pyrimidin-2-yl)-N-(4-methyl-1-azabicyclo[3.2.2]nonan-4-yl)piperidine-4-carboxamide; 4-fluoro-1-(4-(4-(2-fluoroethoxy)phenyl)pyrimidin-2-yl)-N-(quinuclidin-3-yl) piperidine-4-carboxamide; or 4-fluoro-1-(4-(4-(2-fluoroethoxy)phenyl)pyrimidin-2-yl)-N-(4-methyl-1-azabicyclo[3.2.2] nonan-4-yl)piperidine-4-carboxamide) to the PKD patient. Some examples of the methods further include after (f): (g) administering additional doses of the administered treatment identified as being effective (e.g., a CDK inhibitor, such as S-CR8) to the PKD patient.

In some embodiments, the steps (c) and (e) include determining the levels of at least two (e.g., three, four, five, six, or seven) markers selected from the group of: PCNA, cyclin D1, cyclin D3, MEK, S6, and pS6, and the administered treatment is identified as being effective if at least one or both of the two levels is decreased at the second time point as compared to the first time point. In some embodiments, the steps (c) and (e) include determining the levels of at least three (e.g., four, five, six, or seven) markers selected from the group of: PCNA, cyclin D1, cyclin D3, MEK, S6, and pS6, and the administered treatment is identified as being effective if at least one, two, or all three of the three levels is decreased at the second time point as compared to the first time point. In some embodiments, the steps (c) and (e) include determining the levels of at least four (e.g., five, six, or seven) markers selected from the group of: PCNA, cyclin D1, cyclin D3, MEK, S6, and pS6, and the administered treatment is identified as being effective if at least one, two, three, or all four of the levels is decreased at the second time point as compared to the first time point.

In some embodiments of these methods, the concentrating in (b) and (e) includes ultracentrifuging (e.g., differential centrifuging or centrifuging in a density gradient) or filtering the first and second samples, respectively. In some examples, the concentrating in (b) and (e) includes precipitating exosomes in the first and second samples, respectively; passing the first and second samples, respectively through a microfluidic device, respectively; or contacting the first and second samples with an affinity resin that is labeled with an antibody that specifically binds to an epitope present on the surface of exosomes, respectively. Additional methods for concentrating a sample containing a biological fluid for exosomes are known in the art. In some examples, the first and second samples contain urine.

In some examples, determining the level(s) of the one or more marker(s) in (c) and (e) includes determining the level of protein of the at least one marker. For example, the determining in (c) and (e) can include contacting the sample with antibodies that bind specifically to the protein of the at least one marker. In some embodiments, (c) and (e) include determining the level of one or both of cyclin D1 and MEK.

Also provided herein are methods of determining the efficacy of a treatment for PKD in a PKD subject that include: (a) providing a first sample including a biological fluid obtained from the PKD patient at a first time point; (b) determining the level(s) of at least one (e.g., two, three, four, five, six, seven, eight, nine, ten, eleven, or twelve in any combination) marker selected from the group of: PCNA, cyclin D1, cyclin D3, MEK, S6, pS6, ERK, pERK, Akt, pAkt, caspase-2, total S6, and RBBP in the first sample; (c) administering a treatment for PKD to the PKD patient; (d) providing a second sample including a biological fluid obtained from the patient at a second time point after step (c) and performing step (b) on the second sample; and (e) identifying the administered treatment as being effective if the level is decreased at a second time point as compared to the first time point. Some embodiments further include after (e): (f) administering additional doses of the administered GCS inhibitor identified as being effective (e.g., (S)-quinuclidin-3-yl (2-(4'-(2-methoxyethoxy)-[1,1'-biphenyl]-4-yl)propan-2-yl)carbamate; 4-fluoro-1-(5-fluoro-4-(4-((2-methoxyethoxy) methyl)phenyl)pyrimidin-2-yl)-N-(4-methyl-1-azabicyclo[3.2.2]nonan-4-yl)piperidine-4-carboxamide; 4-fluoro-1-(4-(4-((2-methoxyethoxy)methyl)phenyl)pyrimidin-2-yl)-N-(3-methylquinuclidin-3-yl)piperidine-4-carboxamide; 4-fluoro-1-(4-(4-((2-methoxyethoxy)methyl) phenyl)pyrimidin-2-yl)-N-(4-methyl-1-azabicyclo[3.2.2]nonan-4-yl)piperidine-4-carboxamide; 4-fluoro-1-(4-(4-(methoxymethyl)phenyl)pyrimidin-2-yl)-N-(3-methylquinuclidin-3-yl)piperidine-4-carboxamide; 4-fluoro-1-(4-(4-(methoxymethyl) phenyl)pyrimidin-2-yl)-N-(4-methyl-1-azabicyclo[3.2.2]nonan-4-yl)piperidine-4-carboxamide; 4-fluoro-1-(4-(4-(2-methoxyethoxy)phenyl)pyrimidin-2-yl)-N-(3-methylquinuclidin-3-yl)piperidine-4-carboxamide; 4-fluoro-1-(4-(4-(2-methoxyethoxy)phenyl)pyrimidin-2-yl)-N-(4-methyl-1-azabicyclo[3.2.2]nonan-4-yl)piperidine-4-carboxamide; 4-fluoro-1-(4-(4-(2-fluoroethoxy)phenyl) pyrimidin-2-yl)-N-(quinuclidin-3-yl)piperidine-4-carboxamide; or 4-fluoro-1-(4-(4-(2-fluoroethoxy)phenyl)pyrimidin-2-yl)-N-(4-methyl-1-azabicyclo[3.2.2]nonan-4-yl)piperidine-4-carboxamide) to the PKD patient. Some examples of the methods further include after (e): (f) administering additional doses of the administered treatment identified as being effective (e.g., a CDK inhibitor, such as S-CR8) to the PKD patient.

In some embodiments, the steps (b) and (d) include determining the levels of at least two (e.g., three, four, five, six, or seven) markers selected from the group of: PCNA, cyclin D1, cyclin D3, MEK, S6, and pS6, and the administered treatment is identified as being effective if at least one or both of the two levels is decreased at the second time point as compared to the first time point. In some embodiments, the steps (b) and (d) include determining the levels of at least three (e.g., four, five, six, or seven) markers selected from the group of: PCNA, cyclin D1, cyclin D3, MEK, S6, and pS6, and the administered treatment is identified as being effective if at least one, two, or all three of the three levels is decreased at the second time point as compared to the first time point. In some embodiments, the steps (b) and (d) include determining the levels of at least four (e.g., five, six, or seven) markers selected from the group of: PCNA, cyclin D1, cyclin D3, MEK, S6, and pS6, and the administered treatment is identified as being effective if at least one, two, three, or all four of the levels is decreased at the second time point as compared to the first time point.

In some examples, determining the level(s) of the one or more marker(s) in (b) and (d) includes determining the level of protein of the at least one marker. For example, the determining in (b) and (d) can include contacting the sample with antibodies that bind specifically to the protein of the at least one marker. In some embodiments, (b) and (d) include determining the level of at least two of PCNA, cyclin D3, pERK, and Akt.

In some embodiments of any of the methods, the administered treatment is administration of a glucosyl ceramide synthase (GCS) inhibitor (e.g., any of the GCS inhibitors described herein or known in the art). For example, the GCS inhibitor is selected from the group of: (S)-quinuclidin-3-yl (2-(4'-(2-methoxyethoxy)-[1,1'-biphenyl]-4-yl)propan-2-yl) carbamate; 4-fluoro-1-(5-fluoro-4-(4-((2methoxyethoxy) methyl) phenyl)pyrimidin-2-yl)-N-(4-methyl-1-azabicyclo [3.2.2]nonan-4-yl)piperidine-4-carboxamide; 4-fluoro-1-(4-(4-((2-methoxyethoxy)methyl)phenyl) pyrimidin-2-yl)-N-(3-methylquinuclidin-3-yl)piperidine-4-carboxamide; 4-fluoro-1-(4-(4-((2-methoxyethoxy) methyl)phenyl)pyrimidin-2-yl)-N-(4-methyl-1-azabicyclo [3.2.2]nonan-4-yl) piperidine-4-carboxamide; 4-fluoro-1-(4-(4-(methoxymethyl) phenyl)pyrimidin-2-yl)-N-(3-methylquinuclidin-3-yl) piperidine-4-carboxamide; 4-fluoro-1-(4-(4-(methoxymethyl)phenyl)pyrimidin-2-yl)-N-(4-methyl-1-azabicyclo[3.2.2]nonan-4-yl)piperidine-4-carboxamide; 4-fluoro-1-(4-(4-(2-methoxyethoxy)phenyl)pyrimidin-2-yl)-N-(3-methylquinuclidin-3-yl)piperidine-4-carboxamide; 4-fluoro-1-(4-(4-(2-methoxyethoxy)phenyl)pyrimidin-2-yl)-N-(4-methyl-1-azabicyclo[3.2.2]nonan-4-yl)piperidine-4-carboxamide; 4-fluoro-1-(4-(4-(2-fluoroethoxy)phenyl) pyrimidin-2-yl)-N-(quinuclidin-3-yl)piperidine-4-carboxamide; and 4-fluoro-1-(4-(4-(2-fluoroethoxy)phenyl) pyrimidin-2-yl)-N-(4-methyl-1-azabicyclo[3.2.2]nonan-4-yl)piperidine-4-carboxamide.

In some embodiments of any of the methods, the administered treatment is administration of a CDK inhibitor (e.g., any of the CDK inhibitors described herein or known in the art, such as R-roscovitine) to the PKD patient.

Some embodiments of any of the methods further include a step of selecting a patient having PKD or diagnosing a patient having PKD (e.g., using any of the exemplary methods of diagnosing PKD described herein). The patient in any of these methods can be any of the patients described herein. For example, a patient having PKD can have previously been administered a treatment for PKD and the treatment was unsuccessful. Some embodiments of any of the methods further include obtaining the first and/or second samples from the PKD patient.

Some embodiments further include recording the identified efficacy of the administered treatment in the patient's medical record (e.g., a computer readable medium). Some examples further include informing the patient, the patient's family, and/or the patient's primary care physician or attending physician of the identified efficacy of the administered treatment. Some embodiments further include authorization of a refill of an administered treatment identified as being effective.

The difference in time between the first and second time points can be, e.g., between 1 week and 40 weeks, between 1 week and 30 weeks, between 1 week and 20 weeks, between 1 week and 12 weeks, between 1 week and 8 weeks, between 1 week and 4 weeks, between 1 week and 2 weeks, between 2 weeks and 12 weeks, between 2 weeks and 8 weeks, or between 2 weeks and 4 weeks.

Methods of Diagnosing PKD

Also provided are methods of diagnosing PKD in a patient that include (a) providing a sample including a biological fluid from a patient suspected of having PKD; (b) concentrating the sample for exosomes; (c) determining the level(s) of at least one marker selected from the group of: PCNA, cyclin D1, cyclin D3, MEK, S6, pS6, ERK, pERK, Akt, pAkt, caspase-2, total S6, and RBBP in the sample; and (d) identifying the patient as having PKD if the level is elevated as compared to a control level. Some examples of these methods further include after (d): (e) administering a treatment for PKD (e.g., any of the exemplary treatments for PKD described herein) to a patient identified as having PKD. Some embodiments further include after (d): (e) administering a GCS inhibitor (e.g., (S)-quinuclidin-3-yl (2-(4'-(2-methoxyethoxy)-[1,1'-biphenyl]-4-yl)propan-2-yl)carbamate; 4-fluoro-1-(5-fluoro-4-(4-((2methoxyethoxy)methyl) phenyl)pyrimidin-2-yl)-N-(4-methyl-1-azabicyclo [3.2.2] nonan-4-yl)piperidine-4-carboxamide; 4-fluoro-1-(4-(4-((2-methoxyethoxy) methyl)phenyl)pyrimidin-2-yl)-N-(3-methylquinuclidin-3-yl)piperidine-4-carboxamide; 4-fluoro-1-(4-(4-((2-methoxyethoxy) methyl)phenyl)pyrimidin-2-yl)-N-(4-methyl-1-azabicyclo[3.2.2]nonan-4-yl) piperidine-4-carboxamide; 4-fluoro-1-(4-(4-(methoxymethyl)phenyl)pyrimidin-2-yl)-N-(3-methylquinuclidin-3-yl) piperidine-4-carboxamide; 4-fluoro-1-(4-(4-(methoxymethyl)phenyl)pyrimidin-2-yl)-N-(4-methyl-1-azabicyclo[3.2.2]nonan-4-yl)piperidine-4-carboxamide; 4-fluoro-1-(4-(4-(2-methoxyethoxy)phenyl)pyrimidin-2-yl)-N-(3-methylquinuclidin-3-yl)piperidine-4-carboxamide; 4-fluoro-1-(4-(4-(2-methoxyethoxy)phenyl)pyrimidin-2-yl)-N-(4-methyl-1-azabicyclo[3.2.2]nonan-4-yl)piperidine-4-carboxamide; 4-fluoro-1-(4-(4-(2-fluoroethoxy)phenyl) pyrimidin-2-yl)-N-(quinuclidin-3-yl)piperidine-4-carboxamide; or 4-fluoro-1-(4-(4-(2-fluoroethoxy)phenyl) pyrimidin-2-yl)-N-(4-methyl-1-azabicyclo[3.2.2]nonan-4-yl)piperidine-4-carboxamide) to a patient identified as having PKD. Some embodiments further include after (d): (e) administering a CDK inhibitor (e.g., roscovitine) to a patient identified as having PKD. Some embodiments further include after (d): (e) performing one or more additional tests to confirm PKD in the patient (e.g., imaging one or both kidney(s) in a patient identified as having PKD).

In some embodiments, the step (c) includes determining the levels of at least two (e.g., three, four, five, six, or seven) markers selected from the group of: PCNA, cyclin D1, cyclin D3, MEK, S6, and pS6, and the patient is identified as having PKD if at least one or both of the two levels is elevated as compared to the control level. In some embodiments, step (c) includes determining the levels of at least three (e.g., four, five, six, or seven) markers selected from the group of: PCNA, cyclin D1, cyclin D3, MEK, S6, and pS6, and the patient is identified as having PKD if at least one, two, or all three of the three levels is elevated as compared to the control level. In some embodiments, step (c) includes determining the levels of at least four (e.g., five, six, or seven) markers selected from the group of: PCNA, cyclin D1, cyclin D3, MEK, S6, and pS6, and the subject is identified as having PKD if at least one, two, three, or all four of the levels is elevated at compared to the control level.

In some embodiments of these methods, the concentrating in (b) includes ultracentrifuging (e.g., differential centrifuging or centrifuging in a density gradient) or the sample. In some examples, the concentrating in (b) includes precipitating exosomes in the sample; passing the sample through a microfluidic device; or contacting the sample with an affinity resin that is labeled with an antibody that specifically binds to an epitope present on the surface of exosomes. Additional methods for concentrating a sample containing a biological fluid for exosomes are known in the art. In some examples, the sample contains urine.

In some examples, determining the level(s) of the one or more marker(s) in (c) includes determining the level of protein of the at least one marker. For example, the determining in (c) can include contacting the sample with antibodies that bind specifically to the protein of the at least one marker. In some embodiments, (c) includes determining the level of at least two of PCNA, cyclin D1, cyclin D3, MEK, S6, and pS6.

Also provided are methods of diagnosing PKD in a patient that include (a) providing a sample including a biological fluid from a patient suspected of having PKD; (b) determining the level(s) of at least one marker selected from the group of: PCNA, cyclin D1, cyclin D3, MEK, S6, pS6, ERK, pERK, Akt, pAkt, caspase-2, total S6, and RBBP in the sample; and (c) identifying the patient as having PKD if the level is elevated as compared to a control level. Some examples of these methods further include after (c): (d) administering a treatment for PKD (e.g., any of the exemplary treatments for PKD described herein) to a patient identified as having PKD. Some embodiments further include after (c): (d) administering a GCS inhibitor (e.g., (S)-quinuclidin-3-yl (2-(4'-(2-methoxyethoxy)-[1,1'-biphenyl]-4-yl)propan-2-yl)carbamate; 4-fluoro-1-(5-fluoro-4-(4-((2methoxyethoxy)methyl)phenyl) pyrimidin-2-yl)-N-(4-methyl-1-azabicyclo[3.2.2]nonan-4-yl)piperidine-4-carboxamide; 4-fluoro-1-(4-(4-((2-methoxyethoxy)methyl) phenyl)pyrimidin-2-yl)-N-(3-methylquinuclidin-3-yl) piperidine-4-carboxamide; 4-fluoro-1-(4-(4-((2-methoxyethoxy) methyl)phenyl)pyrimidin-2-yl)-N-(4-methyl-1-azabicyclo[3.2.2]nonan-4-yl)piperidine-4-carboxamide; 4-fluoro-1-(4-(4-(methoxymethyl)phenyl) pyrimidin-2-yl)-N-(3-methylquinuclidin-3-yl)piperidine-4-carboxamide; 4-fluoro-1-(4-(4-(methoxymethyl) phenyl)pyrimidin-2-yl)-N-(4-methyl-1-azabicyclo[3.2.2]nonan-4-yl)piperidine-4-carboxamide; 4-fluoro-1-(4-(4-(2-methoxyethoxy)phenyl) pyrimidin-2-yl)-N-(3-methylquinuclidin-3-yl)piperidine-4-carboxamide; 4-fluoro-1-(4-(4-(2-methoxyethoxy) phenyl)pyrimidin-2-yl)-N-(4-methyl-1-azabicyclo[3.2.2]nonan-4-yl)piperidine-4-carboxamide; 4-fluoro-1-(4-(4-(2-fluoroethoxy)phenyl)pyrimidin-2-yl)-N-(quinuclidin-3-yl)piperidine-4-carboxamide; or 4-fluoro-1-(4-(4-(2-fluoroethoxy)phenyl)pyrimidin-2-yl)-N-(4-methyl-1-azabicyclo[3.2.2]nonan-4-yl)piperidine-4-carboxamide) to a patient identified as having PKD. Some embodiments further include after (c): (d) administering a CDK inhibitor (e.g., S-CR8) to a patient identified as having PKD. Some embodiments further include after (c): (d) performing one or more additional tests to confirm PKD in the patient (e.g., imaging one or both kidney(s) in a patient identified as having PKD).

In some embodiments, the step (b) includes determining the levels of at least two (e.g., three, four, five, six, or seven) markers selected from the group of: PCNA, cyclin D1, cyclin D3, MEK, S6, and pS6, and the patient is identified as having PKD if at least one or both of the two levels is elevated as compared to the control level. In some embodiments, step (b) includes determining the levels of at least three (e.g., four, five, six, or seven) markers selected from the group of: PCNA, cyclin D1, cyclin D3, MEK, S6, and pS6, and the patient is identified as having PKD if at least one, two, or all three of the three levels is elevated as compared to the control level. In some embodiments, step (b) includes determining the levels of at least four (e.g., five, six, or seven) markers selected from the group of: PCNA, cyclin D1, cyclin D3, MEK, S6, and pS6, and the subject is identified as having PKD if at least one, two, three, or all four of the levels is elevated As compared to the control level.

In some examples, determining the level(s) of the one or more marker(s) in (b) includes determining the level of protein of the at least one marker. For example, the determining in (b) can include contacting the sample with antibodies that bind specifically to the protein of the at least one marker. In some embodiments, (b) includes determining the level of at least two of cyclin D1, MEK, ERK, pAkt, S6, and pS6.

In any of these methods, a control level can be, e.g., a level of the at least one marker in a subject not presenting with one or more symptoms of PKD and/or not diagnosed as having PKD, a level of the at least one marker in a healthy subject or a population of healthy subjects, or a threshold level (e.g., a level above which indicates that the subject has PKD).

Some embodiments further include recording the identification of PKD in the patient in the patient's medical record (e.g., a computer readable medium). Some examples further include informing the patient, the patient's family, and/or the patient's primary care physician or attending physician of the identification of PKD in the patient. Some examples further include informing the patient's insurance provider of the identification of PKD in the patient.

Methods of Determining the Stage of PKD

Also provided herein are methods of determining the stage of PKD in a patient that include: (a) providing a sample including a biological fluid from a patient suspected of having PKD or identified as having PKD; (b) concentrating the sample for exosomes; (c) determining the level(s) of at least one marker selected from the group of: PCNA, cyclin D1, cyclin D3, MEK, S6, pS6, ERK, pERK, Akt, pAkt, caspase-2, total S6, and RBBP in the sample; and (d) determining the stage of PKD in the patient from the level. In some embodiments, the determining in (d) includes comparing the determined level of at least one marker to a range of values for a particular stage of PKD (e.g., stage I, stage II, stage III, stage IV, or stage V) and identifying a subject as having a particular stage of PKD if the at least one level falls within a range of values for the particular stage of PKD. Some embodiments further include after (d): (e) administering a treatment for stage I, stage II, stage III, stage IV, or stage V PKD to a patient identified as having stage I, stage II, stage III, stage IV, or stage V PKD, respectively. Some embodiments further include after (d): (e) performing one or more assays to confirm the stage of PKD (e.g., imaging one or both kidney(s) in a patient after (d) to confirm the stage of PKD in the patient). Some embodiments further include after (d): (e) hospitalizing a subject identified as having stage IV or stage V PKD. Ranges of levels of the at least one marker described herein in a sample including a biological fluid (e.g., urine or a sample comprising a biological fluid that has been enriched for exosomes) from a subject having a certain stage of PKD (e.g., stage I, stage II, stage III, stage IV, or stage PKD) can be determined using skills known in the art. The five stages of PKD are described on the Kidney Support webpage (kidney-support.org): stage 1 (emergence stage), stage 2 (growth stage), stage 3 (enlargement or swelling stage), stage 4 (cyst rupture stage), and stage 5 (end stage).

In some embodiments, step (c) includes determining the levels of at least two (e.g., three, four, five, six, or seven) markers selected from the group of: PCNA, cyclin D1, cyclin D3, MEK, S6, and pS6, and the stage of PKD is determined from at least one or both of the two levels. In some embodiments, step (c) includes determining the levels of at least three (e.g., four, five, six, or seven) markers selected from the group of: PCNA, cyclin D1, cyclin D3, MEK, S6, and pS6, and the stage of PKD is determined from at least one, two, or all three of the three levels. In some embodiments, step (c) includes determining the levels of at least four (e.g., five, six, or seven) markers selected from the group of: PCNA, cyclin D1, cyclin D3, MEK, S6, and pS6, and the stage of PKD is determined from at least one, two, three, or all four of the levels.

In some embodiments of these methods, the concentrating in (b) includes ultracentrifuging (e.g., differential centrifuging or centrifuging in a density gradient) or the sample. In some examples, the concentrating in (b) includes precipitating exosomes in the sample; passing the sample through a microfluidic device; or contacting the sample with an affinity resin that is labeled with an antibody that specifically binds to an epitope present on the surface of exosomes. Additional methods for concentrating a sample containing a biological fluid for exosomes are known in the art. In some examples, the sample contains urine.

In some examples, determining the level(s) of the one or more marker(s) in (c) includes determining the level of protein of the at least one marker. For example, the determining in (c) can include contacting the sample with antibodies that bind specifically to the protein of the at least one marker. In some embodiments, (c) includes determining the level of at least two of PCNA, cyclin D3, MEK, and phosphorylated S6.

Also provided herein are methods of determining the stage of PKD in a patient that include: (a) providing a sample including a biological fluid from a patient suspected of having PKD or identified as having PKD; (b) determining the level(s) of at least one marker selected from the group of: PCNA, cyclin D1, cyclin D3, MEK, S6, pS6, ERK, pERK, Akt, pAkt, caspase-2, total S6, and RBBP in the sample; and (c) determining the stage of PKD in the patient from the level. In some embodiments, the determining in (c) includes a comparing the determined level of the at least one marker to a range of values for a particular stage of PKD (e.g., stage I, stage II, stage III, stage IV, or stage V) and identifying a subject as having a particular stage of PKD if the at least one level falls within a range of values for the particular stage of PKD. Some embodiments further include after (c): (d) administering a treatment for stage I, stage II, stage III, stage IV, or stage V PKD to a patient identified as having stage I, stage II, stage III, stage IV, or stage V PKD, respectively. Some embodiments further include after (c): (d) performing one or more assays to confirm the stage of PKD (e.g., imaging one or both kidney(s) in a patient after (c) to confirm the stage of PKD in the patient). Some embodiments further include after (c): (d) hospitalizing a subject identified as having stage IV or stage V PKD.

In some embodiments, step (b) includes determining the levels of at least two (e.g., three, four, five, six, or seven) markers selected from the group of: PCNA, cyclin D1, cyclin D3, MEK, S6, and pS6, and the stage of PKD is determined from at least one or both of the two levels. In some embodiments, step (b) includes determining the levels of at least three (e.g., four, five, six, or seven) markers selected from the group of: PCNA, cyclin D1, cyclin D3, MEK, S6, and pS6, and the stage of PKD is determined from at least one, two, or all three of the three levels. In some embodiments, step (b) includes determining the levels of at least four (e.g., five, six, or seven) markers selected from the group of: PCNA, cyclin D1, cyclin D3, MEK, S6, and pS6, and the stage of PKD is determined from at least one, two, three, or all four of the levels.

In some examples, determining the level(s) of the one or more marker(s) in (b) includes determining the level of protein of the at least one marker. For example, the determining in (b) can include contacting the sample with antibodies that bind specifically to the protein of the at least one marker. In some embodiments, (b) includes determining the level of at least two of PCNA, cyclin D3, MEK, and phosphorylated S6.

Methods of Monitoring PKD

Also provided are methods of monitoring a PKD patient that include: (a) providing a first sample including a biological fluid obtained from the PKD patient at a first time point; (b) concentrating the first sample for exosomes; (c) determining the level(s) of at least one marker (e.g., two, three, four, five, six, seven, eight, nine, ten, eleven, or twelve in any combination) marker selected from the group of: PCNA, cyclin D1, cyclin D3, MEK, S6, pS6, ERK, pERK, Akt, pAkt, caspase-2, total S6, and RBBP in the first sample; (d) providing a second sample including a biological fluid obtained from the PKD patient as a second time point after step (c) and performing steps (b) and (c) on the second sample; and (e) identifying the patient as having improving or static PKD if at least one of the two levels is not elevated at the second time point as compared to the first time point. In some embodiments, the steps (c) and (d) include determining the levels of at least two (e.g., three, four, five, six, or seven) markers selected from the group of: PCNA, cyclin D1, cyclin D3, MEK, S6, and pS6, and the patient is identified as having improving or static PKD if at least one or both of the two levels is/are not elevated at the second time point as compared to the first time point. In some embodiments, the steps (c) and (d) include determining the levels of at least three (e.g., four, five, six, or seven) markers selected from the group of: PCNA, cyclin D1, cyclin D3, MEK, S6, and pS6, and the patient is identified as having improving or static PKD if at least one, two, or all three of the three levels is/are not elevated at the second time point as compared to the first time point. In some embodiments, the steps (c) and (d) include determining the levels of at least four (e.g., five, six, or seven) markers selected from the group of: PCNA, cyclin D1, cyclin D3, MEK, S6, and pS6, and the patient is identified as having improving or static PKD if at least one, two, three, or all four of the levels is/are not elevated at the second time point as compared to the first time point.

In some embodiments of these methods, the concentrating in (b) and (d) includes ultracentrifuging (e.g., differential centrifuging or centrifuging in a density gradient) or filtering the first and second samples, respectively. In some examples, the concentrating in (b) and (d) includes precipitating exosomes in the first and second samples, respectively; passing the first and second samples, respectively through a microfluidic device, respectively; or contacting the first and second samples with an affinity resin that is labeled with an antibody that specifically binds to an epitope present on the surface of exosomes, respectively. Additional methods for concentrating a sample containing a biological fluid for exosomes are known in the art. In some examples, the first and second samples contain urine.

In some examples, determining the level(s) of the one or more marker(s) in (c) and (d) include determining the level of protein of the at least one marker. For example, the determining in (c) and (d) can include contacting the sample with antibodies that bind specifically to the protein of the at least one marker. In some embodiments, (c) and (d) include determining the level of at least two (e.g., three or four) of PCNA, cyclin D3, MEK, and phosphorylated S6. Some embodiments further include after (e): (f) administering the same treatment (e.g., any of the exemplary treatments of PKD described herein or known in the art) to a patient identified as having improving or static PKD. For example, the administering in (f) can be the administration of a GCS inhibitor (e.g., (S)-quinuclidin-3-yl (2-(4'-(2-methoxyethoxy)-[1,1'-biphenyl]-4-yl)propan-2-yl)carbamate; 4-fluoro-1-(5-fluoro-4-(4-((2methoxyethoxy)methyl) phenyl)pyrimidin-2-yl)-N-(4-methyl-1-azabicyclo [3.2.2] nonan-4-yl)piperidine-4-carboxamide; 4-fluoro-1-(4-(4-((2-methoxyethoxy) methyl)phenyl)pyrimidin-2-yl)-N-(3-methylquinuclidin-3-yl)piperidine-4-carboxamide; 4-fluoro-1-(4-(4-((2-methoxyethoxy) methyl)phenyl)pyrimidin-2-yl)-N-(4-methyl-1-azabicyclo[3.2.2]nonan-4-yl)piperidine-4-carboxamide; 4-fluoro-1-(4-(4-(methoxymethyl)phenyl)pyrimidin-2-yl)-N-(3-methylquinuclidin-3-yl)piperidine-4-carboxamide; 4-fluoro-1-(4-(4-(methoxymethyl)phenyl)pyrimidin-2-yl)-N-(4-methyl-1-azabicyclo[3.2.2]nonan-4-yl)piperidine-4-carboxamide; 4-fluoro-1-(4-(4-(2-methoxyethoxy)phenyl)pyrimidin-2-yl)-N-(3-methylquinuclidin-3-yl)piperidine-4-carboxamide; 4-fluoro-1-(4-(4-(2-methoxyethoxy)phenyl)pyrimidin-2-yl)-N-(4-methyl-1-azabicyclo[3.2.2]nonan-4-yl)piperidine-4-carboxamide; 4-fluoro-1-(4-(4-(2-fluoroethoxy)phenyl) pyrimidin-2-yl)-N-(quinuclidin-3-yl)piperidine-4-carboxamide; or 4-fluoro-1-(4-(4-(2-fluoroethoxy)phenyl) pyrimidin-2-yl)-N-(4-methyl-1-azabicyclo[3.2.2]nonan-4-yl)piperidine-4-carboxamide).

Also provided are methods of monitoring a PKD patient that include: (a) providing a first sample including a biological fluid obtained from the PKD patient at a first time point; (b) determining the level(s) of at least one marker (e.g., two, three, four, five, six, seven, eight, nine, ten, eleven, or twelve in any combination) marker selected from the group of: PCNA, cyclin D1, cyclin D3, MEK, S6, pS6, ERK, pERK, Akt, pAkt, caspase-2, total S6, and RBBP in the first sample; (c) providing a second sample including a biological fluid obtained from the PKD patient as a second time point after step (b) and performing step (b) on the second sample; and (d) identifying the patient as having improving or static PKD if at least one of the two levels is not elevated at the second time point as compared to the first time point. In some embodiments, the steps (b) and (c) include determining the levels of at least two (e.g., three, four, five, six, or seven) markers selected from the group of: PCNA, cyclin D1, cyclin D3, MEK, S6, and pS6, and the patient is identified as having improving or static PKD if at least one or both of the two levels is/are not elevated at the second time point as compared to the first time point. In some embodiments, the steps (b) and (c) include determining the levels of at least three (e.g., four, five, six, or seven) markers selected from the group of: PCNA, cyclin D1, cyclin D3, MEK, S6, and pS6, and the patient is identified as having improving or static PKD if at least one, two, or all three of the three levels is/are not elevated at the second time point as compared to the first time point. In some embodiments, the steps (c) and (c) include determining the levels of at least four (e.g., five, six, or seven) markers selected from the group of: PCNA, cyclin D1, cyclin D3, MEK, S6, and pS6, and the patient is identified as having improving or static PKD if at least one, two, three, or all four of the levels is/are not elevated at the second time point as compared to the first time point.

In some examples, determining the level(s) of the one or more marker(s) in (b) and (c) include determining the level of protein of the at least one marker. For example, the determining in (b) and (c) can include contacting the sample with antibodies that bind specifically to the protein of the at least one marker. In some embodiments, (b) and (c) include determining the level of at least two (e.g., three or four) of PCNA, cyclin D3, MEK, and phosphorylated S6. Some embodiments further include after (d): (e) administering the same treatment (e.g., any of the exemplary treatments of PKD described herein or known in the art) to a patient identified as having improving or static PKD. For example, the administering in (e) can be the administration of a GCS inhibitor (e.g., (S)-quinuclidin-3-yl (2-(4'-(2-methoxyethoxy)-[1,1'-biphenyl]-4-yl)propan-2-yl)carbamate; 4-fluoro-1-(5-fluoro-4-(4-((2methoxyethoxy)methyl) phenyl)pyrimidin-2-yl)-N-(4-methyl-1-azabicyclo [3.2.2] nonan-4-yl)piperidine-4-carboxamide; 4-fluoro-1-(4-(4-((2-methoxyethoxy) methyl)phenyl)pyrimidin-2-yl)-N-(3-methylquinuclidin-3-yl)piperidine-4-carboxamide; 4-fluoro-1-(4-(4-((2-methoxyethoxy) methyl)phenyl)pyrimidin-2-yl)-N-(4-methyl-1-azabicyclo[3.2.2]nonan-4-yl) piperidine-4-carboxamide; 4-fluoro-1-(4-(4-(methoxymethyl)phenyl)pyrimidin-2-yl)-N-(3-methylquinuclidin-3-yl) piperidine-4-carboxamide; 4-fluoro-1-(4-(4-(methoxymethyl)phenyl)pyrimidin-2-yl)-N-(4-methyl-1-azabicyclo[3.2.2]nonan-4-yl)piperidine-4-carboxamide; 4-fluoro-1-(4-(4-(2-methoxyethoxy)phenyl)pyrimidin-2-yl)-N-(3-methylquinuclidin-3-yl)piperidine-4-carboxamide; 4-fluoro-1-(4-(4-(2-methoxyethoxy)phenyl)pyrimidin-2-yl)-N-(4-methyl-1-azabicyclo[3.2.2]nonan-4-yl)piperidine-4-carboxamide; 4-fluoro-1-(4-(4-(2-fluoroethoxy)phenyl) pyrimidin-2-yl)-N-(quinuclidin-3-yl)piperidine-4-carboxamide; or 4-fluoro-1-(4-(4-(2-fluoroethoxy)phenyl) pyrimidin-2-yl)-N-(4-methyl-1-azabicyclo[3.2.2]nonan-4-yl)piperidine-4-carboxamide).

Some embodiments of any of the methods further include a step of selecting a patient having PKD or diagnosing a patient having PKD (prior to step (a)) (e.g., using any of the exemplary methods of diagnosing PKD described herein). The patient in any of these methods can be any of the patients described herein. Some embodiments of any of the methods further include obtaining the first and/or second samples from the PKD patient.

Some embodiments further include recording the improving or static PKD status of the patient in the patient's medical record (e.g., a computer readable medium). Some examples further include informing the patient, the patient's family, and/or the patient's primary care physician or attending physician of improving or static PKD status of the patient. Some embodiments further include authorization of a refill of a treatment administered to the subject between the first and second time points, when the subject has been identified as having improving or static PKD. Some embodiments include discharging a subject from an inpatient facility (e.g., hospital) based on identification of the subject as having improving or static PKD.

The difference in time between the first and second time points can be, e.g., between 1 week and 40 weeks, between 1 week and 30 weeks, between 1 week and 20 weeks, between 1 week and 12 weeks, between 1 week and 8 weeks, between 1 week and 4 weeks, between 1 week and 2 weeks, between 2 weeks and 12 weeks, between 2 weeks and 8 weeks, or between 2 weeks and 4 weeks.

Kits

Also provided herein are kits that consist essentially of or consist of at least three (e.g., four, five, six, seven, eight, nine, ten, eleven, or twelve) antibodies selected from the group consisting of: an antibody that specifically binds to PCNA, an antibody that specifically binds to cyclin D1, an antibody that specifically binds to cyclin D3, an antibody that specifically binds to MEK, an antibody that specifically binds to S6, an antibody that specifically binds to pS6, an antibody that specifically binds to pERK, an antibody that specifically binds to protein kinase B (Akt), an antibody that specifically binds to pAkt, an antibody that specifically binds to caspase-2, and an antibody that specifically binds to RBBP. In some examples, any combination of the three or more antibodies are labeled (e.g., with a radioisotope, a fluorophore, or a quencher).

Some examples of the kits further include an antibody that specifically binds to one or more exosome protein markers (e.g., aquaporin-2, TSG101, and/or ALIX). Some examples of the kits further include one or more positive control recombinant proteins (e.g., an isolated recombinant PCNA, cyclin D1, cyclin D3, MEK, S6, pS6, pERK, Akt, pAkt, caspase-2, and RBBP. In some examples, the at least three antibodies are covalently attached to a solid surface (e.g., a chip, a bead, or a membrane) by the Fc domain.

Some examples of the kits described herein further include one or more reagents for use in concentrating a sample containing a biological fluid for exosomes (e.g., a nanomembrane filter and/or beads that are coated with an antibody that specifically binds to a epitope present on the surface of an exosome).

Some kits further contain a sample containing a biological fluid (e.g., a sample containing a biological fluid that has been concentrated for exosomes) from a PKD patient (e.g., a PKD patient with a known severity of PKD) or an animal model of PKD (e.g., any of the animal models described in the Examples).

The invention is further described in the following examples, which do not limit the scope of the invention described in the claims.

EXAMPLES

Example 1. Identification of Biomarkers Useful in Methods of Determining Efficacy of Treatment of PKD, Diagnosing PKD, Monitoring PKD, and Staging PKD A set of experiments were performed to determine whether a set of biomarkers would be useful in methods of determining efficacy of treatment of PKD and the diagnosing, monitoring, and staging of PKD.

Materials and Methods

Animals and Urine Collection

C57BL/6J jck/+ mice were maintained for crossing. The cystic jck/jck mice were genotyped as previously described (Smith et al., *J. Am. Soc. Nephrol.* 17:2821-2831, 2006). Pcy mice were maintained on a CD1 genetic background as previously described (Takahashi et al., *J. Am. Soc. Nephrol.* 1:980-989, 1991). GCS inhibitor C9 was administered ad libitum to jck and pcy mice by mixing in powdered 5053 diet at 0.225% from 26 to 64 days and 4 to 30 weeks of age, respectively (as described in Natoli et al., *Nature Medicine* 16:788-792, 2010). Urine samples from the mice were collected in metabolic cages over a 24-hour period and stored at −80° C.

Human Patient Sample Collections

Normal and PKD human patient kidney samples were purchased from the National Disease Research Institute (NDRI). Autosomal dominant PKD urine samples were collected at the University of Toronto and all patients gave informed consent. Briefly, mid void morning urine specimens were collected and stabilized with Complete proteinase inhibitor cocktail (Roche, Basel, Switzerland). The urine was centrifuged at 2000×g for 10 minutes to remove cellular debris and stored at −80° C. Total kidney volume (TKV) was quantified in autosomal dominant PKD patients by magnetic resonance imaging (MRI) (without gadolinium). The profile of each human autosomal dominant PKD human patient who participated in the study is shown in Table 2 below.

2.5× Laemmli Buffer (5×: 15% SDS, 0.575 M sucrose, 0.325 M Tris, pH 6.8, 5% beta-mercapto ethanol, and 0.002% bromophenol blue) for sodium dodecyl sulfate-polyacrylamide gel electrophoresis (SDS-PAGE) and immunoblot analysis.

Immunoblot Analysis

Kidney samples were homogenized on ice in radioimmunoprecipitation assay (RIPA) buffer (Boston BioProducts, Ashland, Mass.) containing 1 mM dithiothreitol, 5 mM ethylenediaminetetraacetic acid (EDTA), 2 mM NaF, 1 mM $Na_3VO_4$ (all supplied by Sigma-Aldrich, St. Louis, Mo.), Pefabloc SC and Complete protease inhibitor cocktail (both from Roche, Basel, Switzerland). Protein concentration was determined by BCA protein assay (Pierce, Rockford, Ill.). The samples were loaded onto 4-12% NuPage Bis-Tris gels following the manufacturer's protocols (Invitrogen, Grand Island, N.Y.). Electrophoretic transfer of the proteins in the gel onto nitrocellulose was performed in a semi-dry apparatus according to the manufacturer's instructions (Invitrogen). After electrophoretic transfer, the resulting membranes were blocked with 5% non-fat milk in tris-buffered saline (TBS) containing 0.1% Tween-20 and incubated with primary antibodies overnight at 4° C. The primary antibodies were detected with horseradish peroxidase-labeled secondary antibodies at a 1:10,000 dilution (Promega, Fitchburg, Wis.). Immunoreactive proteins were revealed by enhanced chemiluminescence (GE Healthcare, Wauwatosa, Wis., and Thermo Scientific, Waltham, Mass.). The primary antibodies to the following antigens were used: PCNA (DAKO, Carpinteria, Calif.), cyclin D1, S6, phospho-S6 (Ser235/236), phospho-AKT (ser473), total ERK, phospho-ERK (Thr202/Tyr204) (Cell Signaling Technology, Danvers, Mass.), cyclin D3, total AKT, caspase-2, RBBP (BD Biosciences, Billerica, Mass.), MEK1 (Upstate Biotechnology, Lake Placid, N.Y.), aquaporin-2 (Millipore, Billerica, Mass.) β-actin, TSG101 (Abcam, Cambridge, Mass.), ALIX (Santa Cruz Biotechnology, Dallas, Tex.), and GAPDH (US Biological, Salem, Mass.).

TABLE 2

Profile of Autosomal Dominant PKD Human Patients[1]

| Patient ID | age at MRI (yr) | Gender | MRI Results | | | |
|---|---|---|---|---|---|---|
| | | | Right kidney volume (ml) | Left kidney volume (ml) | TKV (ml) | HtTKV (ml/m) |
| 175 | 24 | M | 153.9 | 160 | 314 | 190 |
| 181 | 24 | M | 187.4 | 204.8 | 392 | 220 |
| 164/169 | 43 | M | 232.9 | 235.6 | 469 | 270 |
| 167 | 20 | M | 358.4 | 148.3 | 507 | 280 |
| TOR8 | 42 | F | 194.51 | 355.44 | 550 | |
| TOR4 | 52 | F | 348.59 | 493.3 | 842 | |
| TOR6 | 44 | F | 428.49 | 662.91 | 1091 | |
| 198 | 43 | M | 562.1 | 563.3 | 1125 | 630 |
| 212 | 56 | M | 1003.2 | 650.4 | 1654 | 920 |
| 191/199 | 56 | M | 1066.6 | 1096.5 | 2163 | 1200 |
| 211 | 54 | M | 1315.2 | 1331.3 | 2647 | 1470 |
| 204 | 49 | M | 1747.6 | 1880.7 | 3628 | 1840 |
| 178 | 37 | M | 2146.5 | 1984.2 | 4131 | 2360 |

[1]The study population includes both early and late stage autosomal dominant PKD human patients with TKVs ranging from 300 mL to 4,000 mL.

Isolation of Urinary Exosomes

Exosomes were isolated from pooled urine samples (animal studies) or mid void urine samples (human samples) by ultracentrifugation at 100,000 g for 2 hours. Following ultracentrifugation, the exosome pellet was resuspended in Results Markers that can be used for accurate diagnosis and assessment of PKD in human patients in both preclinical and clinical settings were identified using a three-step approach and samples from both PKD human patients and mouse models of PKD. In a first step, markers that were differentially expressed in jck mice (a mouse model of PKD) as compared to normal control mice were identified. Markers from several different pathways were identified, including the cell cycle, Akt/mTOR, and proteins in apoptosis and mitogenic cascades were significantly elevated in exosomes purified from the urine of jck mice as compared to control mice (FIG. 1). The data in FIG. 1 show that the levels of proteins PCNA, cyclin D1, cyclin D3, MEK, Erk, phosphorylated-Akt, Akt, phosphorylated S6, and caspase-2 are elevated in urine exosomes from jck mice as compared to controls. The data in FIG. 1 also show that the levels of proteins PCNA, cyclin D1, cyclin D3, MEK, phosphorylated Erk, Erk, phosphorylated Akt, Akt, phosphorylated S6, and caspase-2 are elevated in kidney lysate sample from human PKD patients and jck mice as compared to healthy controls. These data suggest that the levels of the markers described herein can be used to diagnose a patient as having PKD.

Figure 2:
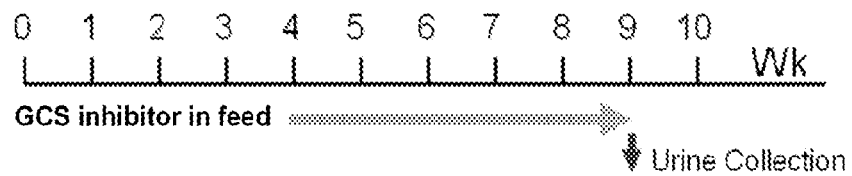
FIG. 2 is a schematic showing experimental design of the continuous treatment of jck mice with the GCS inhibitor C9 for a total of 5 weeks.
Figure 3:
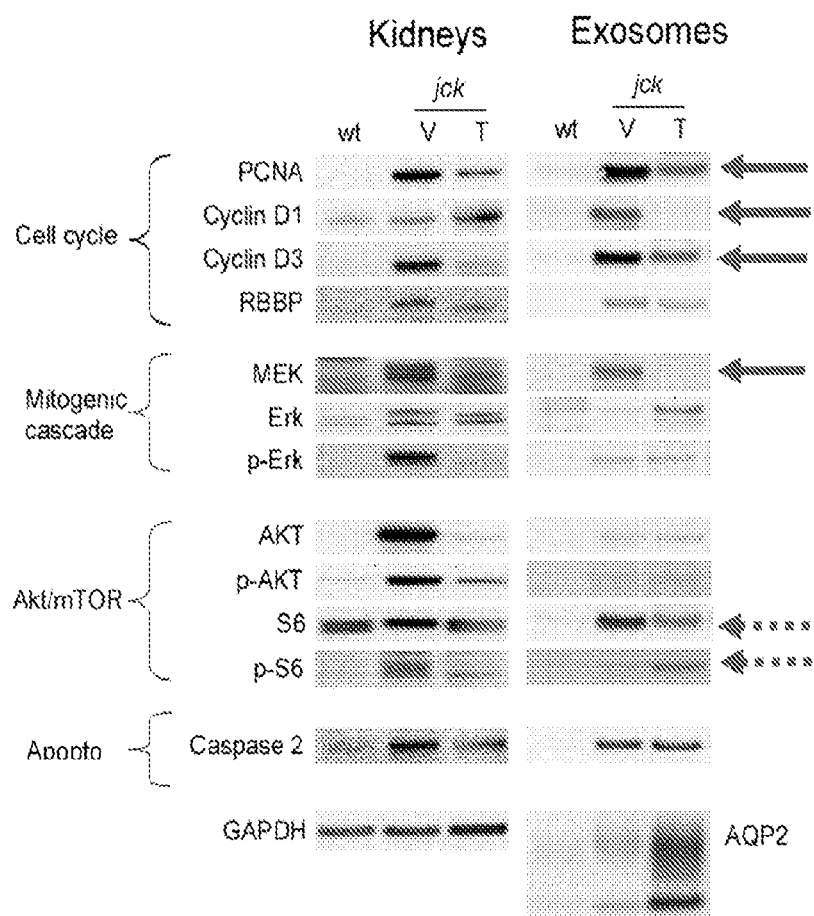
FIG. 3 is an immunoblot showing the levels of markers in kidney lysate from wildtype mice (wt) and jck mice administered vehicle (V) or the GCS inhibitor C9 (T) for five weeks, and the levels of markers in urine exosomes from wildtype mice (wt) or jck mice administered vehicle (V) or the GCS inhibitor C9 (T) for five weeks. The arrows indicate the markers that show more robust change between the vehicle- and GCS inhibitor C9-treated jck mice. The loading controls for the kidney lysate samples (glyceraldehyde 3-phosphate dehydrogenase; GAPDH) and for the urinary exosomes (aquaporin-2; AQP2) are shown.

A further set of experiments was performed to determine whether the same markers could be used to determine the efficacy of a treatment for PKD in a patient having PKD. In these experiments, urine samples from jck mice that were treated with GCS inhibitor C9 continuously for 5 weeks were gathered (FIG. 2) and the levels of each biomarker were analyzed in urine exosomes and kidney lysate samples. A decrease in level was observed for the biomarkers in both the kidney lysate samples and the urine exosomes in the jck mice receiving a GCS inhibitor as compared to the control mice (FIG. 3). For example, these data suggest that the expression of cell cycle markers (PCNA, cyclin D1, and cyclin D3), as well as the mitogenic marker, MEK, and the Akt/mTOR related marker, S6, are robustly decreased in a biological fluid (e.g., urine or a sample comprising a biological fluid (e.g., urine) that has been concentrated for exosomes) in response to treatment with a GCS inhibitor. The data in FIG. 3 show, e.g., that the levels of PCNA, cyclin D3, RBBP, MEK, Erk, phosphorylated ERK, Akt, phosphorylated Akt, S6, phosphorylated S6, and caspase-2 are decreased in kidney lysate samples from jck mice treated with a GCS inhibitor as compared to the levels in kidney lysate samples from control mice. The data in FIG. 3 also show, e.g., that the levels of PCNA, cyclin D1, cyclin D3, MEK, and S6 are decreased in urinary exosomes from jck mice treated with a GCS inhibitor as compared to the levels in urinary exosomes from control mice. These data suggest that levels of the markers described herein can be used to determine the efficacy of a treatment of PKD (e.g., a GCS inhibitor) in a human patient having PKD.

Figure 4:
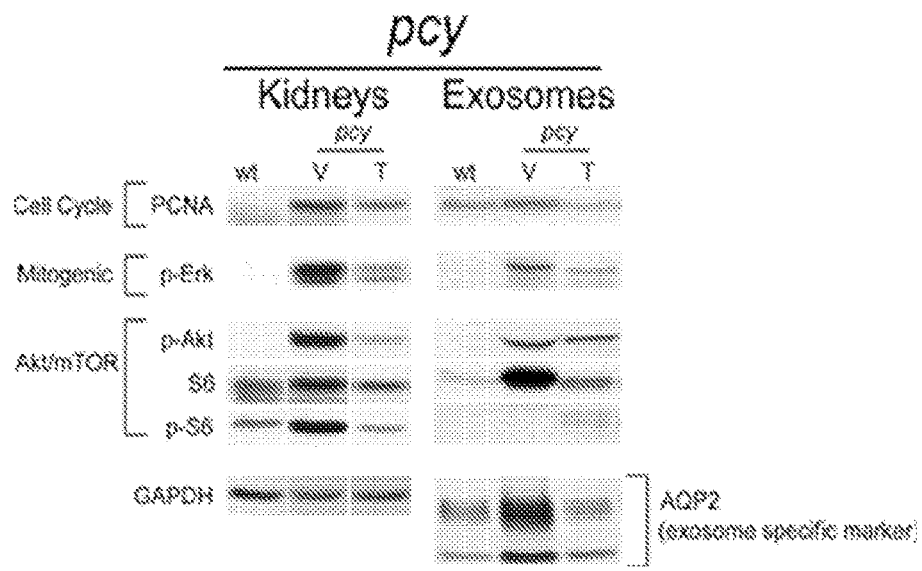
FIG. 4 is an immunoblot showing the levels of markers in kidney lysate from wildtype mice (wt) or pcy mice administered vehicle (V) or the GCS inhibitor C9 (T) for thirty weeks, and the levels of markers in urine exosomes from wildtype mice (wt) or pcy mice administered vehicle (V) or the GCS inhibitor C9 (T) for thirty weeks. The loading controls for the kidney lysate samples (glyceraldehyde 3-phosphate dehydrogenase; GAPDH) and for the urinary exosomes (aquaporin-2; AQP2) are shown.

A further set of experiments was performed to validate the use of the markers described herein for both diagnosing and determining the efficacy of treatment in human patients having PKD. In these experiments, another mouse model of PKD, pcy mice were used. The pcy mouse model is a slowly progressive adult form of PKD characterized by cyst formation and fibrosis. Treatment of pcy mice with GCS inhibitor C9 resulted in effective inhibition of cystogenesis and fibrogenesis (Natoli et al., Nature Medicine 16:788-792, 2010). In these experiments, pcy mice were left untreated or were treated with GCS inhibitor C9 for thirty weeks, and then the expression levels of the markers described herein were determined in both kidney lysate and urine exosome samples. The data from these experiments show the levels of the markers were decreased in both the kidney lysate samples and the urine exosome samples from pcy mice treated with GCS inhibitor C9 as compared to the corresponding levels in the untreated mice (FIG. 4). For example, the data in FIG. 4 show that the levels of PCNA, phosphorylated Erk, phosphorylated Akt, S6, and phosphorylated S6 are decreased in kidney lysate samples from pcy mice treated with GCS inhibitor C9 as compared to the untreated mice. The data in FIG. 4 also show, for example, that the levels of PCNA, phosphorylated Erk, phosphorylated Akt, and S6 are decreased in urinary exosomes from pcy mice treated with GCS inhibitor C9 as compared to the untreated mice.

Figure 5:
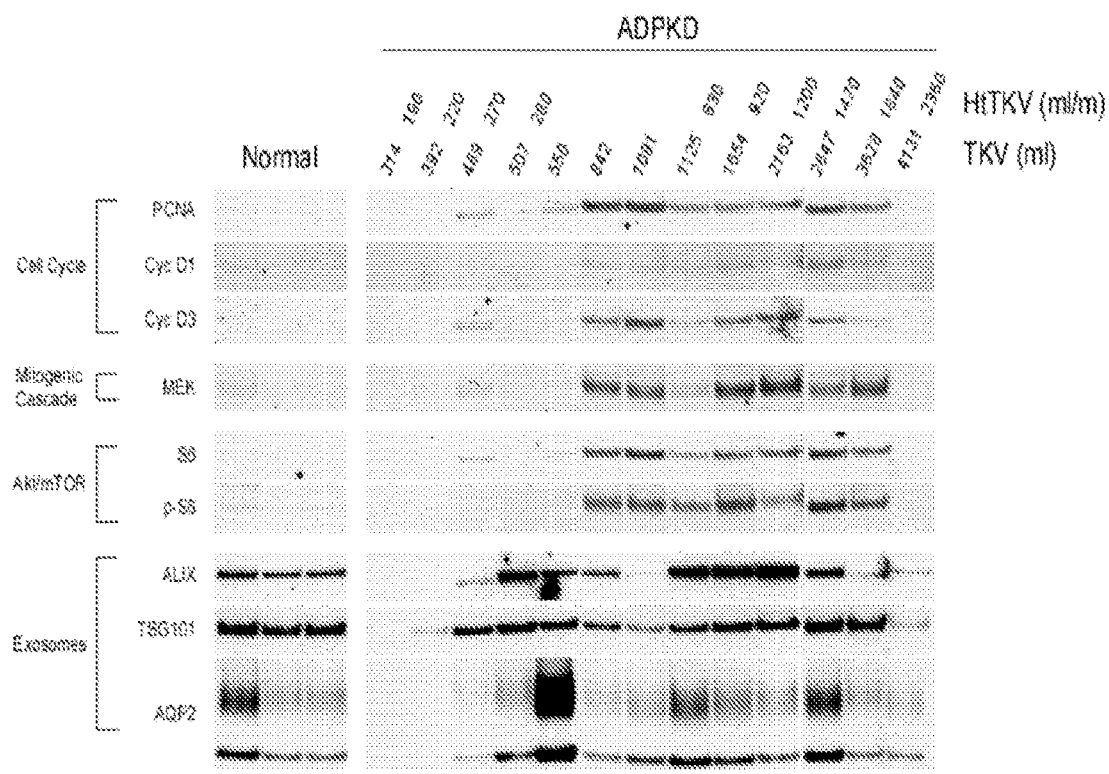
FIG. 5 is an immunoblot showing the levels of markers in urinary exosomes of normal human patients and ADPKD human patients having the listed measured total kidney volume (TKV) and height-adjusted total kidney volume (htTKV). The loading controls for the urinary exosomes (aquaporin-2, AQP2; apoptosis-linked gene 2-interacting protein X, ALIX; and tumor susceptibility gene 101, TSG101) are shown.

A further set of experiments was performed to determine whether levels of the markers described herein can be used to stage PKD in a patient. In these experiments, levels of markers described herein were determined in urinary exosomes from a population of thirteen human PKD patients having different stages of PKD (stages I through V, as evidenced by the total kidney volume and height-adjusted total kidney volume measured for each patient, and shown in FIG. 5). The resulting data show that the levels of the markers described herein become more elevated over each progressing stage of PKD. For example, the data in FIG. 5 show that the levels of PCNA, cyclin D1, cyclin D3, MEK, S6, and phosphorylated S6 in urine exosome samples are progressively elevated in patients having worsening stages of PKD. These data show that the markers described herein can be used to stage PKD in a human patient.

In sum, the data provided herein demonstrate that the markers described herein can be used to accurately determine the efficacy of a treatment of PKD in a patient and to accurately diagnose, monitor, and stage PKD in a patient.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

TABLE 1

Examples of Single Markers and Combinations of Markers

| | |
|---|---|
| PCNA, Cyclin D1, Cyclin D3, MEK | Cyclin D1, MEK, s6, pS6, Erk, pErk, Akt, RBBP |
| PCNA, Cyclin D1, Cyclin D3, s6 | Cyclin D1, MEK, s6, pS6, Erk, pErk, Akt, total S6 |
| PCNA, Cyclin D1, Cyclin D3, pS6 | Cyclin D1, MEK, s6, pS6, Erk, pErk, pAKT, Caspase2 |
| PCNA, Cyclin D1, Cyclin D3, Erk | Cyclin D1, MEK, s6, pS6, Erk, pErk, pAKT, RBBP |
| PCNA, Cyclin D1, Cyclin D3, pErk | Cyclin D1, MEK, s6, pS6, Erk, pErk, pAKT, total S6 |
| PCNA, Cyclin D1, Cyclin D3, Akt | Cyclin D1, MEK, s6, pS6, Erk, pErk, Caspase2, RBBP |
| PCNA, Cyclin D1, Cyclin D3, pAKT | Cyclin D1, MEK, s6, pS6, Erk, pErk, Caspase2, total S6 |
| PCNA, Cyclin D1, Cyclin D3, Caspase2 | Cyclin D1, MEK, s6, pS6, Erk, pErk, RBBP, total S6 |
| PCNA, Cyclin D1, Cyclin D3, RBBP | Cyclin D1, MEK, s6, pS6, Erk, Akt, pAKT, Caspase2 |
| PCNA, Cyclin D1, Cyclin D3, total S6 | Cyclin D1, MEK, s6, pS6, Erk, Akt, pAKT, RBBP |
| PCNA, Cyclin D1, MEK, s6 | Cyclin D1, MEK, s6, pS6, Erk, Akt, pAKT, total S6 |

TABLE 1-continued

Examples of Single Markers and Combinations of Markers

PCNA, Cyclin D1, MEK, pS6
PCNA, Cyclin D1, MEK, Erk
PCNA, Cyclin D1, MEK, pErk
PCNA, Cyclin D1, MEK, Akt
PCNA, Cyclin D1, MEK, pAkt
PCNA, Cyclin D1, MEK, Caspase2
PCNA, Cyclin D1, MEK, RBBP
PCNA, Cyclin D1, MEK, total S6
PCNA, Cyclin D1, s6, pS6
PCNA, Cyclin D1, s6, Erk
PCNA, Cyclin D1, s6, pErk
PCNA, Cyclin D1, s6, Akt
PCNA, Cyclin D1, s6, pAkt
PCNA, Cyclin D1, s6, Caspase2
PCNA, Cyclin D1, s6, RBBP
PCNA, Cyclin D1, s6, total S6
PCNA, Cyclin D1, pS6, Erk
PCNA, Cyclin D1, pS6, pErk
PCNA, Cyclin D1, pS6, Akt
PCNA, Cyclin D1, pS6, pAkt
PCNA, Cyclin D1, pS6, Caspase2
PCNA, Cyclin D1, pS6, RBBP
PCNA, Cyclin D1, pS6, total S6
PCNA, Cyclin D1, Erk, pErk
PCNA, Cyclin D1, Erk, Akt
PCNA, Cyclin D1, Erk, pAkt
PCNA, Cyclin D1, Erk, Caspase2
PCNA, Cyclin D1, Erk, RBBP
PCNA, Cyclin D1, Erk, total S6
PCNA, Cyclin D1, pErk, Akt
PCNA, Cyclin D1, pErk, pAkt
PCNA, Cyclin D1, pErk, Caspase2
PCNA, Cyclin D1, pErk, RBBP
PCNA, Cyclin D1, pErk, total S6
PCNA, Cyclin D1, Akt, pAkt
PCNA, Cyclin D1, Akt, Caspase2
PCNA, Cyclin D1, Akt, RBBP
PCNA, Cyclin D1, Akt, total S6
PCNA, Cyclin D1, pAkt, Caspase2
PCNA, Cyclin D1, pAkt, RBBP
PCNA, Cyclin D1, pAkt, total S6
PCNA, Cyclin D1, Caspase2, RBBP
PCNA, Cyclin D1, Caspase2, total S6
PCNA, Cyclin D1, RBBP, total S6
PCNA, Cyclin D3, MEK, s6
PCNA, Cyclin D3, MEK, pS6
PCNA, Cyclin D3, MEK, Erk
PCNA, Cyclin D3, MEK, pErk
PCNA, Cyclin D3, MEK, Akt
PCNA, Cyclin D3, MEK, pAkt
PCNA, Cyclin D3, MEK, Caspase2
PCNA, Cyclin D3, MEK, RBBP
PCNA, Cyclin D3, MEK, total S6
PCNA, Cyclin D3, s6, pS6
PCNA, Cyclin D3, s6, Erk
PCNA, Cyclin D3, s6, pErk
PCNA, Cyclin D3, s6, Akt
PCNA, Cyclin D3, s6, pAkt
PCNA, Cyclin D3, s6, Caspase2
PCNA, Cyclin D3, s6, RBBP
PCNA, Cyclin D3, s6, total S6
PCNA, Cyclin D3, pS6, Erk
PCNA, Cyclin D3, pS6, pErk
PCNA, Cyclin D3, pS6, Akt
PCNA, Cyclin D3, pS6, pAkt
PCNA, Cyclin D3, pS6, Caspase2
PCNA, Cyclin D3, pS6, RBBP
PCNA, Cyclin D3, pS6, total S6
PCNA, Cyclin D3, Erk, pErk
PCNA, Cyclin D3, Erk, Akt
PCNA, Cyclin D3, Erk, pAkt
PCNA, Cyclin D3, Erk, Caspase2
PCNA, Cyclin D3, Erk, RBBP
PCNA, Cyclin D3, Erk, total S6
PCNA, Cyclin D3, pErk, Akt
PCNA, Cyclin D3, pErk, pAkt
PCNA, Cyclin D3, pErk, Caspase2
PCNA, Cyclin D3, pErk, RBBP
Cyclin D1, MEK, s6, pS6, Erk, Akt, Caspase2, RBBP
Cyclin D1, MEK, s6, pS6, Erk, Akt, Caspase2, total S6
Cyclin D1, MEK, s6, pS6, Erk, Akt, RBBP, total S6
Cyclin D1, MEK, s6, pS6, Erk, pAkt, Caspase2, RBBP
Cyclin D1, MEK, s6, pS6, Erk, pAkt, Caspase2, total S6
Cyclin D1, MEK, s6, pS6, Erk, pAkt, RBBP, total S6
Cyclin D1, MEK, s6, pS6, Erk, Caspase2, RBBP, total S6
Cyclin D1, MEK, s6, pS6, pErk, Akt, pAkt, Caspase2
Cyclin D1, MEK, s6, pS6, pErk, Akt, pAkt, RBBP
Cyclin D1, MEK, s6, pS6, pErk, Akt, pAkt, total S6
Cyclin D1, MEK, s6, pS6, pErk, Akt, Caspase2, RBBP
Cyclin D1, MEK, s6, pS6, pErk, Akt, Caspase2, total S6
Cyclin D1, MEK, s6, pS6, pErk, Akt, RBBP, total S6
Cyclin D1, MEK, s6, pS6, pErk, pAkt, Caspase2, RBBP
Cyclin D1, MEK, s6, pS6, pErk, pAkt, Caspase2, total S6
Cyclin D1, MEK, s6, pS6, pErk, pAkt, RBBP, total S6
Cyclin D1, MEK, s6, pS6, pErk, Caspase2, RBBP, total S6
Cyclin D1, MEK, s6, pS6, Akt, pAkt, Caspase2, RBBP
Cyclin D1, MEK, s6, pS6, Akt, pAkt, Caspase2, total S6
Cyclin D1, MEK, s6, pS6, Akt, pAkt, RBBP, total S6
Cyclin D1, MEK, s6, pS6, Akt, Caspase2, RBBP, total S6
Cyclin D1, MEK, s6, pS6, pAkt, Caspase2, RBBP, total S6
Cyclin D1, MEK, s6, Erk, pErk, Akt, pAkt, Caspase2
Cyclin D1, MEK, s6, Erk, pErk, Akt, pAkt, RBBP
Cyclin D1, MEK, s6, Erk, pErk, Akt, pAkt, total S6
Cyclin D1, MEK, s6, Erk, pErk, Akt, Caspase2, RBBP
Cyclin D1, MEK, s6, Erk, pErk, Akt, Caspase2, total S6
Cyclin D1, MEK, s6, Erk, pErk, Akt, RBBP, total S6
Cyclin D1, MEK, s6, Erk, pErk, pAkt, Caspase2, RBBP
Cyclin D1, MEK, s6, Erk, pErk, pAkt, Caspase2, total S6
Cyclin D1, MEK, s6, Erk, pErk, pAkt, RBBP, total S6
Cyclin D1, MEK, s6, Erk, pErk, Caspase2, RBBP, total S6
Cyclin D1, MEK, s6, Erk, Akt, pAkt, Caspase2, RBBP
Cyclin D1, MEK, s6, Erk, Akt, pAkt, Caspase2, total S6
Cyclin D1, MEK, s6, Erk, Akt, pAkt, RBBP, total S6
Cyclin D1, MEK, s6, Erk, Akt, Caspase2, RBBP, total S6
Cyclin D1, MEK, s6, Erk, pAkt, Caspase2, RBBP, total S6
Cyclin D1, MEK, s6, pErk, Akt, pAkt, Caspase2, RBBP
Cyclin D1, MEK, s6, pErk, Akt, pAkt, Caspase2, total S6
Cyclin D1, MEK, s6, pErk, Akt, pAkt, RBBP, total S6
Cyclin D1, MEK, s6, pErk, Akt, Caspase2, RBBP, total S6
Cyclin D1, MEK, s6, pErk, pAkt, Caspase2, RBBP, total S6
Cyclin D1, MEK, s6, Akt, pAkt, Caspase2, RBBP, total S6
Cyclin D1, MEK, pS6, Erk, pErk, Akt, pAkt, Caspase2
Cyclin D1, MEK, pS6, Erk, pErk, Akt, pAkt, RBBP
Cyclin D1, MEK, pS6, Erk, pErk, Akt, pAkt, total S6
Cyclin D1, MEK, pS6, Erk, pErk, Akt, Caspase2, RBBP
Cyclin D1, MEK, pS6, Erk, pErk, Akt, Caspase2, total S6
Cyclin D1, MEK, pS6, Erk, pErk, Akt, RBBP, total S6
Cyclin D1, MEK, pS6, Erk, pErk, pAkt, Caspase2, RBBP
Cyclin D1, MEK, pS6, Erk, pErk, pAkt, Caspase2, total S6
Cyclin D1, MEK, pS6, Erk, pErk, pAkt, RBBP, total S6
Cyclin D1, MEK, pS6, Erk, pErk, Caspase2, RBBP, total S6
Cyclin D1, MEK, pS6, Erk, Akt, pAkt, Caspase2, RBBP
Cyclin D1, MEK, pS6, Erk, Akt, pAkt, Caspase2, total S6
Cyclin D1, MEK, pS6, Erk, Akt, pAkt, RBBP, total S6
Cyclin D1, MEK, pS6, Erk, Akt, Caspase2, RBBP, total S6
Cyclin D1, MEK, pS6, Erk, pAkt, Caspase2, RBBP, total S6
Cyclin D1, MEK, pS6, pErk, Akt, pAkt, Caspase2, RBBP
Cyclin D1, MEK, pS6, pErk, Akt, pAkt, Caspase2, total S6
Cyclin D1, MEK, pS6, pErk, Akt, pAkt, RBBP, total S6
Cyclin D1, MEK, pS6, pErk, Akt, Caspase2, RBBP, total S6
Cyclin D1, MEK, pS6, pErk, pAkt, Caspase2, RBBP, total S6
Cyclin D1, MEK, pS6, Akt, pAkt, Caspase2, RBBP, total S6
Cyclin D1, MEK, Erk, pErk, Akt, pAkt, Caspase2, RBBP
Cyclin D1, MEK, Erk, pErk, Akt, pAkt, Caspase2, total S6
Cyclin D1, MEK, Erk, pErk, Akt, pAkt, RBBP, total S6
Cyclin D1, MEK, Erk, pErk, Akt, Caspase2, RBBP, total S6
Cyclin D1, MEK, Erk, pErk, pAkt, Caspase2, RBBP, total S6
Cyclin D1, MEK, Erk, Akt, pAkt, Caspase2, RBBP, total S6
Cyclin D1, MEK, pErk, Akt, pAkt, Caspase2, RBBP, total S6
Cyclin D1, s6, pS6, Erk, pErk, Akt, pAkt, Caspase2
Cyclin D1, s6, pS6, Erk, pErk, Akt, pAkt, RBBP
Cyclin D1, s6, pS6, Erk, pErk, Akt, pAkt, total S6
Cyclin D1, s6, pS6, Erk, pErk, Akt, Caspase2, RBBP
Cyclin D1, s6, pS6, Erk, pErk, Akt, Caspase2, total S6
Cyclin D1, s6, pS6, Erk, pErk, Akt, RBBP, total S6
Cyclin D1, s6, pS6, Erk, pErk, pAkt, Caspase2, RBBP TABLE 1-continued Examples of Single Markers and Combinations of Markers PCNA, Cyclin D3, pErk, total S6
PCNA, Cyclin D3, Akt, pAkt
PCNA, Cyclin D3, Akt, Caspase2
PCNA, Cyclin D3, Akt, RBBP
PCNA, Cyclin D3, Akt, total S6
PCNA, Cyclin D3, pAkt, Caspase2
PCNA, Cyclin D3, pAkt, RBBP
PCNA, Cyclin D3, pAkt, total S6
PCNA, Cyclin D3, Caspase2, RBBP
PCNA, Cyclin D3, Caspase2, total S6
PCNA, Cyclin D3, RBBP, total S6
PCNA, MEK, s6, pS6
PCNA, MEK, s6, Erk
PCNA, MEK, s6, pErk
PCNA, MEK, s6, Akt
PCNA, MEK, s6, pAkt
PCNA, MEK, s6, Caspase2
PCNA, MEK, s6, RBBP
PCNA, MEK, s6, total S6
PCNA, MEK, pS6, Erk
PCNA, MEK, pS6, pErk
PCNA, MEK, pS6, Akt
PCNA, MEK, pS6, pAkt
PCNA, MEK, pS6, Caspase2
PCNA, MEK, pS6, RBBP
PCNA, MEK, pS6, total S6
PCNA, MEK, Erk, pErk
PCNA, MEK, Erk, Akt
PCNA, MEK, Erk, pAkt
PCNA, MEK, Erk, Caspase2
PCNA, MEK, Erk, RBBP
PCNA, MEK, Erk, total S6
PCNA, MEK, pErk, Akt
PCNA, MEK, pErk, pAkt
PCNA, MEK, pErk, Caspase2
PCNA, MEK, pErk, RBBP
PCNA, MEK, pErk, total S6
PCNA, MEK, Akt, pAkt
PCNA, MEK, Akt, Caspase2
PCNA, MEK, Akt, RBBP
PCNA, MEK, Akt, total S6
PCNA, MEK, pAkt, Caspase2
PCNA, MEK, pAkt, RBBP
PCNA, MEK, pAkt, total S6
PCNA, MEK, Caspase2, RBBP
PCNA, MEK, Caspase2, total S6
PCNA, MEK, RBBP, total S6
PCNA, s6, pS6, Erk
PCNA, s6, pS6, pErk
PCNA, s6, pS6, Akt
PCNA, s6, pS6, pAkt
PCNA, s6, pS6, Caspase2
PCNA, s6, pS6, RBBP
PCNA, s6, pS6, total S6
PCNA, s6, Erk, pErk
PCNA, s6, Erk, Akt
PCNA, s6, Erk, pAkt
PCNA, s6, Erk, Caspase2
PCNA, s6, Erk, RBBP
PCNA, s6, Erk, total S6
PCNA, s6, pErk, Akt
PCNA, s6, pErk, pAkt
PCNA, s6, pErk, Caspase2
PCNA, s6, pErk, RBBP
PCNA, s6, pErk, total S6
PCNA, s6, Akt, pAkt
PCNA, s6, Akt, Caspase2
PCNA, s6, Akt, RBBP
PCNA, s6, Akt, total S6
PCNA, s6, pAkt, Caspase2
PCNA, s6, pAkt, RBBP
PCNA, s6, pAkt, total S6
PCNA, s6, Caspase2, RBBP
PCNA, s6, Caspase2, total S6
PCNA, s6, RBBP, total S6
PCNA, pS6, Erk, pErk
PCNA, pS6, Erk, Akt
PCNA, pS6, Erk, pAkt Cyclin D1, s6, pS6, Erk, pErk, pAkt, Caspase2, total S6
Cyclin D1, s6, pS6, Erk, pErk, pAkt, RBBP, total S6
Cyclin D1, s6, pS6, Erk, pErk, Caspase2, RBBP, total S6
Cyclin D1, s6, pS6, Erk, Akt, pAkt, Caspase2, RBBP
Cyclin D1, s6, pS6, Erk, Akt, pAkt, Caspase2, total S6
Cyclin D1, s6, pS6, Erk, Akt, pAkt, RBBP, total S6
Cyclin D1, s6, pS6, Erk, Akt, Caspase2, RBBP, total S6
Cyclin D1, s6, pS6, Erk, pAkt, Caspase2, RBBP, total S6
Cyclin D1, s6, pS6, pErk, Akt, pAkt, Caspase2, RBBP
Cyclin D1, s6, pS6, pErk, Akt, pAkt, Caspase2, total S6
Cyclin D1, s6, pS6, pErk, Akt, pAkt, RBBP, total S6
Cyclin D1, s6, pS6, pErk, Akt, Caspase2, RBBP, total S6
Cyclin D1, s6, pS6, pErk, pAkt, Caspase2, RBBP, total S6
Cyclin D1, s6, pS6, Akt, pAkt, Caspase2, RBBP, total S6
Cyclin D1, s6, Erk, pErk, Akt, pAkt, Caspase2, RBBP
Cyclin D1, s6, Erk, pErk, Akt, pAkt, Caspase2, total S6
Cyclin D1, s6, Erk, pErk, Akt, pAkt, RBBP, total S6
Cyclin D1, s6, Erk, pErk, Akt, Caspase2, RBBP, total S6
Cyclin D1, s6, Erk, pErk, pAkt, Caspase2, RBBP, total S6
Cyclin D1, s6, Erk, Akt, pAkt, Caspase2, RBBP, total S6
Cyclin D1, s6, pErk, Akt, pAkt, Caspase2, RBBP, total S6
Cyclin D1, pS6, Erk, pErk, Akt, pAkt, Caspase2, RBBP
Cyclin D1, pS6, Erk, pErk, Akt, pAkt, Caspase2, total S6
Cyclin D1, pS6, Erk, pErk, Akt, pAkt, RBBP, total S6
Cyclin D1, pS6, Erk, pErk, Akt, Caspase2, RBBP, total S6
Cyclin D1, pS6, Erk, pErk, pAkt, Caspase2, RBBP, total S6
Cyclin D1, pS6, Erk, Akt, pAkt, Caspase2, RBBP, total S6
Cyclin D1, pS6, pErk, Akt, pAkt, Caspase2, RBBP, total S6
Cyclin D1, Erk, pErk, Akt, pAkt, Caspase2, RBBP, total S6
Cyclin D3, MEK, s6, pS6, Erk, pErk, Akt, pAkt
Cyclin D3, MEK, s6, pS6, Erk, pErk, Akt, Caspase2
Cyclin D3, MEK, s6, pS6, Erk, pErk, Akt, RBBP
Cyclin D3, MEK, s6, pS6, Erk, pErk, Akt, total S6
Cyclin D3, MEK, s6, pS6, Erk, pErk, pAkt, Caspase2
Cyclin D3, MEK, s6, pS6, Erk, pErk, pAkt, RBBP
Cyclin D3, MEK, s6, pS6, Erk, pErk, pAkt, total S6
Cyclin D3, MEK, s6, pS6, Erk, pErk, Caspase2, RBBP
Cyclin D3, MEK, s6, pS6, Erk, pErk, Caspase2, total S6
Cyclin D3, MEK, s6, pS6, Erk, pErk, RBBP, total S6
Cyclin D3, MEK, s6, pS6, Erk, Akt, pAkt, Caspase2
Cyclin D3, MEK, s6, pS6, Erk, Akt, pAkt, RBBP
Cyclin D3, MEK, s6, pS6, Erk, Akt, pAkt, total S6
Cyclin D3, MEK, s6, pS6, Erk, Akt, Caspase2, RBBP
Cyclin D3, MEK, s6, pS6, Erk, Akt, Caspase2, total S6
Cyclin D3, MEK, s6, pS6, Erk, Akt, RBBP, total S6
Cyclin D3, MEK, s6, pS6, Erk, pAkt, Caspase2, RBBP
Cyclin D3, MEK, s6, pS6, Erk, pAkt, Caspase2, total S6
Cyclin D3, MEK, s6, pS6, Erk, pAkt, RBBP, total S6
Cyclin D3, MEK, s6, pS6, Erk, Caspase2, RBBP, total S6
Cyclin D3, MEK, s6, pS6, pErk, Akt, pAkt, Caspase2
Cyclin D3, MEK, s6, pS6, pErk, Akt, pAkt, RBBP
Cyclin D3, MEK, s6, pS6, pErk, Akt, pAkt, total S6
Cyclin D3, MEK, s6, pS6, pErk, Akt, Caspase2, RBBP
Cyclin D3, MEK, s6, pS6, pErk, Akt, Caspase2, total S6
Cyclin D3, MEK, s6, pS6, pErk, Akt, RBBP, total S6
Cyclin D3, MEK, s6, pS6, pErk, pAkt, Caspase2, RBBP
Cyclin D3, MEK, s6, pS6, pErk, pAkt, Caspase2, total S6
Cyclin D3, MEK, s6, pS6, pErk, pAkt, RBBP, total S6
Cyclin D3, MEK, s6, pS6, pErk, Caspase2, RBBP, total S6
Cyclin D3, MEK, s6, pS6, Akt, pAkt, Caspase2, RBBP
Cyclin D3, MEK, s6, pS6, Akt, pAkt, Caspase2, total S6
Cyclin D3, MEK, s6, pS6, Akt, pAkt, RBBP, total S6
Cyclin D3, MEK, s6, pS6, Akt, Caspase2, RBBP, total S6
Cyclin D3, MEK, s6, pS6, pAkt, Caspase2, RBBP, total S6
Cyclin D3, MEK, s6, Erk, pErk, Akt, pAkt, Caspase2
Cyclin D3, MEK, s6, Erk, pErk, Akt, pAkt, RBBP
Cyclin D3, MEK, s6, Erk, pErk, Akt, pAkt, total S6
Cyclin D3, MEK, s6, Erk, pErk, Akt, Caspase2, RBBP
Cyclin D3, MEK, s6, Erk, pErk, Akt, Caspase2, total S6
Cyclin D3, MEK, s6, Erk, pErk, Akt, RBBP, total S6
Cyclin D3, MEK, s6, Erk, pErk, pAkt, Caspase2, RBBP
Cyclin D3, MEK, s6, Erk, pErk, pAkt, Caspase2, total S6
Cyclin D3, MEK, s6, Erk, pErk, pAkt, RBBP, total S6
Cyclin D3, MEK, s6, Erk, pErk, Caspase2, RBBP, total S6
Cyclin D3, MEK, s6, Erk, Akt, pAkt, Caspase2, RBBP
Cyclin D3, MEK, s6, Erk, Akt, pAkt, Caspase2, total S6
Cyclin D3, MEK, s6, Erk, Akt, pAkt, RBBP, total S6
Cyclin D3, MEK, s6, Erk, Akt, Caspase2, RBBP, total S6

TABLE 1-continued

Examples of Single Markers and Combinations of Markers

PCNA, pS6, Erk, Caspase2
PCNA, pS6, Erk, RBBP
PCNA, pS6, Erk, total S6
PCNA, pS6, pErk, Akt
PCNA, pS6, pErk, pAkt
PCNA, pS6, pErk, Caspase2
PCNA, pS6, pErk, RBBP
PCNA, pS6, pErk, total S6
PCNA, pS6, Akt, pAkt
PCNA, pS6, Akt, Caspase2
PCNA, pS6, Akt, RBBP
PCNA, pS6, Akt, total S6
PCNA, pS6, pAkt, Caspase2
PCNA, pS6, pAkt, RBBP
PCNA, pS6, pAkt, total S6
PCNA, pS6, Caspase2, RBBP
PCNA, pS6, Caspase2, total S6
PCNA, pS6, RBBP, total S6
PCNA, Erk, pErk, Akt
PCNA, Erk, pErk, pAkt
PCNA, Erk, pErk, Caspase2
PCNA, Erk, pErk, RBBP
PCNA, Erk, pErk, total S6
PCNA, Erk, Akt, pAkt
PCNA, Erk, Akt, Caspase2
PCNA, Erk, Akt, RBBP
PCNA, Erk, Akt, total S6
PCNA, Erk, pAkt, Caspase2
PCNA, Erk, pAkt, RBBP
PCNA, Erk, pAkt, total S6
PCNA, Erk, Caspase2, RBBP
PCNA, Erk, Caspase2, total S6
PCNA, Erk, RBBP, total S6
PCNA, pErk, Akt, pAkt
PCNA, pErk, Akt, Caspase2
PCNA, pErk, Akt, RBBP
PCNA, pErk, Akt, total S6
PCNA, pErk, pAkt, Caspase2
PCNA, pErk, pAkt, RBBP
PCNA, pErk, pAkt, total S6
PCNA, pErk, Caspase2, RBBP
PCNA, pErk, Caspase2, total S6
PCNA, pErk, RBBP, total S6
PCNA, Akt, pAkt, Caspase2
PCNA, Akt, pAkt, RBBP
PCNA, Akt, pAkt, total S6
PCNA, Akt, Caspase2, RBBP
PCNA, Akt, Caspase2, total S6
PCNA, Akt, RBBP, total S6
PCNA, pAkt, Caspase2, RBBP
PCNA, pAkt, Caspase2, total S6
PCNA, pAkt, RBBP, total S6
PCNA, Caspase2, RBBP, total S6
Cyclin D1, Cyclin D3, MEK, s6
Cyclin D1, Cyclin D3, MEK, pS6
Cyclin D1, Cyclin D3, MEK, Erk
Cyclin D1, Cyclin D3, MEK, pErk
Cyclin D1, Cyclin D3, MEK, Akt
Cyclin D1, Cyclin D3, MEK, pAkt
Cyclin D1, Cyclin D3, MEK, Caspase2
Cyclin D1, Cyclin D3, MEK, RBBP
Cyclin D1, Cyclin D3, MEK, total S6
Cyclin D1, Cyclin D3, s6, pS6
Cyclin D1, Cyclin D3, s6, Erk
Cyclin D1, Cyclin D3, s6, pErk
Cyclin D1, Cyclin D3, s6, Akt
Cyclin D1, Cyclin D3, s6, pAkt
Cyclin D1, Cyclin D3, s6, Caspase2
Cyclin D1, Cyclin D3, s6, RBBP
Cyclin D1, Cyclin D3, s6, total S6
Cyclin D1, Cyclin D3, pS6, Erk
Cyclin D1, Cyclin D3, pS6, pErk
Cyclin D1, Cyclin D3, pS6, Akt
Cyclin D1, Cyclin D3, pS6, pAkt
Cyclin D1, Cyclin D3, pS6, Caspase2
Cyclin D1, Cyclin D3, pS6, RBBP
Cyclin D1, Cyclin D3, pS6, total S6
Cyclin D1, Cyclin D3, Erk, pErk
Cyclin D3, MEK, s6, Erk, pAkt, Caspase2, RBBP, total S6
Cyclin D3, MEK, s6, pErk, Akt, pAkt, Caspase2, RBBP
Cyclin D3, MEK, s6, pErk, Akt, pAkt, Caspase2, total S6
Cyclin D3, MEK, s6, pErk, Akt, pAkt, RBBP, total S6
Cyclin D3, MEK, s6, pErk, Akt, Caspase2, RBBP, total S6
Cyclin D3, MEK, s6, pErk, pAkt, Caspase2, RBBP, total S6
Cyclin D3, MEK, s6, Akt, pAkt, Caspase2, RBBP, total S6
Cyclin D3, MEK, pS6, Erk, pErk, Akt, pAkt, Caspase2
Cyclin D3, MEK, pS6, Erk, pErk, Akt, pAkt, RBBP
Cyclin D3, MEK, pS6, Erk, pErk, Akt, pAkt, total S6
Cyclin D3, MEK, pS6, Erk, pErk, Akt, Caspase2, RBBP
Cyclin D3, MEK, pS6, Erk, pErk, Akt, Caspase2, total S6
Cyclin D3, MEK, pS6, Erk, pErk, Akt, RBBP, total S6
Cyclin D3, MEK, pS6, Erk, pErk, pAkt, Caspase2, RBBP
Cyclin D3, MEK, pS6, Erk, pErk, pAkt, Caspase2, total S6
Cyclin D3, MEK, pS6, Erk, pErk, pAkt, RBBP, total S6
Cyclin D3, MEK, pS6, Erk, pErk, Caspase2, RBBP, total S6
Cyclin D3, MEK, pS6, Erk, Akt, pAkt, Caspase2, RBBP
Cyclin D3, MEK, pS6, Erk, Akt, pAkt, Caspase2, total S6
Cyclin D3, MEK, pS6, Erk, Akt, pAkt, RBBP, total S6
Cyclin D3, MEK, pS6, Erk, Akt, Caspase2, RBBP, total S6
Cyclin D3, MEK, pS6, Erk, pAkt, Caspase2, RBBP, total S6
Cyclin D3, MEK, pS6, pErk, Akt, pAkt, Caspase2, RBBP
Cyclin D3, MEK, pS6, pErk, Akt, pAkt, Caspase2, total S6
Cyclin D3, MEK, pS6, pErk, Akt, pAkt, RBBP, total S6
Cyclin D3, MEK, pS6, pErk, Akt, Caspase2, RBBP, total S6
Cyclin D3, MEK, pS6, pErk, pAkt, Caspase2, RBBP, total S6
Cyclin D3, MEK, pS6, Akt, pAkt, Caspase2, RBBP, total S6
Cyclin D3, MEK, Erk, pErk, Akt, pAkt, Caspase2, RBBP
Cyclin D3, MEK, Erk, pErk, Akt, pAkt, Caspase2, total S6
Cyclin D3, MEK, Erk, pErk, Akt, pAkt, RBBP, total S6
Cyclin D3, MEK, Erk, pErk, Akt, Caspase2, RBBP, total S6
Cyclin D3, MEK, Erk, pErk, pAkt, Caspase2, RBBP, total S6
Cyclin D3, MEK, Erk, Akt, pAkt, Caspase2, RBBP, total S6
Cyclin D3, MEK, pErk, Akt, pAkt, Caspase2, RBBP, total S6
Cyclin D3, s6, pS6, Erk, pErk, Akt, pAkt, Caspase2
Cyclin D3, s6, pS6, Erk, pErk, Akt, pAkt, RBBP
Cyclin D3, s6, pS6, Erk, pErk, Akt, pAkt, total S6
Cyclin D3, s6, pS6, Erk, pErk, Akt, Caspase2, RBBP
Cyclin D3, s6, pS6, Erk, pErk, Akt, Caspase2, total S6
Cyclin D3, s6, pS6, Erk, pErk, Akt, RBBP, total S6
Cyclin D3, s6, pS6, Erk, pErk, pAkt, Caspase2, RBBP
Cyclin D3, s6, pS6, Erk, pErk, pAkt, Caspase2, total S6
Cyclin D3, s6, pS6, Erk, pErk, pAkt, RBBP, total S6
Cyclin D3, s6, pS6, Erk, pErk, Caspase2, RBBP, total S6
Cyclin D3, s6, pS6, Erk, Akt, pAkt, Caspase2, RBBP
Cyclin D3, s6, pS6, Erk, Akt, pAkt, Caspase2, total S6
Cyclin D3, s6, pS6, Erk, Akt, pAkt, RBBP, total S6
Cyclin D3, s6, pS6, Erk, Akt, Caspase2, RBBP, total S6
Cyclin D3, s6, pS6, Erk, pAkt, Caspase2, RBBP, total S6
Cyclin D3, s6, pS6, pErk, Akt, pAkt, Caspase2, RBBP
Cyclin D3, s6, pS6, pErk, Akt, pAkt, Caspase2, total S6
Cyclin D3, s6, pS6, pErk, Akt, pAkt, RBBP, total S6
Cyclin D3, s6, pS6, pErk, Akt, Caspase2, RBBP, total S6
Cyclin D3, s6, pS6, pErk, pAkt, Caspase2, RBBP, total S6
Cyclin D3, s6, pS6, Akt, pAkt, Caspase2, RBBP, total S6
Cyclin D3, s6, Erk, pErk, Akt, pAkt, Caspase2, RBBP
Cyclin D3, s6, Erk, pErk, Akt, pAkt, Caspase2, total S6
Cyclin D3, s6, Erk, pErk, Akt, pAkt, RBBP, total S6
Cyclin D3, s6, Erk, pErk, Akt, Caspase2, RBBP, total S6
Cyclin D3, s6, Erk, pErk, pAkt, Caspase2, RBBP, total S6
Cyclin D3, s6, Erk, Akt, pAkt, Caspase2, RBBP, total S6
Cyclin D3, s6, pErk, Akt, pAkt, Caspase2, RBBP, total S6
Cyclin D3, pS6, Erk, pErk, Akt, pAkt, Caspase2, RBBP
Cyclin D3, pS6, Erk, pErk, Akt, pAkt, Caspase2, total S6
Cyclin D3, pS6, Erk, pErk, Akt, pAkt, RBBP, total S6
Cyclin D3, pS6, Erk, pErk, Akt, Caspase2, RBBP, total S6
Cyclin D3, pS6, Erk, pErk, pAkt, Caspase2, RBBP, total S6
Cyclin D3, pS6, Erk, Akt, pAkt, Caspase2, RBBP, total S6
Cyclin D3, pS6, pErk, Akt, pAkt, Caspase2, RBBP, total S6
Cyclin D3, Erk, pErk, Akt, pAkt, Caspase2, RBBP, total S6
MEK, s6, pS6, Erk, pErk, Akt, pAkt, Caspase2
MEK, s6, pS6, Erk, pErk, Akt, pAkt, RBBP
MEK, s6, pS6, Erk, pErk, Akt, pAkt, total S6
MEK, s6, pS6, Erk, pErk, Akt, Caspase2, RBBP
MEK, s6, pS6, Erk, pErk, Akt, Caspase2, total S6
MEK, s6, pS6, Erk, pErk, Akt, RBBP, total S6
MEK, s6, pS6, Erk, pErk, pAkt, Caspase2, RBBP TABLE 1-continued Examples of Single Markers and Combinations of Markers Cyclin D1, Cyclin D3, Erk, Akt
Cyclin D1, Cyclin D3, Erk, pAkt
Cyclin D1, Cyclin D3, Erk, Caspase2
Cyclin D1, Cyclin D3, Erk, RBBP
Cyclin D1, Cyclin D3, Erk, total S6
Cyclin D1, Cyclin D3, pErk, Akt
Cyclin D1, Cyclin D3, pErk, pAkt
Cyclin D1, Cyclin D3, pErk, Caspase2
Cyclin D1, Cyclin D3, pErk, RBBP
Cyclin D1, Cyclin D3, pErk, total S6
Cyclin D1, Cyclin D3, Akt, pAkt
Cyclin D1, Cyclin D3, Akt, Caspase2
Cyclin D1, Cyclin D3, Akt, RBBP
Cyclin D1, Cyclin D3, Akt, total S6
Cyclin D1, Cyclin D3, pAkt, Caspase2
Cyclin D1, Cyclin D3, pAkt, RBBP
Cyclin D1, Cyclin D3, pAkt, total S6
Cyclin D1, Cyclin D3, Caspase2, RBBP
Cyclin D1, Cyclin D3, Caspase2, total S6
Cyclin D1, Cyclin D3, RBBP, total S6
Cyclin D1, MEK, s6, pS6
Cyclin D1, MEK, s6, Erk
Cyclin D1, MEK, s6, pErk
Cyclin D1, MEK, s6, Akt
Cyclin D1, MEK, s6, pAkt
Cyclin D1, MEK, s6, Caspase2
Cyclin D1, MEK, s6, RBBP
Cyclin D1, MEK, s6, total S6
Cyclin D1, MEK, pS6, Erk
Cyclin D1, MEK, pS6, pErk
Cyclin D1, MEK, pS6, Akt
Cyclin D1, MEK, pS6, pAkt
Cyclin D1, MEK, pS6, Caspase2
Cyclin D1, MEK, pS6, RBBP
Cyclin D1, MEK, pS6, total S6
Cyclin D1, MEK, Erk, pErk
Cyclin D1, MEK, Erk, Akt
Cyclin D1, MEK, Erk, pAkt
Cyclin D1, MEK, Erk, Caspase2
Cyclin D1, MEK, Erk, RBBP
Cyclin D1, MEK, Erk, total S6
Cyclin D1, MEK, pErk, Akt
Cyclin D1, MEK, pErk, pAkt
Cyclin D1, MEK, pErk, Caspase2
Cyclin D1, MEK, pErk, RBBP
Cyclin D1, MEK, pErk, total S6
Cyclin D1, MEK, Akt, pAkt
Cyclin D1, MEK, Akt, Caspase2
Cyclin D1, MEK, Akt, RBBP
Cyclin D1, MEK, Akt, total S6
Cyclin D1, MEK, pAkt, Caspase2
Cyclin D1, MEK, pAkt, RBBP
Cyclin D1, MEK, pAkt, total S6
Cyclin D1, MEK, Caspase2, RBBP
Cyclin D1, MEK, Caspase2, total S6
Cyclin D1, MEK, RBBP, total S6
Cyclin D1, s6, pS6, Erk
Cyclin D1, s6, pS6, pErk
Cyclin D1, s6, pS6, Akt
Cyclin D1, s6, pS6, pAkt
Cyclin D1, s6, pS6, Caspase2
Cyclin D1, s6, pS6, RBBP
Cyclin D1, s6, pS6, total S6
Cyclin D1, s6, Erk, pErk
Cyclin D1, s6, Erk, Akt
Cyclin D1, s6, Erk, pAkt
Cyclin D1, s6, Erk, Caspase2
Cyclin D1, s6, Erk, RBBP
Cyclin D1, s6, Erk, total S6
Cyclin D1, s6, pErk, Akt
Cyclin D1, s6, pErk, pAkt
Cyclin D1, s6, pErk, Caspase2
Cyclin D1, s6, pErk, RBBP
Cyclin D1, s6, pErk, total S6
Cyclin D1, s6, Akt, pAkt
Cyclin D1, s6, Akt, Caspase2
Cyclin D1, s6, Akt, RBBP
Cyclin D1, s6, Akt, total S6

MEK, s6, pS6, Erk, pErk, pAkt, Caspase2, total S6
MEK, s6, pS6, Erk, pErk, pAkt, RBBP, total S6
MEK, s6, pS6, Erk, pErk, Caspase2, RBBP, total S6
MEK, s6, pS6, Erk, Akt, pAkt, Caspase2, RBBP
MEK, s6, pS6, Erk, Akt, pAkt, Caspase2, total S6
MEK, s6, pS6, Erk, Akt, pAkt, RBBP, total S6
MEK, s6, pS6, Erk, Akt, Caspase2, RBBP, total S6
MEK, s6, pS6, Erk, pAkt, Caspase2, RBBP, total S6
MEK, s6, pS6, pErk, Akt, pAkt, Caspase2, RBBP
MEK, s6, pS6, pErk, Akt, pAkt, Caspase2, total S6
MEK, s6, pS6, pErk, Akt, pAkt, RBBP, total S6
MEK, s6, pS6, pErk, Akt, Caspase2, RBBP, total S6
MEK, s6, pS6, pErk, pAkt, Caspase2, RBBP, total S6
MEK, s6, pS6, Akt, pAkt, Caspase2, RBBP, total S6
MEK, s6, Erk, pErk, Akt, pAkt, Caspase2, RBBP
MEK, s6, Erk, pErk, Akt, pAkt, Caspase2, total S6
MEK, s6, Erk, pErk, Akt, pAkt, RBBP, total S6
MEK, s6, Erk, pErk, Akt, Caspase2, RBBP, total S6
MEK, s6, Erk, pErk, pAkt, Caspase2, RBBP, total S6
MEK, s6, Erk, Akt, pAkt, Caspase2, RBBP, total S6
MEK, s6, pErk, Akt, pAkt, Caspase2, RBBP, total S6
MEK, pS6, Erk, pErk, Akt, pAkt, Caspase2, RBBP
MEK, pS6, Erk, pErk, Akt, pAkt, Caspase2, total S6
MEK, pS6, Erk, pErk, Akt, pAkt, RBBP, total S6
MEK, pS6, Erk, pErk, Akt, Caspase2, RBBP, total S6
MEK, pS6, Erk, pErk, pAkt, Caspase2, RBBP, total S6
MEK, pS6, Erk, Akt, pAkt, Caspase2, RBBP, total S6
MEK, pS6, pErk, Akt, pAkt, Caspase2, RBBP, total S6
MEK, Erk, pErk, Akt, pAkt, Caspase2, RBBP, total S6
s6, pS6, Erk, pErk, Akt, pAkt, Caspase2, RBBP
s6, pS6, Erk, pErk, Akt, pAkt, Caspase2, total S6
s6, pS6, Erk, pErk, Akt, pAkt, RBBP, total S6
s6, pS6, Erk, pErk, Akt, Caspase2, RBBP, total S6
s6, pS6, Erk, pErk, pAkt, Caspase2, RBBP, total S6
s6, pS6, Erk, Akt, pAkt, Caspase2, RBBP, total S6
s6, pS6, pErk, Akt, pAkt, Caspase2, RBBP, total S6
s6, Erk, pErk, Akt, pAkt, Caspase2, RBBP, total S6
pS6, Erk, pErk, Akt, pAkt, Caspase2, RBBP, total S6
PCNA, Cyclin D1, Cyclin D3, MEK, s6, pS6, Erk
PCNA, Cyclin D1, Cyclin D3, MEK, s6, pS6, pErk
PCNA, Cyclin D1, Cyclin D3, MEK, s6, pS6, Akt
PCNA, Cyclin D1, Cyclin D3, MEK, s6, pS6, pAkt
PCNA, Cyclin D1, Cyclin D3, MEK, s6, pS6, Caspase2
PCNA, Cyclin D1, Cyclin D3, MEK, s6, pS6, RBBP
PCNA, Cyclin D1, Cyclin D3, MEK, s6, pS6, total S6
PCNA, Cyclin D1, Cyclin D3, MEK, s6, Erk, pErk
PCNA, Cyclin D1, Cyclin D3, MEK, s6, Erk, Akt
PCNA, Cyclin D1, Cyclin D3, MEK, s6, Erk, pAkt
PCNA, Cyclin D1, Cyclin D3, MEK, s6, Erk, Caspase2
PCNA, Cyclin D1, Cyclin D3, MEK, s6, Erk, RBBP
PCNA, Cyclin D1, Cyclin D3, MEK, s6, Erk, total S6
PCNA, Cyclin D1, Cyclin D3, MEK, s6, pErk, Akt
PCNA, Cyclin D1, Cyclin D3, MEK, s6, pErk, pAkt
PCNA, Cyclin D1, Cyclin D3, MEK, s6, pErk, Caspase2
PCNA, Cyclin D1, Cyclin D3, MEK, s6, pErk, RBBP
PCNA, Cyclin D1, Cyclin D3, MEK, s6, pErk, total S6
PCNA, Cyclin D1, Cyclin D3, MEK, s6, Akt, pAkt
PCNA, Cyclin D1, Cyclin D3, MEK, s6, Akt, Caspase2
PCNA, Cyclin D1, Cyclin D3, MEK, s6, Akt, RBBP
PCNA, Cyclin D1, Cyclin D3, MEK, s6, Akt, total S6
PCNA, Cyclin D1, Cyclin D3, MEK, s6, pAkt, Caspase2
PCNA, Cyclin D1, Cyclin D3, MEK, s6, pAkt, RBBP
PCNA, Cyclin D1, Cyclin D3, MEK, s6, pAkt, total S6
PCNA, Cyclin D1, Cyclin D3, MEK, s6, Caspase2, RBBP
PCNA, Cyclin D1, Cyclin D3, MEK, s6, Caspase2, total S6
PCNA, Cyclin D1, Cyclin D3, MEK, s6, RBBP, total S6
PCNA, Cyclin D1, Cyclin D3, MEK, pS6, Erk, pErk
PCNA, Cyclin D1, Cyclin D3, MEK, pS6, Erk, Akt
PCNA, Cyclin D1, Cyclin D3, MEK, pS6, Erk, pAkt
PCNA, Cyclin D1, Cyclin D3, MEK, pS6, Erk, Caspase2
PCNA, Cyclin D1, Cyclin D3, MEK, pS6, Erk, RBBP
PCNA, Cyclin D1, Cyclin D3, MEK, pS6, Erk, total S6
PCNA, Cyclin D1, Cyclin D3, MEK, pS6, pErk, Akt
PCNA, Cyclin D1, Cyclin D3, MEK, pS6, pErk, pAkt
PCNA, Cyclin D1, Cyclin D3, MEK, pS6, pErk, Caspase2
PCNA, Cyclin D1, Cyclin D3, MEK, pS6, pErk, RBBP
PCNA, Cyclin D1, Cyclin D3, MEK, pS6, pErk, total S6
PCNA, Cyclin D1, Cyclin D3, MEK, pS6, Akt, pAkt TABLE 1-continued Examples of Single Markers and Combinations of Markers Cyclin D1, s6, pAkt, Caspase2
Cyclin D1, s6, pAkt, RBBP
Cyclin D1, s6, pAkt, total S6
Cyclin D1, s6, Caspase2, RBBP
Cyclin D1, s6, Caspase2, total S6
Cyclin D1, s6, RBBP, total S6
Cyclin D1, pS6, Erk, pErk
Cyclin D1, pS6, Erk, Akt
Cyclin D1, pS6, Erk, pAkt
Cyclin D1, pS6, Erk, Caspase2
Cyclin D1, pS6, Erk, RBBP
Cyclin D1, pS6, Erk, total S6
Cyclin D1, pS6, pErk, Akt
Cyclin D1, pS6, pErk, pAkt
Cyclin D1, pS6, pErk, Caspase2
Cyclin D1, pS6, pErk, RBBP
Cyclin D1, pS6, pErk, total S6
Cyclin D1, pS6, Akt, pAkt
Cyclin D1, pS6, Akt, Caspase2
Cyclin D1, pS6, Akt, RBBP
Cyclin D1, pS6, Akt, total S6
Cyclin D1, pS6, pAkt, Caspase2
Cyclin D1, pS6, pAkt, RBBP
Cyclin D1, pS6, pAkt, total S6
Cyclin D1, pS6, Caspase2, RBBP
Cyclin D1, pS6, Caspase2, total S6
Cyclin D1, pS6, RBBP, total S6
Cyclin D1, Erk, pErk, Akt
Cyclin D1, Erk, pErk, pAkt
Cyclin D1, Erk, pErk, Caspase2
Cyclin D1, Erk, pErk, RBBP
Cyclin D1, Erk, pErk, total S6
Cyclin D1, Erk, Akt, pAkt
Cyclin D1, Erk, Akt, Caspase2
Cyclin D1, Erk, Akt, RBBP
Cyclin D1, Erk, Akt, total S6
Cyclin D1, Erk, pAkt, Caspase2
Cyclin D1, Erk, pAkt, RBBP
Cyclin D1, Erk, pAkt, total S6
Cyclin D1, Erk, Caspase2, RBBP
Cyclin D1, Erk, Caspase2, total S6
Cyclin D1, Erk, RBBP, total S6
Cyclin D1, pErk, Akt, pAkt
Cyclin D1, pErk, Akt, Caspase2
Cyclin D1, pErk, Akt, RBBP
Cyclin D1, pErk, Akt, total S6
Cyclin D1, pErk, pAkt, Caspase2
Cyclin D1, pErk, pAkt, RBBP
Cyclin D1, pErk, pAkt, total S6
Cyclin D1, pErk, Caspase2, RBBP
Cyclin D1, pErk, Caspase2, total S6
Cyclin D1, pErk, RBBP, total S6
Cyclin D1, Akt, pAkt, Caspase2
Cyclin D1, Akt, pAkt, RBBP
Cyclin D1, Akt, pAkt, total S6
Cyclin D1, Akt, Caspase2, RBBP
Cyclin D1, Akt, Caspase2, total S6
Cyclin D1, Akt, RBBP, total S6
Cyclin D1, pAkt, Caspase2, RBBP
Cyclin D1, pAkt, Caspase2, total S6
Cyclin D1, pAkt, RBBP, total S6
Cyclin D1, Caspase2, RBBP, total S6
Cyclin D3, MEK, s6, pS6
Cyclin D3, MEK, s6, Erk
Cyclin D3, MEK, s6, pErk
Cyclin D3, MEK, s6, Akt
Cyclin D3, MEK, s6, pAkt
Cyclin D3, MEK, s6, Caspase2
Cyclin D3, MEK, s6, RBBP
Cyclin D3, MEK, s6, total S6
Cyclin D3, MEK, pS6, Erk
Cyclin D3, MEK, pS6, pErk
Cyclin D3, MEK, pS6, Akt
Cyclin D3, MEK, pS6, pAkt
Cyclin D3, MEK, pS6, Caspase2
Cyclin D3, MEK, pS6, RBBP
Cyclin D3, MEK, pS6, total S6
Cyclin D3, MEK, Erk, pErk
PCNA, Cyclin D1, Cyclin D3, MEK, pS6, Akt, Caspase2
PCNA, Cyclin D1, Cyclin D3, MEK, pS6, Akt, RBBP
PCNA, Cyclin D1, Cyclin D3, MEK, pS6, Akt, total S6
PCNA, Cyclin D1, Cyclin D3, MEK, pS6, pAkt, Caspase2
PCNA, Cyclin D1, Cyclin D3, MEK, pS6, pAkt, RBBP
PCNA, Cyclin D1, Cyclin D3, MEK, pS6, pAkt, total S6
PCNA, Cyclin D1, Cyclin D3, MEK, pS6, Caspase2, RBBP
PCNA, Cyclin D1, Cyclin D3, MEK, pS6, Caspase2, total S6
PCNA, Cyclin D1, Cyclin D3, MEK, pS6, RBBP, total S6
PCNA, Cyclin D1, Cyclin D3, MEK, Erk, pErk, Akt
PCNA, Cyclin D1, Cyclin D3, MEK, Erk, pErk, pAkt
PCNA, Cyclin D1, Cyclin D3, MEK, Erk, pErk, Caspase2
PCNA, Cyclin D1, Cyclin D3, MEK, Erk, pErk, RBBP
PCNA, Cyclin D1, Cyclin D3, MEK, Erk, pErk, total S6
PCNA, Cyclin D1, Cyclin D3, MEK, Erk, Akt, pAkt
PCNA, Cyclin D1, Cyclin D3, MEK, Erk, Akt, Caspase2
PCNA, Cyclin D1, Cyclin D3, MEK, Erk, Akt, RBBP
PCNA, Cyclin D1, Cyclin D3, MEK, Erk, Akt, total S6
PCNA, Cyclin D1, Cyclin D3, MEK, Erk, pAkt, Caspase2
PCNA, Cyclin D1, Cyclin D3, MEK, Erk, pAkt, RBBP
PCNA, Cyclin D1, Cyclin D3, MEK, Erk, pAkt, total S6
PCNA, Cyclin D1, Cyclin D3, MEK, Erk, Caspase2, RBBP
PCNA, Cyclin D1, Cyclin D3, MEK, Erk, Caspase2, total S6
PCNA, Cyclin D1, Cyclin D3, MEK, Erk, RBBP, total S6
PCNA, Cyclin D1, Cyclin D3, MEK, pErk, Akt, pAkt
PCNA, Cyclin D1, Cyclin D3, MEK, pErk, Akt, Caspase2
PCNA, Cyclin D1, Cyclin D3, MEK, pErk, Akt, RBBP
PCNA, Cyclin D1, Cyclin D3, MEK, pErk, Akt, total S6
PCNA, Cyclin D1, Cyclin D3, MEK, pErk, pAkt, Caspase2
PCNA, Cyclin D1, Cyclin D3, MEK, pErk, pAkt, RBBP
PCNA, Cyclin D1, Cyclin D3, MEK, pErk, pAkt, total S6
PCNA, Cyclin D1, Cyclin D3, MEK, pErk, Caspase2, RBBP
PCNA, Cyclin D1, Cyclin D3, MEK, pErk, Caspase2, total S6
PCNA, Cyclin D1, Cyclin D3, MEK, pErk, RBBP, total S6
PCNA, Cyclin D1, Cyclin D3, MEK, Akt, pAkt, Caspase2
PCNA, Cyclin D1, Cyclin D3, MEK, Akt, pAkt, RBBP
PCNA, Cyclin D1, Cyclin D3, MEK, Akt, pAkt, total S6
PCNA, Cyclin D1, Cyclin D3, MEK, Akt, Caspase2, RBBP
PCNA, Cyclin D1, Cyclin D3, MEK, Akt, Caspase2, total S6
PCNA, Cyclin D1, Cyclin D3, MEK, Akt, RBBP, total S6
PCNA, Cyclin D1, Cyclin D3, MEK, pAkt, Caspase2, RBBP
PCNA, Cyclin D1, Cyclin D3, MEK, pAkt, Caspase2, total S6
PCNA, Cyclin D1, Cyclin D3, MEK, pAkt, RBBP, total S6
PCNA, Cyclin D1, Cyclin D3, MEK, Caspase2, RBBP, total S6
PCNA, Cyclin D1, Cyclin D3, s6, pS6, Erk, pErk
PCNA, Cyclin D1, Cyclin D3, s6, pS6, Erk, Akt
PCNA, Cyclin D1, Cyclin D3, s6, pS6, Erk, pAkt
PCNA, Cyclin D1, Cyclin D3, s6, pS6, Erk, Caspase2
PCNA, Cyclin D1, Cyclin D3, s6, pS6, Erk, RBBP
PCNA, Cyclin D1, Cyclin D3, s6, pS6, Erk, total S6
PCNA, Cyclin D1, Cyclin D3, s6, pS6, pErk, Akt
PCNA, Cyclin D1, Cyclin D3, s6, pS6, pErk, pAkt
PCNA, Cyclin D1, Cyclin D3, s6, pS6, pErk, Caspase2
PCNA, Cyclin D1, Cyclin D3, s6, pS6, pErk, RBBP
PCNA, Cyclin D1, Cyclin D3, s6, pS6, pErk, total S6
PCNA, Cyclin D1, Cyclin D3, s6, pS6, Akt, pAkt
PCNA, Cyclin D1, Cyclin D3, s6, pS6, Akt, Caspase2
PCNA, Cyclin D1, Cyclin D3, s6, pS6, Akt, RBBP
PCNA, Cyclin D1, Cyclin D3, s6, pS6, Akt, total S6
PCNA, Cyclin D1, Cyclin D3, s6, pS6, pAkt, Caspase2
PCNA, Cyclin D1, Cyclin D3, s6, pS6, pAkt, RBBP
PCNA, Cyclin D1, Cyclin D3, s6, pS6, pAkt, total S6
PCNA, Cyclin D1, Cyclin D3, s6, pS6, Caspase2, RBBP
PCNA, Cyclin D1, Cyclin D3, s6, pS6, Caspase2, total S6
PCNA, Cyclin D1, Cyclin D3, s6, pS6, RBBP, total S6
PCNA, Cyclin D1, Cyclin D3, s6, Erk, pErk, Akt
PCNA, Cyclin D1, Cyclin D3, s6, Erk, pErk, pAkt
PCNA, Cyclin D1, Cyclin D3, s6, Erk, pErk, Caspase2
PCNA, Cyclin D1, Cyclin D3, s6, Erk, pErk, RBBP
PCNA, Cyclin D1, Cyclin D3, s6, Erk, pErk, total S6
PCNA, Cyclin D1, Cyclin D3, s6, Erk, Akt, pAkt
PCNA, Cyclin D1, Cyclin D3, s6, Erk, Akt, Caspase2
PCNA, Cyclin D1, Cyclin D3, s6, Erk, Akt, RBBP
PCNA, Cyclin D1, Cyclin D3, s6, Erk, Akt, total S6
PCNA, Cyclin D1, Cyclin D3, s6, Erk, pAkt, Caspase2
PCNA, Cyclin D1, Cyclin D3, s6, Erk, pAkt, RBBP
PCNA, Cyclin D1, Cyclin D3, s6, Erk, pAkt, total S6
PCNA, Cyclin D1, Cyclin D3, s6, Erk, Caspase2, RBBP

TABLE 1-continued

Examples of Single Markers and Combinations of Markers

Cyclin D3, MEK, Erk, Akt
Cyclin D3, MEK, Erk, pAkt
Cyclin D3, MEK, Erk, Caspase2
Cyclin D3, MEK, Erk, RBBP
Cyclin D3, MEK, Erk, total S6
Cyclin D3, MEK, pErk, Akt
Cyclin D3, MEK, pErk, pAkt
Cyclin D3, MEK, pErk, Caspase2
Cyclin D3, MEK, pErk, RBBP
Cyclin D3, MEK, pErk, total S6
Cyclin D3, MEK, Akt, pAkt
Cyclin D3, MEK, Akt, Caspase2
Cyclin D3, MEK, Akt, RBBP
Cyclin D3, MEK, Akt, total S6
Cyclin D3, MEK, pAkt, Caspase2
Cyclin D3, MEK, pAkt, RBBP
Cyclin D3, MEK, pAkt, total S6
Cyclin D3, MEK, Caspase2, RBBP
Cyclin D3, MEK, Caspase2, total S6
Cyclin D3, MEK, RBBP, total S6
Cyclin D3, s6, pS6, Erk
Cyclin D3, s6, pS6, pErk
Cyclin D3, s6, pS6, Akt
Cyclin D3, s6, pS6, pAkt
Cyclin D3, s6, pS6, Caspase2
Cyclin D3, s6, pS6, RBBP
Cyclin D3, s6, pS6, total S6
Cyclin D3, s6, Erk, pErk
Cyclin D3, s6, Erk, Akt
Cyclin D3, s6, Erk, pAkt
Cyclin D3, s6, Erk, Caspase2
Cyclin D3, s6, Erk, RBBP
Cyclin D3, s6, Erk, total S6
Cyclin D3, s6, pErk, Akt
Cyclin D3, s6, pErk, pAkt
Cyclin D3, s6, pErk, Caspase2
Cyclin D3, s6, pErk, RBBP
Cyclin D3, s6, pErk, total S6
Cyclin D3, s6, Akt, pAkt
Cyclin D3, s6, Akt, Caspase2
Cyclin D3, s6, Akt, RBBP
Cyclin D3, s6, Akt, total S6
Cyclin D3, s6, pAkt, Caspase2
Cyclin D3, s6, pAkt, RBBP
Cyclin D3, s6, pAkt, total S6
Cyclin D3, s6, Caspase2, RBBP
Cyclin D3, s6, Caspase2, total S6
Cyclin D3, s6, RBBP, total S6
Cyclin D3, pS6, Erk, pErk
Cyclin D3, pS6, Erk, Akt
Cyclin D3, pS6, Erk, pAkt
Cyclin D3, pS6, Erk, Caspase2
Cyclin D3, pS6, Erk, RBBP
Cyclin D3, pS6, Erk, total S6
Cyclin D3, pS6, pErk, Akt
Cyclin D3, pS6, pErk, pAkt
Cyclin D3, pS6, pErk, Caspase2
Cyclin D3, pS6, pErk, RBBP
Cyclin D3, pS6, pErk, total S6
Cyclin D3, pS6, Akt, pAkt
Cyclin D3, pS6, Akt, Caspase2
Cyclin D3, pS6, Akt, RBBP
Cyclin D3, pS6, Akt, total S6
Cyclin D3, pS6, pAkt, Caspase2
Cyclin D3, pS6, pAkt, RBBP
Cyclin D3, pS6, pAkt, total S6
Cyclin D3, pS6, Caspase2, RBBP
Cyclin D3, pS6, Caspase2, total S6
Cyclin D3, pS6, RBBP, total S6
Cyclin D3, Erk, pErk, Akt
Cyclin D3, Erk, pErk, pAkt
Cyclin D3, Erk, pErk, Caspase2
Cyclin D3, Erk, pErk, RBBP
Cyclin D3, Erk, pErk, total S6
Cyclin D3, Erk, Akt, pAkt
Cyclin D3, Erk, Akt, Caspase2
Cyclin D3, Erk, Akt, RBBP
Cyclin D3, Erk, Akt, total S6
PCNA, Cyclin D1, Cyclin D3, s6, Erk, Caspase2, total S6
PCNA, Cyclin D1, Cyclin D3, s6, Erk, RBBP, total S6
PCNA, Cyclin D1, Cyclin D3, s6, pErk, Akt, pAkt
PCNA, Cyclin D1, Cyclin D3, s6, pErk, Akt, Caspase2
PCNA, Cyclin D1, Cyclin D3, s6, pErk, Akt, RBBP
PCNA, Cyclin D1, Cyclin D3, s6, pErk, Akt, total S6
PCNA, Cyclin D1, Cyclin D3, s6, pErk, pAkt, Caspase2
PCNA, Cyclin D1, Cyclin D3, s6, pErk, pAkt, RBBP
PCNA, Cyclin D1, Cyclin D3, s6, pErk, pAkt, total S6
PCNA, Cyclin D1, Cyclin D3, s6, pErk, Caspase2, RBBP
PCNA, Cyclin D1, Cyclin D3, s6, pErk, Caspase2, total S6
PCNA, Cyclin D1, Cyclin D3, s6, pErk, RBBP, total S6
PCNA, Cyclin D1, Cyclin D3, s6, Akt, pAkt, Caspase2
PCNA, Cyclin D1, Cyclin D3, s6, Akt, pAkt, RBBP
PCNA, Cyclin D1, Cyclin D3, s6, Akt, pAkt, total S6
PCNA, Cyclin D1, Cyclin D3, s6, Akt, Caspase2, RBBP
PCNA, Cyclin D1, Cyclin D3, s6, Akt, Caspase2, total S6
PCNA, Cyclin D1, Cyclin D3, s6, Akt, RBBP, total S6
PCNA, Cyclin D1, Cyclin D3, s6, pAkt, Caspase2, RBBP
PCNA, Cyclin D1, Cyclin D3, s6, pAkt, Caspase2, total S6
PCNA, Cyclin D1, Cyclin D3, s6, pAkt, RBBP, total S6
PCNA, Cyclin D1, Cyclin D3, s6, Caspase2, RBBP, total S6
PCNA, Cyclin D1, Cyclin D3, pS6, Erk, pErk, Akt
PCNA, Cyclin D1, Cyclin D3, pS6, Erk, pErk, pAkt
PCNA, Cyclin D1, Cyclin D3, pS6, Erk, pErk, Caspase2
PCNA, Cyclin D1, Cyclin D3, pS6, Erk, pErk, RBBP
PCNA, Cyclin D1, Cyclin D3, pS6, Erk, pErk, total S6
PCNA, Cyclin D1, Cyclin D3, pS6, Erk, Akt, pAkt
PCNA, Cyclin D1, Cyclin D3, pS6, Erk, Akt, Caspase2
PCNA, Cyclin D1, Cyclin D3, pS6, Erk, Akt, RBBP
PCNA, Cyclin D1, Cyclin D3, pS6, Erk, Akt, total S6
PCNA, Cyclin D1, Cyclin D3, pS6, Erk, pAkt, Caspase2
PCNA, Cyclin D1, Cyclin D3, pS6, Erk, pAkt, RBBP
PCNA, Cyclin D1, Cyclin D3, pS6, Erk, pAkt, total S6
PCNA, Cyclin D1, Cyclin D3, pS6, Erk, Caspase2, RBBP
PCNA, Cyclin D1, Cyclin D3, pS6, Erk, Caspase2, total S6
PCNA, Cyclin D1, Cyclin D3, pS6, Erk, RBBP, total S6
PCNA, Cyclin D1, Cyclin D3, pS6, pErk, Akt, pAkt
PCNA, Cyclin D1, Cyclin D3, pS6, pErk, Akt, Caspase2
PCNA, Cyclin D1, Cyclin D3, pS6, pErk, Akt, RBBP
PCNA, Cyclin D1, Cyclin D3, pS6, pErk, Akt, total S6
PCNA, Cyclin D1, Cyclin D3, pS6, pErk, pAkt, Caspase2
PCNA, Cyclin D1, Cyclin D3, pS6, pErk, pAkt, RBBP
PCNA, Cyclin D1, Cyclin D3, pS6, pErk, pAkt, total S6
PCNA, Cyclin D1, Cyclin D3, pS6, pErk, Caspase2, RBBP
PCNA, Cyclin D1, Cyclin D3, pS6, pErk, Caspase2, total S6
PCNA, Cyclin D1, Cyclin D3, pS6, pErk, RBBP, total S6
PCNA, Cyclin D1, Cyclin D3, pS6, Akt, pAkt, Caspase2
PCNA, Cyclin D1, Cyclin D3, pS6, Akt, pAkt, RBBP
PCNA, Cyclin D1, Cyclin D3, pS6, Akt, pAkt, total S6
PCNA, Cyclin D1, Cyclin D3, pS6, Akt, Caspase2, RBBP
PCNA, Cyclin D1, Cyclin D3, pS6, Akt, Caspase2, total S6
PCNA, Cyclin D1, Cyclin D3, pS6, Akt, RBBP, total S6
PCNA, Cyclin D1, Cyclin D3, pS6, pAkt, Caspase2, RBBP
PCNA, Cyclin D1, Cyclin D3, pS6, pAkt, Caspase2, total S6
PCNA, Cyclin D1, Cyclin D3, pS6, pAkt, RBBP, total S6
PCNA, Cyclin D1, Cyclin D3, pS6, Caspase2, RBBP, total S6
PCNA, Cyclin D1, Cyclin D3, Erk, pErk, Akt, pAkt
PCNA, Cyclin D1, Cyclin D3, Erk, pErk, Akt, Caspase2
PCNA, Cyclin D1, Cyclin D3, Erk, pErk, Akt, RBBP
PCNA, Cyclin D1, Cyclin D3, Erk, pErk, Akt, total S6
PCNA, Cyclin D1, Cyclin D3, Erk, pErk, pAkt, Caspase2
PCNA, Cyclin D1, Cyclin D3, Erk, pErk, pAkt, RBBP
PCNA, Cyclin D1, Cyclin D3, Erk, pErk, pAkt, total S6
PCNA, Cyclin D1, Cyclin D3, Erk, pErk, Caspase2, RBBP
PCNA, Cyclin D1, Cyclin D3, Erk, pErk, Caspase2, total S6
PCNA, Cyclin D1, Cyclin D3, Erk, pErk, RBBP, total S6
PCNA, Cyclin D1, Cyclin D3, Erk, Akt, pAkt, Caspase2
PCNA, Cyclin D1, Cyclin D3, Erk, Akt, pAkt, RBBP
PCNA, Cyclin D1, Cyclin D3, Erk, Akt, pAkt, total S6
PCNA, Cyclin D1, Cyclin D3, Erk, Akt, Caspase2, RBBP
PCNA, Cyclin D1, Cyclin D3, Erk, Akt, Caspase2, total S6
PCNA, Cyclin D1, Cyclin D3, Erk, Akt, RBBP, total S6
PCNA, Cyclin D1, Cyclin D3, Erk, pAkt, Caspase2, RBBP
PCNA, Cyclin D1, Cyclin D3, Erk, pAkt, Caspase2, total S6
PCNA, Cyclin D1, Cyclin D3, Erk, pAkt, RBBP, total S6
PCNA, Cyclin D1, Cyclin D3, Erk, Caspase2, RBBP, total S6
PCNA, Cyclin D1, Cyclin D3, pErk, Akt, pAkt, Caspase2

TABLE 1-continued

Examples of Single Markers and Combinations of Markers

| | |
|---|---|
| Cyclin D3, Erk, pAkt, Caspase2 | PCNA, Cyclin D1, Cyclin D3, pErk, Akt, pAkt, RBBP |
| Cyclin D3, Erk, pAkt, RBBP | PCNA, Cyclin D1, Cyclin D3, pErk, Akt, pAkt, total S6 |
| Cyclin D3, Erk, pAkt, total S6 | PCNA, Cyclin D1, Cyclin D3, pErk, Akt, Caspase2, RBBP |
| Cyclin D3, Erk, Caspase2, RBBP | PCNA, Cyclin D1, Cyclin D3, pErk, Akt, Caspase2, total S6 |
| Cyclin D3, Erk, Caspase2, total S6 | PCNA, Cyclin D1, Cyclin D3, pErk, Akt, RBBP, total S6 |
| Cyclin D3, Erk, RBBP, total S6 | PCNA, Cyclin D1, Cyclin D3, pErk, pAkt, Caspase2, RBBP |
| Cyclin D3, pErk, Akt, pAkt | PCNA, Cyclin D1, Cyclin D3, pErk, pAkt, Caspase2, total S6 |
| Cyclin D3, pErk, Akt, Caspase2 | PCNA, Cyclin D1, Cyclin D3, pErk, pAkt, RBBP, total S6 |
| Cyclin D3, pErk, Akt, RBBP | PCNA, Cyclin D1, Cyclin D3, pErk, Caspase2, RBBP, total S6 |
| Cyclin D3, pErk, Akt, total S6 | PCNA, Cyclin D1, Cyclin D3, Akt, pAkt, Caspase2, RBBP |
| Cyclin D3, pErk, pAkt, Caspase2 | PCNA, Cyclin D1, Cyclin D3, Akt, pAkt, Caspase2, total S6 |
| Cyclin D3, pErk, pAkt, RBBP | PCNA, Cyclin D1, Cyclin D3, Akt, pAkt, RBBP, total S6 |
| Cyclin D3, pErk, pAkt, total S6 | PCNA, Cyclin D1, Cyclin D3, Akt, Caspase2, RBBP, total S6 |
| Cyclin D3, pErk, Caspase2, RBBP | PCNA, Cyclin D1, Cyclin D3, pAkt, Caspase2, RBBP, total S6 |
| Cyclin D3, pErk, Caspase2, total S6 | PCNA, Cyclin D1, MEK, s6, pS6, Erk, pErk |
| Cyclin D3, pErk, RBBP, total S6 | PCNA, Cyclin D1, MEK, s6, pS6, Erk, Akt |
| Cyclin D3, Akt, pAkt, Caspase2 | PCNA, Cyclin D1, MEK, s6, pS6, Erk, pAkt |
| Cyclin D3, Akt, pAkt, RBBP | PCNA, Cyclin D1, MEK, s6, pS6, Erk, Caspase2 |
| Cyclin D3, Akt, pAkt, total S6 | PCNA, Cyclin D1, MEK, s6, pS6, Erk, RBBP |
| Cyclin D3, Akt, Caspase2, RBBP | PCNA, Cyclin D1, MEK, s6, pS6, Erk, total S6 |
| Cyclin D3, Akt, Caspase2, total S6 | PCNA, Cyclin D1, MEK, s6, pS6, pErk, Akt |
| Cyclin D3, Akt, RBBP, total S6 | PCNA, Cyclin D1, MEK, s6, pS6, pErk, pAkt |
| Cyclin D3, pAkt, Caspase2, RBBP | PCNA, Cyclin D1, MEK, s6, pS6, pErk, Caspase2 |
| Cyclin D3, pAkt, Caspase2, total S6 | PCNA, Cyclin D1, MEK, s6, pS6, pErk, RBBP |
| Cyclin D3, pAkt, RBBP, total S6 | PCNA, Cyclin D1, MEK, s6, pS6, pErk, total S6 |
| Cyclin D3, Caspase2, RBBP, total S6 | PCNA, Cyclin D1, MEK, s6, pS6, Akt, pAkt |
| MEK, s6, pS6, Erk | PCNA, Cyclin D1, MEK, s6, pS6, Akt, Caspase2 |
| MEK, s6, pS6, pErk | PCNA, Cyclin D1, MEK, s6, pS6, Akt, RBBP |
| MEK, s6, pS6, Akt | PCNA, Cyclin D1, MEK, s6, pS6, Akt, total S6 |
| MEK, s6, pS6, pAkt | PCNA, Cyclin D1, MEK, s6, pS6, pAkt, Caspase2 |
| MEK, s6, pS6, Caspase2 | PCNA, Cyclin D1, MEK, s6, pS6, pAkt, RBBP |
| MEK, s6, pS6, RBBP | PCNA, Cyclin D1, MEK, s6, pS6, pAkt, total S6 |
| MEK, s6, pS6, total S6 | PCNA, Cyclin D1, MEK, s6, pS6, Caspase2, RBBP |
| MEK, s6, Erk, pErk | PCNA, Cyclin D1, MEK, s6, pS6, Caspase2, total S6 |
| MEK, s6, Erk, Akt | PCNA, Cyclin D1, MEK, s6, pS6, RBBP, total S6 |
| MEK, s6, Erk, pAkt | PCNA, Cyclin D1, MEK, s6, Erk, pErk, Akt |
| MEK, s6, Erk, Caspase2 | PCNA, Cyclin D1, MEK, s6, Erk, pErk, pAkt |
| MEK, s6, Erk, RBBP | PCNA, Cyclin D1, MEK, s6, Erk, pErk, Caspase2 |
| MEK, s6, Erk, total S6 | PCNA, Cyclin D1, MEK, s6, Erk, pErk, RBBP |
| MEK, s6, pErk, Akt | PCNA, Cyclin D1, MEK, s6, Erk, pErk, total S6 |
| MEK, s6, pErk, pAkt | PCNA, Cyclin D1, MEK, s6, Erk, Akt, pAkt |
| MEK, s6, pErk, Caspase2 | PCNA, Cyclin D1, MEK, s6, Erk, Akt, Caspase2 |
| MEK, s6, pErk, RBBP | PCNA, Cyclin D1, MEK, s6, Erk, Akt, RBBP |
| MEK, s6, pErk, total S6 | PCNA, Cyclin D1, MEK, s6, Erk, Akt, total S6 |
| MEK, s6, Akt, pAkt | PCNA, Cyclin D1, MEK, s6, Erk, pAkt, Caspase2 |
| MEK, s6, Akt, Caspase2 | PCNA, Cyclin D1, MEK, s6, Erk, pAkt, RBBP |
| MEK, s6, Akt, RBBP | PCNA, Cyclin D1, MEK, s6, Erk, pAkt, total S6 |
| MEK, s6, Akt, total S6 | PCNA, Cyclin D1, MEK, s6, Erk, Caspase2, RBBP |
| MEK, s6, pAkt, Caspase2 | PCNA, Cyclin D1, MEK, s6, Erk, Caspase2, total S6 |
| MEK, s6, pAkt, RBBP | PCNA, Cyclin D1, MEK, s6, Erk, RBBP, total S6 |
| MEK, s6, pAkt, total S6 | PCNA, Cyclin D1, MEK, s6, pErk, Akt, pAkt |
| MEK, s6, Caspase2, RBBP | PCNA, Cyclin D1, MEK, s6, pErk, Akt, Caspase2 |
| MEK, s6, Caspase2, total S6 | PCNA, Cyclin D1, MEK, s6, pErk, Akt, RBBP |
| MEK, s6, RBBP, total S6 | PCNA, Cyclin D1, MEK, s6, pErk, Akt, total S6 |
| MEK, pS6, Erk, pErk | PCNA, Cyclin D1, MEK, s6, pErk, pAkt, Caspase2 |
| MEK, pS6, Erk, Akt | PCNA, Cyclin D1, MEK, s6, pErk, pAkt, RBBP |
| MEK, pS6, Erk, pAkt | PCNA, Cyclin D1, MEK, s6, pErk, pAkt, total S6 |
| MEK, pS6, Erk, Caspase2 | PCNA, Cyclin D1, MEK, s6, pErk, Caspase2, RBBP |
| MEK, pS6, Erk, RBBP | PCNA, Cyclin D1, MEK, s6, pErk, Caspase2, total S6 |
| MEK, pS6, Erk, total S6 | PCNA, Cyclin D1, MEK, s6, pErk, RBBP, total S6 |
| MEK, pS6, pErk, Akt | PCNA, Cyclin D1, MEK, s6, Akt, pAkt, Caspase2 |
| MEK, pS6, pErk, pAkt | PCNA, Cyclin D1, MEK, s6, Akt, pAkt, RBBP |
| MEK, pS6, pErk, Caspase2 | PCNA, Cyclin D1, MEK, s6, Akt, pAkt, total S6 |
| MEK, pS6, pErk, RBBP | PCNA, Cyclin D1, MEK, s6, Akt, Caspase2, RBBP |
| MEK, pS6, pErk, total S6 | PCNA, Cyclin D1, MEK, s6, Akt, Caspase2, total S6 |
| MEK, pS6, Akt, pAkt | PCNA, Cyclin D1, MEK, s6, Akt, RBBP, total S6 |
| MEK, pS6, Akt, Caspase2 | PCNA, Cyclin D1, MEK, s6, pAkt, Caspase2, RBBP |
| MEK, pS6, Akt, RBBP | PCNA, Cyclin D1, MEK, s6, pAkt, Caspase2, total S6 |
| MEK, pS6, Akt, total S6 | PCNA, Cyclin D1, MEK, s6, pAkt, RBBP, total S6 |
| MEK, pS6, pAkt, Caspase2 | PCNA, Cyclin D1, MEK, s6, Caspase2, RBBP, total S6 |
| MEK, pS6, pAkt, RBBP | PCNA, Cyclin D1, MEK, pS6, Erk, pErk, Akt |
| MEK, pS6, pAkt, total S6 | PCNA, Cyclin D1, MEK, pS6, Erk, pErk, pAkt |
| MEK, pS6, Caspase2, RBBP | PCNA, Cyclin D1, MEK, pS6, Erk, pErk, Caspase2 |
| MEK, pS6, Caspase2, total S6 | PCNA, Cyclin D1, MEK, pS6, Erk, pErk, RBBP |
| MEK, pS6, RBBP, total S6 | PCNA, Cyclin D1, MEK, pS6, Erk, pErk, total S6 |
| MEK, Erk, pErk, Akt | PCNA, Cyclin D1, MEK, pS6, Erk, Akt, pAkt |
| MEK, Erk, pErk, pAkt | PCNA, Cyclin D1, MEK, pS6, Erk, Akt, Caspase2 |
| MEK, Erk, pErk, Caspase2 | PCNA, Cyclin D1, MEK, pS6, Erk, Akt, RBBP |

TABLE 1-continued

Examples of Single Markers and Combinations of Markers

MEK, Erk, pErk, RBBP
MEK, Erk, pErk, total S6
MEK, Erk, Akt, pAkt
MEK, Erk, Akt, Caspase2
MEK, Erk, Akt, RBBP
MEK, Erk, Akt, total S6
MEK, Erk, pAkt, Caspase2
MEK, Erk, pAkt, RBBP
MEK, Erk, pAkt, total S6
MEK, Erk, Caspase2, RBBP
MEK, Erk, Caspase2, total S6
MEK, Erk, RBBP, total S6
MEK, pErk, Akt, pAkt
MEK, pErk, Akt, Caspase2
MEK, pErk, Akt, RBBP
MEK, pErk, Akt, total S6
MEK, pErk, pAkt, Caspase2
MEK, pErk, pAkt, RBBP
MEK, pErk, pAkt, total S6
MEK, pErk, Caspase2, RBBP
MEK, pErk, Caspase2, total S6
MEK, pErk, RBBP, total S6
MEK, Akt, pAkt, Caspase2
MEK, Akt, pAkt, RBBP
MEK, Akt, pAkt, total S6
MEK, Akt, Caspase2, RBBP
MEK, Akt, Caspase2, total S6
MEK, Akt, RBBP, total S6
MEK, pAkt, Caspase2, RBBP
MEK, pAkt, Caspase2, total S6
MEK, pAkt, RBBP, total S6
MEK, Caspase2, RBBP, total S6
s6, pS6, Erk, pErk
s6, pS6, Erk, Akt
s6, pS6, Erk, pAkt
s6, pS6, Erk, Caspase2
s6, pS6, Erk, RBBP
s6, pS6, Erk, total S6
s6, pS6, pErk, Akt
s6, pS6, pErk, pAkt
s6, pS6, pErk, Caspase2
s6, pS6, pErk, RBBP
s6, pS6, pErk, total S6
s6, pS6, Akt, pAkt
s6, pS6, Akt, Caspase2
s6, pS6, Akt, RBBP
s6, pS6, Akt, total S6
s6, pS6, pAkt, Caspase2
s6, pS6, pAkt, RBBP
s6, pS6, pAkt, total S6
s6, pS6, Caspase2, RBBP
s6, pS6, Caspase2, total S6
s6, pS6, RBBP, total S6
s6, Erk, pErk, Akt
s6, Erk, pErk, pAkt
s6, Erk, pErk, Caspase2
s6, Erk, pErk, RBBP
s6, Erk, pErk, total S6
s6, Erk, Akt, pAkt
s6, Erk, Akt, Caspase2
s6, Erk, Akt, RBBP
s6, Erk, Akt, total S6
s6, Erk, pAkt, Caspase2
s6, Erk, pAkt, RBBP
s6, Erk, pAkt, total S6
s6, Erk, Caspase2, RBBP
s6, Erk, Caspase2, total S6
s6, Erk, RBBP, total S6
s6, pErk, Akt, pAkt
s6, pErk, Akt, Caspase2
s6, pErk, Akt, RBBP
s6, pErk, Akt, total S6
s6, pErk, pAkt, Caspase2
s6, pErk, pAkt, RBBP
s6, pErk, pAkt, total S6
s6, pErk, Caspase2, RBBP
s6, pErk, Caspase2, total S6
s6, pErk, RBBP, total S6
PCNA, Cyclin D1, MEK, pS6, Erk, Akt, total S6
PCNA, Cyclin D1, MEK, pS6, Erk, pAkt, Caspase2
PCNA, Cyclin D1, MEK, pS6, Erk, pAkt, RBBP
PCNA, Cyclin D1, MEK, pS6, Erk, pAkt, total S6
PCNA, Cyclin D1, MEK, pS6, Erk, Caspase2, RBBP
PCNA, Cyclin D1, MEK, pS6, Erk, Caspase2, total S6
PCNA, Cyclin D1, MEK, pS6, Erk, RBBP, total S6
PCNA, Cyclin D1, MEK, pS6, pErk, Akt, pAkt
PCNA, Cyclin D1, MEK, pS6, pErk, Akt, Caspase2
PCNA, Cyclin D1, MEK, pS6, pErk, Akt, RBBP
PCNA, Cyclin D1, MEK, pS6, pErk, Akt, total S6
PCNA, Cyclin D1, MEK, pS6, pErk, pAkt, Caspase2
PCNA, Cyclin D1, MEK, pS6, pErk, pAkt, RBBP
PCNA, Cyclin D1, MEK, pS6, pErk, pAkt, total S6
PCNA, Cyclin D1, MEK, pS6, pErk, Caspase2, RBBP
PCNA, Cyclin D1, MEK, pS6, pErk, Caspase2, total S6
PCNA, Cyclin D1, MEK, pS6, pErk, RBBP, total S6
PCNA, Cyclin D1, MEK, pS6, Akt, pAkt, Caspase2
PCNA, Cyclin D1, MEK, pS6, Akt, pAkt, RBBP
PCNA, Cyclin D1, MEK, pS6, Akt, pAkt, total S6
PCNA, Cyclin D1, MEK, pS6, Akt, Caspase2, RBBP
PCNA, Cyclin D1, MEK, pS6, Akt, Caspase2, total S6
PCNA, Cyclin D1, MEK, pS6, Akt, RBBP, total S6
PCNA, Cyclin D1, MEK, pS6, pAkt, Caspase2, RBBP
PCNA, Cyclin D1, MEK, pS6, pAkt, Caspase2, total S6
PCNA, Cyclin D1, MEK, pS6, pAkt, RBBP, total S6
PCNA, Cyclin D1, MEK, pS6, Caspase2, RBBP, total S6
PCNA, Cyclin D1, MEK, Erk, pErk, Akt, pAkt
PCNA, Cyclin D1, MEK, Erk, pErk, Akt, Caspase2
PCNA, Cyclin D1, MEK, Erk, pErk, Akt, RBBP
PCNA, Cyclin D1, MEK, Erk, pErk, Akt, total S6
PCNA, Cyclin D1, MEK, Erk, pErk, pAkt, Caspase2
PCNA, Cyclin D1, MEK, Erk, pErk, pAkt, RBBP
PCNA, Cyclin D1, MEK, Erk, pErk, pAkt, total S6
PCNA, Cyclin D1, MEK, Erk, pErk, Caspase2, RBBP
PCNA, Cyclin D1, MEK, Erk, pErk, Caspase2, total S6
PCNA, Cyclin D1, MEK, Erk, pErk, RBBP, total S6
PCNA, Cyclin D1, MEK, Erk, Akt, pAkt, Caspase2
PCNA, Cyclin D1, MEK, Erk, Akt, pAkt, RBBP
PCNA, Cyclin D1, MEK, Erk, Akt, pAkt, total S6
PCNA, Cyclin D1, MEK, Erk, Akt, Caspase2, RBBP
PCNA, Cyclin D1, MEK, Erk, Akt, Caspase2, total S6
PCNA, Cyclin D1, MEK, Erk, Akt, RBBP, total S6
PCNA, Cyclin D1, MEK, Erk, pAkt, Caspase2, RBBP
PCNA, Cyclin D1, MEK, Erk, pAkt, Caspase2, total S6
PCNA, Cyclin D1, MEK, Erk, pAkt, RBBP, total S6
PCNA, Cyclin D1, MEK, Erk, Caspase2, RBBP, total S6
PCNA, Cyclin D1, MEK, pErk, Akt, pAkt, Caspase2
PCNA, Cyclin D1, MEK, pErk, Akt, pAkt, RBBP
PCNA, Cyclin D1, MEK, pErk, Akt, pAkt, total S6
PCNA, Cyclin D1, MEK, pErk, Akt, Caspase2, RBBP
PCNA, Cyclin D1, MEK, pErk, Akt, Caspase2, total S6
PCNA, Cyclin D1, MEK, pErk, Akt, RBBP, total S6
PCNA, Cyclin D1, MEK, pErk, pAkt, Caspase2, RBBP
PCNA, Cyclin D1, MEK, pErk, pAkt, Caspase2, total S6
PCNA, Cyclin D1, MEK, pErk, pAkt, RBBP, total S6
PCNA, Cyclin D1, MEK, pErk, Caspase2, RBBP, total S6
PCNA, Cyclin D1, MEK, Akt, pAkt, Caspase2, RBBP
PCNA, Cyclin D1, MEK, Akt, pAkt, Caspase2, total S6
PCNA, Cyclin D1, MEK, Akt, pAkt, RBBP, total S6
PCNA, Cyclin D1, MEK, Akt, Caspase2, RBBP, total S6
PCNA, Cyclin D1, MEK, pAkt, Caspase2, RBBP, total S6
PCNA, Cyclin D1, s6, pS6, Erk, pErk, Akt
PCNA, Cyclin D1, s6, pS6, Erk, pErk, pAkt
PCNA, Cyclin D1, s6, pS6, Erk, pErk, Caspase2
PCNA, Cyclin D1, s6, pS6, Erk, pErk, RBBP
PCNA, Cyclin D1, s6, pS6, Erk, pErk, total S6
PCNA, Cyclin D1, s6, pS6, Erk, Akt, pAkt
PCNA, Cyclin D1, s6, pS6, Erk, Akt, Caspase2
PCNA, Cyclin D1, s6, pS6, Erk, Akt, RBBP
PCNA, Cyclin D1, s6, pS6, Erk, Akt, total S6
PCNA, Cyclin D1, s6, pS6, Erk, pAkt, Caspase2
PCNA, Cyclin D1, s6, pS6, Erk, pAkt, RBBP
PCNA, Cyclin D1, s6, pS6, Erk, pAkt, total S6
PCNA, Cyclin D1, s6, pS6, Erk, Caspase2, RBBP
PCNA, Cyclin D1, s6, pS6, Erk, Caspase2, total S6
PCNA, Cyclin D1, s6, pS6, Erk, RBBP, total S6
PCNA, Cyclin D1, s6, pS6, pErk, Akt, pAkt TABLE 1-continued Examples of Single Markers and Combinations of Markers

| | |
|---|---|
| s6, Akt, pAkt, Caspase2 | PCNA, Cyclin D1, s6, pS6, pErk, Akt, Caspase2 |
| s6, Akt, pAkt, RBBP | PCNA, Cyclin D1, s6, pS6, pErk, Akt, RBBP |
| s6, Akt, pAkt, total S6 | PCNA, Cyclin D1, s6, pS6, pErk, Akt, total S6 |
| s6, Akt, Caspase2, RBBP | PCNA, Cyclin D1, s6, pS6, pErk, pAkt, Caspase2 |
| s6, Akt, Caspase2, total S6 | PCNA, Cyclin D1, s6, pS6, pErk, pAkt, RBBP |
| s6, Akt, RBBP, total S6 | PCNA, Cyclin D1, s6, pS6, pErk, pAkt, total S6 |
| s6, pAkt, Caspase2, RBBP | PCNA, Cyclin D1, s6, pS6, pErk, Caspase2, RBBP |
| s6, pAkt, Caspase2, total S6 | PCNA, Cyclin D1, s6, pS6, pErk, Caspase2, total S6 |
| s6, pAkt, RBBP, total S6 | PCNA, Cyclin D1, s6, pS6, pErk, RBBP, total S6 |
| s6, Caspase2, RBBP, total S6 | PCNA, Cyclin D1, s6, pS6, Akt, pAkt, Caspase2 |
| pS6, Erk, pErk, Akt | PCNA, Cyclin D1, s6, pS6, Akt, pAkt, RBBP |
| pS6, Erk, pErk, pAkt | PCNA, Cyclin D1, s6, pS6, Akt, pAkt, total S6 |
| pS6, Erk, pErk, Caspase2 | PCNA, Cyclin D1, s6, pS6, Akt, Caspase2, RBBP |
| pS6, Erk, pErk, RBBP | PCNA, Cyclin D1, s6, pS6, Akt, Caspase2, total S6 |
| pS6, Erk, pErk, total S6 | PCNA, Cyclin D1, s6, pS6, Akt, RBBP, total S6 |
| pS6, Erk, Akt, pAkt | PCNA, Cyclin D1, s6, pS6, pAkt, Caspase2, RBBP |
| pS6, Erk, Akt, Caspase2 | PCNA, Cyclin D1, s6, pS6, pAkt, Caspase2, total S6 |
| pS6, Erk, Akt, RBBP | PCNA, Cyclin D1, s6, pS6, pAkt, RBBP, total S6 |
| pS6, Erk, Akt, total S6 | PCNA, Cyclin D1, s6, pS6, Caspase2, RBBP, total S6 |
| pS6, Erk, pAkt, Caspase2 | PCNA, Cyclin D1, s6, Erk, pErk, Akt, pAkt |
| pS6, Erk, pAkt, RBBP | PCNA, Cyclin D1, s6, Erk, pErk, Akt, Caspase2 |
| pS6, Erk, pAkt, total S6 | PCNA, Cyclin D1, s6, Erk, pErk, Akt, RBBP |
| pS6, Erk, Caspase2, RBBP | PCNA, Cyclin D1, s6, Erk, pErk, Akt, total S6 |
| pS6, Erk, Caspase2, total S6 | PCNA, Cyclin D1, s6, Erk, pErk, pAkt, Caspase2 |
| pS6, Erk, RBBP, total S6 | PCNA, Cyclin D1, s6, Erk, pErk, pAkt, RBBP |
| pS6, pErk, Akt, pAkt | PCNA, Cyclin D1, s6, Erk, pErk, pAkt, total S6 |
| pS6, pErk, Akt, Caspase2 | PCNA, Cyclin D1, s6, Erk, pErk, Caspase2, RBBP |
| pS6, pErk, Akt, RBBP | PCNA, Cyclin D1, s6, Erk, pErk, Caspase2, total S6 |
| pS6, pErk, Akt, total S6 | PCNA, Cyclin D1, s6, Erk, pErk, RBBP, total S6 |
| pS6, pErk, pAkt, Caspase2 | PCNA, Cyclin D1, s6, Erk, Akt, pAkt, Caspase2 |
| pS6, pErk, pAkt, RBBP | PCNA, Cyclin D1, s6, Erk, Akt, pAkt, RBBP |
| pS6, pErk, pAkt, total S6 | PCNA, Cyclin D1, s6, Erk, Akt, pAkt, total S6 |
| pS6, pErk, Caspase2, RBBP | PCNA, Cyclin D1, s6, Erk, Akt, Caspase2, RBBP |
| pS6, pErk, Caspase2, total S6 | PCNA, Cyclin D1, s6, Erk, Akt, Caspase2, total S6 |
| pS6, pErk, RBBP, total S6 | PCNA, Cyclin D1, s6, Erk, Akt, RBBP, total S6 |
| pS6, Akt, pAkt, Caspase2 | PCNA, Cyclin D1, s6, Erk, pAkt, Caspase2, RBBP |
| pS6, Akt, pAkt, RBBP | PCNA, Cyclin D1, s6, Erk, pAkt, Caspase2, total S6 |
| pS6, Akt, pAkt, total S6 | PCNA, Cyclin D1, s6, Erk, pAkt, RBBP, total S6 |
| pS6, Akt, Caspase2, RBBP | PCNA, Cyclin D1, s6, Erk, Caspase2, RBBP, total S6 |
| pS6, Akt, Caspase2, total S6 | PCNA, Cyclin D1, s6, pErk, Akt, pAkt, Caspase2 |
| pS6, Akt, RBBP, total S6 | PCNA, Cyclin D1, s6, pErk, Akt, pAkt, RBBP |
| pS6, pAkt, Caspase2, RBBP | PCNA, Cyclin D1, s6, pErk, Akt, pAkt, total S6 |
| pS6, pAkt, Caspase2, total S6 | PCNA, Cyclin D1, s6, pErk, Akt, Caspase2, RBBP |
| pS6, pAkt, RBBP, total S6 | PCNA, Cyclin D1, s6, pErk, Akt, Caspase2, total S6 |
| pS6, Caspase2, RBBP, total S6 | PCNA, Cyclin D1, s6, pErk, Akt, RBBP, total S6 |
| Erk, pErk, Akt, pAkt | PCNA, Cyclin D1, s6, pErk, pAkt, Caspase2, RBBP |
| Erk, pErk, Akt, Caspase2 | PCNA, Cyclin D1, s6, pErk, pAkt, Caspase2, total S6 |
| Erk, pErk, Akt, RBBP | PCNA, Cyclin D1, s6, pErk, pAkt, RBBP, total S6 |
| Erk, pErk, Akt, total S6 | PCNA, Cyclin D1, s6, pErk, Caspase2, RBBP, total S6 |
| Erk, pErk, pAkt, Caspase2 | PCNA, Cyclin D1, s6, Akt, pAkt, Caspase2, RBBP |
| Erk, pErk, pAkt, RBBP | PCNA, Cyclin D1, s6, Akt, pAkt, Caspase2, total S6 |
| Erk, pErk, pAkt, total S6 | PCNA, Cyclin D1, s6, Akt, pAkt, RBBP, total S6 |
| Erk, pErk, Caspase2, RBBP | PCNA, Cyclin D1, s6, Akt, Caspase2, RBBP, total S6 |
| Erk, pErk, Caspase2, total S6 | PCNA, Cyclin D1, s6, pAkt, Caspase2, RBBP, total S6 |
| Erk, pErk, RBBP, total S6 | PCNA, Cyclin D1, pS6, Erk, pErk, Akt, pAkt |
| Erk, Akt, pAkt, Caspase2 | PCNA, Cyclin D1, pS6, Erk, pErk, Akt, Caspase2 |
| Erk, Akt, pAkt, RBBP | PCNA, Cyclin D1, pS6, Erk, pErk, Akt, RBBP |
| Erk, Akt, pAkt, total S6 | PCNA, Cyclin D1, pS6, Erk, pErk, Akt, total S6 |
| Erk, Akt, Caspase2, RBBP | PCNA, Cyclin D1, pS6, Erk, pErk, pAkt, Caspase2 |
| Erk, Akt, Caspase2, total S6 | PCNA, Cyclin D1, pS6, Erk, pErk, pAkt, RBBP |
| Erk, Akt, RBBP, total S6 | PCNA, Cyclin D1, pS6, Erk, pErk, pAkt, total S6 |
| Erk, pAkt, Caspase2, RBBP | PCNA, Cyclin D1, pS6, Erk, pErk, Caspase2, RBBP |
| Erk, pAkt, Caspase2, total S6 | PCNA, Cyclin D1, pS6, Erk, pErk, Caspase2, total S6 |
| Erk, pAkt, RBBP, total S6 | PCNA, Cyclin D1, pS6, Erk, pErk, RBBP, total S6 |
| Erk, Caspase2, RBBP, total S6 | PCNA, Cyclin D1, pS6, Erk, Akt, pAkt, Caspase2 |
| pErk, Akt, pAkt, Caspase2 | PCNA, Cyclin D1, pS6, Erk, Akt, pAkt, RBBP |
| pErk, Akt, pAkt, RBBP | PCNA, Cyclin D1, pS6, Erk, Akt, pAkt, total S6 |
| pErk, Akt, pAkt, total S6 | PCNA, Cyclin D1, pS6, Erk, Akt, Caspase2, RBBP |
| pErk, Akt, Caspase2, RBBP | PCNA, Cyclin D1, pS6, Erk, Akt, Caspase2, total S6 |
| pErk, Akt, Caspase2, total S6 | PCNA, Cyclin D1, pS6, Erk, Akt, RBBP, total S6 |
| pErk, Akt, RBBP, total S6 | PCNA, Cyclin D1, pS6, Erk, pAkt, Caspase2, RBBP |
| pErk, pAkt, Caspase2, RBBP | PCNA, Cyclin D1, pS6, Erk, pAkt, Caspase2, total S6 |
| pErk, pAkt, Caspase2, total S6 | PCNA, Cyclin D1, pS6, Erk, pAkt, RBBP, total S6 |
| pErk, pAkt, RBBP, total S6 | PCNA, Cyclin D1, pS6, Erk, Caspase2, RBBP, total S6 |
| pErk, Caspase2, RBBP, total S6 | PCNA, Cyclin D1, pS6, pErk, Akt, pAkt, Caspase2 |
| Akt, pAkt, Caspase2, RBBP | PCNA, Cyclin D1, pS6, pErk, Akt, pAkt, RBBP |
| Akt, pAkt, Caspase2, total S6 | PCNA, Cyclin D1, pS6, pErk, Akt, pAkt, total S6 |
| Akt, pAkt, RBBP, total S6 | PCNA, Cyclin D1, pS6, pErk, Akt, Caspase2, RBBP |

TABLE 1-continued

Examples of Single Markers and Combinations of Markers

Akt, Caspase2, RBBP, total S6
pAkt, Caspase2, RBBP, total S6
PCNA, Cyclin D1, Cyclin D3, MEK, s6
PCNA, Cyclin D1, Cyclin D3, MEK, pS6
PCNA, Cyclin D1, Cyclin D3, MEK, Erk
PCNA, Cyclin D1, Cyclin D3, MEK, pErk
PCNA, Cyclin D1, Cyclin D3, MEK, Akt
PCNA, Cyclin D1, Cyclin D3, MEK, pAkt
PCNA, Cyclin D1, Cyclin D3, MEK, Caspase2
PCNA, Cyclin D1, Cyclin D3, MEK, RBBP
PCNA, Cyclin D1, Cyclin D3, MEK, total S6
PCNA, Cyclin D1, Cyclin D3, s6, pS6
PCNA, Cyclin D1, Cyclin D3, s6, Erk
PCNA, Cyclin D1, Cyclin D3, s6, pErk
PCNA, Cyclin D1, Cyclin D3, s6, Akt
PCNA, Cyclin D1, Cyclin D3, s6, pAkt
PCNA, Cyclin D1, Cyclin D3, s6, Caspase2
PCNA, Cyclin D1, Cyclin D3, s6, RBBP
PCNA, Cyclin D1, Cyclin D3, s6, total S6
PCNA, Cyclin D1, Cyclin D3, pS6, Erk
PCNA, Cyclin D1, Cyclin D3, pS6, pErk
PCNA, Cyclin D1, Cyclin D3, pS6, Akt
PCNA, Cyclin D1, Cyclin D3, pS6, pAkt
PCNA, Cyclin D1, Cyclin D3, pS6, Caspase2
PCNA, Cyclin D1, Cyclin D3, pS6, RBBP
PCNA, Cyclin D1, Cyclin D3, pS6, total S6
PCNA, Cyclin D1, Cyclin D3, Erk, pErk
PCNA, Cyclin D1, Cyclin D3, Erk, Akt
PCNA, Cyclin D1, Cyclin D3, Erk, pAkt
PCNA, Cyclin D1, Cyclin D3, Erk, Caspase2
PCNA, Cyclin D1, Cyclin D3, Erk, RBBP
PCNA, Cyclin D1, Cyclin D3, Erk, total S6
PCNA, Cyclin D1, Cyclin D3, pErk, Akt
PCNA, Cyclin D1, Cyclin D3, pErk, pAkt
PCNA, Cyclin D1, Cyclin D3, pErk, Caspase2
PCNA, Cyclin D1, Cyclin D3, pErk, RBBP
PCNA, Cyclin D1, Cyclin D3, pErk, total S6
PCNA, Cyclin D1, Cyclin D3, Akt, pAkt
PCNA, Cyclin D1, Cyclin D3, Akt, Caspase2
PCNA, Cyclin D1, Cyclin D3, Akt, RBBP
PCNA, Cyclin D1, Cyclin D3, Akt, total S6
PCNA, Cyclin D1, Cyclin D3, pAkt, Caspase2
PCNA, Cyclin D1, Cyclin D3, pAkt, RBBP
PCNA, Cyclin D1, Cyclin D3, pAkt, total S6
PCNA, Cyclin D1, Cyclin D3, Caspase2, RBBP
PCNA, Cyclin D1, Cyclin D3, Caspase2, total S6
PCNA, Cyclin D1, Cyclin D3, RBBP, total S6
PCNA, Cyclin D1, MEK, s6, pS6
PCNA, Cyclin D1, MEK, s6, Erk
PCNA, Cyclin D1, MEK, s6, pErk
PCNA, Cyclin D1, MEK, s6, Akt
PCNA, Cyclin D1, MEK, s6, pAkt
PCNA, Cyclin D1, MEK, s6, Caspase2
PCNA, Cyclin D1, MEK, s6, RBBP
PCNA, Cyclin D1, MEK, s6, total S6
PCNA, Cyclin D1, MEK, pS6, Erk
PCNA, Cyclin D1, MEK, pS6, pErk
PCNA, Cyclin D1, MEK, pS6, Akt
PCNA, Cyclin D1, MEK, pS6, pAkt
PCNA, Cyclin D1, MEK, pS6, Caspase2
PCNA, Cyclin D1, MEK, pS6, RBBP
PCNA, Cyclin D1, MEK, pS6, total S6
PCNA, Cyclin D1, MEK, Erk, pErk
PCNA, Cyclin D1, MEK, Erk, Akt
PCNA, Cyclin D1, MEK, Erk, pAkt
PCNA, Cyclin D1, MEK, Erk, Caspase2
PCNA, Cyclin D1, MEK, Erk, RBBP
PCNA, Cyclin D1, MEK, Erk, total S6
PCNA, Cyclin D1, MEK, pErk, Akt
PCNA, Cyclin D1, MEK, pErk, pAkt
PCNA, Cyclin D1, MEK, pErk, Caspase2
PCNA, Cyclin D1, MEK, pErk, RBBP
PCNA, Cyclin D1, MEK, pErk, total S6
PCNA, Cyclin D1, MEK, Akt, pAkt
PCNA, Cyclin D1, MEK, Akt, Caspase2
PCNA, Cyclin D1, MEK, Akt, RBBP
PCNA, Cyclin D1, MEK, Akt, total S6
PCNA, Cyclin D1, MEK, pAkt, Caspase2
PCNA, Cyclin D1, pS6, pErk, Akt, Caspase2, total S6
PCNA, Cyclin D1, pS6, pErk, Akt, RBBP, total S6
PCNA, Cyclin D1, pS6, pErk, pAkt, Caspase2, RBBP
PCNA, Cyclin D1, pS6, pErk, pAkt, Caspase2, total S6
PCNA, Cyclin D1, pS6, pErk, pAkt, RBBP, total S6
PCNA, Cyclin D1, pS6, pErk, Caspase2, RBBP, total S6
PCNA, Cyclin D1, pS6, Akt, pAkt, Caspase2, RBBP
PCNA, Cyclin D1, pS6, Akt, pAkt, Caspase2, total S6
PCNA, Cyclin D1, pS6, Akt, pAkt, RBBP, total S6
PCNA, Cyclin D1, pS6, Akt, Caspase2, RBBP, total S6
PCNA, Cyclin D1, pS6, pAkt, Caspase2, RBBP, total S6
PCNA, Cyclin D1, Erk, pErk, Akt, pAkt, Caspase2
PCNA, Cyclin D1, Erk, pErk, Akt, pAkt, RBBP
PCNA, Cyclin D1, Erk, pErk, Akt, pAkt, total S6
PCNA, Cyclin D1, Erk, pErk, Akt, Caspase2, RBBP
PCNA, Cyclin D1, Erk, pErk, Akt, Caspase2, total S6
PCNA, Cyclin D1, Erk, pErk, Akt, RBBP, total S6
PCNA, Cyclin D1, Erk, pErk, pAkt, Caspase2, RBBP
PCNA, Cyclin D1, Erk, pErk, pAkt, Caspase2, total S6
PCNA, Cyclin D1, Erk, pErk, pAkt, RBBP, total S6
PCNA, Cyclin D1, Erk, pErk, Caspase2, RBBP, total S6
PCNA, Cyclin D1, Erk, Akt, pAkt, Caspase2, RBBP
PCNA, Cyclin D1, Erk, Akt, pAkt, Caspase2, total S6
PCNA, Cyclin D1, Erk, Akt, pAkt, RBBP, total S6
PCNA, Cyclin D1, Erk, Akt, Caspase2, RBBP, total S6
PCNA, Cyclin D1, Erk, pAkt, Caspase2, RBBP, total S6
PCNA, Cyclin D1, pErk, Akt, pAkt, Caspase2, RBBP
PCNA, Cyclin D1, pErk, Akt, pAkt, Caspase2, total S6
PCNA, Cyclin D1, pErk, Akt, pAkt, RBBP, total S6
PCNA, Cyclin D1, pErk, Akt, Caspase2, RBBP, total S6
PCNA, Cyclin D1, pErk, pAkt, Caspase2, RBBP, total S6
PCNA, Cyclin D1, Akt, pAkt, Caspase2, RBBP, total S6
PCNA, Cyclin D3, MEK, s6, pS6, Erk, pErk
PCNA, Cyclin D3, MEK, s6, pS6, Erk, Akt
PCNA, Cyclin D3, MEK, s6, pS6, Erk, pAkt
PCNA, Cyclin D3, MEK, s6, pS6, Erk, Caspase2
PCNA, Cyclin D3, MEK, s6, pS6, Erk, RBBP
PCNA, Cyclin D3, MEK, s6, pS6, Erk, total S6
PCNA, Cyclin D3, MEK, s6, pS6, pErk, Akt
PCNA, Cyclin D3, MEK, s6, pS6, pErk, pAkt
PCNA, Cyclin D3, MEK, s6, pS6, pErk, Caspase2
PCNA, Cyclin D3, MEK, s6, pS6, pErk, RBBP
PCNA, Cyclin D3, MEK, s6, pS6, pErk, total S6
PCNA, Cyclin D3, MEK, s6, pS6, Akt, pAkt
PCNA, Cyclin D3, MEK, s6, pS6, Akt, Caspase2
PCNA, Cyclin D3, MEK, s6, pS6, Akt, RBBP
PCNA, Cyclin D3, MEK, s6, pS6, Akt, total S6
PCNA, Cyclin D3, MEK, s6, pS6, pAkt, Caspase2
PCNA, Cyclin D3, MEK, s6, pS6, pAkt, RBBP
PCNA, Cyclin D3, MEK, s6, pS6, pAkt, total S6
PCNA, Cyclin D3, MEK, s6, pS6, Caspase2, RBBP
PCNA, Cyclin D3, MEK, s6, pS6, Caspase2, total S6
PCNA, Cyclin D3, MEK, s6, pS6, RBBP, total S6
PCNA, Cyclin D3, MEK, s6, Erk, pErk, Akt
PCNA, Cyclin D3, MEK, s6, Erk, pErk, pAkt
PCNA, Cyclin D3, MEK, s6, Erk, pErk, Caspase2
PCNA, Cyclin D3, MEK, s6, Erk, pErk, RBBP
PCNA, Cyclin D3, MEK, s6, Erk, pErk, total S6
PCNA, Cyclin D3, MEK, s6, Erk, Akt, pAkt
PCNA, Cyclin D3, MEK, s6, Erk, Akt, Caspase2
PCNA, Cyclin D3, MEK, s6, Erk, Akt, RBBP
PCNA, Cyclin D3, MEK, s6, Erk, Akt, total S6
PCNA, Cyclin D3, MEK, s6, Erk, pAkt, Caspase2
PCNA, Cyclin D3, MEK, s6, Erk, pAkt, RBBP
PCNA, Cyclin D3, MEK, s6, Erk, pAkt, total S6
PCNA, Cyclin D3, MEK, s6, Erk, Caspase2, RBBP
PCNA, Cyclin D3, MEK, s6, Erk, Caspase2, total S6
PCNA, Cyclin D3, MEK, s6, Erk, RBBP, total S6
PCNA, Cyclin D3, MEK, s6, pErk, Akt, pAkt
PCNA, Cyclin D3, MEK, s6, pErk, Akt, Caspase2
PCNA, Cyclin D3, MEK, s6, pErk, Akt, RBBP
PCNA, Cyclin D3, MEK, s6, pErk, Akt, total S6
PCNA, Cyclin D3, MEK, s6, pErk, pAkt, Caspase2
PCNA, Cyclin D3, MEK, s6, pErk, pAkt, RBBP
PCNA, Cyclin D3, MEK, s6, pErk, pAkt, total S6
PCNA, Cyclin D3, MEK, s6, pErk, Caspase2, RBBP
PCNA, Cyclin D3, MEK, s6, pErk, Caspase2, total S6
PCNA, Cyclin D3, MEK, s6, pErk, RBBP, total S6

TABLE 1-continued

Examples of Single Markers and Combinations of Markers

PCNA, Cyclin D1, MEK, pAkt, RBBP
PCNA, Cyclin D1, MEK, pAkt, total S6
PCNA, Cyclin D1, MEK, Caspase2, RBBP
PCNA, Cyclin D1, MEK, Caspase2, total S6
PCNA, Cyclin D1, MEK, RBBP, total S6
PCNA, Cyclin D1, s6, pS6, Erk
PCNA, Cyclin D1, s6, pS6, pErk
PCNA, Cyclin D1, s6, pS6, Akt
PCNA, Cyclin D1, s6, pS6, pAkt
PCNA, Cyclin D1, s6, pS6, Caspase2
PCNA, Cyclin D1, s6, pS6, RBBP
PCNA, Cyclin D1, s6, pS6, total S6
PCNA, Cyclin D1, s6, Erk, pErk
PCNA, Cyclin D1, s6, Erk, Akt
PCNA, Cyclin D1, s6, Erk, pAkt
PCNA, Cyclin D1, s6, Erk, Caspase2
PCNA, Cyclin D1, s6, Erk, RBBP
PCNA, Cyclin D1, s6, Erk, total S6
PCNA, Cyclin D1, s6, pErk, Akt
PCNA, Cyclin D1, s6, pErk, pAkt
PCNA, Cyclin D1, s6, pErk, Caspase2
PCNA, Cyclin D1, s6, pErk, RBBP
PCNA, Cyclin D1, s6, pErk, total S6
PCNA, Cyclin D1, s6, Akt, pAkt
PCNA, Cyclin D1, s6, Akt, Caspase2
PCNA, Cyclin D1, s6, Akt, RBBP
PCNA, Cyclin D1, s6, Akt, total S6
PCNA, Cyclin D1, s6, pAkt, Caspase2
PCNA, Cyclin D1, s6, pAkt, RBBP
PCNA, Cyclin D1, s6, pAkt, total S6
PCNA, Cyclin D1, s6, Caspase2, RBBP
PCNA, Cyclin D1, s6, Caspase2, total S6
PCNA, Cyclin D1, s6, RBBP, total S6
PCNA, Cyclin D1, pS6, Erk, pErk
PCNA, Cyclin D1, pS6, Erk, Akt
PCNA, Cyclin D1, pS6, Erk, pAkt
PCNA, Cyclin D1, pS6, Erk, Caspase2
PCNA, Cyclin D1, pS6, Erk, RBBP
PCNA, Cyclin D1, pS6, Erk, total S6
PCNA, Cyclin D1, pS6, pErk, Akt
PCNA, Cyclin D1, pS6, pErk, pAkt
PCNA, Cyclin D1, pS6, pErk, Caspase2
PCNA, Cyclin D1, pS6, pErk, RBBP
PCNA, Cyclin D1, pS6, pErk, total S6
PCNA, Cyclin D1, pS6, Akt, pAkt
PCNA, Cyclin D1, pS6, Akt, Caspase2
PCNA, Cyclin D1, pS6, Akt, RBBP
PCNA, Cyclin D1, pS6, Akt, total S6
PCNA, Cyclin D1, pS6, pAkt, Caspase2
PCNA, Cyclin D1, pS6, pAkt, RBBP
PCNA, Cyclin D1, pS6, pAkt, total S6
PCNA, Cyclin D1, pS6, Caspase2, RBBP
PCNA, Cyclin D1, pS6, Caspase2, total S6
PCNA, Cyclin D1, pS6, RBBP, total S6
PCNA, Cyclin D1, Erk, pErk, Akt
PCNA, Cyclin D1, Erk, pErk, pAkt
PCNA, Cyclin D1, Erk, pErk, Caspase2
PCNA, Cyclin D1, Erk, pErk, RBBP
PCNA, Cyclin D1, Erk, pErk, total S6
PCNA, Cyclin D1, Erk, Akt, pAkt
PCNA, Cyclin D1, Erk, Akt, Caspase2
PCNA, Cyclin D1, Erk, Akt, RBBP
PCNA, Cyclin D1, Erk, Akt, total S6
PCNA, Cyclin D1, Erk, pAkt, Caspase2
PCNA, Cyclin D1, Erk, pAkt, RBBP
PCNA, Cyclin D1, Erk, pAkt, total S6
PCNA, Cyclin D1, Erk, Caspase2, RBBP
PCNA, Cyclin D1, Erk, Caspase2, total S6
PCNA, Cyclin D1, Erk, RBBP, total S6
PCNA, Cyclin D1, pErk, Akt, pAkt
PCNA, Cyclin D1, pErk, Akt, Caspase2
PCNA, Cyclin D1, pErk, Akt, RBBP
PCNA, Cyclin D1, pErk, Akt, total S6
PCNA, Cyclin D1, pErk, pAkt, Caspase2
PCNA, Cyclin D1, pErk, pAkt, RBBP
PCNA, Cyclin D1, pErk, pAkt, total S6
PCNA, Cyclin D1, pErk, Caspase2, RBBP
PCNA, Cyclin D1, pErk, Caspase2, total S6

PCNA, Cyclin D3, MEK, s6, Akt, pAkt, Caspase2
PCNA, Cyclin D3, MEK, s6, Akt, pAkt, RBBP
PCNA, Cyclin D3, MEK, s6, Akt, pAkt, total S6
PCNA, Cyclin D3, MEK, s6, Akt, Caspase2, RBBP
PCNA, Cyclin D3, MEK, s6, Akt, Caspase2, total S6
PCNA, Cyclin D3, MEK, s6, Akt, RBBP, total S6
PCNA, Cyclin D3, MEK, s6, pAkt, Caspase2, RBBP
PCNA, Cyclin D3, MEK, s6, pAkt, Caspase2, total S6
PCNA, Cyclin D3, MEK, s6, pAkt, RBBP, total S6
PCNA, Cyclin D3, MEK, s6, Caspase2, RBBP, total S6
PCNA, Cyclin D3, MEK, pS6, Erk, pErk, Akt
PCNA, Cyclin D3, MEK, pS6, Erk, pErk, pAkt
PCNA, Cyclin D3, MEK, pS6, Erk, pErk, Caspase2
PCNA, Cyclin D3, MEK, pS6, Erk, pErk, RBBP
PCNA, Cyclin D3, MEK, pS6, Erk, pErk, total S6
PCNA, Cyclin D3, MEK, pS6, Erk, Akt, pAkt
PCNA, Cyclin D3, MEK, pS6, Erk, Akt, Caspase2
PCNA, Cyclin D3, MEK, pS6, Erk, Akt, RBBP
PCNA, Cyclin D3, MEK, pS6, Erk, Akt, total S6
PCNA, Cyclin D3, MEK, pS6, Erk, pAkt, Caspase2
PCNA, Cyclin D3, MEK, pS6, Erk, pAkt, RBBP
PCNA, Cyclin D3, MEK, pS6, Erk, pAkt, total S6
PCNA, Cyclin D3, MEK, pS6, Erk, Caspase2, RBBP
PCNA, Cyclin D3, MEK, pS6, Erk, Caspase2, total S6
PCNA, Cyclin D3, MEK, pS6, Erk, RBBP, total S6
PCNA, Cyclin D3, MEK, pS6, pErk, Akt, pAkt
PCNA, Cyclin D3, MEK, pS6, pErk, Akt, Caspase2
PCNA, Cyclin D3, MEK, pS6, pErk, Akt, RBBP
PCNA, Cyclin D3, MEK, pS6, pErk, Akt, total S6
PCNA, Cyclin D3, MEK, pS6, pErk, pAkt, Caspase2
PCNA, Cyclin D3, MEK, pS6, pErk, pAkt, RBBP
PCNA, Cyclin D3, MEK, pS6, pErk, pAkt, total S6
PCNA, Cyclin D3, MEK, pS6, pErk, Caspase2, RBBP
PCNA, Cyclin D3, MEK, pS6, pErk, Caspase2, total S6
PCNA, Cyclin D3, MEK, pS6, pErk, RBBP, total S6
PCNA, Cyclin D3, MEK, pS6, Akt, pAkt, Caspase2
PCNA, Cyclin D3, MEK, pS6, Akt, pAkt, RBBP
PCNA, Cyclin D3, MEK, pS6, Akt, pAkt, total S6
PCNA, Cyclin D3, MEK, pS6, Akt, Caspase2, RBBP
PCNA, Cyclin D3, MEK, pS6, Akt, Caspase2, total S6
PCNA, Cyclin D3, MEK, pS6, Akt, RBBP, total S6
PCNA, Cyclin D3, MEK, pS6, pAkt, Caspase2, RBBP
PCNA, Cyclin D3, MEK, pS6, pAkt, Caspase2, total S6
PCNA, Cyclin D3, MEK, pS6, pAkt, RBBP, total S6
PCNA, Cyclin D3, MEK, pS6, Caspase2, RBBP, total S6
PCNA, Cyclin D3, MEK, Erk, pErk, Akt, pAkt
PCNA, Cyclin D3, MEK, Erk, pErk, Akt, Caspase2
PCNA, Cyclin D3, MEK, Erk, pErk, Akt, RBBP
PCNA, Cyclin D3, MEK, Erk, pErk, Akt, total S6
PCNA, Cyclin D3, MEK, Erk, pErk, pAkt, Caspase2
PCNA, Cyclin D3, MEK, Erk, pErk, pAkt, RBBP
PCNA, Cyclin D3, MEK, Erk, pErk, pAkt, total S6
PCNA, Cyclin D3, MEK, Erk, pErk, Caspase2, RBBP
PCNA, Cyclin D3, MEK, Erk, pErk, Caspase2, total S6
PCNA, Cyclin D3, MEK, Erk, pErk, RBBP, total S6
PCNA, Cyclin D3, MEK, Erk, Akt, pAkt, Caspase2
PCNA, Cyclin D3, MEK, Erk, Akt, pAkt, RBBP
PCNA, Cyclin D3, MEK, Erk, Akt, pAkt, total S6
PCNA, Cyclin D3, MEK, Erk, Akt, Caspase2, RBBP
PCNA, Cyclin D3, MEK, Erk, Akt, Caspase2, total S6
PCNA, Cyclin D3, MEK, Erk, Akt, RBBP, total S6
PCNA, Cyclin D3, MEK, Erk, pAkt, Caspase2, RBBP
PCNA, Cyclin D3, MEK, Erk, pAkt, Caspase2, total S6
PCNA, Cyclin D3, MEK, Erk, pAkt, RBBP, total S6
PCNA, Cyclin D3, MEK, Erk, Caspase2, RBBP, total S6
PCNA, Cyclin D3, MEK, pErk, Akt, pAkt, Caspase2
PCNA, Cyclin D3, MEK, pErk, Akt, pAkt, RBBP
PCNA, Cyclin D3, MEK, pErk, Akt, pAkt, total S6
PCNA, Cyclin D3, MEK, pErk, Akt, Caspase2, RBBP
PCNA, Cyclin D3, MEK, pErk, Akt, Caspase2, total S6
PCNA, Cyclin D3, MEK, pErk, Akt, RBBP, total S6
PCNA, Cyclin D3, MEK, pErk, pAkt, Caspase2, RBBP
PCNA, Cyclin D3, MEK, pErk, pAkt, Caspase2, total S6
PCNA, Cyclin D3, MEK, pErk, pAkt, RBBP, total S6
PCNA, Cyclin D3, MEK, pErk, Caspase2, RBBP, total S6
PCNA, Cyclin D3, MEK, Akt, pAkt, Caspase2, RBBP
PCNA, Cyclin D3, MEK, Akt, pAkt, Caspase2, total S6
PCNA, Cyclin D3, MEK, Akt, pAkt, RBBP, total S6

TABLE 1-continued

Examples of Single Markers and Combinations of Markers

PCNA, Cyclin D1, pErk, RBBP, total S6
PCNA, Cyclin D1, Akt, pAkt, Caspase2
PCNA, Cyclin D1, Akt, pAkt, RBBP
PCNA, Cyclin D1, Akt, pAkt, total S6
PCNA, Cyclin D1, Akt, Caspase2, RBBP
PCNA, Cyclin D1, Akt, Caspase2, total S6
PCNA, Cyclin D1, Akt, RBBP, total S6
PCNA, Cyclin D1, pAkt, Caspase2, RBBP
PCNA, Cyclin D1, pAkt, Caspase2, total S6
PCNA, Cyclin D1, p Akt, RBBP, total S6
PCNA, Cyclin D1, Caspase2, RBBP, total S6
PCNA, Cyclin D3, MEK, s6, pS6
PCNA, Cyclin D3, MEK, s6, Erk
PCNA, Cyclin D3, MEK, s6, pErk
PCNA, Cyclin D3, MEK, s6, Akt
PCNA, Cyclin D3, MEK, s6, pAkt
PCNA, Cyclin D3, MEK, s6, Caspase2
PCNA, Cyclin D3, MEK, s6, RBBP
PCNA, Cyclin D3, MEK, s6, total S6
PCNA, Cyclin D3, MEK, pS6, Erk
PCNA, Cyclin D3, MEK, pS6, pErk
PCNA, Cyclin D3, MEK, pS6, Akt
PCNA, Cyclin D3, MEK, pS6, pAkt
PCNA, Cyclin D3, MEK, pS6, Caspase2
PCNA, Cyclin D3, MEK, pS6, RBBP
PCNA, Cyclin D3, MEK, pS6, total S6
PCNA, Cyclin D3, MEK, Erk, pErk
PCNA, Cyclin D3, MEK, Erk, Akt
PCNA, Cyclin D3, MEK, Erk, pAkt
PCNA, Cyclin D3, MEK, Erk, Caspase2
PCNA, Cyclin D3, MEK, Erk, RBBP
PCNA, Cyclin D3, MEK, Erk, total S6
PCNA, Cyclin D3, MEK, pErk, Akt
PCNA, Cyclin D3, MEK, pErk, pAkt
PCNA, Cyclin D3, MEK, pErk, Caspase2
PCNA, Cyclin D3, MEK, pErk, RBBP
PCNA, Cyclin D3, MEK, pErk, total S6
PCNA, Cyclin D3, MEK, Akt, pAkt
PCNA, Cyclin D3, MEK, Akt, Caspase2
PCNA, Cyclin D3, MEK, Akt, RBBP
PCNA, Cyclin D3, MEK, Akt, total S6
PCNA, Cyclin D3, MEK, pAkt, Caspase2
PCNA, Cyclin D3, MEK, pAkt, RBBP
PCNA, Cyclin D3, MEK, pAkt, total S6
PCNA, Cyclin D3, MEK, Caspase2, RBBP
PCNA, Cyclin D3, MEK, Caspase2, total S6
PCNA, Cyclin D3, MEK, RBBP, total S6
PCNA, Cyclin D3, s6, pS6, Erk
PCNA, Cyclin D3, s6, pS6, pErk
PCNA, Cyclin D3, s6, pS6, Akt
PCNA, Cyclin D3, s6, pS6, pAkt
PCNA, Cyclin D3, s6, pS6, Caspase2
PCNA, Cyclin D3, s6, pS6, RBBP
PCNA, Cyclin D3, s6, pS6, total S6
PCNA, Cyclin D3, s6, Erk, pErk
PCNA, Cyclin D3, s6, Erk, Akt
PCNA, Cyclin D3, s6, Erk, pAkt
PCNA, Cyclin D3, s6, Erk, Caspase2
PCNA, Cyclin D3, s6, Erk, RBBP
PCNA, Cyclin D3, s6, Erk, total S6
PCNA, Cyclin D3, s6, pErk, Akt
PCNA, Cyclin D3, s6, pErk, pAkt
PCNA, Cyclin D3, s6, pErk, Caspase2
PCNA, Cyclin D3, s6, pErk, RBBP
PCNA, Cyclin D3, s6, pErk, total S6
PCNA, Cyclin D3, s6, Akt, pAkt
PCNA, Cyclin D3, s6, Akt, Caspase2
PCNA, Cyclin D3, s6, Akt, RBBP
PCNA, Cyclin D3, s6, Akt, total S6
PCNA, Cyclin D3, s6, pAkt, Caspase2
PCNA, Cyclin D3, s6, pAkt, RBBP
PCNA, Cyclin D3, s6, pAkt, total S6
PCNA, Cyclin D3, s6, Caspase2, RBBP
PCNA, Cyclin D3, s6, Caspase2, total S6
PCNA, Cyclin D3, s6, RBBP, total S6
PCNA, Cyclin D3, pS6, Erk, pErk
PCNA, Cyclin D3, pS6, Erk, Akt
PCNA, Cyclin D3, pS6, Erk, pAkt
PCNA, Cyclin D3, MEK, Akt, Caspase2, RBBP, total S6
PCNA, Cyclin D3, MEK, pAkt, Caspase2, RBBP, total S6
PCNA, Cyclin D3, s6, pS6, Erk, pErk, Akt
PCNA, Cyclin D3, s6, pS6, Erk, pErk, pAkt
PCNA, Cyclin D3, s6, pS6, Erk, pErk, Caspase2
PCNA, Cyclin D3, s6, pS6, Erk, pErk, RBBP
PCNA, Cyclin D3, s6, pS6, Erk, pErk, total S6
PCNA, Cyclin D3, s6, pS6, Erk, Akt, pAkt
PCNA, Cyclin D3, s6, pS6, Erk, Akt, Caspase2
PCNA, Cyclin D3, s6, pS6, Erk, Akt, RBBP
PCNA, Cyclin D3, s6, pS6, Erk, Akt, total S6
PCNA, Cyclin D3, s6, pS6, Erk, pAkt, Caspase2
PCNA, Cyclin D3, s6, pS6, Erk, pAkt, RBBP
PCNA, Cyclin D3, s6, pS6, Erk, pAkt, total S6
PCNA, Cyclin D3, s6, pS6, Erk, Caspase2, RBBP
PCNA, Cyclin D3, s6, pS6, Erk, Caspase2, total S6
PCNA, Cyclin D3, s6, pS6, Erk, RBBP, total S6
PCNA, Cyclin D3, s6, pS6, pErk, Akt, pAkt
PCNA, Cyclin D3, s6, pS6, pErk, Akt, Caspase2
PCNA, Cyclin D3, s6, pS6, pErk, Akt, RBBP
PCNA, Cyclin D3, s6, pS6, pErk, Akt, total S6
PCNA, Cyclin D3, s6, pS6, pErk, pAkt, Caspase2
PCNA, Cyclin D3, s6, pS6, pErk, pAkt, RBBP
PCNA, Cyclin D3, s6, pS6, pErk, pAkt, total S6
PCNA, Cyclin D3, s6, pS6, pErk, Caspase2, RBBP
PCNA, Cyclin D3, s6, pS6, pErk, Caspase2, total S6
PCNA, Cyclin D3, s6, pS6, pErk, RBBP, total S6
PCNA, Cyclin D3, s6, pS6, Akt, pAkt, Caspase2
PCNA, Cyclin D3, s6, pS6, Akt, pAkt, RBBP
PCNA, Cyclin D3, s6, pS6, Akt, pAkt, total S6
PCNA, Cyclin D3, s6, pS6, Akt, Caspase2, RBBP
PCNA, Cyclin D3, s6, pS6, Akt, Caspase2, total S6
PCNA, Cyclin D3, s6, pS6, Akt, RBBP, total S6
PCNA, Cyclin D3, s6, pS6, pAkt, Caspase2, RBBP
PCNA, Cyclin D3, s6, pS6, pAkt, Caspase2, total S6
PCNA, Cyclin D3, s6, pS6, pAkt, RBBP, total S6
PCNA, Cyclin D3, s6, pS6, Caspase2, RBBP, total S6
PCNA, Cyclin D3, s6, Erk, pErk, Akt, pAkt
PCNA, Cyclin D3, s6, Erk, pErk, Akt, Caspase2
PCNA, Cyclin D3, s6, Erk, pErk, Akt, RBBP
PCNA, Cyclin D3, s6, Erk, pErk, Akt, total S6
PCNA, Cyclin D3, s6, Erk, pErk, pAkt, Caspase2
PCNA, Cyclin D3, s6, Erk, pErk, pAkt, RBBP
PCNA, Cyclin D3, s6, Erk, pErk, pAkt, total S6
PCNA, Cyclin D3, s6, Erk, pErk, Caspase2, RBBP
PCNA, Cyclin D3, s6, Erk, pErk, Caspase2, total S6
PCNA, Cyclin D3, s6, Erk, pErk, RBBP, total S6
PCNA, Cyclin D3, s6, Erk, Akt, pAkt, Caspase2
PCNA, Cyclin D3, s6, Erk, Akt, pAkt, RBBP
PCNA, Cyclin D3, s6, Erk, Akt, pAkt, total S6
PCNA, Cyclin D3, s6, Erk, Akt, Caspase2, RBBP
PCNA, Cyclin D3, s6, Erk, Akt, Caspase2, total S6
PCNA, Cyclin D3, s6, Erk, Akt, RBBP, total S6
PCNA, Cyclin D3, s6, Erk, pAkt, Caspase2, RBBP
PCNA, Cyclin D3, s6, Erk, pAkt, Caspase2, total S6
PCNA, Cyclin D3, s6, Erk, pAkt, RBBP, total S6
PCNA, Cyclin D3, s6, Erk, Caspase2, RBBP, total S6
PCNA, Cyclin D3, s6, pErk, Akt, pAkt, Caspase2
PCNA, Cyclin D3, s6, pErk, Akt, pAkt, RBBP
PCNA, Cyclin D3, s6, pErk, Akt, pAkt, total S6
PCNA, Cyclin D3, s6, pErk, Akt, Caspase2, RBBP
PCNA, Cyclin D3, s6, pErk, Akt, Caspase2, total S6
PCNA, Cyclin D3, s6, pErk, Akt, RBBP, total S6
PCNA, Cyclin D3, s6, pErk, pAkt, Caspase2, RBBP
PCNA, Cyclin D3, s6, pErk, pAkt, Caspase2, total S6
PCNA, Cyclin D3, s6, pErk, pAkt, RBBP, total S6
PCNA, Cyclin D3, s6, pErk, Caspase2, RBBP, total S6
PCNA, Cyclin D3, s6, Akt, pAkt, Caspase2, RBBP
PCNA, Cyclin D3, s6, Akt, pAkt, Caspase2, total S6
PCNA, Cyclin D3, s6, Akt, pAkt, RBBP, total S6
PCNA, Cyclin D3, s6, Akt, Caspase2, RBBP, total S6
PCNA, Cyclin D3, s6, pAkt, Caspase2, RBBP, total S6
PCNA, Cyclin D3, pS6, Erk, pErk, Akt, pAkt
PCNA, Cyclin D3, pS6, Erk, pErk, Akt, Caspase2
PCNA, Cyclin D3, pS6, Erk, pErk, Akt, RBBP
PCNA, Cyclin D3, pS6, Erk, pErk, Akt, total S6
PCNA, Cyclin D3, pS6, Erk, pErk, pAkt, Caspase2
PCNA, Cyclin D3, pS6, Erk, pErk, pAkt, RBBP TABLE 1-continued Examples of Single Markers and Combinations of Markers PCNA, Cyclin D3, pS6, Erk, Caspase2
PCNA, Cyclin D3, pS6, Erk, RBBP
PCNA, Cyclin D3, pS6, Erk, total S6
PCNA, Cyclin D3, pS6, pErk, Akt
PCNA, Cyclin D3, pS6, pErk, pAkt
PCNA, Cyclin D3, pS6, pErk, Caspase2
PCNA, Cyclin D3, pS6, pErk, RBBP
PCNA, Cyclin D3, pS6, pErk, total S6
PCNA, Cyclin D3, pS6, Akt, pAkt
PCNA, Cyclin D3, pS6, Akt, Caspase2
PCNA, Cyclin D3, pS6, Akt, RBBP
PCNA, Cyclin D3, pS6, Akt, total S6
PCNA, Cyclin D3, pS6, pAkt, Caspase2
PCNA, Cyclin D3, pS6, pAkt, RBBP
PCNA, Cyclin D3, pS6, pAkt, total S6
PCNA, Cyclin D3, pS6, Caspase2, RBBP
PCNA, Cyclin D3, pS6, Caspase2, total S6
PCNA, Cyclin D3, pS6, RBBP, total S6
PCNA, Cyclin D3, Erk, pErk, Akt
PCNA, Cyclin D3, Erk, pErk, pAkt
PCNA, Cyclin D3, Erk, pErk, Caspase2
PCNA, Cyclin D3, Erk, pErk, RBBP
PCNA, Cyclin D3, Erk, pErk, total S6
PCNA, Cyclin D3, Erk, Akt, pAkt
PCNA, Cyclin D3, Erk, Akt, Caspase2
PCNA, Cyclin D3, Erk, Akt, RBBP
PCNA, Cyclin D3, Erk, Akt, total S6
PCNA, Cyclin D3, Erk, pAkt, Caspase2
PCNA, Cyclin D3, Erk, pAkt, RBBP
PCNA, Cyclin D3, Erk, pAkt, total S6
PCNA, Cyclin D3, Erk, Caspase2, RBBP
PCNA, Cyclin D3, Erk, Caspase2, total S6
PCNA, Cyclin D3, Erk, RBBP, total S6
PCNA, Cyclin D3, pErk, Akt, pAkt
PCNA, Cyclin D3, pErk, Akt, Caspase2
PCNA, Cyclin D3, pErk, Akt, RBBP
PCNA, Cyclin D3, pErk, Akt, total S6
PCNA, Cyclin D3, pErk, pAkt, Caspase2
PCNA, Cyclin D3, pErk, pAkt, RBBP
PCNA, Cyclin D3, pErk, pAkt, total S6
PCNA, Cyclin D3, pErk, Caspase2, RBBP
PCNA, Cyclin D3, pErk, Caspase2, total S6
PCNA, Cyclin D3, pErk, RBBP, total S6
PCNA, Cyclin D3, Akt, pAkt, Caspase2
PCNA, Cyclin D3, Akt, pAkt, RBBP
PCNA, Cyclin D3, Akt, pAkt, total S6
PCNA, Cyclin D3, Akt, Caspase2, RBBP
PCNA, Cyclin D3, Akt, Caspase2, total S6
PCNA, Cyclin D3, Akt, RBBP, total S6
PCNA, Cyclin D3, pAkt, Caspase2, RBBP
PCNA, Cyclin D3, pAkt, Caspase2, total S6
PCNA, Cyclin D3, pAkt, RBBP, total S6
PCNA, Cyclin D3, Caspase2, RBBP, total S6
PCNA, MEK, s6, pS6, Erk
PCNA, MEK, s6, pS6, pErk
PCNA, MEK, s6, pS6, Akt
PCNA, MEK, s6, pS6, pAkt
PCNA, MEK, s6, pS6, Caspase2
PCNA, MEK, s6, pS6, RBBP
PCNA, MEK, s6, pS6, total S6
PCNA, MEK, s6, Erk, pErk
PCNA, MEK, s6, Erk, Akt
PCNA, MEK, s6, Erk, pAkt
PCNA, MEK, s6, Erk, Caspase2
PCNA, MEK, s6, Erk, RBBP
PCNA, MEK, s6, Erk, total S6
PCNA, MEK, s6, pErk, Akt
PCNA, MEK, s6, pErk, pAkt
PCNA, MEK, s6, pErk, Caspase2
PCNA, MEK, s6, pErk, RBBP
PCNA, MEK, s6, pErk, total S6
PCNA, MEK, s6, Akt, pAkt
PCNA, MEK, s6, Akt, Caspase2
PCNA, MEK, s6, Akt, RBBP
PCNA, MEK, s6, Akt, total S6
PCNA, MEK, s6, pAkt, Caspase2
PCNA, MEK, s6, pAkt, RBBP
PCNA, MEK, s6, pAkt, total S6
PCNA, Cyclin D3, pS6, Erk, pErk, pAkt, total S6
PCNA, Cyclin D3, pS6, Erk, pErk, Caspase2, RBBP
PCNA, Cyclin D3, pS6, Erk, pErk, Caspase2, total S6
PCNA, Cyclin D3, pS6, Erk, pErk, RBBP, total S6
PCNA, Cyclin D3, pS6, Erk, Akt, pAkt, Caspase2
PCNA, Cyclin D3, pS6, Erk, Akt, pAkt, RBBP
PCNA, Cyclin D3, pS6, Erk, Akt, pAkt, total S6
PCNA, Cyclin D3, pS6, Erk, Akt, Caspase2, RBBP
PCNA, Cyclin D3, pS6, Erk, Akt, Caspase2, total S6
PCNA, Cyclin D3, pS6, Erk, Akt, RBBP, total S6
PCNA, Cyclin D3, pS6, Erk, pAkt, Caspase2, RBBP
PCNA, Cyclin D3, pS6, Erk, pAkt, Caspase2, total S6
PCNA, Cyclin D3, pS6, Erk, pAkt, RBBP, total S6
PCNA, Cyclin D3, pS6, Erk, Caspase2, RBBP, total S6
PCNA, Cyclin D3, pS6, pErk, Akt, pAkt, Caspase2
PCNA, Cyclin D3, pS6, pErk, Akt, pAkt, RBBP
PCNA, Cyclin D3, pS6, pErk, Akt, pAkt, total S6
PCNA, Cyclin D3, pS6, pErk, Akt, Caspase2, RBBP
PCNA, Cyclin D3, pS6, pErk, Akt, Caspase2, total S6
PCNA, Cyclin D3, pS6, pErk, Akt, RBBP, total S6
PCNA, Cyclin D3, pS6, pErk, pAkt, Caspase2, RBBP
PCNA, Cyclin D3, pS6, pErk, pAkt, Caspase2, total S6
PCNA, Cyclin D3, pS6, pErk, pAkt, RBBP, total S6
PCNA, Cyclin D3, pS6, pErk, Caspase2, RBBP, total S6
PCNA, Cyclin D3, pS6, Akt, pAkt, Caspase2, RBBP
PCNA, Cyclin D3, pS6, Akt, pAkt, Caspase2, total S6
PCNA, Cyclin D3, pS6, Akt, pAkt, RBBP, total S6
PCNA, Cyclin D3, pS6, Akt, Caspase2, RBBP, total S6
PCNA, Cyclin D3, pS6, pAkt, Caspase2, RBBP, total S6
PCNA, Cyclin D3, Erk, pErk, Akt, pAkt, Caspase2
PCNA, Cyclin D3, Erk, pErk, Akt, pAkt, RBBP
PCNA, Cyclin D3, Erk, pErk, Akt, pAkt, total S6
PCNA, Cyclin D3, Erk, pErk, Akt, Caspase2, RBBP
PCNA, Cyclin D3, Erk, pErk, Akt, Caspase2, total S6
PCNA, Cyclin D3, Erk, pErk, Akt, RBBP, total S6
PCNA, Cyclin D3, Erk, pErk, pAkt, Caspase2, RBBP
PCNA, Cyclin D3, Erk, pErk, pAkt, Caspase2, total S6
PCNA, Cyclin D3, Erk, pErk, pAkt, RBBP, total S6
PCNA, Cyclin D3, Erk, pErk, Caspase2, RBBP, total S6
PCNA, Cyclin D3, Erk, Akt, pAkt, Caspase2, RBBP
PCNA, Cyclin D3, Erk, Akt, pAkt, Caspase2, total S6
PCNA, Cyclin D3, Erk, Akt, pAkt, RBBP, total S6
PCNA, Cyclin D3, Erk, Akt, Caspase2, RBBP, total S6
PCNA, Cyclin D3, Erk, pAkt, Caspase2, RBBP, total S6
PCNA, Cyclin D3, pErk, Akt, pAkt, Caspase2, RBBP
PCNA, Cyclin D3, pErk, Akt, pAkt, Caspase2, total S6
PCNA, Cyclin D3, pErk, Akt, pAkt, RBBP, total S6
PCNA, Cyclin D3, pErk, Akt, Caspase2, RBBP, total S6
PCNA, Cyclin D3, pErk, pAkt, Caspase2, RBBP, total S6
PCNA, Cyclin D3, Akt, pAkt, Caspase2, RBBP, total S6
PCNA, MEK, s6, pS6, Erk, pErk, Akt
PCNA, MEK, s6, pS6, Erk, pErk, pAkt
PCNA, MEK, s6, pS6, Erk, pErk, Caspase2
PCNA, MEK, s6, pS6, Erk, pErk, RBBP
PCNA, MEK, s6, pS6, Erk, pErk, total S6
PCNA, MEK, s6, pS6, Erk, Akt, pAkt
PCNA, MEK, s6, pS6, Erk, Akt, Caspase2
PCNA, MEK, s6, pS6, Erk, Akt, RBBP
PCNA, MEK, s6, pS6, Erk, Akt, total S6
PCNA, MEK, s6, pS6, Erk, pAkt, Caspase2
PCNA, MEK, s6, pS6, Erk, pAkt, RBBP
PCNA, MEK, s6, pS6, Erk, pAkt, total S6
PCNA, MEK, s6, pS6, Erk, Caspase2, RBBP
PCNA, MEK, s6, pS6, Erk, Caspase2, total S6
PCNA, MEK, s6, pS6, Erk, RBBP, total S6
PCNA, MEK, s6, pS6, pErk, Akt, pAkt
PCNA, MEK, s6, pS6, pErk, Akt, Caspase2
PCNA, MEK, s6, pS6, pErk, Akt, RBBP
PCNA, MEK, s6, pS6, pErk, Akt, total S6
PCNA, MEK, s6, pS6, pErk, pAkt, Caspase2
PCNA, MEK, s6, pS6, pErk, pAkt, RBBP
PCNA, MEK, s6, pS6, pErk, pAkt, total S6
PCNA, MEK, s6, pS6, pErk, Caspase2, RBBP
PCNA, MEK, s6, pS6, pErk, Caspase2, total S6
PCNA, MEK, s6, pS6, pErk, RBBP, total S6
PCNA, MEK, s6, pS6, Akt, pAkt, Caspase2
PCNA, MEK, s6, pS6, Akt, pAkt, RBBP
PCNA, MEK, s6, pS6, Akt, pAkt, total S6

TABLE 1-continued

Examples of Single Markers and Combinations of Markers

PCNA, MEK, s6, Caspase2, RBBP
PCNA, MEK, s6, Caspase2, total S6
PCNA, MEK, s6, RBBP, total S6
PCNA, MEK, pS6, Erk, pErk
PCNA, MEK, pS6, Erk, Akt
PCNA, MEK, pS6, Erk, pAkt
PCNA, MEK, pS6, Erk, Caspase2
PCNA, MEK, pS6, Erk, RBBP
PCNA, MEK, pS6, Erk, total S6
PCNA, MEK, pS6, pErk, Akt
PCNA, MEK, pS6, pErk, pAkt
PCNA, MEK, pS6, pErk, Caspase2
PCNA, MEK, pS6, pErk, RBBP
PCNA, MEK, pS6, pErk, total S6
PCNA, MEK, pS6, Akt, pAkt
PCNA, MEK, pS6, Akt, Caspase2
PCNA, MEK, pS6, Akt, RBBP
PCNA, MEK, pS6, Akt, total S6
PCNA, MEK, pS6, pAkt, Caspase2
PCNA, MEK, pS6, pAkt, RBBP
PCNA, MEK, pS6, pAkt, total S6
PCNA, MEK, pS6, Caspase2, RBBP
PCNA, MEK, pS6, Caspase2, total S6
PCNA, MEK, pS6, RBBP, total S6
PCNA, MEK, Erk, pErk, Akt
PCNA, MEK, Erk, pErk, pAkt
PCNA, MEK, Erk, pErk, Caspase2
PCNA, MEK, Erk, pErk, RBBP
PCNA, MEK, Erk, pErk, total S6
PCNA, MEK, Erk, Akt, pAkt
PCNA, MEK, Erk, Akt, Caspase2
PCNA, MEK, Erk, Akt, RBBP
PCNA, MEK, Erk, Akt, total S6
PCNA, MEK, Erk, pAkt, Caspase2
PCNA, MEK, Erk, pAkt, RBBP
PCNA, MEK, Erk, pAkt, total S6
PCNA, MEK, Erk, Caspase2, RBBP
PCNA, MEK, Erk, Caspase2, total S6
PCNA, MEK, Erk, RBBP, total S6
PCNA, MEK, pErk, Akt, pAkt
PCNA, MEK, pErk, Akt, Caspase2
PCNA, MEK, pErk, Akt, RBBP
PCNA, MEK, pErk, Akt, total S6
PCNA, MEK, pErk, pAkt, Caspase2
PCNA, MEK, pErk, pAkt, RBBP
PCNA, MEK, pErk, pAkt, total S6
PCNA, MEK, pErk, Caspase2, RBBP
PCNA, MEK, pErk, Caspase2, total S6
PCNA, MEK, pErk, RBBP, total S6
PCNA, MEK, Akt, pAkt, Caspase2
PCNA, MEK, Akt, pAkt, RBBP
PCNA, MEK, Akt, pAkt, total S6
PCNA, MEK, Akt, Caspase2, RBBP
PCNA, MEK, Akt, Caspase2, total S6
PCNA, MEK, Akt, RBBP, total S6
PCNA, MEK, pAkt, Caspase2, RBBP
PCNA, MEK, pAkt, Caspase2, total S6
PCNA, MEK, pAkt, RBBP, total S6
PCNA, MEK, Caspase2, RBBP, total S6
PCNA, s6, pS6, Erk, pErk
PCNA, s6, pS6, Erk, Akt
PCNA, s6, pS6, Erk, pAkt
PCNA, s6, pS6, Erk, Caspase2
PCNA, s6, pS6, Erk, RBBP
PCNA, s6, pS6, Erk, total S6
PCNA, s6, pS6, pErk, Akt
PCNA, s6, pS6, pErk, pAkt
PCNA, s6, pS6, pErk, Caspase2
PCNA, s6, pS6, pErk, RBBP
PCNA, s6, pS6, pErk, total S6
PCNA, s6, pS6, Akt, pAkt
PCNA, s6, pS6, Akt, Caspase2
PCNA, s6, pS6, Akt, RBBP
PCNA, s6, pS6, Akt, total S6
PCNA, s6, pS6, pAkt, Caspase2
PCNA, s6, pS6, pAkt, RBBP
PCNA, s6, pS6, pAkt, total S6
PCNA, s6, pS6, Caspase2, RBBP
PCNA, MEK, s6, pS6, Akt, Caspase2, RBBP
PCNA, MEK, s6, pS6, Akt, Caspase2, total S6
PCNA, MEK, s6, pS6, Akt, RBBP, total S6
PCNA, MEK, s6, pS6, pAkt, Caspase2, RBBP
PCNA, MEK, s6, pS6, pAkt, Caspase2, total S6
PCNA, MEK, s6, pS6, pAkt, RBBP, total S6
PCNA, MEK, s6, pS6, Caspase2, RBBP, total S6
PCNA, MEK, s6, Erk, pErk, Akt, pAkt
PCNA, MEK, s6, Erk, pErk, Akt, Caspase2
PCNA, MEK, s6, Erk, pErk, Akt, RBBP
PCNA, MEK, s6, Erk, pErk, Akt, total S6
PCNA, MEK, s6, Erk, pErk, pAkt, Caspase2
PCNA, MEK, s6, Erk, pErk, pAkt, RBBP
PCNA, MEK, s6, Erk, pErk, pAkt, total S6
PCNA, MEK, s6, Erk, pErk, Caspase2, RBBP
PCNA, MEK, s6, Erk, pErk, Caspase2, total S6
PCNA, MEK, s6, Erk, pErk, RBBP, total S6
PCNA, MEK, s6, Erk, Akt, pAkt, Caspase2
PCNA, MEK, s6, Erk, Akt, pAkt, RBBP
PCNA, MEK, s6, Erk, Akt, pAkt, total S6
PCNA, MEK, s6, Erk, Akt, Caspase2, RBBP
PCNA, MEK, s6, Erk, Akt, Caspase2, total S6
PCNA, MEK, s6, Erk, Akt, RBBP, total S6
PCNA, MEK, s6, Erk, pAkt, Caspase2, RBBP
PCNA, MEK, s6, Erk, pAkt, Caspase2, total S6
PCNA, MEK, s6, Erk, pAkt, RBBP, total S6
PCNA, MEK, s6, Erk, Caspase2, RBBP, total S6
PCNA, MEK, s6, pErk, Akt, pAkt, Caspase2
PCNA, MEK, s6, pErk, Akt, pAkt, RBBP
PCNA, MEK, s6, pErk, Akt, pAkt, total S6
PCNA, MEK, s6, pErk, Akt, Caspase2, RBBP
PCNA, MEK, s6, pErk, Akt, Caspase2, total S6
PCNA, MEK, s6, pErk, Akt, RBBP, total S6
PCNA, MEK, s6, pErk, pAkt, Caspase2, RBBP
PCNA, MEK, s6, pErk, pAkt, Caspase2, total S6
PCNA, MEK, s6, pErk, pAkt, RBBP, total S6
PCNA, MEK, s6, pErk, Caspase2, RBBP, total S6
PCNA, MEK, s6, Akt, pAkt, Caspase2, RBBP
PCNA, MEK, s6, Akt, pAkt, Caspase2, total S6
PCNA, MEK, s6, Akt, pAkt, RBBP, total S6
PCNA, MEK, s6, Akt, Caspase2, RBBP, total S6
PCNA, MEK, s6, pAkt, Caspase2, RBBP, total S6
PCNA, MEK, pS6, Erk, pErk, Akt, pAkt
PCNA, MEK, pS6, Erk, pErk, Akt, Caspase2
PCNA, MEK, pS6, Erk, pErk, Akt, RBBP
PCNA, MEK, pS6, Erk, pErk, Akt, total S6
PCNA, MEK, pS6, Erk, pErk, pAkt, Caspase2
PCNA, MEK, pS6, Erk, pErk, pAkt, RBBP
PCNA, MEK, pS6, Erk, pErk, pAkt, total S6
PCNA, MEK, pS6, Erk, pErk, Caspase2, RBBP
PCNA, MEK, pS6, Erk, pErk, Caspase2, total S6
PCNA, MEK, pS6, Erk, pErk, RBBP, total S6
PCNA, MEK, pS6, Erk, Akt, pAkt, Caspase2
PCNA, MEK, pS6, Erk, Akt, pAkt, RBBP
PCNA, MEK, pS6, Erk, Akt, pAkt, total S6
PCNA, MEK, pS6, Erk, Akt, Caspase2, RBBP
PCNA, MEK, pS6, Erk, Akt, Caspase2, total S6
PCNA, MEK, pS6, Erk, Akt, RBBP, total S6
PCNA, MEK, pS6, Erk, pAkt, Caspase2, RBBP
PCNA, MEK, pS6, Erk, pAkt, Caspase2, total S6
PCNA, MEK, pS6, Erk, pAkt, RBBP, total S6
PCNA, MEK, pS6, Erk, Caspase2, RBBP, total S6
PCNA, MEK, pS6, pErk, Akt, pAkt, Caspase2
PCNA, MEK, pS6, pErk, Akt, pAkt, RBBP
PCNA, MEK, pS6, pErk, Akt, pAkt, total S6
PCNA, MEK, pS6, pErk, Akt, Caspase2, RBBP
PCNA, MEK, pS6, pErk, Akt, Caspase2, total S6
PCNA, MEK, pS6, pErk, Akt, RBBP, total S6
PCNA, MEK, pS6, pErk, pAkt, Caspase2, RBBP
PCNA, MEK, pS6, pErk, pAkt, Caspase2, total S6
PCNA, MEK, pS6, pErk, pAkt, RBBP, total S6
PCNA, MEK, pS6, pErk, Caspase2, RBBP, total S6
PCNA, MEK, pS6, Akt, pAkt, Caspase2, RBBP
PCNA, MEK, pS6, Akt, pAkt, Caspase2, total S6
PCNA, MEK, pS6, Akt, pAkt, RBBP, total S6
PCNA, MEK, pS6, Akt, Caspase2, RBBP, total S6
PCNA, MEK, pS6, pAkt, Caspase2, RBBP, total S6
PCNA, MEK, Erk, pErk, Akt, pAkt, Caspase2

TABLE 1-continued

Examples of Single Markers and Combinations of Markers

PCNA, s6, pS6, Caspase2, total S6
PCNA, s6, pS6, RBBP, total S6
PCNA, s6, Erk, pErk, Akt
PCNA, s6, Erk, pErk, pAkt
PCNA, s6, Erk, pErk, Caspase2
PCNA, s6, Erk, pErk, RBBP
PCNA, s6, Erk, pErk, total S6
PCNA, s6, Erk, Akt, pAkt
PCNA, s6, Erk, Akt, Caspase2
PCNA, s6, Erk, Akt, RBBP
PCNA, s6, Erk, Akt, total S6
PCNA, s6, Erk, pAkt, Caspase2
PCNA, s6, Erk, pAkt, RBBP
PCNA, s6, Erk, pAkt, total S6
PCNA, s6, Erk, Caspase2, RBBP
PCNA, s6, Erk, Caspase2, total S6
PCNA, s6, Erk, RBBP, total S6
PCNA, s6, pErk, Akt, pAkt
PCNA, s6, pErk, Akt, Caspase2
PCNA, s6, pErk, Akt, RBBP
PCNA, s6, pErk, Akt, total S6
PCNA, s6, pErk, pAkt, Caspase2
PCNA, s6, pErk, pAkt, RBBP
PCNA, s6, pErk, pAkt, total S6
PCNA, s6, pErk, Caspase2, RBBP
PCNA, s6, pErk, Caspase2, total S6
PCNA, s6, pErk, RBBP, total S6
PCNA, s6, Akt, pAkt, Caspase2
PCNA, s6, Akt, pAkt, RBBP
PCNA, s6, Akt, pAkt, total S6
PCNA, s6, Akt, Caspase2, RBBP
PCNA, s6, Akt, Caspase2, total S6
PCNA, s6, Akt, RBBP, total S6
PCNA, s6, pAkt, Caspase2, RBBP
PCNA, s6, pAkt, Caspase2, total S6
PCNA, s6, pAkt, RBBP, total S6
PCNA, s6, Caspase2, RBBP, total S6
PCNA, pS6, Erk, pErk, Akt
PCNA, pS6, Erk, pErk, pAkt
PCNA, pS6, Erk, pErk, Caspase2
PCNA, pS6, Erk, pErk, RBBP
PCNA, pS6, Erk, pErk, total S6
PCNA, pS6, Erk, Akt, pAkt
PCNA, pS6, Erk, Akt, Caspase2
PCNA, pS6, Erk, Akt, RBBP
PCNA, pS6, Erk, Akt, total S6
PCNA, pS6, Erk, pAkt, Caspase2
PCNA, pS6, Erk, pAkt, RBBP
PCNA, pS6, Erk, pAkt, total S6
PCNA, pS6, Erk, Caspase2, RBBP
PCNA, pS6, Erk, Caspase2, total S6
PCNA, pS6, Erk, RBBP, total S6
PCNA, pS6, pErk, Akt, pAkt
PCNA, pS6, pErk, Akt, Caspase2
PCNA, pS6, pErk, Akt, RBBP
PCNA, pS6, pErk, Akt, total S6
PCNA, pS6, pErk, pAkt, Caspase2
PCNA, pS6, pErk, pAkt, RBBP
PCNA, pS6, pErk, pAkt, total S6
PCNA, pS6, pErk, Caspase2, RBBP
PCNA, pS6, pErk, Caspase2, total S6
PCNA, pS6, pErk, RBBP, total S6
PCNA, pS6, Akt, pAkt, Caspase2
PCNA, pS6, Akt, pAkt, RBBP
PCNA, pS6, Akt, pAkt, total S6
PCNA, pS6, Akt, Caspase2, RBBP
PCNA, pS6, Akt, Caspase2, total S6
PCNA, pS6, Akt, RBBP, total S6
PCNA, pS6, pAkt, Caspase2, RBBP
PCNA, pS6, pAkt, Caspase2, total S6
PCNA, pS6, pAkt, RBBP, total S6
PCNA, pS6, Caspase2, RBBP, total S6
PCNA, Erk, pErk, Akt, pAkt
PCNA, Erk, pErk, Akt, Caspase2
PCNA, Erk, pErk, Akt, RBBP
PCNA, Erk, pErk, Akt, total S6
PCNA, Erk, pErk, pAkt, Caspase2
PCNA, Erk, pErk, pAkt, RBBP PCNA, MEK, Erk, pErk, Akt, pAkt, RBBP
PCNA, MEK, Erk, pErk, Akt, pAkt, total S6
PCNA, MEK, Erk, pErk, Akt, Caspase2, RBBP
PCNA, MEK, Erk, pErk, Akt, Caspase2, total S6
PCNA, MEK, Erk, pErk, Akt, RBBP, total S6
PCNA, MEK, Erk, pErk, pAkt, Caspase2, RBBP
PCNA, MEK, Erk, pErk, pAkt, Caspase2, total S6
PCNA, MEK, Erk, pErk, pAkt, RBBP, total S6
PCNA, MEK, Erk, pErk, Caspase2, RBBP, total S6
PCNA, MEK, Erk, Akt, pAkt, Caspase2, RBBP
PCNA, MEK, Erk, Akt, pAkt, Caspase2, total S6
PCNA, MEK, Erk, Akt, pAkt, RBBP, total S6
PCNA, MEK, Erk, Akt, Caspase2, RBBP, total S6
PCNA, MEK, Erk, pAkt, Caspase2, RBBP, total S6
PCNA, MEK, pErk, Akt, pAkt, Caspase2, RBBP
PCNA, MEK, pErk, Akt, pAkt, Caspase2, total S6
PCNA, MEK, pErk, Akt, pAkt, RBBP, total S6
PCNA, MEK, pErk, Akt, Caspase2, RBBP, total S6
PCNA, MEK, pErk, pAkt, Caspase2, RBBP, total S6
PCNA, MEK, Akt, pAkt, Caspase2, RBBP, total S6
PCNA, s6, pS6, Erk, pErk, Akt, pAkt
PCNA, s6, pS6, Erk, pErk, Akt, Caspase2
PCNA, s6, pS6, Erk, pErk, Akt, RBBP
PCNA, s6, pS6, Erk, pErk, Akt, total S6
PCNA, s6, pS6, Erk, pErk, pAkt, Caspase2
PCNA, s6, pS6, Erk, pErk, pAkt, RBBP
PCNA, s6, pS6, Erk, pErk, pAkt, total S6
PCNA, s6, pS6, Erk, pErk, Caspase2, RBBP
PCNA, s6, pS6, Erk, pErk, Caspase2, total S6
PCNA, s6, pS6, Erk, pErk, RBBP, total S6
PCNA, s6, pS6, Erk, Akt, pAkt, Caspase2
PCNA, s6, pS6, Erk, Akt, pAkt, RBBP
PCNA, s6, pS6, Erk, Akt, pAkt, total S6
PCNA, s6, pS6, Erk, Akt, Caspase2, RBBP
PCNA, s6, pS6, Erk, Akt, Caspase2, total S6
PCNA, s6, pS6, Erk, Akt, RBBP, total S6
PCNA, s6, pS6, Erk, pAkt, Caspase2, RBBP
PCNA, s6, pS6, Erk, pAkt, Caspase2, total S6
PCNA, s6, pS6, Erk, pAkt, RBBP, total S6
PCNA, s6, pS6, Erk, Caspase2, RBBP, total S6
PCNA, s6, pS6, pErk, Akt, pAkt, Caspase2
PCNA, s6, pS6, pErk, Akt, pAkt, RBBP
PCNA, s6, pS6, pErk, Akt, pAkt, total S6
PCNA, s6, pS6, pErk, Akt, Caspase2, RBBP
PCNA, s6, pS6, pErk, Akt, Caspase2, total S6
PCNA, s6, pS6, pErk, Akt, RBBP, total S6
PCNA, s6, pS6, pErk, pAkt, Caspase2, RBBP
PCNA, s6, pS6, pErk, pAkt, Caspase2, total S6
PCNA, s6, pS6, pErk, pAkt, RBBP, total S6
PCNA, s6, pS6, pErk, Caspase2, RBBP, total S6
PCNA, s6, pS6, Akt, pAkt, Caspase2, RBBP
PCNA, s6, pS6, Akt, pAkt, Caspase2, total S6
PCNA, s6, pS6, Akt, pAkt, RBBP, total S6
PCNA, s6, pS6, Akt, Caspase2, RBBP, total S6
PCNA, s6, pS6, pAkt, Caspase2, RBBP, total S6
PCNA, s6, Erk, pErk, Akt, pAkt, Caspase2
PCNA, s6, Erk, pErk, Akt, pAkt, RBBP
PCNA, s6, Erk, pErk, Akt, pAkt, total S6
PCNA, s6, Erk, pErk, Akt, Caspase2, RBBP
PCNA, s6, Erk, pErk, Akt, Caspase2, total S6
PCNA, s6, Erk, pErk, Akt, RBBP, total S6
PCNA, s6, Erk, pErk, pAkt, Caspase2, RBBP
PCNA, s6, Erk, pErk, pAkt, Caspase2, total S6
PCNA, s6, Erk, pErk, pAkt, RBBP, total S6
PCNA, s6, Erk, pErk, Caspase2, RBBP, total S6
PCNA, s6, Erk, Akt, pAkt, Caspase2, RBBP
PCNA, s6, Erk, Akt, pAkt, Caspase2, total S6
PCNA, s6, Erk, Akt, pAkt, RBBP, total S6
PCNA, s6, Erk, Akt, Caspase2, RBBP, total S6
PCNA, s6, Erk, pAkt, Caspase2, RBBP, total S6
PCNA, s6, pErk, Akt, pAkt, Caspase2, RBBP
PCNA, s6, pErk, Akt, pAkt, Caspase2, total S6
PCNA, s6, pErk, Akt, pAkt, RBBP, total S6
PCNA, s6, pErk, Akt, Caspase2, RBBP, total S6
PCNA, s6, pErk, pAkt, Caspase2, RBBP, total S6
PCNA, s6, Akt, pAkt, Caspase2, RBBP, total S6
PCNA, pS6, Erk, pErk, Akt, pAkt, Caspase2
PCNA, pS6, Erk, pErk, Akt, pAkt, RBBP TABLE 1-continued Examples of Single Markers and Combinations of Markers PCNA, Erk, pErk, pAkt, total S6
PCNA, Erk, pErk, Caspase2, RBBP
PCNA, Erk, pErk, Caspase2, total S6
PCNA, Erk, pErk, RBBP, total S6
PCNA, Erk, Akt, pAkt, Caspase2
PCNA, Erk, Akt, pAkt, RBBP
PCNA, Erk, Akt, pAkt, total S6
PCNA, Erk, Akt, Caspase2, RBBP
PCNA, Erk, Akt, Caspase2, total S6
PCNA, Erk, Akt, RBBP, total S6
PCNA, Erk, pAkt, Caspase2, RBBP
PCNA, Erk, pAkt, Caspase2, total S6
PCNA, Erk, pAkt, RBBP, total S6
PCNA, Erk, Caspase2, RBBP, total S6
PCNA, pErk, Akt, pAkt, Caspase2
PCNA, pErk, Akt, pAkt, RBBP
PCNA, pErk, Akt, pAkt, total S6
PCNA, pErk, Akt, Caspase2, RBBP
PCNA, pErk, Akt, Caspase2, total S6
PCNA, pErk, Akt, RBBP, total S6
PCNA, pErk, pAkt, Caspase2, RBBP
PCNA, pErk, pAkt, Caspase2, total S6
PCNA, pErk, pAkt, RBBP, total S6
PCNA, pErk, Caspase2, RBBP, total S6
PCNA, Akt, pAkt, Caspase2, RBBP
PCNA, Akt, pAkt, Caspase2, total S6
PCNA, Akt, pAkt, RBBP, total S6
PCNA, Akt, Caspase2, RBBP, total S6
PCNA, pAkt, Caspase2, RBBP, total S6
Cyclin D1, Cyclin D3, MEK, s6, pS6
Cyclin D1, Cyclin D3, MEK, s6, Erk
Cyclin D1, Cyclin D3, MEK, s6, pErk
Cyclin D1, Cyclin D3, MEK, s6, Akt
Cyclin D1, Cyclin D3, MEK, s6, pAkt
Cyclin D1, Cyclin D3, MEK, s6, Caspase2
Cyclin D1, Cyclin D3, MEK, s6, RBBP
Cyclin D1, Cyclin D3, MEK, s6, total S6
Cyclin D1, Cyclin D3, MEK, pS6, Erk
Cyclin D1, Cyclin D3, MEK, pS6, pErk
Cyclin D1, Cyclin D3, MEK, pS6, Akt
Cyclin D1, Cyclin D3, MEK, pS6, pAkt
Cyclin D1, Cyclin D3, MEK, pS6, Caspase2
Cyclin D1, Cyclin D3, MEK, pS6, RBBP
Cyclin D1, Cyclin D3, MEK, pS6, total S6
Cyclin D1, Cyclin D3, MEK, Erk, pErk
Cyclin D1, Cyclin D3, MEK, Erk, Akt
Cyclin D1, Cyclin D3, MEK, Erk, pAkt
Cyclin D1, Cyclin D3, MEK, Erk, Caspase2
Cyclin D1, Cyclin D3, MEK, Erk, RBBP
Cyclin D1, Cyclin D3, MEK, Erk, total S6
Cyclin D1, Cyclin D3, MEK, pErk, Akt
Cyclin D1, Cyclin D3, MEK, pErk, pAkt
Cyclin D1, Cyclin D3, MEK, pErk, Caspase2
Cyclin D1, Cyclin D3, MEK, pErk, RBBP
Cyclin D1, Cyclin D3, MEK, pErk, total S6
Cyclin D1, Cyclin D3, MEK, Akt, pAkt
Cyclin D1, Cyclin D3, MEK, Akt, Caspase2
Cyclin D1, Cyclin D3, MEK, Akt, RBBP
Cyclin D1, Cyclin D3, MEK, Akt, total S6
Cyclin D1, Cyclin D3, MEK, pAkt, Caspase2
Cyclin D1, Cyclin D3, MEK, pAkt, RBBP
Cyclin D1, Cyclin D3, MEK, pAkt, total S6
Cyclin D1, Cyclin D3, MEK, Caspase2, RBBP
Cyclin D1, Cyclin D3, MEK, Caspase2, total S6
Cyclin D1, Cyclin D3, MEK, RBBP, total S6
Cyclin D1, Cyclin D3, s6, pS6, Erk
Cyclin D1, Cyclin D3, s6, pS6, pErk
Cyclin D1, Cyclin D3, s6, pS6, Akt
Cyclin D1, Cyclin D3, s6, pS6, pAkt
Cyclin D1, Cyclin D3, s6, pS6, Caspase2
Cyclin D1, Cyclin D3, s6, pS6, RBBP
Cyclin D1, Cyclin D3, s6, pS6, total S6
Cyclin D1, Cyclin D3, s6, Erk, pErk
Cyclin D1, Cyclin D3, s6, Erk, Akt
Cyclin D1, Cyclin D3, s6, Erk, pAkt
Cyclin D1, Cyclin D3, s6, Erk, Caspase2
Cyclin D1, Cyclin D3, s6, Erk, RBBP
Cyclin D1, Cyclin D3, s6, Erk, total S6
PCNA, pS6, Erk, pErk, Akt, pAkt, total S6
PCNA, pS6, Erk, pErk, Akt, Caspase2, RBBP
PCNA, pS6, Erk, pErk, Akt, Caspase2, total S6
PCNA, pS6, Erk, pErk, Akt, RBBP, total S6
PCNA, pS6, Erk, pErk, pAkt, Caspase2, RBBP
PCNA, pS6, Erk, pErk, pAkt, Caspase2, total S6
PCNA, pS6, Erk, pErk, pAkt, RBBP, total S6
PCNA, pS6, Erk, pErk, Caspase2, RBBP, total S6
PCNA, pS6, Erk, Akt, pAkt, Caspase2, RBBP
PCNA, pS6, Erk, Akt, pAkt, Caspase2, total S6
PCNA, pS6, Erk, Akt, pAkt, RBBP, total S6
PCNA, pS6, Erk, Akt, Caspase2, RBBP, total S6
PCNA, pS6, Erk, pAkt, Caspase2, RBBP, total S6
PCNA, pS6, pErk, Akt, pAkt, Caspase2, RBBP
PCNA, pS6, pErk, Akt, pAkt, Caspase2, total S6
PCNA, pS6, pErk, Akt, pAkt, RBBP, total S6
PCNA, pS6, pErk, Akt, Caspase2, RBBP, total S6
PCNA, pS6, pErk, pAkt, Caspase2, RBBP, total S6
PCNA, pS6, Akt, pAkt, Caspase2, RBBP, total S6
PCNA, Erk, pErk, Akt, pAkt, Caspase2, RBBP
PCNA, Erk, pErk, Akt, pAkt, Caspase2, total S6
PCNA, Erk, pErk, Akt, pAkt, RBBP, total S6
PCNA, Erk, pErk, Akt, Caspase2, RBBP, total S6
PCNA, Erk, pErk, pAkt, Caspase2, RBBP, total S6
PCNA, Erk, Akt, pAkt, Caspase2, RBBP, total S6
PCNA, pErk, Akt, pAkt, Caspase2, RBBP, total S6
Cyclin D1, Cyclin D3, MEK, s6, pS6, Erk, pErk
Cyclin D1, Cyclin D3, MEK, s6, pS6, Erk, Akt
Cyclin D1, Cyclin D3, MEK, s6, pS6, Erk, pAkt
Cyclin D1, Cyclin D3, MEK, s6, pS6, Erk, Caspase2
Cyclin D1, Cyclin D3, MEK, s6, pS6, Erk, RBBP
Cyclin D1, Cyclin D3, MEK, s6, pS6, Erk, total S6
Cyclin D1, Cyclin D3, MEK, s6, pS6, pErk, Akt
Cyclin D1, Cyclin D3, MEK, s6, pS6, pErk, pAkt
Cyclin D1, Cyclin D3, MEK, s6, pS6, pErk, Caspase2
Cyclin D1, Cyclin D3, MEK, s6, pS6, pErk, RBBP
Cyclin D1, Cyclin D3, MEK, s6, pS6, pErk, total S6
Cyclin D1, Cyclin D3, MEK, s6, pS6, Akt, pAkt
Cyclin D1, Cyclin D3, MEK, s6, pS6, Akt, Caspase2
Cyclin D1, Cyclin D3, MEK, s6, pS6, Akt, RBBP
Cyclin D1, Cyclin D3, MEK, s6, pS6, Akt, total S6
Cyclin D1, Cyclin D3, MEK, s6, pS6, pAkt, Caspase2
Cyclin D1, Cyclin D3, MEK, s6, pS6, pAkt, RBBP
Cyclin D1, Cyclin D3, MEK, s6, pS6, pAkt, total S6
Cyclin D1, Cyclin D3, MEK, s6, pS6, Caspase2, RBBP
Cyclin D1, Cyclin D3, MEK, s6, pS6, Caspase2, total S6
Cyclin D1, Cyclin D3, MEK, s6, pS6, RBBP, total S6
Cyclin D1, Cyclin D3, MEK, s6, Erk, pErk, Akt
Cyclin D1, Cyclin D3, MEK, s6, Erk, pErk, pAkt
Cyclin D1, Cyclin D3, MEK, s6, Erk, pErk, Caspase2
Cyclin D1, Cyclin D3, MEK, s6, Erk, pErk, RBBP
Cyclin D1, Cyclin D3, MEK, s6, Erk, pErk, total S6
Cyclin D1, Cyclin D3, MEK, s6, Erk, Akt, pAkt
Cyclin D1, Cyclin D3, MEK, s6, Erk, Akt, Caspase2
Cyclin D1, Cyclin D3, MEK, s6, Erk, Akt, RBBP
Cyclin D1, Cyclin D3, MEK, s6, Erk, Akt, total S6
Cyclin D1, Cyclin D3, MEK, s6, Erk, pAkt, Caspase2
Cyclin D1, Cyclin D3, MEK, s6, Erk, pAkt, RBBP
Cyclin D1, Cyclin D3, MEK, s6, Erk, pAkt, total S6
Cyclin D1, Cyclin D3, MEK, s6, Erk, Caspase2, RBBP
Cyclin D1, Cyclin D3, MEK, s6, Erk, Caspase2, total S6
Cyclin D1, Cyclin D3, MEK, s6, Erk, RBBP, total S6
Cyclin D1, Cyclin D3, MEK, s6, pErk, Akt, pAkt
Cyclin D1, Cyclin D3, MEK, s6, pErk, Akt, Caspase2
Cyclin D1, Cyclin D3, MEK, s6, pErk, Akt, RBBP
Cyclin D1, Cyclin D3, MEK, s6, pErk, Akt, total S6
Cyclin D1, Cyclin D3, MEK, s6, pErk, pAkt, Caspase2
Cyclin D1, Cyclin D3, MEK, s6, pErk, pAkt, RBBP
Cyclin D1, Cyclin D3, MEK, s6, pErk, pAkt, total S6
Cyclin D1, Cyclin D3, MEK, s6, pErk, Caspase2, RBBP
Cyclin D1, Cyclin D3, MEK, s6, pErk, Caspase2, total S6
Cyclin D1, Cyclin D3, MEK, s6, pErk, RBBP, total S6
Cyclin D1, Cyclin D3, MEK, s6, Akt, pAkt, Caspase2
Cyclin D1, Cyclin D3, MEK, s6, Akt, pAkt, RBBP
Cyclin D1, Cyclin D3, MEK, s6, Akt, pAkt, total S6
Cyclin D1, Cyclin D3, MEK, s6, Akt, Caspase2, RBBP
Cyclin D1, Cyclin D3, MEK, s6, Akt, Caspase2, total S6
Cyclin D1, Cyclin D3, MEK, s6, Akt, RBBP, total S6

TABLE 1-continued

Examples of Single Markers and Combinations of Markers

Cyclin D1, Cyclin D3, s6, pErk, Akt
Cyclin D1, Cyclin D3, s6, pErk, pAkt
Cyclin D1, Cyclin D3, s6, pErk, Caspase2
Cyclin D1, Cyclin D3, s6, pErk, RBBP
Cyclin D1, Cyclin D3, s6, pErk, total S6
Cyclin D1, Cyclin D3, s6, Akt, pAkt
Cyclin D1, Cyclin D3, s6, Akt, Caspase2
Cyclin D1, Cyclin D3, s6, Akt, RBBP
Cyclin D1, Cyclin D3, s6, Akt, total S6
Cyclin D1, Cyclin D3, s6, pAkt, Caspase2
Cyclin D1, Cyclin D3, s6, pAkt, RBBP
Cyclin D1, Cyclin D3, s6, pAkt, total S6
Cyclin D1, Cyclin D3, s6, Caspase2, RBBP
Cyclin D1, Cyclin D3, s6, Caspase2, total S6
Cyclin D1, Cyclin D3, s6, RBBP, total S6
Cyclin D1, Cyclin D3, pS6, Erk, pErk
Cyclin D1, Cyclin D3, pS6, Erk, Akt
Cyclin D1, Cyclin D3, pS6, Erk, pAkt
Cyclin D1, Cyclin D3, pS6, Erk, Caspase2
Cyclin D1, Cyclin D3, pS6, Erk, RBBP
Cyclin D1, Cyclin D3, pS6, Erk, total S6
Cyclin D1, Cyclin D3, pS6, pErk, Akt
Cyclin D1, Cyclin D3, pS6, pErk, pAkt
Cyclin D1, Cyclin D3, pS6, pErk, Caspase2
Cyclin D1, Cyclin D3, pS6, pErk, RBBP
Cyclin D1, Cyclin D3, pS6, pErk, total S6
Cyclin D1, Cyclin D3, pS6, Akt, pAkt
Cyclin D1, Cyclin D3, pS6, Akt, Caspase2
Cyclin D1, Cyclin D3, pS6, Akt, RBBP
Cyclin D1, Cyclin D3, pS6, Akt, total S6
Cyclin D1, Cyclin D3, pS6, pAkt, Caspase2
Cyclin D1, Cyclin D3, pS6, pAkt, RBBP
Cyclin D1, Cyclin D3, pS6, pAkt, total S6
Cyclin D1, Cyclin D3, pS6, Caspase2, RBBP
Cyclin D1, Cyclin D3, pS6, Caspase2, total S6
Cyclin D1, Cyclin D3, pS6, RBBP, total S6
Cyclin D1, Cyclin D3, Erk, pErk, Akt
Cyclin D1, Cyclin D3, Erk, pErk, pAkt
Cyclin D1, Cyclin D3, Erk, pErk, Caspase2
Cyclin D1, Cyclin D3, Erk, pErk, RBBP
Cyclin D1, Cyclin D3, Erk, pErk, total S6
Cyclin D1, Cyclin D3, Erk, Akt, pAkt
Cyclin D1, Cyclin D3, Erk, Akt, Caspase2
Cyclin D1, Cyclin D3, Erk, Akt, RBBP
Cyclin D1, Cyclin D3, Erk, Akt, total S6
Cyclin D1, Cyclin D3, Erk, pAkt, Caspase2
Cyclin D1, Cyclin D3, Erk, pAkt, RBBP
Cyclin D1, Cyclin D3, Erk, pAkt, total S6
Cyclin D1, Cyclin D3, Erk, Caspase2, RBBP
Cyclin D1, Cyclin D3, Erk, Caspase2, total S6
Cyclin D1, Cyclin D3, Erk, RBBP, total S6
Cyclin D1, Cyclin D3, pErk, Akt, pAkt
Cyclin D1, Cyclin D3, pErk, Akt, Caspase2
Cyclin D1, Cyclin D3, pErk, Akt, RBBP
Cyclin D1, Cyclin D3, pErk, Akt, total S6
Cyclin D1, Cyclin D3, pErk, pAkt, Caspase2
Cyclin D1, Cyclin D3, pErk, pAkt, RBBP
Cyclin D1, Cyclin D3, pErk, pAkt, total S6
Cyclin D1, Cyclin D3, pErk, Caspase2, RBBP
Cyclin D1, Cyclin D3, pErk, Caspase2, total S6
Cyclin D1, Cyclin D3, pErk, RBBP, total S6
Cyclin D1, Cyclin D3, Akt, pAkt, Caspase2
Cyclin D1, Cyclin D3, Akt, pAkt, RBBP
Cyclin D1, Cyclin D3, Akt, pAkt, total S6
Cyclin D1, Cyclin D3, Akt, Caspase2, RBBP
Cyclin D1, Cyclin D3, Akt, Caspase2, total S6
Cyclin D1, Cyclin D3, Akt, RBBP, total S6
Cyclin D1, Cyclin D3, pAkt, Caspase2, RBBP
Cyclin D1, Cyclin D3, pAkt, Caspase2, total S6

Cyclin D1, Cyclin D3, pAkt, RBBP, total S6
Cyclin D1, Cyclin D3, Caspase2, RBBP, total S6

Cyclin D1, MEK, s6, pS6, Erk
Cyclin D1, MEK, s6, pS6, pErk
Cyclin D1, MEK, s6, pS6, Akt
Cyclin D1, MEK, s6, pS6, pAkt
Cyclin D1, MEK, s6, pS6, Caspase2

Cyclin D1, Cyclin D3, MEK, s6, pAkt, Caspase2, RBBP
Cyclin D1, Cyclin D3, MEK, s6, pAkt, Caspase2, total S6
Cyclin D1, Cyclin D3, MEK, s6, pAkt, RBBP, total S6
Cyclin D1, Cyclin D3, MEK, s6, Caspase2, RBBP, total S6
Cyclin D1, Cyclin D3, MEK, pS6, Erk, pErk, Akt
Cyclin D1, Cyclin D3, MEK, pS6, Erk, pErk, pAkt
Cyclin D1, Cyclin D3, MEK, pS6, Erk, pErk, Caspase2
Cyclin D1, Cyclin D3, MEK, pS6, Erk, pErk, RBBP
Cyclin D1, Cyclin D3, MEK, pS6, Erk, pErk, total S6
Cyclin D1, Cyclin D3, MEK, pS6, Erk, Akt, pAkt
Cyclin D1, Cyclin D3, MEK, pS6, Erk, Akt, Caspase2
Cyclin D1, Cyclin D3, MEK, pS6, Erk, Akt, RBBP
Cyclin D1, Cyclin D3, MEK, pS6, Erk, Akt, total S6
Cyclin D1, Cyclin D3, MEK, pS6, Erk, pAkt, Caspase2
Cyclin D1, Cyclin D3, MEK, pS6, Erk, pAkt, RBBP
Cyclin D1, Cyclin D3, MEK, pS6, Erk, pAkt, total S6
Cyclin D1, Cyclin D3, MEK, pS6, Erk, Caspase2, RBBP
Cyclin D1, Cyclin D3, MEK, pS6, Erk, Caspase2, total S6
Cyclin D1, Cyclin D3, MEK, pS6, Erk, RBBP, total S6
Cyclin D1, Cyclin D3, MEK, pS6, pErk, Akt, pAkt
Cyclin D1, Cyclin D3, MEK, pS6, pErk, Akt, Caspase2
Cyclin D1, Cyclin D3, MEK, pS6, pErk, Akt, RBBP
Cyclin D1, Cyclin D3, MEK, pS6, pErk, Akt, total S6
Cyclin D1, Cyclin D3, MEK, pS6, pErk, pAkt, Caspase2
Cyclin D1, Cyclin D3, MEK, pS6, pErk, pAkt, RBBP
Cyclin D1, Cyclin D3, MEK, pS6, pErk, pAkt, total S6
Cyclin D1, Cyclin D3, MEK, pS6, pErk, Caspase2, RBBP
Cyclin D1, Cyclin D3, MEK, pS6, pErk, Caspase2, total S6
Cyclin D1, Cyclin D3, MEK, pS6, pErk, RBBP, total S6
Cyclin D1, Cyclin D3, MEK, pS6, Akt, pAkt, Caspase2
Cyclin D1, Cyclin D3, MEK, pS6, Akt, pAkt, RBBP
Cyclin D1, Cyclin D3, MEK, pS6, Akt, pAkt, total S6
Cyclin D1, Cyclin D3, MEK, pS6, Akt, Caspase2, RBBP
Cyclin D1, Cyclin D3, MEK, pS6, Akt, Caspase2, total S6
Cyclin D1, Cyclin D3, MEK, pS6, Akt, RBBP, total S6
Cyclin D1, Cyclin D3, MEK, pS6, pAkt, Caspase2, RBBP
Cyclin D1, Cyclin D3, MEK, pS6, pAkt, Caspase2, total S6
Cyclin D1, Cyclin D3, MEK, pS6, pAkt, RBBP, total S6
Cyclin D1, Cyclin D3, MEK, pS6, Caspase2, RBBP, total S6
Cyclin D1, Cyclin D3, MEK, Erk, pErk, Akt, pAkt
Cyclin D1, Cyclin D3, MEK, Erk, pErk, Akt, Caspase2
Cyclin D1, Cyclin D3, MEK, Erk, pErk, Akt, RBBP
Cyclin D1, Cyclin D3, MEK, Erk, pErk, Akt, total S6
Cyclin D1, Cyclin D3, MEK, Erk, pErk, pAkt, Caspase2
Cyclin D1, Cyclin D3, MEK, Erk, pErk, pAkt, RBBP
Cyclin D1, Cyclin D3, MEK, Erk, pErk, pAkt, total S6
Cyclin D1, Cyclin D3, MEK, Erk, pErk, Caspase2, RBBP
Cyclin D1, Cyclin D3, MEK, Erk, pErk, Caspase2, total S6
Cyclin D1, Cyclin D3, MEK, Erk, pErk, RBBP, total S6
Cyclin D1, Cyclin D3, MEK, Erk, Akt, pAkt, Caspase2
Cyclin D1, Cyclin D3, MEK, Erk, Akt, pAkt, RBBP
Cyclin D1, Cyclin D3, MEK, Erk, Akt, pAkt, total S6
Cyclin D1, Cyclin D3, MEK, Erk, Akt, Caspase2, RBBP
Cyclin D1, Cyclin D3, MEK, Erk, Akt, Caspase2, total S6
Cyclin D1, Cyclin D3, MEK, Erk, Akt, RBBP, total S6
Cyclin D1, Cyclin D3, MEK, Erk, pAkt, Caspase2, RBBP
Cyclin D1, Cyclin D3, MEK, Erk, pAkt, Caspase2, total S6
Cyclin D1, Cyclin D3, MEK, Erk, pAkt, RBBP, total S6
Cyclin D1, Cyclin D3, MEK, Erk, Caspase2, RBBP, total S6
Cyclin D1, Cyclin D3, MEK, pErk, Akt, pAkt, Caspase2
Cyclin D1, Cyclin D3, MEK, pErk, Akt, pAkt, RBBP
Cyclin D1, Cyclin D3, MEK, pErk, Akt, pAkt, total S6
Cyclin D1, Cyclin D3, MEK, pErk, Akt, Caspase2, RBBP
Cyclin D1, Cyclin D3, MEK, pErk, Akt, Caspase2, total S6
Cyclin D1, Cyclin D3, MEK, pErk, Akt, RBBP, total S6
Cyclin D1, Cyclin D3, MEK, pErk, pAkt, Caspase2, RBBP
Cyclin D1, Cyclin D3, MEK, pErk, pAkt, Caspase2, total S6
Cyclin D1, Cyclin D3, MEK, pErk, pAkt, RBBP, total S6
Cyclin D1, Cyclin D3, MEK, pErk, Caspase2, RBBP, total S6
Cyclin D1, Cyclin D3, MEK, Akt, pAkt, Caspase2, RBBP
Cyclin D1, Cyclin D3, MEK, Akt, pAkt, Caspase2, total S6
Cyclin D1, Cyclin D3, MEK, Akt, pAkt, RBBP, total S6
Cyclin D1, Cyclin D3, MEK, Akt, Caspase2, RBBP, total S6
Cyclin D1, Cyclin D3, MEK, pAkt, Caspase2, RBBP, total S6
Cyclin D1, Cyclin D3, s6, pS6, Erk, pErk, Akt
Cyclin D1, Cyclin D3, s6, pS6, Erk, pErk, pAkt TABLE 1-continued Examples of Single Markers and Combinations of Markers Cyclin D1, MEK, s6, pS6, RBBP
Cyclin D1, MEK, s6, pS6, total S6
Cyclin D1, MEK, s6, Erk, pErk
Cyclin D1, MEK, s6, Erk, Akt
Cyclin D1, MEK, s6, Erk, pAkt
Cyclin D1, MEK, s6, Erk, Caspase2
Cyclin D1, MEK, s6, Erk, RBBP
Cyclin D1, MEK, s6, Erk, total S6
Cyclin D1, MEK, s6, pErk, Akt
Cyclin D1, MEK, s6, pErk, pAkt
Cyclin D1, MEK, s6, pErk, Caspase2
Cyclin D1, MEK, s6, pErk, RBBP
Cyclin D1, MEK, s6, pErk, total S6
Cyclin D1, MEK, s6, Akt, pAkt
Cyclin D1, MEK, s6, Akt, Caspase2
Cyclin D1, MEK, s6, Akt, RBBP
Cyclin D1, MEK, s6, Akt, total S6
Cyclin D1, MEK, s6, pAkt, Caspase2
Cyclin D1, MEK, s6, pAkt, RBBP
Cyclin D1, MEK, s6, pAkt, total S6
Cyclin D1, MEK, s6, Caspase2, RBBP
Cyclin D1, MEK, s6, Caspase2, total S6
Cyclin D1, MEK, s6, RBBP, total S6
Cyclin D1, MEK, pS6, Erk, pErk
Cyclin D1, MEK, pS6, Erk, Akt
Cyclin D1, MEK, pS6, Erk, pAkt
Cyclin D1, MEK, pS6, Erk, Caspase2
Cyclin D1, MEK, pS6, Erk, RBBP
Cyclin D1, MEK, pS6, Erk, total S6
Cyclin D1, MEK, pS6, pErk, Akt
Cyclin D1, MEK, pS6, pErk, pAkt
Cyclin D1, MEK, pS6, pErk, Caspase2
Cyclin D1, MEK, pS6, pErk, RBBP
Cyclin D1, MEK, pS6, pErk, total S6
Cyclin D1, MEK, pS6, Akt, pAkt
Cyclin D1, MEK, pS6, Akt, Caspase2
Cyclin D1, MEK, pS6, Akt, RBBP
Cyclin D1, MEK, pS6, Akt, total S6
Cyclin D1, MEK, pS6, pAkt, Caspase2
Cyclin D1, MEK, pS6, pAkt, RBBP
Cyclin D1, MEK, pS6, pAkt, total S6
Cyclin D1, MEK, pS6, Caspase2, RBBP
Cyclin D1, MEK, pS6, Caspase2, total S6
Cyclin D1, MEK, pS6, RBBP, total S6
Cyclin D1, MEK, Erk, pErk, Akt
Cyclin D1, MEK, Erk, pErk, pAkt
Cyclin D1, MEK, Erk, pErk, Caspase2
Cyclin D1, MEK, Erk, pErk, RBBP
Cyclin D1, MEK, Erk, pErk, total S6
Cyclin D1, MEK, Erk, Akt, pAkt
Cyclin D1, MEK, Erk, Akt, Caspase2
Cyclin D1, MEK, Erk, Akt, RBBP
Cyclin D1, MEK, Erk, Akt, total S6
Cyclin D1, MEK, Erk, pAkt, Caspase2
Cyclin D1, MEK, Erk, pAkt, RBBP
Cyclin D1, MEK, Erk, pAkt, total S6
Cyclin D1, MEK, Erk, Caspase2, RBBP
Cyclin D1, MEK, Erk, Caspase2, total S6
Cyclin D1, MEK, Erk, RBBP, total S6
Cyclin D1, MEK, pErk, Akt, pAkt
Cyclin D1, MEK, pErk, Akt, Caspase2
Cyclin D1, MEK, pErk, Akt, RBBP
Cyclin D1, MEK, pErk, Akt, total S6
Cyclin D1, MEK, pErk, pAkt, Caspase2
Cyclin D1, MEK, pErk, pAkt, RBBP
Cyclin D1, MEK, pErk, pAkt, total S6
Cyclin D1, MEK, pErk, Caspase2, RBBP
Cyclin D1, MEK, pErk, Caspase2, total S6
Cyclin D1, MEK, pErk, RBBP, total S6
Cyclin D1, MEK, Akt, pAkt, Caspase2
Cyclin D1, MEK, Akt, pAkt, RBBP
Cyclin D1, MEK, Akt, pAkt, total S6
Cyclin D1, MEK, Akt, Caspase2, RBBP
Cyclin D1, MEK, Akt, Caspase2, total S6
Cyclin D1, MEK, Akt, RBBP, total S6
Cyclin D1, MEK, pAkt, Caspase2, RBBP
Cyclin D1, MEK, pAkt, Caspase2, total S6
Cyclin D1, MEK, pAkt, RBBP, total S6
Cyclin D1, Cyclin D3, s6, pS6, Erk, pErk, Caspase2
Cyclin D1, Cyclin D3, s6, pS6, Erk, pErk, RBBP
Cyclin D1, Cyclin D3, s6, pS6, Erk, pErk, total S6
Cyclin D1, Cyclin D3, s6, pS6, Erk, Akt, pAkt
Cyclin D1, Cyclin D3, s6, pS6, Erk, Akt, Caspase2
Cyclin D1, Cyclin D3, s6, pS6, Erk, Akt, RBBP
Cyclin D1, Cyclin D3, s6, pS6, Erk, Akt, total S6
Cyclin D1, Cyclin D3, s6, pS6, Erk, pAkt, Caspase2
Cyclin D1, Cyclin D3, s6, pS6, Erk, pAkt, RBBP
Cyclin D1, Cyclin D3, s6, pS6, Erk, pAkt, total S6
Cyclin D1, Cyclin D3, s6, pS6, Erk, Caspase2, RBBP
Cyclin D1, Cyclin D3, s6, pS6, Erk, Caspase2, total S6
Cyclin D1, Cyclin D3, s6, pS6, Erk, RBBP, total S6
Cyclin D1, Cyclin D3, s6, pS6, pErk, Akt, pAkt
Cyclin D1, Cyclin D3, s6, pS6, pErk, Akt, Caspase2
Cyclin D1, Cyclin D3, s6, pS6, pErk, Akt, RBBP
Cyclin D1, Cyclin D3, s6, pS6, pErk, Akt, total S6
Cyclin D1, Cyclin D3, s6, pS6, pErk, pAkt, Caspase2
Cyclin D1, Cyclin D3, s6, pS6, pErk, pAkt, RBBP
Cyclin D1, Cyclin D3, s6, pS6, pErk, pAkt, total S6
Cyclin D1, Cyclin D3, s6, pS6, pErk, Caspase2, RBBP
Cyclin D1, Cyclin D3, s6, pS6, pErk, Caspase2, total S6
Cyclin D1, Cyclin D3, s6, pS6, pErk, RBBP, total S6
Cyclin D1, Cyclin D3, s6, pS6, Akt, pAkt, Caspase2
Cyclin D1, Cyclin D3, s6, pS6, Akt, pAkt, RBBP
Cyclin D1, Cyclin D3, s6, pS6, Akt, pAkt, total S6
Cyclin D1, Cyclin D3, s6, pS6, Akt, Caspase2, RBBP
Cyclin D1, Cyclin D3, s6, pS6, Akt, Caspase2, total S6
Cyclin D1, Cyclin D3, s6, pS6, Akt, RBBP, total S6
Cyclin D1, Cyclin D3, s6, pS6, pAkt, Caspase2, RBBP
Cyclin D1, Cyclin D3, s6, pS6, pAkt, Caspase2, total S6
Cyclin D1, Cyclin D3, s6, pS6, pAkt, RBBP, total S6
Cyclin D1, Cyclin D3, s6, pS6, Caspase2, RBBP, total S6
Cyclin D1, Cyclin D3, s6, Erk, pErk, Akt, pAkt
Cyclin D1, Cyclin D3, s6, Erk, pErk, Akt, Caspase2
Cyclin D1, Cyclin D3, s6, Erk, pErk, Akt, RBBP
Cyclin D1, Cyclin D3, s6, Erk, pErk, Akt, total S6
Cyclin D1, Cyclin D3, s6, Erk, pErk, pAkt, Caspase2
Cyclin D1, Cyclin D3, s6, Erk, pErk, pAkt, RBBP
Cyclin D1, Cyclin D3, s6, Erk, pErk, pAkt, total S6
Cyclin D1, Cyclin D3, s6, Erk, pErk, Caspase2, RBBP
Cyclin D1, Cyclin D3, s6, Erk, pErk, Caspase2, total S6
Cyclin D1, Cyclin D3, s6, Erk, pErk, RBBP, total S6
Cyclin D1, Cyclin D3, s6, Erk, Akt, pAkt, Caspase2
Cyclin D1, Cyclin D3, s6, Erk, Akt, pAkt, RBBP
Cyclin D1, Cyclin D3, s6, Erk, Akt, pAkt, total S6
Cyclin D1, Cyclin D3, s6, Erk, Akt, Caspase2, RBBP
Cyclin D1, Cyclin D3, s6, Erk, Akt, Caspase2, total S6
Cyclin D1, Cyclin D3, s6, Erk, Akt, RBBP, total S6
Cyclin D1, Cyclin D3, s6, Erk, pAkt, Caspase2, RBBP
Cyclin D1, Cyclin D3, s6, Erk, pAkt, Caspase2, total S6
Cyclin D1, Cyclin D3, s6, Erk, pAkt, RBBP, total S6
Cyclin D1, Cyclin D3, s6, Erk, Caspase2, RBBP, total S6
Cyclin D1, Cyclin D3, s6, pErk, Akt, pAkt, Caspase2
Cyclin D1, Cyclin D3, s6, pErk, Akt, pAkt, RBBP
Cyclin D1, Cyclin D3, s6, pErk, Akt, pAkt, total S6
Cyclin D1, Cyclin D3, s6, pErk, Akt, Caspase2, RBBP
Cyclin D1, Cyclin D3, s6, pErk, Akt, Caspase2, total S6
Cyclin D1, Cyclin D3, s6, pErk, Akt, RBBP, total S6
Cyclin D1, Cyclin D3, s6, pErk, pAkt, Caspase2, RBBP
Cyclin D1, Cyclin D3, s6, pErk, pAkt, Caspase2, total S6
Cyclin D1, Cyclin D3, s6, pErk, pAkt, RBBP, total S6
Cyclin D1, Cyclin D3, s6, pErk, Caspase2, RBBP, total S6
Cyclin D1, Cyclin D3, s6, Akt, pAkt, Caspase2, RBBP
Cyclin D1, Cyclin D3, s6, Akt, pAkt, Caspase2, total S6
Cyclin D1, Cyclin D3, s6, Akt, pAkt, RBBP, total S6
Cyclin D1, Cyclin D3, s6, Akt, Caspase2, RBBP, total S6
Cyclin D1, Cyclin D3, s6, pAkt, Caspase2, RBBP, total S6
Cyclin D1, Cyclin D3, pS6, Erk, pErk, Akt, pAkt
Cyclin D1, Cyclin D3, pS6, Erk, pErk, Akt, Caspase2
Cyclin D1, Cyclin D3, pS6, Erk, pErk, Akt, RBBP
Cyclin D1, Cyclin D3, pS6, Erk, pErk, Akt, total S6
Cyclin D1, Cyclin D3, pS6, Erk, pErk, pAkt, Caspase2
Cyclin D1, Cyclin D3, pS6, Erk, pErk, pAkt, RBBP
Cyclin D1, Cyclin D3, pS6, Erk, pErk, pAkt, total S6
Cyclin D1, Cyclin D3, pS6, Erk, pErk, Caspase2, RBBP
Cyclin D1, Cyclin D3, pS6, Erk, pErk, Caspase2, total S6
Cyclin D1, Cyclin D3, pS6, Erk, pErk, RBBP, total S6

TABLE 1-continued

Examples of Single Markers and Combinations of Markers

Cyclin D1, MEK, Caspase2, RBBP, total S6
Cyclin D1, s6, pS6, Erk, pErk
Cyclin D1, s6, pS6, Erk, Akt
Cyclin D1, s6, pS6, Erk, pAkt
Cyclin D1, s6, pS6, Erk, Caspase2
Cyclin D1, s6, pS6, Erk, RBBP
Cyclin D1, s6, pS6, Erk, total S6
Cyclin D1, s6, pS6, pErk, Akt
Cyclin D1, s6, pS6, pErk, pAkt
Cyclin D1, s6, pS6, pErk, Caspase2
Cyclin D1, s6, pS6, pErk, RBBP
Cyclin D1, s6, pS6, pErk, total S6
Cyclin D1, s6, pS6, Akt, pAkt
Cyclin D1, s6, pS6, Akt, Caspase2
Cyclin D1, s6, pS6, Akt, RBBP
Cyclin D1, s6, pS6, Akt, total S6
Cyclin D1, s6, pS6, pAkt, Caspase2
Cyclin D1, s6, pS6, pAkt, RBBP
Cyclin D1, s6, pS6, pAkt, total S6
Cyclin D1, s6, pS6, Caspase2, RBBP
Cyclin D1, s6, pS6, Caspase2, total S6
Cyclin D1, s6, pS6, RBBP, total S6
Cyclin D1, s6, Erk, pErk, Akt
Cyclin D1, s6, Erk, pErk, pAkt
Cyclin D1, s6, Erk, pErk, Caspase2
Cyclin D1, s6, Erk, pErk, RBBP
Cyclin D1, s6, Erk, pErk, total S6
Cyclin D1, s6, Erk, Akt, pAkt
Cyclin D1, s6, Erk, Akt, Caspase2
Cyclin D1, s6, Erk, Akt, RBBP
Cyclin D1, s6, Erk, Akt, total S6
Cyclin D1, s6, Erk, pAkt, Caspase2
Cyclin D1, s6, Erk, pAkt, RBBP
Cyclin D1, s6, Erk, pAkt, total S6
Cyclin D1, s6, Erk, Caspase2, RBBP
Cyclin D1, s6, Erk, Caspase2, total S6
Cyclin D1, s6, Erk, RBBP, total S6
Cyclin D1, s6, pErk, Akt, pAkt
Cyclin D1, s6, pErk, Akt, Caspase2
Cyclin D1, s6, pErk, Akt, RBBP
Cyclin D1, s6, pErk, Akt, total S6
Cyclin D1, s6, pErk, pAkt, Caspase2
Cyclin D1, s6, pErk, pAkt, RBBP
Cyclin D1, s6, pErk, pAkt, total S6
Cyclin D1, s6, pErk, Caspase2, RBBP
Cyclin D1, s6, pErk, Caspase2, total S6
Cyclin D1, s6, pErk, RBBP, total S6
Cyclin D1, s6, Akt, pAkt, Caspase2
Cyclin D1, s6, Akt, pAkt, RBBP
Cyclin D1, s6, Akt, pAkt, total S6
Cyclin D1, s6, Akt, Caspase2, RBBP
Cyclin D1, s6, Akt, Caspase2, total S6
Cyclin D1, s6, Akt, RBBP, total S6
Cyclin D1, s6, pAkt, Caspase2, RBBP
Cyclin D1, s6, pAkt, Caspase2, total S6
Cyclin D1, s6, pAkt, RBBP, total S6
Cyclin D1, s6, Caspase2, RBBP, total S6
Cyclin D1, pS6, Erk, pErk, Akt
Cyclin D1, pS6, Erk, pErk, pAkt
Cyclin D1, pS6, Erk, pErk, Caspase2
Cyclin D1, pS6, Erk, pErk, RBBP
Cyclin D1, pS6, Erk, pErk, total S6
Cyclin D1, pS6, Erk, Akt, pAkt
Cyclin D1, pS6, Erk, Akt, Caspase2
Cyclin D1, pS6, Erk, Akt, RBBP
Cyclin D1, pS6, Erk, Akt, total S6
Cyclin D1, pS6, Erk, pAkt, Caspase2
Cyclin D1, pS6, Erk, pAkt, RBBP
Cyclin D1, pS6, Erk, pAkt, total S6
Cyclin D1, pS6, Erk, Caspase2, RBBP
Cyclin D1, pS6, Erk, Caspase2, total S6
Cyclin D1, pS6, Erk, RBBP, total S6
Cyclin D1, pS6, pErk, Akt, pAkt
Cyclin D1, pS6, pErk, Akt, Caspase2
Cyclin D1, pS6, pErk, Akt, RBBP
Cyclin D1, pS6, pErk, Akt, total S6
Cyclin D1, pS6, pErk, pAkt, Caspase2
Cyclin D1, pS6, pErk, pAkt, RBBP Cyclin D1, Cyclin D3, pS6, Erk, Akt, pAkt, Caspase2
Cyclin D1, Cyclin D3, pS6, Erk, Akt, pAkt, RBBP
Cyclin D1, Cyclin D3, pS6, Erk, Akt, pAkt, total S6
Cyclin D1, Cyclin D3, pS6, Erk, Akt, Caspase2, RBBP
Cyclin D1, Cyclin D3, pS6, Erk, Akt, Caspase2, total S6
Cyclin D1, Cyclin D3, pS6, Erk, Akt, RBBP, total S6
Cyclin D1, Cyclin D3, pS6, Erk, pAkt, Caspase2, RBBP
Cyclin D1, Cyclin D3, pS6, Erk, pAkt, Caspase2, total S6
Cyclin D1, Cyclin D3, pS6, Erk, pAkt, RBBP, total S6
Cyclin D1, Cyclin D3, pS6, Erk, Caspase2, RBBP, total S6
Cyclin D1, Cyclin D3, pS6, pErk, Akt, pAkt, Caspase2
Cyclin D1, Cyclin D3, pS6, pErk, Akt, pAkt, RBBP
Cyclin D1, Cyclin D3, pS6, pErk, Akt, pAkt, total S6
Cyclin D1, Cyclin D3, pS6, pErk, Akt, Caspase2, RBBP
Cyclin D1, Cyclin D3, pS6, pErk, Akt, Caspase2, total S6
Cyclin D1, Cyclin D3, pS6, pErk, Akt, RBBP, total S6
Cyclin D1, Cyclin D3, pS6, pErk, pAkt, Caspase2, RBBP
Cyclin D1, Cyclin D3, pS6, pErk, pAkt, Caspase2, total S6
Cyclin D1, Cyclin D3, pS6, pErk, pAkt, RBBP, total S6
Cyclin D1, Cyclin D3, pS6, pErk, Caspase2, RBBP, total S6
Cyclin D1, Cyclin D3, pS6, Akt, pAkt, Caspase2, RBBP
Cyclin D1, Cyclin D3, pS6, Akt, pAkt, Caspase2, total S6
Cyclin D1, Cyclin D3, pS6, Akt, pAkt, RBBP, total S6
Cyclin D1, Cyclin D3, pS6, Akt, Caspase2, RBBP, total S6
Cyclin D1, Cyclin D3, pS6, pAkt, Caspase2, RBBP, total S6
Cyclin D1, Cyclin D3, Erk, pErk, Akt, pAkt, Caspase2
Cyclin D1, Cyclin D3, Erk, pErk, Akt, pAkt, RBBP
Cyclin D1, Cyclin D3, Erk, pErk, Akt, pAkt, total S6
Cyclin D1, Cyclin D3, Erk, pErk, Akt, Caspase2, RBBP
Cyclin D1, Cyclin D3, Erk, pErk, Akt, Caspase2, total S6
Cyclin D1, Cyclin D3, Erk, pErk, Akt, RBBP, total S6
Cyclin D1, Cyclin D3, Erk, pErk, pAkt, Caspase2, RBBP
Cyclin D1, Cyclin D3, Erk, pErk, pAkt, Caspase2, total S6
Cyclin D1, Cyclin D3, Erk, pErk, pAkt, RBBP, total S6
Cyclin D1, Cyclin D3, Erk, pErk, Caspase2, RBBP, total S6
Cyclin D1, Cyclin D3, Erk, Akt, pAkt, Caspase2, RBBP
Cyclin D1, Cyclin D3, Erk, Akt, pAkt, Caspase2, total S6
Cyclin D1, Cyclin D3, Erk, Akt, pAkt, RBBP, total S6
Cyclin D1, Cyclin D3, Erk, Akt, Caspase2, RBBP, total S6
Cyclin D1, Cyclin D3, Erk, pAkt, Caspase2, RBBP, total S6
Cyclin D1, Cyclin D3, pErk, Akt, pAkt, Caspase2, RBBP
Cyclin D1, Cyclin D3, pErk, Akt, pAkt, Caspase2, total S6
Cyclin D1, Cyclin D3, pErk, Akt, pAkt, RBBP, total S6
Cyclin D1, Cyclin D3, pErk, Akt, Caspase2, RBBP, total S6
Cyclin D1, Cyclin D3, pErk, pAkt, Caspase2, RBBP, total S6
Cyclin D1, Cyclin D3, Akt, pAkt, Caspase2, RBBP, total S6
Cyclin D1, MEK, s6, pS6, Erk, pErk, Akt
Cyclin D1, MEK, s6, pS6, Erk, pErk, pAkt
Cyclin D1, MEK, s6, pS6, Erk, pErk, Caspase2
Cyclin D1, MEK, s6, pS6, Erk, pErk, RBBP
Cyclin D1, MEK, s6, pS6, Erk, pErk, total S6
Cyclin D1, MEK, s6, pS6, Erk, Akt, pAkt
Cyclin D1, MEK, s6, pS6, Erk, Akt, Caspase2
Cyclin D1, MEK, s6, pS6, Erk, Akt, RBBP
Cyclin D1, MEK, s6, pS6, Erk, Akt, total S6
Cyclin D1, MEK, s6, pS6, Erk, pAkt, Caspase2
Cyclin D1, MEK, s6, pS6, Erk, pAkt, RBBP
Cyclin D1, MEK, s6, pS6, Erk, pAkt, total S6
Cyclin D1, MEK, s6, pS6, Erk, Caspase2, RBBP
Cyclin D1, MEK, s6, pS6, Erk, Caspase2, total S6
Cyclin D1, MEK, s6, pS6, Erk, RBBP, total S6
Cyclin D1, MEK, s6, pS6, pErk, Akt, pAkt
Cyclin D1, MEK, s6, pS6, pErk, Akt, Caspase2
Cyclin D1, MEK, s6, pS6, pErk, Akt, RBBP
Cyclin D1, MEK, s6, pS6, pErk, Akt, total S6
Cyclin D1, MEK, s6, pS6, pErk, pAkt, Caspase2
Cyclin D1, MEK, s6, pS6, pErk, pAkt, RBBP
Cyclin D1, MEK, s6, pS6, pErk, pAkt, total S6
Cyclin D1, MEK, s6, pS6, pErk, Caspase2, RBBP
Cyclin D1, MEK, s6, pS6, pErk, Caspase2, total S6
Cyclin D1, MEK, s6, pS6, pErk, RBBP, total S6
Cyclin D1, MEK, s6, pS6, Akt, pAkt, Caspase2
Cyclin D1, MEK, s6, pS6, Akt, pAkt, RBBP
Cyclin D1, MEK, s6, pS6, Akt, pAkt, total S6
Cyclin D1, MEK, s6, pS6, Akt, Caspase2, RBBP
Cyclin D1, MEK, s6, pS6, Akt, Caspase2, total S6
Cyclin D1, MEK, s6, pS6, Akt, RBBP, total S6
Cyclin D1, MEK, s6, pS6, pAkt, Caspase2, RBBP TABLE 1-continued Examples of Single Markers and Combinations of Markers Cyclin D1, pS6, pErk, pAkt, total S6
Cyclin D1, pS6, pErk, Caspase2, RBBP
Cyclin D1, pS6, pErk, Caspase2, total S6
Cyclin D1, pS6, pErk, RBBP, total S6
Cyclin D1, pS6, Akt, pAkt, Caspase2
Cyclin D1, pS6, Akt, pAkt, RBBP
Cyclin D1, pS6, Akt, pAkt, total S6
Cyclin D1, pS6, Akt, Caspase2, RBBP
Cyclin D1, pS6, Akt, Caspase2, total S6
Cyclin D1, pS6, Akt, RBBP, total S6
Cyclin D1, pS6, pAkt, Caspase2, RBBP
Cyclin D1, pS6, pAkt, Caspase2, total S6
Cyclin D1, pS6, pAkt, RBBP, total S6
Cyclin D1, pS6, Caspase2, RBBP, total S6
Cyclin D1, Erk, pErk, Akt, pAkt
Cyclin D1, Erk, pErk, Akt, Caspase2
Cyclin D1, Erk, pErk, Akt, RBBP
Cyclin D1, Erk, pErk, Akt, total S6
Cyclin D1, Erk, pErk, pAkt, Caspase2
Cyclin D1, Erk, pErk, pAkt, RBBP
Cyclin D1, Erk, pErk, pAkt, total S6
Cyclin D1, Erk, pErk, Caspase2, RBBP
Cyclin D1, Erk, pErk, Caspase2, total S6
Cyclin D1, Erk, pErk, RBBP, total S6
Cyclin D1, Erk, Akt, pAkt, Caspase2
Cyclin D1, Erk, Akt, pAkt, RBBP
Cyclin D1, Erk, Akt, pAkt, total S6
Cyclin D1, Erk, Akt, Caspase2, RBBP
Cyclin D1, Erk, Akt, Caspase2, total S6
Cyclin D1, Erk, Akt, RBBP, total S6
Cyclin D1, Erk, pAkt, Caspase2, RBBP
Cyclin D1, Erk, pAkt, Caspase2, total S6
Cyclin D1, Erk, pAkt, RBBP, total S6
Cyclin D1, Erk, Caspase2, RBBP, total S6
Cyclin D1, pErk, Akt, pAkt, Caspase2
Cyclin D1, pErk, Akt, pAkt, RBBP
Cyclin D1, pErk, Akt, pAkt, total S6
Cyclin D1, pErk, Akt, Caspase2, RBBP
Cyclin D1, pErk, Akt, Caspase2, total S6
Cyclin D1, pErk, Akt, RBBP, total S6
Cyclin D1, pErk, pAkt, Caspase2, RBBP
Cyclin D1, pErk, pAkt, Caspase2, total S6
Cyclin D1, pErk, pAkt, RBBP, total S6
Cyclin D1, pErk, Caspase2, RBBP, total S6
Cyclin D1, Akt, pAkt, Caspase2, RBBP
Cyclin D1, Akt, pAkt, Caspase2, total S6
Cyclin D1, Akt, pAkt, RBBP, total S6
Cyclin D1, Akt, Caspase2, RBBP, total S6
Cyclin D1, pAkt, Caspase2, RBBP, total S6
Cyclin D3, MEK, s6, pS6, Erk
Cyclin D3, MEK, s6, pS6, pErk
Cyclin D3, MEK, s6, pS6, Akt
Cyclin D3, MEK, s6, pS6, pAkt
Cyclin D3, MEK, s6, pS6, Caspase2
Cyclin D3, MEK, s6, pS6, RBBP
Cyclin D3, MEK, s6, pS6, total S6
Cyclin D3, MEK, s6, Erk, pErk
Cyclin D3, MEK, s6, Erk, Akt
Cyclin D3, MEK, s6, Erk, pAkt
Cyclin D3, MEK, s6, Erk, Caspase2
Cyclin D3, MEK, s6, Erk, RBBP
Cyclin D3, MEK, s6, Erk, total S6
Cyclin D3, MEK, s6, pErk, Akt
Cyclin D3, MEK, s6, pErk, pAkt
Cyclin D3, MEK, s6, pErk, Caspase2
Cyclin D3, MEK, s6, pErk, RBBP
Cyclin D3, MEK, s6, pErk, total S6
Cyclin D3, MEK, s6, Akt, pAkt
Cyclin D3, MEK, s6, Akt, Caspase2
Cyclin D3, MEK, s6, Akt, RBBP
Cyclin D3, MEK, s6, Akt, total S6
Cyclin D3, MEK, s6, pAkt, Caspase2
Cyclin D3, MEK, s6, pAkt, RBBP
Cyclin D3, MEK, s6, pAkt, total S6
Cyclin D3, MEK, s6, Caspase2, RBBP
Cyclin D3, MEK, s6, Caspase2, total S6
Cyclin D3, MEK, s6, RBBP, total S6
Cyclin D3, MEK, pS6, Erk, pErk
Cyclin D1, MEK, s6, pS6, pAkt, Caspase2, total S6
Cyclin D1, MEK, s6, pS6, pAkt, RBBP, total S6
Cyclin D1, MEK, s6, pS6, Caspase2, RBBP, total S6
Cyclin D1, MEK, s6, Erk, pErk, Akt, pAkt
Cyclin D1, MEK, s6, Erk, pErk, Akt, Caspase2
Cyclin D1, MEK, s6, Erk, pErk, Akt, RBBP
Cyclin D1, MEK, s6, Erk, pErk, Akt, total S6
Cyclin D1, MEK, s6, Erk, pErk, pAkt, Caspase2
Cyclin D1, MEK, s6, Erk, pErk, pAkt, RBBP
Cyclin D1, MEK, s6, Erk, pErk, pAkt, total S6
Cyclin D1, MEK, s6, Erk, pErk, Caspase2, RBBP
Cyclin D1, MEK, s6, Erk, pErk, Caspase2, total S6
Cyclin D1, MEK, s6, Erk, pErk, RBBP, total S6
Cyclin D1, MEK, s6, Erk, Akt, pAkt, Caspase2
Cyclin D1, MEK, s6, Erk, Akt, pAkt, RBBP
Cyclin D1, MEK, s6, Erk, Akt, pAkt, total S6
Cyclin D1, MEK, s6, Erk, Akt, Caspase2, RBBP
Cyclin D1, MEK, s6, Erk, Akt, Caspase2, total S6
Cyclin D1, MEK, s6, Erk, Akt, RBBP, total S6
Cyclin D1, MEK, s6, Erk, pAkt, Caspase2, RBBP
Cyclin D1, MEK, s6, Erk, pAkt, Caspase2, total S6
Cyclin D1, MEK, s6, Erk, pAkt, RBBP, total S6
Cyclin D1, MEK, s6, Erk, Caspase2, RBBP, total S6
Cyclin D1, MEK, s6, pErk, Akt, pAkt, Caspase2
Cyclin D1, MEK, s6, pErk, Akt, pAkt, RBBP
Cyclin D1, MEK, s6, pErk, Akt, pAkt, total S6
Cyclin D1, MEK, s6, pErk, Akt, Caspase2, RBBP
Cyclin D1, MEK, s6, pErk, Akt, Caspase2, total S6
Cyclin D1, MEK, s6, pErk, Akt, RBBP, total S6
Cyclin D1, MEK, s6, pErk, pAkt, Caspase2, RBBP
Cyclin D1, MEK, s6, pErk, pAkt, Caspase2, total S6
Cyclin D1, MEK, s6, pErk, pAkt, RBBP, total S6
Cyclin D1, MEK, s6, pErk, Caspase2, RBBP, total S6
Cyclin D1, MEK, s6, Akt, pAkt, Caspase2, RBBP
Cyclin D1, MEK, s6, Akt, pAkt, Caspase2, total S6
Cyclin D1, MEK, s6, Akt, pAkt, RBBP, total S6
Cyclin D1, MEK, s6, Akt, Caspase2, RBBP, total S6
Cyclin D1, MEK, s6, pAkt, Caspase2, RBBP, total S6
Cyclin D1, MEK, pS6, Erk, pErk, Akt, pAkt
Cyclin D1, MEK, pS6, Erk, pErk, Akt, Caspase2
Cyclin D1, MEK, pS6, Erk, pErk, Akt, RBBP
Cyclin D1, MEK, pS6, Erk, pErk, Akt, total S6
Cyclin D1, MEK, pS6, Erk, pErk, pAkt, Caspase2
Cyclin D1, MEK, pS6, Erk, pErk, pAkt, RBBP
Cyclin D1, MEK, pS6, Erk, pErk, pAkt, total S6
Cyclin D1, MEK, pS6, Erk, pErk, Caspase2, RBBP
Cyclin D1, MEK, pS6, Erk, pErk, Caspase2, total S6
Cyclin D1, MEK, pS6, Erk, pErk, RBBP, total S6
Cyclin D1, MEK, pS6, Erk, Akt, pAkt, Caspase2
Cyclin D1, MEK, pS6, Erk, Akt, pAkt, RBBP
Cyclin D1, MEK, pS6, Erk, Akt, pAkt, total S6
Cyclin D1, MEK, pS6, Erk, Akt, Caspase2, RBBP
Cyclin D1, MEK, pS6, Erk, Akt, Caspase2, total S6
Cyclin D1, MEK, pS6, Erk, Akt, RBBP, total S6
Cyclin D1, MEK, pS6, Erk, pAkt, Caspase2, RBBP
Cyclin D1, MEK, pS6, Erk, pAkt, Caspase2, total S6
Cyclin D1, MEK, pS6, Erk, pAkt, RBBP, total S6
Cyclin D1, MEK, pS6, Erk, Caspase2, RBBP, total S6
Cyclin D1, MEK, pS6, pErk, Akt, pAkt, Caspase2
Cyclin D1, MEK, pS6, pErk, Akt, pAkt, RBBP
Cyclin D1, MEK, pS6, pErk, Akt, pAkt, total S6
Cyclin D1, MEK, pS6, pErk, Akt, Caspase2, RBBP
Cyclin D1, MEK, pS6, pErk, Akt, Caspase2, total S6
Cyclin D1, MEK, pS6, pErk, Akt, RBBP, total S6
Cyclin D1, MEK, pS6, pErk, pAkt, Caspase2, RBBP
Cyclin D1, MEK, pS6, pErk, pAkt, Caspase2, total S6
Cyclin D1, MEK, pS6, pErk, pAkt, RBBP, total S6
Cyclin D1, MEK, pS6, pErk, Caspase2, RBBP, total S6
Cyclin D1, MEK, pS6, Akt, pAkt, Caspase2, RBBP
Cyclin D1, MEK, pS6, Akt, pAkt, Caspase2, total S6
Cyclin D1, MEK, pS6, Akt, pAkt, RBBP, total S6
Cyclin D1, MEK, pS6, Akt, Caspase2, RBBP, total S6
Cyclin D1, MEK, pS6, pAkt, Caspase2, RBBP, total S6
Cyclin D1, MEK, Erk, pErk, Akt, pAkt, Caspase2
Cyclin D1, MEK, Erk, pErk, Akt, pAkt, RBBP
Cyclin D1, MEK, Erk, pErk, Akt, pAkt, total S6
Cyclin D1, MEK, Erk, pErk, Akt, Caspase2, RBBP
Cyclin D1, MEK, Erk, pErk, Akt, Caspase2, total S6

TABLE 1-continued

Examples of Single Markers and Combinations of Markers

Cyclin D3, MEK, pS6, Erk, Akt
Cyclin D3, MEK, pS6, Erk, pAkt
Cyclin D3, MEK, pS6, Erk, Caspase2
Cyclin D3, MEK, pS6, Erk, RBBP
Cyclin D3, MEK, pS6, Erk, total S6
Cyclin D3, MEK, pS6, pErk, Akt
Cyclin D3, MEK, pS6, pErk, pAkt
Cyclin D3, MEK, pS6, pErk, Caspase2
Cyclin D3, MEK, pS6, pErk, RBBP
Cyclin D3, MEK, pS6, pErk, total S6
Cyclin D3, MEK, pS6, Akt, pAkt
Cyclin D3, MEK, pS6, Akt, Caspase2
Cyclin D3, MEK, pS6, Akt, RBBP
Cyclin D3, MEK, pS6, Akt, total S6
Cyclin D3, MEK, pS6, pAkt, Caspase2
Cyclin D3, MEK, pS6, pAkt, RBBP
Cyclin D3, MEK, pS6, pAkt, total S6
Cyclin D3, MEK, pS6, Caspase2, RBBP
Cyclin D3, MEK, pS6, Caspase2, total S6
Cyclin D3, MEK, pS6, RBBP, total S6
Cyclin D3, MEK, Erk, pErk, Akt
Cyclin D3, MEK, Erk, pErk, pAkt
Cyclin D3, MEK, Erk, pErk, Caspase2
Cyclin D3, MEK, Erk, pErk, RBBP
Cyclin D3, MEK, Erk, pErk, total S6
Cyclin D3, MEK, Erk, Akt, pAkt
Cyclin D3, MEK, Erk, Akt, Caspase2
Cyclin D3, MEK, Erk, Akt, RBBP
Cyclin D3, MEK, Erk, Akt, total S6
Cyclin D3, MEK, Erk, pAkt, Caspase2
Cyclin D3, MEK, Erk, pAkt, RBBP
Cyclin D3, MEK, Erk, pAkt, total S6
Cyclin D3, MEK, Erk, Caspase2, RBBP
Cyclin D3, MEK, Erk, Caspase2, total S6
Cyclin D3, MEK, Erk, RBBP, total S6
Cyclin D3, MEK, pErk, Akt, pAkt
Cyclin D3, MEK, pErk, Akt, Caspase2
Cyclin D3, MEK, pErk, Akt, RBBP
Cyclin D3, MEK, pErk, Akt, total S6
Cyclin D3, MEK, pErk, pAkt, Caspase2
Cyclin D3, MEK, pErk, pAkt, RBBP
Cyclin D3, MEK, pErk, pAkt, total S6
Cyclin D3, MEK, pErk, Caspase2, RBBP
Cyclin D3, MEK, pErk, Caspase2, total S6
Cyclin D3, MEK, pErk, RBBP, total S6
Cyclin D3, MEK, Akt, pAkt, Caspase2
Cyclin D3, MEK, Akt, pAkt, RBBP
Cyclin D3, MEK, Akt, pAkt, total S6
Cyclin D3, MEK, Akt, Caspase2, RBBP
Cyclin D3, MEK, Akt, Caspase2, total S6
Cyclin D3, MEK, Akt, RBBP, total S6
Cyclin D3, MEK, pAkt, Caspase2, RBBP
Cyclin D3, MEK, pAkt, Caspase2, total S6
Cyclin D3, MEK, pAkt, RBBP, total S6
Cyclin D3, MEK, Caspase2, RBBP, total S6
Cyclin D3, s6, pS6, Erk, pErk
Cyclin D3, s6, pS6, Erk, Akt
Cyclin D3, s6, pS6, Erk, pAkt
Cyclin D3, s6, pS6, Erk, Caspase2
Cyclin D3, s6, pS6, Erk, RBBP
Cyclin D3, s6, pS6, Erk, total S6
Cyclin D3, s6, pS6, pErk, Akt
Cyclin D3, s6, pS6, pErk, pAkt
Cyclin D3, s6, pS6, pErk, Caspase2
Cyclin D3, s6, pS6, pErk, RBBP
Cyclin D3, s6, pS6, pErk, total S6
Cyclin D3, s6, pS6, Akt, pAkt
Cyclin D3, s6, pS6, Akt, Caspase2
Cyclin D3, s6, pS6, Akt, RBBP
Cyclin D3, s6, pS6, Akt, total S6
Cyclin D3, s6, pS6, pAkt, Caspase2
Cyclin D3, s6, pS6, pAkt, RBBP
Cyclin D3, s6, pS6, pAkt, total S6
Cyclin D3, s6, pS6, Caspase2, RBBP
Cyclin D3, s6, pS6, Caspase2, total S6
Cyclin D3, s6, pS6, RBBP, total S6
Cyclin D3, s6, Erk, pErk, Akt
Cyclin D3, s6, Erk, pErk, pAkt
Cyclin D1, MEK, Erk, pErk, Akt, RBBP, total S6
Cyclin D1, MEK, Erk, pErk, pAkt, Caspase2, RBBP
Cyclin D1, MEK, Erk, pErk, pAkt, Caspase2, total S6
Cyclin D1, MEK, Erk, pErk, pAkt, RBBP, total S6
Cyclin D1, MEK, Erk, pErk, Caspase2, RBBP, total S6
Cyclin D1, MEK, Erk, Akt, pAkt, Caspase2, RBBP
Cyclin D1, MEK, Erk, Akt, pAkt, Caspase2, total S6
Cyclin D1, MEK, Erk, Akt, pAkt, RBBP, total S6
Cyclin D1, MEK, Erk, Akt, Caspase2, RBBP, total S6
Cyclin D1, MEK, Erk, pAkt, Caspase2, RBBP, total S6
Cyclin D1, MEK, pErk, Akt, pAkt, Caspase2, RBBP
Cyclin D1, MEK, pErk, Akt, pAkt, Caspase2, total S6
Cyclin D1, MEK, pErk, Akt, pAkt, RBBP, total S6
Cyclin D1, MEK, pErk, Akt, Caspase2, RBBP, total S6
Cyclin D1, MEK, pErk, pAkt, Caspase2, RBBP, total S6
Cyclin D1, MEK, Akt, pAkt, Caspase2, RBBP, total S6
Cyclin D1, s6, pS6, Erk, pErk, Akt, pAkt
Cyclin D1, s6, pS6, Erk, pErk, Akt, Caspase2
Cyclin D1, s6, pS6, Erk, pErk, Akt, RBBP
Cyclin D1, s6, pS6, Erk, pErk, Akt, total S6
Cyclin D1, s6, pS6, Erk, pErk, pAkt, Caspase2
Cyclin D1, s6, pS6, Erk, pErk, pAkt, RBBP
Cyclin D1, s6, pS6, Erk, pErk, pAkt, total S6
Cyclin D1, s6, pS6, Erk, pErk, Caspase2, RBBP
Cyclin D1, s6, pS6, Erk, pErk, Caspase2, total S6
Cyclin D1, s6, pS6, Erk, pErk, RBBP, total S6
Cyclin D1, s6, pS6, Erk, Akt, pAkt, Caspase2
Cyclin D1, s6, pS6, Erk, Akt, pAkt, RBBP
Cyclin D1, s6, pS6, Erk, Akt, pAkt, total S6
Cyclin D1, s6, pS6, Erk, Akt, Caspase2, RBBP
Cyclin D1, s6, pS6, Erk, Akt, Caspase2, total S6
Cyclin D1, s6, pS6, Erk, Akt, RBBP, total S6
Cyclin D1, s6, pS6, Erk, pAkt, Caspase2, RBBP
Cyclin D1, s6, pS6, Erk, pAkt, Caspase2, total S6
Cyclin D1, s6, pS6, Erk, pAkt, RBBP, total S6
Cyclin D1, s6, pS6, Erk, Caspase2, RBBP, total S6
Cyclin D1, s6, pS6, pErk, Akt, pAkt, Caspase2
Cyclin D1, s6, pS6, pErk, Akt, pAkt, RBBP
Cyclin D1, s6, pS6, pErk, Akt, pAkt, total S6
Cyclin D1, s6, pS6, pErk, Akt, Caspase2, RBBP
Cyclin D1, s6, pS6, pErk, Akt, Caspase2, total S6
Cyclin D1, s6, pS6, pErk, Akt, RBBP, total S6
Cyclin D1, s6, pS6, pErk, pAkt, Caspase2, RBBP
Cyclin D1, s6, pS6, pErk, pAkt, Caspase2, total S6
Cyclin D1, s6, pS6, pErk, pAkt, RBBP, total S6
Cyclin D1, s6, pS6, pErk, Caspase2, RBBP, total S6
Cyclin D1, s6, pS6, Akt, pAkt, Caspase2, RBBP
Cyclin D1, s6, pS6, Akt, pAkt, Caspase2, total S6
Cyclin D1, s6, pS6, Akt, pAkt, RBBP, total S6
Cyclin D1, s6, pS6, Akt, Caspase2, RBBP, total S6
Cyclin D1, s6, pS6, pAkt, Caspase2, RBBP, total S6
Cyclin D1, s6, Erk, pErk, Akt, pAkt, Caspase2
Cyclin D1, s6, Erk, pErk, Akt, pAkt, RBBP
Cyclin D1, s6, Erk, pErk, Akt, pAkt, total S6
Cyclin D1, s6, Erk, pErk, Akt, Caspase2, RBBP
Cyclin D1, s6, Erk, pErk, Akt, Caspase2, total S6
Cyclin D1, s6, Erk, pErk, Akt, RBBP, total S6
Cyclin D1, s6, Erk, pErk, pAkt, Caspase2, RBBP
Cyclin D1, s6, Erk, pErk, pAkt, Caspase2, total S6
Cyclin D1, s6, Erk, pErk, pAkt, RBBP, total S6
Cyclin D1, s6, Erk, pErk, Caspase2, RBBP, total S6
Cyclin D1, s6, Erk, Akt, pAkt, Caspase2, RBBP
Cyclin D1, s6, Erk, Akt, pAkt, Caspase2, total S6
Cyclin D1, s6, Erk, Akt, pAkt, RBBP, total S6
Cyclin D1, s6, Erk, Akt, Caspase2, RBBP, total S6
Cyclin D1, s6, Erk, pAkt, Caspase2, RBBP, total S6
Cyclin D1, s6, pErk, Akt, pAkt, Caspase2, RBBP
Cyclin D1, s6, pErk, Akt, pAkt, Caspase2, total S6
Cyclin D1, s6, pErk, Akt, pAkt, RBBP, total S6
Cyclin D1, s6, pErk, Akt, Caspase2, RBBP, total S6
Cyclin D1, s6, pErk, pAkt, Caspase2, RBBP, total S6
Cyclin D1, s6, Akt, pAkt, Caspase2, RBBP, total S6
Cyclin D1, pS6, Erk, pErk, Akt, pAkt, Caspase2
Cyclin D1, pS6, Erk, pErk, Akt, pAkt, RBBP
Cyclin D1, pS6, Erk, pErk, Akt, pAkt, total S6
Cyclin D1, pS6, Erk, pErk, Akt, Caspase2, RBBP
Cyclin D1, pS6, Erk, pErk, Akt, Caspase2, total S6
Cyclin D1, pS6, Erk, pErk, Akt, RBBP, total S6

TABLE 1-continued

Examples of Single Markers and Combinations of Markers

Cyclin D3, s6, Erk, pErk, Caspase2
Cyclin D3, s6, Erk, pErk, RBBP
Cyclin D3, s6, Erk, pErk, total S6
Cyclin D3, s6, Erk, Akt, pAkt
Cyclin D3, s6, Erk, Akt, Caspase2
Cyclin D3, s6, Erk, Akt, RBBP
Cyclin D3, s6, Erk, Akt, total S6
Cyclin D3, s6, Erk, pAkt, Caspase2
Cyclin D3, s6, Erk, pAkt, RBBP
Cyclin D3, s6, Erk, pAkt, total S6
Cyclin D3, s6, Erk, Caspase2, RBBP
Cyclin D3, s6, Erk, Caspase2, total S6
Cyclin D3, s6, Erk, RBBP, total S6
Cyclin D3, s6, pErk, Akt, pAkt
Cyclin D3, s6, pErk, Akt, Caspase2
Cyclin D3, s6, pErk, Akt, RBBP
Cyclin D3, s6, pErk, Akt, total S6
Cyclin D3, s6, pErk, pAkt, Caspase2
Cyclin D3, s6, pErk, pAkt, RBBP
Cyclin D3, s6, pErk, pAkt, total S6
Cyclin D3, s6, pErk, Caspase2, RBBP
Cyclin D3, s6, pErk, Caspase2, total S6
Cyclin D3, s6, pErk, RBBP, total S6
Cyclin D3, s6, Akt, pAkt, Caspase2
Cyclin D3, s6, Akt, pAkt, RBBP
Cyclin D3, s6, Akt, pAkt, total S6
Cyclin D3, s6, Akt, Caspase2, RBBP
Cyclin D3, s6, Akt, Caspase2, total S6
Cyclin D3, s6, Akt, RBBP, total S6
Cyclin D3, s6, pAkt, Caspase2, RBBP
Cyclin D3, s6, pAkt, Caspase2, total S6
Cyclin D3, s6, pAkt, RBBP, total S6
Cyclin D3, s6, Caspase2, RBBP, total S6
Cyclin D3, pS6, Erk, pErk, Akt
Cyclin D3, pS6, Erk, pErk, pAkt
Cyclin D3, pS6, Erk, pErk, Caspase2
Cyclin D3, pS6, Erk, pErk, RBBP
Cyclin D3, pS6, Erk, pErk, total S6
Cyclin D3, pS6, Erk, Akt, pAkt
Cyclin D3, pS6, Erk, Akt, Caspase2
Cyclin D3, pS6, Erk, Akt, RBBP
Cyclin D3, pS6, Erk, Akt, total S6
Cyclin D3, pS6, Erk, pAkt, Caspase2
Cyclin D3, pS6, Erk, pAkt, RBBP
Cyclin D3, pS6, Erk, pAkt, total S6
Cyclin D3, pS6, Erk, Caspase2, RBBP
Cyclin D3, pS6, Erk, Caspase2, total S6
Cyclin D3, pS6, Erk, RBBP, total S6
Cyclin D3, pS6, pErk, Akt, pAkt
Cyclin D3, pS6, pErk, Akt, Caspase2
Cyclin D3, pS6, pErk, Akt, RBBP
Cyclin D3, pS6, pErk, Akt, total S6
Cyclin D3, pS6, pErk, pAkt, Caspase2
Cyclin D3, pS6, pErk, pAkt, RBBP
Cyclin D3, pS6, pErk, pAkt, total S6
Cyclin D3, pS6, pErk, Caspase2, RBBP
Cyclin D3, pS6, pErk, Caspase2, total S6
Cyclin D3, pS6, pErk, RBBP, total S6
Cyclin D3, pS6, Akt, pAkt, Caspase2
Cyclin D3, pS6, Akt, pAkt, RBBP
Cyclin D3, pS6, Akt, pAkt, total S6
Cyclin D3, pS6, Akt, Caspase2, RBBP
Cyclin D3, pS6, Akt, Caspase2, total S6
Cyclin D3, pS6, Akt, RBBP, total S6
Cyclin D3, pS6, pAkt, Caspase2, RBBP
Cyclin D3, pS6, pAkt, Caspase2, total S6
Cyclin D3, pS6, pAkt, RBBP, total S6
Cyclin D3, pS6, Caspase2, RBBP, total S6
Cyclin D3, Erk, pErk, Akt, pAkt
Cyclin D3, Erk, pErk, Akt, Caspase2
Cyclin D3, Erk, pErk, Akt, RBBP
Cyclin D3, Erk, pErk, Akt, total S6
Cyclin D3, Erk, pErk, pAkt, Caspase2
Cyclin D3, Erk, pErk, pAkt, RBBP
Cyclin D3, Erk, pErk, pAkt, total S6
Cyclin D3, Erk, pErk, Caspase2, RBBP
Cyclin D3, Erk, pErk, Caspase2, total S6
Cyclin D3, Erk, pErk, RBBP, total S6
Cyclin D1, pS6, Erk, pErk, pAkt, Caspase2, RBBP
Cyclin D1, pS6, Erk, pErk, pAkt, Caspase2, total S6
Cyclin D1, pS6, Erk, pErk, pAkt, RBBP, total S6
Cyclin D1, pS6, Erk, pErk, Caspase2, RBBP, total S6
Cyclin D1, pS6, Erk, Akt, pAkt, Caspase2, RBBP
Cyclin D1, pS6, Erk, Akt, pAkt, Caspase2, total S6
Cyclin D1, pS6, Erk, Akt, pAkt, RBBP, total S6
Cyclin D1, pS6, Erk, Akt, Caspase2, RBBP, total S6
Cyclin D1, pS6, Erk, pAkt, Caspase2, RBBP, total S6
Cyclin D1, pS6, pErk, Akt, pAkt, Caspase2, RBBP
Cyclin D1, pS6, pErk, Akt, pAkt, Caspase2, total S6
Cyclin D1, pS6, pErk, Akt, pAkt, RBBP, total S6
Cyclin D1, pS6, pErk, Akt, Caspase2, RBBP, total S6
Cyclin D1, pS6, pErk, pAkt, Caspase2, RBBP, total S6
Cyclin D1, pS6, Akt, pAkt, Caspase2, RBBP, total S6
Cyclin D1, Erk, pErk, Akt, pAkt, Caspase2, RBBP
Cyclin D1, Erk, pErk, Akt, pAkt, Caspase2, total S6
Cyclin D1, Erk, pErk, Akt, pAkt, RBBP, total S6
Cyclin D1, Erk, pErk, Akt, Caspase2, RBBP, total S6
Cyclin D1, Erk, pErk, pAkt, Caspase2, RBBP, total S6
Cyclin D1, Erk, Akt, pAkt, Caspase2, RBBP, total S6
Cyclin D1, pErk, Akt, pAkt, Caspase2, RBBP, total S6
Cyclin D3, MEK, s6, pS6, Erk, pErk, Akt
Cyclin D3, MEK, s6, pS6, Erk, pErk, pAkt
Cyclin D3, MEK, s6, pS6, Erk, pErk, Caspase2
Cyclin D3, MEK, s6, pS6, Erk, pErk, RBBP
Cyclin D3, MEK, s6, pS6, Erk, pErk, total S6
Cyclin D3, MEK, s6, pS6, Erk, Akt, pAkt
Cyclin D3, MEK, s6, pS6, Erk, Akt, Caspase2
Cyclin D3, MEK, s6, pS6, Erk, Akt, RBBP
Cyclin D3, MEK, s6, pS6, Erk, Akt, total S6
Cyclin D3, MEK, s6, pS6, Erk, pAkt, Caspase2
Cyclin D3, MEK, s6, pS6, Erk, pAkt, RBBP
Cyclin D3, MEK, s6, pS6, Erk, pAkt, total S6
Cyclin D3, MEK, s6, pS6, Erk, Caspase2, RBBP
Cyclin D3, MEK, s6, pS6, Erk, Caspase2, total S6
Cyclin D3, MEK, s6, pS6, Erk, RBBP, total S6
Cyclin D3, MEK, s6, pS6, pErk, Akt, pAkt
Cyclin D3, MEK, s6, pS6, pErk, Akt, Caspase2
Cyclin D3, MEK, s6, pS6, pErk, Akt, RBBP
Cyclin D3, MEK, s6, pS6, pErk, Akt, total S6
Cyclin D3, MEK, s6, pS6, pErk, pAkt, Caspase2
Cyclin D3, MEK, s6, pS6, pErk, pAkt, RBBP
Cyclin D3, MEK, s6, pS6, pErk, pAkt, total S6
Cyclin D3, MEK, s6, pS6, pErk, Caspase2, RBBP
Cyclin D3, MEK, s6, pS6, pErk, Caspase2, total S6
Cyclin D3, MEK, s6, pS6, pErk, RBBP, total S6
Cyclin D3, MEK, s6, pS6, Akt, pAkt, Caspase2
Cyclin D3, MEK, s6, pS6, Akt, pAkt, RBBP
Cyclin D3, MEK, s6, pS6, Akt, pAkt, total S6
Cyclin D3, MEK, s6, pS6, Akt, Caspase2, RBBP
Cyclin D3, MEK, s6, pS6, Akt, Caspase2, total S6
Cyclin D3, MEK, s6, pS6, Akt, RBBP, total S6
Cyclin D3, MEK, s6, pS6, pAkt, Caspase2, RBBP
Cyclin D3, MEK, s6, pS6, pAkt, Caspase2, total S6
Cyclin D3, MEK, s6, pS6, pAkt, RBBP, total S6
Cyclin D3, MEK, s6, pS6, Caspase2, RBBP, total S6
Cyclin D3, MEK, s6, Erk, pErk, Akt, pAkt
Cyclin D3, MEK, s6, Erk, pErk, Akt, Caspase2
Cyclin D3, MEK, s6, Erk, pErk, Akt, RBBP
Cyclin D3, MEK, s6, Erk, pErk, Akt, total S6
Cyclin D3, MEK, s6, Erk, pErk, pAkt, Caspase2
Cyclin D3, MEK, s6, Erk, pErk, pAkt, RBBP
Cyclin D3, MEK, s6, Erk, pErk, pAkt, total S6
Cyclin D3, MEK, s6, Erk, pErk, Caspase2, RBBP
Cyclin D3, MEK, s6, Erk, pErk, Caspase2, total S6
Cyclin D3, MEK, s6, Erk, pErk, RBBP, total S6
Cyclin D3, MEK, s6, Erk, Akt, pAkt, Caspase2
Cyclin D3, MEK, s6, Erk, Akt, pAkt, RBBP
Cyclin D3, MEK, s6, Erk, Akt, pAkt, total S6
Cyclin D3, MEK, s6, Erk, Akt, Caspase2, RBBP
Cyclin D3, MEK, s6, Erk, Akt, Caspase2, total S6
Cyclin D3, MEK, s6, Erk, Akt, RBBP, total S6
Cyclin D3, MEK, s6, Erk, pAkt, Caspase2, RBBP
Cyclin D3, MEK, s6, Erk, pAkt, Caspase2, total S6
Cyclin D3, MEK, s6, Erk, pAkt, RBBP, total S6
Cyclin D3, MEK, s6, Erk, Caspase2, RBBP, total S6
Cyclin D3, MEK, s6, pErk, Akt, pAkt, Caspase2

TABLE 1-continued

Examples of Single Markers and Combinations of Markers

Cyclin D3, Erk, Akt, pAkt, Caspase2
Cyclin D3, Erk, Akt, pAkt, RBBP
Cyclin D3, Erk, Akt, pAkt, total S6
Cyclin D3, Erk, Akt, Caspase2, RBBP
Cyclin D3, Erk, Akt, Caspase2, total S6
Cyclin D3, Erk, Akt, RBBP, total S6
Cyclin D3, Erk, pAkt, Caspase2, RBBP
Cyclin D3, Erk, pAkt, Caspase2, total S6
Cyclin D3, Erk, pAkt, RBBP, total S6
Cyclin D3, Erk, Caspase2, RBBP, total S6
Cyclin D3, pErk, Akt, pAkt, Caspase2
Cyclin D3, pErk, Akt, pAkt, RBBP
Cyclin D3, pErk, Akt, pAkt, total S6
Cyclin D3, pErk, Akt, Caspase2, RBBP
Cyclin D3, pErk, Akt, Caspase2, total S6
Cyclin D3, pErk, Akt, RBBP, total S6
Cyclin D3, pErk, pAkt, Caspase2, RBBP
Cyclin D3, pErk, pAkt, Caspase2, total S6
Cyclin D3, pErk, pAkt, RBBP, total S6
Cyclin D3, pErk, Caspase2, RBBP, total S6
Cyclin D3, Akt, pAkt, Caspase2, RBBP
Cyclin D3, Akt, pAkt, Caspase2, total S6
Cyclin D3, Akt, pAkt, RBBP, total S6
Cyclin D3, Akt, Caspase2, RBBP, total S6
Cyclin D3, pAkt, Caspase2, RBBP, total S6
MEK, s6, pS6, Erk, pErk
MEK, s6, pS6, Erk, Akt
MEK, s6, pS6, Erk, pAkt
MEK, s6, pS6, Erk, Caspase2
MEK, s6, pS6, Erk, RBBP
MEK, s6, pS6, Erk, total S6
MEK, s6, pS6, pErk, Akt
MEK, s6, pS6, pErk, pAkt
MEK, s6, pS6, pErk, Caspase2
MEK, s6, pS6, pErk, RBBP
MEK, s6, pS6, pErk, total S6
MEK, s6, pS6, Akt, pAkt
MEK, s6, pS6, Akt, Caspase2
MEK, s6, pS6, Akt, RBBP
MEK, s6, pS6, Akt, total S6
MEK, s6, pS6, pAkt, Caspase2
MEK, s6, pS6, pAkt, RBBP
MEK, s6, pS6, pAkt, total S6
MEK, s6, pS6, Caspase2, RBBP
MEK, s6, pS6, Caspase2, total S6
MEK, s6, pS6, RBBP, total S6
MEK, s6, Erk, pErk, Akt
MEK, s6, Erk, pErk, pAkt
MEK, s6, Erk, pErk, Caspase2
MEK, s6, Erk, pErk, RBBP
MEK, s6, Erk, pErk, total S6
MEK, s6, Erk, Akt, pAkt
MEK, s6, Erk, Akt, Caspase2
MEK, s6, Erk, Akt, RBBP
MEK, s6, Erk, Akt, total S6
MEK, s6, Erk, pAkt, Caspase2
MEK, s6, Erk, pAkt, RBBP
MEK, s6, Erk, pAkt, total S6
MEK, s6, Erk, Caspase2, RBBP
MEK, s6, Erk, Caspase2, total S6
MEK, s6, Erk, RBBP, total S6
MEK, s6, pErk, Akt, pAkt
MEK, s6, pErk, Akt, Caspase2
MEK, s6, pErk, Akt, RBBP
MEK, s6, pErk, Akt, total S6
MEK, s6, pErk, pAkt, Caspase2
MEK, s6, pErk, pAkt, RBBP
MEK, s6, pErk, pAkt, total S6
MEK, s6, pErk, Caspase2, RBBP
MEK, s6, pErk, Caspase2, total S6
MEK, s6, pErk, RBBP, total S6
MEK, s6, Akt, pAkt, Caspase2
MEK, s6, Akt, pAkt, RBBP
MEK, s6, Akt, pAkt, total S6
MEK, s6, Akt, Caspase2, RBBP
MEK, s6, Akt, Caspase2, total S6
MEK, s6, Akt, RBBP, total S6
MEK, s6, pAkt, Caspase2, RBBP
Cyclin D3, MEK, s6, pErk, Akt, pAkt, RBBP
Cyclin D3, MEK, s6, pErk, Akt, pAkt, total S6
Cyclin D3, MEK, s6, pErk, Akt, Caspase2, RBBP
Cyclin D3, MEK, s6, pErk, Akt, Caspase2, total S6
Cyclin D3, MEK, s6, pErk, Akt, RBBP, total S6
Cyclin D3, MEK, s6, pErk, pAkt, Caspase2, RBBP
Cyclin D3, MEK, s6, pErk, pAkt, Caspase2, total S6
Cyclin D3, MEK, s6, pErk, pAkt, RBBP, total S6
Cyclin D3, MEK, s6, pErk, Caspase2, RBBP, total S6
Cyclin D3, MEK, s6, Akt, pAkt, Caspase2, RBBP
Cyclin D3, MEK, s6, Akt, pAkt, Caspase2, total S6
Cyclin D3, MEK, s6, Akt, pAkt, RBBP, total S6
Cyclin D3, MEK, s6, Akt, Caspase2, RBBP, total S6
Cyclin D3, MEK, s6, pAkt, Caspase2, RBBP, total S6
Cyclin D3, MEK, pS6, Erk, pErk, Akt, pAkt
Cyclin D3, MEK, pS6, Erk, pErk, Akt, Caspase2
Cyclin D3, MEK, pS6, Erk, pErk, Akt, RBBP
Cyclin D3, MEK, pS6, Erk, pErk, Akt, total S6
Cyclin D3, MEK, pS6, Erk, pErk, pAkt, Caspase2
Cyclin D3, MEK, pS6, Erk, pErk, pAkt, RBBP
Cyclin D3, MEK, pS6, Erk, pErk, pAkt, total S6
Cyclin D3, MEK, pS6, Erk, pErk, Caspase2, RBBP
Cyclin D3, MEK, pS6, Erk, pErk, Caspase2, total S6
Cyclin D3, MEK, pS6, Erk, pErk, RBBP, total S6
Cyclin D3, MEK, pS6, Erk, Akt, pAkt, Caspase2
Cyclin D3, MEK, pS6, Erk, Akt, pAkt, RBBP
Cyclin D3, MEK, pS6, Erk, Akt, pAkt, total S6
Cyclin D3, MEK, pS6, Erk, Akt, Caspase2, RBBP
Cyclin D3, MEK, pS6, Erk, Akt, Caspase2, total S6
Cyclin D3, MEK, pS6, Erk, Akt, RBBP, total S6
Cyclin D3, MEK, pS6, Erk, pAkt, Caspase2, RBBP
Cyclin D3, MEK, pS6, Erk, pAkt, Caspase2, total S6
Cyclin D3, MEK, pS6, Erk, pAkt, RBBP, total S6
Cyclin D3, MEK, pS6, Erk, Caspase2, RBBP, total S6
Cyclin D3, MEK, pS6, pErk, Akt, pAkt, Caspase2
Cyclin D3, MEK, pS6, pErk, Akt, pAkt, RBBP
Cyclin D3, MEK, pS6, pErk, Akt, pAkt, total S6
Cyclin D3, MEK, pS6, pErk, Akt, Caspase2, RBBP
Cyclin D3, MEK, pS6, pErk, Akt, Caspase2, total S6
Cyclin D3, MEK, pS6, pErk, Akt, RBBP, total S6
Cyclin D3, MEK, pS6, pErk, pAkt, Caspase2, RBBP
Cyclin D3, MEK, pS6, pErk, pAkt, Caspase2, total S6
Cyclin D3, MEK, pS6, pErk, pAkt, RBBP, total S6
Cyclin D3, MEK, pS6, pErk, Caspase2, RBBP, total S6
Cyclin D3, MEK, pS6, Akt, pAkt, Caspase2, RBBP
Cyclin D3, MEK, pS6, Akt, pAkt, Caspase2, total S6
Cyclin D3, MEK, pS6, Akt, pAkt, RBBP, total S6
Cyclin D3, MEK, pS6, Akt, Caspase2, RBBP, total S6
Cyclin D3, MEK, pS6, pAkt, Caspase2, RBBP, total S6
Cyclin D3, MEK, Erk, pErk, Akt, pAkt, Caspase2
Cyclin D3, MEK, Erk, pErk, Akt, pAkt, RBBP
Cyclin D3, MEK, Erk, pErk, Akt, pAkt, total S6
Cyclin D3, MEK, Erk, pErk, Akt, Caspase2, RBBP
Cyclin D3, MEK, Erk, pErk, Akt, Caspase2, total S6
Cyclin D3, MEK, Erk, pErk, Akt, RBBP, total S6
Cyclin D3, MEK, Erk, pErk, pAkt, Caspase2, RBBP
Cyclin D3, MEK, Erk, pErk, pAkt, Caspase2, total S6
Cyclin D3, MEK, Erk, pErk, pAkt, RBBP, total S6
Cyclin D3, MEK, Erk, pErk, Caspase2, RBBP, total S6
Cyclin D3, MEK, Erk, Akt, pAkt, Caspase2, RBBP
Cyclin D3, MEK, Erk, Akt, pAkt, Caspase2, total S6
Cyclin D3, MEK, Erk, Akt, pAkt, RBBP, total S6
Cyclin D3, MEK, Erk, Akt, Caspase2, RBBP, total S6
Cyclin D3, MEK, Erk, pAkt, Caspase2, RBBP, total S6
Cyclin D3, MEK, pErk, Akt, pAkt, Caspase2, RBBP
Cyclin D3, MEK, pErk, Akt, pAkt, Caspase2, total S6
Cyclin D3, MEK, pErk, Akt, pAkt, RBBP, total S6
Cyclin D3, MEK, pErk, Akt, Caspase2, RBBP, total S6
Cyclin D3, MEK, pErk, pAkt, Caspase2, RBBP, total S6
Cyclin D3, MEK, Akt, pAkt, Caspase2, RBBP, total S6
Cyclin D3, s6, pS6, Erk, pErk, Akt, pAkt
Cyclin D3, s6, pS6, Erk, pErk, Akt, Caspase2
Cyclin D3, s6, pS6, Erk, pErk, Akt, RBBP
Cyclin D3, s6, pS6, Erk, pErk, Akt, total S6
Cyclin D3, s6, pS6, Erk, pErk, pAkt, Caspase2
Cyclin D3, s6, pS6, Erk, pErk, pAkt, RBBP
Cyclin D3, s6, pS6, Erk, pErk, pAkt, total S6
Cyclin D3, s6, pS6, Erk, pErk, Caspase2, RBBP TABLE 1-continued Examples of Single Markers and Combinations of Markers

| | |
|---|---|
| MEK, s6, pAkt, Caspase2, total S6 | Cyclin D3, s6, pS6, Erk, pErk, Caspase2, total S6 |
| MEK, s6, pAkt, RBBP, total S6 | Cyclin D3, s6, pS6, Erk, pErk, RBBP, total S6 |
| MEK, s6, Caspase2, RBBP, total S6 | Cyclin D3, s6, pS6, Erk, Akt, pAkt, Caspase2 |
| MEK, pS6, Erk, pErk, Akt | Cyclin D3, s6, pS6, Erk, Akt, pAkt, RBBP |
| MEK, pS6, Erk, pErk, pAkt | Cyclin D3, s6, pS6, Erk, Akt, pAkt, total S6 |
| MEK, pS6, Erk, pErk, Caspase2 | Cyclin D3, s6, pS6, Erk, Akt, Caspase2, RBBP |
| MEK, pS6, Erk, pErk, RBBP | Cyclin D3, s6, pS6, Erk, Akt, Caspase2, total S6 |
| MEK, pS6, Erk, pErk, total S6 | Cyclin D3, s6, pS6, Erk, Akt, RBBP, total S6 |
| MEK, pS6, Erk, Akt, pAkt | Cyclin D3, s6, pS6, Erk, pAkt, Caspase2, RBBP |
| MEK, pS6, Erk, Akt, Caspase2 | Cyclin D3, s6, pS6, Erk, pAkt, Caspase2, total S6 |
| MEK, pS6, Erk, Akt, RBBP | Cyclin D3, s6, pS6, Erk, pAkt, RBBP, total S6 |
| MEK, pS6, Erk, Akt, total S6 | Cyclin D3, s6, pS6, Erk, Caspase2, RBBP, total S6 |
| MEK, pS6, Erk, pAkt, Caspase2 | Cyclin D3, s6, pS6, pErk, Akt, pAkt, Caspase2 |
| MEK, pS6, Erk, pAkt, RBBP | Cyclin D3, s6, pS6, pErk, Akt, pAkt, RBBP |
| MEK, pS6, Erk, pAkt, total S6 | Cyclin D3, s6, pS6, pErk, Akt, pAkt, total S6 |
| MEK, pS6, Erk, Caspase2, RBBP | Cyclin D3, s6, pS6, pErk, Akt, Caspase2, RBBP |
| MEK, pS6, Erk, Caspase2, total S6 | Cyclin D3, s6, pS6, pErk, Akt, Caspase2, total S6 |
| MEK, pS6, Erk, RBBP, total S6 | Cyclin D3, s6, pS6, pErk, Akt, RBBP, total S6 |
| MEK, pS6, pErk, Akt, pAkt | Cyclin D3, s6, pS6, pErk, pAkt, Caspase2, RBBP |
| MEK, pS6, pErk, Akt, Caspase2 | Cyclin D3, s6, pS6, pErk, pAkt, Caspase2, total S6 |
| MEK, pS6, pErk, Akt, RBBP | Cyclin D3, s6, pS6, pErk, pAkt, RBBP, total S6 |
| MEK, pS6, pErk, Akt, total S6 | Cyclin D3, s6, pS6, pErk, Caspase2, RBBP, total S6 |
| MEK, pS6, pErk, pAkt, Caspase2 | Cyclin D3, s6, pS6, Akt, pAkt, Caspase2, RBBP |
| MEK, pS6, pErk, pAkt, RBBP | Cyclin D3, s6, pS6, Akt, pAkt, Caspase2, total S6 |
| MEK, pS6, pErk, pAkt, total S6 | Cyclin D3, s6, pS6, Akt, pAkt, RBBP, total S6 |
| MEK, pS6, pErk, Caspase2, RBBP | Cyclin D3, s6, pS6, Akt, Caspase2, RBBP, total S6 |
| MEK, pS6, pErk, Caspase2, total S6 | Cyclin D3, s6, pS6, pAkt, Caspase2, RBBP, total S6 |
| MEK, pS6, pErk, RBBP, total S6 | Cyclin D3, s6, Erk, pErk, Akt, pAkt, Caspase2 |
| MEK, pS6, Akt, pAkt, Caspase2 | Cyclin D3, s6, Erk, pErk, Akt, pAkt, RBBP |
| MEK, pS6, Akt, pAkt, RBBP | Cyclin D3, s6, Erk, pErk, Akt, pAkt, total S6 |
| MEK, pS6, Akt, pAkt, total S6 | Cyclin D3, s6, Erk, pErk, Akt, Caspase2, RBBP |
| MEK, pS6, Akt, Caspase2, RBBP | Cyclin D3, s6, Erk, pErk, Akt, Caspase2, total S6 |
| MEK, pS6, Akt, Caspase2, total S6 | Cyclin D3, s6, Erk, pErk, Akt, RBBP, total S6 |
| MEK, pS6, Akt, RBBP, total S6 | Cyclin D3, s6, Erk, pErk, pAkt, Caspase2, RBBP |
| MEK, pS6, pAkt, Caspase2, RBBP | Cyclin D3, s6, Erk, pErk, pAkt, Caspase2, total S6 |
| MEK, pS6, pAkt, Caspase2, total S6 | Cyclin D3, s6, Erk, pErk, pAkt, RBBP, total S6 |
| MEK, pS6, pAkt, RBBP, total S6 | Cyclin D3, s6, Erk, pErk, Caspase2, RBBP, total S6 |
| MEK, pS6, Caspase2, RBBP, total S6 | Cyclin D3, s6, Erk, Akt, pAkt, Caspase2, RBBP |
| MEK, Erk, pErk, Akt, pAkt | Cyclin D3, s6, Erk, Akt, pAkt, Caspase2, total S6 |
| MEK, Erk, pErk, Akt, Caspase2 | Cyclin D3, s6, Erk, Akt, pAkt, RBBP, total S6 |
| MEK, Erk, pErk, Akt, RBBP | Cyclin D3, s6, Erk, Akt, Caspase2, RBBP, total S6 |
| MEK, Erk, pErk, Akt, total S6 | Cyclin D3, s6, Erk, pAkt, Caspase2, RBBP, total S6 |
| MEK, Erk, pErk, pAkt, Caspase2 | Cyclin D3, s6, pErk, Akt, pAkt, Caspase2, RBBP |
| MEK, Erk, pErk, pAkt, RBBP | Cyclin D3, s6, pErk, Akt, pAkt, Caspase2, total S6 |
| MEK, Erk, pErk, pAkt, total S6 | Cyclin D3, s6, pErk, Akt, pAkt, RBBP, total S6 |
| MEK, Erk, pErk, Caspase2, RBBP | Cyclin D3, s6, pErk, Akt, Caspase2, RBBP, total S6 |
| MEK, Erk, pErk, Caspase2, total S6 | Cyclin D3, s6, pErk, pAkt, Caspase2, RBBP, total S6 |
| MEK, Erk, pErk, RBBP, total S6 | Cyclin D3, s6, Akt, pAkt, Caspase2, RBBP, total S6 |
| MEK, Erk, Akt, pAkt, Caspase2 | Cyclin D3, pS6, Erk, pErk, Akt, pAkt, Caspase2 |
| MEK, Erk, Akt, pAkt, RBBP | Cyclin D3, pS6, Erk, pErk, Akt, pAkt, RBBP |
| MEK, Erk, Akt, pAkt, total S6 | Cyclin D3, pS6, Erk, pErk, Akt, pAkt, total S6 |
| MEK, Erk, Akt, Caspase2, RBBP | Cyclin D3, pS6, Erk, pErk, Akt, Caspase2, RBBP |
| MEK, Erk, Akt, Caspase2, total S6 | Cyclin D3, pS6, Erk, pErk, Akt, Caspase2, total S6 |
| MEK, Erk, Akt, RBBP, total S6 | Cyclin D3, pS6, Erk, pErk, Akt, RBBP, total S6 |
| MEK, Erk, pAkt, Caspase2, RBBP | Cyclin D3, pS6, Erk, pErk, pAkt, Caspase2, RBBP |
| MEK, Erk, pAkt, Caspase2, total S6 | Cyclin D3, pS6, Erk, pErk, pAkt, Caspase2, total S6 |
| MEK, Erk, pAkt, RBBP, total S6 | Cyclin D3, pS6, Erk, pErk, pAkt, RBBP, total S6 |
| MEK, Erk, Caspase2, RBBP, total S6 | Cyclin D3, pS6, Erk, pErk, Caspase2, RBBP, total S6 |
| MEK, pErk, Akt, pAkt, Caspase2 | Cyclin D3, pS6, Erk, Akt, pAkt, Caspase2, RBBP |
| MEK, pErk, Akt, pAkt, RBBP | Cyclin D3, pS6, Erk, Akt, pAkt, Caspase2, total S6 |
| MEK, pErk, Akt, pAkt, total S6 | Cyclin D3, pS6, Erk, Akt, pAkt, RBBP, total S6 |
| MEK, pErk, Akt, Caspase2, RBBP | Cyclin D3, pS6, Erk, Akt, Caspase2, RBBP, total S6 |
| MEK, pErk, Akt, Caspase2, total S6 | Cyclin D3, pS6, Erk, pAkt, Caspase2, RBBP, total S6 |
| MEK, pErk, Akt, RBBP, total S6 | Cyclin D3, pS6, pErk, Akt, pAkt, Caspase2, RBBP |
| MEK, pErk, pAkt, Caspase2, RBBP | Cyclin D3, pS6, pErk, Akt, pAkt, Caspase2, total S6 |
| MEK, pErk, pAkt, Caspase2, total S6 | Cyclin D3, pS6, pErk, Akt, pAkt, RBBP, total S6 |
| MEK, pErk, pAkt, RBBP, total S6 | Cyclin D3, pS6, pErk, Akt, Caspase2, RBBP, total S6 |
| MEK, pErk, Caspase2, RBBP, total S6 | Cyclin D3, pS6, pErk, pAkt, Caspase2, RBBP, total S6 |
| MEK, Akt, pAkt, Caspase2, RBBP | Cyclin D3, pS6, Akt, pAkt, Caspase2, RBBP, total S6 |
| MEK, Akt, pAkt, Caspase2, total S6 | Cyclin D3, Erk, pErk, Akt, pAkt, Caspase2, RBBP |
| MEK, Akt, pAkt, RBBP, total S6 | Cyclin D3, Erk, pErk, Akt, pAkt, Caspase2, total S6 |
| MEK, Akt, Caspase2, RBBP, total S6 | Cyclin D3, Erk, pErk, Akt, pAkt, RBBP, total S6 |
| MEK, pAkt, Caspase2, RBBP, total S6 | Cyclin D3, Erk, pErk, Akt, Caspase2, RBBP, total S6 |
| s6, pS6, Erk, pErk, Akt | Cyclin D3, Erk, pErk, pAkt, Caspase2, RBBP, total S6 |
| s6, pS6, Erk, pErk, pAkt | Cyclin D3, Erk, Akt, pAkt, Caspase2, RBBP, total S6 |
| s6, pS6, Erk, pErk, Caspase2 | Cyclin D3, pErk, Akt, pAkt, Caspase2, RBBP, total S6 |
| s6, pS6, Erk, pErk, RBBP | MEK, s6, pS6, Erk, pErk, Akt, pAkt |
| s6, pS6, Erk, pErk, total S6 | MEK, s6, pS6, Erk, pErk, Akt, Caspase2 |

TABLE 1-continued

Examples of Single Markers and Combinations of Markers s6, pS6, Erk, Akt, pAkt
s6, pS6, Erk, Akt, Caspase2
s6, pS6, Erk, Akt, RBBP
s6, pS6, Erk, Akt, total S6
s6, pS6, Erk, pAkt, Caspase2
s6, pS6, Erk, pAkt, RBBP
s6, pS6, Erk, pAkt, total S6
s6, pS6, Erk, Caspase2, RBBP
s6, pS6, Erk, Caspase2, total S6
s6, pS6, Erk, RBBP, total S6
s6, pS6, pErk, Akt, pAkt
s6, pS6, pErk, Akt, Caspase2
s6, pS6, pErk, Akt, RBBP
s6, pS6, pErk, Akt, total S6
s6, pS6, pErk, pAkt, Caspase2
s6, pS6, pErk, pAkt, RBBP
s6, pS6, pErk, pAkt, total S6
s6, pS6, pErk, Caspase2, RBBP
s6, pS6, pErk, Caspase2, total S6
s6, pS6, pErk, RBBP, total S6
s6, pS6, Akt, pAkt, Caspase2
s6, pS6, Akt, pAkt, RBBP
s6, pS6, Akt, pAkt, total S6
s6, pS6, Akt, Caspase2, RBBP
s6, pS6, Akt, Caspase2, total S6
s6, pS6, Akt, RBBP, total S6
s6, pS6, pAkt, Caspase2, RBBP
s6, pS6, pAkt, Caspase2, total S6
s6, pS6, pAkt, RBBP, total S6
s6, pS6, Caspase2, RBBP, total S6
s6, Erk, pErk, Akt, pAkt
s6, Erk, pErk, Akt, Caspase2
s6, Erk, pErk, Akt, RBBP
s6, Erk, pErk, Akt, total S6
s6, Erk, pErk, pAkt, Caspase2
s6, Erk, pErk, pAkt, RBBP
s6, Erk, pErk, pAkt, total S6
s6, Erk, pErk, Caspase2, RBBP
s6, Erk, pErk, Caspase2, total S6
s6, Erk, pErk, RBBP, total S6
s6, Erk, Akt, pAkt, Caspase2
s6, Erk, Akt, pAkt, RBBP
s6, Erk, Akt, pAkt, total S6
s6, Erk, Akt, Caspase2, RBBP
s6, Erk, Akt, Caspase2, total S6
s6, Erk, Akt, RBBP, total S6
s6, Erk, pAkt, Caspase2, RBBP
s6, Erk, pAkt, Caspase2, total S6
s6, Erk, pAkt, RBBP, total S6
s6, Erk, Caspase2, RBBP, total S6
s6, pErk, Akt, pAkt, Caspase2
s6, pErk, Akt, pAkt, RBBP
s6, pErk, Akt, pAkt, total S6
s6, pErk, Akt, Caspase2, RBBP
s6, pErk, Akt, Caspase2, total S6
s6, pErk, Akt, RBBP, total S6
s6, pErk, pAkt, Caspase2, RBBP
s6, pErk, pAkt, Caspase2, total S6
s6, pErk, pAkt, RBBP, total S6
s6, pErk, Caspase2, RBBP, total S6
s6, Akt, pAkt, Caspase2, RBBP
s6, Akt, pAkt, Caspase2, total S6
s6, Akt, pAkt, RBBP, total S6
s6, Akt, Caspase2, RBBP, total S6
s6, pAkt, Caspase2, RBBP, total S6
pS6, Erk, pErk, Akt, pAkt
pS6, Erk, pErk, Akt, Caspase2
pS6, Erk, pErk, Akt, RBBP
pS6, Erk, pErk, Akt, total S6
pS6, Erk, pErk, pAkt, Caspase2
pS6, Erk, pErk, pAkt, RBBP
pS6, Erk, pErk, pAkt, total S6
pS6, Erk, pErk, Caspase2, RBBP
pS6, Erk, pErk, Caspase2, total S6
pS6, Erk, pErk, RBBP, total S6
pS6, Erk, Akt, pAkt, Caspase2
pS6, Erk, Akt, pAkt, RBBP
pS6, Erk, Akt, pAkt, total S6
MEK, s6, pS6, Erk, pErk, Akt, RBBP
MEK, s6, pS6, Erk, pErk, Akt, total S6
MEK, s6, pS6, Erk, pErk, pAkt, Caspase2
MEK, s6, pS6, Erk, pErk, pAkt, RBBP
MEK, s6, pS6, Erk, pErk, pAkt, total S6
MEK, s6, pS6, Erk, pErk, Caspase2, RBBP
MEK, s6, pS6, Erk, pErk, Caspase2, total S6
MEK, s6, pS6, Erk, pErk, RBBP, total S6
MEK, s6, pS6, Erk, Akt, pAkt, Caspase2
MEK, s6, pS6, Erk, Akt, pAkt, RBBP
MEK, s6, pS6, Erk, Akt, pAkt, total S6
MEK, s6, pS6, Erk, Akt, Caspase2, RBBP
MEK, s6, pS6, Erk, Akt, Caspase2, total S6
MEK, s6, pS6, Erk, Akt, RBBP, total S6
MEK, s6, pS6, Erk, pAkt, Caspase2, RBBP
MEK, s6, pS6, Erk, pAkt, Caspase2, total S6
MEK, s6, pS6, Erk, pAkt, RBBP, total S6
MEK, s6, pS6, Erk, Caspase2, RBBP, total S6
MEK, s6, pS6, pErk, Akt, pAkt, Caspase2
MEK, s6, pS6, pErk, Akt, pAkt, RBBP
MEK, s6, pS6, pErk, Akt, pAkt, total S6
MEK, s6, pS6, pErk, Akt, Caspase2, RBBP
MEK, s6, pS6, pErk, Akt, Caspase2, total S6
MEK, s6, pS6, pErk, Akt, RBBP, total S6
MEK, s6, pS6, pErk, pAkt, Caspase2, RBBP
MEK, s6, pS6, pErk, pAkt, Caspase2, total S6
MEK, s6, pS6, pErk, pAkt, RBBP, total S6
MEK, s6, pS6, pErk, Caspase2, RBBP, total S6
MEK, s6, pS6, Akt, pAkt, Caspase2, RBBP
MEK, s6, pS6, Akt, pAkt, Caspase2, total S6
MEK, s6, pS6, Akt, pAkt, RBBP, total S6
MEK, s6, pS6, Akt, Caspase2, RBBP, total S6
MEK, s6, pS6, pAkt, Caspase2, RBBP, total S6
MEK, s6, Erk, pErk, Akt, pAkt, Caspase2
MEK, s6, Erk, pErk, Akt, pAkt, RBBP
MEK, s6, Erk, pErk, Akt, pAkt, total S6
MEK, s6, Erk, pErk, Akt, Caspase2, RBBP
MEK, s6, Erk, pErk, Akt, Caspase2, total S6
MEK, s6, Erk, pErk, Akt, RBBP, total S6
MEK, s6, Erk, pErk, pAkt, Caspase2, RBBP
MEK, s6, Erk, pErk, pAkt, Caspase2, total S6
MEK, s6, Erk, pErk, pAkt, RBBP, total S6
MEK, s6, Erk, pErk, Caspase2, RBBP, total S6
MEK, s6, Erk, Akt, pAkt, Caspase2, RBBP
MEK, s6, Erk, Akt, pAkt, Caspase2, total S6
MEK, s6, Erk, Akt, pAkt, RBBP, total S6
MEK, s6, Erk, Akt, Caspase2, RBBP, total S6
MEK, s6, Erk, pAkt, Caspase2, RBBP, total S6
MEK, s6, pErk, Akt, pAkt, Caspase2, RBBP
MEK, s6, pErk, Akt, pAkt, Caspase2, total S6
MEK, s6, pErk, Akt, pAkt, RBBP, total S6
MEK, s6, pErk, Akt, Caspase2, RBBP, total S6
MEK, s6, pErk, pAkt, Caspase2, RBBP, total S6
MEK, s6, Akt, pAkt, Caspase2, RBBP, total S6
MEK, pS6, Erk, pErk, Akt, pAkt, Caspase2
MEK, pS6, Erk, pErk, Akt, pAkt, RBBP
MEK, pS6, Erk, pErk, Akt, pAkt, total S6
MEK, pS6, Erk, pErk, Akt, Caspase2, RBBP
MEK, pS6, Erk, pErk, Akt, Caspase2, total S6
MEK, pS6, Erk, pErk, Akt, RBBP, total S6
MEK, pS6, Erk, pErk, pAkt, Caspase2, RBBP
MEK, pS6, Erk, pErk, pAkt, Caspase2, total S6
MEK, pS6, Erk, pErk, pAkt, RBBP, total S6
MEK, pS6, Erk, pErk, Caspase2, RBBP, total S6
MEK, pS6, Erk, Akt, pAkt, Caspase2, RBBP
MEK, pS6, Erk, Akt, pAkt, Caspase2, total S6
MEK, pS6, Erk, Akt, pAkt, RBBP, total S6
MEK, pS6, Erk, Akt, Caspase2, RBBP, total S6
MEK, pS6, Erk, pAkt, Caspase2, RBBP, total S6
MEK, pS6, pErk, Akt, pAkt, Caspase2, RBBP
MEK, pS6, pErk, Akt, pAkt, Caspase2, total S6
MEK, pS6, pErk, Akt, pAkt, RBBP, total S6
MEK, pS6, pErk, Akt, Caspase2, RBBP, total S6
MEK, pS6, pErk, pAkt, Caspase2, RBBP, total S6
MEK, pS6, Akt, pAkt, Caspase2, RBBP, total S6
MEK, Erk, pErk, Akt, pAkt, Caspase2, RBBP
MEK, Erk, pErk, Akt, pAkt, Caspase2, total S6
MEK, Erk, pErk, Akt, pAkt, RBBP, total S6

TABLE 1-continued

Examples of Single Markers and Combinations of Markers pS6, Erk, Akt, Caspase2, RBBP
pS6, Erk, Akt, Caspase2, total S6
pS6, Erk, Akt, RBBP, total S6
pS6, Erk, pAkt, Caspase2, RBBP
pS6, Erk, pAkt, Caspase2, total S6
pS6, Erk, pAkt, RBBP, total S6
pS6, Erk, Caspase2, RBBP, total S6
pS6, pErk, Akt, pAkt, Caspase2
pS6, pErk, Akt, pAkt, RBBP
pS6, pErk, Akt, pAkt, total S6
pS6, pErk, Akt, Caspase2, RBBP
pS6, pErk, Akt, Caspase2, total S6
pS6, pErk, Akt, RBBP, total S6
pS6, pErk, pAkt, Caspase2, RBBP
pS6, pErk, pAkt, Caspase2, total S6
pS6, pErk, pAkt, RBBP, total S6
pS6, pErk, Caspase2, RBBP, total S6
pS6, Akt, pAkt, Caspase2, RBBP
pS6, Akt, pAkt, Caspase2, total S6
pS6, Akt, pAkt, RBBP, total S6
pS6, Akt, Caspase2, RBBP, total S6
pS6, pAkt, Caspase2, RBBP, total S6
Erk, pErk, Akt, pAkt, Caspase2
Erk, pErk, Akt, pAkt, RBBP
Erk, pErk, Akt, pAkt, total S6
Erk, pErk, Akt, Caspase2, RBBP
Erk, pErk, Akt, Caspase2, total S6
Erk, pErk, Akt, RBBP, total S6
Erk, pErk, pAkt, Caspase2, RBBP
Erk, pErk, pAkt, Caspase2, total S6
Erk, pErk, pAkt, RBBP, total S6
Erk, pErk, Caspase2, RBBP, total S6
Erk, Akt, pAkt, Caspase2, RBBP
Erk, Akt, pAkt, Caspase2, total S6
Erk, Akt, pAkt, RBBP, total S6
Erk, Akt, Caspase2, RBBP, total S6
Erk, pAkt, Caspase2, RBBP, total S6
pErk, Akt, pAkt, Caspase2, RBBP
pErk, Akt, pAkt, Caspase2, total S6
pErk, Akt, pAkt, RBBP, total S6
pErk, Akt, Caspase2, RBBP, total S6
pErk, pAkt, Caspase2, RBBP, total S6
Akt, pAkt, Caspase2, RBBP, total S6
PCNA, Cyclin D1, Cyclin D3, MEK, s6, pS6, Erk, pErk, Akt, pAkt, Caspase2, RBBP, total S6
PCNA, Cyclin D1, Cyclin D3, MEK, s6, pS6, Erk, pErk, Akt, pAkt, Caspase2, RBBP
PCNA, Cyclin D1, Cyclin D3, MEK, s6, pS6, Erk, pErk, Akt, pAkt, Caspase2, total S6
PCNA, Cyclin D1, Cyclin D3, MEK, s6, pS6, Erk, pErk, Akt, pAkt, RBBP, total S6
PCNA, Cyclin D1, Cyclin D3, MEK, s6, pS6, Erk, pErk, Akt, Caspase2, RBBP, total S6
PCNA, Cyclin D1, Cyclin D3, MEK, s6, pS6, Erk, pErk, pAkt, Caspase2, RBBP, total S6
PCNA, Cyclin D1, Cyclin D3, MEK, s6, pS6, Erk, Akt, pAkt, Caspase2, RBBP, total S6
PCNA, Cyclin D1, Cyclin D3, MEK, s6, pS6, pErk, Akt, pAkt, Caspase2, RBBP, total S6
PCNA, Cyclin D1, Cyclin D3, MEK, s6, Erk, pErk, Akt, pAkt, Caspase2, RBBP, total S6
PCNA, Cyclin D1, Cyclin D3, MEK, pS6, Erk, pErk, Akt, pAkt, Caspase2, RBBP, total S6
PCNA, Cyclin D1, Cyclin D3, s6, pS6, Erk, pErk, Akt, pAkt, Caspase2, RBBP, total S6
PCNA, Cyclin D1, MEK, s6, pS6, Erk, pErk, Akt, pAkt, Caspase2, RBBP, total S6
PCNA, Cyclin D3, MEK, s6, pS6, Erk, pErk, Akt, pAkt, Caspase2, RBBP, total S6
Cyclin D1, Cyclin D3, MEK, s6, pS6, Erk, pErk, Akt, pAkt, Caspase2, RBBP, total S6
PCNA, Cyclin D1, Cyclin D3, MEK, s6, pS6, Erk, pErk, Akt, pAkt, Caspase2
PCNA, Cyclin D1, Cyclin D3, MEK, s6, pS6, Erk, pErk, Akt, pAkt, RBBP
PCNA, Cyclin D1, Cyclin D3, MEK, s6, pS6, Erk, pErk, Akt, pAkt, total S6
MEK, Erk, pErk, Akt, Caspase2, RBBP, total S6
MEK, Erk, pErk, pAkt, Caspase2, RBBP, total S6
MEK, Erk, Akt, pAkt, Caspase2, RBBP, total S6
MEK, pErk, Akt, pAkt, Caspase2, RBBP, total S6
s6, pS6, Erk, pErk, Akt, pAkt, Caspase2
s6, pS6, Erk, pErk, Akt, pAkt, RBBP
s6, pS6, Erk, pErk, Akt, pAkt, total S6
s6, pS6, Erk, pErk, Akt, Caspase2, RBBP
s6, pS6, Erk, pErk, Akt, Caspase2, total S6
s6, pS6, Erk, pErk, Akt, RBBP, total S6
s6, pS6, Erk, pErk, pAkt, Caspase2, RBBP
s6, pS6, Erk, pErk, pAkt, Caspase2, total S6
s6, pS6, Erk, pErk, pAkt, RBBP, total S6
s6, pS6, Erk, pErk, Caspase2, RBBP, total S6
s6, pS6, Erk, Akt, pAkt, Caspase2, RBBP
s6, pS6, Erk, Akt, pAkt, Caspase2, total S6
s6, pS6, Erk, Akt, pAkt, RBBP, total S6
s6, pS6, Erk, Akt, Caspase2, RBBP, total S6
s6, pS6, Erk, pAkt, Caspase2, RBBP, total S6
s6, pS6, pErk, Akt, pAkt, Caspase2, RBBP
s6, pS6, pErk, Akt, pAkt, Caspase2, total S6
s6, pS6, pErk, Akt, pAkt, RBBP, total S6
s6, pS6, pErk, Akt, Caspase2, RBBP, total S6
s6, pS6, pErk, pAkt, Caspase2, RBBP, total S6
s6, pS6, Akt, pAkt, Caspase2, RBBP, total S6
s6, Erk, pErk, Akt, pAkt, Caspase2, RBBP
s6, Erk, pErk, Akt, pAkt, Caspase2, total S6
s6, Erk, pErk, Akt, pAkt, RBBP, total S6
s6, Erk, pErk, Akt, Caspase2, RBBP, total S6
s6, Erk, pErk, pAkt, Caspase2, RBBP, total S6
s6, Erk, Akt, pAkt, Caspase2, RBBP, total S6
s6, pErk, Akt, pAkt, Caspase2, RBBP, total S6
pS6, Erk, pErk, Akt, pAkt, Caspase2, RBBP
pS6, Erk, pErk, Akt, pAkt, Caspase2, total S6
pS6, Erk, pErk, Akt, pAkt, RBBP, total S6
pS6, Erk, pErk, Akt, Caspase2, RBBP, total S6
pS6, Erk, pErk, pAkt, Caspase2, RBBP, total S6
pS6, Erk, Akt, pAkt, Caspase2, RBBP, total S6
pS6, pErk, Akt, pAkt, Caspase2, RBBP, total S6
Erk, pErk, Akt, pAkt, Caspase2, RBBP, total S6
PCNA, Cyclin D1, Cyclin D3, MEK, s6, pS6
PCNA, Cyclin D1, Cyclin D3, MEK, s6, Erk
PCNA, Cyclin D1, Cyclin D3, MEK, s6, pErk
PCNA, Cyclin D1, Cyclin D3, MEK, s6, Akt
PCNA, Cyclin D1, Cyclin D3, MEK, s6, pAkt
PCNA, Cyclin D1, Cyclin D3, MEK, s6, Caspase2
PCNA, Cyclin D1, Cyclin D3, MEK, s6, RBBP
PCNA, Cyclin D1, Cyclin D3, MEK, s6, total S6
PCNA, Cyclin D1, Cyclin D3, MEK, pS6, Erk
PCNA, Cyclin D1, Cyclin D3, MEK, pS6, pErk
PCNA, Cyclin D1, Cyclin D3, MEK, pS6, Akt
PCNA, Cyclin D1, Cyclin D3, MEK, pS6, pAkt
PCNA, Cyclin D1, Cyclin D3, MEK, pS6, Caspase2
PCNA, Cyclin D1, Cyclin D3, MEK, pS6, RBBP
PCNA, Cyclin D1, Cyclin D3, MEK, pS6, total S6
PCNA, Cyclin D1, Cyclin D3, MEK, Erk, pErk
PCNA, Cyclin D1, Cyclin D3, MEK, Erk, Akt
PCNA, Cyclin D1, Cyclin D3, MEK, Erk, pAkt
PCNA, Cyclin D1, Cyclin D3, MEK, Erk, Caspase2
PCNA, Cyclin D1, Cyclin D3, MEK, Erk, RBBP

TABLE 1-continued

Examples of Single Markers and Combinations of Markers

PCNA, Cyclin D1, Cyclin D3, MEK, s6, pS6, Erk, pErk, Akt, Caspase2, RBBP
PCNA, Cyclin D1, Cyclin D3, MEK, s6, pS6, Erk, pErk, Akt, Caspase2, total S6
PCNA, Cyclin D1, Cyclin D3, MEK, s6, pS6, Erk, pErk, Akt, RBBP, total S6
PCNA, Cyclin D1, Cyclin D3, MEK, s6, pS6, Erk, pErk, pAkt, Caspase2, RBBP
PCNA, Cyclin D1, Cyclin D3, MEK, s6, pS6, Erk, pErk, pAkt, Caspase2, total S6
PCNA, Cyclin D1, Cyclin D3, MEK, s6, pS6, Erk, pErk, pAkt, RBBP, total S6
PCNA, Cyclin D1, Cyclin D3, MEK, s6, pS6, Erk, pErk, Caspase2, RBBP, total S6
PCNA, Cyclin D1, Cyclin D3, MEK, s6, pS6, Erk, Akt, pAkt, Caspase2, RBBP
PCNA, Cyclin D1, Cyclin D3, MEK, s6, pS6, Erk, Akt, pAkt, Caspase2, total S6
PCNA, Cyclin D1, Cyclin D3, MEK, s6, pS6, Erk, Akt, pAkt, RBBP, total S6
PCNA, Cyclin D1, Cyclin D3, MEK, s6, pS6, Erk, Akt, Caspase2, RBBP, total S6
PCNA, Cyclin D1, Cyclin D3, MEK, s6, pS6, Erk, pAkt, Caspase2, RBBP, total S6
PCNA, Cyclin D1, Cyclin D3, MEK, s6, pS6, pErk, Akt, pAkt, Caspase2, RBBP
PCNA, Cyclin D1, Cyclin D3, MEK, s6, pS6, pErk, Akt, pAkt, Caspase2, total S6
PCNA, Cyclin D1, Cyclin D3, MEK, s6, pS6, pErk, Akt, pAkt, RBBP, total S6
PCNA, Cyclin D1, Cyclin D3, MEK, s6, pS6, pErk, Akt, Caspase2, RBBP, total S6
PCNA, Cyclin D1, Cyclin D3, MEK, s6, pS6, pErk, pAkt, Caspase2, RBBP, total S6
PCNA, Cyclin D1, Cyclin D3, MEK, s6, pS6, Akt, pAkt, Caspase2, RBBP, total S6
PCNA, Cyclin D1, Cyclin D3, MEK, s6, Erk, pErk, Akt, pAkt, Caspase2, RBBP
PCNA, Cyclin D1, Cyclin D3, MEK, s6, Erk, pErk, Akt, pAkt, Caspase2, total S6
PCNA, Cyclin D1, Cyclin D3, MEK, s6, Erk, pErk, Akt, pAkt, RBBP, total S6
PCNA, Cyclin D1, Cyclin D3, MEK, s6, Erk, pErk, Akt, Caspase2, RBBP, total S6
PCNA, Cyclin D1, Cyclin D3, MEK, s6, Erk, pErk, pAkt, Caspase2, RBBP, total S6
PCNA, Cyclin D1, Cyclin D3, MEK, s6, Erk, Akt, pAkt, Caspase2, RBBP, total S6
PCNA, Cyclin D1, Cyclin D3, MEK, s6, pErk, Akt, pAkt, Caspase2, RBBP, total S6
PCNA, Cyclin D1, Cyclin D3, MEK, pS6, Erk, pErk, Akt, pAkt, Caspase2, RBBP
PCNA, Cyclin D1, Cyclin D3, MEK, pS6, Erk, pErk, Akt, pAkt, Caspase2, total S6
PCNA, Cyclin D1, Cyclin D3, MEK, pS6, Erk, pErk, Akt, pAkt, RBBP, total S6
PCNA, Cyclin D1, Cyclin D3, MEK, pS6, Erk, pErk, Akt, Caspase2, RBBP, total S6
PCNA, Cyclin D1, Cyclin D3, MEK, pS6, Erk, pErk, pAkt, Caspase2, RBBP, total S6
PCNA, Cyclin D1, Cyclin D3, MEK, pS6, Erk, Akt, pAkt, Caspase2, RBBP, total S6
PCNA, Cyclin D1, Cyclin D3, MEK, pS6, pErk, Akt, pAkt, Caspase2, RBBP, total S6
PCNA, Cyclin D1, Cyclin D3, MEK, Erk, pErk, Akt, pAkt, Caspase2, RBBP, total S6
PCNA, Cyclin D1, Cyclin D3, s6, pS6, Erk, pErk, Akt, pAkt, Caspase2, RBBP
PCNA, Cyclin D1, Cyclin D3, s6, pS6, Erk, pErk, Akt, pAkt, Caspase2, total S6
PCNA, Cyclin D1, Cyclin D3, s6, pS6, Erk, pErk, Akt, pAkt, RBBP, total S6
PCNA, Cyclin D1, Cyclin D3, s6, pS6, Erk, pErk, Akt, Caspase2, RBBP, total S6
PCNA, Cyclin D1, Cyclin D3, s6, pS6, Erk, pErk, pAkt, Caspase2, RBBP, total S6
PCNA, Cyclin D1, Cyclin D3, s6, pS6, Erk, Akt, pAkt, Caspase2, RBBP, total S6

PCNA, Cyclin D1, Cyclin D3, MEK, Erk, total S6
PCNA, Cyclin D1, Cyclin D3, MEK, pErk, Akt
PCNA, Cyclin D1, Cyclin D3, MEK, pErk, pAkt
PCNA, Cyclin D1, Cyclin D3, MEK, pErk, Caspase2
PCNA, Cyclin D1, Cyclin D3, MEK, pErk, RBBP
PCNA, Cyclin D1, Cyclin D3, MEK, pErk, total S6
PCNA, Cyclin D1, Cyclin D3, MEK, Akt, pAkt
PCNA, Cyclin D1, Cyclin D3, MEK, Akt, Caspase2
PCNA, Cyclin D1, Cyclin D3, MEK, Akt, RBBP
PCNA, Cyclin D1, Cyclin D3, MEK, Akt, total S6
PCNA, Cyclin D1, Cyclin D3, MEK, pAkt, Caspase2
PCNA, Cyclin D1, Cyclin D3, MEK, pAkt, RBBP
PCNA, Cyclin D1, Cyclin D3, MEK, pAkt, total S6
PCNA, Cyclin D1, Cyclin D3, MEK, Caspase2, RBBP
PCNA, Cyclin D1, Cyclin D3, MEK, Caspase2, total S6
PCNA, Cyclin D1, Cyclin D3, MEK, RBBP, total S6
PCNA, Cyclin D1, Cyclin D3, s6, pS6, Erk
PCNA, Cyclin D1, Cyclin D3, s6, pS6, pErk
PCNA, Cyclin D1, Cyclin D3, s6, pS6, Akt
PCNA, Cyclin D1, Cyclin D3, s6, pS6, pAkt
PCNA, Cyclin D1, Cyclin D3, s6, pS6, Caspase2
PCNA, Cyclin D1, Cyclin D3, s6, pS6, RBBP
PCNA, Cyclin D1, Cyclin D3, s6, pS6, total S6
PCNA, Cyclin D1, Cyclin D3, s6, Erk, pErk
PCNA, Cyclin D1, Cyclin D3, s6, Erk, Akt
PCNA, Cyclin D1, Cyclin D3, s6, Erk, pAkt
PCNA, Cyclin D1, Cyclin D3, s6, Erk, Caspase2
PCNA, Cyclin D1, Cyclin D3, s6, Erk, RBBP
PCNA, Cyclin D1, Cyclin D3, s6, Erk, total S6
PCNA, Cyclin D1, Cyclin D3, s6, pErk, Akt
PCNA, Cyclin D1, Cyclin D3, s6, pErk, pAkt
PCNA, Cyclin D1, Cyclin D3, s6, pErk, Caspase2
PCNA, Cyclin D1, Cyclin D3, s6, pErk, RBBP
PCNA, Cyclin D1, Cyclin D3, s6, pErk, total S6
PCNA, Cyclin D1, Cyclin D3, s6, Akt, pAkt
PCNA, Cyclin D1, Cyclin D3, s6, Akt, Caspase2
PCNA, Cyclin D1, Cyclin D3, s6, Akt, RBBP
PCNA, Cyclin D1, Cyclin D3, s6, Akt, total S6
PCNA, Cyclin D1, Cyclin D3, s6, pAkt, Caspase2

TABLE 1-continued

Examples of Single Markers and Combinations of Markers

PCNA, Cyclin D1, Cyclin D3, s6, pS6, pErk, Akt, pAkt, Caspase2, RBBP, total S6
PCNA, Cyclin D1, Cyclin D3, s6, pS6, Erk, pErk, Akt, pAkt, Caspase2, RBBP, total S6
PCNA, Cyclin D1, Cyclin D3, pS6, Erk, pErk, Akt, pAkt, Caspase2, RBBP, total S6
PCNA, Cyclin D1, MEK, s6, pS6, Erk, pErk, Akt, pAkt, Caspase2, RBBP
PCNA, Cyclin D1, MEK, s6, pS6, Erk, pErk, Akt, pAkt, Caspase2, total S6
PCNA, Cyclin D1, MEK, s6, pS6, Erk, pErk, Akt, pAkt, RBBP, total S6
PCNA, Cyclin D1, MEK, s6, pS6, Erk, pErk, Akt, Caspase2, RBBP, total S6
PCNA, Cyclin D1, MEK, s6, pS6, Erk, pErk, pAkt, Caspase2, RBBP, total S6
PCNA, Cyclin D1, MEK, s6, pS6, Erk, Akt, pAkt, Caspase2, RBBP, total S6
PCNA, Cyclin D1, MEK, s6, pS6, pErk, Akt, pAkt, Caspase2, RBBP, total S6
PCNA, Cyclin D1, MEK, s6, Erk, pErk, Akt, pAkt, Caspase2, RBBP, total S6
PCNA, Cyclin D1, MEK, pS6, Erk, pErk, Akt, pAkt, Caspase2, RBBP, total S6
PCNA, Cyclin D1, s6, pS6, Erk, pErk, Akt, pAkt, Caspase2, RBBP, total S6
PCNA, Cyclin D3, MEK, s6, pS6, Erk, pErk, Akt, pAkt, Caspase2, RBBP
PCNA, Cyclin D3, MEK, s6, pS6, Erk, pErk, Akt, pAkt, Caspase2, total S6
PCNA, Cyclin D3, MEK, s6, pS6, Erk, pErk, Akt, pAkt, RBBP, total S6
PCNA, Cyclin D3, MEK, s6, pS6, Erk, pErk, Akt, Caspase2, RBBP, total S6
PCNA, Cyclin D3, MEK, s6, pS6, Erk, pErk, pAkt, Caspase2, RBBP, total S6
PCNA, Cyclin D3, MEK, s6, pS6, Erk, Akt, pAkt, Caspase2, RBBP, total S6
PCNA, Cyclin D3, MEK, s6, pS6, pErk, Akt, pAkt, Caspase2, RBBP, total S6
PCNA, Cyclin D3, MEK, s6, Erk, pErk, Akt, pAkt, Caspase2, RBBP, total S6
PCNA, Cyclin D3, MEK, pS6, Erk, pErk, Akt, pAkt, Caspase2, RBBP, total S6
PCNA, Cyclin D3, s6, pS6, Erk, pErk, Akt, pAkt, Caspase2, RBBP, total S6
PCNA, MEK, s6, pS6, Erk, pErk, Akt, pAkt, Caspase2, RBBP, total S6
Cyclin D1, Cyclin D3, MEK, s6, pS6, Erk, pErk, Akt, pAkt, Caspase2, RBBP
Cyclin D1, Cyclin D3, MEK, s6, pS6, Erk, pErk, Akt, pAkt, Caspase2, total S6
Cyclin D1, Cyclin D3, MEK, s6, pS6, Erk, pErk, Akt, pAkt, RBBP, total S6
Cyclin D1, Cyclin D3, MEK, s6, pS6, Erk, pErk, Akt, Caspase2, RBBP, total S6
Cyclin D1, Cyclin D3, MEK, s6, pS6, Erk, pErk, pAkt, Caspase2, RBBP, total S6
Cyclin D1, Cyclin D3, MEK, s6, pS6, Erk, Akt, pAkt, Caspase2, RBBP, total S6
Cyclin D1, Cyclin D3, MEK, s6, pS6, pErk, Akt, pAkt, Caspase2, RBBP, total S6
Cyclin D1, Cyclin D3, MEK, s6, Erk, pErk, Akt, pAkt, Caspase2, RBBP, total S6
Cyclin D1, Cyclin D3, MEK, pS6, Erk, pErk, Akt, pAkt, Caspase2, RBBP, total S6
Cyclin D1, Cyclin D3, s6, pS6, Erk, pErk, Akt, pAkt, Caspase2, RBBP, total S6
Cyclin D1, MEK, s6, pS6, Erk, pErk, Akt, pAkt, Caspase2, RBBP, total S6
Cyclin D3, MEK, s6, pS6, Erk, pErk, Akt, pAkt, Caspase2, RBBP, total S6
PCNA, Cyclin D1, Cyclin D3, MEK, s6, pS6, Erk, pErk, Akt, pAkt
PCNA, Cyclin D1, Cyclin D3, MEK, s6, pS6, Erk, pErk, Akt, Caspase2
PCNA, Cyclin D1, Cyclin D3, MEK, s6, pS6, Erk, pErk, Akt, RBBP
PCNA, Cyclin D1, Cyclin D3, s6, pAkt, RBBP
PCNA, Cyclin D1, Cyclin D3, s6, pAkt, total S6
PCNA, Cyclin D1, Cyclin D3, s6, Caspase2, RBBP
PCNA, Cyclin D1, Cyclin D3, s6, Caspase2, total S6
PCNA, Cyclin D1, Cyclin D3, s6, RBBP, total S6
PCNA, Cyclin D1, Cyclin D3, pS6, Erk, pErk
PCNA, Cyclin D1, Cyclin D3, pS6, Erk, Akt
PCNA, Cyclin D1, Cyclin D3, pS6, Erk, pAkt
PCNA, Cyclin D1, Cyclin D3, pS6, Erk, Caspase2
PCNA, Cyclin D1, Cyclin D3, pS6, Erk, RBBP
PCNA, Cyclin D1, Cyclin D3, pS6, Erk, total S6
PCNA, Cyclin D1, Cyclin D3, pS6, pErk, Akt
PCNA, Cyclin D1, Cyclin D3, pS6, pErk, pAkt
PCNA, Cyclin D1, Cyclin D3, pS6, pErk, Caspase2
PCNA, Cyclin D1, Cyclin D3, pS6, pErk, RBBP
PCNA, Cyclin D1, Cyclin D3, pS6, pErk, total S6
PCNA, Cyclin D1, Cyclin D3, pS6, Akt, pAkt
PCNA, Cyclin D1, Cyclin D3, pS6, Akt, Caspase2
PCNA, Cyclin D1, Cyclin D3, pS6, Akt, RBBP
PCNA, Cyclin D1, Cyclin D3, pS6, Akt, total S6
PCNA, Cyclin D1, Cyclin D3, pS6, pAkt, Caspase2
PCNA, Cyclin D1, Cyclin D3, pS6, pAkt, RBBP
PCNA, Cyclin D1, Cyclin D3, pS6, pAkt, total S6
PCNA, Cyclin D1, Cyclin D3, pS6, Caspase2, RBBP
PCNA, Cyclin D1, Cyclin D3, pS6, Caspase2, total S6
PCNA, Cyclin D1, Cyclin D3, pS6, RBBP, total S6
PCNA, Cyclin D1, Cyclin D3, Erk, pErk, Akt
PCNA, Cyclin D1, Cyclin D3, Erk, pErk, pAkt
PCNA, Cyclin D1, Cyclin D3, Erk, pErk, Caspase2
PCNA, Cyclin D1, Cyclin D3, Erk, pErk, RBBP
PCNA, Cyclin D1, Cyclin D3, Erk, pErk, total S6
PCNA, Cyclin D1, Cyclin D3, Erk, Akt, pAkt
PCNA, Cyclin D1, Cyclin D3, Erk, Akt, Caspase2
PCNA, Cyclin D1, Cyclin D3, Erk, Akt, RBBP
PCNA, Cyclin D1, Cyclin D3, Erk, Akt, total S6
PCNA, Cyclin D1, Cyclin D3, Erk, pAkt, Caspase2
PCNA, Cyclin D1, Cyclin D3, Erk, pAkt, RBBP
PCNA, Cyclin D1, Cyclin D3, Erk, pAkt, total S6
PCNA, Cyclin D1, Cyclin D3, Erk, Caspase2, RBBP

TABLE 1-continued

Examples of Single Markers and Combinations of Markers

PCNA, Cyclin D1, Cyclin D3, MEK, s6, pS6, Erk, pErk, Akt, total S6
PCNA, Cyclin D1, Cyclin D3, MEK, s6, pS6, Erk, pErk, pAkt, Caspase2
PCNA, Cyclin D1, Cyclin D3, MEK, s6, pS6, Erk, pErk, pAkt, RBBP
PCNA, Cyclin D1, Cyclin D3, MEK, s6, pS6, Erk, pErk, pAkt, total S6
PCNA, Cyclin D1, Cyclin D3, MEK, s6, pS6, Erk, pErk, Caspase2, RBBP
PCNA, Cyclin D1, Cyclin D3, MEK, s6, pS6, Erk, pErk, Caspase2, total S6
PCNA, Cyclin D1, Cyclin D3, MEK, s6, pS6, Erk, pErk, RBBP, total S6
PCNA, Cyclin D1, Cyclin D3, MEK, s6, pS6, Erk, Akt, pAkt, Caspase2
PCNA, Cyclin D1, Cyclin D3, MEK, s6, pS6, Erk, Akt, pAkt, RBBP
PCNA, Cyclin D1, Cyclin D3, MEK, s6, pS6, Erk, Akt, pAkt, total S6
PCNA, Cyclin D1, Cyclin D3, MEK, s6, pS6, Erk, Akt, Caspase2, RBBP
PCNA, Cyclin D1, Cyclin D3, MEK, s6, pS6, Erk, Akt, Caspase2, total S6
PCNA, Cyclin D1, Cyclin D3, MEK, s6, pS6, Erk, Akt, RBBP, total S6
PCNA, Cyclin D1, Cyclin D3, MEK, s6, pS6, Erk, pAkt, Caspase2, RBBP
PCNA, Cyclin D1, Cyclin D3, MEK, s6, pS6, Erk, pAkt, Caspase2, total S6
PCNA, Cyclin D1, Cyclin D3, MEK, s6, pS6, Erk, pAkt, RBBP, total S6
PCNA, Cyclin D1, Cyclin D3, MEK, s6, pS6, Erk, Caspase2, RBBP, total S6
PCNA, Cyclin D1, Cyclin D3, MEK, s6, pS6, pErk, Akt, pAkt, Caspase2
PCNA, Cyclin D1, Cyclin D3, MEK, s6, pS6, pErk, Akt, pAkt, RBBP
PCNA, Cyclin D1, Cyclin D3, MEK, s6, pS6, pErk, Akt, pAkt, total S6
PCNA, Cyclin D1, Cyclin D3, MEK, s6, pS6, pErk, Akt, Caspase2, RBBP
PCNA, Cyclin D1, Cyclin D3, MEK, s6, pS6, pErk, Akt, Caspase2, total S6
PCNA, Cyclin D1, Cyclin D3, MEK, s6, pS6, pErk, Akt, RBBP, total S6
PCNA, Cyclin D1, Cyclin D3, MEK, s6, pS6, pErk, pAkt, Caspase2, RBBP
PCNA, Cyclin D1, Cyclin D3, MEK, s6, pS6, pErk, pAkt, Caspase2, total S6
PCNA, Cyclin D1, Cyclin D3, MEK, s6, pS6, pErk, pAkt, RBBP, total S6
PCNA, Cyclin D1, Cyclin D3, MEK, s6, pS6, pErk, Caspase2, RBBP, total S6
PCNA, Cyclin D1, Cyclin D3, MEK, s6, pS6, Akt, pAkt, Caspase2, RBBP
PCNA, Cyclin D1, Cyclin D3, MEK, s6, pS6, Akt, pAkt, Caspase2, total S6
PCNA, Cyclin D1, Cyclin D3, MEK, s6, pS6, Akt, pAkt, RBBP, total S6
PCNA, Cyclin D1, Cyclin D3, MEK, s6, pS6, Akt, Caspase2, RBBP, total S6
PCNA, Cyclin D1, Cyclin D3, MEK, s6, pS6, pAkt, Caspase2, RBBP, total S6
PCNA, Cyclin D1, Cyclin D3, MEK, s6, Erk, pErk, Akt, pAkt, Caspase2
PCNA, Cyclin D1, Cyclin D3, MEK, s6, Erk, pErk, Akt, pAkt, RBBP
PCNA, Cyclin D1, Cyclin D3, MEK, s6, Erk, pErk, Akt, pAkt, total S6
PCNA, Cyclin D1, Cyclin D3, MEK, s6, Erk, pErk, Akt, Caspase2, RBBP
PCNA, Cyclin D1, Cyclin D3, MEK, s6, Erk, pErk, Akt, Caspase2, total S6
PCNA, Cyclin D1, Cyclin D3, MEK, s6, Erk, pErk, Akt, RBBP, total S6
PCNA, Cyclin D1, Cyclin D3, MEK, s6, Erk, pErk, pAkt, Caspase2, RBBP PCNA, Cyclin D1, Cyclin D3, Erk, Caspase2, total S6
PCNA, Cyclin D1, Cyclin D3, Erk, RBBP, total S6
PCNA, Cyclin D1, Cyclin D3, pErk, Akt, pAkt
PCNA, Cyclin D1, Cyclin D3, pErk, Akt, Caspase2
PCNA, Cyclin D1, Cyclin D3, pErk, Akt, RBBP
PCNA, Cyclin D1, Cyclin D3, pErk, Akt, total S6
PCNA, Cyclin D1, Cyclin D3, pErk, pAkt, Caspase2
PCNA, Cyclin D1, Cyclin D3, pErk, pAkt, RBBP
PCNA, Cyclin D1, Cyclin D3, pErk, pAkt, total S6
PCNA, Cyclin D1, Cyclin D3, pErk, Caspase2, RBBP
PCNA, Cyclin D1, Cyclin D3, pErk, Caspase2, total S6
PCNA, Cyclin D1, Cyclin D3, pErk, RBBP, total S6
PCNA, Cyclin D1, Cyclin D3, Akt, pAkt, Caspase2
PCNA, Cyclin D1, Cyclin D3, Akt, pAkt, RBBP
PCNA, Cyclin D1, Cyclin D3, Akt, pAkt, total S6
PCNA, Cyclin D1, Cyclin D3, Akt, Caspase2, RBBP
PCNA, Cyclin D1, Cyclin D3, Akt, Caspase2, total S6
PCNA, Cyclin D1, Cyclin D3, Akt, RBBP, total S6
PCNA, Cyclin D1, Cyclin D3, pAkt, Caspase2, RBBP
PCNA, Cyclin D1, Cyclin D3, pAkt, Caspase2, total S6
PCNA, Cyclin D1, Cyclin D3, pAkt, RBBP, total S6
PCNA, Cyclin D1, Cyclin D3, Caspase2, RBBP, total S6
PCNA, Cyclin D1, MEK, s6, pS6, Erk
PCNA, Cyclin D1, MEK, s6, pS6, pErk
PCNA, Cyclin D1, MEK, s6, pS6, Akt
PCNA, Cyclin D1, MEK, s6, pS6, pAkt
PCNA, Cyclin D1, MEK, s6, pS6, Caspase2
PCNA, Cyclin D1, MEK, s6, pS6, RBBP
PCNA, Cyclin D1, MEK, s6, pS6, total S6
PCNA, Cyclin D1, MEK, s6, Erk, pErk
PCNA, Cyclin D1, MEK, s6, Erk, Akt
PCNA, Cyclin D1, MEK, s6, Erk, pAkt
PCNA, Cyclin D1, MEK, s6, Erk, Caspase2
PCNA, Cyclin D1, MEK, s6, Erk, RBBP
PCNA, Cyclin D1, MEK, s6, Erk, total S6
PCNA, Cyclin D1, MEK, s6, pErk, Akt
PCNA, Cyclin D1, MEK, s6, pErk, pAkt
PCNA, Cyclin D1, MEK, s6, pErk, Caspase2
PCNA, Cyclin D1, MEK, s6, pErk, RBBP

TABLE 1-continued

Examples of Single Markers and Combinations of Markers

PCNA, Cyclin D1, Cyclin D3, MEK, s6, Erk, pErk, pAkt, Caspase2, total S6
PCNA, Cyclin D1, Cyclin D3, MEK, s6, Erk, pErk, pAkt, RBBP, total S6
PCNA, Cyclin D1, Cyclin D3, MEK, s6, Erk, pErk, Caspase2, RBBP, total S6
PCNA, Cyclin D1, Cyclin D3, MEK, s6, Erk, Akt, pAkt, Caspase2, RBBP
PCNA, Cyclin D1, Cyclin D3, MEK, s6, Erk, Akt, pAkt, Caspase2, total S6
PCNA, Cyclin D1, Cyclin D3, MEK, s6, Erk, Akt, pAkt, RBBP, total S6
PCNA, Cyclin D1, Cyclin D3, MEK, s6, Erk, Akt, Caspase2, RBBP, total S6
PCNA, Cyclin D1, Cyclin D3, MEK, s6, Erk, pAkt, Caspase2, RBBP, total S6
PCNA, Cyclin D1, Cyclin D3, MEK, s6, pErk, Akt, pAkt, Caspase2, RBBP
PCNA, Cyclin D1, Cyclin D3, MEK, s6, pErk, Akt, pAkt, Caspase2, total S6
PCNA, Cyclin D1, Cyclin D3, MEK, s6, pErk, Akt, pAkt, RBBP, total S6
PCNA, Cyclin D1, Cyclin D3, MEK, s6, pErk, Akt, Caspase2, RBBP, total S6
PCNA, Cyclin D1, Cyclin D3, MEK, s6, pErk, pAkt, Caspase2, RBBP, total S6
PCNA, Cyclin D1, Cyclin D3, MEK, s6, Akt, pAkt, Caspase2, RBBP, total S6
PCNA, Cyclin D1, Cyclin D3, MEK, pS6, Erk, pErk, Akt, pAkt, Caspase2
PCNA, Cyclin D1, Cyclin D3, MEK, pS6, Erk, pErk, Akt, pAkt, RBBP
PCNA, Cyclin D1, Cyclin D3, MEK, pS6, Erk, pErk, Akt, pAkt, total S6
PCNA, Cyclin D1, Cyclin D3, MEK, pS6, Erk, pErk, Akt, Caspase2, RBBP
PCNA, Cyclin D1, Cyclin D3, MEK, pS6, Erk, pErk, Akt, Caspase2, total S6
PCNA, Cyclin D1, Cyclin D3, MEK, pS6, Erk, pErk, Akt, RBBP, total S6
PCNA, Cyclin D1, Cyclin D3, MEK, pS6, Erk, pErk, pAkt, Caspase2, RBBP
PCNA, Cyclin D1, Cyclin D3, MEK, pS6, Erk, pErk, pAkt, Caspase2, total S6
PCNA, Cyclin D1, Cyclin D3, MEK, pS6, Erk, pErk, pAkt, RBBP, total S6
PCNA, Cyclin D1, Cyclin D3, MEK, pS6, Erk, pErk, Caspase2, RBBP, total S6
PCNA, Cyclin D1, Cyclin D3, MEK, pS6, Erk, Akt, pAkt, Caspase2, RBBP
PCNA, Cyclin D1, Cyclin D3, MEK, pS6, Erk, Akt, pAkt, Caspase2, total S6
PCNA, Cyclin D1, Cyclin D3, MEK, pS6, Erk, Akt, pAkt, RBBP, total S6
PCNA, Cyclin D1, Cyclin D3, MEK, pS6, Erk, Akt, Caspase2, RBBP, total S6
PCNA, Cyclin D1, Cyclin D3, MEK, pS6, Erk, pAkt, Caspase2, RBBP, total S6
PCNA, Cyclin D1, Cyclin D3, MEK, pS6, pErk, Akt, pAkt, Caspase2, RBBP
PCNA, Cyclin D1, Cyclin D3, MEK, pS6, pErk, Akt, pAkt, Caspase2, total S6
PCNA, Cyclin D1, Cyclin D3, MEK, pS6, pErk, Akt, pAkt, RBBP, total S6
PCNA, Cyclin D1, Cyclin D3, MEK, pS6, pErk, Akt, Caspase2, RBBP, total S6
PCNA, Cyclin D1, Cyclin D3, MEK, pS6, pErk, pAkt, Caspase2, RBBP, total S6
PCNA, Cyclin D1, Cyclin D3, MEK, pS6, Akt, pAkt, Caspase2, RBBP, total S6
PCNA, Cyclin D1, Cyclin D3, MEK, Erk, pErk, Akt, pAkt, Caspase2, RBBP
PCNA, Cyclin D1, Cyclin D3, MEK, Erk, pErk, Akt, pAkt, Caspase2, total S6
PCNA, Cyclin D1, Cyclin D3, MEK, Erk, pErk, Akt, pAkt, RBBP, total S6
PCNA, Cyclin D1, Cyclin D3, MEK, Erk, pErk, Akt, Caspase2, RBBP, total S6

PCNA, Cyclin D1, MEK, s6, pErk, total S6
PCNA, Cyclin D1, MEK, s6, Akt, pAkt
PCNA, Cyclin D1, MEK, s6, Akt, Caspase2
PCNA, Cyclin D1, MEK, s6, Akt, RBBP
PCNA, Cyclin D1, MEK, s6, Akt, total S6
PCNA, Cyclin D1, MEK, s6, pAkt, Caspase2
PCNA, Cyclin D1, MEK, s6, pAkt, RBBP
PCNA, Cyclin D1, MEK, s6, pAkt, total S6
PCNA, Cyclin D1, MEK, s6, Caspase2, RBBP
PCNA, Cyclin D1, MEK, s6, Caspase2, total S6
PCNA, Cyclin D1, MEK, s6, RBBP, total S6
PCNA, Cyclin D1, MEK, pS6, Erk, pErk
PCNA, Cyclin D1, MEK, pS6, Erk, Akt
PCNA, Cyclin D1, MEK, pS6, Erk, pAkt
PCNA, Cyclin D1, MEK, pS6, Erk, Caspase2
PCNA, Cyclin D1, MEK, pS6, Erk, RBBP
PCNA, Cyclin D1, MEK, pS6, Erk, total S6
PCNA, Cyclin D1, MEK, pS6, pErk, Akt
PCNA, Cyclin D1, MEK, pS6, pErk, pAkt
PCNA, Cyclin D1, MEK, pS6, pErk, Caspase2
PCNA, Cyclin D1, MEK, pS6, pErk, RBBP
PCNA, Cyclin D1, MEK, pS6, pErk, total S6
PCNA, Cyclin D1, MEK, pS6, Akt, pAkt
PCNA, Cyclin D1, MEK, pS6, Akt, Caspase2
PCNA, Cyclin D1, MEK, pS6, Akt, RBBP
PCNA, Cyclin D1, MEK, pS6, Akt, total S6
PCNA, Cyclin D1, MEK, pS6, pAkt, Caspase2
PCNA, Cyclin D1, MEK, pS6, pAkt, RBBP
PCNA, Cyclin D1, MEK, pS6, pAkt, total S6
PCNA, Cyclin D1, MEK, pS6, Caspase2, RBBP
PCNA, Cyclin D1, MEK, pS6, Caspase2, total S6
PCNA, Cyclin D1, MEK, pS6, RBBP, total S6
PCNA, Cyclin D1, MEK, Erk, pErk, Akt
PCNA, Cyclin D1, MEK, Erk, pErk, pAkt
PCNA, Cyclin D1, MEK, Erk, pErk, Caspase2
PCNA, Cyclin D1, MEK, Erk, pErk, RBBP
PCNA, Cyclin D1, MEK, Erk, pErk, total S6
PCNA, Cyclin D1, MEK, Erk, Akt, pAkt
PCNA, Cyclin D1, MEK, Erk, Akt, Caspase2

TABLE 1-continued

Examples of Single Markers and Combinations of Markers

PCNA, Cyclin D1, Cyclin D3, MEK, Erk, pErk, pAkt, Caspase2, RBBP, total S6
PCNA, Cyclin D1, Cyclin D3, MEK, Erk, Akt, pAkt, Caspase2, RBBP, total S6
PCNA, Cyclin D1, Cyclin D3, MEK, pErk, Akt, pAkt, Caspase2, RBBP, total S6
PCNA, Cyclin D1, Cyclin D3, s6, pS6, Erk, pErk, Akt, pAkt, Caspase2
PCNA, Cyclin D1, Cyclin D3, s6, pS6, Erk, pErk, Akt, pAkt, RBBP
PCNA, Cyclin D1, Cyclin D3, s6, pS6, Erk, pErk, Akt, pAkt, total S6
PCNA, Cyclin D1, Cyclin D3, s6, pS6, Erk, pErk, Akt, Caspase2, RBBP
PCNA, Cyclin D1, Cyclin D3, s6, pS6, Erk, pErk, Akt, Caspase2, total S6
PCNA, Cyclin D1, Cyclin D3, s6, pS6, Erk, pErk, Akt, RBBP, total S6
PCNA, Cyclin D1, Cyclin D3, s6, pS6, Erk, pErk, pAkt, Caspase2, RBBP
PCNA, Cyclin D1, Cyclin D3, s6, pS6, Erk, pErk, pAkt, Caspase2, total S6
PCNA, Cyclin D1, Cyclin D3, s6, pS6, Erk, pErk, pAkt, RBBP, total S6
PCNA, Cyclin D1, Cyclin D3, s6, pS6, Erk, pErk, Caspase2, RBBP, total S6
PCNA, Cyclin D1, Cyclin D3, s6, pS6, Erk, Akt, pAkt, Caspase2, RBBP
PCNA, Cyclin D1, Cyclin D3, s6, pS6, Erk, Akt, pAkt, Caspase2, total S6
PCNA, Cyclin D1, Cyclin D3, s6, pS6, Erk, Akt, pAkt, RBBP, total S6
PCNA, Cyclin D1, Cyclin D3, s6, pS6, Erk, Akt, Caspase2, RBBP, total S6
PCNA, Cyclin D1, Cyclin D3, s6, pS6, Erk, pAkt, Caspase2, RBBP, total S6
PCNA, Cyclin D1, Cyclin D3, s6, pS6, pErk, Akt, pAkt, Caspase2, RBBP
PCNA, Cyclin D1, Cyclin D3, s6, pS6, pErk, Akt, pAkt, Caspase2, total S6
PCNA, Cyclin D1, Cyclin D3, s6, pS6, pErk, Akt, pAkt, RBBP, total S6
PCNA, Cyclin D1, Cyclin D3, s6, pS6, pErk, Akt, Caspase2, RBBP, total S6
PCNA, Cyclin D1, Cyclin D3, s6, pS6, pErk, pAkt, Caspase2, RBBP, total S6
PCNA, Cyclin D1, Cyclin D3, s6, pS6, Akt, pAkt, Caspase2, RBBP, total S6
PCNA, Cyclin D1, Cyclin D3, s6, Erk, pErk, Akt, pAkt, Caspase2, RBBP
PCNA, Cyclin D1, Cyclin D3, s6, Erk, pErk, Akt, pAkt, Caspase2, total S6
PCNA, Cyclin D1, Cyclin D3, s6, Erk, pErk, Akt, pAkt, RBBP, total S6
PCNA, Cyclin D1, Cyclin D3, s6, Erk, pErk, Akt, Caspase2, RBBP, total S6
PCNA, Cyclin D1, Cyclin D3, s6, Erk, pErk, pAkt, Caspase2, RBBP, total S6
PCNA, Cyclin D1, Cyclin D3, s6, Erk, Akt, pAkt, Caspase2, RBBP, total S6
PCNA, Cyclin D1, Cyclin D3, s6, pErk, Akt, pAkt, Caspase2, RBBP, total S6
PCNA, Cyclin D1, Cyclin D3, pS6, Erk, pErk, Akt, pAkt, Caspase2, RBBP
PCNA, Cyclin D1, Cyclin D3, pS6, Erk, pErk, Akt, pAkt, Caspase2, total S6
PCNA, Cyclin D1, Cyclin D3, pS6, Erk, pErk, Akt, pAkt, RBBP, total S6
PCNA, Cyclin D1, Cyclin D3, pS6, Erk, pErk, Akt, Caspase2, RBBP, total S6
PCNA, Cyclin D1, Cyclin D3, pS6, Erk, pErk, pAkt, Caspase2, RBBP, total S6
PCNA, Cyclin D1, Cyclin D3, pS6, Erk, Akt, pAkt, Caspase2, RBBP, total S6
PCNA, Cyclin D1, Cyclin D3, pS6, pErk, Akt, pAkt, Caspase2, RBBP, total S6
PCNA, Cyclin D1, Cyclin D3, Erk, pErk, Akt, pAkt, Caspase2, RBBP, total S6
PCNA, Cyclin D1, MEK, Erk, Akt, RBBP
PCNA, Cyclin D1, MEK, Erk, Akt, total S6
PCNA, Cyclin D1, MEK, Erk, pAkt, Caspase2
PCNA, Cyclin D1, MEK, Erk, pAkt, RBBP
PCNA, Cyclin D1, MEK, Erk, pAkt, total S6
PCNA, Cyclin D1, MEK, Erk, Caspase2, RBBP
PCNA, Cyclin D1, MEK, Erk, Caspase2, total S6
PCNA, Cyclin D1, MEK, Erk, RBBP, total S6
PCNA, Cyclin D1, MEK, pErk, Akt, pAkt
PCNA, Cyclin D1, MEK, pErk, Akt, Caspase2
PCNA, Cyclin D1, MEK, pErk, Akt, RBBP
PCNA, Cyclin D1, MEK, pErk, Akt, total S6
PCNA, Cyclin D1, MEK, pErk, pAkt, Caspase2
PCNA, Cyclin D1, MEK, pErk, pAkt, RBBP
PCNA, Cyclin D1, MEK, pErk, pAkt, total S6
PCNA, Cyclin D1, MEK, pErk, Caspase2, RBBP
PCNA, Cyclin D1, MEK, pErk, Caspase2, total S6
PCNA, Cyclin D1, MEK, pErk, RBBP, total S6
PCNA, Cyclin D1, MEK, Akt, pAkt, Caspase2
PCNA, Cyclin D1, MEK, Akt, pAkt, RBBP
PCNA, Cyclin D1, MEK, Akt, pAkt, total S6
PCNA, Cyclin D1, MEK, Akt, Caspase2, RBBP
PCNA, Cyclin D1, MEK, Akt, Caspase2, total S6
PCNA, Cyclin D1, MEK, Akt, RBBP, total S6
PCNA, Cyclin D1, MEK, pAkt, Caspase2, RBBP
PCNA, Cyclin D1, MEK, pAkt, Caspase2, total S6
PCNA, Cyclin D1, MEK, pAkt, RBBP, total S6
PCNA, Cyclin D1, MEK, Caspase2, RBBP, total S6
PCNA, Cyclin D1, s6, pS6, Erk, pErk
PCNA, Cyclin D1, s6, pS6, Erk, Akt
PCNA, Cyclin D1, s6, pS6, Erk, pAkt
PCNA, Cyclin D1, s6, pS6, Erk, Caspase2
PCNA, Cyclin D1, s6, pS6, Erk, RBBP
PCNA, Cyclin D1, s6, pS6, Erk, total S6
PCNA, Cyclin D1, s6, pS6, pErk, Akt
PCNA, Cyclin D1, s6, pS6, pErk, pAkt
PCNA, Cyclin D1, s6, pS6, pErk, Caspase2
PCNA, Cyclin D1, s6, pS6, pErk, RBBP
PCNA, Cyclin D1, s6, pS6, pErk, total S6

TABLE 1-continued

Examples of Single Markers and Combinations of Markers

PCNA, Cyclin D1, MEK, s6, pS6, Erk, pErk, Akt, pAkt, Caspase2
PCNA, Cyclin D1, MEK, s6, pS6, Erk, pErk, Akt, pAkt, RBBP
PCNA, Cyclin D1, MEK, s6, pS6, Erk, pErk, Akt, pAkt, total S6
PCNA, Cyclin D1, MEK, s6, pS6, Erk, pErk, Akt, Caspase2, RBBP
PCNA, Cyclin D1, MEK, s6, pS6, Erk, pErk, Akt, Caspase2, total S6
PCNA, Cyclin D1, MEK, s6, pS6, Erk, pErk, Akt, RBBP, total S6
PCNA, Cyclin D1, MEK, s6, pS6, Erk, pErk, pAkt, Caspase2, RBBP
PCNA, Cyclin D1, MEK, s6, pS6, Erk, pErk, pAkt, Caspase2, total S6
PCNA, Cyclin D1, MEK, s6, pS6, Erk, pErk, pAkt, RBBP, total S6
PCNA, Cyclin D1, MEK, s6, pS6, Erk, pErk, Caspase2, RBBP, total S6
PCNA, Cyclin D1, MEK, s6, pS6, Erk, Akt, pAkt, Caspase2, RBBP
PCNA, Cyclin D1, MEK, s6, pS6, Erk, Akt, pAkt, Caspase2, total S6
PCNA, Cyclin D1, MEK, s6, pS6, Erk, Akt, pAkt, RBBP, total S6
PCNA, Cyclin D1, MEK, s6, pS6, Erk, Akt, Caspase2, RBBP, total S6
PCNA, Cyclin D1, MEK, s6, pS6, Erk, pAkt, Caspase2, RBBP, total S6
PCNA, Cyclin D1, MEK, s6, pS6, pErk, Akt, pAkt, Caspase2, RBBP
PCNA, Cyclin D1, MEK, s6, pS6, pErk, Akt, pAkt, Caspase2, total S6
PCNA, Cyclin D1, MEK, s6, pS6, pErk, Akt, pAkt, RBBP, total S6
PCNA, Cyclin D1, MEK, s6, pS6, pErk, Akt, Caspase2, RBBP, total S6
PCNA, Cyclin D1, MEK, s6, pS6, pErk, pAkt, Caspase2, RBBP, total S6
PCNA, Cyclin D1, MEK, s6, pS6, Akt, pAkt, Caspase2, RBBP, total S6
PCNA, Cyclin D1, MEK, s6, Erk, pErk, Akt, pAkt, Caspase2, RBBP
PCNA, Cyclin D1, MEK, s6, Erk, pErk, Akt, pAkt, Caspase2, total S6
PCNA, Cyclin D1, MEK, s6, Erk, pErk, Akt, pAkt, RBBP, total S6
PCNA, Cyclin D1, MEK, s6, Erk, pErk, Akt, Caspase2, RBBP, total S6
PCNA, Cyclin D1, MEK, s6, Erk, pErk, pAkt, Caspase2, RBBP, total S6
PCNA, Cyclin D1, MEK, s6, Erk, Akt, pAkt, Caspase2, RBBP, total S6
PCNA, Cyclin D1, MEK, s6, pErk, Akt, pAkt, Caspase2, RBBP, total S6
PCNA, Cyclin D1, MEK, pS6, Erk, pErk, Akt, pAkt, Caspase2, RBBP
PCNA, Cyclin D1, MEK, pS6, Erk, pErk, Akt, pAkt, Caspase2, total S6
PCNA, Cyclin D1, MEK, pS6, Erk, pErk, Akt, pAkt, RBBP, total S6
PCNA, Cyclin D1, MEK, pS6, Erk, pErk, Akt, Caspase2, RBBP, total S6
PCNA, Cyclin D1, MEK, pS6, Erk, pErk, pAkt, Caspase2, RBBP, total S6
PCNA, Cyclin D1, MEK, pS6, Erk, Akt, pAkt, Caspase2, RBBP, total S6
PCNA, Cyclin D1, MEK, pS6, pErk, Akt, pAkt, Caspase2, RBBP, total S6
PCNA, Cyclin D1, MEK, Erk, pErk, Akt, pAkt, Caspase2, RBBP, total S6
PCNA, Cyclin D1, s6, pS6, Erk, pErk, Akt, pAkt, Caspase2, RBBP
PCNA, Cyclin D1, s6, pS6, Erk, pErk, Akt, pAkt, Caspase2, total S6
PCNA, Cyclin D1, s6, pS6, Erk, pErk, Akt, pAkt, RBBP, total S6
PCNA, Cyclin D1, s6, pS6, Erk, pErk, Akt, Caspase2, RBBP, total S6
PCNA, Cyclin D1, s6, pS6, Erk, pErk, pAkt, Caspase2, RBBP, total S6
PCNA, Cyclin D1, s6, pS6, Akt, pAkt
PCNA, Cyclin D1, s6, pS6, Akt, Caspase2
PCNA, Cyclin D1, s6, pS6, Akt, RBBP
PCNA, Cyclin D1, s6, pS6, Akt, total S6
PCNA, Cyclin D1, s6, pS6, pAkt, Caspase2
PCNA, Cyclin D1, s6, pS6, pAkt, RBBP
PCNA, Cyclin D1, s6, pS6, pAkt, total S6
PCNA, Cyclin D1, s6, pS6, Caspase2, RBBP
PCNA, Cyclin D1, s6, pS6, Caspase2, total S6
PCNA, Cyclin D1, s6, pS6, RBBP, total S6
PCNA, Cyclin D1, s6, Erk, pErk, Akt
PCNA, Cyclin D1, s6, Erk, pErk, pAkt
PCNA, Cyclin D1, s6, Erk, pErk, Caspase2
PCNA, Cyclin D1, s6, Erk, pErk, RBBP
PCNA, Cyclin D1, s6, Erk, pErk, total S6
PCNA, Cyclin D1, s6, Erk, Akt, pAkt
PCNA, Cyclin D1, s6, Erk, Akt, Caspase2
PCNA, Cyclin D1, s6, Erk, Akt, RBBP
PCNA, Cyclin D1, s6, Erk, Akt, total S6
PCNA, Cyclin D1, s6, Erk, pAkt, Caspase2
PCNA, Cyclin D1, s6, Erk, pAkt, RBBP
PCNA, Cyclin D1, s6, Erk, pAkt, total S6
PCNA, Cyclin D1, s6, Erk, Caspase2, RBBP
PCNA, Cyclin D1, s6, Erk, Caspase2, total S6
PCNA, Cyclin D1, s6, Erk, RBBP, total S6
PCNA, Cyclin D1, s6, pErk, Akt, pAkt
PCNA, Cyclin D1, s6, pErk, Akt, Caspase2
PCNA, Cyclin D1, s6, pErk, Akt, RBBP
PCNA, Cyclin D1, s6, pErk, Akt, total S6
PCNA, Cyclin D1, s6, pErk, pAkt, Caspase2
PCNA, Cyclin D1, s6, pErk, pAkt, RBBP
PCNA, Cyclin D1, s6, pErk, pAkt, total S6
PCNA, Cyclin D1, s6, pErk, Caspase2, RBBP
PCNA, Cyclin D1, s6, pErk, Caspase2, total S6
PCNA, Cyclin D1, s6, pErk, RBBP, total S6
PCNA, Cyclin D1, s6, Akt, pAkt, Caspase2
PCNA, Cyclin D1, s6, Akt, pAkt, RBBP
PCNA, Cyclin D1, s6, Akt, pAkt, total S6
PCNA, Cyclin D1, s6, Akt, Caspase2, RBBP
PCNA, Cyclin D1, s6, Akt, Caspase2, total S6
PCNA, Cyclin D1, s6, Akt, RBBP, total S6

TABLE 1-continued

Examples of Single Markers and Combinations of Markers

PCNA, Cyclin D1, s6, pS6, Erk, Akt, pAkt, Caspase2, RBBP, total S6
PCNA, Cyclin D1, s6, pS6, pErk, Akt, pAkt, Caspase2, RBBP, total S6
PCNA, Cyclin D1, s6, Erk, pErk, Akt, pAkt, Caspase2, RBBP, total S6
PCNA, Cyclin D1, pS6, Erk, pErk, Akt, pAkt, Caspase2, RBBP, total S6
PCNA, Cyclin D3, MEK, s6, pS6, Erk, pErk, Akt, pAkt, Caspase2
PCNA, Cyclin D3, MEK, s6, pS6, Erk, pErk, Akt, pAkt, RBBP
PCNA, Cyclin D3, MEK, s6, pS6, Erk, pErk, Akt, pAkt, total S6
PCNA, Cyclin D3, MEK, s6, pS6, Erk, pErk, Akt, Caspase2, RBBP
PCNA, Cyclin D3, MEK, s6, pS6, Erk, pErk, Akt, Caspase2, total S6
PCNA, Cyclin D3, MEK, s6, pS6, Erk, pErk, Akt, RBBP, total S6
PCNA, Cyclin D3, MEK, s6, pS6, Erk, pErk, pAkt, Caspase2, RBBP
PCNA, Cyclin D3, MEK, s6, pS6, Erk, pErk, pAkt, Caspase2, total S6
PCNA, Cyclin D3, MEK, s6, pS6, Erk, pErk, pAkt, RBBP, total S6
PCNA, Cyclin D3, MEK, s6, pS6, Erk, pErk, Caspase2, RBBP, total S6
PCNA, Cyclin D3, MEK, s6, pS6, Erk, Akt, pAkt, Caspase2, RBBP
PCNA, Cyclin D3, MEK, s6, pS6, Erk, Akt, pAkt, Caspase2, total S6
PCNA, Cyclin D3, MEK, s6, pS6, Erk, Akt, pAkt, RBBP, total S6
PCNA, Cyclin D3, MEK, s6, pS6, Erk, Akt, Caspase2, RBBP, total S6
PCNA, Cyclin D3, MEK, s6, pS6, Erk, pAkt, Caspase2, RBBP, total S6
PCNA, Cyclin D3, MEK, s6, pS6, pErk, Akt, pAkt, Caspase2, RBBP
PCNA, Cyclin D3, MEK, s6, pS6, pErk, Akt, pAkt, Caspase2, total S6
PCNA, Cyclin D3, MEK, s6, pS6, pErk, Akt, pAkt, RBBP, total S6
PCNA, Cyclin D3, MEK, s6, pS6, pErk, Akt, Caspase2, RBBP, total S6
PCNA, Cyclin D3, MEK, s6, pS6, pErk, pAkt, Caspase2, RBBP, total S6
PCNA, Cyclin D3, MEK, s6, pS6, Akt, pAkt, Caspase2, RBBP, total S6
PCNA, Cyclin D3, MEK, s6, Erk, pErk, Akt, pAkt, Caspase2, RBBP
PCNA, Cyclin D3, MEK, s6, Erk, pErk, Akt, pAkt, Caspase2, total S6
PCNA, Cyclin D3, MEK, s6, Erk, pErk, Akt, pAkt, RBBP, total S6
PCNA, Cyclin D3, MEK, s6, Erk, pErk, Akt, Caspase2, RBBP, total S6
PCNA, Cyclin D3, MEK, s6, Erk, pErk, pAkt, Caspase2, RBBP, total S6
PCNA, Cyclin D3, MEK, s6, Erk, Akt, pAkt, Caspase2, RBBP, total S6
PCNA, Cyclin D3, MEK, s6, pErk, Akt, pAkt, Caspase2, RBBP, total S6
PCNA, Cyclin D3, MEK, pS6, Erk, pErk, Akt, pAkt, Caspase2, RBBP
PCNA, Cyclin D3, MEK, pS6, Erk, pErk, Akt, pAkt, Caspase2, total S6
PCNA, Cyclin D3, MEK, pS6, Erk, pErk, Akt, pAkt, RBBP, total S6
PCNA, Cyclin D3, MEK, pS6, Erk, pErk, Akt, Caspase2, RBBP, total S6
PCNA, Cyclin D3, MEK, pS6, Erk, pErk, pAkt, Caspase2, RBBP, total S6
PCNA, Cyclin D3, MEK, pS6, Erk, Akt, pAkt, Caspase2, RBBP, total S6
PCNA, Cyclin D3, MEK, pS6, pErk, Akt, pAkt, Caspase2, RBBP, total S6

PCNA, Cyclin D1, s6, pAkt, Caspase2, RBBP
PCNA, Cyclin D1, s6, pAkt, Caspase2, total S6
PCNA, Cyclin D1, s6, pAkt, RBBP, total S6
PCNA, Cyclin D1, s6, Caspase2, RBBP, total S6
PCNA, Cyclin D1, pS6, Erk, pErk, Akt
PCNA, Cyclin D1, pS6, Erk, pErk, pAkt
PCNA, Cyclin D1, pS6, Erk, pErk, Caspase2
PCNA, Cyclin D1, pS6, Erk, pErk, RBBP
PCNA, Cyclin D1, pS6, Erk, pErk, total S6
PCNA, Cyclin D1, pS6, Erk, Akt, pAkt
PCNA, Cyclin D1, pS6, Erk, Akt, Caspase2
PCNA, Cyclin D1, pS6, Erk, Akt, RBBP
PCNA, Cyclin D1, pS6, Erk, Akt, total S6
PCNA, Cyclin D1, pS6, Erk, pAkt, Caspase2
PCNA, Cyclin D1, pS6, Erk, pAkt, RBBP
PCNA, Cyclin D1, pS6, Erk, pAkt, total S6
PCNA, Cyclin D1, pS6, Erk, Caspase2, RBBP
PCNA, Cyclin D1, pS6, Erk, Caspase2, total S6
PCNA, Cyclin D1, pS6, Erk, RBBP, total S6
PCNA, Cyclin D1, pS6, pErk, Akt, pAkt
PCNA, Cyclin D1, pS6, pErk, Akt, Caspase2
PCNA, Cyclin D1, pS6, pErk, Akt, RBBP
PCNA, Cyclin D1, pS6, pErk, Akt, total S6
PCNA, Cyclin D1, pS6, pErk, pAkt, Caspase2
PCNA, Cyclin D1, pS6, pErk, pAkt, RBBP
PCNA, Cyclin D1, pS6, pErk, pAkt, total S6
PCNA, Cyclin D1, pS6, pErk, Caspase2, RBBP
PCNA, Cyclin D1, pS6, pErk, Caspase2, total S6
PCNA, Cyclin D1, pS6, pErk, RBBP, total S6
PCNA, Cyclin D1, pS6, Akt, pAkt, Caspase2
PCNA, Cyclin D1, pS6, Akt, pAkt, RBBP
PCNA, Cyclin D1, pS6, Akt, pAkt, total S6
PCNA, Cyclin D1, pS6, Akt, Caspase2, RBBP
PCNA, Cyclin D1, pS6, Akt, Caspase2, total S6
PCNA, Cyclin D1, pS6, Akt, RBBP, total S6
PCNA, Cyclin D1, pS6, pAkt, Caspase2, RBBP
PCNA, Cyclin D1, pS6, pAkt, Caspase2, total S6
PCNA, Cyclin D1, pS6, pAkt, RBBP, total S6
PCNA, Cyclin D1, pS6, Caspase2, RBBP, total S6

TABLE 1-continued

Examples of Single Markers and Combinations of Markers

PCNA, Cyclin D3, MEK, Erk, pErk, Akt, pAkt, Caspase2, RBBP, total S6
PCNA, Cyclin D3, s6, pS6, Erk, pErk, Akt, pAkt, Caspase2, RBBP
PCNA, Cyclin D3, s6, pS6, Erk, pErk, Akt, pAkt, Caspase2, total S6
PCNA, Cyclin D3, s6, pS6, Erk, pErk, Akt, pAkt, RBBP, total S6
PCNA, Cyclin D3, s6, pS6, Erk, pErk, Akt, Caspase2, RBBP, total S6
PCNA, Cyclin D3, s6, pS6, Erk, pErk, pAkt, Caspase2, RBBP, total S6
PCNA, Cyclin D3, s6, pS6, Erk, Akt, pAkt, Caspase2, RBBP, total S6
PCNA, Cyclin D3, s6, pS6, pErk, Akt, pAkt, Caspase2, RBBP, total S6
PCNA, Cyclin D3, s6, Erk, pErk, Akt, pAkt, Caspase2, RBBP, total S6
PCNA, Cyclin D3, pS6, Erk, pErk, Akt, pAkt, Caspase2, RBBP, total S6
PCNA, MEK, s6, pS6, Erk, pErk, Akt, pAkt, Caspase2, RBBP
PCNA, MEK, s6, pS6, Erk, pErk, Akt, pAkt, Caspase2, total S6
PCNA, MEK, s6, pS6, Erk, pErk, Akt, pAkt, RBBP, total S6
PCNA, MEK, s6, pS6, Erk, pErk, Akt, Caspase2, RBBP, total S6
PCNA, MEK, s6, pS6, Erk, pErk, pAkt, Caspase2, RBBP, total S6
PCNA, MEK, s6, pS6, Erk, Akt, pAkt, Caspase2, RBBP, total S6
PCNA, MEK, s6, pS6, pErk, Akt, pAkt, Caspase2, RBBP, total S6
PCNA, MEK, s6, Erk, pErk, Akt, pAkt, Caspase2, RBBP, total S6
PCNA, MEK, pS6, Erk, pErk, Akt, pAkt, Caspase2, RBBP, total S6
PCNA, s6, pS6, Erk, pErk, Akt, pAkt, Caspase2, RBBP, total S6
Cyclin D1, Cyclin D3, MEK, s6, pS6, Erk, pErk, Akt, pAkt, Caspase2
Cyclin D1, Cyclin D3, MEK, s6, pS6, Erk, pErk, Akt, pAkt, RBBP
Cyclin D1, Cyclin D3, MEK, s6, pS6, Erk, pErk, Akt, pAkt, total S6
Cyclin D1, Cyclin D3, MEK, s6, pS6, Erk, pErk, Akt, Caspase2, RBBP
Cyclin D1, Cyclin D3, MEK, s6, pS6, Erk, pErk, Akt, Caspase2, total S6
Cyclin D1, Cyclin D3, MEK, s6, pS6, Erk, pErk, Akt, RBBP, total S6
Cyclin D1, Cyclin D3, MEK, s6, pS6, Erk, pErk, pAkt, Caspase2, RBBP
Cyclin D1, Cyclin D3, MEK, s6, pS6, Erk, pErk, pAkt, Caspase2, total S6
Cyclin D1, Cyclin D3, MEK, s6, pS6, Erk, pErk, pAkt, RBBP, total S6
Cyclin D1, Cyclin D3, MEK, s6, pS6, Erk, pErk, Caspase2, RBBP, total S6
Cyclin D1, Cyclin D3, MEK, s6, pS6, Erk, Akt, pAkt, Caspase2, RBBP
Cyclin D1, Cyclin D3, MEK, s6, pS6, Erk, Akt, pAkt, Caspase2, total S6
Cyclin D1, Cyclin D3, MEK, s6, pS6, Erk, Akt, pAkt, RBBP, total S6
Cyclin D1, Cyclin D3, MEK, s6, pS6, Erk, Akt, Caspase2, RBBP, total S6
Cyclin D1, Cyclin D3, MEK, s6, pS6, Erk, pAkt, Caspase2, RBBP, total S6
Cyclin D1, Cyclin D3, MEK, s6, pS6, pErk, Akt, pAkt, Caspase2, RBBP
Cyclin D1, Cyclin D3, MEK, s6, pS6, pErk, Akt, pAkt, Caspase2, total S6
Cyclin D1, Cyclin D3, MEK, s6, pS6, pErk, Akt, pAkt, RBBP, total S6
Cyclin D1, Cyclin D3, MEK, s6, pS6, pErk, Akt, Caspase2, RBBP, total S6
Cyclin D1, Cyclin D3, MEK, s6, pS6, pErk, pAkt, Caspase2, RBBP, total S6
PCNA, Cyclin D1, Erk, pErk, Akt, pAkt
PCNA, Cyclin D1, Erk, pErk, Akt, Caspase2
PCNA, Cyclin D1, Erk, pErk, Akt, RBBP
PCNA, Cyclin D1, Erk, pErk, Akt, total S6
PCNA, Cyclin D1, Erk, pErk, pAkt, Caspase2
PCNA, Cyclin D1, Erk, pErk, pAkt, RBBP
PCNA, Cyclin D1, Erk, pErk, pAkt, total S6
PCNA, Cyclin D1, Erk, pErk, Caspase2, RBBP
PCNA, Cyclin D1, Erk, pErk, Caspase2, total S6
PCNA, Cyclin D1, Erk, pErk, RBBP, total S6
PCNA, Cyclin D1, Erk, Akt, pAkt, Caspase2
PCNA, Cyclin D1, Erk, Akt, pAkt, RBBP
PCNA, Cyclin D1, Erk, Akt, pAkt, total S6
PCNA, Cyclin D1, Erk, Akt, Caspase2, RBBP
PCNA, Cyclin D1, Erk, Akt, Caspase2, total S6
PCNA, Cyclin D1, Erk, Akt, RBBP, total S6
PCNA, Cyclin D1, Erk, pAkt, Caspase2, RBBP
PCNA, Cyclin D1, Erk, pAkt, Caspase2, total S6
PCNA, Cyclin D1, Erk, pAkt, RBBP, total S6
PCNA, Cyclin D1, Erk, Caspase2, RBBP, total S6
PCNA, Cyclin D1, pErk, Akt, pAkt, Caspase2
PCNA, Cyclin D1, pErk, Akt, pAkt, RBBP
PCNA, Cyclin D1, pErk, Akt, pAkt, total S6
PCNA, Cyclin D1, pErk, Akt, Caspase2, RBBP
PCNA, Cyclin D1, pErk, Akt, Caspase2, total S6
PCNA, Cyclin D1, pErk, Akt, RBBP, total S6
PCNA, Cyclin D1, pErk, pAkt, Caspase2, RBBP
PCNA, Cyclin D1, pErk, pAkt, Caspase2, total S6
PCNA, Cyclin D1, pErk, pAkt, RBBP, total S6
PCNA, Cyclin D1, pErk, Caspase2, RBBP, total S6
PCNA, Cyclin D1, Akt, pAkt, Caspase2, RBBP
PCNA, Cyclin D1, Akt, pAkt, Caspase2, total S6
PCNA, Cyclin D1, Akt, pAkt, RBBP, total S6
PCNA, Cyclin D1, Akt, Caspase2, RBBP, total S6
PCNA, Cyclin D1, pAkt, Caspase2, RBBP, total S6
PCNA, Cyclin D3, MEK, s6, pS6, Erk
PCNA, Cyclin D3, MEK, s6, pS6, pErk
PCNA, Cyclin D3, MEK, s6, pS6, Akt
PCNA, Cyclin D3, MEK, s6, pS6, pAkt
PCNA, Cyclin D3, MEK, s6, pS6, Caspase2

TABLE 1-continued

Examples of Single Markers and Combinations of Markers

Cyclin D1, Cyclin D3, MEK, s6, pS6, Akt, pAkt, Caspase2, RBBP, total S6
Cyclin D1, Cyclin D3, MEK, s6, Erk, pErk, Akt, pAkt, Caspase2, RBBP
Cyclin D1, Cyclin D3, MEK, s6, Erk, pErk, Akt, pAkt, Caspase2, total S6
Cyclin D1, Cyclin D3, MEK, s6, Erk, pErk, Akt, pAkt, RBBP, total S6
Cyclin D1, Cyclin D3, MEK, s6, Erk, pErk, Akt, Caspase2, RBBP, total S6
Cyclin D1, Cyclin D3, MEK, s6, Erk, pErk, pAkt, Caspase2, RBBP, total S6
Cyclin D1, Cyclin D3, MEK, s6, Erk, Akt, pAkt, Caspase2, RBBP, total S6
Cyclin D1, Cyclin D3, MEK, s6, pErk, Akt, pAkt, Caspase2, RBBP, total S6
Cyclin D1, Cyclin D3, MEK, pS6, Erk, pErk, Akt, pAkt, Caspase2, RBBP
Cyclin D1, Cyclin D3, MEK, pS6, Erk, pErk, Akt, pAkt, Caspase2, total S6
Cyclin D1, Cyclin D3, MEK, pS6, Erk, pErk, Akt, pAkt, RBBP, total S6
Cyclin D1, Cyclin D3, MEK, pS6, Erk, pErk, Akt, Caspase2, RBBP, total S6
Cyclin D1, Cyclin D3, MEK, pS6, Erk, pErk, pAkt, Caspase2, RBBP, total S6
Cyclin D1, Cyclin D3, MEK, pS6, Erk, Akt, pAkt, Caspase2, RBBP, total S6
Cyclin D1, Cyclin D3, MEK, pS6, pErk, Akt, pAkt, Caspase2, RBBP, total S6
Cyclin D1, Cyclin D3, MEK, Erk, pErk, Akt, pAkt, Caspase2, RBBP, total S6
Cyclin D1, Cyclin D3, s6, pS6, Erk, pErk, Akt, pAkt, Caspase2, RBBP
Cyclin D1, Cyclin D3, s6, pS6, Erk, pErk, Akt, pAkt, Caspase2, total S6
Cyclin D1, Cyclin D3, s6, pS6, Erk, pErk, Akt, pAkt, RBBP, total S6
Cyclin D1, Cyclin D3, s6, pS6, Erk, pErk, Akt, Caspase2, RBBP, total S6
Cyclin D1, Cyclin D3, s6, pS6, Erk, pErk, pAkt, Caspase2, RBBP, total S6
Cyclin D1, Cyclin D3, s6, pS6, Erk, Akt, pAkt, Caspase2, RBBP, total S6
Cyclin D1, Cyclin D3, s6, pS6, pErk, Akt, pAkt, Caspase2, RBBP, total S6
Cyclin D1, Cyclin D3, s6, Erk, pErk, Akt, pAkt, Caspase2, RBBP, total S6
Cyclin D1, Cyclin D3, pS6, Erk, pErk, Akt, pAkt, Caspase2, RBBP, total S6
Cyclin D1, MEK, s6, pS6, Erk, pErk, Akt, pAkt, Caspase2, RBBP
Cyclin D1, MEK, s6, pS6, Erk, pErk, Akt, pAkt, Caspase2, total S6
Cyclin D1, MEK, s6, pS6, Erk, pErk, Akt, pAkt, RBBP, total S6
Cyclin D1, MEK, s6, pS6, Erk, pErk, Akt, Caspase2, RBBP, total S6
Cyclin D1, MEK, s6, pS6, Erk, pErk, pAkt, Caspase2, RBBP, total S6
Cyclin D1, MEK, s6, pS6, Erk, Akt, pAkt, Caspase2, RBBP, total S6
Cyclin D1, MEK, s6, pS6, pErk, Akt, pAkt, Caspase2, RBBP, total S6
Cyclin D1, MEK, s6, Erk, pErk, Akt, pAkt, Caspase2, RBBP, total S6
Cyclin D1, MEK, pS6, Erk, pErk, Akt, pAkt, Caspase2, RBBP, total S6
Cyclin D1, s6, pS6, Erk, pErk, Akt, pAkt, Caspase2, RBBP, total S6
Cyclin D3, MEK, s6, pS6, Erk, pErk, Akt, pAkt, Caspase2, RBBP
Cyclin D3, MEK, s6, pS6, Erk, pErk, Akt, pAkt, Caspase2, total S6
Cyclin D3, MEK, s6, pS6, Erk, pErk, Akt, pAkt, RBBP, total S6
Cyclin D3, MEK, s6, pS6, Erk, pErk, Akt, Caspase2, RBBP, total S6
Cyclin D3, MEK, s6, pS6, Erk, pErk, pAkt, Caspase2, RBBP, total S6
PCNA, Cyclin D3, MEK, s6, pS6, RBBP
PCNA, Cyclin D3, MEK, s6, pS6, total S6
PCNA, Cyclin D3, MEK, s6, Erk, pErk
PCNA, Cyclin D3, MEK, s6, Erk, Akt
PCNA, Cyclin D3, MEK, s6, Erk, pAkt
PCNA, Cyclin D3, MEK, s6, Erk, Caspase2
PCNA, Cyclin D3, MEK, s6, Erk, RBBP
PCNA, Cyclin D3, MEK, s6, Erk, total S6
PCNA, Cyclin D3, MEK, s6, pErk, Akt
PCNA, Cyclin D3, MEK, s6, pErk, pAkt
PCNA, Cyclin D3, MEK, s6, pErk, Caspase2
PCNA, Cyclin D3, MEK, s6, pErk, RBBP
PCNA, Cyclin D3, MEK, s6, pErk, total S6
PCNA, Cyclin D3, MEK, s6, Akt, pAkt
PCNA, Cyclin D3, MEK, s6, Akt, Caspase2
PCNA, Cyclin D3, MEK, s6, Akt, RBBP
PCNA, Cyclin D3, MEK, s6, Akt, total S6
PCNA, Cyclin D3, MEK, s6, pAkt, Caspase2
PCNA, Cyclin D3, MEK, s6, pAkt, RBBP
PCNA, Cyclin D3, MEK, s6, pAkt, total S6
PCNA, Cyclin D3, MEK, s6, Caspase2, RBBP
PCNA, Cyclin D3, MEK, s6, Caspase2, total S6
PCNA, Cyclin D3, MEK, s6, RBBP, total S6
PCNA, Cyclin D3, MEK, pS6, Erk, pErk
PCNA, Cyclin D3, MEK, pS6, Erk, Akt
PCNA, Cyclin D3, MEK, pS6, Erk, pAkt
PCNA, Cyclin D3, MEK, pS6, Erk, Caspase2
PCNA, Cyclin D3, MEK, pS6, Erk, RBBP
PCNA, Cyclin D3, MEK, pS6, Erk, total S6
PCNA, Cyclin D3, MEK, pS6, pErk, Akt
PCNA, Cyclin D3, MEK, pS6, pErk, pAkt
PCNA, Cyclin D3, MEK, pS6, pErk, Caspase2
PCNA, Cyclin D3, MEK, pS6, pErk, RBBP
PCNA, Cyclin D3, MEK, pS6, pErk, total S6
PCNA, Cyclin D3, MEK, pS6, Akt, pAkt
PCNA, Cyclin D3, MEK, pS6, Akt, Caspase2
PCNA, Cyclin D3, MEK, pS6, Akt, RBBP
PCNA, Cyclin D3, MEK, pS6, Akt, total S6
PCNA, Cyclin D3, MEK, pS6, pAkt, Caspase2
PCNA, Cyclin D3, MEK, pS6, pAkt, RBBP TABLE 1-continued Examples of Single Markers and Combinations of Markers Cyclin D3, MEK, s6, pS6, Erk, Akt, pAkt, Caspase2, RBBP, total S6
Cyclin D3, MEK, s6, pS6, pErk, Akt, pAkt, Caspase2, RBBP, total S6
Cyclin D3, MEK, s6, Erk, pErk, Akt, pAkt, Caspase2, RBBP, total S6
Cyclin D3, MEK, pS6, Erk, pErk, Akt, pAkt, Caspase2, RBBP, total S6
Cyclin D3, s6, pS6, Erk, pErk, Akt, pAkt, Caspase2, RBBP, total S6
MEK, s6, pS6, Erk, pErk, Akt, pAkt, Caspase2, RBBP, total S6
PCNA, Cyclin D1, Cyclin D3, MEK, s6, pS6, Erk, pErk, Akt
PCNA, Cyclin D1, Cyclin D3, MEK, s6, pS6, Erk, pErk, pAkt
PCNA, Cyclin D1, Cyclin D3, MEK, s6, pS6, Erk, pErk, Caspase2
PCNA, Cyclin D1, Cyclin D3, MEK, s6, pS6, Erk, pErk, RBBP
PCNA, Cyclin D1, Cyclin D3, MEK, s6, pS6, Erk, pErk, total S6
PCNA, Cyclin D1, Cyclin D3, MEK, s6, pS6, Erk, Akt, pAkt
PCNA, Cyclin D1, Cyclin D3, MEK, s6, pS6, Erk, Akt, Caspase2
PCNA, Cyclin D1, Cyclin D3, MEK, s6, pS6, Erk, Akt, RBBP
PCNA, Cyclin D1, Cyclin D3, MEK, s6, pS6, Erk, Akt, total S6
PCNA, Cyclin D1, Cyclin D3, MEK, s6, pS6, Erk, pAkt, Caspase2
PCNA, Cyclin D1, Cyclin D3, MEK, s6, pS6, Erk, pAkt, RBBP
PCNA, Cyclin D1, Cyclin D3, MEK, s6, pS6, Erk, pAkt, total S6
PCNA, Cyclin D1, Cyclin D3, MEK, s6, pS6, Erk, Caspase2, RBBP
PCNA, Cyclin D1, Cyclin D3, MEK, s6, pS6, Erk, Caspase2, total S6
PCNA, Cyclin D1, Cyclin D3, MEK, s6, pS6, Erk, RBBP, total S6
PCNA, Cyclin D1, Cyclin D3, MEK, s6, pS6, pErk, Akt, pAkt
PCNA, Cyclin D1, Cyclin D3, MEK, s6, pS6, pErk, Akt, Caspase2
PCNA, Cyclin D1, Cyclin D3, MEK, s6, pS6, pErk, Akt, RBBP
PCNA, Cyclin D1, Cyclin D3, MEK, s6, pS6, pErk, Akt, total S6
PCNA, Cyclin D1, Cyclin D3, MEK, s6, pS6, pErk, pAkt, Caspase2
PCNA, Cyclin D1, Cyclin D3, MEK, s6, pS6, pErk, pAkt, RBBP
PCNA, Cyclin D1, Cyclin D3, MEK, s6, pS6, pErk, pAkt, total S6
PCNA, Cyclin D1, Cyclin D3, MEK, s6, pS6, pErk, Caspase2, RBBP
PCNA, Cyclin D1, Cyclin D3, MEK, s6, pS6, pErk, Caspase2, total S6
PCNA, Cyclin D1, Cyclin D3, MEK, s6, pS6, pErk, RBBP, total S6
PCNA, Cyclin D1, Cyclin D3, MEK, s6, pS6, Akt, pAkt, Caspase2
PCNA, Cyclin D1, Cyclin D3, MEK, s6, pS6, Akt, pAkt, RBBP
PCNA, Cyclin D1, Cyclin D3, MEK, s6, pS6, Akt, pAkt, total S6
PCNA, Cyclin D1, Cyclin D3, MEK, s6, pS6, Akt, Caspase2, RBBP
PCNA, Cyclin D1, Cyclin D3, MEK, s6, pS6, Akt, Caspase2, total S6
PCNA, Cyclin D1, Cyclin D3, MEK, s6, pS6, Akt, RBBP, total S6
PCNA, Cyclin D1, Cyclin D3, MEK, s6, pS6, pAkt, Caspase2, RBBP
PCNA, Cyclin D1, Cyclin D3, MEK, s6, pS6, pAkt, Caspase2, total S6
PCNA, Cyclin D1, Cyclin D3, MEK, s6, pS6, pAkt, RBBP, total S6
PCNA, Cyclin D1, Cyclin D3, MEK, s6, pS6, Caspase2, RBBP, total S6
PCNA, Cyclin D1, Cyclin D3, MEK, s6, Erk, pErk, Akt, pAkt
PCNA, Cyclin D1, Cyclin D3, MEK, s6, Erk, pErk, Akt, Caspase2
PCNA, Cyclin D1, Cyclin D3, MEK, s6, Erk, pErk, Akt, RBBP
PCNA, Cyclin D3, MEK, pS6, pAkt, total S6
PCNA, Cyclin D3, MEK, pS6, Caspase2, RBBP
PCNA, Cyclin D3, MEK, pS6, Caspase2, total S6
PCNA, Cyclin D3, MEK, pS6, RBBP, total S6
PCNA, Cyclin D3, MEK, Erk, pErk, Akt
PCNA, Cyclin D3, MEK, Erk, pErk, pAkt
PCNA, Cyclin D3, MEK, Erk, pErk, Caspase2
PCNA, Cyclin D3, MEK, Erk, pErk, RBBP
PCNA, Cyclin D3, MEK, Erk, pErk, total S6
PCNA, Cyclin D3, MEK, Erk, Akt, pAkt
PCNA, Cyclin D3, MEK, Erk, Akt, Caspase2
PCNA, Cyclin D3, MEK, Erk, Akt, RBBP
PCNA, Cyclin D3, MEK, Erk, Akt, total S6
PCNA, Cyclin D3, MEK, Erk, pAkt, Caspase2
PCNA, Cyclin D3, MEK, Erk, pAkt, RBBP
PCNA, Cyclin D3, MEK, Erk, pAkt, total S6
PCNA, Cyclin D3, MEK, Erk, Caspase2, RBBP
PCNA, Cyclin D3, MEK, Erk, Caspase2, total S6
PCNA, Cyclin D3, MEK, Erk, RBBP, total S6
PCNA, Cyclin D3, MEK, pErk, Akt, pAkt
PCNA, Cyclin D3, MEK, pErk, Akt, Caspase2
PCNA, Cyclin D3, MEK, pErk, Akt, RBBP
PCNA, Cyclin D3, MEK, pErk, Akt, total S6
PCNA, Cyclin D3, MEK, pErk, pAkt, Caspase2
PCNA, Cyclin D3, MEK, pErk, pAkt, RBBP
PCNA, Cyclin D3, MEK, pErk, pAkt, total S6
PCNA, Cyclin D3, MEK, pErk, Caspase2, RBBP
PCNA, Cyclin D3, MEK, pErk, Caspase2, total S6
PCNA, Cyclin D3, MEK, pErk, RBBP, total S6
PCNA, Cyclin D3, MEK, Akt, pAkt, Caspase2
PCNA, Cyclin D3, MEK, Akt, pAkt, RBBP
PCNA, Cyclin D3, MEK, Akt, pAkt, total S6
PCNA, Cyclin D3, MEK, Akt, Caspase2, RBBP
PCNA, Cyclin D3, MEK, Akt, Caspase2, total S6
PCNA, Cyclin D3, MEK, Akt, RBBP, total S6
PCNA, Cyclin D3, MEK, pAkt, Caspase2, RBBP
PCNA, Cyclin D3, MEK, pAkt, Caspase2, total S6
PCNA, Cyclin D3, MEK, pAkt, RBBP, total S6
PCNA, Cyclin D3, MEK, Caspase2, RBBP, total S6
PCNA, Cyclin D3, s6, pS6, Erk, pErk
PCNA, Cyclin D3, s6, pS6, Erk, Akt
PCNA, Cyclin D3, s6, pS6, Erk, pAkt
PCNA, Cyclin D3, s6, pS6, Erk, Caspase2
PCNA, Cyclin D3, s6, pS6, Erk, RBBP TABLE 1-continued Examples of Single Markers and Combinations of Markers PCNA, Cyclin D1, Cyclin D3, MEK, s6, Erk, pErk, Akt, total S6
PCNA, Cyclin D1, Cyclin D3, MEK, s6, Erk, pErk, pAkt, Caspase2
PCNA, Cyclin D1, Cyclin D3, MEK, s6, Erk, pErk, pAkt, RBBP
PCNA, Cyclin D1, Cyclin D3, MEK, s6, Erk, pErk, pAkt, total S6
PCNA, Cyclin D1, Cyclin D3, MEK, s6, Erk, pErk, Caspase2, RBBP
PCNA, Cyclin D1, Cyclin D3, MEK, s6, Erk, pErk, Caspase2, total S6
PCNA, Cyclin D1, Cyclin D3, MEK, s6, Erk, pErk, RBBP, total S6
PCNA, Cyclin D1, Cyclin D3, MEK, s6, Erk, Akt, pAkt, Caspase2
PCNA, Cyclin D1, Cyclin D3, MEK, s6, Erk, Akt, pAkt, RBBP
PCNA, Cyclin D1, Cyclin D3, MEK, s6, Erk, Akt, pAkt, total S6
PCNA, Cyclin D1, Cyclin D3, MEK, s6, Erk, Akt, Caspase2, RBBP
PCNA, Cyclin D1, Cyclin D3, MEK, s6, Erk, Akt, Caspase2, total S6
PCNA, Cyclin D1, Cyclin D3, MEK, s6, Erk, Akt, RBBP, total S6
PCNA, Cyclin D1, Cyclin D3, MEK, s6, Erk, pAkt, Caspase2, RBBP
PCNA, Cyclin D1, Cyclin D3, MEK, s6, Erk, pAkt, Caspase2, total S6
PCNA, Cyclin D1, Cyclin D3, MEK, s6, Erk, pAkt, RBBP, total S6
PCNA, Cyclin D1, Cyclin D3, MEK, s6, Erk, Caspase2, RBBP, total S6
PCNA, Cyclin D1, Cyclin D3, MEK, s6, pErk, Akt, pAkt, Caspase2
PCNA, Cyclin D1, Cyclin D3, MEK, s6, pErk, Akt, pAkt, RBBP
PCNA, Cyclin D1, Cyclin D3, MEK, s6, pErk, Akt, pAkt, total S6
PCNA, Cyclin D1, Cyclin D3, MEK, s6, pErk, Akt, Caspase2, RBBP
PCNA, Cyclin D1, Cyclin D3, MEK, s6, pErk, Akt, Caspase2, total S6
PCNA, Cyclin D1, Cyclin D3, MEK, s6, pErk, Akt, RBBP, total S6
PCNA, Cyclin D1, Cyclin D3, MEK, s6, pErk, pAkt, Caspase2, RBBP
PCNA, Cyclin D1, Cyclin D3, MEK, s6, pErk, pAkt, Caspase2, total S6
PCNA, Cyclin D1, Cyclin D3, MEK, s6, pErk, pAkt, RBBP, total S6
PCNA, Cyclin D1, Cyclin D3, MEK, s6, pErk, Caspase2, RBBP, total S6
PCNA, Cyclin D1, Cyclin D3, MEK, s6, Akt, pAkt, Caspase2, RBBP
PCNA, Cyclin D1, Cyclin D3, MEK, s6, Akt, pAkt, Caspase2, total S6
PCNA, Cyclin D1, Cyclin D3, MEK, s6, Akt, pAkt, RBBP, total S6
PCNA, Cyclin D1, Cyclin D3, MEK, s6, Akt, Caspase2, RBBP, total S6
PCNA, Cyclin D1, Cyclin D3, MEK, s6, pAkt, Caspase2, RBBP, total S6
PCNA, Cyclin D1, Cyclin D3, MEK, pS6, Erk, pErk, Akt, pAkt
PCNA, Cyclin D1, Cyclin D3, MEK, pS6, Erk, pErk, Akt, Caspase2
PCNA, Cyclin D1, Cyclin D3, MEK, pS6, Erk, pErk, Akt, RBBP
PCNA, Cyclin D1, Cyclin D3, MEK, pS6, Erk, pErk, Akt, total S6
PCNA, Cyclin D1, Cyclin D3, MEK, pS6, Erk, pErk, pAkt, Caspase2
PCNA, Cyclin D1, Cyclin D3, MEK, pS6, Erk, pErk, pAkt, RBBP
PCNA, Cyclin D1, Cyclin D3, MEK, pS6, Erk, pErk, pAkt, total S6
PCNA, Cyclin D1, Cyclin D3, MEK, pS6, Erk, pErk, Caspase2, RBBP
PCNA, Cyclin D1, Cyclin D3, MEK, pS6, Erk, pErk, Caspase2, total S6
PCNA, Cyclin D1, Cyclin D3, MEK, pS6, Erk, pErk, RBBP, total S6
PCNA, Cyclin D1, Cyclin D3, MEK, pS6, Erk, Akt, pAkt, Caspase2
PCNA, Cyclin D1, Cyclin D3, MEK, pS6, Erk, Akt, pAkt, RBBP
PCNA, Cyclin D3, s6, pS6, Erk, total S6
PCNA, Cyclin D3, s6, pS6, pErk, Akt
PCNA, Cyclin D3, s6, pS6, pErk, pAkt
PCNA, Cyclin D3, s6, pS6, pErk, Caspase2
PCNA, Cyclin D3, s6, pS6, pErk, RBBP
PCNA, Cyclin D3, s6, pS6, pErk, total S6
PCNA, Cyclin D3, s6, pS6, Akt, pAkt
PCNA, Cyclin D3, s6, pS6, Akt, Caspase2
PCNA, Cyclin D3, s6, pS6, Akt, RBBP
PCNA, Cyclin D3, s6, pS6, Akt, total S6
PCNA, Cyclin D3, s6, pS6, pAkt, Caspase2
PCNA, Cyclin D3, s6, pS6, pAkt, RBBP
PCNA, Cyclin D3, s6, pS6, pAkt, total S6
PCNA, Cyclin D3, s6, pS6, Caspase2, RBBP
PCNA, Cyclin D3, s6, pS6, Caspase2, total S6
PCNA, Cyclin D3, s6, pS6, RBBP, total S6
PCNA, Cyclin D3, s6, Erk, pErk, Akt
PCNA, Cyclin D3, s6, Erk, pErk, pAkt
PCNA, Cyclin D3, s6, Erk, pErk, Caspase2
PCNA, Cyclin D3, s6, Erk, pErk, RBBP
PCNA, Cyclin D3, s6, Erk, pErk, total S6
PCNA, Cyclin D3, s6, Erk, Akt, pAkt
PCNA, Cyclin D3, s6, Erk, Akt, Caspase2
PCNA, Cyclin D3, s6, Erk, Akt, RBBP
PCNA, Cyclin D3, s6, Erk, Akt, total S6
PCNA, Cyclin D3, s6, Erk, pAkt, Caspase2
PCNA, Cyclin D3, s6, Erk, pAkt, RBBP
PCNA, Cyclin D3, s6, Erk, pAkt, total S6
PCNA, Cyclin D3, s6, Erk, Caspase2, RBBP
PCNA, Cyclin D3, s6, Erk, Caspase2, total S6
PCNA, Cyclin D3, s6, Erk, RBBP, total S6
PCNA, Cyclin D3, s6, pErk, Akt, pAkt
PCNA, Cyclin D3, s6, pErk, Akt, Caspase2
PCNA, Cyclin D3, s6, pErk, Akt, RBBP
PCNA, Cyclin D3, s6, pErk, Akt, total S6
PCNA, Cyclin D3, s6, pErk, pAkt, Caspase2
PCNA, Cyclin D3, s6, pErk, pAkt, RBBP
PCNA, Cyclin D3, s6, pErk, pAkt, total S6
PCNA, Cyclin D3, s6, pErk, Caspase2, RBBP
PCNA, Cyclin D3, s6, pErk, Caspase2, total S6
PCNA, Cyclin D3, s6, pErk, RBBP, total S6
PCNA, Cyclin D3, s6, Akt, pAkt, Caspase2
PCNA, Cyclin D3, s6, Akt, pAkt, RBBP
PCNA, Cyclin D3, s6, Akt, pAkt, total S6

TABLE 1-continued

Examples of Single Markers and Combinations of Markers

PCNA, Cyclin D1, Cyclin D3, MEK, pS6, Erk, Akt, pAkt, total S6
PCNA, Cyclin D1, Cyclin D3, MEK, pS6, Erk, Akt, Caspase2, RBBP
PCNA, Cyclin D1, Cyclin D3, MEK, pS6, Erk, Akt, Caspase2, total S6
PCNA, Cyclin D1, Cyclin D3, MEK, pS6, Erk, Akt, RBBP, total S6
PCNA, Cyclin D1, Cyclin D3, MEK, pS6, Erk, pAkt, Caspase2, RBBP
PCNA, Cyclin D1, Cyclin D3, MEK, pS6, Erk, pAkt, Caspase2, total S6
PCNA, Cyclin D1, Cyclin D3, MEK, pS6, Erk, pAkt, RBBP, total S6
PCNA, Cyclin D1, Cyclin D3, MEK, pS6, Erk, Caspase2, RBBP, total S6
PCNA, Cyclin D1, Cyclin D3, MEK, pS6, pErk, Akt, pAkt, Caspase2
PCNA, Cyclin D1, Cyclin D3, MEK, pS6, pErk, Akt, pAkt, RBBP
PCNA, Cyclin D1, Cyclin D3, MEK, pS6, pErk, Akt, pAkt, total S6
PCNA, Cyclin D1, Cyclin D3, MEK, pS6, pErk, Akt, Caspase2, RBBP
PCNA, Cyclin D1, Cyclin D3, MEK, pS6, pErk, Akt, Caspase2, total S6
PCNA, Cyclin D1, Cyclin D3, MEK, pS6, pErk, Akt, RBBP, total S6
PCNA, Cyclin D1, Cyclin D3, MEK, pS6, pErk, pAkt, Caspase2, RBBP
PCNA, Cyclin D1, Cyclin D3, MEK, pS6, pErk, pAkt, Caspase2, total S6
PCNA, Cyclin D1, Cyclin D3, MEK, pS6, pErk, pAkt, RBBP, total S6
PCNA, Cyclin D1, Cyclin D3, MEK, pS6, pErk, Caspase2, RBBP, total S6
PCNA, Cyclin D1, Cyclin D3, MEK, pS6, Akt, pAkt, Caspase2, RBBP
PCNA, Cyclin D1, Cyclin D3, MEK, pS6, Akt, pAkt, Caspase2, total S6
PCNA, Cyclin D1, Cyclin D3, MEK, pS6, Akt, pAkt, RBBP, total S6
PCNA, Cyclin D1, Cyclin D3, MEK, pS6, Akt, Caspase2, RBBP, total S6
PCNA, Cyclin D1, Cyclin D3, MEK, pS6, pAkt, Caspase2, RBBP, total S6
PCNA, Cyclin D1, Cyclin D3, MEK, Erk, pErk, Akt, pAkt, Caspase2
PCNA, Cyclin D1, Cyclin D3, MEK, Erk, pErk, Akt, pAkt, RBBP
PCNA, Cyclin D1, Cyclin D3, MEK, Erk, pErk, Akt, pAkt, total S6
PCNA, Cyclin D1, Cyclin D3, MEK, Erk, pErk, Akt, Caspase2, RBBP
PCNA, Cyclin D1, Cyclin D3, MEK, Erk, pErk, Akt, Caspase2, total S6
PCNA, Cyclin D1, Cyclin D3, MEK, Erk, pErk, Akt, RBBP, total S6
PCNA, Cyclin D1, Cyclin D3, MEK, Erk, pErk, pAkt, Caspase2, RBBP
PCNA, Cyclin D1, Cyclin D3, MEK, Erk, pErk, pAkt, Caspase2, total S6
PCNA, Cyclin D1, Cyclin D3, MEK, Erk, pErk, pAkt, RBBP, total S6
PCNA, Cyclin D1, Cyclin D3, MEK, Erk, pErk, Caspase2, RBBP, total S6
PCNA, Cyclin D1, Cyclin D3, MEK, Erk, Akt, pAkt, Caspase2, RBBP
PCNA, Cyclin D1, Cyclin D3, MEK, Erk, Akt, pAkt, Caspase2, total S6
PCNA, Cyclin D1, Cyclin D3, MEK, Erk, Akt, pAkt, RBBP, total S6
PCNA, Cyclin D1, Cyclin D3, MEK, Erk, Akt, Caspase2, RBBP, total S6
PCNA, Cyclin D1, Cyclin D3, MEK, Erk, pAkt, Caspase2, RBBP, total S6
PCNA, Cyclin D1, Cyclin D3, MEK, pErk, Akt, pAkt, Caspase2, RBBP
PCNA, Cyclin D3, s6, Akt, Caspase2, RBBP
PCNA, Cyclin D3, s6, Akt, Caspase2, total S6
PCNA, Cyclin D3, s6, Akt, RBBP, total S6
PCNA, Cyclin D3, s6, pAkt, Caspase2, RBBP
PCNA, Cyclin D3, s6, pAkt, Caspase2, total S6
PCNA, Cyclin D3, s6, pAkt, RBBP, total S6
PCNA, Cyclin D3, s6, Caspase2, RBBP, total S6
PCNA, Cyclin D3, pS6, Erk, pErk, Akt
PCNA, Cyclin D3, pS6, Erk, pErk, pAkt
PCNA, Cyclin D3, pS6, Erk, pErk, Caspase2
PCNA, Cyclin D3, pS6, Erk, pErk, RBBP
PCNA, Cyclin D3, pS6, Erk, pErk, total S6
PCNA, Cyclin D3, pS6, Erk, Akt, pAkt
PCNA, Cyclin D3, pS6, Erk, Akt, Caspase2
PCNA, Cyclin D3, pS6, Erk, Akt, RBBP
PCNA, Cyclin D3, pS6, Erk, Akt, total S6
PCNA, Cyclin D3, pS6, Erk, pAkt, Caspase2
PCNA, Cyclin D3, pS6, Erk, pAkt, RBBP
PCNA, Cyclin D3, pS6, Erk, pAkt, total S6
PCNA, Cyclin D3, pS6, Erk, Caspase2, RBBP
PCNA, Cyclin D3, pS6, Erk, Caspase2, total S6
PCNA, Cyclin D3, pS6, Erk, RBBP, total S6
PCNA, Cyclin D3, pS6, pErk, Akt, pAkt
PCNA, Cyclin D3, pS6, pErk, Akt, Caspase2
PCNA, Cyclin D3, pS6, pErk, Akt, RBBP
PCNA, Cyclin D3, pS6, pErk, Akt, total S6
PCNA, Cyclin D3, pS6, pErk, pAkt, Caspase2
PCNA, Cyclin D3, pS6, pErk, pAkt, RBBP
PCNA, Cyclin D3, pS6, pErk, pAkt, total S6
PCNA, Cyclin D3, pS6, pErk, Caspase2, RBBP
PCNA, Cyclin D3, pS6, pErk, Caspase2, total S6
PCNA, Cyclin D3, pS6, pErk, RBBP, total S6
PCNA, Cyclin D3, pS6, Akt, pAkt, Caspase2
PCNA, Cyclin D3, pS6, Akt, pAkt, RBBP
PCNA, Cyclin D3, pS6, Akt, pAkt, total S6
PCNA, Cyclin D3, pS6, Akt, Caspase2, RBBP
PCNA, Cyclin D3, pS6, Akt, Caspase2, total S6
PCNA, Cyclin D3, pS6, Akt, RBBP, total S6
PCNA, Cyclin D3, pS6, pAkt, Caspase2, RBBP TABLE 1-continued Examples of Single Markers and Combinations of Markers PCNA, Cyclin D1, Cyclin D3, MEK, pErk, Akt, pAkt, Caspase2, total S6
PCNA, Cyclin D1, Cyclin D3, MEK, pErk, Akt, pAkt, RBBP, total S6
PCNA, Cyclin D1, Cyclin D3, MEK, pErk, Akt, Caspase2, RBBP, total S6
PCNA, Cyclin D1, Cyclin D3, MEK, pErk, pAkt, Caspase2, RBBP, total S6
PCNA, Cyclin D1, Cyclin D3, MEK, Akt, pAkt, Caspase2, RBBP, total S6
PCNA, Cyclin D1, Cyclin D3, s6, pS6, Erk, pErk, Akt, pAkt
PCNA, Cyclin D1, Cyclin D3, s6, pS6, Erk, pErk, Akt, Caspase2
PCNA, Cyclin D1, Cyclin D3, s6, pS6, Erk, pErk, Akt, RBBP
PCNA, Cyclin D1, Cyclin D3, s6, pS6, Erk, pErk, Akt, total S6
PCNA, Cyclin D1, Cyclin D3, s6, pS6, Erk, pErk, pAkt, Caspase2
PCNA, Cyclin D1, Cyclin D3, s6, pS6, Erk, pErk, pAkt, RBBP
PCNA, Cyclin D1, Cyclin D3, s6, pS6, Erk, pErk, pAkt, total S6
PCNA, Cyclin D1, Cyclin D3, s6, pS6, Erk, pErk, Caspase2, RBBP
PCNA, Cyclin D1, Cyclin D3, s6, pS6, Erk, pErk, Caspase2, total S6
PCNA, Cyclin D1, Cyclin D3, s6, pS6, Erk, pErk, RBBP, total S6
PCNA, Cyclin D1, Cyclin D3, s6, pS6, Erk, Akt, pAkt, Caspase2
PCNA, Cyclin D1, Cyclin D3, s6, pS6, Erk, Akt, pAkt, RBBP
PCNA, Cyclin D1, Cyclin D3, s6, pS6, Erk, Akt, pAkt, total S6
PCNA, Cyclin D1, Cyclin D3, s6, pS6, Erk, Akt, Caspase2, RBBP
PCNA, Cyclin D1, Cyclin D3, s6, pS6, Erk, Akt, Caspase2, total S6
PCNA, Cyclin D1, Cyclin D3, s6, pS6, Erk, Akt, RBBP, total S6
PCNA, Cyclin D1, Cyclin D3, s6, pS6, Erk, pAkt, Caspase2, RBBP
PCNA, Cyclin D1, Cyclin D3, s6, pS6, Erk, pAkt, Caspase2, total S6
PCNA, Cyclin D1, Cyclin D3, s6, pS6, Erk, pAkt, RBBP, total S6
PCNA, Cyclin D1, Cyclin D3, s6, pS6, Erk, Caspase2, RBBP, total S6
PCNA, Cyclin D1, Cyclin D3, s6, pS6, pErk, Akt, pAkt, Caspase2
PCNA, Cyclin D1, Cyclin D3, s6, pS6, pErk, Akt, pAkt, RBBP
PCNA, Cyclin D1, Cyclin D3, s6, pS6, pErk, Akt, pAkt, total S6
PCNA, Cyclin D1, Cyclin D3, s6, pS6, pErk, Akt, Caspase2, RBBP
PCNA, Cyclin D1, Cyclin D3, s6, pS6, pErk, Akt, Caspase2, total S6
PCNA, Cyclin D1, Cyclin D3, s6, pS6, pErk, Akt, RBBP, total S6
PCNA, Cyclin D1, Cyclin D3, s6, pS6, pErk, pAkt, Caspase2, RBBP
PCNA, Cyclin D1, Cyclin D3, s6, pS6, pErk, pAkt, Caspase2, total S6
PCNA, Cyclin D1, Cyclin D3, s6, pS6, pErk, pAkt, RBBP, total S6
PCNA, Cyclin D1, Cyclin D3, s6, pS6, pErk, Caspase2, RBBP, total S6
PCNA, Cyclin D1, Cyclin D3, s6, pS6, Akt, pAkt, Caspase2, RBBP
PCNA, Cyclin D1, Cyclin D3, s6, pS6, Akt, pAkt, Caspase2, total S6
PCNA, Cyclin D1, Cyclin D3, s6, pS6, Akt, pAkt, RBBP, total S6
PCNA, Cyclin D1, Cyclin D3, s6, pS6, Akt, Caspase2, RBBP, total S6
PCNA, Cyclin D1, Cyclin D3, s6, pS6, pAkt, Caspase2, RBBP, total S6
PCNA, Cyclin D1, Cyclin D3, s6, Erk, pErk, Akt, pAkt, Caspase2
PCNA, Cyclin D1, Cyclin D3, s6, Erk, pErk, Akt, pAkt, RBBP
PCNA, Cyclin D1, Cyclin D3, s6, Erk, pErk, Akt, pAkt, total S6

PCNA, Cyclin D3, pS6, pAkt, Caspase2, total S6
PCNA, Cyclin D3, pS6, pAkt, RBBP, total S6
PCNA, Cyclin D3, pS6, Caspase2, RBBP, total S6
PCNA, Cyclin D3, Erk, pErk, Akt, pAkt
PCNA, Cyclin D3, Erk, pErk, Akt, Caspase2
PCNA, Cyclin D3, Erk, pErk, Akt, RBBP
PCNA, Cyclin D3, Erk, pErk, Akt, total S6
PCNA, Cyclin D3, Erk, pErk, pAkt, Caspase2
PCNA, Cyclin D3, Erk, pErk, pAkt, RBBP
PCNA, Cyclin D3, Erk, pErk, pAkt, total S6
PCNA, Cyclin D3, Erk, pErk, Caspase2, RBBP
PCNA, Cyclin D3, Erk, pErk, Caspase2, total S6
PCNA, Cyclin D3, Erk, pErk, RBBP, total S6
PCNA, Cyclin D3, Erk, Akt, pAkt, Caspase2
PCNA, Cyclin D3, Erk, Akt, pAkt, RBBP
PCNA, Cyclin D3, Erk, Akt, pAkt, total S6
PCNA, Cyclin D3, Erk, Akt, Caspase2, RBBP
PCNA, Cyclin D3, Erk, Akt, Caspase2, total S6
PCNA, Cyclin D3, Erk, Akt, RBBP, total S6
PCNA, Cyclin D3, Erk, pAkt, Caspase2, RBBP
PCNA, Cyclin D3, Erk, pAkt, Caspase2, total S6
PCNA, Cyclin D3, Erk, pAkt, RBBP, total S6
PCNA, Cyclin D3, Erk, Caspase2, RBBP, total S6
PCNA, Cyclin D3, pErk, Akt, pAkt, Caspase2
PCNA, Cyclin D3, pErk, Akt, pAkt, RBBP
PCNA, Cyclin D3, pErk, Akt, pAkt, total S6
PCNA, Cyclin D3, pErk, Akt, Caspase2, RBBP
PCNA, Cyclin D3, pErk, Akt, Caspase2, total S6
PCNA, Cyclin D3, pErk, Akt, RBBP, total S6
PCNA, Cyclin D3, pErk, pAkt, Caspase2, RBBP
PCNA, Cyclin D3, pErk, pAkt, Caspase2, total S6
PCNA, Cyclin D3, pErk, pAkt, RBBP, total S6
PCNA, Cyclin D3, pErk, Caspase2, RBBP, total S6
PCNA, Cyclin D3, Akt, pAkt, Caspase2, RBBP
PCNA, Cyclin D3, Akt, pAkt, Caspase2, total S6
PCNA, Cyclin D3, Akt, pAkt, RBBP, total S6
PCNA, Cyclin D3, Akt, Caspase2, RBBP, total S6
PCNA, Cyclin D3, pAkt, Caspase2, RBBP, total S6
PCNA, MEK, s6, pS6, Erk, pErk
PCNA, MEK, s6, pS6, Erk, Akt
PCNA, MEK, s6, pS6, Erk, pAkt
PCNA, MEK, s6, pS6, Erk, Caspase2
PCNA, MEK, s6, pS6, Erk, RBBP TABLE 1-continued Examples of Single Markers and Combinations of Markers PCNA, Cyclin D1, Cyclin D3, s6, Erk, pErk, Akt, Caspase2, RBBP
PCNA, Cyclin D1, Cyclin D3, s6, Erk, pErk, Akt, Caspase2, total S6
PCNA, Cyclin D1, Cyclin D3, s6, Erk, pErk, Akt, RBBP, total S6
PCNA, Cyclin D1, Cyclin D3, s6, Erk, pErk, pAkt, Caspase2, RBBP
PCNA, Cyclin D1, Cyclin D3, s6, Erk, pErk, pAkt, Caspase2, total S6
PCNA, Cyclin D1, Cyclin D3, s6, Erk, pErk, pAkt, RBBP, total S6
PCNA, Cyclin D1, Cyclin D3, s6, Erk, pErk, Caspase2, RBBP, total S6
PCNA, Cyclin D1, Cyclin D3, s6, Erk, Akt, pAkt, Caspase2, RBBP
PCNA, Cyclin D1, Cyclin D3, s6, Erk, Akt, pAkt, Caspase2, total S6
PCNA, Cyclin D1, Cyclin D3, s6, Erk, Akt, pAkt, RBBP, total S6
PCNA, Cyclin D1, Cyclin D3, s6, Erk, Akt, Caspase2, RBBP, total S6
PCNA, Cyclin D1, Cyclin D3, s6, Erk, pAkt, Caspase2, RBBP, total S6
PCNA, Cyclin D1, Cyclin D3, s6, pErk, Akt, pAkt, Caspase2, RBBP
PCNA, Cyclin D1, Cyclin D3, s6, pErk, Akt, pAkt, Caspase2, total S6
PCNA, Cyclin D1, Cyclin D3, s6, pErk, Akt, pAkt, RBBP, total S6
PCNA, Cyclin D1, Cyclin D3, s6, pErk, Akt, Caspase2, RBBP, total S6
PCNA, Cyclin D1, Cyclin D3, s6, pErk, pAkt, Caspase2, RBBP, total S6
PCNA, Cyclin D1, Cyclin D3, s6, Akt, pAkt, Caspase2, RBBP, total S6
PCNA, Cyclin D1, Cyclin D3, pS6, Erk, pErk, Akt, pAkt, Caspase2
PCNA, Cyclin D1, Cyclin D3, pS6, Erk, pErk, Akt, pAkt, RBBP
PCNA, Cyclin D1, Cyclin D3, pS6, Erk, pErk, Akt, pAkt, total S6
PCNA, Cyclin D1, Cyclin D3, pS6, Erk, pErk, Akt, Caspase2, RBBP
PCNA, Cyclin D1, Cyclin D3, pS6, Erk, pErk, Akt, Caspase2, total S6
PCNA, Cyclin D1, Cyclin D3, pS6, Erk, pErk, Akt, RBBP, total S6
PCNA, Cyclin D1, Cyclin D3, pS6, Erk, pErk, pAkt, Caspase2, RBBP
PCNA, Cyclin D1, Cyclin D3, pS6, Erk, pErk, pAkt, Caspase2, total S6
PCNA, Cyclin D1, Cyclin D3, pS6, Erk, pErk, pAkt, RBBP, total S6
PCNA, Cyclin D1, Cyclin D3, pS6, Erk, pErk, Caspase2, RBBP, total S6
PCNA, Cyclin D1, Cyclin D3, pS6, Erk, Akt, pAkt, Caspase2, RBBP
PCNA, Cyclin D1, Cyclin D3, pS6, Erk, Akt, pAkt, Caspase2, total S6
PCNA, Cyclin D1, Cyclin D3, pS6, Erk, Akt, pAkt, RBBP, total S6
PCNA, Cyclin D1, Cyclin D3, pS6, Erk, Akt, Caspase2, RBBP, total S6
PCNA, Cyclin D1, Cyclin D3, pS6, Erk, pAkt, Caspase2, RBBP, total S6
PCNA, Cyclin D1, Cyclin D3, pS6, pErk, Akt, pAkt, Caspase2, RBBP
PCNA, Cyclin D1, Cyclin D3, pS6, pErk, Akt, pAkt, Caspase2, total S6
PCNA, Cyclin D1, Cyclin D3, pS6, pErk, Akt, pAkt, RBBP, total S6
PCNA, Cyclin D1, Cyclin D3, pS6, pErk, Akt, Caspase2, RBBP, total S6
PCNA, Cyclin D1, Cyclin D3, pS6, pErk, pAkt, Caspase2, RBBP, total S6
PCNA, Cyclin D1, Cyclin D3, pS6, Akt, pAkt, Caspase2, RBBP, total S6
PCNA, Cyclin D1, Cyclin D3, Erk, pErk, Akt, pAkt, Caspase2, RBBP
PCNA, Cyclin D1, Cyclin D3, Erk, pErk, Akt, pAkt, Caspase2, total S6
PCNA, Cyclin D1, Cyclin D3, Erk, pErk, Akt, pAkt, RBBP, total S6
PCNA, Cyclin D1, Cyclin D3, Erk, pErk, Akt, Caspase2, RBBP, total S6
PCNA, Cyclin D1, Cyclin D3, Erk, pErk, pAkt, Caspase2, RBBP, total S6
PCNA, Cyclin D1, Cyclin D3, Erk, Akt, pAkt, Caspase2, RBBP, total S6
PCNA, Cyclin D1, Cyclin D3, pErk, Akt, pAkt, Caspase2, RBBP, total S6
PCNA, Cyclin D1, MEK, s6, pS6, Erk, pErk, Akt, pAkt
PCNA, Cyclin D1, MEK, s6, pS6, Erk, pErk, Akt, Caspase2
PCNA, Cyclin D1, MEK, s6, pS6, Erk, pErk, Akt, RBBP
PCNA, Cyclin D1, MEK, s6, pS6, Erk, pErk, Akt, total S6
PCNA, Cyclin D1, MEK, s6, pS6, Erk, pErk, pAkt, Caspase2
PCNA, Cyclin D1, MEK, s6, pS6, Erk, pErk, pAkt, RBBP
PCNA, Cyclin D1, MEK, s6, pS6, Erk, pErk, pAkt, total S6
PCNA, Cyclin D1, MEK, s6, pS6, Erk, pErk, Caspase2, RBBP
PCNA, MEK, s6, pS6, Erk, total S6
PCNA, MEK, s6, pS6, pErk, Akt
PCNA, MEK, s6, pS6, pErk, pAkt
PCNA, MEK, s6, pS6, pErk, Caspase2
PCNA, MEK, s6, pS6, pErk, RBBP
PCNA, MEK, s6, pS6, pErk, total S6
PCNA, MEK, s6, pS6, Akt, pAkt
PCNA, MEK, s6, pS6, Akt, Caspase2
PCNA, MEK, s6, pS6, Akt, RBBP
PCNA, MEK, s6, pS6, Akt, total S6
PCNA, MEK, s6, pS6, pAkt, Caspase2
PCNA, MEK, s6, pS6, pAkt, RBBP
PCNA, MEK, s6, pS6, pAkt, total S6
PCNA, MEK, s6, pS6, Caspase2, RBBP
PCNA, MEK, s6, pS6, Caspase2, total S6
PCNA, MEK, s6, pS6, RBBP, total S6
PCNA, MEK, s6, Erk, pErk, Akt
PCNA, MEK, s6, Erk, pErk, pAkt
PCNA, MEK, s6, Erk, pErk, Caspase2
PCNA, MEK, s6, Erk, pErk, RBBP
PCNA, MEK, s6, Erk, pErk, total S6
PCNA, MEK, s6, Erk, Akt, pAkt
PCNA, MEK, s6, Erk, Akt, Caspase2
PCNA, MEK, s6, Erk, Akt, RBBP
PCNA, MEK, s6, Erk, Akt, total S6
PCNA, MEK, s6, Erk, pAkt, Caspase2
PCNA, MEK, s6, Erk, pAkt, RBBP
PCNA, MEK, s6, Erk, pAkt, total S6
PCNA, MEK, s6, Erk, Caspase2, RBBP
PCNA, MEK, s6, Erk, Caspase2, total S6
PCNA, MEK, s6, Erk, RBBP, total S6
PCNA, MEK, s6, pErk, Akt, pAkt
PCNA, MEK, s6, pErk, Akt, Caspase2
PCNA, MEK, s6, pErk, Akt, RBBP
PCNA, MEK, s6, pErk, Akt, total S6
PCNA, MEK, s6, pErk, pAkt, Caspase2
PCNA, MEK, s6, pErk, pAkt, RBBP
PCNA, MEK, s6, pErk, pAkt, total S6
PCNA, MEK, s6, pErk, Caspase2, RBBP
PCNA, MEK, s6, pErk, Caspase2, total S6
PCNA, MEK, s6, pErk, RBBP, total S6
PCNA, MEK, s6, Akt, pAkt, Caspase2
PCNA, MEK, s6, Akt, pAkt, RBBP
PCNA, MEK, s6, Akt, pAkt, total S6
PCNA, MEK, s6, Akt, Caspase2, RBBP
PCNA, MEK, s6, Akt, Caspase2, total S6
PCNA, MEK, s6, Akt, RBBP, total S6
PCNA, MEK, s6, pAkt, Caspase2, RBBP
PCNA, MEK, s6, pAkt, Caspase2, total S6
PCNA, MEK, s6, pAkt, RBBP, total S6
PCNA, MEK, s6, Caspase2, RBBP, total S6
PCNA, MEK, pS6, Erk, pErk, Akt
PCNA, MEK, pS6, Erk, pErk, pAkt
PCNA, MEK, pS6, Erk, pErk, Caspase2

TABLE 1-continued

Examples of Single Markers and Combinations of Markers

PCNA, Cyclin D1, MEK, s6, pS6, Erk, pErk, Caspase2, total S6
PCNA, Cyclin D1, MEK, s6, pS6, Erk, pErk, RBBP, total S6
PCNA, Cyclin D1, MEK, s6, pS6, Erk, Akt, pAkt, Caspase2
PCNA, Cyclin D1, MEK, s6, pS6, Erk, Akt, pAkt, RBBP
PCNA, Cyclin D1, MEK, s6, pS6, Erk, Akt, pAkt, total S6
PCNA, Cyclin D1, MEK, s6, pS6, Erk, Akt, Caspase2, RBBP
PCNA, Cyclin D1, MEK, s6, pS6, Erk, Akt, Caspase2, total S6
PCNA, Cyclin D1, MEK, s6, pS6, Erk, Akt, RBBP, total S6
PCNA, Cyclin D1, MEK, s6, pS6, Erk, pAkt, Caspase2, RBBP
PCNA, Cyclin D1, MEK, s6, pS6, Erk, pAkt, Caspase2, total S6
PCNA, Cyclin D1, MEK, s6, pS6, Erk, pAkt, RBBP, total S6
PCNA, Cyclin D1, MEK, s6, pS6, Erk, Caspase2, RBBP, total S6
PCNA, Cyclin D1, MEK, s6, pS6, pErk, Akt, pAkt, Caspase2
PCNA, Cyclin D1, MEK, s6, pS6, pErk, Akt, pAkt, RBBP
PCNA, Cyclin D1, MEK, s6, pS6, pErk, Akt, pAkt, total S6
PCNA, Cyclin D1, MEK, s6, pS6, pErk, Akt, Caspase2, RBBP
PCNA, Cyclin D1, MEK, s6, pS6, pErk, Akt, Caspase2, total S6
PCNA, Cyclin D1, MEK, s6, pS6, pErk, Akt, RBBP, total S6
PCNA, Cyclin D1, MEK, s6, pS6, pErk, pAkt, Caspase2, RBBP
PCNA, Cyclin D1, MEK, s6, pS6, pErk, pAkt, Caspase2, total S6
PCNA, Cyclin D1, MEK, s6, pS6, pErk, pAkt, RBBP, total S6
PCNA, Cyclin D1, MEK, s6, pS6, pErk, Caspase2, RBBP, total S6
PCNA, Cyclin D1, MEK, s6, pS6, Akt, pAkt, Caspase2, RBBP
PCNA, Cyclin D1, MEK, s6, pS6, Akt, pAkt, Caspase2, total S6
PCNA, Cyclin D1, MEK, s6, pS6, Akt, pAkt, RBBP, total S6
PCNA, Cyclin D1, MEK, s6, pS6, Akt, Caspase2, RBBP, total S6
PCNA, Cyclin D1, MEK, s6, pS6, pAkt, Caspase2, RBBP, total S6

PCNA, Cyclin D1, MEK, s6, Erk, pErk, Akt, pAkt, Caspase2
PCNA, Cyclin D1, MEK, s6, Erk, pErk, Akt, pAkt, RBBP
PCNA, Cyclin D1, MEK, s6, Erk, pErk, Akt, pAkt, total S6
PCNA, Cyclin D1, MEK, s6, Erk, pErk, Akt, Caspase2, RBBP
PCNA, Cyclin D1, MEK, s6, Erk, pErk, Akt, Caspase2, total S6

PCNA, Cyclin D1, MEK, s6, Erk, pErk, Akt, RBBP, total S6
PCNA, Cyclin D1, MEK, s6, Erk, pErk, pAkt, Caspase2, RBBP
PCNA, Cyclin D1, MEK, s6, Erk, pErk, pAkt, Caspase2, total S6
PCNA, Cyclin D1, MEK, s6, Erk, pErk, pAkt, RBBP, total S6
PCNA, Cyclin D1, MEK, s6, Erk, pErk, Caspase2, RBBP, total S6
PCNA, Cyclin D1, MEK, s6, Erk, Akt, pAkt, Caspase2, RBBP
PCNA, Cyclin D1, MEK, s6, Erk, Akt, pAkt, Caspase2, total S6
PCNA, Cyclin D1, MEK, s6, Erk, Akt, pAkt, RBBP, total S6
PCNA, Cyclin D1, MEK, s6, Erk, Akt, Caspase2, RBBP, total S6
PCNA, Cyclin D1, MEK, s6, Erk, pAkt, Caspase2, RBBP, total S6
PCNA, Cyclin D1, MEK, s6, pErk, Akt, pAkt, Caspase2, RBBP
PCNA, Cyclin D1, MEK, s6, pErk, Akt, pAkt, Caspase2, total S6
PCNA, Cyclin D1, MEK, s6, pErk, Akt, pAkt, RBBP, total S6
PCNA, Cyclin D1, MEK, s6, pErk, Akt, Caspase2, RBBP, total S6
PCNA, Cyclin D1, MEK, s6, pErk, pAkt, Caspase2, RBBP, total S6

PCNA, Cyclin D1, MEK, s6, Akt, pAkt, Caspase2, RBBP, total S6
PCNA, Cyclin D1, MEK, pS6, Erk, pErk, Akt, pAkt, Caspase2
PCNA, Cyclin D1, MEK, pS6, Erk, pErk, Akt, pAkt, RBBP
PCNA, Cyclin D1, MEK, pS6, Erk, pErk, Akt, pAkt, total S6
PCNA, Cyclin D1, MEK, pS6, Erk, pErk, Akt, Caspase2, RBBP
PCNA, Cyclin D1, MEK, pS6, Erk, pErk, Akt, Caspase2, total S6
PCNA, Cyclin D1, MEK, pS6, Erk, pErk, Akt, RBBP, total S6
PCNA, Cyclin D1, MEK, pS6, Erk, pErk, pAkt, Caspase2, RBBP
PCNA, Cyclin D1, MEK, pS6, Erk, pErk, pAkt, Caspase2, total S6
PCNA, Cyclin D1, MEK, pS6, Erk, pErk, pAkt, RBBP, total S6
PCNA, Cyclin D1, MEK, pS6, Erk, pErk, Caspase2, RBBP, total S6
PCNA, Cyclin D1, MEK, pS6, Erk, Akt, pAkt, Caspase2, RBBP
PCNA, Cyclin D1, MEK, pS6, Erk, Akt, pAkt, Caspase2, total S6

PCNA, Cyclin D1, MEK, pS6, Erk, Akt, pAkt, RBBP, total S6
PCNA, Cyclin D1, MEK, pS6, Erk, Akt, Caspase2, RBBP, total S6
PCNA, Cyclin D1, MEK, pS6, Erk, pAkt, Caspase2, RBBP, total S6
PCNA, Cyclin D1, MEK, pS6, pErk, Akt, pAkt, Caspase2, RBBP
PCNA, Cyclin D1, MEK, pS6, pErk, Akt, pAkt, Caspase2, total S6
PCNA, Cyclin D1, MEK, pS6, pErk, Akt, pAkt, RBBP, total S6

PCNA, Cyclin D1, MEK, pS6, pErk, Akt, Caspase2, RBBP, total S6
PCNA, Cyclin D1, MEK, pS6, pErk, pAkt, Caspase2, RBBP, total S6
PCNA, Cyclin D1, MEK, pS6, Akt, pAkt, Caspase2, RBBP, total S6
PCNA, Cyclin D1, MEK, Erk, pErk, Akt, pAkt, Caspase2, RBBP PCNA, MEK, pS6, Erk, pErk, RBBP
PCNA, MEK, pS6, Erk, pErk, total S6
PCNA, MEK, pS6, Erk, Akt, pAkt
PCNA, MEK, pS6, Erk, Akt, Caspase2
PCNA, MEK, pS6, Erk, Akt, RBBP
PCNA, MEK, pS6, Erk, Akt, total S6
PCNA, MEK, pS6, Erk, pAkt, Caspase2
PCNA, MEK, pS6, Erk, pAkt, RBBP
PCNA, MEK, pS6, Erk, pAkt, total S6
PCNA, MEK, pS6, Erk, Caspase2, RBBP
PCNA, MEK, pS6, Erk, Caspase2, total S6
PCNA, MEK, pS6, Erk, RBBP, total S6
PCNA, MEK, pS6, pErk, Akt, pAkt
PCNA, MEK, pS6, pErk, Akt, Caspase2
PCNA, MEK, pS6, pErk, Akt, RBBP
PCNA, MEK, pS6, pErk, Akt, total S6
PCNA, MEK, pS6, pErk, pAkt, Caspase2
PCNA, MEK, pS6, pErk, pAkt, RBBP
PCNA, MEK, pS6, pErk, pAkt, total S6
PCNA, MEK, pS6, pErk, Caspase2, RBBP
PCNA, MEK, pS6, pErk, Caspase2, total S6
PCNA, MEK, pS6, pErk, RBBP, total S6
PCNA, MEK, pS6, Akt, pAkt, Caspase2
PCNA, MEK, pS6, Akt, pAkt, RBBP
PCNA, MEK, pS6, Akt, pAkt, total S6
PCNA, MEK, pS6, Akt, Caspase2, RBBP
PCNA, MEK, pS6, Akt, Caspase2, total S6
PCNA, MEK, pS6, Akt, RBBP, total S6
PCNA, MEK, pS6, pAkt, Caspase2, RBBP
PCNA, MEK, pS6, pAkt, Caspase2, total S6
PCNA, MEK, pS6, pAkt, RBBP, total S6
PCNA, MEK, pS6, Caspase2, RBBP, total S6
PCNA, MEK, Erk, pErk, Akt, pAkt
PCNA, MEK, Erk, pErk, Akt, Caspase2
PCNA, MEK, Erk, pErk, Akt, RBBP
PCNA, MEK, Erk, pErk, Akt, total S6
PCNA, MEK, Erk, pErk, pAkt, Caspase2
PCNA, MEK, Erk, pErk, pAkt, RBBP
PCNA, MEK, Erk, pErk, pAkt, total S6
PCNA, MEK, Erk, pErk, Caspase2, RBBP
PCNA, MEK, Erk, pErk, Caspase2, total S6
PCNA, MEK, Erk, pErk, RBBP, total S6
PCNA, MEK, Erk, Akt, pAkt, Caspase2
PCNA, MEK, Erk, Akt, pAkt, RBBP
PCNA, MEK, Erk, Akt, pAkt, total S6
PCNA, MEK, Erk, Akt, Caspase2, RBBP
PCNA, MEK, Erk, Akt, Caspase2, total S6
PCNA, MEK, Erk, Akt, RBBP, total S6
PCNA, MEK, Erk, pAkt, Caspase2, RBBP
PCNA, MEK, Erk, pAkt, Caspase2, total S6
PCNA, MEK, Erk, pAkt, RBBP, total S6
PCNA, MEK, Erk, Caspase2, RBBP, total S6
PCNA, MEK, pErk, Akt, pAkt, Caspase2
PCNA, MEK, pErk, Akt, pAkt, RBBP
PCNA, MEK, pErk, Akt, pAkt, total S6
PCNA, MEK, pErk, Akt, Caspase2, RBBP
PCNA, MEK, pErk, Akt, Caspase2, total S6
PCNA, MEK, pErk, Akt, RBBP, total S6
PCNA, MEK, pErk, pAkt, Caspase2, RBBP
PCNA, MEK, pErk, pAkt, Caspase2, total S6
PCNA, MEK, pErk, pAkt, RBBP, total S6
PCNA, MEK, pErk, Caspase2, RBBP, total S6
PCNA, MEK, Akt, pAkt, Caspase2, RBBP
PCNA, MEK, Akt, pAkt, Caspase2, total S6
PCNA, MEK, Akt, pAkt, RBBP, total S6
PCNA, MEK, Akt, Caspase2, RBBP, total S6
PCNA, MEK, pAkt, Caspase2, RBBP, total S6
PCNA, s6, pS6, Erk, pErk, Akt
PCNA, s6, pS6, Erk, pErk, pAkt
PCNA, s6, pS6, Erk, pErk, Caspase2

TABLE 1-continued

Examples of Single Markers and Combinations of Markers

PCNA, Cyclin D1, MEK, Erk, pErk, Akt, pAkt, Caspase2, total S6
PCNA, Cyclin D1, MEK, Erk, pErk, Akt, pAkt, RBBP, total S6
PCNA, Cyclin D1, MEK, Erk, pErk, Akt, Caspase2, RBBP, total S6
PCNA, Cyclin D1, MEK, Erk, pErk, pAkt, Caspase2, RBBP, total S6
PCNA, Cyclin D1, MEK, Erk, Akt, pAkt, Caspase2, RBBP, total S6
PCNA, Cyclin D1, MEK, pErk, Akt, pAkt, Caspase2, RBBP, total S6
PCNA, Cyclin D1, s6, pS6, Erk, pErk, Akt, pAkt, Caspase2
PCNA, Cyclin D1, s6, pS6, Erk, pErk, Akt, pAkt, RBBP
PCNA, Cyclin D1, s6, pS6, Erk, pErk, Akt, pAkt, total S6
PCNA, Cyclin D1, s6, pS6, Erk, pErk, Akt, Caspase2, RBBP
PCNA, Cyclin D1, s6, pS6, Erk, pErk, Akt, Caspase2, total S6
PCNA, Cyclin D1, s6, pS6, Erk, pErk, Akt, RBBP, total S6
PCNA, Cyclin D1, s6, pS6, Erk, pErk, pAkt, Caspase2, RBBP
PCNA, Cyclin D1, s6, pS6, Erk, pErk, pAkt, Caspase2, total S6
PCNA, Cyclin D1, s6, pS6, Erk, pErk, pAkt, RBBP, total S6
PCNA, Cyclin D1, s6, pS6, Erk, pErk, Caspase2, RBBP, total S6
PCNA, Cyclin D1, s6, pS6, Erk, Akt, pAkt, Caspase2, RBBP
PCNA, Cyclin D1, s6, pS6, Erk, Akt, pAkt, Caspase2, total S6
PCNA, Cyclin D1, s6, pS6, Erk, Akt, pAkt, RBBP, total S6
PCNA, Cyclin D1, s6, pS6, Erk, Akt, Caspase2, RBBP, total S6
PCNA, Cyclin D1, s6, pS6, Erk, pAkt, Caspase2, RBBP, total S6
PCNA, Cyclin D1, s6, pS6, pErk, Akt, pAkt, Caspase2, RBBP
PCNA, Cyclin D1, s6, pS6, pErk, Akt, pAkt, Caspase2, total S6
PCNA, Cyclin D1, s6, pS6, pErk, Akt, pAkt, RBBP, total S6
PCNA, Cyclin D1, s6, pS6, pErk, Akt, Caspase2, RBBP, total S6
PCNA, Cyclin D1, s6, pS6, pErk, pAkt, Caspase2, RBBP, total S6
PCNA, Cyclin D1, s6, pS6, Akt, pAkt, Caspase2, RBBP, total S6
PCNA, Cyclin D1, s6, Erk, pErk, Akt, pAkt, Caspase2, RBBP
PCNA, Cyclin D1, s6, Erk, pErk, Akt, pAkt, Caspase2, total S6
PCNA, Cyclin D1, s6, Erk, pErk, Akt, pAkt, RBBP, total S6
PCNA, Cyclin D1, s6, Erk, pErk, Akt, Caspase2, RBBP, total S6
PCNA, Cyclin D1, s6, Erk, pErk, pAkt, Caspase2, RBBP, total S6
PCNA, Cyclin D1, s6, Erk, Akt, pAkt, Caspase2, RBBP, total S6
PCNA, Cyclin D1, s6, pErk, Akt, pAkt, Caspase2, RBBP, total S6
PCNA, Cyclin D1, pS6, Erk, pErk, Akt, pAkt, Caspase2, RBBP
PCNA, Cyclin D1, pS6, Erk, pErk, Akt, pAkt, Caspase2, total S6
PCNA, Cyclin D1, pS6, Erk, pErk, Akt, pAkt, RBBP, total S6
PCNA, Cyclin D1, pS6, Erk, pErk, Akt, Caspase2, RBBP, total S6
PCNA, Cyclin D1, pS6, Erk, pErk, pAkt, Caspase2, RBBP, total S6
PCNA, Cyclin D1, pS6, Erk, Akt, pAkt, Caspase2, RBBP, total S6
PCNA, Cyclin D1, pS6, pErk, Akt, pAkt, Caspase2, RBBP, total S6
PCNA, Cyclin D1, Erk, pErk, Akt, pAkt, Caspase2, RBBP, total S6
PCNA, Cyclin D3, MEK, s6, pS6, Erk, pErk, Akt, pAkt
PCNA, Cyclin D3, MEK, s6, pS6, Erk, pErk, Akt, Caspase2
PCNA, Cyclin D3, MEK, s6, pS6, Erk, pErk, Akt, RBBP
PCNA, Cyclin D3, MEK, s6, pS6, Erk, pErk, Akt, total S6
PCNA, Cyclin D3, MEK, s6, pS6, Erk, pErk, pAkt, Caspase2
PCNA, Cyclin D3, MEK, s6, pS6, Erk, pErk, pAkt, RBBP
PCNA, Cyclin D3, MEK, s6, pS6, Erk, pErk, pAkt, total S6
PCNA, Cyclin D3, MEK, s6, pS6, Erk, pErk, Caspase2, RBBP
PCNA, Cyclin D3, MEK, s6, pS6, Erk, pErk, Caspase2, total S6
PCNA, Cyclin D3, MEK, s6, pS6, Erk, pErk, RBBP, total S6
PCNA, Cyclin D3, MEK, s6, pS6, Erk, Akt, pAkt, Caspase2
PCNA, Cyclin D3, MEK, s6, pS6, Erk, Akt, pAkt, RBBP
PCNA, Cyclin D3, MEK, s6, pS6, Erk, Akt, pAkt, total S6
PCNA, Cyclin D3, MEK, s6, pS6, Erk, Akt, Caspase2, RBBP
PCNA, Cyclin D3, MEK, s6, pS6, Erk, Akt, Caspase2, total S6
PCNA, Cyclin D3, MEK, s6, pS6, Erk, Akt, RBBP, total S6
PCNA, Cyclin D3, MEK, s6, pS6, Erk, pAkt, Caspase2, RBBP
PCNA, Cyclin D3, MEK, s6, pS6, Erk, pAkt, Caspase2, total S6
PCNA, Cyclin D3, MEK, s6, pS6, Erk, pAkt, RBBP, total S6
PCNA, Cyclin D3, MEK, s6, pS6, Erk, Caspase2, RBBP, total S6
PCNA, Cyclin D3, MEK, s6, pS6, pErk, Akt, pAkt, Caspase2
PCNA, Cyclin D3, MEK, s6, pS6, pErk, Akt, pAkt, RBBP
PCNA, Cyclin D3, MEK, s6, pS6, pErk, Akt, pAkt, total S6
PCNA, Cyclin D3, MEK, s6, pS6, pErk, Akt, Caspase2, RBBP
PCNA, Cyclin D3, MEK, s6, pS6, pErk, Akt, Caspase2, total S6
PCNA, Cyclin D3, MEK, s6, pS6, pErk, Akt, RBBP, total S6
PCNA, Cyclin D3, MEK, s6, pS6, pErk, pAkt, Caspase2, RBBP
PCNA, Cyclin D3, MEK, s6, pS6, pErk, pAkt, Caspase2, total S6
PCNA, Cyclin D3, MEK, s6, pS6, pErk, pAkt, RBBP, total S6
PCNA, Cyclin D3, MEK, s6, pS6, pErk, Caspase2, RBBP, total S6
PCNA, Cyclin D3, MEK, s6, pS6, Akt, pAkt, Caspase2, RBBP
PCNA, Cyclin D3, MEK, s6, pS6, Akt, pAkt, Caspase2, total S6
PCNA, Cyclin D3, MEK, s6, pS6, Akt, pAkt, RBBP, total S6
PCNA, Cyclin D3, MEK, s6, pS6, Akt, Caspase2, RBBP, total S6
PCNA, Cyclin D3, MEK, s6, pS6, pAkt, Caspase2, RBBP, total S6
PCNA, Cyclin D3, MEK, s6, Erk, pErk, Akt, pAkt, Caspase2

PCNA, s6, pS6, Erk, pErk, RBBP
PCNA, s6, pS6, Erk, pErk, total S6
PCNA, s6, pS6, Erk, Akt, pAkt
PCNA, s6, pS6, Erk, Akt, Caspase2
PCNA, s6, pS6, Erk, Akt, RBBP
PCNA, s6, pS6, Erk, Akt, total S6
PCNA, s6, pS6, Erk, pAkt, Caspase2
PCNA, s6, pS6, Erk, pAkt, RBBP
PCNA, s6, pS6, Erk, pAkt, total S6
PCNA, s6, pS6, Erk, Caspase2, RBBP
PCNA, s6, pS6, Erk, Caspase2, total S6
PCNA, s6, pS6, Erk, RBBP, total S6
PCNA, s6, pS6, pErk, Akt, pAkt
PCNA, s6, pS6, pErk, Akt, Caspase2
PCNA, s6, pS6, pErk, Akt, RBBP
PCNA, s6, pS6, pErk, Akt, total S6
PCNA, s6, pS6, pErk, pAkt, Caspase2
PCNA, s6, pS6, pErk, pAkt, RBBP
PCNA, s6, pS6, pErk, pAkt, total S6
PCNA, s6, pS6, pErk, Caspase2, RBBP
PCNA, s6, pS6, pErk, Caspase2, total S6
PCNA, s6, pS6, pErk, RBBP, total S6
PCNA, s6, pS6, Akt, pAkt, Caspase2
PCNA, s6, pS6, Akt, pAkt, RBBP
PCNA, s6, pS6, Akt, pAkt, total S6
PCNA, s6, pS6, Akt, Caspase2, RBBP
PCNA, s6, pS6, Akt, Caspase2, total S6
PCNA, s6, pS6, Akt, RBBP, total S6
PCNA, s6, pS6, pAkt, Caspase2, RBBP
PCNA, s6, pS6, pAkt, Caspase2, total S6
PCNA, s6, pS6, pAkt, RBBP, total S6
PCNA, s6, pS6, Caspase2, RBBP, total S6
PCNA, s6, Erk, pErk, Akt, pAkt
PCNA, s6, Erk, pErk, Akt, Caspase2
PCNA, s6, Erk, pErk, Akt, RBBP
PCNA, s6, Erk, pErk, Akt, total S6
PCNA, s6, Erk, pErk, pAkt, Caspase2
PCNA, s6, Erk, pErk, pAkt, RBBP
PCNA, s6, Erk, pErk, pAkt, total S6
PCNA, s6, Erk, pErk, Caspase2, RBBP
PCNA, s6, Erk, pErk, Caspase2, total S6
PCNA, s6, Erk, pErk, RBBP, total S6
PCNA, s6, Erk, Akt, pAkt, Caspase2
PCNA, s6, Erk, Akt, pAkt, RBBP
PCNA, s6, Erk, Akt, pAkt, total S6
PCNA, s6, Erk, Akt, Caspase2, RBBP
PCNA, s6, Erk, Akt, Caspase2, total S6
PCNA, s6, Erk, Akt, RBBP, total S6
PCNA, s6, Erk, pAkt, Caspase2, RBBP
PCNA, s6, Erk, pAkt, Caspase2, total S6
PCNA, s6, Erk, pAkt, RBBP, total S6
PCNA, s6, Erk, Caspase2, RBBP, total S6
PCNA, s6, pErk, Akt, pAkt, Caspase2
PCNA, s6, pErk, Akt, pAkt, RBBP
PCNA, s6, pErk, Akt, pAkt, total S6
PCNA, s6, pErk, Akt, Caspase2, RBBP
PCNA, s6, pErk, Akt, Caspase2, total S6
PCNA, s6, pErk, Akt, RBBP, total S6
PCNA, s6, pErk, pAkt, Caspase2, RBBP
PCNA, s6, pErk, pAkt, Caspase2, total S6
PCNA, s6, pErk, pAkt, RBBP, total S6
PCNA, s6, pErk, Caspase2, RBBP, total S6
PCNA, s6, Akt, pAkt, Caspase2, RBBP
PCNA, s6, Akt, pAkt, Caspase2, total S6
PCNA, s6, Akt, pAkt, RBBP, total S6
PCNA, s6, Akt, Caspase2, RBBP, total S6
PCNA, s6, pAkt, Caspase2, RBBP, total S6
PCNA, pS6, Erk, pErk, Akt, pAkt
PCNA, pS6, Erk, pErk, Akt, Caspase2
PCNA, pS6, Erk, pErk, Akt, RBBP
PCNA, pS6, Erk, pErk, Akt, total S6
PCNA, pS6, Erk, pErk, pAkt, Caspase2
PCNA, pS6, Erk, pErk, pAkt, RBBP
PCNA, pS6, Erk, pErk, pAkt, total S6
PCNA, pS6, Erk, pErk, Caspase2, RBBP
PCNA, pS6, Erk, pErk, Caspase2, total S6
PCNA, pS6, Erk, pErk, RBBP, total S6
PCNA, pS6, Erk, Akt, pAkt, Caspase2

TABLE 1-continued

Examples of Single Markers and Combinations of Markers

PCNA, Cyclin D3, MEK, s6, Erk, pErk, Akt, pAkt, RBBP
PCNA, Cyclin D3, MEK, s6, Erk, pErk, Akt, pAkt, total S6
PCNA, Cyclin D3, MEK, s6, Erk, pErk, Akt, Caspase2, RBBP
PCNA, Cyclin D3, MEK, s6, Erk, pErk, Akt, Caspase2, total S6
PCNA, Cyclin D3, MEK, s6, Erk, pErk, Akt, RBBP, total S6
PCNA, Cyclin D3, MEK, s6, Erk, pErk, pAkt, Caspase2, RBBP
PCNA, Cyclin D3, MEK, s6, Erk, pErk, pAkt, Caspase2, total S6
PCNA, Cyclin D3, MEK, s6, Erk, pErk, pAkt, RBBP, total S6
PCNA, Cyclin D3, MEK, s6, Erk, pErk, Caspase2, RBBP, total S6

PCNA, Cyclin D3, MEK, s6, Erk, Akt, pAkt, Caspase2, RBBP
PCNA, Cyclin D3, MEK, s6, Erk, Akt, pAkt, Caspase2, total S6
PCNA, Cyclin D3, MEK, s6, Erk, Akt, pAkt, RBBP, total S6
PCNA, Cyclin D3, MEK, s6, Erk, Akt, Caspase2, RBBP, total S6
PCNA, Cyclin D3, MEK, s6, Erk, pAkt, Caspase2, RBBP, total S6
PCNA, Cyclin D3, MEK, s6, pErk, Akt, pAkt, Caspase2, RBBP
PCNA, Cyclin D3, MEK, s6, pErk, Akt, pAkt, Caspase2, total S6
PCNA, Cyclin D3, MEK, s6, pErk, Akt, pAkt, RBBP, total S6
PCNA, Cyclin D3, MEK, s6, pErk, Akt, Caspase2, RBBP, total S6
PCNA, Cyclin D3, MEK, s6, pErk, pAkt, Caspase2, RBBP, total S6
PCNA, Cyclin D3, MEK, s6, Akt, pAkt, Caspase2, RBBP, total S6
PCNA, Cyclin D3, MEK, pS6, Erk, pErk, Akt, pAkt, Caspase2
PCNA, Cyclin D3, MEK, pS6, Erk, pErk, Akt, pAkt, RBBP
PCNA, Cyclin D3, MEK, pS6, Erk, pErk, Akt, pAkt, total S6
PCNA, Cyclin D3, MEK, pS6, Erk, pErk, Akt, Caspase2, RBBP
PCNA, Cyclin D3, MEK, pS6, Erk, pErk, Akt, Caspase2, total S6
PCNA, Cyclin D3, MEK, pS6, Erk, pErk, Akt, RBBP, total S6
PCNA, Cyclin D3, MEK, pS6, Erk, pErk, pAkt, Caspase2, RBBP
PCNA, Cyclin D3, MEK, pS6, Erk, pErk, pAkt, Caspase2, total S6
PCNA, Cyclin D3, MEK, pS6, Erk, pErk, pAkt, RBBP, total S6
PCNA, Cyclin D3, MEK, pS6, Erk, pErk, Caspase2, RBBP, total S6
PCNA, Cyclin D3, MEK, pS6, Erk, Akt, pAkt, Caspase2, RBBP
PCNA, Cyclin D3, MEK, pS6, Erk, Akt, pAkt, Caspase2, total S6
PCNA, Cyclin D3, MEK, pS6, Erk, Akt, pAkt, RBBP, total S6
PCNA, Cyclin D3, MEK, pS6, Erk, Akt, Caspase2, RBBP, total S6
PCNA, Cyclin D3, MEK, pS6, Erk, pAkt, Caspase2, RBBP, total S6
PCNA, Cyclin D3, MEK, pS6, pErk, Akt, pAkt, Caspase2, RBBP
PCNA, Cyclin D3, MEK, pS6, pErk, Akt, pAkt, Caspase2, total S6
PCNA, Cyclin D3, MEK, pS6, pErk, Akt, pAkt, RBBP, total S6
PCNA, Cyclin D3, MEK, pS6, pErk, Akt, Caspase2, RBBP, total S6
PCNA, Cyclin D3, MEK, pS6, pErk, pAkt, Caspase2, RBBP, total S6
PCNA, Cyclin D3, MEK, pS6, Akt, pAkt, Caspase2, RBBP, total S6
PCNA, Cyclin D3, MEK, Erk, pErk, Akt, pAkt, Caspase2, RBBP
PCNA, Cyclin D3, MEK, Erk, pErk, Akt, pAkt, Caspase2, total S6
PCNA, Cyclin D3, MEK, Erk, pErk, Akt, pAkt, RBBP, total S6
PCNA, Cyclin D3, MEK, Erk, pErk, Akt, Caspase2, RBBP, total S6
PCNA, Cyclin D3, MEK, Erk, pErk, pAkt, Caspase2, RBBP, total S6
PCNA, Cyclin D3, MEK, Erk, Akt, pAkt, Caspase2, RBBP, total S6
PCNA, Cyclin D3, MEK, pErk, Akt, pAkt, Caspase2, RBBP, total S6
PCNA, Cyclin D3, s6, pS6, Erk, pErk, Akt, pAkt, Caspase2
PCNA, Cyclin D3, s6, pS6, Erk, pErk, Akt, pAkt, RBBP
PCNA, Cyclin D3, s6, pS6, Erk, pErk, Akt, pAkt, total S6
PCNA, Cyclin D3, s6, pS6, Erk, pErk, Akt, Caspase2, RBBP
PCNA, Cyclin D3, s6, pS6, Erk, pErk, Akt, Caspase2, total S6
PCNA, Cyclin D3, s6, pS6, Erk, pErk, Akt, RBBP, total S6
PCNA, Cyclin D3, s6, pS6, Erk, pErk, pAkt, Caspase2, RBBP
PCNA, Cyclin D3, s6, pS6, Erk, pErk, pAkt, Caspase2, total S6

PCNA, Cyclin D3, s6, pS6, Erk, pErk, pAkt, RBBP, total S6
PCNA, Cyclin D3, s6, pS6, Erk, pErk, Caspase2, RBBP, total S6
PCNA, Cyclin D3, s6, pS6, Erk, Akt, pAkt, Caspase2, RBBP
PCNA, Cyclin D3, s6, pS6, Erk, Akt, pAkt, Caspase2, total S6
PCNA, Cyclin D3, s6, pS6, Erk, Akt, pAkt, RBBP, total S6

PCNA, pS6, Erk, Akt, pAkt, RBBP
PCNA, pS6, Erk, Akt, pAkt, total S6
PCNA, pS6, Erk, Akt, Caspase2, RBBP
PCNA, pS6, Erk, Akt, Caspase2, total S6
PCNA, pS6, Erk, Akt, RBBP, total S6
PCNA, pS6, Erk, pAkt, Caspase2, RBBP
PCNA, pS6, Erk, pAkt, Caspase2, total S6
PCNA, pS6, Erk, pAkt, RBBP, total S6
PCNA, pS6, Erk, Caspase2, RBBP, total S6

PCNA, pS6, pErk, Akt, pAkt, Caspase2
PCNA, pS6, pErk, Akt, pAkt, RBBP
PCNA, pS6, pErk, Akt, pAkt, total S6
PCNA, pS6, pErk, Akt, Caspase2, RBBP
PCNA, pS6, pErk, Akt, Caspase2, total S6
PCNA, pS6, pErk, Akt, RBBP, total S6
PCNA, pS6, pErk, pAkt, Caspase2, RBBP
PCNA, pS6, pErk, pAkt, Caspase2, total S6
PCNA, pS6, pErk, pAkt, RBBP, total S6
PCNA, pS6, pErk, Caspase2, RBBP, total S6

PCNA, pS6, Akt, pAkt, Caspase2, RBBP
PCNA, pS6, Akt, pAkt, Caspase2, total S6
PCNA, pS6, Akt, pAkt, RBBP, total S6
PCNA, pS6, Akt, Caspase2, RBBP, total S6
PCNA, pS6, pAkt, Caspase2, RBBP, total S6
PCNA, Erk, pErk, Akt, pAkt, Caspase2
PCNA, Erk, pErk, Akt, pAkt, RBBP
PCNA, Erk, pErk, Akt, pAkt, total S6
PCNA, Erk, pErk, Akt, Caspase2, RBBP
PCNA, Erk, pErk, Akt, Caspase2, total S6
PCNA, Erk, pErk, Akt, RBBP, total S6

PCNA, Erk, pErk, pAkt, Caspase2, RBBP
PCNA, Erk, pErk, pAkt, Caspase2, total S6
PCNA, Erk, pErk, pAkt, RBBP, total S6
PCNA, Erk, pErk, Caspase2, RBBP, total S6

PCNA, Erk, Akt, pAkt, Caspase2, RBBP

PCNA, Erk, Akt, pAkt, Caspase2, total S6
PCNA, Erk, Akt, pAkt, RBBP, total S6
PCNA, Erk, Akt, Caspase2, RBBP, total S6
PCNA, Erk, pAkt, Caspase2, RBBP, total S6

PCNA, pErk, Akt, pAkt, Caspase2, RBBP

PCNA, pErk, Akt, pAkt, Caspase2, total S6

PCNA, pErk, Akt, pAkt, RBBP, total S6
PCNA, pErk, Akt, Caspase2, RBBP, total S6

PCNA, pErk, pAkt, Caspase2, RBBP, total S6

PCNA, Akt, pAkt, Caspase2, RBBP, total S6

Cyclin D1, Cyclin D3, MEK, s6, pS6, Erk

Cyclin D1, Cyclin D3, MEK, s6, pS6, pErk

Cyclin D1, Cyclin D3, MEK, s6, pS6, Akt

Cyclin D1, Cyclin D3, MEK, s6, pS6, pAkt
Cyclin D1, Cyclin D3, MEK, s6, pS6, Caspase2
Cyclin D1, Cyclin D3, MEK, s6, pS6, RBBP
Cyclin D1, Cyclin D3, MEK, s6, pS6, total S6
Cyclin D1, Cyclin D3, MEK, s6, Erk, pErk
Cyclin D1, Cyclin D3, MEK, s6, Erk, Akt
Cyclin D1, Cyclin D3, MEK, s6, Erk, pAkt
Cyclin D1, Cyclin D3, MEK, s6, Erk, Caspase2
Cyclin D1, Cyclin D3, MEK, s6, Erk, RBBP
Cyclin D1, Cyclin D3, MEK, s6, Erk, total S6
Cyclin D1, Cyclin D3, MEK, s6, pErk, Akt
Cyclin D1, Cyclin D3, MEK, s6, pErk, pAkt
Cyclin D1, Cyclin D3, MEK, s6, pErk, Caspase2

TABLE 1-continued

Examples of Single Markers and Combinations of Markers

PCNA, Cyclin D3, s6, pS6, Erk, Akt, Caspase2, RBBP, total S6
PCNA, Cyclin D3, s6, pS6, Erk, pAkt, Caspase2, RBBP, total S6
PCNA, Cyclin D3, s6, pS6, pErk, Akt, pAkt, Caspase2, RBBP
PCNA, Cyclin D3, s6, pS6, pErk, Akt, pAkt, Caspase2, total S6
PCNA, Cyclin D3, s6, pS6, pErk, Akt, pAkt, RBBP, total S6
PCNA, Cyclin D3, s6, pS6, pErk, Akt, Caspase2, RBBP, total S6
PCNA, Cyclin D3, s6, pS6, pErk, pAkt, Caspase2, RBBP, total S6
PCNA, Cyclin D3, s6, pS6, Akt, pAkt, Caspase2, RBBP, total S6
PCNA, Cyclin D3, s6, Erk, pErk, Akt, pAkt, Caspase2, RBBP
PCNA, Cyclin D3, s6, Erk, pErk, Akt, pAkt, Caspase2, total S6
PCNA, Cyclin D3, s6, Erk, pErk, Akt, pAkt, RBBP, total S6
PCNA, Cyclin D3, s6, Erk, pErk, Akt, Caspase2, RBBP, total S6
PCNA, Cyclin D3, s6, Erk, pErk, pAkt, Caspase2, RBBP, total S6
PCNA, Cyclin D3, s6, Erk, Akt, pAkt, Caspase2, RBBP, total S6
PCNA, Cyclin D3, s6, pErk, Akt, pAkt, Caspase2, RBBP, total S6
PCNA, Cyclin D3, pS6, Erk, pErk, Akt, pAkt, Caspase2, RBBP
PCNA, Cyclin D3, pS6, Erk, pErk, Akt, pAkt, Caspase2, total S6
PCNA, Cyclin D3, pS6, Erk, pErk, Akt, pAkt, RBBP, total S6
PCNA, Cyclin D3, pS6, Erk, pErk, Akt, Caspase2, RBBP, total S6
PCNA, Cyclin D3, pS6, Erk, pErk, pAkt, Caspase2, RBBP, total S6
PCNA, Cyclin D3, pS6, Erk, Akt, pAkt, Caspase2, RBBP, total S6
PCNA, Cyclin D3, pS6, pErk, Akt, pAkt, Caspase2, RBBP, total S6
PCNA, Cyclin D3, Erk, pErk, Akt, pAkt, Caspase2, RBBP, total S6
PCNA, MEK, s6, pS6, Erk, pErk, Akt, pAkt, Caspase2
PCNA, MEK, s6, pS6, Erk, pErk, Akt, pAkt, RBBP
PCNA, MEK, s6, pS6, Erk, pErk, Akt, pAkt, total S6
PCNA, MEK, s6, pS6, Erk, pErk, Akt, Caspase2, RBBP
PCNA, MEK, s6, pS6, Erk, pErk, Akt, Caspase2, total S6
PCNA, MEK, s6, pS6, Erk, pErk, Akt, RBBP, total S6
PCNA, MEK, s6, pS6, Erk, pErk, pAkt, Caspase2, RBBP
PCNA, MEK, s6, pS6, Erk, pErk, pAkt, Caspase2, total S6
PCNA, MEK, s6, pS6, Erk, pErk, pAkt, RBBP, total S6
PCNA, MEK, s6, pS6, Erk, pErk, Caspase2, RBBP, total S6
PCNA, MEK, s6, pS6, Erk, Akt, pAkt, Caspase2, RBBP
PCNA, MEK, s6, pS6, Erk, Akt, pAkt, Caspase2, total S6
PCNA, MEK, s6, pS6, Erk, Akt, pAkt, RBBP, total S6
PCNA, MEK, s6, pS6, Erk, Akt, Caspase2, RBBP, total S6
PCNA, MEK, s6, pS6, Erk, pAkt, Caspase2, RBBP, total S6
PCNA, MEK, s6, pS6, pErk, Akt, pAkt, Caspase2, RBBP
PCNA, MEK, s6, pS6, pErk, Akt, pAkt, Caspase2, total S6
PCNA, MEK, s6, pS6, pErk, Akt, pAkt, RBBP, total S6
PCNA, MEK, s6, pS6, pErk, Akt, Caspase2, RBBP, total S6
PCNA, MEK, s6, pS6, pErk, pAkt, Caspase2, RBBP, total S6
PCNA, MEK, s6, pS6, Akt, pAkt, Caspase2, RBBP, total S6
PCNA, MEK, s6, Erk, pErk, Akt, pAkt, Caspase2, RBBP
PCNA, MEK, s6, Erk, pErk, Akt, pAkt, Caspase2, total S6
PCNA, MEK, s6, Erk, pErk, Akt, pAkt, RBBP, total S6
PCNA, MEK, s6, Erk, pErk, Akt, Caspase2, RBBP, total S6
PCNA, MEK, s6, Erk, pErk, pAkt, Caspase2, RBBP, total S6
PCNA, MEK, s6, Erk, Akt, pAkt, Caspase2, RBBP, total S6
Cyclin D1, Cyclin D3, MEK, s6, pErk, RBBP
Cyclin D1, Cyclin D3, MEK, s6, pErk, total S6
Cyclin D1, Cyclin D3, MEK, s6, Akt, pAkt
Cyclin D1, Cyclin D3, MEK, s6, Akt, Caspase2
Cyclin D1, Cyclin D3, MEK, s6, Akt, RBBP
Cyclin D1, Cyclin D3, MEK, s6, Akt, total S6
Cyclin D1, Cyclin D3, MEK, s6, pAkt, Caspase2
Cyclin D1, Cyclin D3, MEK, s6, pAkt, RBBP
Cyclin D1, Cyclin D3, MEK, s6, pAkt, total S6
Cyclin D1, Cyclin D3, MEK, s6, Caspase2, RBBP
Cyclin D1, Cyclin D3, MEK, s6, Caspase2, total S6
Cyclin D1, Cyclin D3, MEK, s6, RBBP, total S6
Cyclin D1, Cyclin D3, MEK, pS6, Erk, pErk
Cyclin D1, Cyclin D3, MEK, pS6, Erk, Akt
Cyclin D1, Cyclin D3, MEK, pS6, Erk, pAkt
Cyclin D1, Cyclin D3, MEK, pS6, Erk, Caspase2
Cyclin D1, Cyclin D3, MEK, pS6, Erk, RBBP
Cyclin D1, Cyclin D3, MEK, pS6, Erk, total S6
Cyclin D1, Cyclin D3, MEK, pS6, pErk, Akt
Cyclin D1, Cyclin D3, MEK, pS6, pErk, pAkt
Cyclin D1, Cyclin D3, MEK, pS6, pErk, Caspase2
Cyclin D1, Cyclin D3, MEK, pS6, pErk, RBBP
Cyclin D1, Cyclin D3, MEK, pS6, pErk, total S6
Cyclin D1, Cyclin D3, MEK, pS6, Akt, pAkt
Cyclin D1, Cyclin D3, MEK, pS6, Akt, Caspase2
Cyclin D1, Cyclin D3, MEK, pS6, Akt, RBBP
Cyclin D1, Cyclin D3, MEK, pS6, Akt, total S6
Cyclin D1, Cyclin D3, MEK, pS6, pAkt, Caspase2
Cyclin D1, Cyclin D3, MEK, pS6, pAkt, RBBP
Cyclin D1, Cyclin D3, MEK, pS6, pAkt, total S6
Cyclin D1, Cyclin D3, MEK, pS6, Caspase2, RBBP
Cyclin D1, Cyclin D3, MEK, pS6, Caspase2, total S6
Cyclin D1, Cyclin D3, MEK, pS6, RBBP, total S6
Cyclin D1, Cyclin D3, MEK, Erk, pErk, Akt
Cyclin D1, Cyclin D3, MEK, Erk, pErk, pAkt
Cyclin D1, Cyclin D3, MEK, Erk, pErk, Caspase2
Cyclin D1, Cyclin D3, MEK, Erk, pErk, RBBP
Cyclin D1, Cyclin D3, MEK, Erk, pErk, total S6
Cyclin D1, Cyclin D3, MEK, Erk, Akt, pAkt
Cyclin D1, Cyclin D3, MEK, Erk, Akt, Caspase2
Cyclin D1, Cyclin D3, MEK, Erk, Akt, RBBP
Cyclin D1, Cyclin D3, MEK, Erk, Akt, total S6
Cyclin D1, Cyclin D3, MEK, Erk, pAkt, Caspase2
Cyclin D1, Cyclin D3, MEK, Erk, pAkt, RBBP
Cyclin D1, Cyclin D3, MEK, Erk, pAkt, total S6
Cyclin D1, Cyclin D3, MEK, Erk, Caspase2, RBBP
Cyclin D1, Cyclin D3, MEK, Erk, Caspase2, total S6
Cyclin D1, Cyclin D3, MEK, Erk, RBBP, total S6
Cyclin D1, Cyclin D3, MEK, pErk, Akt, pAkt
Cyclin D1, Cyclin D3, MEK, pErk, Akt, Caspase2

TABLE 1-continued

| Examples of Single Markers and Combinations of Markers | |
|---|---|
| PCNA, MEK, s6, pErk, Akt, pAkt, Caspase2, RBBP, total S6 | Cyclin D1, Cyclin D3, MEK, pErk, Akt, RBBP |
| PCNA, MEK, pS6, Erk, pErk, Akt, pAkt, Caspase2, RBBP | Cyclin D1, Cyclin D3, MEK, pErk, Akt, total S6 |
| PCNA, MEK, pS6, Erk, pErk, Akt, pAkt, Caspase2, total S6 | Cyclin D1, Cyclin D3, MEK, pErk, pAkt, Caspase2 |
| PCNA, MEK, pS6, Erk, pErk, Akt, pAkt, RBBP, total S6 | Cyclin D1, Cyclin D3, MEK, pErk, pAkt, RBBP |
| PCNA, MEK, pS6, Erk, pErk, Akt, Caspase2, RBBP, total S6 | Cyclin D1, Cyclin D3, MEK, pErk, pAkt, total S6 |
| PCNA, MEK, pS6, Erk, pErk, pAkt, Caspase2, RBBP, total S6 | Cyclin D1, Cyclin D3, MEK, pErk, Caspase2, RBBP |
| PCNA, MEK, pS6, Erk, Akt, pAkt, Caspase2, RBBP, total S6 | Cyclin D1, Cyclin D3, MEK, pErk, Caspase2, total S6 |
| PCNA, MEK, pS6, pErk, Akt, pAkt, Caspase2, RBBP, total S6 | Cyclin D1, Cyclin D3, MEK, pErk, RBBP, total S6 |
| PCNA, MEK, Erk, pErk, Akt, pAkt, Caspase2, RBBP, total S6 | Cyclin D1, Cyclin D3, MEK, Akt, pAkt, Caspase2 |
| PCNA, s6, pS6, Erk, pErk, Akt, pAkt, Caspase2, RBBP | Cyclin D1, Cyclin D3, MEK, Akt, pAkt, RBBP |
| PCNA, s6, pS6, Erk, pErk, Akt, pAkt, Caspase2, total S6 | Cyclin D1, Cyclin D3, MEK, Akt, pAkt, total S6 |
| PCNA, s6, pS6, Erk, pErk, Akt, pAkt, RBBP, total S6 | Cyclin D1, Cyclin D3, MEK, Akt, Caspase2, RBBP |
| PCNA, s6, pS6, Erk, pErk, Akt, Caspase2, RBBP, total S6 | Cyclin D1, Cyclin D3, MEK, Akt, Caspase2, total S6 |
| PCNA, s6, pS6, Erk, pErk, pAkt, Caspase2, RBBP, total S6 | Cyclin D1, Cyclin D3, MEK, Akt, RBBP, total S6 |
| PCNA, s6, pS6, Erk, Akt, pAkt, Caspase2, RBBP, total S6 | Cyclin D1, Cyclin D3, MEK, pAkt, Caspase2, RBBP |
| PCNA, s6, pS6, pErk, Akt, pAkt, Caspase2, RBBP, total S6 | Cyclin D1, Cyclin D3, MEK, pAkt, Caspase2, total S6 |
| PCNA, s6, Erk, pErk, Akt, pAkt, Caspase2, RBBP, total S6 | Cyclin D1, Cyclin D3, MEK, pAkt, RBBP, total S6 |
| PCNA, pS6, Erk, pErk, Akt, pAkt, Caspase2, RBBP, total S6 | Cyclin D1, Cyclin D3, MEK, Caspase2, RBBP, total S6 |
| Cyclin D1, Cyclin D3, MEK, s6, pS6, Erk, pErk, Akt, pAkt | Cyclin D1, Cyclin D3, s6, pS6, Erk, pErk |
| Cyclin D1, Cyclin D3, MEK, s6, pS6, Erk, pErk, Akt, Caspase2 | Cyclin D1, Cyclin D3, s6, pS6, Erk, Akt |
| Cyclin D1, Cyclin D3, MEK, s6, pS6, Erk, pErk, Akt, RBBP | Cyclin D1, Cyclin D3, s6, pS6, Erk, pAkt |
| Cyclin D1, Cyclin D3, MEK, s6, pS6, Erk, pErk, Akt, total S6 | Cyclin D1, Cyclin D3, s6, pS6, Erk, Caspase2 |
| Cyclin D1, Cyclin D3, MEK, s6, pS6, Erk, pErk, pAkt, Caspase2 | Cyclin D1, Cyclin D3, s6, pS6, Erk, RBBP |
| Cyclin D1, Cyclin D3, MEK, s6, pS6, Erk, pErk, pAkt, RBBP | Cyclin D1, Cyclin D3, s6, pS6, Erk, total S6 |
| Cyclin D1, Cyclin D3, MEK, s6, pS6, Erk, pErk, pAkt, total S6 | Cyclin D1, Cyclin D3, s6, pS6, pErk, Akt |
| Cyclin D1, Cyclin D3, MEK, s6, pS6, Erk, pErk, Caspase2, RBBP | Cyclin D1, Cyclin D3, s6, pS6, pErk, pAkt |
| Cyclin D1, Cyclin D3, MEK, s6, pS6, Erk, pErk, Caspase2, total S6 | Cyclin D1, Cyclin D3, s6, pS6, pErk, Caspase2 |
| Cyclin D1, Cyclin D3, MEK, s6, pS6, Erk, pErk, RBBP, total S6 | Cyclin D1, Cyclin D3, s6, pS6, pErk, RBBP |
| Cyclin D1, Cyclin D3, MEK, s6, pS6, Erk, Akt, pAkt, Caspase2 | Cyclin D1, Cyclin D3, s6, pS6, pErk, total S6 |
| Cyclin D1, Cyclin D3, MEK, s6, pS6, Erk, Akt, pAkt, RBBP | Cyclin D1, Cyclin D3, s6, pS6, Akt, pAkt |
| Cyclin D1, Cyclin D3, MEK, s6, pS6, Erk, Akt, pAkt, total S6 | Cyclin D1, Cyclin D3, s6, pS6, Akt, Caspase2 |
| Cyclin D1, Cyclin D3, MEK, s6, pS6, Erk, Akt, Caspase2, RBBP | Cyclin D1, Cyclin D3, s6, pS6, Akt, RBBP |
| Cyclin D1, Cyclin D3, MEK, s6, pS6, Erk, Akt, Caspase2, total S6 | Cyclin D1, Cyclin D3, s6, pS6, Akt, total S6 |
| Cyclin D1, Cyclin D3, MEK, s6, pS6, Erk, Akt, RBBP, total S6 | Cyclin D1, Cyclin D3, s6, pS6, pAkt, Caspase2 |
| Cyclin D1, Cyclin D3, MEK, s6, pS6, Erk, pAkt, Caspase2, RBBP | Cyclin D1, Cyclin D3, s6, pS6, pAkt, RBBP |
| Cyclin D1, Cyclin D3, MEK, s6, pS6, Erk, pAkt, Caspase2, total S6 | Cyclin D1, Cyclin D3, s6, pS6, pAkt, total S6 |
| Cyclin D1, Cyclin D3, MEK, s6, pS6, Erk, pAkt, RBBP, total S6 | Cyclin D1, Cyclin D3, s6, pS6, Caspase2, RBBP |
| Cyclin D1, Cyclin D3, MEK, s6, pS6, Erk, Caspase2, RBBP, total S6 | Cyclin D1, Cyclin D3, s6, pS6, Caspase2, total S6 |
| Cyclin D1, Cyclin D3, MEK, s6, pS6, pErk, Akt, pAkt, Caspase2 | Cyclin D1, Cyclin D3, s6, pS6, RBBP, total S6 |
| Cyclin D1, Cyclin D3, MEK, s6, pS6, pErk, Akt, pAkt, RBBP | Cyclin D1, Cyclin D3, s6, Erk, pErk, Akt |
| Cyclin D1, Cyclin D3, MEK, s6, pS6, pErk, Akt, pAkt, total S6 | Cyclin D1, Cyclin D3, s6, Erk, pErk, pAkt |
| Cyclin D1, Cyclin D3, MEK, s6, pS6, pErk, Akt, Caspase2, RBBP | Cyclin D1, Cyclin D3, s6, Erk, pErk, Caspase2 |
| Cyclin D1, Cyclin D3, MEK, s6, pS6, pErk, Akt, Caspase2, total S6 | Cyclin D1, Cyclin D3, s6, Erk, pErk, RBBP |
| Cyclin D1, Cyclin D3, MEK, s6, pS6, pErk, Akt, RBBP, total S6 | Cyclin D1, Cyclin D3, s6, Erk, pErk, total S6 |
| Cyclin D1, Cyclin D3, MEK, s6, pS6, pErk, pAkt, Caspase2, RBBP | Cyclin D1, Cyclin D3, s6, Erk, Akt, pAkt |
| Cyclin D1, Cyclin D3, MEK, s6, pS6, pErk, pAkt, Caspase2, total S6 | Cyclin D1, Cyclin D3, s6, Erk, Akt, Caspase2 |
| Cyclin D1, Cyclin D3, MEK, s6, pS6, pErk, pAkt, RBBP, total S6 | Cyclin D1, Cyclin D3, s6, Erk, Akt, RBBP |
| Cyclin D1, Cyclin D3, MEK, s6, pS6, pErk, Caspase2, RBBP, total S6 | Cyclin D1, Cyclin D3, s6, Erk, Akt, total S6 |

TABLE 1-continued

Examples of Single Markers and Combinations of Markers

Cyclin D1, Cyclin D3, MEK, s6, pS6, Akt, pAkt, Caspase2, RBBP
Cyclin D1, Cyclin D3, MEK, s6, pS6, Akt, pAkt, Caspase2, total S6
Cyclin D1, Cyclin D3, MEK, s6, pS6, Akt, pAkt, RBBP, total S6
Cyclin D1, Cyclin D3, MEK, s6, pS6, Akt, Caspase2, RBBP, total S6
Cyclin D1, Cyclin D3, MEK, s6, pS6, pAkt, Caspase2, RBBP, total S6
Cyclin D1, Cyclin D3, MEK, s6, Erk, pErk, Akt, pAkt, Caspase2
Cyclin D1, Cyclin D3, MEK, s6, Erk, pErk, Akt, pAkt, RBBP
Cyclin D1, Cyclin D3, MEK, s6, Erk, pErk, Akt, pAkt, total S6
Cyclin D1, Cyclin D3, MEK, s6, Erk, pErk, Akt, Caspase2, RBBP
Cyclin D1, Cyclin D3, MEK, s6, Erk, pErk, Akt, Caspase2, total S6
Cyclin D1, Cyclin D3, MEK, s6, Erk, pErk, Akt, RBBP, total S6
Cyclin D1, Cyclin D3, MEK, s6, Erk, pErk, pAkt, Caspase2, RBBP
Cyclin D1, Cyclin D3, MEK, s6, Erk, pErk, pAkt, Caspase2, total S6
Cyclin D1, Cyclin D3, MEK, s6, Erk, pErk, pAkt, RBBP, total S6
Cyclin D1, Cyclin D3, MEK, s6, Erk, pErk, Caspase2, RBBP, total S6
Cyclin D1, Cyclin D3, MEK, s6, Erk, Akt, pAkt, Caspase2, RBBP
Cyclin D1, Cyclin D3, MEK, s6, Erk, Akt, pAkt, Caspase2, total S6
Cyclin D1, Cyclin D3, MEK, s6, Erk, Akt, pAkt, RBBP, total S6
Cyclin D1, Cyclin D3, MEK, s6, Erk, Akt, Caspase2, RBBP, total S6
Cyclin D1, Cyclin D3, MEK, s6, Erk, pAkt, Caspase2, RBBP, total S6
Cyclin D1, Cyclin D3, MEK, s6, pErk, Akt, pAkt, Caspase2, RBBP
Cyclin D1, Cyclin D3, MEK, s6, pErk, Akt, pAkt, Caspase2, total S6
Cyclin D1, Cyclin D3, MEK, s6, pErk, Akt, pAkt, RBBP, total S6
Cyclin D1, Cyclin D3, MEK, s6, pErk, Akt, Caspase2, RBBP, total S6
Cyclin D1, Cyclin D3, MEK, s6, pErk, pAkt, Caspase2, RBBP, total S6
Cyclin D1, Cyclin D3, MEK, s6, Akt, pAkt, Caspase2, RBBP, total S6
Cyclin D1, Cyclin D3, MEK, pS6, Erk, pErk, Akt, pAkt, Caspase2
Cyclin D1, Cyclin D3, MEK, pS6, Erk, pErk, Akt, pAkt, RBBP
Cyclin D1, Cyclin D3, MEK, pS6, Erk, pErk, Akt, pAkt, total S6
Cyclin D1, Cyclin D3, MEK, pS6, Erk, pErk, Akt, Caspase2, RBBP
Cyclin D1, Cyclin D3, MEK, pS6, Erk, pErk, Akt, Caspase2, total S6
Cyclin D1, Cyclin D3, MEK, pS6, Erk, pErk, Akt, RBBP, total S6
Cyclin D1, Cyclin D3, MEK, pS6, Erk, pErk, pAkt, Caspase2, RBBP
Cyclin D1, Cyclin D3, MEK, pS6, Erk, pErk, pAkt, Caspase2, total S6
Cyclin D1, Cyclin D3, MEK, pS6, Erk, pErk, pAkt, RBBP, total S6
Cyclin D1, Cyclin D3, MEK, pS6, Erk, pErk, Caspase2, RBBP, total S6
Cyclin D1, Cyclin D3, MEK, pS6, Erk, Akt, pAkt, Caspase2, RBBP
Cyclin D1, Cyclin D3, MEK, pS6, Erk, Akt, pAkt, Caspase2, total S6
Cyclin D1, Cyclin D3, MEK, pS6, Erk, Akt, pAkt, RBBP, total S6
Cyclin D1, Cyclin D3, s6, Erk, pAkt, Caspase2
Cyclin D1, Cyclin D3, s6, Erk, pAkt, RBBP
Cyclin D1, Cyclin D3, s6, Erk, pAkt, total S6
Cyclin D1, Cyclin D3, s6, Erk, Caspase2, RBBP
Cyclin D1, Cyclin D3, s6, Erk, Caspase2, total S6
Cyclin D1, Cyclin D3, s6, Erk, RBBP, total S6
Cyclin D1, Cyclin D3, s6, pErk, Akt, pAkt
Cyclin D1, Cyclin D3, s6, pErk, Akt, Caspase2
Cyclin D1, Cyclin D3, s6, pErk, Akt, RBBP
Cyclin D1, Cyclin D3, s6, pErk, Akt, total S6
Cyclin D1, Cyclin D3, s6, pErk, pAkt, Caspase2
Cyclin D1, Cyclin D3, s6, pErk, pAkt, RBBP
Cyclin D1, Cyclin D3, s6, pErk, pAkt, total S6
Cyclin D1, Cyclin D3, s6, pErk, Caspase2, RBBP
Cyclin D1, Cyclin D3, s6, pErk, Caspase2, total S6
Cyclin D1, Cyclin D3, s6, pErk, RBBP, total S6
Cyclin D1, Cyclin D3, s6, Akt, pAkt, Caspase2
Cyclin D1, Cyclin D3, s6, Akt, pAkt, RBBP
Cyclin D1, Cyclin D3, s6, Akt, pAkt, total S6
Cyclin D1, Cyclin D3, s6, Akt, Caspase2, RBBP
Cyclin D1, Cyclin D3, s6, Akt, Caspase2, total S6
Cyclin D1, Cyclin D3, s6, Akt, RBBP, total S6
Cyclin D1, Cyclin D3, s6, pAkt, Caspase2, RBBP
Cyclin D1, Cyclin D3, s6, pAkt, Caspase2, total S6
Cyclin D1, Cyclin D3, s6, pAkt, RBBP, total S6
Cyclin D1, Cyclin D3, s6, Caspase2, RBBP, total S6
Cyclin D1, Cyclin D3, pS6, Erk, pErk, Akt
Cyclin D1, Cyclin D3, pS6, Erk, pErk, pAkt
Cyclin D1, Cyclin D3, pS6, Erk, pErk, Caspase2
Cyclin D1, Cyclin D3, pS6, Erk, pErk, RBBP
Cyclin D1, Cyclin D3, pS6, Erk, pErk, total S6
Cyclin D1, Cyclin D3, pS6, Erk, Akt, pAkt
Cyclin D1, Cyclin D3, pS6, Erk, Akt, Caspase2
Cyclin D1, Cyclin D3, pS6, Erk, Akt, RBBP
Cyclin D1, Cyclin D3, pS6, Erk, Akt, total S6
Cyclin D1, Cyclin D3, pS6, Erk, pAkt, Caspase2
Cyclin D1, Cyclin D3, pS6, Erk, pAkt, RBBP
Cyclin D1, Cyclin D3, pS6, Erk, pAkt, total S6
Cyclin D1, Cyclin D3, pS6, Erk, Caspase2, RBBP TABLE 1-continued Examples of Single Markers and Combinations of Markers

| | |
|---|---|
| Cyclin D1, Cyclin D3, MEK, pS6, Erk, Akt, Caspase2, RBBP, total S6 | Cyclin D1, Cyclin D3, pS6, Erk, Caspase2, total S6 |
| Cyclin D1, Cyclin D3, MEK, pS6, Erk, pAkt, Caspase2, RBBP, total S6 | Cyclin D1, Cyclin D3, pS6, Erk, RBBP, total S6 |
| Cyclin D1, Cyclin D3, MEK, pS6, pErk, Akt, pAkt, Caspase2, RBBP | Cyclin D1, Cyclin D3, pS6, pErk, Akt, pAkt |
| Cyclin D1, Cyclin D3, MEK, pS6, pErk, Akt, pAkt, Caspase2, total S6 | Cyclin D1, Cyclin D3, pS6, pErk, Akt, Caspase2 |
| Cyclin D1, Cyclin D3, MEK, pS6, pErk, Akt, pAkt, RBBP, total S6 | Cyclin D1, Cyclin D3, pS6, pErk, Akt, RBBP |
| Cyclin D1, Cyclin D3, MEK, pS6, pErk, Akt, Caspase2, RBBP, total S6 | Cyclin D1, Cyclin D3, pS6, pErk, Akt, total S6 |
| Cyclin D1, Cyclin D3, MEK, pS6, pErk, pAkt, Caspase2, RBBP, total S6 | Cyclin D1, Cyclin D3, pS6, pErk, pAkt, Caspase2 |
| Cyclin D1, Cyclin D3, MEK, pS6, Akt, pAkt, Caspase2, RBBP, total S6 | Cyclin D1, Cyclin D3, pS6, pErk, pAkt, RBBP |
| Cyclin D1, Cyclin D3, MEK, Erk, pErk, Akt, pAkt, Caspase2, RBBP | Cyclin D1, Cyclin D3, pS6, pErk, pAkt, total S6 |
| Cyclin D1, Cyclin D3, MEK, Erk, pErk, Akt, pAkt, Caspase2, total S6 | Cyclin D1, Cyclin D3, pS6, pErk, Caspase2, RBBP |
| Cyclin D1, Cyclin D3, MEK, Erk, pErk, Akt, pAkt, RBBP, total S6 | Cyclin D1, Cyclin D3, pS6, pErk, Caspase2, total S6 |
| Cyclin D1, Cyclin D3, MEK, Erk, pErk, Akt, Caspase2, RBBP, total S6 | Cyclin D1, Cyclin D3, pS6, pErk, RBBP, total S6 |
| Cyclin D1, Cyclin D3, MEK, Erk, pErk, pAkt, Caspase2, RBBP, total S6 | Cyclin D1, Cyclin D3, pS6, Akt, pAkt, Caspase2 |
| Cyclin D1, Cyclin D3, MEK, Erk, Akt, pAkt, Caspase2, RBBP, total S6 | Cyclin D1, Cyclin D3, pS6, Akt, pAkt, RBBP |
| Cyclin D1, Cyclin D3, MEK, pErk, Akt, pAkt, Caspase2, RBBP, total S6 | Cyclin D1, Cyclin D3, pS6, Akt, pAkt, total S6 |
| Cyclin D1, Cyclin D3, s6, pS6, Erk, pErk, Akt, pAkt, Caspase2 | Cyclin D1, Cyclin D3, pS6, Akt, Caspase2, RBBP |
| Cyclin D1, Cyclin D3, s6, pS6, Erk, pErk, Akt, pAkt, RBBP | Cyclin D1, Cyclin D3, pS6, Akt, Caspase2, total S6 |
| Cyclin D1, Cyclin D3, s6, pS6, Erk, pErk, Akt, pAkt, total S6 | Cyclin D1, Cyclin D3, pS6, Akt, RBBP, total S6 |
| Cyclin D1, Cyclin D3, s6, pS6, Erk, pErk, Akt, Caspase2, RBBP | Cyclin D1, Cyclin D3, pS6, pAkt, Caspase2, RBBP |
| Cyclin D1, Cyclin D3, s6, pS6, Erk, pErk, Akt, Caspase2, total S6 | Cyclin D1, Cyclin D3, pS6, pAkt, Caspase2, total S6 |
| Cyclin D1, Cyclin D3, s6, pS6, Erk, pErk, Akt, RBBP, total S6 | Cyclin D1, Cyclin D3, pS6, pAkt, RBBP, total S6 |
| Cyclin D1, Cyclin D3, s6, pS6, Erk, pErk, pAkt, Caspase2, RBBP | Cyclin D1, Cyclin D3, pS6, Caspase2, RBBP, total S6 |
| Cyclin D1, Cyclin D3, s6, pS6, Erk, pErk, pAkt, Caspase2, total S6 | Cyclin D1, Cyclin D3, Erk, pErk, Akt, pAkt |
| Cyclin D1, Cyclin D3, s6, pS6, Erk, pErk, pAkt, RBBP, total S6 | Cyclin D1, Cyclin D3, Erk, pErk, Akt, Caspase2 |
| Cyclin D1, Cyclin D3, s6, pS6, Erk, pErk, Caspase2, RBBP, total S6 | Cyclin D1, Cyclin D3, Erk, pErk, Akt, RBBP |
| Cyclin D1, Cyclin D3, s6, pS6, Erk, Akt, pAkt, Caspase2, RBBP | Cyclin D1, Cyclin D3, Erk, pErk, Akt, total S6 |
| Cyclin D1, Cyclin D3, s6, pS6, Erk, Akt, pAkt, Caspase2, total S6 | Cyclin D1, Cyclin D3, Erk, pErk, pAkt, Caspase2 |
| Cyclin D1, Cyclin D3, s6, pS6, Erk, Akt, pAkt, RBBP, total S6 | Cyclin D1, Cyclin D3, Erk, pErk, pAkt, RBBP |
| Cyclin D1, Cyclin D3, s6, pS6, Erk, Akt, Caspase2, RBBP, total S6 | Cyclin D1, Cyclin D3, Erk, pErk, pAkt, total S6 |
| Cyclin D1, Cyclin D3, s6, pS6, Erk, pAkt, Caspase2, RBBP, total S6 | Cyclin D1, Cyclin D3, Erk, pErk, Caspase2, RBBP |
| Cyclin D1, Cyclin D3, s6, pS6, pErk, Akt, pAkt, Caspase2, RBBP | Cyclin D1, Cyclin D3, Erk, pErk, Caspase2, total S6 |
| Cyclin D1, Cyclin D3, s6, pS6, pErk, Akt, pAkt, Caspase2, total S6 | Cyclin D1, Cyclin D3, Erk, pErk, RBBP, total S6 |
| Cyclin D1, Cyclin D3, s6, pS6, pErk, Akt, pAkt, RBBP, total S6 | Cyclin D1, Cyclin D3, Erk, Akt, pAkt, Caspase2 |
| Cyclin D1, Cyclin D3, s6, pS6, pErk, Akt, Caspase2, RBBP, total S6 | Cyclin D1, Cyclin D3, Erk, Akt, pAkt, RBBP |
| Cyclin D1, Cyclin D3, s6, pS6, pErk, pAkt, Caspase2, RBBP, total S6 | Cyclin D1, Cyclin D3, Erk, Akt, pAkt, total S6 |
| Cyclin D1, Cyclin D3, s6, pS6, Akt, pAkt, Caspase2, RBBP, total S6 | Cyclin D1, Cyclin D3, Erk, Akt, Caspase2, RBBP |
| Cyclin D1, Cyclin D3, s6, Erk, pErk, Akt, pAkt, Caspase2, RBBP | Cyclin D1, Cyclin D3, Erk, Akt, Caspase2, total S6 |
| Cyclin D1, Cyclin D3, s6, Erk, pErk, Akt, pAkt, Caspase2, total S6 | Cyclin D1, Cyclin D3, Erk, Akt, RBBP, total S6 |
| Cyclin D1, Cyclin D3, s6, Erk, pErk, Akt, pAkt, RBBP, total S6 | Cyclin D1, Cyclin D3, Erk, pAkt, Caspase2, RBBP |

TABLE 1-continued

Examples of Single Markers and Combinations of Markers

Cyclin D1, Cyclin D3, s6, Erk, pErk, Akt, Caspase2, RBBP, total S6
Cyclin D1, Cyclin D3, s6, Erk, pErk, pAkt, Caspase2, RBBP, total S6
Cyclin D1, Cyclin D3, s6, Erk, Akt, pAkt, Caspase2, RBBP, total S6
Cyclin D1, Cyclin D3, s6, pErk, Akt, pAkt, Caspase2, RBBP, total S6
Cyclin D1, Cyclin D3, pS6, Erk, pErk, Akt, pAkt, Caspase2, RBBP
Cyclin D1, Cyclin D3, pS6, Erk, pErk, Akt, pAkt, Caspase2, total S6
Cyclin D1, Cyclin D3, pS6, Erk, pErk, Akt, pAkt, RBBP, total S6
Cyclin D1, Cyclin D3, pS6, Erk, pErk, Akt, Caspase2, RBBP, total S6
Cyclin D1, Cyclin D3, pS6, Erk, pErk, pAkt, Caspase2, RBBP, total S6
Cyclin D1, Cyclin D3, pS6, Erk, Akt, pAkt, Caspase2, RBBP, total S6
Cyclin D1, Cyclin D3, pS6, pErk, Akt, pAkt, Caspase2, RBBP, total S6
Cyclin D1, Cyclin D3, Erk, pErk, Akt, pAkt, Caspase2, RBBP, total S6
Cyclin D1, MEK, s6, pS6, Erk, pErk, Akt, pAkt, Caspase2
Cyclin D1, MEK, s6, pS6, Erk, pErk, Akt, pAkt, RBBP
Cyclin D1, MEK, s6, pS6, Erk, pErk, Akt, pAkt, total S6
Cyclin D1, MEK, s6, pS6, Erk, pErk, Akt, Caspase2, RBBP
Cyclin D1, MEK, s6, pS6, Erk, pErk, Akt, Caspase2, total S6
Cyclin D1, MEK, s6, pS6, Erk, pErk, Akt, RBBP, total S6
Cyclin D1, MEK, s6, pS6, Erk, pErk, pAkt, Caspase2, RBBP
Cyclin D1, MEK, s6, pS6, Erk, pErk, pAkt, Caspase2, total S6
Cyclin D1, MEK, s6, pS6, Erk, pErk, pAkt, RBBP, total S6
Cyclin D1, MEK, s6, pS6, Erk, pErk, Caspase2, RBBP, total S6
Cyclin D1, MEK, s6, pS6, Erk, Akt, pAkt, Caspase2, RBBP
Cyclin D1, MEK, s6, pS6, Erk, Akt, pAkt, Caspase2, total S6
Cyclin D1, MEK, s6, pS6, Erk, Akt, pAkt, RBBP, total S6
Cyclin D1, MEK, s6, pS6, Erk, Akt, Caspase2, RBBP, total S6
Cyclin D1, MEK, s6, pS6, Erk, pAkt, Caspase2, RBBP, total S6
Cyclin D1, MEK, s6, pS6, pErk, Akt, pAkt, Caspase2, RBBP
Cyclin D1, MEK, s6, pS6, pErk, Akt, pAkt, Caspase2, total S6
Cyclin D1, MEK, s6, pS6, pErk, Akt, pAkt, RBBP, total S6
Cyclin D1, MEK, s6, pS6, pErk, Akt, Caspase2, RBBP, total S6
Cyclin D1, MEK, s6, pS6, pErk, pAkt, Caspase2, RBBP, total S6
Cyclin D1, MEK, s6, pS6, Akt, pAkt, Caspase2, RBBP, total S6
Cyclin D1, MEK, s6, Erk, pErk, Akt, pAkt, Caspase2, RBBP
Cyclin D1, MEK, s6, Erk, pErk, Akt, pAkt, Caspase2, total S6
Cyclin D1, MEK, s6, Erk, pErk, Akt, pAkt, RBBP, total S6
Cyclin D1, MEK, s6, Erk, pErk, Akt, Caspase2, RBBP, total S6
Cyclin D1, MEK, s6, Erk, pErk, pAkt, Caspase2, RBBP, total S6
Cyclin D1, MEK, s6, Erk, Akt, pAkt, Caspase2, RBBP, total S6
Cyclin D1, MEK, s6, pErk, Akt, pAkt, Caspase2, RBBP, total S6
Cyclin D1, MEK, pS6, Erk, pErk, Akt, pAkt, Caspase2, RBBP
Cyclin D1, MEK, pS6, Erk, pErk, Akt, pAkt, Caspase2, total S6
Cyclin D1, MEK, pS6, Erk, pErk, Akt, pAkt, RBBP, total S6
Cyclin D1, MEK, pS6, Erk, pErk, Akt, Caspase2, RBBP, total S6
Cyclin D1, MEK, pS6, Erk, pErk, pAkt, Caspase2, RBBP, total S6
Cyclin D1, MEK, pS6, Erk, Akt, pAkt, Caspase2, RBBP, total S6
Cyclin D1, MEK, pS6, pErk, Akt, pAkt, Caspase2, RBBP, total S6
Cyclin D1, MEK, Erk, pErk, Akt, pAkt, Caspase2, RBBP, total S6
Cyclin D1, s6, pS6, Erk, pErk, Akt, pAkt, Caspase2, RBBP
Cyclin D1, s6, pS6, Erk, pErk, Akt, pAkt, Caspase2, total S6
Cyclin D1, s6, pS6, Erk, pErk, Akt, pAkt, RBBP, total S6
Cyclin D1, s6, pS6, Erk, pErk, Akt, Caspase2, RBBP, total S6
Cyclin D1, s6, pS6, Erk, pErk, pAkt, Caspase2, RBBP, total S6
Cyclin D1, s6, pS6, Erk, Akt, pAkt, Caspase2, RBBP, total S6
Cyclin D1, s6, pS6, pErk, Akt, pAkt, Caspase2, RBBP, total S6
Cyclin D1, s6, Erk, pErk, Akt, pAkt, Caspase2, RBBP, total S6
Cyclin D1, pS6, Erk, pErk, Akt, pAkt, Caspase2, RBBP, total S6
Cyclin D3, MEK, s6, pS6, Erk, pErk, Akt, pAkt, Caspase2
Cyclin D3, MEK, s6, pS6, Erk, pErk, Akt, pAkt, RBBP
Cyclin D1, Cyclin D3, Erk, pAkt, Caspase2, total S6
Cyclin D1, Cyclin D3, Erk, pAkt, RBBP, total S6
Cyclin D1, Cyclin D3, Erk, Caspase2, RBBP, total S6
Cyclin D1, Cyclin D3, pErk, Akt, pAkt, Caspase2
Cyclin D1, Cyclin D3, pErk, Akt, pAkt, RBBP
Cyclin D1, Cyclin D3, pErk, Akt, pAkt, total S6
Cyclin D1, Cyclin D3, pErk, Akt, Caspase2, RBBP
Cyclin D1, Cyclin D3, pErk, Akt, Caspase2, total S6
Cyclin D1, Cyclin D3, pErk, Akt, RBBP, total S6
Cyclin D1, Cyclin D3, pErk, pAkt, Caspase2, RBBP
Cyclin D1, Cyclin D3, pErk, pAkt, Caspase2, total S6
Cyclin D1, Cyclin D3, pErk, pAkt, RBBP, total S6
Cyclin D1, Cyclin D3, pErk, Caspase2, RBBP, total S6
Cyclin D1, Cyclin D3, Akt, pAkt, Caspase2, RBBP
Cyclin D1, Cyclin D3, Akt, pAkt, Caspase2, total S6
Cyclin D1, Cyclin D3, Akt, pAkt, RBBP, total S6
Cyclin D1, Cyclin D3, Akt, Caspase2, RBBP, total S6
Cyclin D1, Cyclin D3, pAkt, Caspase2, RBBP, total S6
Cyclin D1, MEK, s6, pS6, Erk, pErk
Cyclin D1, MEK, s6, pS6, Erk, Akt
Cyclin D1, MEK, s6, pS6, Erk, pAkt
Cyclin D1, MEK, s6, pS6, Erk, Caspase2
Cyclin D1, MEK, s6, pS6, Erk, RBBP
Cyclin D1, MEK, s6, pS6, Erk, total S6
Cyclin D1, MEK, s6, pS6, pErk, Akt
Cyclin D1, MEK, s6, pS6, pErk, pAkt
Cyclin D1, MEK, s6, pS6, pErk, Caspase2
Cyclin D1, MEK, s6, pS6, pErk, RBBP
Cyclin D1, MEK, s6, pS6, pErk, total S6
Cyclin D1, MEK, s6, pS6, Akt, pAkt
Cyclin D1, MEK, s6, pS6, Akt, Caspase2
Cyclin D1, MEK, s6, pS6, Akt, RBBP
Cyclin D1, MEK, s6, pS6, Akt, total S6
Cyclin D1, MEK, s6, pS6, pAkt, Caspase2
Cyclin D1, MEK, s6, pS6, pAkt, RBBP
Cyclin D1, MEK, s6, pS6, pAkt, total S6
Cyclin D1, MEK, s6, pS6, Caspase2, RBBP
Cyclin D1, MEK, s6, pS6, Caspase2, total S6
Cyclin D1, MEK, s6, pS6, RBBP, total S6
Cyclin D1, MEK, s6, Erk, pErk, Akt
Cyclin D1, MEK, s6, Erk, pErk, pAkt
Cyclin D1, MEK, s6, Erk, pErk, Caspase2
Cyclin D1, MEK, s6, Erk, pErk, RBBP
Cyclin D1, MEK, s6, Erk, pErk, total S6
Cyclin D1, MEK, s6, Erk, Akt, pAkt
Cyclin D1, MEK, s6, Erk, Akt, Caspase2
Cyclin D1, MEK, s6, Erk, Akt, RBBP
Cyclin D1, MEK, s6, Erk, Akt, total S6
Cyclin D1, MEK, s6, Erk, pAkt, Caspase2
Cyclin D1, MEK, s6, Erk, pAkt, RBBP
Cyclin D1, MEK, s6, Erk, pAkt, total S6
Cyclin D1, MEK, s6, Erk, Caspase2, RBBP
Cyclin D1, MEK, s6, Erk, Caspase2, total S6
Cyclin D1, MEK, s6, Erk, RBBP, total S6
Cyclin D1, MEK, s6, pErk, Akt, pAkt
Cyclin D1, MEK, s6, pErk, Akt, Caspase2
Cyclin D1, MEK, s6, pErk, Akt, RBBP
Cyclin D1, MEK, s6, pErk, Akt, total S6
Cyclin D1, MEK, s6, pErk, pAkt, Caspase2

TABLE 1-continued

Examples of Single Markers and Combinations of Markers

Cyclin D3, MEK, s6, pS6, Erk, pErk, Akt, pAkt, total S6
Cyclin D3, MEK, s6, pS6, Erk, pErk, Akt, Caspase2, RBBP
Cyclin D3, MEK, s6, pS6, Erk, pErk, Akt, Caspase2, total S6
Cyclin D3, MEK, s6, pS6, Erk, pErk, Akt, RBBP, total S6
Cyclin D3, MEK, s6, pS6, Erk, pErk, pAkt, Caspase2, RBBP
Cyclin D3, MEK, s6, pS6, Erk, pErk, pAkt, Caspase2, total S6
Cyclin D3, MEK, s6, pS6, Erk, pErk, pAkt, RBBP, total S6
Cyclin D3, MEK, s6, pS6, Erk, pErk, Caspase2, RBBP, total S6
Cyclin D3, MEK, s6, pS6, Erk, Akt, pAkt, Caspase2, RBBP
Cyclin D3, MEK, s6, pS6, Erk, Akt, pAkt, Caspase2, total S6
Cyclin D3, MEK, s6, pS6, Erk, Akt, pAkt, RBBP, total S6
Cyclin D3, MEK, s6, pS6, Erk, Akt, Caspase2, RBBP, total S6
Cyclin D3, MEK, s6, pS6, Erk, pAkt, Caspase2, RBBP, total S6

Cyclin D3, MEK, s6, pS6, pErk, Akt, pAkt, Caspase2, RBBP
Cyclin D3, MEK, s6, pS6, pErk, Akt, pAkt, Caspase2, total S6

Cyclin D3, MEK, s6, pS6, pErk, Akt, pAkt, RBBP, total S6
Cyclin D3, MEK, s6, pS6, pErk, Akt, Caspase2, RBBP, total S6
Cyclin D3, MEK, s6, pS6, pErk, pAkt, Caspase2, RBBP, total S6
Cyclin D3, MEK, s6, pS6, Akt, pAkt, Caspase2, RBBP, total S6
Cyclin D3, MEK, s6, Erk, pErk, Akt, pAkt, Caspase2, RBBP
Cyclin D3, MEK, s6, Erk, pErk, Akt, pAkt, Caspase2, total S6
Cyclin D3, MEK, s6, Erk, pErk, Akt, pAkt, RBBP, total S6
Cyclin D3, MEK, s6, Erk, pErk, Akt, Caspase2, RBBP, total S6
Cyclin D3, MEK, s6, Erk, pErk, pAkt, Caspase2, RBBP, total S6
Cyclin D3, MEK, s6, Erk, Akt, pAkt, Caspase2, RBBP, total S6
Cyclin D3, MEK, s6, pErk, Akt, pAkt, Caspase2, RBBP, total S6
Cyclin D3, MEK, pS6, Erk, pErk, Akt, pAkt, Caspase2, RBBP
Cyclin D3, MEK, pS6, Erk, pErk, Akt, pAkt, Caspase2, total S6

Cyclin D3, MEK, pS6, Erk, pErk, Akt, pAkt, RBBP, total S6
Cyclin D3, MEK, pS6, Erk, pErk, Akt, Caspase2, RBBP, total S6
Cyclin D3, MEK, pS6, Erk, pErk, pAkt, Caspase2, RBBP, total S6
Cyclin D3, MEK, pS6, Erk, Akt, pAkt, Caspase2, RBBP, total S6
Cyclin D3, MEK, pS6, pErk, Akt, pAkt, Caspase2, RBBP, total S6
Cyclin D3, MEK, Erk, pErk, Akt, pAkt, Caspase2, RBBP, total S6
Cyclin D3, s6, pS6, Erk, pErk, Akt, pAkt, Caspase2, RBBP
Cyclin D3, s6, pS6, Erk, pErk, Akt, pAkt, Caspase2, total S6
Cyclin D3, s6, pS6, Erk, pErk, Akt, pAkt, RBBP, total S6
Cyclin D3, s6, pS6, Erk, pErk, Akt, Caspase2, RBBP, total S6
Cyclin D3, s6, pS6, Erk, pErk, pAkt, Caspase2, RBBP, total S6

Cyclin D3, s6, pS6, Erk, Akt, pAkt, Caspase2, RBBP, total S6
Cyclin D3, s6, pS6, pErk, Akt, pAkt, Caspase2, RBBP, total S6
Cyclin D3, s6, Erk, pErk, Akt, pAkt, Caspase2, RBBP, total S6
Cyclin D3, pS6, Erk, pErk, Akt, pAkt, Caspase2, RBBP, total S6
MEK, s6, pS6, Erk, pErk, Akt, pAkt, Caspase2, RBBP
MEK, s6, pS6, Erk, pErk, Akt, pAkt, Caspase2, total S6
MEK, s6, pS6, Erk, pErk, Akt, pAkt, RBBP, total S6
MEK, s6, pS6, Erk, pErk, Akt, Caspase2, RBBP, total S6
MEK, s6, pS6, Erk, pErk, pAkt, Caspase2, RBBP, total S6
MEK, s6, pS6, Erk, Akt, pAkt, Caspase2, RBBP, total S6
MEK, s6, pS6, pErk, Akt, pAkt, Caspase2, RBBP, total S6
MEK, s6, Erk, pErk, Akt, pAkt, Caspase2, RBBP, total S6
MEK, pS6, Erk, pErk, Akt, pAkt, Caspase2, RBBP, total S6
s6, pS6, Erk, pErk, Akt, pAkt, Caspase2, RBBP, total S6
PCNA, Cyclin D1, Cyclin D3, MEK, s6, pS6, Erk, pErk
PCNA, Cyclin D1, Cyclin D3, MEK, s6, pS6, Erk, Akt
PCNA, Cyclin D1, Cyclin D3, MEK, s6, pS6, Erk, pAkt
PCNA, Cyclin D1, Cyclin D3, MEK, s6, pS6, Erk, Caspase2
PCNA, Cyclin D1, Cyclin D3, MEK, s6, pS6, Erk, RBBP
PCNA, Cyclin D1, Cyclin D3, MEK, s6, pS6, Erk, total S6
PCNA, Cyclin D1, Cyclin D3, MEK, s6, pS6, pErk, Akt
PCNA, Cyclin D1, Cyclin D3, MEK, s6, pS6, pErk, pAkt
PCNA, Cyclin D1, Cyclin D3, MEK, s6, pS6, pErk, Caspase2
PCNA, Cyclin D1, Cyclin D3, MEK, s6, pS6, pErk, RBBP
PCNA, Cyclin D1, Cyclin D3, MEK, s6, pS6, pErk, total S6
PCNA, Cyclin D1, Cyclin D3, MEK, s6, pS6, Akt, pAkt
PCNA, Cyclin D1, Cyclin D3, MEK, s6, pS6, Akt, Caspase2
PCNA, Cyclin D1, Cyclin D3, MEK, s6, pS6, Akt, RBBP
PCNA, Cyclin D1, Cyclin D3, MEK, s6, pS6, Akt, total S6
PCNA, Cyclin D1, Cyclin D3, MEK, s6, pS6, pAkt, Caspase2
PCNA, Cyclin D1, Cyclin D3, MEK, s6, pS6, pAkt, RBBP
PCNA, Cyclin D1, Cyclin D3, MEK, s6, pS6, pAkt, total S6
PCNA, Cyclin D1, Cyclin D3, MEK, s6, pS6, Caspase2, RBBP
PCNA, Cyclin D1, Cyclin D3, MEK, s6, pS6, Caspase2, total S6

Cyclin D1, MEK, s6, pErk, pAkt, RBBP
Cyclin D1, MEK, s6, pErk, pAkt, total S6
Cyclin D1, MEK, s6, pErk, Caspase2, RBBP
Cyclin D1, MEK, s6, pErk, Caspase2, total S6
Cyclin D1, MEK, s6, pErk, RBBP, total S6
Cyclin D1, MEK, s6, Akt, pAkt, Caspase2
Cyclin D1, MEK, s6, Akt, pAkt, RBBP
Cyclin D1, MEK, s6, Akt, pAkt, total S6
Cyclin D1, MEK, s6, Akt, Caspase2, RBBP
Cyclin D1, MEK, s6, Akt, Caspase2, total S6
Cyclin D1, MEK, s6, Akt, RBBP, total S6
Cyclin D1, MEK, s6, pAkt, Caspase2, RBBP
Cyclin D1, MEK, s6, pAkt, Caspase2, total S6
Cyclin D1, MEK, s6, pAkt, RBBP, total S6
Cyclin D1, MEK, s6, Caspase2, RBBP, total S6
Cyclin D1, MEK, pS6, Erk, pErk, Akt
Cyclin D1, MEK, pS6, Erk, pErk, pAkt
Cyclin D1, MEK, pS6, Erk, pErk, Caspase2
Cyclin D1, MEK, pS6, Erk, pErk, RBBP
Cyclin D1, MEK, pS6, Erk, pErk, total S6
Cyclin D1, MEK, pS6, Erk, Akt, pAkt
Cyclin D1, MEK, pS6, Erk, Akt, Caspase2
Cyclin D1, MEK, pS6, Erk, Akt, RBBP
Cyclin D1, MEK, pS6, Erk, Akt, total S6
Cyclin D1, MEK, pS6, Erk, pAkt, Caspase2
Cyclin D1, MEK, pS6, Erk, pAkt, RBBP
Cyclin D1, MEK, pS6, Erk, pAkt, total S6
Cyclin D1, MEK, pS6, Erk, Caspase2, RBBP
Cyclin D1, MEK, pS6, Erk, Caspase2, total S6
Cyclin D1, MEK, pS6, Erk, RBBP, total S6
Cyclin D1, MEK, pS6, pErk, Akt, pAkt
Cyclin D1, MEK, pS6, pErk, Akt, Caspase2
Cyclin D1, MEK, pS6, pErk, Akt, RBBP
Cyclin D1, MEK, pS6, pErk, Akt, total S6
Cyclin D1, MEK, pS6, pErk, pAkt, Caspase2
Cyclin D1, MEK, pS6, pErk, pAkt, RBBP
Cyclin D1, MEK, pS6, pErk, pAkt, total S6
Cyclin D1, MEK, pS6, pErk, Caspase2, RBBP
Cyclin D1, MEK, pS6, pErk, Caspase2, total S6
Cyclin D1, MEK, pS6, pErk, RBBP, total S6
Cyclin D1, MEK, pS6, Akt, pAkt, Caspase2
Cyclin D1, MEK, pS6, Akt, pAkt, RBBP
Cyclin D1, MEK, pS6, Akt, pAkt, total S6
Cyclin D1, MEK, pS6, Akt, Caspase2, RBBP
Cyclin D1, MEK, pS6, Akt, Caspase2, total S6
Cyclin D1, MEK, pS6, Akt, RBBP, total S6
Cyclin D1, MEK, pS6, pAkt, Caspase2, RBBP
Cyclin D1, MEK, pS6, pAkt, Caspase2, total S6
Cyclin D1, MEK, pS6, pAkt, RBBP, total S6
Cyclin D1, MEK, pS6, Caspase2, RBBP, total S6
Cyclin D1, MEK, Erk, pErk, Akt, pAkt
Cyclin D1, MEK, Erk, pErk, Akt, Caspase2
Cyclin D1, MEK, Erk, pErk, Akt, RBBP
Cyclin D1, MEK, Erk, pErk, Akt, total S6
Cyclin D1, MEK, Erk, pErk, pAkt, Caspase2
Cyclin D1, MEK, Erk, pErk, pAkt, RBBP
Cyclin D1, MEK, Erk, pErk, pAkt, total S6
Cyclin D1, MEK, Erk, pErk, Caspase2, RBBP
Cyclin D1, MEK, Erk, pErk, Caspase2, total S6
Cyclin D1, MEK, Erk, pErk, RBBP, total S6
Cyclin D1, MEK, Erk, Akt, pAkt, Caspase2
Cyclin D1, MEK, Erk, Akt, pAkt, RBBP
Cyclin D1, MEK, Erk, Akt, pAkt, total S6
Cyclin D1, MEK, Erk, Akt, Caspase2, RBBP
Cyclin D1, MEK, Erk, Akt, Caspase2, total S6
Cyclin D1, MEK, Erk, Akt, RBBP, total S6
Cyclin D1, MEK, Erk, pAkt, Caspase2, RBBP
Cyclin D1, MEK, Erk, pAkt, Caspase2, total S6
Cyclin D1, MEK, Erk, pAkt, RBBP, total S6
Cyclin D1, MEK, Erk, Caspase2, RBBP, total S6
Cyclin D1, MEK, pErk, Akt, pAkt, Caspase2
Cyclin D1, MEK, pErk, Akt, pAkt, RBBP
Cyclin D1, MEK, pErk, Akt, pAkt, total S6

TABLE 1-continued

Examples of Single Markers and Combinations of Markers

PCNA, Cyclin D1, Cyclin D3, MEK, s6, pS6, RBBP, total S6
PCNA, Cyclin D1, Cyclin D3, MEK, s6, Erk, pErk, Akt
PCNA, Cyclin D1, Cyclin D3, MEK, s6, Erk, pErk, pAkt
PCNA, Cyclin D1, Cyclin D3, MEK, s6, Erk, pErk, Caspase2
PCNA, Cyclin D1, Cyclin D3, MEK, s6, Erk, pErk, RBBP
PCNA, Cyclin D1, Cyclin D3, MEK, s6, Erk, pErk, total S6
PCNA, Cyclin D1, Cyclin D3, MEK, s6, Erk, Akt, pAkt
PCNA, Cyclin D1, Cyclin D3, MEK, s6, Erk, Akt, Caspase2
PCNA, Cyclin D1, Cyclin D3, MEK, s6, Erk, Akt, RBBP
PCNA, Cyclin D1, Cyclin D3, MEK, s6, Erk, Akt, total S6
PCNA, Cyclin D1, Cyclin D3, MEK, s6, Erk, pAkt, Caspase2

PCNA, Cyclin D1, Cyclin D3, MEK, s6, Erk, pAkt, RBBP
PCNA, Cyclin D1, Cyclin D3, MEK, s6, Erk, pAkt, total S6
PCNA, Cyclin D1, Cyclin D3, MEK, s6, Erk, Caspase2, RBBP
PCNA, Cyclin D1, Cyclin D3, MEK, s6, Erk, Caspase2, total S6
PCNA, Cyclin D1, Cyclin D3, MEK, s6, Erk, RBBP, total S6
PCNA, Cyclin D1, Cyclin D3, MEK, s6, pErk, Akt, pAkt
PCNA, Cyclin D1, Cyclin D3, MEK, s6, pErk, Akt, Caspase2
PCNA, Cyclin D1, Cyclin D3, MEK, s6, pErk, Akt, RBBP
PCNA, Cyclin D1, Cyclin D3, MEK, s6, pErk, Akt, total S6
PCNA, Cyclin D1, Cyclin D3, MEK, s6, pErk, pAkt, Caspase2
PCNA, Cyclin D1, Cyclin D3, MEK, s6, pErk, pAkt, RBBP
PCNA, Cyclin D1, Cyclin D3, MEK, s6, pErk, pAkt, total S6
PCNA, Cyclin D1, Cyclin D3, MEK, s6, pErk, Caspase2, RBBP
PCNA, Cyclin D1, Cyclin D3, MEK, s6, pErk, Caspase2, total S6
PCNA, Cyclin D1, Cyclin D3, MEK, s6, pErk, RBBP, total S6
PCNA, Cyclin D1, Cyclin D3, MEK, s6, Akt, pAkt, Caspase2
PCNA, Cyclin D1, Cyclin D3, MEK, s6, Akt, pAkt, RBBP
PCNA, Cyclin D1, Cyclin D3, MEK, s6, Akt, pAkt, total S6
PCNA, Cyclin D1, Cyclin D3, MEK, s6, Akt, Caspase2, RBBP
PCNA, Cyclin D1, Cyclin D3, MEK, s6, Akt, Caspase2, total S6
PCNA, Cyclin D1, Cyclin D3, MEK, s6, Akt, RBBP, total S6
PCNA, Cyclin D1, Cyclin D3, MEK, s6, pAkt, Caspase2, RBBP
PCNA, Cyclin D1, Cyclin D3, MEK, s6, pAkt, Caspase2, total S6
PCNA, Cyclin D1, Cyclin D3, MEK, s6, pAkt, RBBP, total S6
PCNA, Cyclin D1, Cyclin D3, MEK, s6, Caspase2, RBBP, total S6

PCNA, Cyclin D1, Cyclin D3, MEK, pS6, Erk, pErk, Akt
PCNA, Cyclin D1, Cyclin D3, MEK, pS6, Erk, pErk, pAkt
PCNA, Cyclin D1, Cyclin D3, MEK, pS6, Erk, pErk, Caspase2
PCNA, Cyclin D1, Cyclin D3, MEK, pS6, Erk, pErk, RBBP
PCNA, Cyclin D1, Cyclin D3, MEK, pS6, Erk, pErk, total S6
PCNA, Cyclin D1, Cyclin D3, MEK, pS6, Erk, Akt, pAkt
PCNA, Cyclin D1, Cyclin D3, MEK, pS6, Erk, Akt, Caspase2
PCNA, Cyclin D1, Cyclin D3, MEK, pS6, Erk, Akt, RBBP
PCNA, Cyclin D1, Cyclin D3, MEK, pS6, Erk, Akt, total S6
PCNA, Cyclin D1, Cyclin D3, MEK, pS6, Erk, pAkt, Caspase2
PCNA, Cyclin D1, Cyclin D3, MEK, pS6, Erk, pAkt, RBBP
PCNA, Cyclin D1, Cyclin D3, MEK, pS6, Erk, pAkt, total S6
PCNA, Cyclin D1, Cyclin D3, MEK, pS6, Erk, Caspase2, RBBP
PCNA, Cyclin D1, Cyclin D3, MEK, pS6, Erk, Caspase2, total S6
PCNA, Cyclin D1, Cyclin D3, MEK, pS6, Erk, RBBP, total S6
PCNA, Cyclin D1, Cyclin D3, MEK, pS6, pErk, Akt, pAkt
PCNA, Cyclin D1, Cyclin D3, MEK, pS6, pErk, Akt, Caspase2
PCNA, Cyclin D1, Cyclin D3, MEK, pS6, pErk, Akt, RBBP
PCNA, Cyclin D1, Cyclin D3, MEK, pS6, pErk, Akt, total S6
PCNA, Cyclin D1, Cyclin D3, MEK, pS6, pErk, pAkt, Caspase2
PCNA, Cyclin D1, Cyclin D3, MEK, pS6, pErk, pAkt, RBBP
PCNA, Cyclin D1, Cyclin D3, MEK, pS6, pErk, pAkt, total S6
PCNA, Cyclin D1, Cyclin D3, MEK, pS6, pErk, Caspase2, RBBP
PCNA, Cyclin D1, Cyclin D3, MEK, pS6, pErk, Caspase2, total S6
PCNA, Cyclin D1, Cyclin D3, MEK, pS6, pErk, RBBP, total S6
PCNA, Cyclin D1, Cyclin D3, MEK, pS6, Akt, pAkt, Caspase2
PCNA, Cyclin D1, Cyclin D3, MEK, pS6, Akt, pAkt, RBBP
PCNA, Cyclin D1, Cyclin D3, MEK, pS6, Akt, pAkt, total S6
PCNA, Cyclin D1, Cyclin D3, MEK, pS6, Akt, Caspase2, RBBP PCNA, Cyclin D1, Cyclin D3, MEK, pS6, Akt, Caspase2, total S6
PCNA, Cyclin D1, Cyclin D3, MEK, pS6, Akt, RBBP, total S6
PCNA, Cyclin D1, Cyclin D3, MEK, pS6, pAkt, Caspase2, RBBP PCNA, Cyclin D1, Cyclin D3, MEK, pS6, pAkt, Caspase2, total S6
PCNA, Cyclin D1, Cyclin D3, MEK, pS6, pAkt, RBBP, total S6
PCNA, Cyclin D1, Cyclin D3, MEK, pS6, Caspase2, RBBP, total S6

PCNA, Cyclin D1, Cyclin D3, MEK, Erk, pErk, Akt, pAkt
PCNA, Cyclin D1, Cyclin D3, MEK, Erk, pErk, Akt, Caspase2

Cyclin D1, MEK, pErk, Akt, Caspase2, RBBP
Cyclin D1, MEK, pErk, Akt, Caspase2, total S6
Cyclin D1, MEK, pErk, Akt, RBBP, total S6
Cyclin D1, MEK, pErk, pAkt, Caspase2, RBBP
Cyclin D1, MEK, pErk, pAkt, Caspase2, total S6
Cyclin D1, MEK, pErk, pAkt, RBBP, total S6
Cyclin D1, MEK, pErk, Caspase2, RBBP, total S6
Cyclin D1, MEK, Akt, pAkt, Caspase2, RBBP
Cyclin D1, MEK, Akt, pAkt, Caspase2, total S6
Cyclin D1, MEK, Akt, pAkt, RBBP, total S6
Cyclin D1, MEK, Akt, Caspase2, RBBP, total S6

Cyclin D1, MEK, pAkt, Caspase2, RBBP, total S6
Cyclin D1, s6, pS6, Erk, pErk, Akt
Cyclin D1, s6, pS6, Erk, pErk, pAkt
Cyclin D1, s6, pS6, Erk, pErk, Caspase2
Cyclin D1, s6, pS6, Erk, pErk, RBBP
Cyclin D1, s6, pS6, Erk, pErk, total S6
Cyclin D1, s6, pS6, Erk, Akt, pAkt
Cyclin D1, s6, pS6, Erk, Akt, Caspase2
Cyclin D1, s6, pS6, Erk, Akt, RBBP
Cyclin D1, s6, pS6, Erk, Akt, total S6
Cyclin D1, s6, pS6, Erk, pAkt, Caspase2
Cyclin D1, s6, pS6, Erk, pAkt, RBBP
Cyclin D1, s6, pS6, Erk, pAkt, total S6
Cyclin D1, s6, pS6, Erk, Caspase2, RBBP
Cyclin D1, s6, pS6, Erk, Caspase2, total S6
Cyclin D1, s6, pS6, Erk, RBBP, total S6
Cyclin D1, s6, pS6, pErk, Akt, pAkt
Cyclin D1, s6, pS6, pErk, Akt, Caspase2
Cyclin D1, s6, pS6, pErk, Akt, RBBP
Cyclin D1, s6, pS6, pErk, Akt, total S6
Cyclin D1, s6, pS6, pErk, pAkt, Caspase2
Cyclin D1, s6, pS6, pErk, pAkt, RBBP
Cyclin D1, s6, pS6, pErk, pAkt, total S6
Cyclin D1, s6, pS6, pErk, Caspase2, RBBP
Cyclin D1, s6, pS6, pErk, Caspase2, total S6
Cyclin D1, s6, pS6, pErk, RBBP, total S6
Cyclin D1, s6, pS6, Akt, pAkt, Caspase2
Cyclin D1, s6, pS6, Akt, pAkt, RBBP
Cyclin D1, s6, pS6, Akt, pAkt, total S6
Cyclin D1, s6, pS6, Akt, Caspase2, RBBP
Cyclin D1, s6, pS6, Akt, Caspase2, total S6
Cyclin D1, s6, pS6, Akt, RBBP, total S6
Cyclin D1, s6, pS6, pAkt, Caspase2, RBBP
Cyclin D1, s6, pS6, pAkt, Caspase2, total S6
Cyclin D1, s6, pS6, pAkt, RBBP, total S6
Cyclin D1, s6, pS6, Caspase2, RBBP, total S6
Cyclin D1, s6, Erk, pErk, Akt, pAkt
Cyclin D1, s6, Erk, pErk, Akt, Caspase2
Cyclin D1, s6, Erk, pErk, Akt, RBBP
Cyclin D1, s6, Erk, pErk, Akt, total S6
Cyclin D1, s6, Erk, pErk, pAkt, Caspase2
Cyclin D1, s6, Erk, pErk, pAkt, RBBP
Cyclin D1, s6, Erk, pErk, pAkt, total S6
Cyclin D1, s6, Erk, pErk, Caspase2, RBBP
Cyclin D1, s6, Erk, pErk, Caspase2, total S6
Cyclin D1, s6, Erk, pErk, RBBP, total S6
Cyclin D1, s6, Erk, Akt, pAkt, Caspase2
Cyclin D1, s6, Erk, Akt, pAkt, RBBP
Cyclin D1, s6, Erk, Akt, pAkt, total S6
Cyclin D1, s6, Erk, Akt, Caspase2, RBBP
Cyclin D1, s6, Erk, Akt, Caspase2, total S6
Cyclin D1, s6, Erk, Akt, RBBP, total S6
Cyclin D1, s6, Erk, pAkt, Caspase2, RBBP
Cyclin D1, s6, Erk, pAkt, Caspase2, total S6
Cyclin D1, s6, Erk, pAkt, RBBP, total S6
Cyclin D1, s6, Erk, Caspase2, RBBP, total S6
Cyclin D1, s6, pErk, Akt, pAkt, Caspase2
Cyclin D1, s6, pErk, Akt, pAkt, RBBP
Cyclin D1, s6, pErk, Akt, pAkt, total S6
Cyclin D1, s6, pErk, Akt, Caspase2, RBBP
Cyclin D1, s6, pErk, Akt, Caspase2, total S6
Cyclin D1, s6, pErk, Akt, RBBP, total S6

TABLE 1-continued

Examples of Single Markers and Combinations of Markers

PCNA, Cyclin D1, Cyclin D3, MEK, Erk, pErk, Akt, RBBP
PCNA, Cyclin D1, Cyclin D3, MEK, Erk, pErk, Akt, total S6
PCNA, Cyclin D1, Cyclin D3, MEK, Erk, pErk, pAkt, Caspase2
PCNA, Cyclin D1, Cyclin D3, MEK, Erk, pErk, pAkt, RBBP
PCNA, Cyclin D1, Cyclin D3, MEK, Erk, pErk, pAkt, total S6
PCNA, Cyclin D1, Cyclin D3, MEK, Erk, pErk, Caspase2, RBBP
PCNA, Cyclin D1, Cyclin D3, MEK, Erk, pErk, Caspase2, total S6
PCNA, Cyclin D1, Cyclin D3, MEK, Erk, pErk, RBBP, total S6
PCNA, Cyclin D1, Cyclin D3, MEK, Erk, Akt, pAkt, Caspase2
PCNA, Cyclin D1, Cyclin D3, MEK, Erk, Akt, pAkt, RBBP
PCNA, Cyclin D1, Cyclin D3, MEK, Erk, Akt, pAkt, total S6
PCNA, Cyclin D1, Cyclin D3, MEK, Erk, Akt, Caspase2, RBBP
PCNA, Cyclin D1, Cyclin D3, MEK, Erk, Akt, Caspase2, total S6
PCNA, Cyclin D1, Cyclin D3, MEK, Erk, Akt, RBBP, total S6
PCNA, Cyclin D1, Cyclin D3, MEK, Erk, pAkt, Caspase2, RBBP
PCNA, Cyclin D1, Cyclin D3, MEK, Erk, pAkt, Caspase2, total S6
PCNA, Cyclin D1, Cyclin D3, MEK, Erk, pAkt, RBBP, total S6
PCNA, Cyclin D1, Cyclin D3, MEK, Erk, Caspase2, RBBP, total S6
PCNA, Cyclin D1, Cyclin D3, MEK, pErk, Akt, pAkt, Caspase2
PCNA, Cyclin D1, Cyclin D3, MEK, pErk, Akt, pAkt, RBBP
PCNA, Cyclin D1, Cyclin D3, MEK, pErk, Akt, pAkt, total S6
PCNA, Cyclin D1, Cyclin D3, MEK, pErk, Akt, Caspase2, RBBP
PCNA, Cyclin D1, Cyclin D3, MEK, pErk, Akt, Caspase2, total S6
PCNA, Cyclin D1, Cyclin D3, MEK, pErk, Akt, RBBP, total S6
PCNA, Cyclin D1, Cyclin D3, MEK, pErk, pAkt, Caspase2, RBBP
PCNA, Cyclin D1, Cyclin D3, MEK, pErk, pAkt, Caspase2, total S6
PCNA, Cyclin D1, Cyclin D3, MEK, pErk, pAkt, RBBP, total S6
PCNA, Cyclin D1, Cyclin D3, MEK, pErk, Caspase2, RBBP, total S6
PCNA, Cyclin D1, Cyclin D3, MEK, Akt, pAkt, Caspase2, RBBP
PCNA, Cyclin D1, Cyclin D3, MEK, Akt, pAkt, Caspase2, total S6
PCNA, Cyclin D1, Cyclin D3, MEK, Akt, pAkt, RBBP, total S6
PCNA, Cyclin D1, Cyclin D3, MEK, Akt, Caspase2, RBBP, total S6
PCNA, Cyclin D1, Cyclin D3, MEK, pAkt, Caspase2, RBBP, total S6
PCNA, Cyclin D1, Cyclin D3, s6, pS6, Erk, pErk, Akt
PCNA, Cyclin D1, Cyclin D3, s6, pS6, Erk, pErk, pAkt
PCNA, Cyclin D1, Cyclin D3, s6, pS6, Erk, pErk, Caspase2
PCNA, Cyclin D1, Cyclin D3, s6, pS6, Erk, pErk, RBBP
PCNA, Cyclin D1, Cyclin D3, s6, pS6, Erk, pErk, total S6
PCNA, Cyclin D1, Cyclin D3, s6, pS6, Erk, Akt, pAkt
PCNA, Cyclin D1, Cyclin D3, s6, pS6, Erk, Akt, Caspase2
PCNA, Cyclin D1, Cyclin D3, s6, pS6, Erk, Akt, RBBP
PCNA, Cyclin D1, Cyclin D3, s6, pS6, Erk, Akt, total S6
PCNA, Cyclin D1, Cyclin D3, s6, pS6, Erk, pAkt, Caspase2
PCNA, Cyclin D1, Cyclin D3, s6, pS6, Erk, pAkt, RBBP
PCNA, Cyclin D1, Cyclin D3, s6, pS6, Erk, pAkt, total S6
PCNA, Cyclin D1, Cyclin D3, s6, pS6, Erk, Caspase2, RBBP
PCNA, Cyclin D1, Cyclin D3, s6, pS6, Erk, Caspase2, total S6
PCNA, Cyclin D1, Cyclin D3, s6, pS6, Erk, RBBP, total S6
PCNA, Cyclin D1, Cyclin D3, s6, pS6, pErk, Akt, pAkt
PCNA, Cyclin D1, Cyclin D3, s6, pS6, pErk, Akt, Caspase2
PCNA, Cyclin D1, Cyclin D3, s6, pS6, pErk, Akt, RBBP
PCNA, Cyclin D1, Cyclin D3, s6, pS6, pErk, Akt, total S6
PCNA, Cyclin D1, Cyclin D3, s6, pS6, pErk, pAkt, Caspase2
PCNA, Cyclin D1, Cyclin D3, s6, pS6, pErk, pAkt, RBBP
PCNA, Cyclin D1, Cyclin D3, s6, pS6, pErk, pAkt, total S6
PCNA, Cyclin D1, Cyclin D3, s6, pS6, pErk, Caspase2, RBBP
PCNA, Cyclin D1, Cyclin D3, s6, pS6, pErk, Caspase2, total S6
PCNA, Cyclin D1, Cyclin D3, s6, pS6, pErk, RBBP, total S6
PCNA, Cyclin D1, Cyclin D3, s6, pS6, Akt, pAkt, Caspase2
PCNA, Cyclin D1, Cyclin D3, s6, pS6, Akt, pAkt, RBBP
PCNA, Cyclin D1, Cyclin D3, s6, pS6, Akt, pAkt, total S6
PCNA, Cyclin D1, Cyclin D3, s6, pS6, Akt, Caspase2, RBBP
PCNA, Cyclin D1, Cyclin D3, s6, pS6, Akt, Caspase2, total S6

Cyclin D1, s6, pErk, pAkt, Caspase2, RBBP
Cyclin D1, s6, pErk, pAkt, Caspase2, total S6
Cyclin D1, s6, pErk, pAkt, RBBP, total S6
Cyclin D1, s6, pErk, Caspase2, RBBP, total S6
Cyclin D1, s6, Akt, pAkt, Caspase2, RBBP
Cyclin D1, s6, Akt, pAkt, Caspase2, total S6
Cyclin D1, s6, Akt, pAkt, RBBP, total S6
Cyclin D1, s6, Akt, Caspase2, RBBP, total S6
Cyclin D1, s6, pAkt, Caspase2, RBBP, total S6
Cyclin D1, pS6, Erk, pErk, Akt, pAkt
Cyclin D1, pS6, Erk, pErk, Akt, Caspase2
Cyclin D1, pS6, Erk, pErk, Akt, RBBP
Cyclin D1, pS6, Erk, pErk, Akt, total S6
Cyclin D1, pS6, Erk, pErk, pAkt, Caspase2
Cyclin D1, pS6, Erk, pErk, pAkt, RBBP
Cyclin D1, pS6, Erk, pErk, pAkt, total S6
Cyclin D1, pS6, Erk, pErk, Caspase2, RBBP
Cyclin D1, pS6, Erk, pErk, Caspase2, total S6
Cyclin D1, pS6, Erk, pErk, RBBP, total S6
Cyclin D1, pS6, Erk, Akt, pAkt, Caspase2
Cyclin D1, pS6, Erk, Akt, pAkt, RBBP
Cyclin D1, pS6, Erk, Akt, pAkt, total S6
Cyclin D1, pS6, Erk, Akt, Caspase2, RBBP
Cyclin D1, pS6, Erk, Akt, Caspase2, total S6
Cyclin D1, pS6, Erk, Akt, RBBP, total S6
Cyclin D1, pS6, Erk, pAkt, Caspase2, RBBP
Cyclin D1, pS6, Erk, pAkt, Caspase2, total S6
Cyclin D1, pS6, Erk, pAkt, RBBP, total S6
Cyclin D1, pS6, Erk, Caspase2, RBBP, total S6
Cyclin D1, pS6, pErk, Akt, pAkt, Caspase2
Cyclin D1, pS6, pErk, Akt, pAkt, RBBP
Cyclin D1, pS6, pErk, Akt, pAkt, total S6
Cyclin D1, pS6, pErk, Akt, Caspase2, RBBP
Cyclin D1, pS6, pErk, Akt, Caspase2, total S6
Cyclin D1, pS6, pErk, Akt, RBBP, total S6
Cyclin D1, pS6, pErk, pAkt, Caspase2, RBBP
Cyclin D1, pS6, pErk, pAkt, Caspase2, total S6
Cyclin D1, pS6, pErk, pAkt, RBBP, total S6
Cyclin D1, pS6, pErk, Caspase2, RBBP, total S6
Cyclin D1, pS6, Akt, pAkt, Caspase2, RBBP
Cyclin D1, pS6, Akt, pAkt, Caspase2, total S6
Cyclin D1, pS6, Akt, pAkt, RBBP, total S6
Cyclin D1, pS6, Akt, Caspase2, RBBP, total S6
Cyclin D1, pS6, pAkt, Caspase2, RBBP, total S6
Cyclin D1, Erk, pErk, Akt, pAkt, Caspase2
Cyclin D1, Erk, pErk, Akt, pAkt, RBBP
Cyclin D1, Erk, pErk, Akt, pAkt, total S6
Cyclin D1, Erk, pErk, Akt, Caspase2, RBBP
Cyclin D1, Erk, pErk, Akt, Caspase2, total S6
Cyclin D1, Erk, pErk, Akt, RBBP, total S6
Cyclin D1, Erk, pErk, pAkt, Caspase2, RBBP
Cyclin D1, Erk, pErk, pAkt, Caspase2, total S6
Cyclin D1, Erk, pErk, pAkt, RBBP, total S6
Cyclin D1, Erk, pErk, Caspase2, RBBP, total S6
Cyclin D1, Erk, Akt, pAkt, Caspase2, RBBP
Cyclin D1, Erk, Akt, pAkt, Caspase2, total S6
Cyclin D1, Erk, Akt, pAkt, RBBP, total S6
Cyclin D1, Erk, Akt, Caspase2, RBBP, total S6
Cyclin D1, Erk, pAkt, Caspase2, RBBP, total S6
Cyclin D1, pErk, Akt, pAkt, Caspase2, RBBP
Cyclin D1, pErk, Akt, pAkt, Caspase2, total S6
Cyclin D1, pErk, Akt, pAkt, RBBP, total S6
Cyclin D1, pErk, Akt, Caspase2, RBBP, total S6

TABLE 1-continued

Examples of Single Markers and Combinations of Markers

PCNA, Cyclin D1, Cyclin D3, s6, pS6, Akt, RBBP, total S6
PCNA, Cyclin D1, Cyclin D3, s6, pS6, pAkt, Caspase2, RBBP
PCNA, Cyclin D1, Cyclin D3, s6, pS6, pAkt, Caspase2, total S6
PCNA, Cyclin D1, Cyclin D3, s6, pS6, pAkt, RBBP, total S6
PCNA, Cyclin D1, Cyclin D3, s6, pS6, Caspase2, RBBP, total S6
PCNA, Cyclin D1, Cyclin D3, s6, Erk, pErk, Akt, pAkt
PCNA, Cyclin D1, Cyclin D3, s6, Erk, pErk, Akt, Caspase2
PCNA, Cyclin D1, Cyclin D3, s6, Erk, pErk, Akt, RBBP
PCNA, Cyclin D1, Cyclin D3, s6, Erk, pErk, Akt, total S6
PCNA, Cyclin D1, Cyclin D3, s6, Erk, pErk, pAkt, Caspase2
PCNA, Cyclin D1, Cyclin D3, s6, Erk, pErk, pAkt, RBBP
PCNA, Cyclin D1, Cyclin D3, s6, Erk, pErk, pAkt, total S6
PCNA, Cyclin D1, Cyclin D3, s6, Erk, pErk, Caspase2, RBBP
PCNA, Cyclin D1, Cyclin D3, s6, Erk, pErk, Caspase2, total S6
PCNA, Cyclin D1, Cyclin D3, s6, Erk, pErk, RBBP, total S6
PCNA, Cyclin D1, Cyclin D3, s6, Erk, Akt, pAkt, Caspase2
PCNA, Cyclin D1, Cyclin D3, s6, Erk, Akt, pAkt, RBBP
PCNA, Cyclin D1, Cyclin D3, s6, Erk, Akt, pAkt, total S6
PCNA, Cyclin D1, Cyclin D3, s6, Erk, Akt, Caspase2, RBBP
PCNA, Cyclin D1, Cyclin D3, s6, Erk, Akt, Caspase2, total S6
PCNA, Cyclin D1, Cyclin D3, s6, Erk, Akt, RBBP, total S6
PCNA, Cyclin D1, Cyclin D3, s6, Erk, pAkt, Caspase2, RBBP
PCNA, Cyclin D1, Cyclin D3, s6, Erk, pAkt, Caspase2, total S6
PCNA, Cyclin D1, Cyclin D3, s6, Erk, pAkt, RBBP, total S6
PCNA, Cyclin D1, Cyclin D3, s6, Erk, Caspase2, RBBP, total S6
PCNA, Cyclin D1, Cyclin D3, s6, pErk, Akt, pAkt, Caspase2
PCNA, Cyclin D1, Cyclin D3, s6, pErk, Akt, pAkt, RBBP
PCNA, Cyclin D1, Cyclin D3, s6, pErk, Akt, pAkt, total S6
PCNA, Cyclin D1, Cyclin D3, s6, pErk, Akt, Caspase2, RBBP
PCNA, Cyclin D1, Cyclin D3, s6, pErk, Akt, Caspase2, total S6
PCNA, Cyclin D1, Cyclin D3, s6, pErk, Akt, RBBP, total S6
PCNA, Cyclin D1, Cyclin D3, s6, pErk, pAkt, Caspase2, RBBP
PCNA, Cyclin D1, Cyclin D3, s6, pErk, pAkt, Caspase2, total S6
PCNA, Cyclin D1, Cyclin D3, s6, pErk, pAkt, RBBP, total S6
PCNA, Cyclin D1, Cyclin D3, s6, pErk, Caspase2, RBBP, total S6
PCNA, Cyclin D1, Cyclin D3, s6, Akt, pAkt, Caspase2, RBBP
PCNA, Cyclin D1, Cyclin D3, s6, Akt, pAkt, Caspase2, total S6
PCNA, Cyclin D1, Cyclin D3, s6, Akt, pAkt, RBBP, total S6
PCNA, Cyclin D1, Cyclin D3, s6, Akt, Caspase2, RBBP, total S6
PCNA, Cyclin D1, Cyclin D3, s6, pAkt, Caspase2, RBBP, total S6
PCNA, Cyclin D1, Cyclin D3, pS6, Erk, pErk, Akt, pAkt
PCNA, Cyclin D1, Cyclin D3, pS6, Erk, pErk, Akt, Caspase2
PCNA, Cyclin D1, Cyclin D3, pS6, Erk, pErk, Akt, RBBP
PCNA, Cyclin D1, Cyclin D3, pS6, Erk, pErk, Akt, total S6
PCNA, Cyclin D1, Cyclin D3, pS6, Erk, pErk, pAkt, Caspase2
PCNA, Cyclin D1, Cyclin D3, pS6, Erk, pErk, pAkt, RBBP
PCNA, Cyclin D1, Cyclin D3, pS6, Erk, pErk, pAkt, total S6
PCNA, Cyclin D1, Cyclin D3, pS6, Erk, pErk, Caspase2, RBBP
PCNA, Cyclin D1, Cyclin D3, pS6, Erk, pErk, Caspase2, total S6
PCNA, Cyclin D1, Cyclin D3, pS6, Erk, pErk, RBBP, total S6
PCNA, Cyclin D1, Cyclin D3, pS6, Erk, Akt, pAkt, Caspase2
PCNA, Cyclin D1, Cyclin D3, pS6, Erk, Akt, pAkt, RBBP
PCNA, Cyclin D1, Cyclin D3, pS6, Erk, Akt, pAkt, total S6
PCNA, Cyclin D1, Cyclin D3, pS6, Erk, Akt, Caspase2, RBBP
PCNA, Cyclin D1, Cyclin D3, pS6, Erk, Akt, Caspase2, total S6
PCNA, Cyclin D1, Cyclin D3, pS6, Erk, Akt, RBBP, total S6
PCNA, Cyclin D1, Cyclin D3, pS6, Erk, pAkt, Caspase2, RBBP
PCNA, Cyclin D1, Cyclin D3, pS6, Erk, pAkt, Caspase2, total S6

PCNA, Cyclin D1, Cyclin D3, pS6, Erk, pAkt, RBBP, total S6
PCNA, Cyclin D1, Cyclin D3, pS6, Erk, Caspase2, RBBP, total S6
PCNA, Cyclin D1, Cyclin D3, pS6, pErk, Akt, pAkt, Caspase2
PCNA, Cyclin D1, Cyclin D3, pS6, pErk, Akt, pAkt, RBBP
PCNA, Cyclin D1, Cyclin D3, pS6, pErk, Akt, pAkt, total S6
PCNA, Cyclin D1, Cyclin D3, pS6, pErk, Akt, Caspase2, RBBP
PCNA, Cyclin D1, Cyclin D3, pS6, pErk, Akt, Caspase2, total S6
PCNA, Cyclin D1, Cyclin D3, pS6, pErk, Akt, RBBP, total S6
PCNA, Cyclin D1, Cyclin D3, pS6, pErk, pAkt, Caspase2, RBBP
PCNA, Cyclin D1, Cyclin D3, pS6, pErk, pAkt, Caspase2, total S6

PCNA, Cyclin D1, Cyclin D3, pS6, pErk, pAkt, RBBP, total S6
PCNA, Cyclin D1, Cyclin D3, pS6, pErk, Caspase2, RBBP, total S6

PCNA, Cyclin D1, Cyclin D3, pS6, Akt, pAkt, Caspase2, RBBP
PCNA, Cyclin D1, Cyclin D3, pS6, Akt, pAkt, Caspase2, total S6

Cyclin D1, pErk, pAkt, Caspase2, RBBP, total S6
Cyclin D1, Akt, pAkt, Caspase2, RBBP, total S6
Cyclin D3, MEK, s6, pS6, Erk, pErk
Cyclin D3, MEK, s6, pS6, Erk, Akt
Cyclin D3, MEK, s6, pS6, Erk, pAkt
Cyclin D3, MEK, s6, pS6, Erk, Caspase2
Cyclin D3, MEK, s6, pS6, Erk, RBBP
Cyclin D3, MEK, s6, pS6, Erk, total S6
Cyclin D3, MEK, s6, pS6, pErk, Akt
Cyclin D3, MEK, s6, pS6, pErk, pAkt
Cyclin D3, MEK, s6, pS6, pErk, Caspase2
Cyclin D3, MEK, s6, pS6, pErk, RBBP
Cyclin D3, MEK, s6, pS6, pErk, total S6
Cyclin D3, MEK, s6, pS6, Akt, pAkt
Cyclin D3, MEK, s6, pS6, Akt, Caspase2
Cyclin D3, MEK, s6, pS6, Akt, RBBP
Cyclin D3, MEK, s6, pS6, Akt, total S6
Cyclin D3, MEK, s6, pS6, pAkt, Caspase2
Cyclin D3, MEK, s6, pS6, pAkt, RBBP
Cyclin D3, MEK, s6, pS6, pAkt, total S6
Cyclin D3, MEK, s6, pS6, Caspase2, RBBP
Cyclin D3, MEK, s6, pS6, Caspase2, total S6
Cyclin D3, MEK, s6, pS6, RBBP, total S6
Cyclin D3, MEK, s6, Erk, pErk, Akt
Cyclin D3, MEK, s6, Erk, pErk, pAkt
Cyclin D3, MEK, s6, Erk, pErk, Caspase2
Cyclin D3, MEK, s6, Erk, pErk, RBBP
Cyclin D3, MEK, s6, Erk, pErk, total S6
Cyclin D3, MEK, s6, Erk, Akt, pAkt
Cyclin D3, MEK, s6, Erk, Akt, Caspase2
Cyclin D3, MEK, s6, Erk, Akt, RBBP
Cyclin D3, MEK, s6, Erk, Akt, total S6
Cyclin D3, MEK, s6, Erk, pAkt, Caspase2
Cyclin D3, MEK, s6, Erk, pAkt, RBBP
Cyclin D3, MEK, s6, Erk, pAkt, total S6
Cyclin D3, MEK, s6, Erk, Caspase2, RBBP
Cyclin D3, MEK, s6, Erk, Caspase2, total S6
Cyclin D3, MEK, s6, Erk, RBBP, total S6
Cyclin D3, MEK, s6, pErk, Akt, pAkt
Cyclin D3, MEK, s6, pErk, Akt, Caspase2
Cyclin D3, MEK, s6, pErk, Akt, RBBP
Cyclin D3, MEK, s6, pErk, Akt, total S6
Cyclin D3, MEK, s6, pErk, pAkt, Caspase2
Cyclin D3, MEK, s6, pErk, pAkt, RBBP
Cyclin D3, MEK, s6, pErk, pAkt, total S6
Cyclin D3, MEK, s6, pErk, Caspase2, RBBP
Cyclin D3, MEK, s6, pErk, Caspase2, total S6
Cyclin D3, MEK, s6, pErk, RBBP, total S6
Cyclin D3, MEK, s6, Akt, pAkt, Caspase2
Cyclin D3, MEK, s6, Akt, pAkt, RBBP
Cyclin D3, MEK, s6, Akt, pAkt, total S6
Cyclin D3, MEK, s6, Akt, Caspase2, RBBP
Cyclin D3, MEK, s6, Akt, Caspase2, total S6
Cyclin D3, MEK, s6, Akt, RBBP, total S6
Cyclin D3, MEK, s6, pAkt, Caspase2, RBBP
Cyclin D3, MEK, s6, pAkt, Caspase2, total S6
Cyclin D3, MEK, s6, pAkt, RBBP, total S6
Cyclin D3, MEK, s6, Caspase2, RBBP, total S6

Cyclin D3, MEK, pS6, Erk, pErk, Akt
Cyclin D3, MEK, pS6, Erk, pErk, pAkt
Cyclin D3, MEK, pS6, Erk, pErk, Caspase2
Cyclin D3, MEK, pS6, Erk, pErk, RBBP
Cyclin D3, MEK, pS6, Erk, pErk, total S6
Cyclin D3, MEK, pS6, Erk, Akt, pAkt
Cyclin D3, MEK, pS6, Erk, Akt, Caspase2
Cyclin D3, MEK, pS6, Erk, Akt, RBBP
Cyclin D3, MEK, pS6, Erk, Akt, total S6
Cyclin D3, MEK, pS6, Erk, pAkt, Caspase2
Cyclin D3, MEK, pS6, Erk, pAkt, RBBP
Cyclin D3, MEK, pS6, Erk, pAkt, total S6
Cyclin D3, MEK, pS6, Erk, Caspase2, RBBP
Cyclin D3, MEK, pS6, Erk, Caspase2, total S6

TABLE 1-continued

Examples of Single Markers and Combinations of Markers

PCNA, Cyclin D1, Cyclin D3, pS6, Akt, pAkt, RBBP, total S6
PCNA, Cyclin D1, Cyclin D3, pS6, Akt, Caspase2, RBBP, total S6
PCNA, Cyclin D1, Cyclin D3, pS6, pAkt, Caspase2, RBBP, total S6

PCNA, Cyclin D1, Cyclin D3, Erk, pErk, Akt, pAkt, Caspase2
PCNA, Cyclin D1, Cyclin D3, Erk, pErk, Akt, pAkt, RBBP
PCNA, Cyclin D1, Cyclin D3, Erk, pErk, Akt, pAkt, total S6
PCNA, Cyclin D1, Cyclin D3, Erk, pErk, Akt, Caspase2, RBBP
PCNA, Cyclin D1, Cyclin D3, Erk, pErk, Akt, Caspase2, total S6
PCNA, Cyclin D1, Cyclin D3, Erk, pErk, Akt, RBBP, total S6
PCNA, Cyclin D1, Cyclin D3, Erk, pErk, pAkt, Caspase2, RBBP PCNA, Cyclin D1, Cyclin D3, Erk, pErk, pAkt, Caspase2, total S6

PCNA, Cyclin D1, Cyclin D3, Erk, pErk, pAkt, RBBP, total S6

PCNA, Cyclin D1, Cyclin D3, Erk, pErk, Caspase2, RBBP, total S6
PCNA, Cyclin D1, Cyclin D3, Erk, Akt, pAkt, Caspase2, RBBP
PCNA, Cyclin D1, Cyclin D3, Erk, Akt, pAkt, Caspase2, total S6

PCNA, Cyclin D1, Cyclin D3, Erk, Akt, pAkt, RBBP, total S6
PCNA, Cyclin D1, Cyclin D3, Erk, Akt, Caspase2, RBBP, total S6

PCNA, Cyclin D1, Cyclin D3, Erk, pAkt, Caspase2, RBBP, total S6

PCNA, Cyclin D1, Cyclin D3, pErk, Akt, pAkt, Caspase2, RBBP

PCNA, Cyclin D1, Cyclin D3, pErk, Akt, pAkt, Caspase2, total S6

PCNA, Cyclin D1, Cyclin D3, pErk, Akt, pAkt, RBBP, total S6

PCNA, Cyclin D1, Cyclin D3, pErk, Akt, Caspase2, RBBP, total S6
PCNA, Cyclin D1, Cyclin D3, pErk, pAkt, Caspase2, RBBP, total S6

PCNA, Cyclin D1, Cyclin D3, Akt, pAkt, Caspase2, RBBP, total S6

PCNA, Cyclin D1, MEK, s6, pS6, Erk, pErk, Akt
PCNA, Cyclin D1, MEK, s6, pS6, Erk, pErk, pAkt
PCNA, Cyclin D1, MEK, s6, pS6, Erk, pErk, Caspase2
PCNA, Cyclin D1, MEK, s6, pS6, Erk, pErk, RBBP
PCNA, Cyclin D1, MEK, s6, pS6, Erk, pErk, total S6

PCNA, Cyclin D1, MEK, s6, pS6, Erk, Akt, pAkt

PCNA, Cyclin D1, MEK, s6, pS6, Erk, Akt, Caspase2
PCNA, Cyclin D1, MEK, s6, pS6, Erk, Akt, RBBP
PCNA, Cyclin D1, MEK, s6, pS6, Erk, Akt, total S6
PCNA, Cyclin D1, MEK, s6, pS6, Erk, pAkt, Caspase2
PCNA, Cyclin D 1, MEK, s6, pS6, Erk, pAkt, RBBP
PCNA, Cyclin D 1, MEK, s6, pS6, Erk, pAkt, total S6
PCNA, Cyclin D 1, MEK, s6, pS6, Erk, Caspase2, RBBP
PCNA, Cyclin D1, MEK, s6, pS6, Erk, Caspase2, total S6
PCNA, Cyclin D 1, MEK, s6, pS6, Erk, RBBP, total S6
PCNA, Cyclin D1, MEK, s6, pS6, pErk, Akt, pAkt
PCNA, Cyclin D1, MEK, s6, pS6, pErk, Akt, Caspase2
PCNA, Cyclin D 1, MEK, s6, pS6, pErk, Akt, RBBP
PCNA, Cyclin D1, MEK, s6, pS6, pErk, Akt, total S6
PCNA, Cyclin D1, MEK, s6, pS6, pErk, pAkt, Caspase2
PCNA, Cyclin D 1, MEK, s6, pS6, pErk, pAkt, RBBP
PCNA, Cyclin D 1, MEK, s6, pS6, pErk, pAkt, total S6
PCNA, Cyclin D1, MEK, s6, pS6, pErk, Caspase2, RBBP
PCNA, Cyclin D1, MEK, s6, pS6, pErk, Caspase2, total S6
PCNA, Cyclin D 1, MEK, s6, pS6, pErk, RBBP, total S6
PCNA, Cyclin D 1, MEK, s6, pS6, Akt, pAkt, Caspase2
PCNA, Cyclin D 1, MEK, s6, pS6, Akt, pAkt, RBBP
PCNA, Cyclin D 1, MEK, s6, pS6, Akt, pAkt, total S6
PCNA, Cyclin D 1, MEK, s6, pS6, Akt, Caspase2, RBBP
PCNA, Cyclin D1, MEK, s6, pS6, Akt, Caspase2, total S6
PCNA, Cyclin D1, MEK, s6, pS6, Akt, RBBP, total S6
PCNA, Cyclin D1, MEK, s6, pS6, pAkt, Caspase2, RBBP
PCNA, Cyclin D1, MEK, s6, pS6, pAkt, Caspase2, total S6
PCNA, Cyclin D1, MEK, s6, pS6, pAkt, RBBP, total S6
PCNA, Cyclin D 1, MEK, s6, pS6, Caspase2, RBBP, total S6
PCNA, Cyclin D 1, MEK, s6, Erk, pErk, Akt, pAkt
PCNA, Cyclin D 1, MEK, s6, Erk, pErk, Akt, Caspase2
PCNA, Cyclin D 1, MEK, s6, Erk, pErk, Akt, RBBP
PCNA, Cyclin D 1, MEK, s6, Erk, pErk, Akt, total S6
PCNA, Cyclin D1, MEK, s6, Erk, pErk, pAkt, Caspase2

Cyclin D3, MEK, pS6, Erk, RBBP, total S6
Cyclin D3, MEK, pS6, pErk, Akt, pAkt
Cyclin D3, MEK, pS6, pErk, Akt, Caspase2
Cyclin D3, MEK, pS6, pErk, Akt, RBBP
Cyclin D3, MEK, pS6, pErk, Akt, total S6
Cyclin D3, MEK, pS6, pErk, pAkt, Caspase2
Cyclin D3, MEK, pS6, pErk, pAkt, RBBP
Cyclin D3, MEK, pS6, pErk, pAkt, total S6
Cyclin D3, MEK, pS6, pErk, Caspase2, RBBP
Cyclin D3, MEK, pS6, pErk, Caspase2, total S6
Cyclin D3, MEK, pS6, pErk, RBBP, total S6
Cyclin D3, MEK, pS6, Akt, pAkt, Caspase2
Cyclin D3, MEK, pS6, Akt, pAkt, RBBP
Cyclin D3, MEK, pS6, Akt, pAkt, total S6
Cyclin D3, MEK, pS6, Akt, Caspase2, RBBP
Cyclin D3, MEK, pS6, Akt, Caspase2, total S6
Cyclin D3, MEK, pS6, Akt, RBBP, total S6
Cyclin D3, MEK, pS6, pAkt, Caspase2, RBBP
Cyclin D3, MEK, pS6, pAkt, Caspase2, total S6
Cyclin D3, MEK, pS6, pAkt, RBBP, total S6
Cyclin D3, MEK, pS6, Caspase2, RBBP, total S6
Cyclin D3, MEK, Erk, pErk, Akt, pAkt
Cyclin D3, MEK, Erk, pErk, Akt, Caspase2
Cyclin D3, MEK, Erk, pErk, Akt, RBBP
Cyclin D3, MEK, Erk, pErk, Akt, total S6
Cyclin D3, MEK, Erk, pErk, pAkt, Caspase2
Cyclin D3, MEK, Erk, pErk, pAkt, RBBP
Cyclin D3, MEK, Erk, pErk, pAkt, total S6
Cyclin D3, MEK, Erk, pErk, Caspase2, RBBP
Cyclin D3, MEK, Erk, pErk, Caspase2, total S6
Cyclin D3, MEK, Erk, pErk, RBBP, total S6
Cyclin D3, MEK, Erk, Akt, pAkt, Caspase2
Cyclin D3, MEK, Erk, Akt, pAkt, RBBP
Cyclin D3, MEK, Erk, Akt, pAkt, total S6
Cyclin D3, MEK, Erk, Akt, Caspase2, RBBP
Cyclin D3, MEK, Erk, Akt, Caspase2, total S6
Cyclin D3, MEK, Erk, Akt, RBBP, total S6
Cyclin D3, MEK, Erk, pAkt, Caspase2, RBBP
Cyclin D3, MEK, Erk, pAkt, Caspase2, total S6
Cyclin D3, MEK, Erk, pAkt, RBBP, total S6
Cyclin D3, MEK, Erk, Caspase2, RBBP, total S6
Cyclin D3, MEK, pErk, Akt, pAkt, Caspase2
Cyclin D3, MEK, pErk, Akt, pAkt, RBBP
Cyclin D3, MEK, pErk, Akt, pAkt, total S6
Cyclin D3, MEK, pErk, Akt, Caspase2, RBBP
Cyclin D3, MEK, pErk, Akt, Caspase2, total S6
Cyclin D3, MEK, pErk, Akt, RBBP, total S6
Cyclin D3, MEK, pErk, pAkt, Caspase2, RBBP
Cyclin D3, MEK, pErk, pAkt, Caspase2, total S6
Cyclin D3, MEK, pErk, pAkt, RBBP, total S6
Cyclin D3, MEK, pErk, Caspase2, RBBP, total S6
Cyclin D3, MEK, Akt, pAkt, Caspase2, RBBP
Cyclin D3, MEK, Akt, pAkt, Caspase2, total S6
Cyclin D3, MEK, Akt, pAkt, RBBP, total S6
Cyclin D3, MEK, Akt, Caspase2, RBBP, total S6
Cyclin D3, MEK, pAkt, Caspase2, RBBP, total S6
Cyclin D3, s6, pS6, Erk, pErk, Akt
Cyclin D3, s6, pS6, Erk, pErk, pAkt
Cyclin D3, s6, pS6, Erk, pErk, Caspase2
Cyclin D3, s6, pS6, Erk, pErk, RBBP
Cyclin D3, s6, pS6, Erk, pErk, total S6
Cyclin D3, s6, pS6, Erk, Akt, pAkt
Cyclin D3, s6, pS6, Erk, Akt, Caspase2
Cyclin D3, s6, pS6, Erk, Akt, RBBP TABLE 1-continued Examples of Single Markers and Combinations of Markers PCNA, Cyclin D1, MEK, s6, Erk, pErk, pAkt, RBBP
PCNA, Cyclin D 1, MEK, s6, Erk, pErk, pAkt, total S6
PCNA, Cyclin D 1, MEK, s6, Erk, pErk, Caspase2, RBBP
PCNA, Cyclin D1, MEK, s6, Erk, pErk, Caspase2, total S6
PCNA, Cyclin D1, MEK, s6, Erk, pErk, RBBP, total S6
PCNA, Cyclin D1, MEK, s6, Erk, Akt, pAkt, Caspase2
PCNA, Cyclin D1, MEK, s6, Erk, Akt, pAkt, RBBP
PCNA, Cyclin D1, MEK, s6, Erk, Akt, pAkt, total S6
PCNA, Cyclin D1, MEK, s6, Erk, Akt, Caspase2, RBBP
PCNA, Cyclin D1, MEK, s6, Erk, Akt, Caspase2, total S6
PCNA, Cyclin D1, MEK, s6, Erk, Akt, RBBP, total S6
PCNA, Cyclin D1, MEK, s6, Erk, pAkt, Caspase2, RBBP
PCNA, Cyclin D1, MEK, s6, Erk, pAkt, Caspase2, total S6
PCNA, Cyclin D1, MEK, s6, Erk, pAkt, RBBP, total S6
PCNA, Cyclin D1, MEK, s6, Erk, Caspase2, RBBP, total S6
PCNA, Cyclin D1, MEK, s6, pErk, Akt, pAkt, Caspase2
PCNA, Cyclin D1, MEK, s6, pErk, Akt, pAkt, RBBP
PCNA, Cyclin D1, MEK, s6, pErk, Akt, pAkt, total S6
PCNA, Cyclin D1, MEK, s6, pErk, Akt, Caspase2, RBBP
PCNA, Cyclin D1, MEK, s6, pErk, Akt, Caspase2, total S6
PCNA, Cyclin D1, MEK, s6, pErk, Akt, RBBP, total S6
PCNA, Cyclin D1, MEK, s6, pErk, pAkt, Caspase2, RBBP
PCNA, Cyclin D1, MEK, s6, pErk, pAkt, Caspase2, total S6
PCNA, Cyclin D1, MEK, s6, pErk, pAkt, RBBP, total S6
PCNA, Cyclin D1, MEK, s6, pErk, Caspase2, RBBP, total S6
PCNA, Cyclin D1, MEK, s6, Akt, pAkt, Caspase2, RBBP
PCNA, Cyclin D1, MEK, s6, Akt, pAkt, Caspase2, total S6
PCNA, Cyclin D1, MEK, s6, Akt, pAkt, RBBP, total S6
PCNA, Cyclin D1, MEK, s6, Akt, Caspase2, RBBP, total S6
PCNA, Cyclin D1, MEK, s6, pAkt, Caspase2, RBBP, total S6
PCNA, Cyclin D1, MEK, pS6, Erk, pErk, Akt, pAkt
PCNA, Cyclin D1, MEK, pS6, Erk, pErk, Akt, Caspase2
PCNA, Cyclin D1, MEK, pS6, Erk, pErk, Akt, RBBP
PCNA, Cyclin D1, MEK, pS6, Erk, pErk, Akt, total S6
PCNA, Cyclin D1, MEK, pS6, Erk, pErk, pAkt, Caspase2
PCNA, Cyclin D1, MEK, pS6, Erk, pErk, pAkt, RBBP
PCNA, Cyclin D1, MEK, pS6, Erk, pErk, pAkt, total S6
PCNA, Cyclin D1, MEK, pS6, Erk, pErk, Caspase2, RBBP
PCNA, Cyclin D1, MEK, pS6, Erk, pErk, Caspase2, total S6
PCNA, Cyclin D1, MEK, pS6, Erk, pErk, RBBP, total S6
PCNA, Cyclin D1, MEK, pS6, Erk, Akt, pAkt, Caspase2
PCNA, Cyclin D1, MEK, pS6, Erk, Akt, pAkt, RBBP
PCNA, Cyclin D1, MEK, pS6, Erk, Akt, pAkt, total S6
PCNA, Cyclin D1, MEK, pS6, Erk, Akt, Caspase2, RBBP
PCNA, Cyclin D1, MEK, pS6, Erk, Akt, Caspase2, total S6
PCNA, Cyclin D1, MEK, pS6, Erk, Akt, RBBP, total S6
PCNA, Cyclin D1, MEK, pS6, Erk, pAkt, Caspase2, RBBP
PCNA, Cyclin D1, MEK, pS6, Erk, pAkt, Caspase2, total S6
PCNA, Cyclin D1, MEK, pS6, Erk, pAkt, RBBP, total S6
PCNA, Cyclin D1, MEK, pS6, Erk, Caspase2, RBBP, total S6
PCNA, Cyclin D1, MEK, pS6, pErk, Akt, pAkt, Caspase2
PCNA, Cyclin D1, MEK, pS6, pErk, Akt, pAkt, RBBP
PCNA, Cyclin D1, MEK, pS6, pErk, Akt, pAkt, total S6
PCNA, Cyclin D1, MEK, pS6, pErk, Akt, Caspase2, RBBP
PCNA, Cyclin D1, MEK, pS6, pErk, Akt, Caspase2, total S6
PCNA, Cyclin D1, MEK, pS6, pErk, Akt, RBBP, total S6
PCNA, Cyclin D1, MEK, pS6, pErk, pAkt, Caspase2, RBBP
PCNA, Cyclin D1, MEK, pS6, pErk, pAkt, Caspase2, total S6
PCNA, Cyclin D1, MEK, pS6, pErk, pAkt, RBBP, total S6
PCNA, Cyclin D1, MEK, pS6, pErk, Caspase2, RBBP, total S6
PCNA, Cyclin D1, MEK, pS6, Akt, pAkt, Caspase2, RBBP
PCNA, Cyclin D1, MEK, pS6, Akt, pAkt, Caspase2, total S6
PCNA, Cyclin D1, MEK, pS6, Akt, pAkt, RBBP, total S6
PCNA, Cyclin D1, MEK, pS6, Akt, Caspase2, RBBP, total S6
PCNA, Cyclin D1, MEK, pS6, pAkt, Caspase2, RBBP, total S6
PCNA, Cyclin D1, MEK, Erk, pErk, Akt, pAkt, Caspase2
PCNA, Cyclin D1, MEK, Erk, pErk, Akt, pAkt, RBBP
PCNA, Cyclin D1, MEK, Erk, pErk, Akt, pAkt, total S6
PCNA, Cyclin D1, MEK, Erk, pErk, Akt, Caspase2, RBBP
PCNA, Cyclin D1, MEK, Erk, pErk, Akt, Caspase2, total S6
PCNA, Cyclin D1, MEK, Erk, pErk, Akt, RBBP, total S6
PCNA, Cyclin D1, MEK, Erk, pErk, pAkt, Caspase2, RBBP
PCNA, Cyclin D1, MEK, Erk, pErk, pAkt, Caspase2, total S6
PCNA, Cyclin D1, MEK, Erk, pErk, pAkt, RBBP, total S6
PCNA, Cyclin D1, MEK, Erk, pErk, Caspase2, RBBP, total S6
PCNA, Cyclin D1, MEK, Erk, Akt, pAkt, Caspase2, RBBP
PCNA, Cyclin D1, MEK, Erk, Akt, pAkt, Caspase2, total S6
PCNA, Cyclin D1, MEK, Erk, Akt, pAkt, RBBP, total S6
Cyclin D3, s6, pS6, Erk, Akt, total S6
Cyclin D3, s6, pS6, Erk, pAkt, Caspase2
Cyclin D3, s6, pS6, Erk, pAkt, RBBP
Cyclin D3, s6, pS6, Erk, pAkt, total S6
Cyclin D3, s6, pS6, Erk, Caspase2, RBBP
Cyclin D3, s6, pS6, Erk, Caspase2, total S6
Cyclin D3, s6, pS6, Erk, RBBP, total S6
Cyclin D3, s6, pS6, pErk, Akt, pAkt
Cyclin D3, s6, pS6, pErk, Akt, Caspase2
Cyclin D3, s6, pS6, pErk, Akt, RBBP
Cyclin D3, s6, pS6, pErk, Akt, total S6
Cyclin D3, s6, pS6, pErk, pAkt, Caspase2
Cyclin D3, s6, pS6, pErk, pAkt, RBBP
Cyclin D3, s6, pS6, pErk, pAkt, total S6
Cyclin D3, s6, pS6, pErk, Caspase2, RBBP
Cyclin D3, s6, pS6, pErk, Caspase2, total S6
Cyclin D3, s6, pS6, pErk, RBBP, total S6
Cyclin D3, s6, pS6, Akt, pAkt, Caspase2
Cyclin D3, s6, pS6, Akt, pAkt, RBBP
Cyclin D3, s6, pS6, Akt, pAkt, total S6
Cyclin D3, s6, pS6, Akt, Caspase2, RBBP
Cyclin D3, s6, pS6, Akt, Caspase2, total S6
Cyclin D3, s6, pS6, Akt, RBBP, total S6
Cyclin D3, s6, pS6, pAkt, Caspase2, RBBP
Cyclin D3, s6, pS6, pAkt, Caspase2, total S6
Cyclin D3, s6, pS6, pAkt, RBBP, total S6
Cyclin D3, s6, pS6, Caspase2, RBBP, total S6
Cyclin D3, s6, Erk, pErk, Akt, pAkt
Cyclin D3, s6, Erk, pErk, Akt, Caspase2
Cyclin D3, s6, Erk, pErk, Akt, RBBP
Cyclin D3, s6, Erk, pErk, Akt, total S6
Cyclin D3, s6, Erk, pErk, pAkt, Caspase2
Cyclin D3, s6, Erk, pErk, pAkt, RBBP
Cyclin D3, s6, Erk, pErk, pAkt, total S6
Cyclin D3, s6, Erk, pErk, Caspase2, RBBP
Cyclin D3, s6, Erk, pErk, Caspase2, total S6
Cyclin D3, s6, Erk, pErk, RBBP, total S6
Cyclin D3, s6, Erk, Akt, pAkt, Caspase2
Cyclin D3, s6, Erk, Akt, pAkt, RBBP
Cyclin D3, s6, Erk, Akt, pAkt, total S6
Cyclin D3, s6, Erk, Akt, Caspase2, RBBP
Cyclin D3, s6, Erk, Akt, Caspase2, total S6
Cyclin D3, s6, Erk, Akt, RBBP, total S6
Cyclin D3, s6, Erk, pAkt, Caspase2, RBBP
Cyclin D3, s6, Erk, pAkt, Caspase2, total S6
Cyclin D3, s6, Erk, pAkt, RBBP, total S6
Cyclin D3, s6, Erk, Caspase2, RBBP, total S6
Cyclin D3, s6, pErk, Akt, pAkt, Caspase2
Cyclin D3, s6, pErk, Akt, pAkt, RBBP
Cyclin D3, s6, pErk, Akt, pAkt, total S6
Cyclin D3, s6, pErk, Akt, Caspase2, RBBP
Cyclin D3, s6, pErk, Akt, Caspase2, total S6
Cyclin D3, s6, pErk, Akt, RBBP, total S6
Cyclin D3, s6, pErk, pAkt, Caspase2, RBBP
Cyclin D3, s6, pErk, pAkt, Caspase2, total S6
Cyclin D3, s6, pErk, pAkt, RBBP, total S6
Cyclin D3, s6, pErk, Caspase2, RBBP, total S6
Cyclin D3, s6, Akt, pAkt, Caspase2, RBBP
Cyclin D3, s6, Akt, pAkt, Caspase2, total S6
Cyclin D3, s6, Akt, pAkt, RBBP, total S6
Cyclin D3, s6, Akt, Caspase2, RBBP, total S6
Cyclin D3, s6, pAkt, Caspase2, RBBP, total S6
Cyclin D3, pS6, Erk, pErk, Akt, pAkt
Cyclin D3, pS6, Erk, pErk, Akt, Caspase2
Cyclin D3, pS6, Erk, pErk, Akt, RBBP
Cyclin D3, pS6, Erk, pErk, Akt, total S6
Cyclin D3, pS6, Erk, pErk, pAkt, Caspase2
Cyclin D3, pS6, Erk, pErk, pAkt, RBBP
Cyclin D3, pS6, Erk, pErk, pAkt, total S6
Cyclin D3, pS6, Erk, pErk, Caspase2, RBBP
Cyclin D3, pS6, Erk, pErk, Caspase2, total S6
Cyclin D3, pS6, Erk, pErk, RBBP, total S6
Cyclin D3, pS6, Erk, Akt, pAkt, Caspase2
Cyclin D3, pS6, Erk, Akt, pAkt, RBBP
Cyclin D3, pS6, Erk, Akt, pAkt, total S6
Cyclin D3, pS6, Erk, Akt, Caspase2, RBBP
Cyclin D3, pS6, Erk, Akt, Caspase2, total S6
Cyclin D3, pS6, Erk, Akt, RBBP, total S6

TABLE 1-continued

Examples of Single Markers and Combinations of Markers

PCNA, Cyclin D1, MEK, Erk, Akt, Caspase2, RBBP, total S6
PCNA, Cyclin D1, MEK, Erk, pAkt, Caspase2, RBBP, total S6
PCNA, Cyclin D1, MEK, pErk, Akt, pAkt, Caspase2, RBBP
PCNA, Cyclin D1, MEK, pErk, Akt, pAkt, Caspase2, total S6
PCNA, Cyclin D1, MEK, pErk, Akt, pAkt, RBBP, total S6
PCNA, Cyclin D1, MEK, pErk, Akt, Caspase2, RBBP, total S6
PCNA, Cyclin D1, MEK, pErk, pAkt, Caspase2, RBBP, total S6
PCNA, Cyclin D1, MEK, Akt, pAkt, Caspase2, RBBP, total S6
PCNA, Cyclin D1, s6, pS6, Erk, pErk, Akt, pAkt
PCNA, Cyclin D1, s6, pS6, Erk, pErk, Akt, Caspase2
PCNA, Cyclin D1, s6, pS6, Erk, pErk, Akt, RBBP
PCNA, Cyclin D1, s6, pS6, Erk, pErk, Akt, total S6
PCNA, Cyclin D1, s6, pS6, Erk, pErk, pAkt, Caspase2
PCNA, Cyclin D1, s6, pS6, Erk, pErk, pAkt, RBBP
PCNA, Cyclin D1, s6, pS6, Erk, pErk, pAkt, total S6
PCNA, Cyclin D1, s6, pS6, Erk, pErk, Caspase2, RBBP
PCNA, Cyclin D1, s6, pS6, Erk, pErk, Caspase2, total S6
PCNA, Cyclin D1, s6, pS6, Erk, pErk, RBBP, total S6
PCNA, Cyclin D1, s6, pS6, Erk, Akt, pAkt, Caspase2
PCNA, Cyclin D1, s6, pS6, Erk, Akt, pAkt, RBBP
PCNA, Cyclin D1, s6, pS6, Erk, Akt, pAkt, total S6
PCNA, Cyclin D1, s6, pS6, Erk, Akt, Caspase2, RBBP
PCNA, Cyclin D1, s6, pS6, Erk, Akt, Caspase2, total S6
PCNA, Cyclin D1, s6, pS6, Erk, Akt, RBBP, total S6
PCNA, Cyclin D1, s6, pS6, Erk, pAkt, Caspase2, RBBP
PCNA, Cyclin D1, s6, pS6, Erk, pAkt, Caspase2, total S6
PCNA, Cyclin D1, s6, pS6, Erk, pAkt, RBBP, total S6
PCNA, Cyclin D1, s6, pS6, Erk, Caspase2, RBBP, total S6
PCNA, Cyclin D1, s6, pS6, pErk, Akt, pAkt, Caspase2
PCNA, Cyclin D1, s6, pS6, pErk, Akt, pAkt, RBBP
PCNA, Cyclin D1, s6, pS6, pErk, Akt, pAkt, total S6
PCNA, Cyclin D1, s6, pS6, pErk, Akt, Caspase2, RBBP
PCNA, Cyclin D1, s6, pS6, pErk, Akt, Caspase2, total S6
PCNA, Cyclin D1, s6, pS6, pErk, Akt, RBBP, total S6
PCNA, Cyclin D1, s6, pS6, pErk, pAkt, Caspase2, RBBP
PCNA, Cyclin D1, s6, pS6, pErk, pAkt, Caspase2, total S6
PCNA, Cyclin D1, s6, pS6, pErk, pAkt, RBBP, total S6
PCNA, Cyclin D1, s6, pS6, pErk, Caspase2, RBBP, total S6
PCNA, Cyclin D1, s6, pS6, Akt, pAkt, Caspase2, RBBP
PCNA, Cyclin D1, s6, pS6, Akt, pAkt, Caspase2, total S6
PCNA, Cyclin D1, s6, pS6, Akt, pAkt, RBBP, total S6
PCNA, Cyclin D1, s6, pS6, Akt, Caspase2, RBBP, total S6
PCNA, Cyclin D1, s6, pS6, pAkt, Caspase2, RBBP, total S6
PCNA, Cyclin D1, s6, Erk, pErk, Akt, pAkt, Caspase2
PCNA, Cyclin D1, s6, Erk, pErk, Akt, pAkt, RBBP
PCNA, Cyclin D1, s6, Erk, pErk, Akt, pAkt, total S6
PCNA, Cyclin D1, s6, Erk, pErk, Akt, Caspase2, RBBP
PCNA, Cyclin D1, s6, Erk, pErk, Akt, Caspase2, total S6
PCNA, Cyclin D1, s6, Erk, pErk, Akt, RBBP, total S6
PCNA, Cyclin D1, s6, Erk, pErk, pAkt, Caspase2, RBBP
PCNA, Cyclin D1, s6, Erk, pErk, pAkt, Caspase2, total S6
PCNA, Cyclin D1, s6, Erk, pErk, pAkt, RBBP, total S6
PCNA, Cyclin D1, s6, Erk, pErk, Caspase2, RBBP, total S6
PCNA, Cyclin D1, s6, Erk, Akt, pAkt, Caspase2, RBBP
PCNA, Cyclin D1, s6, Erk, Akt, pAkt, Caspase2, total S6
PCNA, Cyclin D1, s6, Erk, Akt, pAkt, RBBP, total S6
PCNA, Cyclin D1, s6, Erk, Akt, Caspase2, RBBP, total S6
PCNA, Cyclin D1, s6, Erk, pAkt, Caspase2, RBBP, total S6
PCNA, Cyclin D1, s6, pErk, Akt, pAkt, Caspase2, RBBP
PCNA, Cyclin D1, s6, pErk, Akt, pAkt, Caspase2, total S6
PCNA, Cyclin D1, s6, pErk, Akt, pAkt, RBBP, total S6
PCNA, Cyclin D1, s6, pErk, Akt, Caspase2, RBBP, total S6
PCNA, Cyclin D1, s6, pErk, pAkt, Caspase2, RBBP, total S6
PCNA, Cyclin D1, s6, Akt, pAkt, Caspase2, RBBP, total S6
PCNA, Cyclin D1, pS6, Erk, pErk, Akt, pAkt, Caspase2
PCNA, Cyclin D1, pS6, Erk, pErk, Akt, pAkt, RBBP
PCNA, Cyclin D1, pS6, Erk, pErk, Akt, pAkt, total S6
PCNA, Cyclin D1, pS6, Erk, pErk, Akt, Caspase2, RBBP
PCNA, Cyclin D1, pS6, Erk, pErk, Akt, Caspase2, total S6
PCNA, Cyclin D1, pS6, Erk, pErk, Akt, RBBP, total S6
PCNA, Cyclin D1, pS6, Erk, pErk, pAkt, Caspase2, RBBP
PCNA, Cyclin D1, pS6, Erk, pErk, pAkt, Caspase2, total S6
PCNA, Cyclin D1, pS6, Erk, pErk, pAkt, RBBP, total S6
PCNA, Cyclin D1, pS6, Erk, pErk, Caspase2, RBBP, total S6
PCNA, Cyclin D1, pS6, Erk, Akt, pAkt, Caspase2, RBBP
PCNA, Cyclin D1, pS6, Erk, Akt, pAkt, Caspase2, total S6
PCNA, Cyclin D1, pS6, Erk, Akt, pAkt, RBBP, total S6
Cyclin D3, pS6, Erk, pAkt, Caspase2, RBBP
Cyclin D3, pS6, Erk, pAkt, Caspase2, total S6
Cyclin D3, pS6, Erk, pAkt, RBBP, total S6
Cyclin D3, pS6, Erk, Caspase2, RBBP, total S6
Cyclin D3, pS6, pErk, Akt, pAkt, Caspase2
Cyclin D3, pS6, pErk, Akt, pAkt, RBBP
Cyclin D3, pS6, pErk, Akt, pAkt, total S6
Cyclin D3, pS6, pErk, Akt, Caspase2, RBBP
Cyclin D3, pS6, pErk, Akt, Caspase2, total S6
Cyclin D3, pS6, pErk, Akt, RBBP, total S6
Cyclin D3, pS6, pErk, pAkt, Caspase2, RBBP
Cyclin D3, pS6, pErk, pAkt, Caspase2, total S6
Cyclin D3, pS6, pErk, pAkt, RBBP, total S6
Cyclin D3, pS6, pErk, Caspase2, RBBP, total S6
Cyclin D3, pS6, Akt, pAkt, Caspase2, RBBP
Cyclin D3, pS6, Akt, pAkt, Caspase2, total S6
Cyclin D3, pS6, Akt, pAkt, RBBP, total S6
Cyclin D3, pS6, Akt, Caspase2, RBBP, total S6
Cyclin D3, pS6, pAkt, Caspase2, RBBP, total S6
Cyclin D3, Erk, pErk, Akt, pAkt, Caspase2
Cyclin D3, Erk, pErk, Akt, pAkt, RBBP
Cyclin D3, pErk, Akt, pAkt, total S6
Cyclin D3, Erk, pErk, Akt, Caspase2, RBBP
Cyclin D3, Erk, pErk, Akt, Caspase2, total S6
Cyclin D3, Erk, pErk, Akt, RBBP, total S6
Cyclin D3, Erk, pErk, pAkt, Caspase2, RBBP
Cyclin D3, Erk, pErk, pAkt, Caspase2, total S6
Cyclin D3, Erk, pErk, pAkt, RBBP, total S6
Cyclin D3, Erk, pErk, Caspase2, RBBP, total S6
Cyclin D3, Erk, Akt, pAkt, Caspase2, RBBP
Cyclin D3, Erk, Akt, pAkt, Caspase2, total S6
Cyclin D3, Erk, Akt, pAkt, RBBP, total S6
Cyclin D3, Erk, Akt, Caspase2, RBBP, total S6
Cyclin D3, Erk, pAkt, Caspase2, RBBP, total S6
Cyclin D3, pErk, Akt, pAkt, Caspase2, RBBP
Cyclin D3, pErk, Akt, pAkt, Caspase2, total S6
Cyclin D3, pErk, Akt, pAkt, RBBP, total S6
Cyclin D3, pErk, Akt, Caspase2, RBBP, total S6
Cyclin D3, pErk, pAkt, Caspase2, RBBP, total S6
Cyclin D3, Akt, pAkt, Caspase2, RBBP, total S6
MEK, s6, pS6, Erk, pErk, Akt
MEK, s6, pS6, Erk, pErk, pAkt
MEK, s6, pS6, Erk, pErk, Caspase2
MEK, s6, pS6, Erk, pErk, RBBP
MEK, s6, pS6, Erk, pErk, total S6
MEK, s6, pS6, Erk, Akt, pAkt
MEK, s6, pS6, Erk, Akt, Caspase2
MEK, s6, pS6, Erk, Akt, RBBP
MEK, s6, pS6, Erk, Akt, total S6
MEK, s6, pS6, Erk, pAkt, Caspase2
MEK, s6, pS6, Erk, pAkt, RBBP
MEK, s6, pS6, Erk, pAkt, total S6
MEK, s6, pS6, Erk, Caspase2, RBBP
MEK, s6, pS6, Erk, Caspase2, total S6
MEK, s6, pS6, Erk, RBBP, total S6
MEK, s6, pS6, pErk, Akt, pAkt
MEK, s6, pS6, pErk, Akt, Caspase2
MEK, s6, pS6, pErk, Akt, RBBP
MEK, s6, pS6, pErk, Akt, total S6
MEK, s6, pS6, pErk, pAkt, Caspase2
MEK, s6, pS6, pErk, pAkt, RBBP
MEK, s6, pS6, pErk, pAkt, total S6
MEK, s6, pS6, pErk, Caspase2, RBBP
MEK, s6, pS6, pErk, Caspase2, total S6
MEK, s6, pS6, pErk, RBBP, total S6
MEK, s6, pS6, Akt, pAkt, Caspase2
MEK, s6, pS6, Akt, pAkt, RBBP
MEK, s6, pS6, Akt, pAkt, total S6
MEK, s6, pS6, Akt, Caspase2, RBBP
MEK, s6, pS6, Akt, Caspase2, total S6
MEK, s6, pS6, Akt, RBBP, total S6
MEK, s6, pS6, pAkt, Caspase2, RBBP
MEK, s6, pS6, pAkt, Caspase2, total S6
MEK, s6, pS6, pAkt, RBBP, total S6
MEK, s6, pS6, Caspase2, RBBP, total S6
MEK, s6, Erk, pErk, Akt, pAkt
MEK, s6, Erk, pErk, Akt, Caspase2

TABLE 1-continued

Examples of Single Markers and Combinations of Markers

PCNA, Cyclin D1, pS6, Erk, Akt, Caspase2, RBBP, total S6
PCNA, Cyclin D1, pS6, Erk, pAkt, Caspase2, RBBP, total S6
PCNA, Cyclin D1, pS6, pErk, Akt, pAkt, Caspase2, RBBP
PCNA, Cyclin D1, pS6, pErk, Akt, pAkt, Caspase2, total S6
PCNA, Cyclin D1, pS6, pErk, Akt, pAkt, RBBP, total S6
PCNA, Cyclin D1, pS6, pErk, Akt, Caspase2, RBBP, total S6
PCNA, Cyclin D1, pS6, pErk, pAkt, Caspase2, RBBP, total S6
PCNA, Cyclin D1, pS6, Akt, pAkt, Caspase2, RBBP, total S6
PCNA, Cyclin D1, Erk, pErk, Akt, pAkt, Caspase2, RBBP
PCNA, Cyclin D1, Erk, pErk, Akt, pAkt, Caspase2, total S6
PCNA, Cyclin D1, Erk, pErk, Akt, pAkt, RBBP, total S6
PCNA, Cyclin D1, Erk, pErk, Akt, Caspase2, RBBP, total S6
PCNA, Cyclin D1, Erk, pErk, pAkt, Caspase2, RBBP, total S6
PCNA, Cyclin D1, Erk, Akt, pAkt, Caspase2, RBBP, total S6
PCNA, Cyclin D1, pErk, Akt, pAkt, Caspase2, RBBP, total S6
PCNA, Cyclin D3, MEK, s6, pS6, Erk, pErk, Akt
PCNA, Cyclin D3, MEK, s6, pS6, Erk, pErk, pAkt
PCNA, Cyclin D3, MEK, s6, pS6, Erk, pErk, Caspase2
PCNA, Cyclin D3, MEK, s6, pS6, Erk, pErk, RBBP
PCNA, Cyclin D3, MEK, s6, pS6, Erk, pErk, total S6
PCNA, Cyclin D3, MEK, s6, pS6, Erk, Akt, pAkt
PCNA, Cyclin D3, MEK, s6, pS6, Erk, Akt, Caspase2
PCNA, Cyclin D3, MEK, s6, pS6, Erk, Akt, RBBP
PCNA, Cyclin D3, MEK, s6, pS6, Erk, Akt, total S6
PCNA, Cyclin D3, MEK, s6, pS6, Erk, pAkt, Caspase2
PCNA, Cyclin D3, MEK, s6, pS6, Erk, pAkt, RBBP
PCNA, Cyclin D3, MEK, s6, pS6, Erk, pAkt, total S6
PCNA, Cyclin D3, MEK, s6, pS6, Erk, Caspase2, RBBP
PCNA, Cyclin D3, MEK, s6, pS6, Erk, Caspase2, total S6
PCNA, Cyclin D3, MEK, s6, pS6, Erk, RBBP, total S6
PCNA, Cyclin D3, MEK, s6, pS6, pErk, Akt, pAkt
PCNA, Cyclin D3, MEK, s6, pS6, pErk, Akt, Caspase2
PCNA, Cyclin D3, MEK, s6, pS6, pErk, Akt, RBBP
PCNA, Cyclin D3, MEK, s6, pS6, pErk, Akt, total S6
PCNA, Cyclin D3, MEK, s6, pS6, pErk, pAkt, Caspase2
PCNA, Cyclin D3, MEK, s6, pS6, pErk, pAkt, RBBP
PCNA, Cyclin D3, MEK, s6, pS6, pErk, pAkt, total S6
PCNA, Cyclin D3, MEK, s6, pS6, pErk, Caspase2, RBBP
PCNA, Cyclin D3, MEK, s6, pS6, pErk, Caspase2, total S6
PCNA, Cyclin D3, MEK, s6, pS6, pErk, RBBP, total S6
PCNA, Cyclin D3, MEK, s6, pS6, Akt, pAkt, Caspase2
PCNA, Cyclin D3, MEK, s6, pS6, Akt, pAkt, RBBP
PCNA, Cyclin D3, MEK, s6, pS6, Akt, pAkt, total S6
PCNA, Cyclin D3, MEK, s6, pS6, Akt, Caspase2, RBBP
PCNA, Cyclin D3, MEK, s6, pS6, Akt, Caspase2, total S6
PCNA, Cyclin D3, MEK, s6, pS6, Akt, RBBP, total S6
PCNA, Cyclin D3, MEK, s6, pS6, pAkt, Caspase2, RBBP
PCNA, Cyclin D3, MEK, s6, pS6, pAkt, Caspase2, total S6
PCNA, Cyclin D3, MEK, s6, pS6, pAkt, RBBP, total S6
PCNA, Cyclin D3, MEK, s6, pS6, Caspase2, RBBP, total S6
PCNA, Cyclin D3, MEK, s6, Erk, pErk, Akt, pAkt
PCNA, Cyclin D3, MEK, s6, Erk, pErk, Akt, Caspase2
PCNA, Cyclin D3, MEK, s6, Erk, pErk, Akt, RBBP
PCNA, Cyclin D3, MEK, s6, Erk, pErk, Akt, total S6
PCNA, Cyclin D3, MEK, s6, Erk, pErk, pAkt, Caspase2
PCNA, Cyclin D3, MEK, s6, Erk, pErk, pAkt, RBBP
PCNA, Cyclin D3, MEK, s6, Erk, pErk, pAkt, total S6
PCNA, Cyclin D3, MEK, s6, Erk, pErk, Caspase2, RBBP
PCNA, Cyclin D3, MEK, s6, Erk, pErk, Caspase2, total S6
PCNA, Cyclin D3, MEK, s6, Erk, pErk, RBBP, total S6
PCNA, Cyclin D3, MEK, s6, Erk, Akt, pAkt, Caspase2
PCNA, Cyclin D3, MEK, s6, Erk, Akt, pAkt, RBBP
PCNA, Cyclin D3, MEK, s6, Erk, Akt, pAkt, total S6
PCNA, Cyclin D3, MEK, s6, Erk, Akt, Caspase2, RBBP
PCNA, Cyclin D3, MEK, s6, Erk, Akt, Caspase2, total S6
PCNA, Cyclin D3, MEK, s6, Erk, Akt, RBBP, total S6
PCNA, Cyclin D3, MEK, s6, Erk, pAkt, Caspase2, RBBP
PCNA, Cyclin D3, MEK, s6, Erk, pAkt, Caspase2, total S6
PCNA, Cyclin D3, MEK, s6, Erk, pAkt, RBBP, total S6
PCNA, Cyclin D3, MEK, s6, Erk, Caspase2, RBBP, total S6
PCNA, Cyclin D3, MEK, s6, pErk, Akt, pAkt, Caspase2
PCNA, Cyclin D3, MEK, s6, pErk, Akt, pAkt, RBBP
PCNA, Cyclin D3, MEK, s6, pErk, Akt, pAkt, total S6
PCNA, Cyclin D3, MEK, s6, pErk, Akt, Caspase2, RBBP
PCNA, Cyclin D3, MEK, s6, pErk, Akt, Caspase2, total S6
PCNA, Cyclin D3, MEK, s6, pErk, Akt, RBBP, total S6
PCNA, Cyclin D3, MEK, s6, pErk, pAkt, Caspase2, RBBP
PCNA, Cyclin D3, MEK, s6, pErk, pAkt, Caspase2, total S6

MEK, s6, Erk, pErk, Akt, RBBP
MEK, s6, Erk, pErk, Akt, total S6
MEK, s6, Erk, pErk, pAkt, Caspase2
MEK, s6, Erk, pErk, pAkt, RBBP
MEK, s6, Erk, pErk, pAkt, total S6
MEK, s6, Erk, pErk, Caspase2, RBBP
MEK, s6, Erk, pErk, Caspase2, total S6
MEK, s6, Erk, pErk, RBBP, total S6
MEK, s6, Erk, Akt, pAkt, Caspase2
MEK, s6, Erk, Akt, pAkt, RBBP
MEK, s6, Erk, Akt, pAkt, total S6
MEK, s6, Erk, Akt, Caspase2, RBBP
MEK, s6, Erk, Akt, Caspase2, total S6
MEK, s6, Erk, Akt, RBBP, total S6
MEK, s6, Erk, pAkt, Caspase2, RBBP
MEK, s6, Erk, pAkt, Caspase2, total S6
MEK, s6, Erk, pAkt, RBBP, total S6
MEK, s6, Erk, Caspase2, RBBP, total S6
MEK, s6, pErk, Akt, pAkt, Caspase2
MEK, s6, pErk, Akt, pAkt, RBBP
MEK, s6, pErk, Akt, pAkt, total S6
MEK, s6, pErk, Akt, Caspase2, RBBP
MEK, s6, pErk, Akt, Caspase2, total S6
MEK, s6, pErk, Akt, RBBP, total S6
MEK, s6, pErk, pAkt, Caspase2, RBBP
MEK, s6, pErk, pAkt, Caspase2, total S6
MEK, s6, pErk, pAkt, RBBP, total S6
MEK, s6, pErk, Caspase2, RBBP, total S6
MEK, s6, Akt, pAkt, Caspase2, RBBP
MEK, s6, Akt, pAkt, Caspase2, total S6
MEK, s6, Akt, pAkt, RBBP, total S6
MEK, s6, Akt, Caspase2, RBBP, total S6
MEK, s6, pAkt, Caspase2, RBBP, total S6
MEK, pS6, Erk, pErk, Akt, pAkt
MEK, pS6, Erk, pErk, Akt, Caspase2
MEK, pS6, Erk, pErk, Akt, RBBP
MEK, pS6, Erk, pErk, Akt, total S6
MEK, pS6, Erk, pErk, pAkt, Caspase2
MEK, pS6, Erk, pErk, pAkt, RBBP
MEK, pS6, Erk, pErk, pAkt, total S6
MEK, pS6, Erk, pErk, Caspase2, RBBP
MEK, pS6, Erk, pErk, Caspase2, total S6
MEK, pS6, Erk, pErk, RBBP, total S6
MEK, pS6, Erk, Akt, pAkt, Caspase2
MEK, pS6, Erk, Akt, pAkt, RBBP
MEK, pS6, Erk, Akt, pAkt, total S6
MEK, pS6, Erk, Akt, Caspase2, RBBP
MEK, pS6, Erk, Akt, Caspase2, total S6
MEK, pS6, Erk, Akt, RBBP, total S6
MEK, pS6, Erk, pAkt, Caspase2, RBBP
MEK, pS6, Erk, pAkt, Caspase2, total S6
MEK, pS6, Erk, pAkt, RBBP, total S6
MEK, pS6, Erk, Caspase2, RBBP, total S6
MEK, pS6, pErk, Akt, pAkt, Caspase2
MEK, pS6, pErk, Akt, pAkt, RBBP
MEK, pS6, pErk, Akt, pAkt, total S6
MEK, pS6, pErk, Akt, Caspase2, RBBP
MEK, pS6, pErk, Akt, Caspase2, total S6
MEK, pS6, pErk, Akt, RBBP, total S6
MEK, pS6, pErk, pAkt, Caspase2, RBBP
MEK, pS6, pErk, pAkt, Caspase2, total S6
MEK, pS6, pErk, pAkt, RBBP, total S6
MEK, pS6, pErk, Caspase2, RBBP, total S6
MEK, pS6, Akt, pAkt, Caspase2, RBBP
MEK, pS6, Akt, pAkt, Caspase2, total S6
MEK, pS6, Akt, pAkt, RBBP, total S6
MEK, pS6, Akt, Caspase2, RBBP, total S6
MEK, pS6, pAkt, Caspase2, RBBP, total S6
MEK, Erk, pErk, Akt, pAkt, Caspase2
MEK, Erk, pErk, Akt, pAkt, RBBP
MEK, Erk, pErk, Akt, pAkt, total S6
MEK, Erk, pErk, Akt, Caspase2, RBBP
MEK, Erk, pErk, Akt, Caspase2, total S6
MEK, Erk, pErk, Akt, RBBP, total S6
MEK, Erk, pErk, pAkt, Caspase2, RBBP
MEK, Erk, pErk, pAkt, Caspase2, total S6
MEK, Erk, pErk, pAkt, RBBP, total S6
MEK, Erk, pErk, Caspase2, RBBP, total S6

TABLE 1-continued

Examples of Single Markers and Combinations of Markers

PCNA, Cyclin D3, MEK, s6, pErk, pAkt, RBBP, total S6
PCNA, Cyclin D3, MEK, s6, pErk, Caspase2, RBBP, total S6
PCNA, Cyclin D3, MEK, s6, Akt, pAkt, Caspase2, RBBP
PCNA, Cyclin D3, MEK, s6, Akt, pAkt, Caspase2, total S6
PCNA, Cyclin D3, MEK, s6, Akt, pAkt, RBBP, total S6
PCNA, Cyclin D3, MEK, s6, Akt, Caspase2, RBBP, total S6
PCNA, Cyclin D3, MEK, s6, pAkt, Caspase2, RBBP, total S6
PCNA, Cyclin D3, MEK, pS6, Erk, pErk, Akt, pAkt
PCNA, Cyclin D3, MEK, pS6, Erk, pErk, Akt, Caspase2
PCNA, Cyclin D3, MEK, pS6, Erk, pErk, Akt, RBBP
PCNA, Cyclin D3, MEK, pS6, Erk, pErk, Akt, total S6
PCNA, Cyclin D3, MEK, pS6, Erk, pErk, pAkt, Caspase2
PCNA, Cyclin D3, MEK, pS6, Erk, pErk, pAkt, RBBP
PCNA, Cyclin D3, MEK, pS6, Erk, pErk, pAkt, total S6
PCNA, Cyclin D3, MEK, pS6, Erk, pErk, Caspase2, RBBP
PCNA, Cyclin D3, MEK, pS6, Erk, pErk, Caspase2, total S6
PCNA, Cyclin D3, MEK, pS6, Erk, pErk, RBBP, total S6
PCNA, Cyclin D3, MEK, pS6, Erk, Akt, pAkt, Caspase2
PCNA, Cyclin D3, MEK, pS6, Erk, Akt, pAkt, RBBP
PCNA, Cyclin D3, MEK, pS6, Erk, Akt, pAkt, total S6
PCNA, Cyclin D3, MEK, pS6, Erk, Akt, Caspase2, RBBP
PCNA, Cyclin D3, MEK, pS6, Erk, Akt, Caspase2, total S6
PCNA, Cyclin D3, MEK, pS6, Erk, Akt, RBBP, total S6
PCNA, Cyclin D3, MEK, pS6, Erk, pAkt, Caspase2, RBBP
PCNA, Cyclin D3, MEK, pS6, Erk, pAkt, Caspase2, total S6
PCNA, Cyclin D3, MEK, pS6, Erk, pAkt, RBBP, total S6
PCNA, Cyclin D3, MEK, pS6, Erk, Caspase2, RBBP, total S6
PCNA, Cyclin D3, MEK, pS6, pErk, Akt, pAkt, Caspase2
PCNA, Cyclin D3, MEK, pS6, pErk, Akt, pAkt, RBBP
PCNA, Cyclin D3, MEK, pS6, pErk, Akt, pAkt, total S6
PCNA, Cyclin D3, MEK, pS6, pErk, Akt, Caspase2, RBBP
PCNA, Cyclin D3, MEK, pS6, pErk, Akt, Caspase2, total S6
PCNA, Cyclin D3, MEK, pS6, pErk, Akt, RBBP, total S6
PCNA, Cyclin D3, MEK, pS6, pErk, pAkt, Caspase2, RBBP
PCNA, Cyclin D3, MEK, pS6, pErk, pAkt, Caspase2, total S6
PCNA, Cyclin D3, MEK, pS6, pErk, pAkt, RBBP, total S6
PCNA, Cyclin D3, MEK, pS6, pErk, Caspase2, RBBP, total S6
PCNA, Cyclin D3, MEK, pS6, Akt, pAkt, Caspase2, RBBP
PCNA, Cyclin D3, MEK, pS6, Akt, pAkt, Caspase2, total S6
PCNA, Cyclin D3, MEK, pS6, Akt, pAkt, RBBP, total S6
PCNA, Cyclin D3, MEK, pS6, Akt, Caspase2, RBBP, total S6
PCNA, Cyclin D3, MEK, pS6, pAkt, Caspase2, RBBP, total S6
PCNA, Cyclin D3, MEK, Erk, pErk, Akt, pAkt, Caspase2
PCNA, Cyclin D3, MEK, Erk, pErk, Akt, pAkt, RBBP
PCNA, Cyclin D3, MEK, Erk, pErk, Akt, pAkt, total S6
PCNA, Cyclin D3, MEK, Erk, pErk, Akt, Caspase2, RBBP
PCNA, Cyclin D3, MEK, Erk, pErk, Akt, Caspase2, total S6
PCNA, Cyclin D3, MEK, Erk, pErk, Akt, RBBP, total S6
PCNA, Cyclin D3, MEK, Erk, pErk, pAkt, Caspase2, RBBP
PCNA, Cyclin D3, MEK, Erk, pErk, pAkt, Caspase2, total S6
PCNA, Cyclin D3, MEK, Erk, pErk, pAkt, RBBP, total S6
PCNA, Cyclin D3, MEK, Erk, pErk, Caspase2, RBBP, total S6
PCNA, Cyclin D3, MEK, Erk, Akt, pAkt, Caspase2, RBBP
PCNA, Cyclin D3, MEK, Erk, Akt, pAkt, Caspase2, total S6
PCNA, Cyclin D3, MEK, Erk, Akt, pAkt, RBBP, total S6
PCNA, Cyclin D3, MEK, Erk, Akt, Caspase2, RBBP, total S6
PCNA, Cyclin D3, MEK, Erk, pAkt, Caspase2, RBBP, total S6
PCNA, Cyclin D3, MEK, pErk, Akt, pAkt, Caspase2, RBBP
PCNA, Cyclin D3, MEK, pErk, Akt, pAkt, Caspase2, total S6
PCNA, Cyclin D3, MEK, pErk, Akt, pAkt, RBBP, total S6
PCNA, Cyclin D3, MEK, pErk, Akt, Caspase2, RBBP, total S6
PCNA, Cyclin D3, MEK, pErk, pAkt, Caspase2, RBBP, total S6
PCNA, Cyclin D3, MEK, Akt, pAkt, Caspase2, RBBP, total S6
PCNA, Cyclin D3, s6, pS6, Erk, pErk, Akt, pAkt
PCNA, Cyclin D3, s6, pS6, Erk, pErk, Akt, Caspase2
PCNA, Cyclin D3, s6, pS6, Erk, pErk, Akt, RBBP
PCNA, Cyclin D3, s6, pS6, Erk, pErk, Akt, total S6
PCNA, Cyclin D3, s6, pS6, Erk, pErk, pAkt, Caspase2
PCNA, Cyclin D3, s6, pS6, Erk, pErk, pAkt, RBBP
PCNA, Cyclin D3, s6, pS6, Erk, pErk, pAkt, total S6
PCNA, Cyclin D3, s6, pS6, Erk, pErk, Caspase2, RBBP
PCNA, Cyclin D3, s6, pS6, Erk, pErk, Caspase2, total S6
PCNA, Cyclin D3, s6, pS6, Erk, pErk, RBBP, total S6
PCNA, Cyclin D3, s6, pS6, Erk, Akt, pAkt, Caspase2
PCNA, Cyclin D3, s6, pS6, Erk, Akt, pAkt, RBBP
PCNA, Cyclin D3, s6, pS6, Erk, Akt, pAkt, total S6
PCNA, Cyclin D3, s6, pS6, Erk, Akt, Caspase2, RBBP
PCNA, Cyclin D3, s6, pS6, Erk, Akt, Caspase2, total S6

MEK, Erk, Akt, pAkt, Caspase2, RBBP
MEK, Erk, Akt, pAkt, Caspase2, total S6
MEK, Erk, Akt, pAkt, RBBP, total S6
MEK, Erk, Akt, Caspase2, RBBP, total S6
MEK, Erk, pAkt, Caspase2, RBBP, total S6
MEK, pErk, Akt, pAkt, Caspase2, RBBP
MEK, pErk, Akt, pAkt, Caspase2, total S6
MEK, pErk, Akt, pAkt, RBBP, total S6
MEK, pErk, Akt, Caspase2, RBBP, total S6
MEK, pErk, pAkt, Caspase2, RBBP, total S6
MEK, Akt, pAkt, Caspase2, RBBP, total S6
s6, pS6, Erk, pErk, Akt, pAkt
s6, pS6, Erk, pErk, Akt, Caspase2
s6, pS6, Erk, pErk, Akt, RBBP
s6, pS6, Erk, pErk, Akt, total S6
s6, pS6, Erk, pErk, pAkt, Caspase2
s6, pS6, Erk, pErk, pAkt, RBBP
s6, pS6, Erk, pErk, pAkt, total S6
s6, pS6, Erk, pErk, Caspase2, RBBP
s6, pS6, Erk, pErk, Caspase2, total S6
s6, pS6, Erk, pErk, RBBP, total S6
s6, pS6, Erk, Akt, pAkt, Caspase2
s6, pS6, Erk, Akt, pAkt, RBBP
s6, pS6, Erk, Akt, pAkt, total S6
s6, pS6, Erk, Akt, Caspase2, RBBP
s6, pS6, Erk, Akt, Caspase2, total S6
s6, pS6, Erk, Akt, RBBP, total S6
s6, pS6, Erk, pAkt, Caspase2, RBBP
s6, pS6, Erk, pAkt, Caspase2, total S6
s6, pS6, Erk, pAkt, RBBP, total S6
s6, pS6, Erk, Caspase2, RBBP, total S6
s6, pS6, pErk, Akt, pAkt, Caspase2
s6, pS6, pErk, Akt, pAkt, RBBP
s6, pS6, pErk, Akt, pAkt, total S6
s6, pS6, pErk, Akt, Caspase2, RBBP
s6, pS6, pErk, Akt, Caspase2, total S6
s6, pS6, pErk, Akt, RBBP, total S6
s6, pS6, pErk, pAkt, Caspase2, RBBP
s6, pS6, pErk, pAkt, Caspase2, total S6
s6, pS6, pErk, pAkt, RBBP, total S6
s6, pS6, pErk, Caspase2, RBBP, total S6
s6, pS6, Akt, pAkt, Caspase2, RBBP
s6, pS6, Akt, pAkt, Caspase2, total S6
s6, pS6, Akt, pAkt, RBBP, total S6
s6, pS6, Akt, Caspase2, RBBP, total S6
s6, pS6, pAkt, Caspase2, RBBP, total S6
s6, Erk, pErk, Akt, pAkt, Caspase2
s6, Erk, pErk, Akt, pAkt, RBBP
s6, Erk, pErk, Akt, pAkt, total S6
s6, Erk, pErk, Akt, Caspase2, RBBP
s6, Erk, pErk, Akt, Caspase2, total S6
s6, Erk, pErk, Akt, RBBP, total S6
s6, Erk, pErk, pAkt, Caspase2, RBBP
s6, Erk, pErk, pAkt, Caspase2, total S6
s6, Erk, pErk, pAkt, RBBP, total S6
s6, Erk, pErk, Caspase2, RBBP, total S6
s6, Erk, Akt, pAkt, Caspase2, RBBP
s6, Erk, Akt, pAkt, Caspase2, total S6
s6, Erk, Akt, pAkt, RBBP, total S6
s6, Erk, Akt, Caspase2, RBBP, total S6
s6, Erk, pAkt, Caspase2, RBBP, total S6
s6, pErk, Akt, pAkt, Caspase2, RBBP
s6, pErk, Akt, pAkt, Caspase2, total S6
s6, pErk, Akt, pAkt, RBBP, total S6
s6, pErk, Akt, Caspase2, RBBP, total S6
s6, pErk, pAkt, Caspase2, RBBP, total S6
s6, Akt, pAkt, Caspase2, RBBP, total S6
pS6, Erk, pErk, Akt, pAkt, Caspase2
pS6, Erk, pErk, Akt, pAkt, RBBP
pS6, Erk, pErk, Akt, pAkt, total S6
pS6, Erk, pErk, Akt, Caspase2, RBBP
pS6, Erk, pErk, Akt, Caspase2, total S6
pS6, Erk, pErk, Akt, RBBP, total S6
pS6, Erk, pErk, pAkt, Caspase2, RBBP
pS6, Erk, pErk, pAkt, Caspase2, total S6
pS6, Erk, pErk, pAkt, RBBP, total S6
pS6, Erk, pErk, Caspase2, RBBP, total S6
pS6, Erk, Akt, pAkt, Caspase2, RBBP TABLE 1-continued Examples of Single Markers and Combinations of Markers PCNA, Cyclin D3, s6, pS6, Erk, Akt, RBBP, total S6
PCNA, Cyclin D3, s6, pS6, Erk, pAkt, Caspase2, RBBP
PCNA, Cyclin D3, s6, pS6, Erk, pAkt, Caspase2, total S6
PCNA, Cyclin D3, s6, pS6, Erk, pAkt, RBBP, total S6
PCNA, Cyclin D3, s6, pS6, Erk, Caspase2, RBBP, total S6
PCNA, Cyclin D3, s6, pS6, pErk, Akt, pAkt, Caspase2
PCNA, Cyclin D3, s6, pS6, pErk, Akt, pAkt, RBBP
PCNA, Cyclin D3, s6, pS6, pErk, Akt, pAkt, total S6
PCNA, Cyclin D3, s6, pS6, pErk, Akt, Caspase2, RBBP
PCNA, Cyclin D3, s6, pS6, pErk, Akt, Caspase2, total S6
PCNA, Cyclin D3, s6, pS6, pErk, Akt, RBBP, total S6
PCNA, Cyclin D3, s6, pS6, pErk, pAkt, Caspase2, RBBP
PCNA, Cyclin D3, s6, pS6, pErk, pAkt, Caspase2, total S6
PCNA, Cyclin D3, s6, pS6, pErk, pAkt, RBBP, total S6
PCNA, Cyclin D3, s6, pS6, pErk, Caspase2, RBBP, total S6
PCNA, Cyclin D3, s6, pS6, Akt, pAkt, Caspase2, RBBP
PCNA, Cyclin D3, s6, pS6, Akt, pAkt, Caspase2, total S6
PCNA, Cyclin D3, s6, pS6, Akt, pAkt, RBBP, total S6
PCNA, Cyclin D3, s6, pS6, Akt, Caspase2, RBBP, total S6
PCNA, Cyclin D3, s6, pS6, pAkt, Caspase2, RBBP, total S6
PCNA, Cyclin D3, s6, Erk, pErk, Akt, pAkt, Caspase2
PCNA, Cyclin D3, s6, Erk, pErk, Akt, pAkt, RBBP
PCNA, Cyclin D3, s6, Erk, pErk, Akt, pAkt, total S6
PCNA, Cyclin D3, s6, Erk, pErk, Akt, Caspase2, RBBP
PCNA, Cyclin D3, s6, Erk, pErk, Akt, Caspase2, total S6
PCNA, Cyclin D3, s6, Erk, pErk, Akt, RBBP, total S6
PCNA, Cyclin D3, s6, Erk, pErk, pAkt, Caspase2, RBBP
PCNA, Cyclin D3, s6, Erk, pErk, pAkt, Caspase2, total S6
PCNA, Cyclin D3, s6, Erk, pErk, pAkt, RBBP, total S6
PCNA, Cyclin D3, s6, Erk, pErk, Caspase2, RBBP, total S6
PCNA, Cyclin D3, s6, Erk, Akt, pAkt, Caspase2, RBBP
PCNA, Cyclin D3, s6, Erk, Akt, pAkt, Caspase2, total S6
PCNA, Cyclin D3, s6, Erk, Akt, pAkt, RBBP, total S6
PCNA, Cyclin D3, s6, Erk, Akt, Caspase2, RBBP, total S6
PCNA, Cyclin D3, s6, Erk, pAkt, Caspase2, RBBP, total S6
PCNA, Cyclin D3, s6, pErk, Akt, pAkt, Caspase2, RBBP
PCNA, Cyclin D3, s6, pErk, Akt, pAkt, Caspase2, total S6
PCNA, Cyclin D3, s6, pErk, Akt, pAkt, RBBP, total S6
PCNA, Cyclin D3, s6, pErk, Akt, Caspase2, RBBP, total S6
PCNA, Cyclin D3, s6, pErk, pAkt, Caspase2, RBBP, total S6
PCNA, Cyclin D3, s6, Akt, pAkt, Caspase2, RBBP, total S6
PCNA, Cyclin D3, pS6, Erk, pErk, Akt, pAkt, Caspase2
PCNA, Cyclin D3, pS6, Erk, pErk, Akt, pAkt, RBBP
PCNA, Cyclin D3, pS6, Erk, pErk, Akt, pAkt, total S6
PCNA, Cyclin D3, pS6, Erk, pErk, Akt, Caspase2, RBBP
PCNA, Cyclin D3, pS6, Erk, pErk, Akt, Caspase2, total S6
PCNA, Cyclin D3, pS6, Erk, pErk, Akt, RBBP, total S6
PCNA, Cyclin D3, pS6, Erk, pErk, pAkt, Caspase2, RBBP
PCNA, Cyclin D3, pS6, Erk, pErk, pAkt, Caspase2, total S6
PCNA, Cyclin D3, pS6, Erk, pErk, pAkt, RBBP, total S6
PCNA, Cyclin D3, pS6, Erk, pErk, Caspase2, RBBP, total S6
PCNA, Cyclin D3, pS6, Erk, Akt, pAkt, Caspase2, RBBP
PCNA, Cyclin D3, pS6, Erk, Akt, pAkt, Caspase2, total S6
PCNA, Cyclin D3, pS6, Erk, Akt, pAkt, RBBP, total S6
PCNA, Cyclin D3, pS6, Erk, Akt, Caspase2, RBBP, total S6
PCNA, Cyclin D3, pS6, Erk, pAkt, Caspase2, RBBP, total S6
PCNA, Cyclin D3, pS6, pErk, Akt, pAkt, Caspase2, RBBP
PCNA, Cyclin D3, pS6, pErk, Akt, pAkt, Caspase2, total S6
PCNA, Cyclin D3, pS6, pErk, Akt, pAkt, RBBP, total S6
PCNA, Cyclin D3, pS6, pErk, Akt, Caspase2, RBBP, total S6
PCNA, Cyclin D3, pS6, pErk, pAkt, Caspase2, RBBP, total S6
PCNA, Cyclin D3, pS6, Akt, pAkt, Caspase2, RBBP, total S6
PCNA, Cyclin D3, Erk, pErk, Akt, pAkt, Caspase2, RBBP
PCNA, Cyclin D3, Erk, pErk, Akt, pAkt, Caspase2, total S6
PCNA, Cyclin D3, Erk, pErk, Akt, pAkt, RBBP, total S6
PCNA, Cyclin D3, Erk, pErk, Akt, Caspase2, RBBP, total S6
PCNA, Cyclin D3, Erk, pErk, pAkt, Caspase2, RBBP, total S6
PCNA, Cyclin D3, Erk, Akt, pAkt, Caspase2, RBBP, total S6
PCNA, Cyclin D3, pErk, Akt, pAkt, Caspase2, RBBP, total S6
PCNA, MEK, s6, pS6, Erk, pErk, Akt, pAkt
PCNA, MEK, s6, pS6, Erk, pErk, Akt, Caspase2
PCNA, MEK, s6, pS6, Erk, pErk, Akt, RBBP
PCNA, MEK, s6, pS6, Erk, pErk, Akt, total S6
PCNA, MEK, s6, pS6, Erk, pErk, pAkt, Caspase2
PCNA, MEK, s6, pS6, Erk, pErk, pAkt, RBBP
PCNA, MEK, s6, pS6, Erk, pErk, pAkt, total S6
PCNA, MEK, s6, pS6, Erk, pErk, Caspase2, RBBP
PCNA, MEK, s6, pS6, Erk, pErk, Caspase2, total S6 pS6, Erk, Akt, pAkt, Caspase2, total S6
pS6, Erk, Akt, pAkt, RBBP, total S6
pS6, Erk, Akt, Caspase2, RBBP, total S6
pS6, Erk, pAkt, Caspase2, RBBP, total S6
pS6, pErk, Akt, pAkt, Caspase2, RBBP
pS6, pErk, Akt, pAkt, Caspase2, total S6
pS6, pErk, Akt, pAkt, RBBP, total S6
pS6, pErk, Akt, Caspase2, RBBP, total S6
pS6, pErk, pAkt, Caspase2, RBBP, total S6
pS6, Akt, pAkt, Caspase2, RBBP, total S6
Erk, pErk, Akt, pAkt, Caspase2, RBBP
Erk, pErk, Akt, pAkt, Caspase2, total S6
Erk, pErk, Akt, pAkt, RBBP, total S6
Erk, pErk, Akt, Caspase2, RBBP, total S6
Erk, pErk, pAkt, Caspase2, RBBP, total S6
Erk, Akt, pAkt, Caspase2, RBBP, total S6
pErk, Akt, pAkt, Caspase2, RBBP, total S6
PCNA, Cyclin D1, Cyclin D3
PCNA, Cyclin D1, MEK
PCNA, Cyclin D1, s6
PCNA, Cyclin D1, pS6
PCNA, Cyclin D1, Erk
PCNA, Cyclin D1, pErk
PCNA, Cyclin D1, Akt
PCNA, Cyclin D1, pAkt
PCNA, Cyclin D1, Caspase2
PCNA, Cyclin D1, RBBP
PCNA, Cyclin D1, total S6
PCNA, Cyclin D3, MEK
PCNA, Cyclin D3, s6
PCNA, Cyclin D3, pS6
PCNA, Cyclin D3, Erk
PCNA, Cyclin D3, pErk
PCNA, Cyclin D3, Akt
PCNA, Cyclin D3, pAkt
PCNA, Cyclin D3, Caspase2
PCNA, Cyclin D3, RBBP
PCNA, Cyclin D3, total S6
PCNA, MEK, s6
PCNA, MEK, pS6
PCNA, MEK, Erk
PCNA, MEK, pErk
PCNA, MEK, Akt
PCNA, MEK, pAkt
PCNA, MEK, Caspase2
PCNA, MEK, RBBP
PCNA, MEK, total S6
PCNA, s6, pS6
PCNA, s6, Erk
PCNA, s6, pErk
PCNA, s6, Akt
PCNA, s6, pAkt
PCNA, s6, Caspase2
PCNA, s6, RBBP
PCNA, s6, total S6
PCNA, pS6, Erk
PCNA, pS6, pErk
PCNA, pS6, Akt
PCNA, pS6, pAkt
PCNA, pS6, Caspase2
PCNA, pS6, RBBP
PCNA, pS6, total S6
PCNA, Erk, pErk
PCNA, Erk, Akt
PCNA, Erk, pAkt
PCNA, Erk, Caspase2
PCNA, Erk, RBBP
PCNA, Erk, total S6
PCNA, pErk, Akt
PCNA, pErk, pAkt
PCNA, pErk, Caspase2
PCNA, pErk, RBBP
PCNA, pErk, total S6
PCNA, Akt, pAkt
PCNA, Akt, Caspase2
PCNA, Akt, RBBP
PCNA, Akt, total S6
PCNA, pAkt, Caspase2

TABLE 1-continued

Examples of Single Markers and Combinations of Markers

PCNA, MEK, s6, pS6, Erk, pErk, RBBP, total S6
PCNA, MEK, s6, pS6, Erk, Akt, pAkt, Caspase2
PCNA, MEK, s6, pS6, Erk, Akt, pAkt, RBBP
PCNA, MEK, s6, pS6, Erk, Akt, pAkt, total S6
PCNA, MEK, s6, pS6, Erk, Akt, Caspase2, RBBP
PCNA, MEK, s6, pS6, Erk, Akt, Caspase2, total S6
PCNA, MEK, s6, pS6, Erk, Akt, RBBP, total S6
PCNA, MEK, s6, pS6, Erk, pAkt, Caspase2, RBBP
PCNA, MEK, s6, pS6, Erk, pAkt, Caspase2, total S6
PCNA, MEK, s6, pS6, Erk, pAkt, RBBP, total S6
PCNA, MEK, s6, pS6, Erk, Caspase2, RBBP, total S6
PCNA, MEK, s6, pS6, pErk, Akt, pAkt, Caspase2
PCNA, MEK, s6, pS6, pErk, Akt, pAkt, RBBP
PCNA, MEK, s6, pS6, pErk, Akt, pAkt, total S6
PCNA, MEK, s6, pS6, pErk, Akt, Caspase2, RBBP
PCNA, MEK, s6, pS6, pErk, Akt, Caspase2, total S6
PCNA, MEK, s6, pS6, pErk, Akt, RBBP, total S6
PCNA, MEK, s6, pS6, pErk, pAkt, Caspase2, RBBP
PCNA, MEK, s6, pS6, pErk, pAkt, Caspase2, total S6
PCNA, MEK, s6, pS6, pErk, pAkt, RBBP, total S6
PCNA, MEK, s6, pS6, pErk, Caspase2, RBBP, total S6
PCNA, MEK, s6, pS6, Akt, pAkt, Caspase2, RBBP
PCNA, MEK, s6, pS6, Akt, pAkt, Caspase2, total S6
PCNA, MEK, s6, pS6, Akt, pAkt, RBBP, total S6
PCNA, MEK, s6, pS6, Akt, Caspase2, RBBP, total S6
PCNA, MEK, s6, pS6, pAkt, Caspase2, RBBP, total S6
PCNA, MEK, s6, Erk, pErk, Akt, pAkt, Caspase2
PCNA, MEK, s6, Erk, pErk, Akt, pAkt, RBBP
PCNA, MEK, s6, Erk, pErk, Akt, pAkt, total S6
PCNA, MEK, s6, Erk, pErk, Akt, Caspase2, RBBP
PCNA, MEK, s6, Erk, pErk, Akt, Caspase2, total S6
PCNA, MEK, s6, Erk, pErk, Akt, RBBP, total S6
PCNA, MEK, s6, Erk, pErk, pAkt, Caspase2, RBBP
PCNA, MEK, s6, Erk, pErk, pAkt, Caspase2, total S6
PCNA, MEK, s6, Erk, pErk, pAkt, RBBP, total S6
PCNA, MEK, s6, Erk, pErk, Caspase2, RBBP, total S6
PCNA, MEK, s6, Erk, Akt, pAkt, Caspase2, RBBP
PCNA, MEK, s6, Erk, Akt, pAkt, Caspase2, total S6
PCNA, MEK, s6, Erk, Akt, pAkt, RBBP, total S6
PCNA, MEK, s6, Erk, Akt, Caspase2, RBBP, total S6
PCNA, MEK, s6, Erk, pAkt, Caspase2, RBBP, total S6
PCNA, MEK, s6, pErk, Akt, pAkt, Caspase2, RBBP
PCNA, MEK, s6, pErk, Akt, pAkt, Caspase2, total S6
PCNA, MEK, s6, pErk, Akt, pAkt, RBBP, total S6
PCNA, MEK, s6, pErk, Akt, Caspase2, RBBP, total S6
PCNA, MEK, s6, pErk, pAkt, Caspase2, RBBP, total S6
PCNA, MEK, s6, Akt, pAkt, Caspase2, RBBP, total S6
PCNA, MEK, pS6, Erk, pErk, Akt, pAkt, Caspase2
PCNA, MEK, pS6, Erk, pErk, Akt, pAkt, RBBP
PCNA, MEK, pS6, Erk, pErk, Akt, pAkt, total S6
PCNA, MEK, pS6, Erk, pErk, Akt, Caspase2, RBBP
PCNA, MEK, pS6, Erk, pErk, Akt, Caspase2, total S6
PCNA, MEK, pS6, Erk, pErk, Akt, RBBP, total S6
PCNA, MEK, pS6, Erk, pErk, pAkt, Caspase2, RBBP
PCNA, MEK, pS6, Erk, pErk, pAkt, Caspase2, total S6
PCNA, MEK, pS6, Erk, pErk, pAkt, RBBP, total S6
PCNA, MEK, pS6, Erk, pErk, Caspase2, RBBP, total S6
PCNA, MEK, pS6, Erk, Akt, pAkt, Caspase2, RBBP
PCNA, MEK, pS6, Erk, Akt, pAkt, Caspase2, total S6
PCNA, MEK, pS6, Erk, Akt, pAkt, RBBP, total S6
PCNA, MEK, pS6, Erk, Akt, Caspase2, RBBP, total S6
PCNA, MEK, pS6, Erk, pAkt, Caspase2, RBBP, total S6
PCNA, MEK, pS6, pErk, Akt, pAkt, Caspase2, RBBP
PCNA, MEK, pS6, pErk, Akt, pAkt, Caspase2, total S6
PCNA, MEK, pS6, pErk, Akt, pAkt, RBBP, total S6
PCNA, MEK, pS6, pErk, Akt, Caspase2, RBBP, total S6
PCNA, MEK, pS6, pErk, pAkt, Caspase2, RBBP, total S6
PCNA, MEK, pS6, Akt, pAkt, Caspase2, RBBP, total S6
PCNA, MEK, Erk, pErk, Akt, pAkt, Caspase2, RBBP
PCNA, MEK, Erk, pErk, Akt, pAkt, Caspase2, total S6
PCNA, MEK, Erk, pErk, Akt, pAkt, RBBP, total S6
PCNA, MEK, Erk, pErk, Akt, Caspase2, RBBP, total S6
PCNA, MEK, Erk, pErk, pAkt, Caspase2, RBBP, total S6
PCNA, MEK, Erk, Akt, pAkt, Caspase2, RBBP, total S6
PCNA, MEK, pErk, Akt, pAkt, Caspase2, RBBP, total S6
PCNA, s6, pS6, Erk, pErk, Akt, pAkt, Caspase2
PCNA, s6, pS6, Erk, pErk, Akt, pAkt, RBBP
PCNA, s6, pS6, Erk, pErk, Akt, pAkt, total S6
PCNA, pAkt, RBBP
PCNA, pAkt, total S6
PCNA, Caspase2, RBBP
PCNA, Caspase2, total S6
PCNA, RBBP, total S6
Cyclin D1, Cyclin D3, MEK
Cyclin D1, Cyclin D3, s6
Cyclin D1, Cyclin D3, pS6
Cyclin D1, Cyclin D3, Erk
Cyclin D1, Cyclin D3, pErk
Cyclin D1, Cyclin D3, Akt
Cyclin D1, Cyclin D3, pAkt
Cyclin D1, Cyclin D3, Caspase2
Cyclin D1, Cyclin D3, RBBP
Cyclin D1, Cyclin D3, total S6
Cyclin D1, MEK, s6
Cyclin D1, MEK, pS6
Cyclin D1, MEK, Erk
Cyclin D1, MEK, pErk
Cyclin D1, MEK, Akt
Cyclin D1, MEK, pAkt
Cyclin D1, MEK, Caspase2
Cyclin D1, MEK, RBBP
Cyclin D1, MEK, total S6
Cyclin D1, s6, pS6
Cyclin D1, s6, Erk
Cyclin D1, s6, pErk
Cyclin D1, s6, Akt
Cyclin D1, s6, pAkt
Cyclin D1, s6, Caspase2
Cyclin D1, s6, RBBP
Cyclin D1, s6, total S6
Cyclin D1, pS6, Erk
Cyclin D1, pS6, pErk
Cyclin D1, pS6, Akt
Cyclin D1, pS6, pAkt
Cyclin D1, pS6, Caspase2
Cyclin D1, pS6, RBBP
Cyclin D1, pS6, total S6
Cyclin D1, Erk, pErk
Cyclin D1, Erk, Akt
Cyclin D1, Erk, pAkt
Cyclin D1, Erk, Caspase2
Cyclin D1, Erk, RBBP
Cyclin D1, Erk, total S6
Cyclin D1, pErk, Akt
Cyclin D1, pErk, pAkt
Cyclin D1, pErk, Caspase2
Cyclin D1, pErk, RBBP
Cyclin D1, pErk, total S6
Cyclin D1, Akt, pAkt
Cyclin D1, Akt, Caspase2
Cyclin D1, Akt, RBBP
Cyclin D1, Akt, total S6
Cyclin D1, pAkt, Caspase2
Cyclin D1, pAkt, RBBP
Cyclin D1, pAkt, total S6
Cyclin D1, Caspase2, RBBP
Cyclin D1, Caspase2, total S6
Cyclin D1, RBBP, total S6
Cyclin D3, MEK, s6
Cyclin D3, MEK, pS6
Cyclin D3, MEK, Erk
Cyclin D3, MEK, pErk
Cyclin D3, MEK, Akt
Cyclin D3, MEK, pAkt
Cyclin D3, MEK, Caspase2
Cyclin D3, MEK, RBBP
Cyclin D3, MEK, total S6
Cyclin D3, s6, pS6
Cyclin D3, s6, Erk
Cyclin D3, s6, pErk
Cyclin D3, s6, Akt
Cyclin D3, s6, pAkt
Cyclin D3, s6, Caspase2
Cyclin D3, s6, RBBP
Cyclin D3, s6, total S6
Cyclin D3, pS6, Erk TABLE 1-continued Examples of Single Markers and Combinations of Markers PCNA, s6, pS6, Erk, pErk, Akt, Caspase2, RBBP
PCNA, s6, pS6, Erk, pErk, Akt, Caspase2, total S6
PCNA, s6, pS6, Erk, pErk, Akt, RBBP, total S6
PCNA, s6, pS6, Erk, pErk, pAkt, Caspase2, RBBP
PCNA, s6, pS6, Erk, pErk, pAkt, Caspase2, total S6
PCNA, s6, pS6, Erk, pErk, pAkt, RBBP, total S6
PCNA, s6, pS6, Erk, pErk, Caspase2, RBBP, total S6
PCNA, s6, pS6, Erk, Akt, pAkt, Caspase2, RBBP
PCNA, s6, pS6, Erk, Akt, pAkt, Caspase2, total S6
PCNA, s6, pS6, Erk, Akt, pAkt, RBBP, total S6
PCNA, s6, pS6, Erk, Akt, Caspase2, RBBP, total S6
PCNA, s6, pS6, Erk, pAkt, Caspase2, RBBP, total S6
PCNA, s6, pS6, pErk, Akt, pAkt, Caspase2, RBBP
PCNA, s6, pS6, pErk, Akt, pAkt, Caspase2, total S6
PCNA, s6, pS6, pErk, Akt, pAkt, RBBP, total S6
PCNA, s6, pS6, pErk, Akt, Caspase2, RBBP, total S6
PCNA, s6, pS6, pErk, pAkt, Caspase2, RBBP, total S6
PCNA, s6, pS6, Akt, pAkt, Caspase2, RBBP, total S6
PCNA, s6, Erk, pErk, Akt, pAkt, Caspase2, RBBP
PCNA, s6, Erk, pErk, Akt, pAkt, Caspase2, total S6
PCNA, s6, Erk, pErk, Akt, pAkt, RBBP, total S6
PCNA, s6, Erk, pErk, Akt, Caspase2, RBBP, total S6
PCNA, s6, Erk, pErk, pAkt, Caspase2, RBBP, total S6
PCNA, s6, Erk, Akt, pAkt, Caspase2, RBBP, total S6
PCNA, s6, pErk, Akt, pAkt, Caspase2, RBBP, total S6
PCNA, pS6, Erk, pErk, Akt, pAkt, Caspase2, RBBP
PCNA, pS6, Erk, pErk, Akt, pAkt, Caspase2, total S6
PCNA, pS6, Erk, pErk, Akt, pAkt, RBBP, total S6
PCNA, pS6, Erk, pErk, Akt, Caspase2, RBBP, total S6
PCNA, pS6, Erk, pErk, pAkt, Caspase2, RBBP, total S6
PCNA, pS6, Erk, Akt, pAkt, Caspase2, RBBP, total S6
PCNA, pS6, pErk, Akt, pAkt, Caspase2, RBBP, total S6
PCNA, Erk, pErk, Akt, pAkt, Caspase2, RBBP, total S6
Cyclin D1, Cyclin D3, MEK, s6, pS6, Erk, pErk, Akt
Cyclin D1, Cyclin D3, MEK, s6, pS6, Erk, pErk, pAkt
Cyclin D1, Cyclin D3, MEK, s6, pS6, Erk, pErk, Caspase2
Cyclin D1, Cyclin D3, MEK, s6, pS6, Erk, pErk, RBBP
Cyclin D1, Cyclin D3, MEK, s6, pS6, Erk, pErk, total S6
Cyclin D1, Cyclin D3, MEK, s6, pS6, Erk, Akt, pAkt
Cyclin D1, Cyclin D3, MEK, s6, pS6, Erk, Akt, Caspase2
Cyclin D1, Cyclin D3, MEK, s6, pS6, Erk, Akt, RBBP
Cyclin D1, Cyclin D3, MEK, s6, pS6, Erk, Akt, total S6
Cyclin D1, Cyclin D3, MEK, s6, pS6, Erk, pAkt, Caspase2
Cyclin D1, Cyclin D3, MEK, s6, pS6, Erk, pAkt, RBBP
Cyclin D1, Cyclin D3, MEK, s6, pS6, Erk, pAkt, total S6
Cyclin D1, Cyclin D3, MEK, s6, pS6, Erk, Caspase2, RBBP
Cyclin D1, Cyclin D3, MEK, s6, pS6, Erk, Caspase2, total S6
Cyclin D1, Cyclin D3, MEK, s6, pS6, Erk, RBBP, total S6
Cyclin D1, Cyclin D3, MEK, s6, pS6, pErk, Akt, pAkt
Cyclin D1, Cyclin D3, MEK, s6, pS6, pErk, Akt, Caspase2
Cyclin D1, Cyclin D3, MEK, s6, pS6, pErk, Akt, RBBP
Cyclin D1, Cyclin D3, MEK, s6, pS6, pErk, Akt, total S6
Cyclin D1, Cyclin D3, MEK, s6, pS6, pErk, pAkt, Caspase2
Cyclin D1, Cyclin D3, MEK, s6, pS6, pErk, pAkt, RBBP
Cyclin D1, Cyclin D3, MEK, s6, pS6, pErk, pAkt, total S6
Cyclin D1, Cyclin D3, MEK, s6, pS6, pErk, Caspase2, RBBP
Cyclin D1, Cyclin D3, MEK, s6, pS6, pErk, Caspase2, total S6
Cyclin D1, Cyclin D3, MEK, s6, pS6, pErk, RBBP, total S6
Cyclin D1, Cyclin D3, MEK, s6, pS6, Akt, pAkt, Caspase2
Cyclin D1, Cyclin D3, MEK, s6, pS6, Akt, pAkt, RBBP
Cyclin D1, Cyclin D3, MEK, s6, pS6, Akt, pAkt, total S6
Cyclin D1, Cyclin D3, MEK, s6, pS6, Akt, Caspase2, RBBP
Cyclin D1, Cyclin D3, MEK, s6, pS6, Akt, Caspase2, total S6
Cyclin D1, Cyclin D3, MEK, s6, pS6, Akt, RBBP, total S6
Cyclin D1, Cyclin D3, MEK, s6, pS6, pAkt, Caspase2, RBBP
Cyclin D1, Cyclin D3, MEK, s6, pS6, pAkt, Caspase2, total S6
Cyclin D1, Cyclin D3, MEK, s6, pS6, pAkt, RBBP, total S6
Cyclin D1, Cyclin D3, MEK, s6, pS6, Caspase2, RBBP, total S6
Cyclin D1, Cyclin D3, MEK, s6, Erk, pErk, Akt, pAkt
Cyclin D1, Cyclin D3, MEK, s6, Erk, pErk, Akt, Caspase2
Cyclin D1, Cyclin D3, MEK, s6, Erk, pErk, Akt, RBBP
Cyclin D1, Cyclin D3, MEK, s6, Erk, pErk, Akt, total S6
Cyclin D1, Cyclin D3, MEK, s6, Erk, pErk, pAkt, Caspase2
Cyclin D1, Cyclin D3, MEK, s6, Erk, pErk, pAkt, RBBP
Cyclin D1, Cyclin D3, MEK, s6, Erk, pErk, pAkt, total S6
Cyclin D1, Cyclin D3, MEK, s6, Erk, pErk, Caspase2, RBBP
Cyclin D1, Cyclin D3, MEK, s6, Erk, pErk, Caspase2, total S6
Cyclin D1, Cyclin D3, MEK, s6, Erk, pErk, RBBP, total S6

Cyclin D3, pS6, pErk
Cyclin D3, pS6, Akt
Cyclin D3, pS6, pAkt
Cyclin D3, pS6, Caspase2
Cyclin D3, pS6, RBBP
Cyclin D3, pS6, total S6
Cyclin D3, Erk, pErk
Cyclin D3, Erk, Akt
Cyclin D3, Erk, pAkt
Cyclin D3, Erk, Caspase2
Cyclin D3, Erk, RBBP
Cyclin D3, Erk, total S6
Cyclin D3, pErk, Akt
Cyclin D3, pErk, pAkt
Cyclin D3, pErk, Caspase2
Cyclin D3, pErk, RBBP
Cyclin D3, pErk, total S6
Cyclin D3, Akt, pAkt
Cyclin D3, Akt, Caspase2
Cyclin D3, Akt, RBBP
Cyclin D3, Akt, total S6
Cyclin D3, pAkt, Caspase2
Cyclin D3, pAkt, RBBP
Cyclin D3, pAkt, total S6
Cyclin D3, Caspase2, RBBP
Cyclin D3, Caspase2, total S6
Cyclin D3, RBBP, total S6
MEK, s6, pS6
MEK, s6, Erk
MEK, s6, pErk
MEK, s6, Akt
MEK, s6, pAkt
MEK, s6, Caspase2
MEK, s6, RBBP
MEK, s6, total S6
MEK, pS6, Erk
MEK, pS6, pErk
MEK, pS6, Akt
MEK, pS6, pAkt
MEK, pS6, Caspase2
MEK, pS6, RBBP
MEK, pS6, total S6
MEK, Erk, pErk
MEK, Erk, Akt
MEK, Erk, pAkt
MEK, Erk, Caspase2
MEK, Erk, RBBP
MEK, Erk, total S6
MEK, pErk, Akt
MEK, pErk, pAkt
MEK, pErk, Caspase2
MEK, pErk, RBBP
MEK, pErk, total S6
MEK, Akt, pAkt
MEK, Akt, Caspase2
MEK, Akt, RBBP
MEK, Akt, total S6
MEK, pAkt, Caspase2
MEK, pAkt, RBBP
MEK, pAkt, total S6
MEK, Caspase2, RBBP
MEK, Caspase2, total S6
MEK, RBBP, total S6
s6, pS6, Erk
s6, pS6, pErk
s6, pS6, Akt
s6, pS6, pAkt
s6, pS6, Caspase2
s6, pS6, RBBP
s6, pS6, total S6
s6, Erk, pErk
s6, Erk, Akt
s6, Erk, pAkt
s6, Erk, Caspase2
s6, Erk, RBBP
s6, Erk, total S6
s6, pErk, Akt
s6, pErk, pAkt TABLE 1-continued Examples of Single Markers and Combinations of Markers

| | |
|---|---|
| Cyclin D1, Cyclin D3, MEK, s6, Erk, Akt, pAkt, Caspase2 | s6, pErk, Caspase2 |
| Cyclin D1, Cyclin D3, MEK, s6, Erk, Akt, pAkt, RBBP | s6, pErk, RBBP |
| Cyclin D1, Cyclin D3, MEK, s6, Erk, Akt, pAkt, total S6 | s6, pErk, total S6 |
| Cyclin D1, Cyclin D3, MEK, s6, Erk, Akt, Caspase2, RBBP | s6, Akt, pAkt |
| Cyclin D1, Cyclin D3, MEK, s6, Erk, Akt, Caspase2, total S6 | s6, Akt, Caspase2 |
| Cyclin D1, Cyclin D3, MEK, s6, Erk, Akt, RBBP, total S6 | s6, Akt, RBBP |
| Cyclin D1, Cyclin D3, MEK, s6, Erk, pAkt, Caspase2, RBBP | s6, Akt, total S6 |
| Cyclin D1, Cyclin D3, MEK, s6, Erk, pAkt, Caspase2, total S6 | s6, pAkt, Caspase2 |
| Cyclin D1, Cyclin D3, MEK, s6, Erk, pAkt, RBBP, total S6 | s6, pAkt, RBBP |
| Cyclin D1, Cyclin D3, MEK, s6, Erk, Caspase2, RBBP, total S6 | s6, pAkt, total S6 |
| Cyclin D1, Cyclin D3, MEK, s6, pErk, Akt, pAkt, Caspase2 | s6, Caspase2, RBBP |
| Cyclin D1, Cyclin D3, MEK, s6, pErk, Akt, pAkt, RBBP | s6, Caspase2, total S6 |
| Cyclin D1, Cyclin D3, MEK, s6, pErk, Akt, pAkt, total S6 | s6, RBBP, total S6 |
| Cyclin D1, Cyclin D3, MEK, s6, pErk, Akt, Caspase2, RBBP | pS6, Erk, pErk |
| Cyclin D1, Cyclin D3, MEK, s6, pErk, Akt, Caspase2, total S6 | pS6, Erk, Akt |
| Cyclin D1, Cyclin D3, MEK, s6, pErk, Akt, RBBP, total S6 | pS6, Erk, pAkt |
| Cyclin D1, Cyclin D3, MEK, s6, pErk, pAkt, Caspase2, RBBP | pS6, Erk, Caspase2 |
| Cyclin D1, Cyclin D3, MEK, s6, pErk, pAkt, Caspase2, total S6 | pS6, Erk, RBBP |
| Cyclin D1, Cyclin D3, MEK, s6, pErk, pAkt, RBBP, total S6 | pS6, Erk, total S6 |
| Cyclin D1, Cyclin D3, MEK, s6, pErk, Caspase2, RBBP, total S6 | pS6, pErk, Akt |
| Cyclin D1, Cyclin D3, MEK, s6, Akt, pAkt, Caspase2, RBBP | pS6, pErk, pAkt |
| Cyclin D1, Cyclin D3, MEK, s6, Akt, pAkt, Caspase2, total S6 | pS6, pErk, Caspase2 |
| Cyclin D1, Cyclin D3, MEK, s6, Akt, pAkt, RBBP, total S6 | pS6, pErk, RBBP |
| Cyclin D1, Cyclin D3, MEK, s6, Akt, Caspase2, RBBP, total S6 | pS6, pErk, total S6 |
| Cyclin D1, Cyclin D3, MEK, s6, pAkt, Caspase2, RBBP, total S6 | pS6, Akt, pAkt |
| Cyclin D1, Cyclin D3, MEK, pS6, Erk, pErk, Akt, pAkt | pS6, Akt, Caspase2 |
| Cyclin D1, Cyclin D3, MEK, pS6, Erk, pErk, Akt, Caspase2 | pS6, Akt, RBBP |
| Cyclin D1, Cyclin D3, MEK, pS6, Erk, pErk, Akt, total S6 | pS6, Akt, total S6 |
| Cyclin D1, Cyclin D3, MEK, pS6, Erk, pErk, pAkt, Caspase2 | pS6, pAkt, Caspase2 |
| Cyclin D1, Cyclin D3, MEK, pS6, Erk, pErk, pAkt, RBBP | pS6, pAkt, RBBP |
| Cyclin D1, Cyclin D3, MEK, pS6, Erk, pErk, pAkt, total S6 | pS6, pAkt, total S6 |
| Cyclin D1, Cyclin D3, MEK, pS6, Erk, pErk, Caspase2, RBBP | pS6, Caspase2, RBBP |
| Cyclin D1, Cyclin D3, MEK, pS6, Erk, pErk, Caspase2, total S6 | pS6, Caspase2, total S6 |
| Cyclin D1, Cyclin D3, MEK, pS6, Erk, pErk, RBBP, total S6 | pS6, RBBP, total S6 |
| Cyclin D1, Cyclin D3, MEK, pS6, Erk, Akt, pAkt, Caspase2 | Erk, pErk, Akt |
| Cyclin D1, Cyclin D3, MEK, pS6, Erk, Akt, pAkt, RBBP | Erk, pErk, pAkt |
| Cyclin D1, Cyclin D3, MEK, pS6, Erk, Akt, pAkt, total S6 | Erk, pErk, Caspase2 |
| Cyclin D1, Cyclin D3, MEK, pS6, Erk, Akt, Caspase2, RBBP | Erk, pErk, RBBP |
| Cyclin D1, Cyclin D3, MEK, pS6, Erk, Akt, Caspase2, total S6 | Erk, pErk, total S6 |
| Cyclin D1, Cyclin D3, MEK, pS6, Erk, Akt, RBBP, total S6 | Erk, Akt, pAkt |
| Cyclin D1, Cyclin D3, MEK, pS6, Erk, pAkt, Caspase2, RBBP | Erk, Akt, Caspase2 |
| Cyclin D1, Cyclin D3, MEK, pS6, Erk, pAkt, Caspase2, total S6 | Erk, Akt, RBBP |
| Cyclin D1, Cyclin D3, MEK, pS6, Erk, pAkt, RBBP, total S6 | Erk, Akt, total S6 |
| Cyclin D1, Cyclin D3, MEK, pS6, Erk, Caspase2, RBBP, total S6 | Erk, pAkt, Caspase2 |
| Cyclin D1, Cyclin D3, MEK, pS6, pErk, Akt, pAkt, Caspase2 | Erk, pAkt, RBBP |
| Cyclin D1, Cyclin D3, MEK, pS6, pErk, Akt, pAkt, RBBP | Erk, pAkt, total S6 |
| Cyclin D1, Cyclin D3, MEK, pS6, pErk, Akt, pAkt, total S6 | Erk, Caspase2, RBBP |
| Cyclin D1, Cyclin D3, MEK, pS6, pErk, Akt, Caspase2, RBBP | Erk, Caspase2, total S6 |
| Cyclin D1, Cyclin D3, MEK, pS6, pErk, Akt, Caspase2, total S6 | Erk, RBBP, total S6 |
| Cyclin D1, Cyclin D3, MEK, pS6, pErk, Akt, RBBP, total S6 | pErk, Akt, pAkt |
| Cyclin D1, Cyclin D3, MEK, pS6, pErk, pAkt, Caspase2, RBBP | pErk, Akt, Caspase2 |
| Cyclin D1, Cyclin D3, MEK, pS6, pErk, pAkt, Caspase2, total S6 | pErk, Akt, RBBP |
| Cyclin D1, Cyclin D3, MEK, pS6, pErk, pAkt, RBBP, total S6 | pErk, Akt, total S6 |
| Cyclin D1, Cyclin D3, MEK, pS6, pErk, Caspase2, RBBP, total S6 | pErk, pAkt, Caspase2 |
| Cyclin D1, Cyclin D3, MEK, pS6, Akt, pAkt, Caspase2, RBBP | pErk, pAkt, RBBP |
| Cyclin D1, Cyclin D3, MEK, pS6, Akt, pAkt, Caspase2, total S6 | pErk, pAkt, total S6 |
| Cyclin D1, Cyclin D3, MEK, pS6, Akt, pAkt, RBBP, total S6 | pErk, Caspase2, RBBP |
| Cyclin D1, Cyclin D3, MEK, pS6, Akt, Caspase2, RBBP, total S6 | pErk, Caspase2, total S6 |
| Cyclin D1, Cyclin D3, MEK, pS6, pAkt, Caspase2, RBBP, total S6 | pErk, RBBP, total S6 |
| Cyclin D1, Cyclin D3, MEK, Erk, pErk, Akt, pAkt, Caspase2 | Akt, pAkt, Caspase2 |
| Cyclin D1, Cyclin D3, MEK, Erk, pErk, Akt, pAkt, RBBP | Akt, pAkt, RBBP |
| Cyclin D1, Cyclin D3, MEK, Erk, pErk, Akt, pAkt, total S6 | Akt, pAkt, total S6 |
| Cyclin D1, Cyclin D3, MEK, Erk, pErk, Akt, Caspase2, RBBP | Akt, Caspase2, RBBP |
| Cyclin D1, Cyclin D3, MEK, Erk, pErk, Akt, Caspase2, total S6 | Akt, Caspase2, total S6 |
| Cyclin D1, Cyclin D3, MEK, Erk, pErk, Akt, RBBP, total S6 | Akt, RBBP, total S6 |
| Cyclin D1, Cyclin D3, MEK, Erk, pErk, pAkt, Caspase2, RBBP | pAkt, Caspase2, RBBP |
| Cyclin D1, Cyclin D3, MEK, Erk, pErk, pAkt, Caspase2, total S6 | pAkt, Caspase2, total S6 |
| Cyclin D1, Cyclin D3, MEK, Erk, pErk, pAkt, RBBP, total S6 | pAkt, RBBP, total S6 |
| Cyclin D1, Cyclin D3, MEK, Erk, pErk, Caspase2, RBBP, total S6 | Caspase2, RBBP, total S6 |
| Cyclin D1, Cyclin D3, MEK, Erk, Akt, pAkt, Caspase2, RBBP | PCNA, Cyclin D1 |
| Cyclin D1, Cyclin D3, MEK, Erk, Akt, pAkt, Caspase2, total S6 | PCNA, Cyclin D3 |
| Cyclin D1, Cyclin D3, MEK, Erk, Akt, pAkt, RBBP, total S6 | PCNA, MEK |
| Cyclin D1, Cyclin D3, MEK, Erk, Akt, Caspase2, RBBP, total S6 | PCNA, s6 |
| Cyclin D1, Cyclin D3, MEK, Erk, pAkt, Caspase2, RBBP, total S6 | PCNA, pS6 |
| Cyclin D1, Cyclin D3, MEK, pErk, Akt, pAkt, Caspase2, RBBP | PCNA, Erk |
| Cyclin D1, Cyclin D3, MEK, pErk, Akt, pAkt, Caspase2, total S6 | PCNA, pErk |
| Cyclin D1, Cyclin D3, MEK, pErk, Akt, pAkt, RBBP, total S6 | PCNA, Akt |
| | PCNA, pAkt |

TABLE 1-continued

Examples of Single Markers and Combinations of Markers

| | |
|---|---|
| Cyclin D1, Cyclin D3, MEK, pErk, Akt, Caspase2, RBBP, total S6 | PCNA, Caspase2 |
| Cyclin D1, Cyclin D3, MEK, pErk, pAkt, Caspase2, RBBP, total S6 | PCNA, RBBP |
| Cyclin D1, Cyclin D3, MEK, Akt, pAkt, Caspase2, RBBP, total S6 | PCNA, total S6 |
| Cyclin D1, Cyclin D3, s6, pS6, Erk, pErk, Akt, pAkt | Cyclin D1, Cyclin D3 |
| Cyclin D1, Cyclin D3, s6, pS6, Erk, pErk, Akt, Caspase2 | Cyclin D1, MEK |
| Cyclin D1, Cyclin D3, s6, pS6, Erk, pErk, Akt, RBBP | Cyclin D1, s6 |
| Cyclin D1, Cyclin D3, s6, pS6, Erk, pErk, Akt, total S6 | Cyclin D1, pS6 |
| Cyclin D1, Cyclin D3, s6, pS6, Erk, pErk, pAkt, Caspase2 | Cyclin D1, Erk |
| Cyclin D1, Cyclin D3, s6, pS6, Erk, pErk, pAkt, RBBP | Cyclin D1, pErk |
| Cyclin D1, Cyclin D3, s6, pS6, Erk, pErk, pAkt, total S6 | Cyclin D1, Akt |
| Cyclin D1, Cyclin D3, s6, pS6, Erk, pErk, Caspase2, RBBP | Cyclin D1, pAkt |
| Cyclin D1, Cyclin D3, s6, pS6, Erk, pErk, Caspase2, total S6 | Cyclin D1, Caspase2 |
| Cyclin D1, Cyclin D3, s6, pS6, Erk, pErk, RBBP, total S6 | Cyclin D1, RBBP |
| Cyclin D1, Cyclin D3, s6, pS6, Erk, Akt, pAkt, Caspase2 | Cyclin D1, total S6 |
| Cyclin D1, Cyclin D3, s6, pS6, Erk, Akt, pAkt, RBBP | Cyclin D3, MEK |
| Cyclin D1, Cyclin D3, s6, pS6, Erk, Akt, pAkt, total S6 | Cyclin D3, s6 |
| Cyclin D1, Cyclin D3, s6, pS6, Erk, Akt, Caspase2, RBBP | Cyclin D3, pS6 |
| Cyclin D1, Cyclin D3, s6, pS6, Erk, Akt, Caspase2, total S6 | Cyclin D3, Erk |
| Cyclin D1, Cyclin D3, s6, pS6, Erk, Akt, RBBP, total S6 | Cyclin D3, pErk |
| Cyclin D1, Cyclin D3, s6, pS6, Erk, pAkt, Caspase2, RBBP | Cyclin D3, Akt |
| Cyclin D1, Cyclin D3, s6, pS6, Erk, pAkt, Caspase2, total S6 | Cyclin D3, pAkt |
| Cyclin D1, Cyclin D3, s6, pS6, Erk, pAkt, RBBP, total S6 | Cyclin D3, Caspase2 |
| Cyclin D1, Cyclin D3, s6, pS6, Erk, Caspase2, RBBP, total S6 | Cyclin D3, RBBP |
| Cyclin D1, Cyclin D3, s6, pS6, pErk, Akt, pAkt, Caspase2 | Cyclin D3, total S6 |
| Cyclin D1, Cyclin D3, s6, pS6, pErk, Akt, pAkt, RBBP | MEK, s6 |
| Cyclin D1, Cyclin D3, s6, pS6, pErk, Akt, pAkt, total S6 | MEK, pS6 |
| Cyclin D1, Cyclin D3, s6, pS6, pErk, Akt, Caspase2, RBBP | MEK, Erk |
| Cyclin D1, Cyclin D3, s6, pS6, pErk, Akt, Caspase2, total S6 | MEK, pErk |
| Cyclin D1, Cyclin D3, s6, pS6, pErk, Akt, RBBP, total S6 | MEK, Akt |
| Cyclin D1, Cyclin D3, s6, pS6, pErk, pAkt, Caspase2, RBBP | MEK, pAkt |
| Cyclin D1, Cyclin D3, s6, pS6, pErk, pAkt, Caspase2, total S6 | MEK, Caspase2 |
| Cyclin D1, Cyclin D3, s6, pS6, pErk, pAkt, RBBP, total S6 | MEK, RBBP |
| Cyclin D1, Cyclin D3, s6, pS6, pErk, Caspase2, RBBP, total S6 | MEK, total S6 |
| Cyclin D1, Cyclin D3, s6, pS6, Akt, pAkt, Caspase2, RBBP | s6, pS6 |
| Cyclin D1, Cyclin D3, s6, pS6, Akt, pAkt, Caspase2, total S6 | s6, Erk |
| Cyclin D1, Cyclin D3, s6, pS6, Akt, pAkt, RBBP, total S6 | s6, pErk |
| Cyclin D1, Cyclin D3, s6, pS6, Akt, Caspase2, RBBP, total S6 | s6, Akt |
| Cyclin D1, Cyclin D3, s6, pS6, pAkt, Caspase2, RBBP, total S6 | s6, pAkt |
| Cyclin D1, Cyclin D3, s6, Erk, pErk, Akt, pAkt, Caspase2 | s6, Caspase2 |
| Cyclin D1, Cyclin D3, s6, Erk, pErk, Akt, pAkt, RBBP | s6, RBBP |
| Cyclin D1, Cyclin D3, s6, Erk, pErk, Akt, pAkt, total S6 | s6, total S6 |
| Cyclin D1, Cyclin D3, s6, Erk, pErk, Akt, Caspase2, RBBP | pS6, Erk |
| Cyclin D1, Cyclin D3, s6, Erk, pErk, Akt, Caspase2, total S6 | pS6, pErk |
| Cyclin D1, Cyclin D3, s6, Erk, pErk, Akt, RBBP, total S6 | pS6, Akt |
| Cyclin D1, Cyclin D3, s6, Erk, pErk, pAkt, Caspase2, RBBP | pS6, pAkt |
| Cyclin D1, Cyclin D3, s6, Erk, pErk, pAkt, Caspase2, total S6 | pS6, Caspase2 |
| Cyclin D1, Cyclin D3, s6, Erk, pErk, pAkt, RBBP, total S6 | pS6, RBBP |
| Cyclin D1, Cyclin D3, s6, Erk, pErk, Caspase2, RBBP, total S6 | pS6, total S6 |
| Cyclin D1, Cyclin D3, s6, Erk, Akt, pAkt, Caspase2, RBBP | Erk, pErk |
| Cyclin D1, Cyclin D3, s6, Erk, Akt, pAkt, Caspase2, total S6 | Erk, Akt |
| Cyclin D1, Cyclin D3, s6, Erk, Akt, pAkt, RBBP, total S6 | Erk, pAkt |
| Cyclin D1, Cyclin D3, s6, Erk, Akt, Caspase2, RBBP, total S6 | Erk, Caspase2 |
| Cyclin D1, Cyclin D3, s6, Erk, pAkt, Caspase2, RBBP, total S6 | Erk, RBBP |
| Cyclin D1, Cyclin D3, s6, pErk, Akt, pAkt, Caspase2, RBBP | Erk, total S6 |
| Cyclin D1, Cyclin D3, s6, pErk, Akt, pAkt, Caspase2, total S6 | pErk, Akt |
| Cyclin D1, Cyclin D3, s6, pErk, Akt, pAkt, RBBP, total S6 | pErk, pAkt |
| Cyclin D1, Cyclin D3, s6, pErk, Akt, Caspase2, RBBP, total S6 | pErk, Caspase2 |
| Cyclin D1, Cyclin D3, s6, pErk, pAkt, Caspase2, RBBP, total S6 | pErk, RBBP |
| Cyclin D1, Cyclin D3, s6, Akt, pAkt, Caspase2, RBBP, total S6 | pErk, total S6 |
| Cyclin D1, Cyclin D3, pS6, Erk, pErk, Akt, pAkt, Caspase2 | Akt, pAkt |
| Cyclin D1, Cyclin D3, pS6, Erk, pErk, Akt, pAkt, RBBP | Akt, Caspase2 |
| Cyclin D1, Cyclin D3, pS6, Erk, pErk, Akt, pAkt, total S6 | Akt, RBBP |
| Cyclin D1, Cyclin D3, pS6, Erk, pErk, Akt, Caspase2, RBBP | Akt, total S6 |
| Cyclin D1, Cyclin D3, pS6, Erk, pErk, Akt, Caspase2, total S6 | pAkt, Caspase2 |
| Cyclin D1, Cyclin D3, pS6, Erk, pErk, Akt, RBBP, total S6 | pAkt, RBBP |
| Cyclin D1, Cyclin D3, pS6, Erk, pErk, pAkt, Caspase2, RBBP | pAkt, total S6 |
| Cyclin D1, Cyclin D3, pS6, Erk, pErk, pAkt, Caspase2, total S6 | Caspase2, RBBP |
| Cyclin D1, Cyclin D3, pS6, Erk, pErk, pAkt, RBBP, total S6 | Caspase2, total S6 |
| Cyclin D1, Cyclin D3, pS6, Erk, pErk, Caspase2, RBBP, total S6 | RBBP, total S6 |
| Cyclin D1, Cyclin D3, pS6, Erk, Akt, pAkt, Caspase2, RBBP | PCNA |
| Cyclin D1, Cyclin D3, pS6, Erk, Akt, pAkt, Caspase2, total S6 | Cyclin D1 |
| Cyclin D1, Cyclin D3, pS6, Erk, Akt, pAkt, RBBP, total S6 | Cyclin D3 |
| Cyclin D1, Cyclin D3, pS6, Erk, Akt, Caspase2, RBBP, total S6 | MEK |
| Cyclin D1, Cyclin D3, pS6, Erk, pAkt, Caspase2, RBBP, total S6 | s6 |
| Cyclin D1, Cyclin D3, pS6, pErk, Akt, pAkt, Caspase2, RBBP | pS6 |
| Cyclin D1, Cyclin D3, pS6, pErk, Akt, pAkt, Caspase2, total S6 | Erk |
| Cyclin D1, Cyclin D3, pS6, pErk, Akt, pAkt, RBBP, total S6 | pErk |
| Cyclin D1, Cyclin D3, pS6, pErk, Akt, Caspase2, RBBP, total S6 | Akt |

TABLE 1-continued

Examples of Single Markers and Combinations of Markers

| | |
|---|---|
| Cyclin D1, Cyclin D3, pS6, pErk, pAkt, Caspase2, RBBP, total S6 | pAkt |
| Cyclin D1, Cyclin D3, pS6, Akt, pAkt, Caspase2, RBBP, total S6 | Caspase2 |
| Cyclin D1, Cyclin D3, Erk, pErk, Akt, pAkt, Caspase2, RBBP | RBBP |
| Cyclin D1, Cyclin D3, Erk, pErk, Akt, pAkt, Caspase2, total S6 | total S6 |
| Cyclin D1, Cyclin D3, Erk, pErk, Akt, pAkt, RBBP, total S6 | Cyclin D1, MEK, s6, pS6, Erk, pErk, Akt, Caspase2 |
| Cyclin D1, Cyclin D3, Erk, pErk, Akt, Caspase2, RBBP, total S6 | Cyclin D1, MEK, s6, pS6, Erk, pErk, Akt, pAkt |
| Cyclin D1, Cyclin D3, Erk, pErk, pAkt, Caspase2, RBBP, total S6 | Cyclin D1, Cyclin D3, pErk, Akt, pAkt, Caspase2, RBBP, total S6 |
| Cyclin D1, Cyclin D3, Erk, Akt, pAkt, Caspase2, RBBP, total S6 | |

What is claimed is:

1. A method of determining the efficacy of treatment for polycystic kidney disease (PKD) in a PKD patient, the method comprising:
    (a) providing a first sample comprising urine obtained from the PKD patient at a first time point;
    (b) concentrating the first sample for exosomes;
    (c) determining the level(s) of at least one marker selected from the group consisting of Proliferating Cell Nuclear Antigen (PCNA), cyclin D1, cyclin D3, MAPK-ERK kinase 1 (MEK), and ribosomal protein S6 (S6) in the first sample after step (b);
    (d) administering a glucosyl ceramide synthase (GCS) inhibitor to the PKD patient;
    (e) providing a second sample comprising urine obtained from the PKD patient at a second time point after step (d) and performing steps (b) and (c) on the second sample; and
    (f) identifying the administered treatment as being effective if the level of the at least one marker is decreased at the second time point as compared to the first time point.

2. The method of claim 1, wherein the GCS inhibitor is selected from the group consisting of:
    (S)-quinuclidin-3-yl (2-(4'-(2-methoxyethoxy)-[1,1'-biphenyl]-4-yl)propan-2-yl)carbamate;
    4-fluoro-1-(5-fluoro-4-(4-((2-methoxyethoxy)methyl)phenyl)pyrimidin-2-yl)-N-(4-methyl-1-azabicyclo[3.2.2]nonan-4-yl)piperidine-4-carboxamide;
    4-fluoro-1-(4-(4-((2-methoxyethoxy)methyl)phenyl)pyrimidin-2-yl)-N-(3-methylquinuclidin-3-yl)piperidine-4-carboxamide;
    4-fluoro-1-(4-(4-((2-methoxyethoxy)methyl)phenyl)pyrimidin-2-yl)-N-(4-methyl-1-azabicyclo[3.2.2]nonan-4-yl)piperidine-4-carboxamide;
    4-fluoro-1-(4-(4-(methoxymethyl)phenyl)pyrimidin-2-yl)-N-(3-methylquinuclidin-3-yl)piperidine-4-carboxamide;
    4-fluoro-1-(4-(4-(methoxymethyl)phenyl)pyrimidin-2-yl)-N-(4-methyl-1-azabicyclo[3.2.2]nonan-4-yl)piperidine-4-carboxamide;
    4-fluoro-1-(4-(4-(2-methoxyethoxy)phenyl)pyrimidin-2-yl)-N-(3-methylquinuclidin-3-yl)piperidine-4-carboxamide;
    4-fluoro-1-(4-(4-(2-methoxyethoxy)phenyl)pyrimidin-2-yl)-N-(4-methyl-1-azabicyclo[3.2.2]nonan-4-yl)piperidine-4-carboxamide;
    4-fluoro-1-(4-(4-(2-fluoroethoxy)phenyl)pyrimidin-2-yl)-N-(quinuclidin-3-yl)piperidine-4-carboxamide; and
    4-fluoro-1-(4-(4-(2-fluoroethoxy)phenyl)pyrimidin-2-yl)-N-(4-methyl-1-azabicyclo[3.2.2]nonan-4-yl)piperidine-4-carboxamide.

3. The method of claim 1, wherein steps (c) and (e) comprise determining the levels of at least two markers selected from the group consisting of PCNA, cyclin D1, cyclin D3, MEK, and S6, and the administered GCS inhibitor is identified as being effective if at least one of the two levels is decreased at the second time point as compared to the first time point.

4. The method of claim 3, wherein the administered GCS inhibitor is identified being effective if both levels are decreased at the second time point as compared to the first time point.

* * * * *

```
SEQUENCE LISTING

<160> NUMBER OF SEQ ID NOS: 16

<210> SEQ ID NO 1
<211> LENGTH: 261
<212> TYPE: PRT
<213> ORGANISM: Homo sapiens

<400> SEQUENCE: 1

Met Phe Glu Ala Arg Leu Val Gln Gly Ser Ile Leu Lys Lys Val Leu
1               5                   10                  15

Glu Ala Leu Lys Asp Leu Ile Asn Glu Ala Cys Trp Asp Ile Ser Ser
            20                  25                  30

Ser Gly Val Asn Leu Gln Ser Met Asp Ser Ser His Val Ser Leu Val
        35                  40                  45

Gln Leu Thr Leu Arg Ser Glu Gly Phe Asp Thr Tyr Arg Cys Asp Arg
    50                  55                  60

Asn Leu Ala Met Gly Val Asn Leu Thr Ser Met Ser Lys Ile Leu Lys
65                  70                  75                  80

Cys Ala Gly Asn Glu Asp Ile Ile Thr Leu Arg Ala Glu Asp Asn Ala
                85                  90                  95

Asp Thr Leu Ala Leu Val Phe Glu Ala Pro Asn Gln Glu Lys Val Ser
            100                 105                 110

Asp Tyr Glu Met Lys Leu Met Asp Leu Asp Val Glu Gln Leu Gly Ile
        115                 120                 125

Pro Glu Gln Glu Tyr Ser Cys Val Val Lys Met Pro Ser Gly Glu Phe
    130                 135                 140

Ala Arg Ile Cys Arg Asp Leu Ser His Ile Gly Asp Ala Val Val Ile
145                 150                 155                 160

Ser Cys Ala Lys Asp Gly Val Lys Phe Ser Ala Ser Gly Glu Leu Gly
                165                 170                 175

Asn Gly Asn Ile Lys Leu Ser Gln Thr Ser Asn Val Asp Lys Glu Glu
            180                 185                 190

Glu Ala Val Thr Ile Glu Met Asn Glu Pro Val Gln Leu Thr Phe Ala
        195                 200                 205

Leu Arg Tyr Leu Asn Phe Phe Thr Lys Ala Thr Pro Leu Ser Ser Thr
    210                 215                 220

Val Thr Leu Ser Met Ser Ala Asp Val Pro Leu Val Val Glu Tyr Lys
225                 230                 235                 240

Ile Ala Asp Met Gly His Leu Lys Tyr Tyr Leu Ala Pro Lys Ile Glu
                245                 250                 255

Asp Glu Glu Gly Ser
            260
```

<210> SEQ ID NO 2
<211> LENGTH: 295
<212> TYPE: PRT
<213> ORGANISM: Homo sapiens

<400> SEQUENCE: 2

Met Glu His Gln Leu Leu Cys Cys Glu Val Glu Thr Ile Arg Arg Ala
1               5                   10                  15

Tyr Pro Asp Ala Asn Leu Leu Asn Asp Arg Val Leu Arg Ala Met Leu
            20                  25                  30

Lys Ala Glu Glu Thr Cys Ala Pro Ser Val Ser Tyr Phe Lys Cys Val
        35                  40                  45

Gln Lys Glu Val Leu Pro Ser Met Arg Lys Ile Val Ala Thr Trp Met
    50                  55                  60

Leu Glu Val Cys Glu Glu Gln Lys Cys Glu Glu Val Phe Pro Leu
65                  70                  75                  80

Ala Met Asn Tyr Leu Asp Arg Phe Leu Ser Glu Pro Val Lys Lys
                85                  90                  95

Ser Arg Leu Gln Leu Leu Gly Ala Thr Cys Met Phe Val Ala Ser Lys
            100                 105                 110

Met Lys Glu Thr Ile Pro Leu Thr Ala Glu Lys Leu Cys Ile Tyr Thr
        115                 120                 125

Asp Asn Ser Ile Arg Pro Glu Glu Leu Leu Gln Met Glu Leu Leu Leu
    130                 135                 140

Val Asn Lys Leu Lys Trp Asn Leu Ala Ala Met Thr Pro His Asp Phe
145                 150                 155                 160

Ile Glu His Phe Leu Ser Lys Met Pro Glu Ala Glu Glu Asn Lys Gln
                165                 170                 175

Ile Ile Arg Lys His Ala Gln Thr Phe Val Ala Leu Cys Ala Thr Asp
            180                 185                 190

Val Lys Phe Ile Ser Asn Pro Pro Ser Met Val Ala Ala Gly Ser Val
        195                 200                 205

Val Ala Ala Val Gln Gly Leu Asn Leu Arg Ser Pro Asn Asn Phe Leu
    210                 215                 220

Ser Tyr Tyr Arg Leu Thr Arg Phe Leu Ser Arg Val Ile Lys Cys Asp
225                 230                 235                 240

Pro Asp Cys Leu Arg Ala Cys Gln Glu Gln Ile Glu Ala Leu Leu Glu
                245                 250                 255

Ser Ser Leu Arg Gln Ala Gln Gln Asn Met Asp Pro Lys Ala Ala Glu
            260                 265                 270

Glu Glu Glu Glu Glu Glu Glu Glu Val Asp Leu Ala Cys Thr Pro Thr
        275                 280                 285

Asp Val Arg Asp Val Asp Ile
    290                 295

<210> SEQ ID NO 3
<211> LENGTH: 292
<212> TYPE: PRT
<213> ORGANISM: Homo sapiens

<400> SEQUENCE: 3

Met Glu Leu Leu Cys Cys Glu Gly Thr Arg His Ala Pro Arg Ala Gly
1               5                   10                  15

Pro Asp Pro Arg Leu Leu Gly Asp Gln Arg Val Leu Gln Ser Leu Leu
            20                  25                  30

Arg Leu Glu Glu Arg Tyr Val Pro Arg Ala Ser Tyr Phe Gln Cys Val
            35                  40                  45

Gln Arg Glu Ile Lys Pro His Met Arg Lys Met Leu Ala Tyr Trp Met
 50                  55                  60

Leu Glu Val Cys Glu Glu Gln Arg Cys Glu Glu Val Phe Pro Leu
 65                  70                  75                  80

Ala Met Asn Tyr Leu Asp Arg Tyr Leu Ser Cys Val Pro Thr Arg Lys
                85                  90                  95

Ala Gln Leu Gln Leu Leu Gly Ala Val Cys Met Leu Leu Ala Ser Lys
            100                 105                 110

Leu Arg Glu Thr Thr Pro Leu Thr Ile Glu Lys Leu Cys Ile Tyr Thr
            115                 120                 125

Asp His Ala Val Ser Pro Arg Gln Leu Arg Asp Trp Glu Val Leu Val
        130                 135                 140

Leu Gly Lys Leu Lys Trp Asp Leu Ala Ala Val Ile Ala His Asp Phe
145                 150                 155                 160

Leu Ala Phe Ile Leu His Arg Leu Ser Leu Pro Arg Asp Arg Gln Ala
                165                 170                 175

Leu Val Lys Lys His Ala Gln Thr Phe Leu Ala Leu Cys Ala Thr Asp
            180                 185                 190

Tyr Thr Phe Ala Met Tyr Pro Pro Ser Met Ile Ala Thr Gly Ser Ile
        195                 200                 205

Gly Ala Ala Val Gln Gly Leu Gly Ala Cys Ser Met Ser Gly Asp Glu
    210                 215                 220

Leu Thr Glu Leu Leu Ala Gly Ile Thr Gly Thr Glu Val Asp Cys Leu
225                 230                 235                 240

Arg Ala Cys Gln Glu Gln Ile Glu Ala Ala Leu Arg Glu Ser Leu Arg
                245                 250                 255

Glu Ala Ser Gln Thr Ser Ser Pro Ala Pro Lys Ala Pro Arg Gly
            260                 265                 270

Ser Ser Ser Gln Gly Pro Ser Gln Thr Ser Thr Pro Thr Asp Val Thr
    275                 280                 285

Ala Ile His Leu
    290

<210> SEQ ID NO 4
<211> LENGTH: 393
<212> TYPE: PRT
<213> ORGANISM: Homo sapiens

<400> SEQUENCE: 4

Met Pro Lys Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile

```
            100                 105                 110
Arg Glu Leu Gln Val Leu His Glu Cys Asn Ser Pro Tyr Ile Val Gly
            115                 120                 125

Phe Tyr Gly Ala Phe Tyr Ser Asp Gly Glu Ile Ser Ile Cys Met Glu
            130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
            195                 200                 205

Phe Gly Val Ser Gly Gln Leu Ile Asp Ser Met Ala Asn Ser Phe Val
210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Pro Asp Ala Lys Glu Leu Glu
            260                 265                 270

Leu Met Phe Gly Cys Gln Val Glu Gly Asp Ala Ala Glu Thr Pro Pro
            275                 280                 285

Arg Pro Arg Thr Pro Gly Arg Pro Leu Ser Ser Tyr Gly Met Asp Ser
290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
            340                 345                 350

Lys Gln Leu Met Val His Ala Phe Ile Lys Arg Ser Asp Ala Glu Glu
            355                 360                 365

Val Asp Phe Ala Gly Trp Leu Cys Ser Thr Ile Gly Leu Asn Gln Pro
370                 375                 380

Ser Thr Pro Thr His Ala Ala Gly Val
385                 390

<210> SEQ ID NO 5
<211> LENGTH: 367
<212> TYPE: PRT
<213> ORGANISM: Homo sapiens

<400> SEQUENCE: 5

Met Pro Lys Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80
```

```
Val Val Phe Lys Val Ser His Lys Pro Ser Gly Leu Val Met Ala Arg
                85                  90                  95
Lys Leu Ile His Leu Glu Ile Lys Pro Ala Ile Arg Asn Gln Ile Ile
            100                 105                 110
Arg Glu Leu Gln Val Leu His Glu Cys Asn Ser Pro Tyr Ile Val Gly
        115                 120                 125
Phe Tyr Gly Ala Phe Tyr Ser Asp Gly Glu Ile Ser Ile Cys Met Glu
    130                 135                 140
His Met Val Ile Lys Gly Leu Thr Tyr Leu Arg Glu Lys His Lys Ile
145                 150                 155                 160
Met His Arg Asp Val Lys Pro Ser Asn Ile Leu Val Asn Ser Arg Gly
                165                 170                 175
Glu Ile Lys Leu Cys Asp Phe Gly Val Ser Gly Gln Leu Ile Asp Ser
            180                 185                 190
Met Ala Asn Ser Phe Val Gly Thr Arg Ser Tyr Met Ser Pro Glu Arg
        195                 200                 205
Leu Gln Gly Thr His Tyr Ser Val Gln Ser Asp Ile Trp Ser Met Gly
    210                 215                 220
Leu Ser Leu Val Glu Met Ala Val Gly Arg Tyr Pro Ile Pro Pro Pro
225                 230                 235                 240
Asp Ala Lys Glu Leu Glu Leu Met Phe Gly Cys Gln Val Glu Gly Asp
                245                 250                 255
Ala Ala Glu Thr Pro Pro Arg Pro Arg Thr Pro Gly Arg Pro Leu Ser
            260                 265                 270
Ser Tyr Gly Met Asp Ser Arg Pro Pro Met Ala Ile Phe Glu Leu Leu
        275                 280                 285
Asp Tyr Ile Val Asn Glu Pro Pro Pro Lys Leu Pro Ser Gly Val Phe
    290                 295                 300
Ser Leu Glu Phe Gln Asp Phe Val Asn Lys Cys Leu Ile Lys Asn Pro
305                 310                 315                 320
Ala Glu Arg Ala Asp Leu Lys Gln Leu Met Val His Ala Phe Ile Lys
                325                 330                 335
Arg Ser Asp Ala Glu Glu Val Asp Phe Ala Gly Trp Leu Cys Ser Thr
            340                 345                 350
Ile Gly Leu Asn Gln Pro Ser Thr Pro Thr His Ala Ala Gly Val
        355                 360                 365

<210> SEQ ID NO 6
<211> LENGTH: 249
<212> TYPE: PRT
<213> ORGANISM: Homo sapiens

<400> SEQUENCE: 6

Met Lys Leu Asn Ile Ser Phe Pro Ala Thr Gly Cys Gln Lys Leu Ile
1               5                   10                  15
Glu Val Asp Asp Glu Arg Lys Leu Arg Thr Phe Tyr Glu Lys Arg Met
            20                  25                  30
Ala Thr Glu Val Ala Ala Asp Ala Leu Gly Glu Glu Trp Lys Gly Tyr
        35                  40                  45
Val Val Arg Ile Ser Gly Gly Asn Asp Lys Gln Gly Phe Pro Met Lys
    50                  55                  60
Gln Gly Val Leu Thr His Gly Arg Val Arg Leu Leu Leu Ser Lys Gly
65                  70                  75                  80
His Ser Cys Tyr Arg Pro Arg Arg Thr Gly Glu Arg Lys Arg Lys Ser
                85                  90                  95
```

```
Val Arg Gly Cys Ile Val Asp Ala Asn Leu Ser Val Leu Asn Leu Val
            100                 105                 110

Ile Val Lys Lys Gly Glu Lys Asp Ile Pro Gly Leu Thr Asp Thr Thr
        115                 120                 125

Val Pro Arg Arg Leu Gly Pro Lys Arg Ala Ser Arg Ile Arg Lys Leu
130                 135                 140

Phe Asn Leu Ser Lys Glu Asp Val Arg Gln Tyr Val Val Arg Lys
145                 150                 155                 160

Pro Leu Asn Lys Glu Gly Lys Lys Pro Arg Thr Lys Ala Pro Lys Ile
                165                 170                 175

Gln Arg Leu Val Thr Pro Arg Val Leu Gln His Lys Arg Arg Arg Ile
            180                 185                 190

Ala Leu Lys Lys Gln Arg Thr Lys Lys Asn Lys Glu Glu Ala Ala Glu
        195                 200                 205

Tyr Ala Lys Leu Leu Ala Lys Arg Met Lys Glu Ala Lys Glu Lys Arg
    210                 215                 220

Gln Glu Gln Ile Ala Lys Arg Arg Arg Leu Ser Ser Leu Arg Ala Ser
225                 230                 235                 240

Thr Ser Lys Ser Glu Ser Ser Gln Lys
                245

<210> SEQ ID NO 7
<211> LENGTH: 379
<212> TYPE: PRT
<213> ORGANISM: Homo sapiens

<400> SEQUENCE: 7

Met Ala Ala Ala Ala Gln Gly Gly Gly Gly Glu Pro Arg Arg
1               5                   10                  15

Thr Glu Gly Val Gly Pro Gly Val Pro Gly Glu Val Glu Met Val Lys
            20                  25                  30

Gly Gln Pro Phe Asp Val Gly Pro Arg Tyr Thr Gln Leu Gln Tyr Ile
        35                  40                  45

Gly Glu Gly Ala Tyr Gly Met Val Ser Ser Ala Tyr Asp His Val Arg
    50                  55                  60

Lys Thr Arg Val Ala Ile Lys Lys Ile Ser Pro Phe Glu His Gln Thr
65                  70                  75                  80

Tyr Cys Gln Arg Thr Leu Arg Glu Ile Gln Ile Leu Leu Arg Phe Arg
                85                  90                  95

His Glu Asn Val Ile Gly Ile Arg Asp Ile Leu Arg Ala Ser Thr Leu
            100                 105                 110

Glu Ala Met Arg Asp Val Tyr Ile Val Gln Asp Leu Met Glu Thr Asp
        115                 120                 125

Leu Tyr Lys Leu Leu Lys Ser Gln Gln Leu Ser Asn Asp His Ile Cys
130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                165                 170                 175

Thr Cys Asp Leu Lys Ile Cys Asp Phe Gly Leu Ala Arg Ile Ala Asp
            180                 185                 190

Pro Glu His Asp His Thr Gly Phe Leu Thr Glu Tyr Val Ala Thr Arg
        195                 200                 205

Trp Tyr Arg Ala Pro Glu Ile Met Leu Asn Ser Lys Gly Tyr Thr Lys
```

```
                210                 215                 220
Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255

Ile Leu Gly Ile Leu Gly Ser Pro Ser Gln Glu Asp Leu Asn Cys Ile
            260                 265                 270

Ile Asn Met Lys Ala Arg Asn Tyr Leu Gln Ser Leu Pro Ser Lys Thr
        275                 280                 285

Lys Val Ala Trp Ala Lys Leu Phe Pro Lys Ser Asp Ser Lys Ala Leu
    290                 295                 300

Asp Leu Leu Asp Arg Met Leu Thr Phe Asn Pro Asn Lys Arg Ile Thr
305                 310                 315                 320

Val Glu Glu Ala Leu Ala His Pro Tyr Leu Gln Tyr Tyr Asp Pro
                325                 330                 335

Thr Asp Glu Pro Val Ala Glu Pro Phe Thr Phe Ala Met Glu Leu
            340                 345                 350

Asp Asp Leu Pro Lys Glu Arg Leu Lys Glu Leu Ile Phe Gln Glu Thr
        355                 360                 365

Ala Arg Phe Gln Pro Gly Val Leu Glu Ala Pro
    370                 375

<210> SEQ ID NO 8
<211> LENGTH: 335
<212> TYPE: PRT
<213> ORGANISM: Homo sapiens

<400> SEQUENCE: 8

Met Ala Ala Ala Ala Gln Gly Gly Gly Gly Glu Pro Arg Arg
1               5                   10                  15

Thr Glu Gly Val Gly Pro Gly Val Pro Gly Glu Val Glu Met Val Lys
                20                  25                  30

Gly Gln Pro Phe Asp Val Gly Pro Arg Tyr Thr Gln Leu Gln Tyr Ile
            35                  40                  45

Gly Glu Gly Ala Tyr Gly Met Val Ser Ser Ala Tyr Asp His Val Arg
        50                  55                  60

Lys Thr Arg Val Ala Ile Lys Lys Ile Ser Pro Phe Glu His Gln Thr
65                  70                  75                  80

Tyr Cys Gln Arg Thr Leu Arg Glu Ile Gln Ile Leu Leu Arg Phe Arg
                85                  90                  95

His Glu Asn Val Ile Gly Ile Arg Asp Ile Leu Arg Ala Ser Thr Leu
            100                 105                 110

Glu Ala Met Arg Asp Val Tyr Ile Val Gln Asp Leu Met Glu Thr Asp
        115                 120                 125

Leu Tyr Lys Leu Leu Lys Ser Gln Gln Leu Ser Asn Asp His Ile Cys
    130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                165                 170                 175

Thr Cys Asp Leu Lys Ile Cys Asp Phe Gly Leu Ala Arg Ile Ala Asp
            180                 185                 190

Pro Glu His Asp His Thr Gly Phe Leu Thr Glu Tyr Val Ala Thr Arg
        195                 200                 205
```

```
Trp Tyr Arg Ala Pro Glu Ile Met Leu Asn Ser Lys Gly Tyr Thr Lys
    210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255

Ile Leu Ala Leu Asp Leu Leu Asp Arg Met Leu Thr Phe Asn Pro Asn
                260                 265                 270

Lys Arg Ile Thr Val Glu Glu Ala Leu Ala His Pro Tyr Leu Glu Gln
            275                 280                 285

Tyr Tyr Asp Pro Thr Asp Glu Pro Val Ala Glu Pro Phe Thr Phe
    290                 295                 300

Ala Met Glu Leu Asp Asp Leu Pro Lys Glu Arg Leu Lys Glu Leu Ile
305                 310                 315                 320

Phe Gln Glu Thr Ala Arg Phe Gln Pro Gly Val Leu Glu Ala Pro
                325                 330                 335

<210> SEQ ID NO 9
<211> LENGTH: 357
<212> TYPE: PRT
<213> ORGANISM: Homo sapiens

<400> SEQUENCE: 9

Met Ala Ala Ala Ala Gln Gly Gly Gly Gly Gly Glu Pro Arg Arg
1               5                   10                  15

Thr Glu Gly Val Gly Pro Gly Val Pro Gly Glu Val Glu Met Val Lys
                20                  25                  30

Gly Gln Pro Phe Asp Val Gly Pro Arg Tyr Thr Gln Leu Gln Tyr Ile
            35                  40                  45

Gly Glu Gly Ala Tyr Gly Met Val Ser Ser Ala Tyr Asp His Val Arg
        50                  55                  60

Lys Thr Arg Val Ala Ile Lys Lys Ile Ser Pro Phe Glu His Gln Thr
65                  70                  75                  80

Tyr Cys Gln Arg Thr Leu Arg Glu Ile Gln Ile Leu Leu Arg Phe Arg
                85                  90                  95

His Glu Asn Val Ile Gly Ile Arg Asp Ile Leu Arg Ala Ser Thr Leu
                100                 105                 110

Glu Ala Met Arg Asp Val Tyr Ile Val Gln Asp Leu Met Glu Thr Asp
            115                 120                 125

Leu Tyr Lys Leu Leu Lys Ser Gln Gln Leu Ser Asn Asp His Ile Cys
130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                165                 170                 175

Thr Cys Asp Leu Lys Ile Cys Asp Phe Gly Leu Ala Arg Ile Ala Asp
                180                 185                 190

Pro Glu His Asp His Thr Gly Phe Leu Thr Glu Tyr Val Ala Thr Arg
            195                 200                 205

Trp Tyr Arg Ala Pro Glu Ile Met Leu Asn Ser Lys Gly Tyr Thr Lys
    210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255
```

```
Ile Leu Gly Ile Leu Gly Ser Pro Ser Gln Glu Asp Leu Asn Cys Ile
                260                 265                 270

Ile Asn Met Lys Ala Arg Asn Tyr Leu Gln Ser Leu Pro Ser Lys Thr
            275                 280                 285

Lys Val Ala Trp Ala Lys Leu Phe Pro Lys Ser Asp Ser Lys Ala Leu
        290                 295                 300

Asp Leu Leu Asp Arg Met Leu Thr Phe Asn Pro Asn Lys Arg Ile Thr
305                 310                 315                 320

Val Glu Glu Ala Leu Ala His Pro Tyr Leu Glu Gln Tyr Tyr Asp Pro
                325                 330                 335

Thr Asp Glu Val Gly Gln Ser Pro Ala Ala Val Gly Leu Gly Ala Gly
            340                 345                 350

Glu Gln Gly Gly Thr
        355

<210> SEQ ID NO 10
<211> LENGTH: 360
<212> TYPE: PRT
<213> ORGANISM: Homo sapiens

<400> SEQUENCE: 10

Met Ala Ala Ala Ala Ala Gly Ala Gly Pro Glu Met Val Arg Gly
1               5                   10                  15

Gln Val Phe Asp Val Gly Pro Arg Tyr Thr Asn Leu Ser Tyr Ile Gly
            20                  25                  30

Glu Gly Ala Tyr Gly Met Val Cys Ser Ala Tyr Asp Asn Val Asn Lys
        35                  40                  45

Val Arg Val Ala Ile Lys Lys Ile Ser Pro Phe Glu His Gln Thr Tyr
    50                  55                  60

Cys Gln Arg Thr Leu Arg Glu Ile Lys Ile Leu Leu Arg Phe Arg His
65                  70                  75                  80

Glu Asn Ile Ile Gly Ile Asn Asp Ile Ile Arg Ala Pro Thr Ile Glu
                85                  90                  95

Gln Met Lys Asp Val Tyr Ile Val Gln Asp Leu Met Glu Thr Asp Leu
            100                 105                 110

Tyr Lys Leu Leu Lys Thr Gln His Leu Ser Asn Asp His Ile Cys Tyr
        115                 120                 125

Phe Leu Tyr Gln Ile Leu Arg Gly Leu Lys Tyr Ile His Ser Ala Asn
    130                 135                 140

Val Leu His Arg Asp Leu Lys Pro Ser Asn Leu Leu Asn Thr Thr
145                 150                 155                 160

Cys Asp Leu Lys Ile Cys Asp Phe Gly Leu Ala Arg Val Ala Asp Pro
                165                 170                 175

Asp His Asp His Thr Gly Phe Leu Thr Glu Tyr Val Ala Thr Arg Trp
            180                 185                 190

Tyr Arg Ala Pro Glu Ile Met Leu Asn Ser Lys Gly Tyr Thr Lys Ser
        195                 200                 205

Ile Asp Ile Trp Ser Val Gly Cys Ile Leu Ala Glu Met Leu Ser Asn
    210                 215                 220

Arg Pro Ile Phe Pro Gly Lys His Tyr Leu Asp Gln Leu Asn His Ile
225                 230                 235                 240

Leu Gly Ile Leu Gly Ser Pro Ser Gln Glu Asp Leu Asn Cys Ile Ile
                245                 250                 255

Asn Leu Lys Ala Arg Asn Tyr Leu Leu Ser Leu Pro His Lys Asn Lys
```

Val Pro Trp Asn Arg Leu Phe Pro Asn Ala Asp Ser Lys Ala Leu Asp
             260                 265                 270
        275                 280                 285

Leu Leu Asp Lys Met Leu Thr Phe Asn Pro His Lys Arg Ile Glu Val
        290                 295                 300

Glu Gln Ala Leu Ala His Pro Tyr Leu Glu Gln Tyr Tyr Asp Pro Ser
305                 310                 315                 320

Asp Glu Pro Ile Ala Glu Ala Pro Phe Lys Phe Asp Met Glu Leu Asp
                    325                 330                 335

Asp Leu Pro Lys Glu Lys Leu Lys Glu Leu Ile Phe Glu Glu Thr Ala
                340                 345                 350

Arg Phe Gln Pro Gly Tyr Arg Ser
                355                 360

<210> SEQ ID NO 11
<211> LENGTH: 316
<212> TYPE: PRT
<213> ORGANISM: Homo sapiens

<400> SEQUENCE: 11

Met Ala Ala Ala Ala Ala Gly Ala Gly Pro Glu Met Val Arg Gly
1               5                   10                  15

Gln Val Phe Asp Val Gly Pro Arg Tyr Thr Asn Leu Ser Tyr Ile Gly
                20                  25                  30

Glu Gly Ala Tyr Gly Met Val Cys Ser Ala Tyr Asp Asn Val Asn Lys
            35                  40                  45

Val Arg Val Ala Ile Lys Lys Ile Ser Pro Phe Glu His Gln Thr Tyr
        50                  55                  60

Cys Gln Arg Thr Leu Arg Glu Ile Lys Ile Leu Leu Arg Phe Arg His
65                  70                  75                  80

Glu Asn Ile Ile Gly Ile Asn Asp Ile Ile Arg Ala Pro Thr Ile Glu
                85                  90                  95

Gln Met Lys Asp Val Tyr Ile Val Gln Asp Leu Met Glu Thr Asp Leu
                100                 105                 110

Tyr Lys Leu Leu Lys Thr Gln His Leu Ser Asn Asp His Ile Cys Tyr
            115                 120                 125

Phe Leu Tyr Gln Ile Leu Arg Gly Leu Lys Tyr Ile His Ser Ala Asn
        130                 135                 140

Val Leu His Arg Asp Leu Lys Pro Ser Asn Leu Leu Leu Asn Thr Thr
145                 150                 155                 160

Cys Asp Leu Lys Ile Cys Asp Phe Gly Leu Ala Arg Val Ala Asp Pro
                165                 170                 175

Asp His Asp His Thr Gly Phe Leu Thr Glu Tyr Val Ala Thr Arg Trp
                180                 185                 190

Tyr Arg Ala Pro Glu Ile Met Leu Asn Ser Lys Gly Tyr Thr Lys Ser
            195                 200                 205

Ile Asp Ile Trp Ser Val Gly Cys Ile Leu Ala Glu Met Leu Ser Asn
        210                 215                 220

Arg Pro Ile Phe Pro Gly Lys His Tyr Leu Asp Gln Leu Asn His Ile
225                 230                 235                 240

Leu Ala Leu Asp Leu Leu Asp Lys Met Leu Thr Phe Asn Pro His Lys
                245                 250                 255

Arg Ile Glu Val Glu Gln Ala Leu Ala His Pro Tyr Leu Glu Gln Tyr
                260                 265                 270

```
Tyr Asp Pro Ser Asp Glu Pro Ile Ala Glu Ala Pro Phe Lys Phe Asp
            275                 280                 285

Met Glu Leu Asp Asp Leu Pro Lys Glu Lys Leu Lys Glu Leu Ile Phe
    290                 295                 300

Glu Glu Thr Ala Arg Phe Gln Pro Gly Tyr Arg Ser
305                 310                 315

<210> SEQ ID NO 12
<211> LENGTH: 480
<212> TYPE: PRT
<213> ORGANISM: Homo sapiens

<400> SEQUENCE: 12

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335
```

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
            355                 360                 365

Pro Arg Thr Leu Gly Pro Glu Ala Lys Ser Leu Leu Ser Gly Leu Leu
        370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
            435                 440                 445

Ile Thr Pro Pro Asp Gln Asp Asp Ser Met Glu Cys Val Asp Ser Glu
        450                 455                 460

Arg Arg Pro His Phe Pro Gln Phe Ser Tyr Ser Ala Ser Gly Thr Ala
465                 470                 475                 480

<210> SEQ ID NO 13
<211> LENGTH: 450
<212> TYPE: PRT
<213> ORGANISM: Homo sapiens

<400> SEQUENCE: 13

Met Ala Ala Pro Ser Ala Gly Ser Trp Ser Thr Phe Gln His Lys Glu
1               5                   10                  15

Leu Met Ala Ala Asp Arg Gly Arg Arg Ile Leu Gly Val Cys Gly Met
            20                  25                  30

His Pro His His Gln Glu Thr Leu Lys Lys Asn Arg Val Val Leu Ala
        35                  40                  45

Lys Gln Leu Leu Leu Ser Glu Leu Leu Glu His Leu Leu Glu Lys Asp
50                  55                  60

Ile Ile Thr Leu Glu Met Arg Glu Leu Ile Gln Ala Lys Val Gly Ser
65                  70                  75                  80

Phe Ser Gln Asn Val Glu Leu Leu Asn Leu Leu Pro Lys Arg Gly Pro
                85                  90                  95

Gln Ala Phe Asp Ala Phe Cys Glu Ala Leu Arg Glu Thr Lys Gln Gly
            100                 105                 110

His Leu Glu Asp Met Leu Leu Thr Thr Leu Ser Gly Leu Gln His Val
        115                 120                 125

Leu Pro Pro Leu Ser Cys Asp Tyr Asp Leu Ser Leu Pro Phe Pro Val
    130                 135                 140

Cys Glu Ser Cys Pro Leu Tyr Lys Lys Leu Arg Leu Ser Thr Asp Thr
145                 150                 155                 160

Val Glu His Ser Leu Asp Asn Lys Asp Gly Pro Val Cys Leu Gln Val
                165                 170                 175

Lys Pro Cys Thr Pro Glu Phe Tyr Gln Thr His Phe Gln Leu Ala Tyr
            180                 185                 190

Arg Leu Gln Ser Arg Pro Arg Gly Leu Ala Leu Val Leu Ser Asn Val
        195                 200                 205

His Phe Thr Gly Glu Lys Glu Leu Glu Phe Arg Ser Gly Gly Asp Val
    210                 215                 220

Asp His Ser Thr Leu Val Thr Leu Phe Lys Leu Leu Gly Tyr Asp Val

```
                225                 230                 235                 240
        His Val Leu Cys Asp Gln Thr Ala Gln Glu Met Gln Glu Lys Leu Gln
                        245                 250                 255

Asn Phe Ala Gln Leu Pro Ala His Arg Val Thr Asp Ser Cys Ile Val
                        260                 265                 270

Ala Leu Leu Ser His Gly Val Glu Gly Ala Ile Tyr Gly Val Asp Gly
                        275                 280                 285

Lys Leu Leu Gln Leu Gln Glu Val Phe Gln Leu Phe Asp Asn Ala Asn
                        290                 295                 300

Cys Pro Ser Leu Gln Asn Lys Pro Lys Met Phe Phe Ile Gln Ala Cys
        305                 310                 315                 320

Arg Gly Asp Glu Thr Asp Arg Gly Val Asp Gln Gln Asp Gly Lys Asn
                        325                 330                 335

His Ala Gly Ser Pro Gly Cys Glu Glu Ser Asp Ala Gly Lys Glu Lys
                        340                 345                 350

Leu Pro Lys Met Arg Leu Pro Thr Arg Ser Asp Met Ile Cys Gly Tyr
                        355                 360                 365

Ala Cys Leu Lys Gly Thr Ala Ala Met Arg Asn Thr Lys Arg Gly Ser
                        370                 375                 380

Trp Tyr Ile Glu Ala Leu Ala Gln Val Phe Ser Glu Arg Ala Cys Asp
        385                 390                 395                 400

Met His Val Ala Asp Met Leu Val Lys Val Asn Ala Leu Ile Lys Asp
                        405                 410                 415

Arg Glu Gly Tyr Ala Pro Gly Thr Glu Phe His Arg Cys Lys Glu Met
                        420                 425                 430

Ser Glu Tyr Cys Ser Thr Leu Cys Arg His Leu Tyr Leu Phe Pro Gly
                        435                 440                 445

His Pro
            450

<210> SEQ ID NO 14
<211> LENGTH: 313
<212> TYPE: PRT
<213> ORGANISM: Homo sapiens

<400> SEQUENCE: 14

Met His Pro His His Gln Glu Thr Leu Lys Lys Asn Arg Val Val Leu
        1               5                   10                  15

Ala Lys Gln Leu Leu Leu Ser Glu Leu Leu Glu His Leu Leu Glu Lys
                        20                  25                  30

Asp Ile Ile Thr Leu Glu Met Arg Glu Leu Ile Gln Ala Lys Val Gly
                        35                  40                  45

Ser Phe Ser Gln Asn Val Glu Leu Leu Asn Leu Leu Pro Lys Arg Gly
                        50                  55                  60

Pro Gln Ala Phe Asp Ala Phe Cys Glu Ala Leu Arg Glu Thr Lys Gln
        65                  70                  75                  80

Gly His Leu Glu Asp Met Leu Leu Thr Thr Leu Ser Gly Leu Gln His
                        85                  90                  95

Val Leu Pro Pro Leu Ser Cys Asp Tyr Asp Leu Ser Leu Pro Phe Pro
                        100                 105                 110

Val Cys Glu Ser Cys Pro Leu Tyr Lys Lys Leu Arg Leu Ser Thr Asp
                        115                 120                 125

Thr Val Glu His Ser Leu Asp Asn Lys Asp Gly Pro Val Cys Leu Gln
                        130                 135                 140
```

```
Val Lys Pro Cys Thr Pro Glu Phe Tyr Gln Thr His Phe Gln Leu Ala
145                 150                 155                 160

Tyr Arg Leu Gln Ser Arg Pro Arg Gly Leu Ala Leu Val Leu Ser Asn
            165                 170                 175

Val His Phe Thr Gly Glu Lys Glu Leu Glu Phe Arg Ser Gly Gly Asp
                180                 185                 190

Val Asp His Ser Thr Leu Val Thr Leu Phe Lys Leu Leu Gly Tyr Asp
            195                 200                 205

Val His Val Leu Cys Asp Gln Thr Ala Gln Met Gln Glu Lys Leu
        210                 215                 220

Gln Asn Phe Ala Gln Leu Pro Ala His Arg Val Thr Asp Ser Cys Ile
225                 230                 235                 240

Val Ala Leu Leu Ser His Gly Val Glu Gly Ala Ile Tyr Gly Val Asp
            245                 250                 255

Gly Lys Leu Leu Gln Leu Gln Glu Val Phe Gln Leu Phe Asp Asn Ala
            260                 265                 270

Asn Cys Pro Ser Leu Gln Asn Lys Pro Lys Met Phe Phe Ile Gln Ala
            275                 280                 285

Cys Arg Gly Gly Gly Ala Ile Gly Ser Leu Gly His Leu Leu Leu Phe
            290                 295                 300

Thr Ala Ala Thr Ala Ser Leu Ala Leu
305                 310
```

<210> SEQ ID NO 15
<211> LENGTH: 91
<212> TYPE: PRT
<213> ORGANISM: Homo sapiens

<400> SEQUENCE: 15

```
Met Ala Ala Asp Arg Gly Arg Arg Ile Leu Gly Val Cys Gly Met His
1               5                   10                  15

Pro His His Gln Glu Thr Leu Lys Lys Asn Arg Val Val Leu Ala Lys
                20                  25                  30

Gln Leu Leu Leu Ser Glu Leu Leu Glu His Leu Leu Glu Lys Asp Ile
            35                  40                  45

Ile Thr Leu Glu Met Arg Glu Leu Ile Gln Ala Lys Val Gly Ser Phe
50                  55                  60

Ser Gln Asn Val Glu Leu Leu Asn Leu Leu Pro Lys Arg Gly Pro Gln
65                  70                  75                  80

Ala Phe Asp Ala Phe Cys Glu Ala Leu His Ser
                85                  90
```

<210> SEQ ID NO 16
<211> LENGTH: 425
<212> TYPE: PRT
<213> ORGANISM: Homo sapiens

<400> SEQUENCE: 16

```
Met Ala Asp Lys Glu Ala Ala Phe Asp Asp Ala Val Glu Glu Arg Val
1               5                   10                  15

Ile Asn Glu Glu Tyr Lys Ile Trp Lys Lys Asn Thr Pro Phe Leu Tyr
                20                  25                  30

Asp Leu Val Met Thr His Ala Leu Glu Trp Pro Ser Leu Thr Ala Gln
            35                  40                  45

Trp Leu Pro Asp Val Thr Arg Pro Glu Gly Lys Asp Phe Ser Ile His
50                  55                  60
```

-continued

| | | | | | | | | | | | | | | |
|---|---|---|---|---|---|---|---|---|---|---|---|---|---|---|
|Arg|Leu|Val|Leu|Gly|Thr|His|Thr|Ser|Asp|Glu|Gln|Asn|His|Leu|Val|
|65| | | | |70| | | |75| | | | |80|

Ile Ala Ser Val Gln Leu Pro Asn Asp Asp Ala Gln Phe Asp Ala Ser
                85                  90                  95

His Tyr Asp Ser Glu Lys Gly Glu Phe Gly Phe Gly Ser Val Ser
            100                 105                 110

Gly Lys Ile Glu Ile Glu Ile Lys Ile Asn His Glu Gly Glu Val Asn
            115                 120                 125

Arg Ala Arg Tyr Met Pro Gln Asn Pro Cys Ile Ile Ala Thr Lys Thr
130             135                 140

Pro Ser Ser Asp Val Leu Val Phe Asp Tyr Thr Lys His Pro Ser Lys
145                 150                 155                 160

Pro Asp Pro Ser Gly Glu Cys Asn Pro Asp Leu Arg Leu Arg Gly His
                165                 170                 175

Gln Lys Glu Gly Tyr Gly Leu Ser Trp Asn Pro Asn Leu Ser Gly His
            180                 185                 190

Leu Leu Ser Ala Ser Asp Asp His Thr Ile Cys Leu Trp Asp Ile Ser
            195                 200                 205

Ala Val Pro Lys Glu Gly Lys Val Val Asp Ala Lys Thr Ile Phe Thr
            210                 215                 220

Gly His Thr Ala Val Val Glu Asp Val Ser Trp His Leu Leu His Glu
225                 230                 235                 240

Ser Leu Phe Gly Ser Val Ala Asp Asp Gln Lys Leu Met Ile Trp Asp
                245                 250                 255

Thr Arg Ser Asn Asn Thr Ser Lys Pro Ser His Ser Val Asp Ala His
                260                 265                 270

Thr Ala Glu Val Asn Cys Leu Ser Phe Asn Pro Tyr Ser Glu Phe Ile
            275                 280                 285

Leu Ala Thr Gly Ser Ala Asp Lys Thr Val Ala Leu Trp Asp Leu Arg
            290                 295                 300

Asn Leu Lys Leu Lys Leu His Ser Phe Glu Ser His Lys Asp Glu Ile
305                 310                 315                 320

Phe Gln Val Gln Trp Ser Pro His Asn Glu Thr Ile Leu Ala Ser Ser
                325                 330                 335

Gly Thr Asp Arg Arg Leu Asn Val Trp Asp Leu Ser Lys Ile Gly Glu
                340                 345                 350

Glu Gln Ser Pro Glu Asp Ala Glu Asp Gly Pro Pro Glu Leu Leu Phe
            355                 360                 365

Ile His Gly Gly His Thr Ala Lys Ile Ser Asp Phe Ser Trp Asn Pro
            370                 375                 380

Asn Glu Pro Trp Val Ile Cys Ser Val Ser Glu Asp Asn Ile Met Gln
385                 390                 395                 400

Val Trp Gln Met Ala Glu Asn Ile Tyr Asn Asp Glu Asp Pro Glu Gly
                405                 410                 415

Ser Val Asp Pro Glu Gly Gln Gly Ser
                420                 425